United States Patent
Argiriadi et al.

(10) Patent No.: US 10,160,748 B2
(45) Date of Patent: Dec. 25, 2018

(54) INDAZOLONES AS MODULATORS OF TNF SIGNALING

(71) Applicant: AbbVie Inc., North Chicago, IL (US)

(72) Inventors: Maria Argiriadi, Southborough, MA (US); Eric Breinlinger, Charlton, MA (US); Justin D. Dietrich, Lindenhust, IL (US); Michael Friedman, Brookline, MA (US); David Ihle, Worcester, MA (US); Michael Morytko, Framingham, MA (US); Kelly Mullen, Charlton, MA (US); Augustine Osuma, Lindenhurst, IL (US); Gloria Y. LoSchiavo, Worcester, MA (US); Noel S. Wilson, Kenosha, WI (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/670,708

(22) Filed: Aug. 7, 2017

(65) Prior Publication Data
US 2018/0086737 A1   Mar. 29, 2018

Related U.S. Application Data

(63) Continuation of application No. 15/130,279, filed on Apr. 15, 2016, now abandoned.

(60) Provisional application No. 62/258,651, filed on Nov. 23, 2015, provisional application No. 62/149,232, filed on Apr. 17, 2015.

(51) Int. Cl.
| | |
|---|---|
| *C07D 403/04* | (2006.01) |
| *C07F 9/6558* | (2006.01) |
| *C07D 413/04* | (2006.01) |
| *C07D 471/04* | (2006.01) |
| *C07D 405/04* | (2006.01) |
| *C07D 491/107* | (2006.01) |
| *C07D 487/04* | (2006.01) |
| *C07D 401/14* | (2006.01) |
| *C07D 417/04* | (2006.01) |
| *C07D 403/14* | (2006.01) |
| *C07D 498/04* | (2006.01) |
| *C07D 401/04* | (2006.01) |
| *C07D 413/14* | (2006.01) |
| *C07D 405/14* | (2006.01) |
| *C07D 417/14* | (2006.01) |

(52) U.S. Cl.
CPC ......... *C07D 403/04* (2013.01); *C07D 401/04* (2013.01); *C07D 401/14* (2013.01); *C07D 403/14* (2013.01); *C07D 405/04* (2013.01); *C07D 405/14* (2013.01); *C07D 413/04* (2013.01); *C07D 413/14* (2013.01); *C07D 417/04* (2013.01); *C07D 417/14* (2013.01); *C07D 471/04* (2013.01); *C07D 487/04* (2013.01); *C07D 491/107* (2013.01); *C07D 498/04* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 4,898,863 | A | 2/1990 | Brown et al. |
| 2007/0021337 | A1 | 1/2007 | Lee et al. |
| 2007/0213337 | A1 | 9/2007 | Wacker et al. |
| 2008/0287448 | A1 | 11/2008 | Zoller et al. |
| 2010/0029616 | A1 | 2/2010 | Kinney et al. |
| 2010/0204214 | A1 | 8/2010 | Chytil et al. |
| 2014/0235675 | A1 | 8/2014 | Papeo et al. |
| 2016/0039811 | A1 | 2/2016 | Yoshida et al. |
| 2016/0304496 | A1 | 10/2016 | Argiriadi et al. |

FOREIGN PATENT DOCUMENTS

| | | |
|---|---|---|
| JP | 2009035531 A | 2/2009 |
| WO | WO-2004/063163 A1 | 7/2004 |
| WO | WO-2004/093872 A1 | 11/2004 |
| WO | WO-2005/100353 A1 | 10/2005 |
| WO | WO-2005/121096 A2 | 12/2005 |
| WO | WO-2006/047516 | 5/2006 |
| WO | WO-2006/108948 A2 | 10/2006 |
| WO | WO-2007/042178 A1 | 4/2007 |
| WO | WO-2007/110216 A1 | 10/2007 |
| WO | WO-2007/126122 A1 | 11/2007 |
| WO | WO-2007/126128 A1 | 11/2007 |
| WO | WO-2008/008432 A2 | 1/2008 |
| WO | WO-2008/051403 A2 | 5/2008 |
| WO | WO-2008/051493 A2 | 5/2008 |
| WO | WO-2008/141385 A1 | 11/2008 |
| WO | WO-2010/054278 A2 | 5/2010 |
| WO | WO-2010/084402 A2 | 7/2010 |
| WO | WO-2010/115491 A2 | 10/2010 |
| WO | WO-2011/062864 A2 | 5/2011 |
| WO | WO-2011/116356 A2 | 9/2011 |
| WO | WO-2011/119565 A1 | 9/2011 |
| WO | WO-2012/072019 A1 | 6/2012 |
| WO | WO-2012/088124 A2 | 6/2012 |
| WO | WO-2013/000994 A1 | 1/2013 |
| WO | WO-2013/186229 A1 | 12/2013 |
| WO | WO-2014/009295 A1 | 1/2014 |
| WO | WO-2014/009296 A1 | 1/2014 |
| WO | WO-2014/157569 A1 | 10/2014 |
| WO | WO-2015/086496 A1 | 6/2015 |
| WO | WO-2015/086498 A1 | 6/2015 |
| WO | WO-2015/086499 A1 | 6/2015 |

(Continued)

OTHER PUBLICATIONS

U.S. Appl. No. 62/134,769, Bristol-Myers Squibb Company.

(Continued)

*Primary Examiner* — Brian J Davis

(57) ABSTRACT

The disclosure provides indazolone compounds, pharmaceutically acceptable salts, pro-drugs, biologically active metabolites, stereoisomers and isomers thereof wherein the variables are defined herein. The compounds of the disclosure may be useful for treating immunological and oncological conditions.

20 Claims, No Drawings

(56) References Cited

FOREIGN PATENT DOCUMENTS

| | | |
|---|---|---|
| WO | WO-2015/086500 A1 | 6/2015 |
| WO | WO-2015/086501 A1 | 6/2015 |
| WO | WO-2015/086502 A1 | 6/2015 |
| WO | WO-2015/086503 A1 | 6/2015 |
| WO | WO-2015/086504 A1 | 6/2015 |
| WO | WO-2015/086505 A1 | 6/2015 |
| WO | WO-2015/086506 A1 | 6/2015 |
| WO | WO-2015/086507 A1 | 6/2015 |
| WO | WO-2015/086508 A1 | 6/2015 |
| WO | WO-2015/086509 A1 | 6/2015 |
| WO | WO-2015/086511 A1 | 6/2015 |
| WO | WO-2015/086512 A1 | 6/2015 |
| WO | WO-2015/086513 A1 | 6/2015 |
| WO | WO-2015/086519 A1 | 6/2015 |
| WO | WO-2015/086520 A1 | 6/2015 |
| WO | WO-2015/086521 A1 | 6/2015 |
| WO | WO-2015/086523 A1 | 6/2015 |
| WO | WO-2015/086525 A1 | 6/2015 |
| WO | WO-2015/086526 A1 | 6/2015 |
| WO | WO-2015/086527 A1 | 6/2015 |
| WO | WO-2016/050975 A1 | 4/2016 |
| WO | WO-2016/149436 A1 | 9/2016 |
| WO | WO-2016/149437 A1 | 9/2016 |
| WO | WO-2016/149439 A1 | 9/2016 |
| WO | WO-2016/168633 A1 | 10/2016 |
| WO | WO-2016/168638 A1 | 10/2016 |
| WO | WO-2016/168641 A1 | 10/2016 |
| WO | WO-2016/198398 A1 | 12/2016 |
| WO | WO-2016/198400 A1 | 12/2016 |
| WO | WO-2016/198401 A1 | 12/2016 |
| WO | WO-2016/202411 A1 | 12/2016 |
| WO | WO-2016/202412 A1 | 12/2016 |
| WO | WO-2016/202413 A1 | 12/2016 |
| WO | WO-2016/202414 A1 | 12/2016 |
| WO | WO-2016/202415 A1 | 12/2016 |
| WO | WO-2017/023902 A1 | 2/2017 |
| WO | WO-2017/023905 A1 | 2/2017 |

OTHER PUBLICATIONS

Cappelli et al., "Design, Synthesis, and Biological Evaluation of AT1 Angiotensin II Receptor antagonists Based on the Pyrazolo[3,4-b]pyridine and Related Heteroaromatic Bicyclic Systems," J Med Chem, 51: 2137-2146 (2008).

Chimirri et al., "Synthesis and Antitumor Activity of 1 H,3H-thiazolo[3,4-a]benzimidazole Derivatives", Archiv der Pharmazie, 334(6): 203-208 (2001).

Database CAPLUS in STN, Acc. No. 2005:1154552, Vidal et al., WO 2005/100353 A1 (Oct. 27, 2005) (abstract).

Database CAPLUS in STN, Acc. No. 2009: 1290752, Vidal'-Khuan et al., RU 23700496 C2 (Oct. 20, 2009) (abstract).

International Search Report and Written Opinion for International Application No. PCT/2016/027799 dated May 25, 2016.

International Search Report and Written Opinion for International Application No. PCT/2016/027808 dated Jun. 1, 2016.

International Search Report and Written Opinion for International Application No. PCT/2016/027814 dated Jun. 10, 2016.

Kumar K.S., et al., "A New Three-Component Reaction: Green Synthesis of Novel Soindolo[2,1-a]quinazoline Derivative as Potent Inhibitors of TNF-a," Chemical Communications, 47(17): 5010-5012 (2011).

U.S. Appl. No. 15/130,323, filed Apr. 15, 2016; (107 pages).

U.S. Appl. No. 15/130,362, filed Apr. 15, 2016; (377 pages).

INDAZOLONES AS MODULATORS OF TNF SIGNALING

PRIORITY CLAIM

This application is a continuation application of U.S. patent application Ser. No. 15/130,279, filed Apr. 15, 2016, which claims the benefit of priority to U.S. Provisional Application Nos. 62/258,651, filed Nov. 23, 2015, and 62/149,232, filed Apr. 17, 2015.

FIELD OF THE DISCLOSURE

The present disclosure relates to a class of indazolone derivatives, and to their use in therapy. More particularly, this disclosure is concerned with pharmacologically active substituted indazolone derivatives. These compounds are modulators of the signaling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

BACKGROUND

TNFα is the prototypical member of the Tumor Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, Drug Discovery Today, 2009, 14, 1082-1088; and F. S. Carneiro et al., J. Sexual Medicine, 2010, 7, 3823-3834).

SUMMARY OF THE DISCLOSURE

The compounds in accordance with the present disclosure, being potent modulators of human TNFα activity, may be beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present disclosure may be beneficial as pharmacological standards for use in the development of new biological tests and in the search for new pharmacological agents. Thus, in one embodiment, the compounds of this disclosure may be useful as radioligands in assays for detecting pharmacologically active compounds. In an alternative embodiment, certain compounds of this disclosure may be useful for coupling to a fluorophore to provide fluorescent conjugates that can be utilized in assays (e.g., a fluorescence polarization assay) for detecting pharmacologically active compounds.

The compounds in accordance with the present disclosure potently neutralize the activity of TNFα using the TNFα fluorescence polarization competitive binding assay. When tested in this assay, the compounds of the present disclosure exhibit an $IC_{50}$ value of 50 μM or less, generally of 10 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

In a first embodiment, the present disclosure provides a compound of Formula (I),

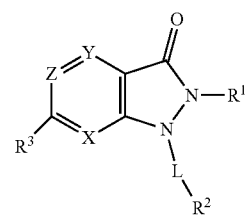

Formula (I)

or a pharmaceutically acceptable salt, prodrug or stereoisomer thereof, wherein:

X, Y and Z are independently $CR^4$ or N;

provided that Y and Z are not both N;

L is a bond, optionally substituted $(C_1-C_3)$alkylene or —C(O)—;

$R^1$ is H, $CD_3$, optionally substituted $(C_1-C_3)$alkyl, optionally substituted $(C_3-C_6)$cycloalkyl, —$(CH_2)_q$-optionally substituted $(C_3-C_6)$aryl, or —$(CH_2)_q$-optionally substituted $(C_3-C_6)$heteroaryl;

$R^2$ is optionally substituted aryl or optionally substituted heteroaryl;

$R^3$ is —$R^{3a}$-$R^{3b}$, wherein:

$R^{3a}$ is an optionally substituted saturated, unsaturated or partially saturated heterocyclyl or optionally substituted heteroaryl;

$R^{3b}$ is —$N(R^a)(R^b)$, —$O(R^a)$, optionally substituted $(C_1-C_5)$alkyl, optionally substituted $(C_3-C_6)$cycloalkyl, or —$(CH_2)_p$-optionally substituted heterocyclyl; wherein $R^a$ and $R^b$ are independently selected from H, optionally substituted $(C_1-C_5)$alkyl, and —$(CH_2)_n$-optionally substituted heterocyclyl;

$R^4$ is independently H, Cl, CN, F, $CF_3$ methoxy, or optionally substituted $(C_1-C_3)$alkyl; and n is 0 or 1;

p is 0, 1 or 2;

q is 0 or 1.

In a second embodiment, the disclosure provides a compound according to the first embodiment wherein the compound is a compound of Formula (Ia), Formula (Ib), Formula (Ic), Formula (Id) or Formula (Ie)

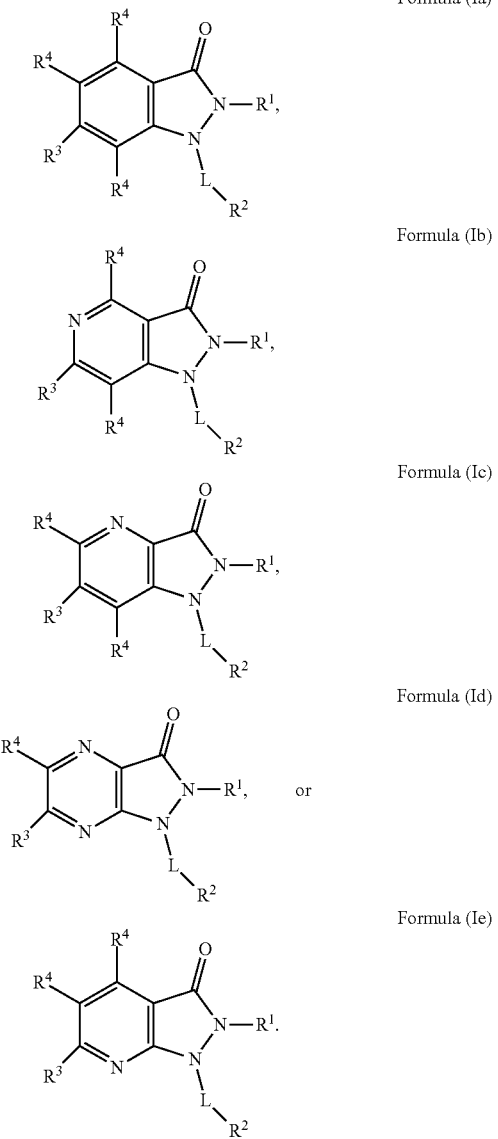

In a third embodiment, the disclosure provides a compound according to any of the foregoing embodiments wherein $R^1$ is optionally substituted (C1-C3)alkyl or optionally substituted cyclopropyl.

In a fourth embodiment, the disclosure provides a compound according to any of the foregoing embodiments wherein $R^2$ is optionally substituted heteroaryl, or optionally substituted phenyl.

In a fifth embodiment, the disclosure provides a compound according to any of the foregoing embodiments wherein $R^{3a}$ is optionally substituted 1,2,4-oxadiazolyl, optionally substituted pyrazolyl, optionally substituted pyridinyl, optionally substituted pyrimidinyl, optionally substituted pyrazinyl, or optionally substituted 1,2,4-thiadiazolyl.

In a sixth embodiment, the disclosure provides a compound according to any of the foregoing embodiments wherein $R^{3b}$ is —N($R^a$)($R^b$), —O($R^a$), optionally substituted ($C_1$-$C_3$)alkyl, —($CH_2$)$_p$-optionally substituted 2-oxa-6-azaspiro[3.3]heptanyl, —($CH_2$)$_p$-optionally substituted 2-azaspiro[3.3]heptanyl, —($CH_2$)$_p$-optionally substituted 5-azaspiro[2.3]hexanyl, —($CH_2$)$_p$-optionally substituted azetidinyl, —($CH_2$)$_p$-optionally substituted morpholinyl, —($CH_2$)$_p$-optionally substituted oxetanyl, —($CH_2$)$_p$-optionally substituted piperazinyl, —($CH_2$)$_p$-optionally substituted piperidinyl, —($CH_2$)$_p$-optionally substituted pyrrolidinyl, —($CH_2$)$_p$-optionally substituted tetrahydropyranyl, —($CH_2$)$_p$-optionally substituted 6-oxohexahydropyrrolo[1,2-a]pyrazinyl, —($CH_2$)$_p$-optionally substituted tetrahydro-1H-oxazolo[3,4-a]pyrazin-3(5H)-one or —($CH_2$)$_p$-optionally substituted hexahydroimidazo[1,5-a]pyrazin-3(2H)-one; wherein $R^a$ and $R^b$ are independently selected from H, optionally substituted ($C_1$-$C_3$)alkyl, —($CH_2$)$_n$-oxoazepanyl, —($CH_2$)$_n$-optionally substituted tetrahydrofuranyl, —($CH_2$)$_n$-optionally substituted oxetanyl, —($CH_2$)$_n$-optionally substituted tetrahydropyranyl, and —($CH_2$)$_n$-optionally substituted pyrrolidinyl.

In a seventh embodiment, the disclosure provides a compound according to any of the foregoing embodiments wherein L is a bond or optionally substituted ($C_1$-$C_2$) alkylene.

In an eighth embodiment, the disclosure provides a compound according to any of the foregoing embodiments wherein $R^2$ is phenyl, pyridinyl or pyrimidinyl, and $R^2$ is optionally substituted by one or more substituents independently selected from halogen, CN, haloalkoxy. $CF_3$, or optionally substituted ($C_1$-$C_3$)alkyl.

In a ninth embodiment, the disclosure provides a compound according to any of the foregoing embodiments wherein $R^{3b}$ is —N(H)$CH_2$-optionally substituted pyrrolidinyl, —O($R^a$), —N(H)-optionally substituted oxetanyl, optionally substituted ($C_1$-$C_3$)alkyl, optionally substituted 2-oxa-6-azaspiro[3.3]heptanyl, optionally substituted 5-azaspiro[2.3]hexanyl, optionally substituted azetidinyl, optionally substituted morpholinyl, —($CH_2$)$_p$-optionally substituted oxetanyl, optionally substituted piperazinyl, optionally substituted piperidinyl, —($CH_2$)$_p$-optionally substituted pyrrolidinyl, or optionally substituted tetrahydropyranyl; wherein $R^a$ is selected from H, optionally substituted ($C_1$-$C_3$)alkyl, —($CH_2$)$_n$-oxoazepanyl, —($CH_2$)$_n$-optionally substituted tetrahydrofuranyl, —($CH_2$)$_n$-optionally substituted oxetanyl, —($CH_2$)$_n$-optionally substituted tetrahydropyranyl, and —($CH_2$)$_n$-optionally substituted pyrrolidinyl.

In a tenth embodiment, the disclosure provides a compound according to any of the foregoing embodiments wherein $R^{3b}$ is optionally substituted by one or more substituents independently selected from halogen, CN, —C(O)OH, —C(O)$CH_3$, —C(O)$NH_2$, $NH_2$, =O, —OH, optionally substituted ($C_1$-$C_3$)alkyl, optionally substituted ($C_1$-$C_3$)alkoxy and optionally substituted oxetanyl.

In an eleventh embodiment, the disclosure provides a compound according to any of the foregoing embodiments wherein Y is $CR^4$.

In a twelfth embodiment, the disclosure provides a compound according to any of the foregoing embodiments wherein Z is $CR^4$.

In a thirteenth embodiment, the disclosure provides a compound according to any of the foregoing embodiments wherein the compound is:

1-(2-(difluoromethoxy)benzyl)-2-methyl-6-(2-(((1-methyl-5-oxopyrrolidin-3-yl)methyl)amino)pyrimidin-5-yl)-1H-indazol-3(2H)-one;

(R)-1-(5-(1-(2-(difluoromethoxy)benzyl)-2-methyl-3-oxo-2,3-dihydro-1H-indazol-6-yl)pyrimidin-2-yl)pyrrolidine-3-carboxylic acid;

(S)-1-(5-(1-(2-(difluoromethoxy)benzyl)-2-methyl-3-oxo-2,3-dihydro-1H-indazol-6-yl)pyrimidin-2-yl)pyrrolidine-3-carboxylic acid;

1-((4-chloropyridin-3-yl)methyl)-2-methyl-6-(2-morpholinopyrimidin-5-yl)-1H-indazol-3(2H)-one;

(R)-1-(2-(difluoromethoxy)benzyl)-6-(2-(3-hydroxypyrrolidin-1-yl)pyrimidin-5-yl)-2-methyl-1H-indazol-3(2H)-one;

2-(5-(1-(2-(difluoromethoxy)benzyl)-2-methyl-3-oxo-2,3-dihydro-1H-indazol-6-yl)pyrimidin-2-yl)-2-azaspiro[3.3]heptane-6-carboxylic acid;

5-(5-(1-(2-(difluoromethoxy)benzyl)-2-methyl-3-oxo-2,3-dihydro-1H-indazol-6-yl)pyrimidin-2-yl)-5-azaspiro[2.3]hexane-1-carboxylic acid;

1-(2-(difluoromethoxy)benzyl)-2-ethyl-6-(2-morpholinopyrimidin-5-yl)-1H-indazol-3(2H)-one;

1-(2-(difluoromethoxy)-5-fluorobenzyl)-2-methyl-6-(2-morpholinopyrimidin-5-yl)-1H-indazol-3(2H)-one;

6-(2-(2-oxa-6-azaspiro[3.3]heptan-6-yl)pyrimidin-5-yl)-1-(2-(difluoromethoxy)benzyl)-2-methyl-1H-indazol-3(2H)-one;

1-(5-(1-(2-(difluoromethoxy)benzyl)-2,5-dimethyl-3-oxo-2,3-dihydro-1H-indazol-6-yl)pyrimidin-2-yl)piperidine-4-carboxylic acid;

1-(2-(difluoromethoxy)benzyl)-2,5-dimethyl-6-(2-morpholinopyrimidin-5-yl)-1H-indazol-3(2H)-one;

1-(2-(difluoromethoxy)benzyl)-2,5-dimethyl-6-(2-(3-oxopiperazin-1-yl)pyrimidin-5-yl)-1H-indazol-3(2H)-one;

1-((3,6-dichloropyridin-2-yl)methyl)-2-methyl-6-(2-morpholinopyrimidin-5-yl)-1H-indazol-3(2H)-one;

6-(2-((1-acetylpyrrolidin-3-yl)amino)pyrimidin-5-yl)-1-(2-(difluoromethoxy)benzyl)-2-methyl-1H-indazol-3(2H)-one;

1-(5-(1-(2-(difluoromethoxy)benzyl)-2-methyl-3-oxo-2,3-dihydro-1H-indazol-6-yl)pyrimidin-2-yl)azetidine-3-carboxylic acid;

1-(2-(difluoromethoxy)benzyl)-6-(2-(2,2-dimethylmorpholino)pyrimidin-5-yl)-2-methyl-1H-indazol-3(2H)-one;

1-(2-(difluoromethoxy)benzyl)-6-(2-(3-(hydroxymethyl)azetidin-1-yl)pyrimidin-5-yl)-2-methyl-1H-indazol-3(2H)-one;

1-(2-(difluoromethoxy)benzyl)-6-(2-(3-hydroxyazetidin-1-yl)pyrimidin-5-yl)-2-methyl-1H-indazol-3(2H)-one;

1-(5-(1-(2,5-dichlorobenzyl)-2-methyl-3-oxo-2,3-dihydro-1H-indazol-6-yl)pyrimidin-2-yl)piperidine-4-carboxylic acid;

6-(5-chloro-2-morpholinopyridin-4-yl)-1-(2-(difluoromethoxy)benzyl)-2-methyl-1H-indazol-3(2H)-one;

1-(2-(difluoromethoxy)benzyl)-2-methyl-6-(2-(oxetan-3-ylamino)pyrimidin-5-yl)-1H-indazol-3(2H)-one;

1-benzoyl-2-methyl-6-(2-morpholinopyrimidin-5-yl)-1H-indazol-3(2H)-one;

6-(5-chloro-2-morpholinopyridin-4-yl)-1-(3-fluorobenzyl)-2-methyl-1H-indazol-3(2H)-one;

1-(2-(difluoromethoxy)benzoyl)-2-methyl-6-(2-morpholinopyrimidin-5-yl)-1H-indazol-3(2H)-one;

1-(2-(difluoromethoxy)benzyl)-6-(2-((2-hydroxyethyl)amino)pyrimidin-5-yl)-2-methyl-1H-indazol-3(2H)-one;

2-(1-(5-(1-(2-(difluoromethoxy)benzyl)-2-methyl-3-oxo-2,3-dihydro-1H-indazol-6-yl)pyrimidin-2-yl)azetidin-3-yl)acetic acid;

1-(2-(difluoromethoxy)benzyl)-2-methyl-6-(1-(tetrahydro-2H-pyran-4-yl)-1H-pyrazol-4-yl)-1H-indazol-3(2H)-one;

1-(2-(difluoromethoxy)benzyl)-2-methyl-6-(2-morpholinopyridin-4-yl)-1H-indazol-3(2H)-one;

1-(3-fluorobenzyl)-2-methyl-6-(1-(tetrahydro-2H-pyran-4-yl)-1H-pyrazol-4-yl)-1H-indazol-3(2H)-one;

1-(3-fluorobenzyl)-2-methyl-6-(2-morpholinopyridin-4-yl)-1H-indazol-3(2H)-one;

1-(2-(difluoromethoxy)-6-fluorobenzyl)-2-methyl-6-(2-morpholinopyrimidin-5-yl)-1H-indazol-3(2H)-one;

1-(1-(2-(difluoromethoxy)phenyl)ethyl)-2-methyl-6-(2-morpholinopyrimidin-5-yl)-1H-indazol-3(2H)-one;

2-methyl-6-(2-morpholinopyrimidin-5-yl)-1-phenethyl-1H-indazol-3(2H)-one;

2-methyl-1-(2-methylbenzyl)-6-(2-morpholinopyrimidin-5-yl)-1H-indazol-3(2H)-one;

1-(2,6-dichlorobenzyl)-2-methyl-6-(2-morpholinopyrimidin-5-yl)-1H-indazol-3(2H)-one;

1-(3-(difluoromethoxy)benzyl)-2-methyl-6-(2-morpholinopyrimidin-5-yl)-1H-indazol-3(2H)-one;

1-(3-fluorobenzyl)-2-methyl-6-(2-morpholinopyrimidin-5-yl)-1H-indazol-3(2H)-one;

1-(2-fluorophenethyl)-2-methyl-6-(2-morpholinopyrimidin-5-yl)-1H-indazol-3(2H)-one;

1-(2-fluorobenzyl)-2-methyl-6-(2-morpholinopyrimidin-5-yl)-1H-indazol-3(2H)-one;

2-((2-methyl-6-(2-morpholinopyrimidin-5-yl)-3-oxo-2,3-dihydro-1H-indazol-1-yl)methyl)benzonitrile;

2-methyl-1-(3-methylbenzyl)-6-(2-morpholinopyrimidin-5-yl)-1H-indazol-3(2H)-one;

1-(4-fluorobenzyl)-2-methyl-6-(2-morpholinopyrimidin-5-yl)-1H-indazol-3(2H)-one;

1-benzyl-2-methyl-6-(2-morpholinopyrimidin-5-yl)-1H-indazol-3(2H)-one;

1-(2,6-dichlorobenzyl)-2-methyl-6-(2-(3-oxopiperazin-1-yl)pyrimidin-5-yl)-1H-indazol-3(2H)-one;

1-(5-(1-(2-(difluoromethoxy)benzyl)-2-methyl-3-oxo-2,3-dihydro-1H-indazol-6-yl)pyrimidin-2-yl)piperidine-4-carboxylic acid;

1-(2-(difluoromethoxy)benzyl)-6-(2-methoxypyrimidin-5-yl)-2-methyl-1H-indazol-3(2H)-one;

1-(2-(difluoromethoxy)benzyl)-2-methyl-6-(2-(3-oxopiperazin-1-yl)pyrimidin-5-yl)-1H-indazol-3(2H)-one;

1-(2-(difluoromethoxy)benzyl)-6-(2-morpholinopyrimidin-5-yl)-1H-indazol-3(2H)-one;

1-(2,5-dichlorobenzyl)-2-methyl-6-(2-(piperazin-1-yl)pyrimidin-5-yl)-1H-indazol-3(2H)-one;

1-(2,5-dichlorobenzyl)-2-methyl-6-(2-morpholinopyrimidin-5-yl)-1H-indazol-3(2H)-one;

1-(2-(difluoromethoxy)benzyl)-2-methyl-6-(2-morpholinopyrimidin-5-yl)-1H-indazol-3(2H)-one;

1-(2-(difluoromethoxy)benzyl)-2-methyl-6-(6-(3-oxopiperazin-1-yl)pyridin-3-yl)-1H-indazol-3(2H)-one;

1-(2-(difluoromethoxy)benzyl)-2-methyl-6-(6-(piperazin-1-yl)pyridin-3-yl)-1H-indazol-3(2H)-one;

1-(2-(difluoromethoxy)benzyl)-2-methyl-6-(6-morpholinopyridin-3-yl)-1H-indazol-3(2H)-one;

1-(2-(difluoromethoxy)benzyl)-6-(2-(2-hydroxypropan-2-yl)pyrimidin-5-yl)-2-methyl-1H-indazol-3(2H)-one;

1-(2-(difluoromethoxy)benzyl)-2-methyl-6-(2-(3-(oxetan-3-yl)azetidin-1-yl)pyrimidin-5-yl)-1H-indazol-3(2H)-one;

2-((5-(1-(2-(difluoromethoxy)benzyl)-2-methyl-3-oxo-2,3-dihydro-1H-indazol-6-yl)pyrimidin-2-yl)amino)propanamide;

1-(2-(difluoromethoxy)benzyl)-2-methyl-6-(5-morpholinopyrazin-2-yl)-1H-indazol-3(2H)-one;

1-((5-(1-(2-(difluoromethoxy)benzyl)-2-methyl-3-oxo-2,3-dihydro-1H-indazol-6-yl)pyrimidin-2-yl)methyl)azetidine-3-carboxylic acid;

1-(2-(difluoromethoxy)benzyl)-2-methyl-6-(2-(((5-oxopyr-rolidin-3-yl)methyl)amino)pyrimidin-5-yl)-1H-indazol-3(2H)-one;

1-((3-chloropyridin-2-yl)methyl)-2-methyl-6-(2-morpholinopyrimidin-5-yl)-1H-indazol-3(2H)-one;

2-cyclopropyl-1-(2-(difluoromethoxy)benzyl)-6-(2-morpholinopyrimidin-5-yl)-1H-indazol-3(2H)-one;

1-(2,5-dichlorophenyl)-2-methyl-6-(2-morpholinopyrimidin-5-yl)-1H-indazol-3(2H)-one 1-(2-(difluoromethoxy)-6-fluorobenzyl)-2-methyl-6-(2-morpholinopyrimidin-5-yl)-1H-indazol-3(2H)-one;

4-(5-(1-(2-(difluoromethoxy)benzyl)-2-methyl-3-oxo-2,3-dihydro-1H-indazol-6-yl)pyrimidin-2-yl)piperazine-1-carboxamide;

1-(1-(2-(difluoromethoxy)phenyl)ethyl)-6-(2-((R)-2-(methoxymethyl)pyrrolidin-1-yl)pyrimidin-5-yl)-2-methyl-1H-indazol-3(2H)-one;

6-(2-(4-acetylpiperazin-1-yl)pyrimidin-5-yl)-1-(2-(difluoromethoxy)benzyl)-2-methyl-1H-indazol-3(2H)-one;

1-(2-(difluoromethoxy)benzyl)-2-methyl-6-(2-((2-oxoazepan-3-yl)amino)pyrimidin-5-yl)-1H-indazol-3(2H)-one;

1-(3-(difluoromethoxy)benzyl)-2-methyl-6-(2-((tetrahydrofuran-3-yl)amino)pyrimidin-5-yl)-1H-indazol-3(2H)-one;

1-(2-(difluoromethoxy)benzyl)-2-methyl-6-(2-((tetrahydro-2H-pyran-3-yl)amino)pyrimidin-5-yl)-1H-indazol-3(2H)-one;

1-(2-(difluoromethoxy)benzyl)-6-(2-((3-methoxypropyl)amino)pyrimidin-5-yl)-2-methyl-1H-indazol-3(2H)-one;

1-(2,5-dichlorobenzyl)-2-methyl-6-(2-morpholinopyrimidin-5-yl)-1H-indazol-3(2H)-one;

1-(5-(1-(2-(difluoromethoxy)benzyl)-2-methyl-3-oxo-2,3-dihydro-1H-indazol-6-yl)pyrazin-2-yl)piperidine-4-carboxylic acid;

1-(2-(difluoromethoxy)benzyl)-2-methyl-6-(5-morpholino-1,2,4-thiadiazol-3-yl)-1H-indazol-3(2H)-one;

1-(2-(difluoromethoxy)benzyl)-2-methyl-6-(2-morpholinopyrimidin-5-yl)-1H-pyrazolo[4,3-b]pyridin-3(2H)-one;

1-(2-(difluoromethoxy)benzyl)-2-methyl-6-(2-((3-methyloxetan-3-yl)methyl)pyrimidin-5-yl)-1H-indazol-3(2H)-one;

1-(2-(difluoromethoxy)benzyl)-2-methyl-6-(3-morpholino-1,2,4-oxadiazol-5-yl)-1H-indazol-3(2H)-one;

1-(2-(difluoromethoxy)benzyl)-2-methyl-6-(2-morpholinopyrimidin-5-yl)-1H-pyrazolo[3,4-b]pyridin-3(2H)-one;

1-(2-(difluoromethoxy)benzyl)-6-(2-(2-hydroxypropan-2-yl)pyrimidin-5-yl)-2-methyl-1H-pyrazolo[3,4-b]pyridin-3(2H)-one;

1-(2-(difluoromethoxy)benzyl)-2-methyl-6-(2-morpholinopyrimidin-5-yl)-1H-pyrazolo[4,3-c]pyridin-3(2H)-one;

1-(2-(difluoromethoxy)benzyl)-2-methyl-6-(2-(6-oxohexahydropyrrolo[1,2-a]pyrazin-2(1H)-yl)pyrimidin-5-yl)-1H-indazol-3(2H)-one;

(R)-1-(2-(difluoromethoxy)benzyl)-2-methyl-6-(2-((tetrahydrofuran-3-yl)amino)pyrimidin-5-yl)-1H-indazol-3(2H)-one;

(R)-7-(5-(1-(2-(difluoromethoxy)benzyl)-2-methyl-3-oxo-2,3-dihydro-1H-indazol-6-yl)pyrimidin-2-yl)tetrahydro-1H-oxazolo[3,4-a]pyrazin-3(5H)-one;

(S)-7-(5-(1-(2-(difluoromethoxy)benzyl)-2-methyl-3-oxo-2,3-dihydro-1H-indazol-6-yl)pyrimidin-2-yl)tetrahydro-1H-oxazolo[3,4-a]pyrazin-3(5H)-one;

7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;

(R)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;

(S)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;

1-(2-(difluoromethoxy)-5-methylbenzyl)-2-methyl-6-(2-morpholinopyrimidin-5-yl)-1H-indazol-3(2H)-one;

1-(2-(difluoromethoxy)-5-(hydroxymethyl)benzyl)-2-methyl-6-(2-morpholinopyrimidin-5-yl)-1H-indazol-3(2H)-one;

(R)-7-(5-(1-(2-(difluoromethoxy)-5-methylbenzyl)-2-methyl-3-oxo-2,3-dihydro-1H-indazol-6-yl)pyrimidin-2-yl)hexahydroimidazo[1,5-a]pyrazin-3(2H)-one;

(S)-7-(5-(1-(2-(difluoromethoxy)-5-methylbenzyl)-2-methyl-3-oxo-2,3-dihydro-1H-indazol-6-yl)pyrimidin-2-yl)hexahydroimidazo[1,5-a]pyrazin-3(2H)-one;

(S)-7-(5-(1-(2-(Difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one; or 7-(5-(1-(2-(difluoromethoxy)-5-(hydroxymethyl)benzyl)-2-methyl-3-oxo-2,3-dihydro-1H-indazol-6-yl)pyrimidin-2-yl)-5,6,7,8-tetrahydroimidazo[1,5-a]pyrazin-3(2H)-one;

1-(2-(difluoromethoxy)-5-methylbenzyl)-5-fluoro-6-(2-(2-hydroxypropan-2-yl)pyrimidin-5-yl)-2-methyl-1H-indazol-3(2H)-one; or (R)-1-(2-(difluoromethoxy)benzyl-6-(2-(4-(2-hydroxyacetyl)-3-methylpiperazin-1-yl)pyrimidin-5-yl)-2-methyl-1H-indazol-3(2H)-one.

In a fourteenth embodiment, the present disclosure provides a compound of Formula (I), or a pharmaceutically acceptable salt, prodrug or stereoisomer thereof, wherein
X, Y and Z are independently $CR^4$ or N;
provided that Y and Z are not both N;
L is a bond, optionally substituted $(C_1-C_3)$alkylene or —C(O)—;
$R^1$ is H, $CD_3$, CN, optionally substituted $(C_1-C_3)$alkyl, —$(CH_2)_n$-optionally substituted phenyl, —$(CH_2)_n$-optionally substituted heteroaryl or —$(CH_2)_n$-optionally substituted heterocyclyl;
$R^2$ is optionally substituted aryl, optionally substituted heteroaryl, optionally substituted heterocyclyl or optionally substituted cycloalkyl;
$R^3$ is —$R^{3a}$—$R^{3b}$, wherein:
$R^{3a}$ is an optionally substituted saturated, unsaturated or partially saturated heterocyclyl or optionally substituted heteroaryl;
$R^{3b}$ is —$N(R^a)(R^b)$, —$O(R^a)$, optionally substituted $(C_1-C_5)$alkyl, optionally substituted $(C_3-C_6)$cycloalkyl, or —$(CH_2)_p$-optionally substituted heterocyclyl; wherein $R^a$ and $R^b$ are independently selected from H, optionally substituted $(C_1-C_5)$alkyl, and —$(CH_2)_n$-optionally substituted heterocyclyl;
$R^4$ is independently H, Cl, CN, F, $CF_3$, optionally substituted $(C_1-C_3)$alkyl or optionally substituted $(C_1-C_3)$ alkoxy; and
n is 0 or 1;
p is 0, 1 or 2.

In a fifteenth embodiment, the disclosure provides a compound according to any of the foregoing embodiments wherein $R^1$ is H, $CD_3$, optionally substituted $(C_1-C_3)$alkyl or —$CH_2$-pyrimidinyl.

In a sixteenth embodiment, the disclosure provides a compound according to any of the foregoing embodiments wherein $R^2$ is optionally substituted heteroaryl, optionally substituted heterocyclyl or optionally substituted phenyl.

In a seventeenth embodiment, the disclosure provides a compound according to any of the foregoing embodiments wherein $R^{3a}$ is optionally substituted dihydropyranyl, optionally substituted imidazo[1,2-b]pyridazinyl, optionally substituted 1,2,4-oxadiazolyl, optionally substituted pyrazolyl, optionally substituted 3,6-dihydro-2H-pyranyl, optionally substituted pyridinyl, optionally substituted pyrimidinyl, optionally substituted pyrazinyl, or optionally substituted 1,2,4-thiadiazolyl.

In a eighteenth embodiment, the disclosure provides a compound according to any of the foregoing embodiments wherein $R^{3b}$ is —N($R^a$)($R^b$), —O($R^a$), optionally substituted ($C_1$-$C_3$)alkyl, —$(CH_2)_p$-optionally substituted imidazo[1,2-b]pyridazinyl, —$(CH_2)_p$-optionally substituted morpholinyl, —$(CH_2)_p$-optionally substituted piperazinyl, —$(CH_2)_p$-optionally substituted piperidinyl, —$(CH_2)_p$-optionally substituted pyrrolidinyl, —$(CH_2)_p$-optionally substituted tetrahydropyranyl, —$(CH_2)_p$-optionally substituted tetrahydro-1H-oxazolo[3,4-a]pyrazin-3(5H)-one, —$(CH_2)_p$-optionally substituted hydroimidazo[1,2-b]pyridazin-3(2H)-one; or —$(CH_2)_p$-optionally substituted hexahydroimidazo[1,5-a]pyrazin-3(2H)-one; wherein $R^a$ and $R^b$ are independently selected from H, optionally substituted ($C_1$-$C_3$)alkyl, —$(CH_2)_n$-morpholinyl —$(CH_2)_n$-oxoazepanyl, —$(CH_2)_n$-optionally substituted tetrahydrofuranyl, —$(CH_2)_n$-optionally substituted oxetanyl, —$(CH_2)_n$-optionally substituted piperidinyl, —$(CH_2)_n$-optionally substituted tetrahydropyranyl, —$(CH_2)_p$-optionally substituted hexahydroimidazo[1,5-a]pyrazin-3(2H)-one, and —$(CH_2)_n$-optionally substituted pyrrolidinyl.

In an nineteenth embodiment, the disclosure provides a compound according to any of the foregoing embodiments wherein L is a bond or optionally substituted ($C_1$-$C_2$) alkylene.

In a twentieth embodiment, the disclosure provides a compound according to any of the foregoing embodiments wherein $R^2$ is 4,5-dihydrobenzo[f][1,5]thiazepin-3(2h)-one, 1,3-dihydroisobenzofuranyl, phenyl, pyridinyl, pyrimidinyl or pyrrolyl, and $R^2$ is optionally substituted by one or more substituents independently selected from halogen, CN, haloalkoxy, $CF_3$, —$SCHF_2$, optionally substituted ($C_1$-$C_3$) alkyl, optionally substituted ($C_3$-$C_5$)cycloalkyl, —$CH_2OC(O)C(H)NH_2CH_3$, —$CH_2NHC(O)OCH_3$, —$CH_2$-pyridinyl, —$CH_2$-pyrrolyl, —$CH_2$-optionally substituted pyrazolyl, —$CH_2$-triazolyl-, —$CH_2$-O-pyrazolyl, —$C(O)CH_3$, —N(H)$CH_2C(OH)(CH_3)_2$, —N(H)$CH_2C(H)(OH)CH_3$, or —N(H)($R^c$); wherein $R^c$ is —$(CH_2)_n$-optionally substituted heterocyclyl or —$(CH_2)$ optionally substituted heteroaryl, wherein n is 0 or 1.

In a twenty-first embodiment, the disclosure provides a compound according to any of the foregoing embodiments wherein $R^{3b}$ is —N(H)-optionally substituted oxetanyl, —N(H)-optionally substituted piperidin-2-one, —N(H)-optionally substituted tetrahydropyranyl, —O-tetrahydropyranyl, optionally substituted ($C_1$-$C_3$)alkyl, optionally substituted morpholinyl, optionally substituted piperazinyl, optionally substituted piperidinyl, optionally substituted pyrrolidinyl, -optionally substituted tetrahydro-1H-oxazolo[3,4-a]pyrazin-3(5H)-one —$(CH_2)_p$-optionally substituted hexahydroimidazo[1,5-a]pyrazin-3(2H)-one, or optionally substituted tetrahydropyranyl.

In a twenty-second embodiment, the disclosure provides a compound according to any of the foregoing embodiments wherein $R^{3b}$ is optionally substituted by one or more substituents independently selected from halogen, —CHO, CN, —C(O)OH, —$C(O)CH_3$, —$C(O)CH_2CN$, —$C(O)CH_2OH$, —$C(O)CH_2NH_2$, $C(O)CH_2OCH_3$, —$C(O)C(H)(CH_3)NH_2$, —C(O)C(H)(OH)$CH_2OH$, —C(O)C(H)(OH)$CH_2C(O)OH$, —C(O)C(H)(OH)$CH_2NH_2$. —$C(O)CH_2OC(O)C(H)(NH_2)CH(CH_3)_2$, —$C(O)NH_2$, —$C(O)OCH_3$, $C(O)CH_2OP(O)(OH)$, —C(O)-oxetanyl, $NH_2$, =O, —OH, —$S(O)_2CH_3$, optionally substituted ($C_1$-$C_3$)alkyl, optionally substituted ($C_1$-$C_3$)alkoxy and optionally substituted oxetanyl.

In a twenty-third embodiment, the disclosure provides a compound according to any of the foregoing embodiments wherein Y is $CR^4$ and $R^4$ is H.

In a twenty-fourth embodiment, the disclosure provides a compound according to any of the foregoing embodiments wherein Z is $CR^4$ and $R^4$ is H or F.

In a twenty-fifth embodiment, the disclosure provides a compound according to any of the foregoing embodiments wherein the compound is:

(R)-1-(5-((1H-pyrazol-4-yl)methyl)-2-(difluoromethoxy)benzyl)-6-(2-(4-acetyl-3-methylpiperazin-1-yl)pyrimidin-5-yl)-2-methyl-1H-indazol-3(2H)-one;

(R)-1-(2-(difluoromethoxy)benzyl)-7-fluoro-6-(2-(4-(2-hydroxyacetyl)-3-methylpiperazin-1-yl)pyrimidin-5-yl)-2-methyl-1H-indazol-3(2H)-one;

(R)-2-(4-(difluoromethoxy)-3-((6-(2-(4-(2-hydroxyacetyl)-3-methylpiperazin-1-yl)pyrimidin-5-yl)-2-methyl-3-oxo-2,3-dihydro-1H-indazol-1-yl)methyl)phenyl)acetonitrile;

(R)-2-(4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-2-oxoethyl dihydrogen phosphate;

(R)-1-(2-(difluoromethoxy)benzyl)-5,7-difluoro-6-(2-(4-(2-hydroxyacetyl)-3-methylpiperazin-1-yl)pyrimidin-5-yl)-2-methyl-1H-indazol-3(2H)-one;

(R)-1-(2-chlorobenzyl)-7-fluoro-6-(2-(4-(2-hydroxyacetyl)-3-methylpiperazin-1-yl)pyrimidin-5-yl)-2-methyl-1H-indazol-3(2H)-one;

(R)-1-(2-chlorobenzyl)-7-fluoro-6-(2-(4-(2-hydroxyacetyl)-3-methylpiperazin-1-yl)pyrimidin-5-yl)-2-methyl-1H-indazol-3(2H)-one;

(R)-1-(2-(difluoromethoxy)-5-methylbenzyl)-5-fluoro-6-(2-(4-(2-hydroxyacetyl)-2-methylpiperazin-1-yl)pyrimidin-5-yl)-2-methyl-1H-indazol-3(2H)-one;

1-(5-((1H-pyrazol-5-yl)methyl)-2-(difluoromethoxy)benzyl)-6-(2-(2-hydroxypropan-2-yl)pyrimidin-5-yl)-2-methyl-1H-indazol-3(2H)-one;

1-(2-(difluoromethoxy)-5-methylbenzyl)-6-(3-(2-hydroxypropan-2-yl)imidazo[1,2-b]pyridazin-7-yl)-2-methyl-1H-indazol-3(2H)-one;

1-(2-(difluoromethoxy)-5-methylbenzyl)-2-methyl-6-(2-(3-methylpyrrolidin-3-yl)pyrimidin-5-yl)-1H-indazol-3(2H)-one;

1-(1-(2,5-difluorophenyl)ethyl)-6-(2-((R)-4-(2-hydroxyacetyl)-3-methylpiperazin-1-yl)pyrimidin-5-yl)-2-methyl-1H-indazol-3(2H)-one;

1-(2-(difluoromethoxy)-5-methylbenzyl)-5-fluoro-6-(6-(1-hydroxyethyl)-5,6-dihydro-2H-pyran-3-yl)-2-methyl-1H-indazol-3(2H)-one;

1-(2-chloro-5-((2-hydroxy-2-methylpropyl)amino)benzyl)-6-(2-(2-hydroxypropan-2-yl)pyrimidin-5-yl)-2-methyl-1H-indazol-3(2H)-one;

1(2-(difluoromethoxy)-5-methylbenzyl)-6-(2-(1,3-dimethylpyrrolidin-3-yl)pyrimidin-5-yl)-2-methyl-1H-indazol-3(2H)-one acetate, 1-(2-(difluoromethoxy)-5-methylbenzyl)-6-(2-(1,3-dimethylpyrrolidin-3-yl)pyrimidin-5-yl)-2-methyl-1H-indazol-3(2H)-one;

(R)-1-(2-(difluoromethoxy)benzyl)-5-fluoro-6-(2-(4-(2-hydroxyacetyl)-3-methylpiperazin-1-yl)pyrimidin-5-yl)-2-methyl-1H-indazol-3(2H)-one;

6-[2-[(3R)-4-acetyl-3-methyl-piperazin-1-yl]pyrimidin-5-yl]-1-[[2-(difluoromethoxy)-5-methyl-phenyl]methyl]-2(trideuteriomethyl)indazol-3-one;

(S)-6-(2-(4-acetyl-2-methylpiperazin-1-yl)pyrimidin-5-yl)-1-(2-(difluoromethoxy)-5-methylbenzyl)-2-methyl-1H-indazol-3(2H)-one;

(R)-1-(2-(difluoromethoxy)-5-methylbenzyl)-6-(2-(4-(2-hydroxyacetyl)-3-methylpiperazin-1-yl)pyrimidin-5-yl)-2-methyl-1H-indazol-3(2H)-one;

1-[[2-(difluoromethoxy)-5-methyl-phenyl]methyl]-6-[2-[(3R)-4-(2-hydroxyacetyl)-3-methyl-piperazin-1-yl]pyrimidin-5-yl]-2-(trideuteriomethyl)indazol-3-one;

(R)-1-(2-(difluoromethoxy)-5-methylbenzyl)-6-(2-(4-(2-hydroxyacetyl)-2-methylpiperazin-1-yl)pyrimidin-5-yl)-2-methyl-1H-indazol-3(2H)-one;

(R)-6-(2-(4-acetyl-2-methylpiperazin-1-yl)pyrimidin-5-yl)-1-(2-(difluoromethoxy)-6-(hydroxymethyl)benzyl)-2-methyl-1H-indazol-3(2H)-one;

(R)-1-(2-(difluoromethoxy)benzyl)-6-(2-(4-(2-hydroxyacetyl)-3-methylpiperazin-1-yl)-4-methylpyrimidin-5-yl)-2-methyl-1H-indazol-3(2H)-one;

1-(2-(difluoromethoxy)-5-methylbenzyl)-5-fluoro-6-(6-(2-hydroxypropan-2-yl)-5,6-dihydro-2H-pyran-3-yl)-2-methyl-1H-indazol-3(2H)-one;

1-((S)-1-(2,6-difluorophenyl)ethyl)-6-(2-((R)-4-(2-hydroxyacetyl)-3-methylpiperazin-1-yl)pyrimidin-5-yl)-2-methyl-1H-indazol-3(2H)-one;

(R)-1-(2-(difluoromethoxy)-5-methylbenzyl)-2-methyl-6-(2-(3-methyl-4-(methylsulfonyl)piperazin-1-yl)pyrimidin-5-yl)-1H-indazol-3(2H)-one;

(R)-methyl 4-(5-(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate;

(R)-6-(2-(4-acetyl-3-methylpiperazin-1-yl)pyrimidin-5-yl)-1-(2-(difluoromethoxy)-6-(hydroxymethyl)benzyl)-2-methyl-1H-indazol-3(2H)-one;

(S)-7-(5-(1-(2-(difluoromethoxy)-5-methylbenzyl)-2-methyl-3-oxo-2,3-dihydro-1H-indazol-6-yl)pyrimidin-2-yl)tetrahydro-1H-oxazolo[3,4-a]pyrazin-3(5H)-one;

(R)-6-(2-(4-acetyl-2-methylpiperazin-1-yl)pyrimidin-5-yl)-1-(2-(difluoromethoxy)-5-methylbenzyl)-2-methyl-1H-indazol-3(2H)-one;

(R)-1-(2-(difluoromethoxy)benzyl)-6-(2-(4-(2-hydroxyacetyl)-2-methylpiperazin-1-yl)-4-methylpyrimidin-5-yl)-2-methyl-1H-indazol-3(2H)-one;

(R)-7-(5-(1-(5-((1,2,4-triazol-1-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;

(R)-7-(5-(1-(2-(difluoromethoxy)-6-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one;

1-(5-((1H-pyrazol-4-yl)methyl)-2-(difluoromethoxy)benzyl)-6-(2-(2-hydroxypropan-2-yl)pyrimidin-5-yl)-2-methyl-1H-indazol-3(2H)-one;

(R)-6-(2-(4-acetyl-3-methylpiperazin-1-yl)pyrimidin-5-yl)-1-(2-((difluoromethyl)thio)-5-methylbenzyl)-2-methyl-1H-pyrazolo[3,4-b]pyridin-3(2H)-one;

(R)-6-(2-(4-acetyl-3-methylpiperazin-1-yl)pyrimidin-5-yl)-1-(2-chloro-5-methylbenzyl)-2-methyl-1H-pyrazolo[3,4-b]pyridin-3(2H)-one;

(R)-6-(2-(4-acetyl-3-methylpiperazin-1-yl)pyrimidin-5-yl)-1-(2-((difluoromethyl)thio)-5-methylbenzyl)-2-methyl-1H-indazol-3(2H)-one;

(R)-6-(2-(4-acetyl-3-methylpiperazin-1-yl)pyrimidin-5-yl)-1-(2-(difluoromethoxy)-5-methylbenzyl)-2-methyl-1H-indazol-3(2H)-one;

(R)-2-(4-(difluoromethoxy)-3-((2-methyl-3-oxo-6-(2-(3-oxotetrahydro-1H-oxazolo[3,4-a]pyrazin-7(3H)-yl)pyrimidin-5-yl)-2,3-dihydro-1H-indazol-1-yl)methyl)phenyl)acetonitrile;

(S)-1-(2-(difluoromethoxy)benzyl)-6-(2-(4-(2-hydroxyacetyl)-2-methylpiperazin-1-yl)-4-methylpyrimidin-5-yl)-2-methyl-1H-indazol-3(2H)-one;

(R)-6-(2-(4-(2-hydroxyacetyl)-3-methylpiperazin-1-yl)pyrimidin-5-yl)-2-methyl-1-((6-methyl-3-(trifluoromethyl)pyridin-2-yl)methyl)-1H-indazol-3(2H)-one;

(R)-7-(5-(1-(2-(difluoromethoxy)-6-(methoxymethyl)benzyl)-2-methyl-3-oxo-2,3-dihydro-1H-indazol-6-yl)pyrimidin-2-yl)hexahydroimidazo[1,5-a]pyrazin-3(2H)-one;

(S)-1-(2-(difluoromethoxy)-5-methylbenzyl)-2-methyl-6-(2-(3-methyl-4-(methylsulfonyl)piperazin-1-yl)pyrimidin-5-yl)-1H-indazol-3(2H)-one:

(R)-1-(2-(difluoromethoxy)benzyl)-5-fluoro-6-(2-(4-(2-hydroxyacetyl)-3-methylpiperazin-1-yl)pyrimidin-5-yl)-2-methyl-1H-pyrazolo[3,4-b]pyridin-3(2H)-one;

6-(2-((R)-4-(2-hydroxyacetyl)-3-methylpiperazin-1-yl)pyrimidin-5-yl)-2-methyl-1-((S)-1-(m-tolyl)ethyl)-1H-indazol-3(2H)-one;

6-(2-(4-(3-amino-2-hydroxypropanoyl)-3-methylpiperazin-1-yl)pyrimidin-5-yl)-1-(2-(difluoromethoxy)-5-methylbenzyl)-2-methyl-1H-indazol-3(2H)-one;

1-(2-(difluoromethoxy)benzyl)-6-(2-((R)-4-((S)-2,3-dihydroxypropanoyl)-3-methylpiperazin-1-yl)pyrimidin-5-yl)-2-methyl-1H-indazol-3(2H)-one;

(R)-1-(2-(difluoromethoxy)benzyl)-5-fluoro-6-(2-(4-(2-hydroxyacetyl)-2-methylpiperazin-1-yl)pyrimidin-5-yl)-2-methyl-1H-indazol-3(2H)-one;

1-(2-(difluoromethoxy)-5-methylbenzyl)-2-methyl-6-(2-((3R)-3-methyl-4-(oxetane-2-carbonyl)piperazin-1-yl)pyrimidin-5-yl)-1H-indazol-3(2H)-one;

(R)-2-(4-(5-(1-(2-(difluoromethoxy)benzyl)-2-methyl-3-oxo-2,3-dihydro-1H-indazol-6-yl)pyrimidin-2-yl)-2-methylpiperazin-1-yl)-2-oxoethyl phosphate;

(R)-1-(2-(difluoromethoxy)benzyl)-6-(2-(4-(2-hydroxyacetyl)-3-methylpiperazin-1-yl)pyrimidin-5-yl)-2-methyl-1H-indazol-3(2H)-one;

(R)-3-(4-(5-(1(2-(difluoromethoxy)-5-methylbenzyl)-2-methyl-3-oxo-2,3-dihydro-1H-indazol-6-yl)pyrimidin-2-yl)-2-methylpiperazin-1-yl)-3-oxopropanenitrile;

1-(1-(2,6-difluorophenylethyl)-6-(2-((R)-4-(2-hydroxyacetyl)-3-methylpiperazin-1-yl)pyrimidin-5-yl)-2-methyl-1H-indazol-3(2H)-one;

(S)-1-(2-(difluoromethoxy)benzyl)-6-(2-(4-(2-hydroxyacetyl)-2-methylpiperazin-1-yl)pyrimidin-5-yl)-2-methyl-1H-indazol-3(2H)-one;

1-(2-(difluoromethoxy)benzyl)-6-(2-((R)-4-((R)-2,3-dihydroxypropanoyl)-3-methylpiperazin-1-yl)pyrimidin-5-yl)-2-methyl-1H-indazol-3(2H)-one;

(R)-6-(2-(4-acetyl-2-ethylpiperazin-1-yl)pyrimidin-5-yl)-1-(2-(difluoromethoxy)-5-methylbenzyl)-2-methyl-1H-indazol-3(2H)-one;

(R)-1-(2-(difluoromethoxy)-5-(hydroxymethyl)benzyl)-2-methyl-6-(2-((2-oxopiperidin-4-yl)amino)pyrimidin-5-yl)-1H-indazol-3(2H)-one;

(S)-7-(5-(1(2-(difluoromethoxy)-5-(hydroxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one;

(R)-1-(2-(difluoromethoxy)benzyl)-5-fluoro-6-(6-(4-(2-hydroxyacetyl)-3-methylpiperazin-1-yl)pyridin-3-yl)-2-methyl-1H-indazol-3(2H)-one;

(R)-1-(2-chlorobenzyl)-6-(2-(4-(2-hydroxyacetyl)-3-methylpiperazin-1-yl)pyrimidin-5-yl)-2-methyl-1H-indazol-3(2H)-one;

(R)-1-(2-(difluoromethoxy)-5-methylbenzyl)-2-methyl-6-(2-(3-methyl-4-(oxetane-3-carbonyl)piperazin-1-yl)pyrimidin-5-yl)-1H-indazol-3(2H)-one;

4-(5-(1-(2-(difluoromethoxy)-5-(hydroxymethyl)benzyl)-2-methyl-3-oxo-2,3-dihydro-1H-indazol-6-yl)pyrimidin-2-yl)piperazine-1-carbaldehyde;

(S)-2-((R)-4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-2-oxoethyl 2-amino-3-methylbutanoate hydrochloride;

(R)-7-(5-(1-(2-(difluoromethoxy)-5-(hydroxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one;

(S)-7-(5-(1-(2-chloro-5-methylbenzyl)-2-methyl-3-oxo-2,3-dihydro-1H-indazol-6-yl)pyrimidin-2-yl)hexahydroimidazo[1,5-a]pyrazin-3(2H)-one;

(R)-1-(2-(difluoromethoxy)benzyl)-7-fluoro-6-(2-(4-(2-hydroxyacetyl)-2-methylpiperazin-1-yl)pyrimidin-5-yl)-2-methyl-1H-indazol-3(2H)-one;

(R)-6-(2-(4-acetyl-3-methylpiperazin-1-yl)pyrimidin-5-yl)-2-methyl-1-((6-methyl-3-(trifluoromethyl)pyridin-2-yl)methyl)-1H-indazol-3(2H)-one;

(R)-7-(5-(1-(2-(Difluoromethoxy)-5-methylbenzyl)-2-(methyl-d₃)-3-oxo-2,3-dihydro-1H-indazol-6-yl)pyrimidin-2-yl)hexahydro-3H-oxazolo[3,4-a]pyrazin-3-one;

(R)-1-(2-(difluoromethoxy)-5-methylbenzyl)-6-(2-(4-(2-methoxyacetyl)-3-methylpiperazin-1-yl)pyrimidin-5-yl)-2-methyl-1H-indazol-3(2H)-one;

(S)-7-(5-(2-methyl-1-(5-methyl-2-(trifluoromethyl)benzyl)-3-oxo-2,3-dihydro-1H-indazol-6-yl)pyrimidin-2-yl)hexahydroimidazo[1,5-a]pyrazin-3(2H)-one;

6-(2-(4-acetylpiperazin-1-yl)pyrimidin-5-yl)-1-(2-(difluoromethoxy)-5-(hydroxymethyl)benzyl)-2-methyl-1H-indazol-3(2H)-one;

(S)-1-(2-(difluoromethoxy)-5-methylbenzyl)-6-(2-(4-(2-hydroxyacetyl)-3-methylpiperazin-1-yl)pyrimidin-5-yl)-2-methyl-1H-indazol-3(2H)-one;

6-(2-((R)-4-(2-hydroxyacetyl)-3-methylpiperazin-1-yl)pyrimidin-5-yl)-2-methyl-1-(1-(m-tolyl)propyl)-1H-indazol-3(2H)-one;

(S)-7-(5-(1(5-((4H-1,2,4-triazol-4-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;

(R)-1-(2-(difluoromethoxy)benzyl)-6-(2-(4-(2-hydroxyacetyl)-2-methylpiperazin-1-yl)pyrimidin-5-yl)-2-methyl-1H-indazol-3(2H)-one;

(R)-6-(2-(4-acetyl-3-methylpiperazin-1-yl)pyrimidin-5-yl)-1-(2-(difluoromethoxy)-5-methylbenzyl)-2-methyl-1H-pyrazolo[3,4-b]pyridin-3(2H)-one;

(R)-7-(5-(1-((3-(difluoromethoxy)-6-(hydroxymethyl)pyridin-2-yl)methyl)-2-methyl-3-oxo-2,3-dihydro-1H-indazol-6-yl)pyrimidin-2-yl)hexahydroimidazo[1,5-a]pyrazin-3(2H)-one;

(R)-6-(2-(4-acetyl-3-methylpiperazin-1-yl)pyrimidin-5-yl)-1-(2-(difluoromethoxy)benzyl)-2-methyl-1H-indazol-3(2H)-one;

(R)-6-(2-(4-acetyl-3-methylpiperazin-1-yl)pyrimidin-5-yl)-2-methyl-1-((6-methyl-3-(trifluoromethyl)pyridin-2-yl)methyl)-1H-pyrazolo[3,4-b]pyridin-3(2H)-one;

(S)-4-(difluoromethoxy)-3-((2-methyl-3-oxo-6-(2-((R)-3-oxohexahydroimidazo[1,5-a]pyrazin-7(1H)-yl)pyrimidin-5-yl)-2,3-dihydro-1H-indazol-1-yl)methyl)benzyl 2-aminopropanoate hydrochloride;

(R)-6-(2-(4-acetyl-3-methylpiperazin-1-yl)pyrimidin-5-yl)-2-methyl-1-((4-(trifluoromethyl)-1H-pyrrol-3-yl)methyl)-1H-indazol-3(2H)-one;

1-(2-(difluoromethoxy)-5-methylbenzyl)-6-(2-(2-hydroxypropan-2-yl)-4-methylpyrimidin-5-yl)-2-methyl-1H-indazol-3(2H)-one;

6-(2-((R)-4-(2-hydroxyacetyl)-3-methylpiperazin-1-yl)pyrimidin-5-yl)-2-methyl-1-(1-(m-tolyl)ethyl)-1H-indazol-3(2H)-one;

1-(2-chloro-5-((4,5,6,7-tetrahydro-1H-indazol-7-yl)amino)benzyl)-6-(2-(2-hydroxypropan-2-yl)pyrimidin-5-yl)-2-methyl-1H-indazol-3(2H)-one;

(R)-2-(4-(difluoromethoxy)-3-((2-methyl-3-oxo-6-(2-(3-oxohexahydroimidazo[1,5-a]pyrazin-7(1H)-yl)pyrimidin-5-yl)-2,3-dihydro-1H-indazol-1-yl)methyl)phenyl)acetonitrile;

(R)-6-(2-(4-(2-aminoacetyl)-3-methylpiperazin-1-yl)pyrimidin-5-yl)-1-(2-(difluoromethoxy)-5-methylbenzyl)-2-methyl-1H-indazol-3(2H)-one;

1-(2-(difluoromethoxy)-5-methylbenzyl)-6-(2-(4-(2-hydroxyacetyl)piperazin-1-yl)pyrimidin-5-yl)-2-methyl-1H-indazol-3(2H)-one;

(R)-1-(5-(((1H-pyrazol-5-yl)oxy)methyl)-2-(difluoromethoxy)benzyl)-6-(2-(4-acetyl-3-methylpiperazin-1-yl)pyrimidin-5-yl)-2-methyl-1H-indazol-3(2H)-one;

(S)-6-(2-(4-acetyl-3-methylpiperazin-1-yl)pyrimidin-5-yl)-1-(2-(difluoromethoxy)-5-methylbenzyl)-2-methyl-1H-indazol-3(2H)-one;

1-(5-((1H-1,2,4-triazol-1-yl)methyl)-2-(difluoromethoxy)benzyl)-5-fluoro-6-(2-(2-hydroxypropan-2-yl)pyrimidin-5-yl)-2-methyl-1H-indazol-3(2H)-one;

(R)-7-(5-(1-(2-(difluoromethoxy)-5-methylbenzyl)-2-methyl-3-oxo-2,3-dihydro-1H-indazol-6-yl)pyrimidin-2-yl)tetrahydro-1H-oxazolo[3,4-a]pyrazin-3(5H)-one;

(R)-1-(2-(difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one;

(R)-1-(2-(difluoromethoxy)benzyl)-6-(2-(4-(2-hydroxyacetyl)-3-methylpiperazin-1-yl)pyrimidin-5-yl)-7-methoxy-2-methyl-1H-indazol-3(2H)-one;

1-((S)-1-(2-fluorophenyl)ethyl)-6-(2-((R)-4-(2-hydroxyacetyl)-3-methylpiperazin-1-yl)pyrimidin-5-yl)-2-methyl-1H-indazol-3(2H)-one;

(R)-6-(2-(4-acetyl-2-methylpiperazin-1-yl)pyrimidin-5-yl)-1-(2-(difluoromethoxy)benzyl)-2-methyl-1H-indazol-3(2H)-one;

6-(2-((R)-4-((S)-2-aminopropanoyl)-3-methylpiperazin-1-yl)pyrimidin-5-yl)-1-(2-(difluoromethoxy)-5-methylbenzyl)-2-methyl-1H-indazol-3(2H)-one;

1-(2-(difluoromethoxy)-5-methylbenzyl)-5-fluoro-6-(2-(2-hydroxypropan-2-yl)pyrimidin-5-yl)-2-methyl-1H-indazol-3(2H)-one;

1-(2-(difluoromethoxy)-5-(hydroxymethyl)benzyl)-2-methyl-6-(2-((2-oxopiperidin-4-yl)amino)pyrimidin-5-yl)-1H-indazol-3(2H)-one;

(R)-methyl 3-((6-(2-(4-acetyl-3-methylpiperazin-1-yl)pyrimidin-5-yl)-2-methyl-3-oxo-2,3-dihydro-1H-indazol-1-yl)methyl)-4-(difluoromethoxy)benzylcarbamate;

1-(2-(difluoromethoxy)-5-methylbenzyl)-2-methyl-6-(2-((tetrahydro-2H-pyran-4-yl)oxy)pyridin-4-yl)-1H-indazol-3(2H)-one;

(S)-3-(4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-3-oxopropanenitrile;

(S)-2-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-2-oxoethyl 2-amino-3-methylbutanoate;

(R)-7-(5-(1(2-(difluoromethoxy)benzyl)-2-methyl-3-oxo-2,3-dihydro-1H-indazol-6-yl)pyrimidin-2-yl)-2-(2-hydroxyethyl)hexahydroimidazo[1,5-a]pyrazin-3(2H)-one;

(R)-6-(2-(4-(2-hydroxyacetyl)-2-methylpiperazin-1-yl)pyrimidin-5-yl)-2-methyl-1-((6-methyl-3-(trifluoromethyl)pyridin-2-yl)methyl)-1H-indazol-3(2H)-one;

(R)-7-(5-(2-methyl-1-((6-methyl-3-(trifluoromethyl)pyridin-2-yl)methyl)-3-oxo-2,3-dihydro-1H-indazol-6-yl)pyrimidin-2-yl)tetrahydro-1H-oxazolo[3,4-a]pyrazin-3(5H)-one;

(R)-6-(2-(4-acetyl-3-methylpiperazin-1-yl)pyrimidin-5-yl)-1-((1-acetyl-4-(trifluoromethyl)-1H-pyrrol-3-yl)methyl)-2-methyl-1H-indazol-3(2H)-one;

(R)-1-(2-(difluoromethoxy)-5-methylbenzyl)-6-(3-(1-hydroxyethyl)imidazo[1,2-b]pyridazin-7-yl)-2-methyl-1H-indazol-3(2H)-one;

(R)-2-(6-((6-(2-(4-acetyl-3-methylpiperazin-1-yl)pyrimidin-5-yl)-2-methyl-3-oxo-2,3-dihydro-1H-indazol-1-yl)methyl)-5-(trifluoromethyl)pyridin-2-yl)acetonitrile;

(R)-1-(2-(difluoromethoxy)benzyl)-6-(2-(4-(2-hydroxyacetyl)-3-methylpiperazin-1-yl)pyrimidin-5-yl)-2-methyl-3-oxo-2,3-dihydro-1H-indazole-7-carbonitrile;

1-(2-(difluoromethoxy)-5-methylbenzyl)-5-fluoro-6-(2-(2-hydroxypropan-2-yl)-4-methylpyrimidin-5-yl)-2-methyl-1H-indazol-3(2H)-one;

(R)-4-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoic acid;

1-(2-(difluoromethoxy)benzyl)-6-(2-((2R,4R)-4-hydroxy-2-methylpiperidin-1-yl)pyrimidin-5-yl)-2-methyl-1H-indazol-3(2H)-one;

6-(2-(2-hydroxypropan-2-yl)pyrimidin-5-yl)-1-((1-((4-methoxy-1H-pyrazol-3-yl)methyl)-4-(trifluoromethyl)-1H-pyrrol-3-yl)methyl)-2-methyl-1H-indazol-3(2H)-one;

(R)-2-(4-(difluoromethoxy)-3-((6-(2-(4-(2-hydroxyacetyl)-2-methylpiperazin-1-yl)pyrimidin-5-yl)-2-methyl-3-oxo-2,3-dihydro-1H-indazol-1-yl)methyl)phenyl)acetonitrile;

(R)-2-(2-((6-(2-(4-acetyl-3-methylpiperazin-1-yl)pyrimidin-5-yl)-2-methyl-3-oxo-2,3-dihydro-1H-indazol-1-yl)methyl)-3-(difluoromethoxy)phenyl)acetonitrile;

(R)-2-((R)-4-(5-(1(2-(difluoromethoxy)benzyl)-2-methyl-3-oxo-2,3-dihydro-1H-indazol-6-yl)pyrimidin-2-yl)-2-methylpiperazin-1-yl)-2-oxoethyl 2-amino-3-methylbutanoate;

1-(2-(difluoromethoxy)-5-(hydroxymethyl)benzyl)-2-methyl-6-(2-(((1-methyl-2-oxopiperidin-4-yl)amino)pyrimidin-5-yl)-1H-indazol-3(2H)-one;

6-(2-(4-acetylpiperazin-1-yl)pyrimidin-5-yl)-1-(2-(difluoromethoxy)-5-methylbenzyl)-2-methyl-1H-indazol-3(2H)-one;

1-(2,5-dimethylbenzyl)-2-methyl-6-(2-morpholinopyrimidin-5-yl)-1H-indazol-3(2H)-one;

(R)-1-(2-(difluoromethoxy)benzyl)-6-(2-(4-(2-hydroxyacetyl)-3-methylpiperazin-1-yl)pyrimidin-5-yl)-2,7-dimethyl-1H-indazol-3(2H)-one;

1-(2-(difluoromethoxy)-5-(hydroxymethyl)benzyl)-6-(2-(2-hydroxypropan-2-yl)pyrimidin-5-yl)-2-methyl-1H-indazol-3(2H)-one;

(S)-7-(5-(2-methyl-1-((6-methyl-3-(trifluoromethyl)pyridin-2-yl)methyl)-3-oxo-2,3-dihydro-1H-indazol-6-yl)pyrimidin-2-yl)hexahydroimidazo[1,5-a]pyrazin-3(2H)-one;

(R)-6-(2-(4-acetyl-2-methylpiperazin-1-yl)pyrimidin-5-yl)-2-methyl-1-((6-methyl-3-(trifluoromethyl)pyridin-2-yl)methyl)-1H-indazol-3(2H)-one;

6-(2-(2-hydroxypropan-2-yl)pyrimidin-5-yl)-2-methyl-1-((1-(pyridin-3-ylmethyl)-4-(trifluoromethyl)-1H-pyrrol-3-yl)methyl)-1H-indazol-3(2H)-one;

6-(2-(4-(3-amino-2-hydroxypropanoyl)-3-methylpiperazin-1-yl)pyrimidin-5-yl)-1-(2-(difluoromethoxy)benzyl)-2-methyl-1H-indazol-3(2H)-one dihydrochloride;

1-(2-(difluoromethoxy)-5-methylbenzyl)-5-fluoro-6-(2-(1-hydroxy-2-methylpropan-2-yl)pyrimidin-5-yl)-2-methyl-1H-indazol-3(2H)-one;

(R)-1-(2-chloro-5-methylbenzyl)-6-(2-(4-(2-hydroxyacetyl)-2-methylpiperazin-1-yl)pyrimidin-5-yl)-2-methyl-1H-pyrazolo[3,4-b]pyridin-3(2H)-one;

1-(2-(difluoromethoxy)-5-methylbenzyl)-6-(3-(1-hydroxyethyl)imidazo[1,2-b]pyridazin-7-yl)-2-methyl-1H-indazol-3(2H)-one;

6-(2-(2-aminopropan-2-yl)pyrimidin-5-yl)-1-(2-(difluoromethoxy)-5-methylbenzyl)-2-methyl-1H-indazol-3(2H)-one;

(1S,3S)-3-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentanecarbonitrile;

(S)-1-(2-(difluoromethoxy)-5-methylbenzyl)-6-(3-(1-hydroxyethyl)imidazo[1,2-b]pyridazin-7-yl)-2-methyl-1H-indazol-3(2H)-one;

(S)-7-(5-(1-(5-chloro-2-(trifluoromethyl)benzyl)-2-methyl-3-oxo-2,3-dihydro-1H-imidazol-6-yl)pyrimidin-2-yl)hexahydroimidazo[1,5-a]pyrazin-3(2H)-one;

(R)-6-(2-(4-acetyl-3-methylpiperazin-1-yl)pyrimidin-5-yl)-1-((3-chloro-6-methylpyridin-2-yl)methyl)-2-methyl-1H-indazol-3(2H)-one;

(R)-7-(5-(1-(2-(difluoromethoxy)benzyl)-2-methyl-3-oxo-2,3-dihydro-1H-indazol-6-yl)pyrimidin-2-yl)-2-methyl-hexahydroimidazo[1,5-a]pyrazin-3(2H)-one;

(S)-7-(5-(2-methyl-1-((1-methyl-4-(trifluoromethyl)-1H-pyrrol-3-yl)methyl)-3-oxo-2,3-dihydro-1H-indazol-6-yl)pyrimidin-2-yl)hexahydroimidazo[1,5-a]pyrazin-3(2H)-one;

(R)-1-(2-chlorobenzyl)-6-(2-(4-(2-hydroxyacetyl)-3-methylpiperazin-1-yl)pyrimidin-5-yl)-2-methyl-1H-pyrazolo[3,4-b]pyridin-3(2H)-one;

(S)-1-(2-(difluoromethoxy)-5-(hydroxymethyl)benzyl)-2-methyl-6-(2-((2-oxopiperidin-4-yl)amino)pyrimidin-5-yl)-1H-indazol-3(2H)-one;

1-(2-(difluoromethoxy)benzyl)-2-methyl-6-(2-((tetrahydro-2H-pyran-4-yl)oxy)pyridin-4-yl)-1H-indazol-3(2H)-one;

6-(2-((R)-4-(2-hydroxyacetyl)-3-methylpiperazin-1-yl)pyrimidin-5-yl)-2-methyl-1-(1-phenylethyl)-1H-indazol-3(2H)-one;

1-(1-(2-fluorophenyl)ethyl)-6-(2-((R)-4-(2-hydroxyacetyl)-3-methylpiperazin-1-yl)pyrimidin-5-yl)-2-methyl-1H-indazol-3(2H)-one;

(R)-1-((3-(difluoromethoxy)-6-methylpyridin-2-yl)methyl)-6-(2-(4-(2-hydroxyacetyl)-3-methylpiperazin-1-yl)pyrimidin-5-yl)-2-methyl-1H-indazol-3(2H)-one;

(R)-6-(2-(4-acetyl-3-methylpiperazin-1-yl)pyrimidin-5-yl)-1-((1-(2-hydroxyethyl)-4-(trifluoromethyl)-1H-pyrrol-3-yl)methyl)-2-methyl-1H-indazol-3(2H)-one;

1-(5-((1H-1,2,4-triazol-1-yl)methyl)-2-(difluoromethoxy) benzyl)-6-(2-(2-hydroxypropan-2-yl)pyrimidin-5-yl)-2-methyl-1H-indazol-3(2H)-one;

1-(2-(difluoromethoxy)-5-methylbenzyl)-6-(2-(4-hydroxypiperidin-1-yl)pyrimidin-5-yl)-2-methyl-1H-indazol-3(2H)-one;

1-(2-(difluoromethoxy)-5-methylbenzyl)-6-(2-isopropylpyrimidin-5-yl)-2-methyl-1H-indazol-3(2H)-one;

(R)-1-(2-chlorobenzyl)-6-(2-(4-(2-hydroxyacetyl)-3-methylpiperazin-1-yl)pyrimidin-5-yl)-2,7-dimethyl-1H-indazol-3(2H)-one;

6-(6-(2-aminopropan-2-yl)pyridin-3-yl)-1-(2-(difluoromethoxy)-5-methylbenzyl)-5-fluoro-2-methyl-1H-indazol-3(2H)-one;

(S)-4-(difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-aminopropanoate;

1-(2-(difluoromethoxy)benzyl)-6-(2-((2R,4S)-4-hydroxy-2-methylpiperidin-1-yl)pyrimidin-5-yl)-2-methyl-1H-indazol-3(2H)-one;

(R)-4-(difluoromethoxy)-3-((2-methyl-3-oxo-6-(2-(3-oxohexahydroimidazo[1,5-a]pyrazin-7(1H)-yl)pyrimidin-5-yl)-2,3-dihydro-1H-indazol-1-yl)methyl)benzyldimethylcarbamate;

(S)-6-(2-(4-(2-aminoacetyl)-3-methylpiperazin-1-yl)pyrimidin-5-yl)-1-(2-(difluoromethoxy)-5-methylbenzyl)-2-methyl-1H-indazol-3(2H)-one hydrochloride;

(R)-7-(5-(1-((6-(hydroxymethyl)-3-(trifluoromethyl)pyridin-2-yl)methyl)-2-methyl-3-oxo-2,3-dihydro-1H-indazol-6-yl)pyrimidin-2-yl)hexahydroimidazo[1,5-a]pyrazin-3(2H)-one;

(S)-7-(5-(1-(((5-chloro-1,3-dihydroisobenzofuran-4-yl) methyl)-2-methyl-3-oxo-2,3-dihydro-1H-indazol-6-yl)pyrimidin-2-yl)hexahydroimidazo[1,5-a]pyrazin-3(2H)-one;

1-(2-(difluoromethoxy)-5-methylbenzyl)-7-fluoro-6-(2-(2-hydroxypropan-2-yl)-4-methylpyrimidin-5-yl)-2-methyl-1H-indazol-3(2H)-one;

1-(2-(difluoromethoxy)-5-methylbenzyl)-5-fluoro-6-(2-(2-hydroxypropan-2-yl)-4-methylpyrimidin-5-yl)-2-methyl-1H-pyrazolo[3,4-b]pyridin-3(2H)-one;

1-(2-chloro-5-methylbenzyl)-6-(2-(2-hydroxypropan-2-yl)-4-methylpyrimidin-5-yl)-2-methyl-1H-pyrazolo[3,4-b]pyridin-3(2H)-one;

(R)-1-(2-(difluoromethoxy)benzyl)-2-(difluoromethyl)-6-(2-(4-(2-hydroxyacetyl)-3-methylpiperazin-1-yl)pyrimidin-5-yl)-1H-indazol-3(2H)-one;

1-(2-(difluoromethoxy)benzyl)-6-(2-(4-(2-hydroxyacetyl) piperazin-1-yl)pyrimidin-5-yl)-2-methyl-1H-indazol-3 (2H)-one;

6-(2-((S)-4-((S)-2-aminopropanoyl)-3-methylpiperazin-1-yl)pyrimidin-5-yl)-1-(2-(difluoromethoxy)-5-methylbenzyl)-2-methyl-1H-indazol-3(2H)-one;

(S)-4-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoic acid;

(S)-6-(2-(4-acetyl-3-(hydroxymethyl)piperazin-1-yl)pyrimidin-5-yl)-1-(2-(difluoromethoxy)-5-methylbenzyl)-2-methyl-1H-indazol-3(2H)-one;

(R)-6-(2-(4-acetyl-3-methylpiperazin-1-yl)pyrimidin-5-yl)-1-(((3-(difluoromethoxy)-6-methylpyridin-2-yl)methyl)-2-methyl-1H-indazol-3(2H)-one;

6-(2-(4-acetylpiperazin-1-yl)pyrimidin-5-yl)-1-(5-(hydroxymethyl)-2-(trifluoromethyl)benzyl)-2-methyl-1H-indazol-3(2H)-one;

(R)-1-(2-chlorobenzyl)-6-(2-(4-(2-hydroxyacetyl)-3-methylpiperazin-1-yl)pyrimidin-5-yl)-7-methoxy-2-methyl-1H-indazol-3(2H)-one;

(R)-6-(2-(4-acetyl-3-(hydroxymethyl)piperazin-1-yl)pyrimidin-5-yl)-1-(2-(difluoromethoxy)-5-methylbenzyl)-2-methyl-1H-indazol-3(2H)-one;

(R)-1-(2-(difluoromethoxy)-5-methylbenzyl)-6-(2-(4-(2-hydroxyacetyl)-2-methylpiperazin-1-yl)pyrimidin-5-yl)-2-methyl-1H-pyrazolo[3,4-b]pyridin-3(2H)-one;

(S)-4-(difluoromethoxy)-3-((2-methyl-3-oxo-6-(2-((R)-3-oxohexahydroimidazo[1,5-a]pyrazin-7(1H)-yl)pyrimidin-5-yl)-2,3-dihydro-1H-indazol-1-yl)methyl)benzyl 2-amino-3-methylbutanoate hydrochloride;

(S)-7-(5-(1-(((3-(difluoromethoxy)-6-methylpyridin-2-yl) methyl)-2-methyl-3-oxo-2,3-dihydro-1H-indazol-6-yl) pyrimidin-2-yl)hexahydroimidazo[1,5-a]pyrazin-3(2H)-one;

(R)-9-((6-(2-(4-acetyl-3-methylpiperazin-1-yl)pyrimidin-5-yl)-2-methyl-3-oxo-2,3-dihydro-1H-indazol-1-yl) methyl)-4,5-dihydrobenzo[t][1,4]thiazepin-3(2H)-one;

1-(2-(difluoromethoxy)benzyl)-5-fluoro-6-(2-(2-hydroxypropan-2-yl)pyrimidin-5-yl)-2-methyl-1H-indazol-3 (2H)-one;

6-(2-((R)-4-acetyl-3-methylpiperazin-1-yl)pyrimidin-5-yl)-1-(2-(difluoromethoxy)-5-(2-hydroxypropyl)benzyl)-2-methyl-1H-indazol-3(2H)-one;

1-(2-(difluoromethoxy)-5-methylbenzyl)-5-fluoro-6-(2-(2-hydroxypropan-2-yl)pyrimidin-5-yl)-2-methyl-1H-pyrazolo[3,4-b]pyridin-3(2H)-one;

(R)-1-(2-(difluoromethoxy)benzyl)-6-(2-(4-(2-hydroxyacetyl)-3-methylpiperazin-1-yl)pyrimidin-5-yl)-5-methoxy-2-methyl-1H-indazol-3(2H)-one;

(R)-1-(2-(difluoromethoxy)-5-methylbenzyl)-2-methyl-6-(2-(3-methylpiperazin-1-yl)pyrimidin-5-yl)-1H-indazol-3 (2H)-one;

1-(5-(1-(2-(difluoromethoxy)-5-methylbenzyl)-2-methyl-3-oxo-2,3-dihydro-1H-indazol-6-yl)pyrimidin-2-yl)pyrrolidine-3-carboxamide;

1-(2-(difluoromethoxy)-5-methylbenzyl)-6-(2-(2-hydroxypropan-2-yl)-4-methylpyrimidin-5-yl)-2-methyl-1H-pyrazolo[3,4-b]pyridin-3(2H)-one;

1-(2-(difluoromethoxy)-5-methylbenzyl)-2-methyl-6-(2-((3aS,6aS)-4-oxohexahydropyrrolo[3,4-c]pyrrol-2(1H)-yl)pyrimidin-5-yl)-1H-indazol-3(2H)-one;

(R)-6-(2-(4-acetyl-3-methylpiperazin-1-yl)pyrimidin-5-yl)-1-(2-(difluoromethoxy)-5-((3-methyl-2-oxoimidazolidin-1-yl)methyl)benzyl)-2-methyl-1H-indazol-3(2H)-one;

1-(2-(difluoromethoxy)-5-(hydroxymethyl)benzyl)-2-methyl-6-(2-((2-oxopyrrolidin-3-yl)amino)pyrimidin-5-yl)-1H-indazol-3(2H)-one;

2-(4-(difluoromethoxy)-3-((5-fluoro-6-(2-(2-hydroxypropan-2-yl)pyrimidin-5-yl)-2-methyl-3-oxo-2,3-dihydro-1H-indazol-1-yl)methyl)phenyl)acetonitrile;

1-(5-((4H-1,2,4-triazol-4-yl)methyl)-2-(difluoromethoxy) benzyl)-5-fluoro-6-(2-(2-hydroxypropan-2-yl)pyrimidin-5-yl)-2-methyl-1H-indazol-3(2H)-one;

1-(2-(difluoromethoxy)-5-methylbenzyl)-6-(2-(1-hydroxy-2-methylpropan-2-yl)pyrimidin-5-yl)-2-methyl-1H-indazol-3(2H)-one;

1-(2-(difluoromethoxy)-5-(hydroxymethyl)benzyl)-2-methyl-6-(4-((1-methyl-2-oxopyrrolidin-3-yl)amino)phenyl)-1H-indazol-3(2H)-one;

(S)-1-(2-(difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one;

6-(2-((R)-4-(2-hydroxyacetyl)-3-methylpiperazin-1-yl)pyrimidin-5-yl)-2-methyl-1-(1-(6-methylpyridin-2-yl)ethyl)-1H-indazol-3(2H)-one;

1-(2-(difluoromethoxy)benzyl)-2-methyl-6-(2-((tetrahydro-2H-pyran-3-yl)oxy)pyridin-4-yl)-1H-indazol-3(2H)-one;

1-(2-(difluoromethoxy)-5-methylbenzyl)-7-fluoro-6-(2-(2-hydroxypropan-2-yl)pyrimidin-5-yl)-2-methyl-1H-indazol-3(2H)-one;

6-(2-((R)-4-(2-hydroxyacetyl)-3-methylpiperazin-1-yl)pyrimidin-5-yl)-2-methyl-1-(1-(4-methylpyridin-2-yl)ethyl)-1H-indazol-3(2H)-one;

1-(2-chloro-5-((1-methyl-2-oxopiperidin-3-yl)amino)benzyl)-6-(2-(2-hydroxypropan-2-yl)pyrimidin-5-yl)-2-methyl-1H-indazol-3(2H)-one;

(R)—N-(3-((6-(2-(4-acetyl-3-methylpiperazin-1-yl)pyrimidin-5-yl)-2-methyl-3-oxo-2,3-dihydro-1H-indazol-1-yl)methyl)-4-(difluoromethoxy)benzyl)acetamide;

(R)-6-(2-(4-acetyl-3-methylpiperazin-1-yl)pyrimidin-5-yl)-1-(2-chlorobenzyl)-2-(pyridin-4-ylmethyl)-1H-indazol-3(2H)-one;

(S)-4-(difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-amino-3-methylbutanoate;

(R)-1-(2-(difluoromethoxy)-5-methylbenzyl)-6-(2-(2-(hydroxymethyl)pyrrolidin-1-yl)pyrimidin-5-yl)-2-methyl-1H-indazol-3(2H)-one;

(S)-1-(2-(difluoromethoxy)-5-methylbenzyl)-6-(2-(2-(hydroxymethyl)pyrrolidin-1-yl)pyrimidin-5-yl)-2-methyl-1H-indazol-3(2H)-one;

(S)-7-(5-(2-methyl-1-((5-methyl-2-(trifluoromethyl)pyridin-3-yl)methyl)-3-oxo-2,3-dihydro-1H-indazol-6-yl)pyrimidin-2-yl)hexahydroimidazo[1,5-a]pyrazin-3(2H)-one;

(R)-1-(2-(difluoromethoxy)benzyl)-6-(2-(4-(2-hydroxyacetyl)-3-methylpiperazin-1-yl)pyrimidin-5-yl)-2-methyl-3-oxo-2,3-dihydro-1H-indazole-5-carbonitrile;

(S)-4-methyl-2-((2-methyl-3-oxo-6-(2-(3-oxohexahydroimidazo[1,5-a]pyrazin-7(1H)-yl)pyrimidin-5-yl)-2,3-dihydro-1H-indazol-1-yl)methyl)benzonitrile;

3-(3-((6-(2-((R)-4-acetyl-3-methylpiperazin-1-yl)pyrimidin-5-yl)-2-methyl-3-oxo-2,3-dihydro-1H-indazol-1-yl)methyl)-4-(difluoromethoxy)phenyl)-2-methylpropanenitrile;

2-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)acetonitrile;

(R)-6-(2-(4-acetyl-3-methylpiperazin-1-yl)pyrimidin-5-yl)-1-(2-(difluoromethoxy)-5-((3-oxo-2,3-dihydro-1H-pyrazol-1-yl)methyl)benzyl)-2-methyl-1H-indazol-3(2H)-one;

1-(1-(2-chlorophenyl)ethyl)-6-(2-((R)-4-(2-hydroxyacetyl)-3-methylpiperazin-1-yl)pyrimidin-5-yl)-2-methyl-1H-indazol-3(2H)-one;

(R)-3-((6-(2-(4-acetyl-3-methylpiperazin-1-yl)pyrimidin-5-yl)-1-(2-chlorobenzyl)-3-oxo-1H-indazol-2(3H)-yl)methyl)benzonitrile;

1-(2-(difluoromethoxy)-6-(methoxymethyl)benzyl)-6-(2-(2-hydroxypropan-2-yl)pyrimidin-5-yl)-2-methyl-1H-indazol-3(2H)-one;

1-((R)-1-(2-fluorophenyl)ethyl)-6-(2-((R)-4-(2-hydroxyacetyl)-3-methylpiperazin-1-yl)pyrimidin-5-yl)-2-methyl-1H-indazol-3(2H)-one;

1-(2-chloro-5-((pyridin-3-ylmethyl)amino)benzyl)-6-(2-(2-hydroxypropan-2-yl)pyrimidin-5-yl)-2-methyl-1H-indazol-3(2H)-one;

(R)-1-(2-chlorobenzyl)-6-(2-(4-(2-hydroxyacetyl)-3-methylpiperazin-1-yl)pyrimidin-5-yl)-2-methyl-3-oxo-2,3-dihydro-1H-indazole-7-carbonitrile;

(R)-6-(2-(4-acetyl-3-methylpiperazin-1-yl)pyrimidin-5-yl)-1-(2-(difluoromethoxy)benzyl)-2-(pyridin-4-ylmethyl)-1H-indazol-3(2H)-one;

(S)-7-(5-(2-methyl-1-((1-methyl-4-(trifluoromethyl)-1H-pyrazol-3-yl)methyl)-3-oxo-2,3-dihydro-1H-indazol-6-yl)pyrimidin-2-yl)hexahydroimidazo[1,5-a]pyrazin-3(2H)-one;

3-(1-(5-(1-(2-(difluoromethoxy)benzyl)-2-methyl-3-oxo-2,3-dihydro-1H-indazol-6-yl)pyrimidin-2-yl)piperidin-4-yl)-1,2,4-thiadiazol-5(4H)-one;

1-(2-chloro-5-((1-methyl-2-oxopyrrolidin-3-yl)amino)benzyl)-6-(2-(2-hydroxypropan-2-yl)pyrimidin-5-yl)-2-methyl-1H-indazol-3(2H)-one;

1-(2-chloro-5-((pyridin-2-ylmethyl)amino)benzyl)-6-(2-(2-hydroxypropan-2-yl)pyrimidin-5-yl)-2-methyl-1H-indazol-3(2H)-one;

methyl 4-(difluoromethoxy)-3-((6-(2-(2-hydroxypropan-2-yl)pyrimidin-5-yl)-2-methyl-3-oxo-2,3-dihydro-1H-indazol-1-yl)methyl)benzylcarbamate;

(S)-7-(5-(2-methyl-3-oxo-1-((2-(trifluoromethyl)pyridin-3-yl)methyl)-2,3-dihydro-1H-indazol-6-yl)pyrimidin-2-yl)hexahydroimidazo[1,5-a]pyrazin-3(2H)-one;

1-(5-(hydroxymethyl)-2-methylbenzyl)-2-methyl-6-(2-morpholinopyrimidin-5-yl)-1H-indazol-3(2H)-one;

1-(5-(((1H-pyrazol-3-yl)methyl)amino)-2-chlorobenzyl)-6-(2-(2-hydroxypropan-2-yl)pyrimidin-5-yl)-2-methyl-1H-indazol-3(2H)-one;

6-(2-(4-acetylpiperazin-1-yl)pyrimidin-5-yl)-1-(2-(difluoromethoxy)-5-(methoxymethyl)benzyl)-2-methyl-1H-indazol-3(2H)-one;

(R)—N-(3-((6-(2-(4-acetyl-3-methylpiperazin-1-yl)pyrimidin-5-yl)-2-methyl-3-oxo-2,3-dihydro-1H-indazol-1-yl)methyl)-4-(difluoromethoxy)benzyl)-N-ethylacetamide;

1-((1-((4-ethylpyridin-3-yl)methyl)-4-(trifluoromethyl)-1H-pyrrol-3-yl)methyl)-6-(2-(2-hydroxypropan-2-yl)pyrimidin-5-yl)-2-methyl-1H-indazol-3(2H)-one;

1-(2-(difluoromethoxy)benzyl)-6-(2-(dimethylamino)pyrimidin-5-yl)-2-methyl-1H-indazol-3(2H)-one;

6-(2-(1-acetyl-4-hydroxypiperidin-4-yl)pyrimidin-5-yl)-1-(2-(difluoromethoxy)benzyl)-2-methyl-1H-indazol-3(2H)-one;

1-(5-((1-acetylazetidin-3-yl)methyl)-2-(difluoromethoxy)benzyl)-5-fluoro-6-(2-(2-hydroxypropan-2-yl)pyrimidin-5-yl)-2-methyl-1H-indazol-3(2H)-one;

1-(2-(difluoromethoxy)-5-((5-oxo-1H-1,2,4-triazol-4(5H)-yl)methyl)benzyl)-6-(2-(2-hydroxypropan-2-yl)pyrimidin-5-yl)-2-methyl-1H-indazol-3(2H)-one;

6-(2-((R)-4-(2-hydroxyacetyl)-3-methylpiperazin-1-yl)pyrimidin-5-yl)-2-methyl-1-((R)-1-(m-tolyl)ethyl)-1H-indazol-3(2H)-one;

6-(2-(2-hydroxypropan-2-yl)pyrimidin-5-yl)-2-methyl-1-((1-(pyridazin-4-ylmethyl)-4-(trifluoromethyl)-1H-pyrrol-3-yl)methyl)-1H-indazol-3(2H)-one;

1-(2-(difluoromethoxy)-5-methylbenzyl)-2-(difluoromethyl)-6-(2-(2-hydroxypropan-2-yl)pyrimidin-5-yl)-1H-indazol-3(2H)-one;

(1R,2S)-2-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentanecarbonitrile;

(1R,3S)-3-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentanecarbonitrile;

6-(2-(1-(2-aminoacetyl)-4-hydroxypiperidin-4-yl)pyrimidin-5-yl)-1-(2-(difluoromethoxy)benzyl)-2-methyl-1H-indazol-3(2H)-one;

4-(5-(1-(2-(difluoromethoxy)benzyl)-2-methyl-3-oxo-2,3-dihydro-1H-indazol-6-yl)pyrimidin-2-yl)-4-hydroxypiperidine-1-carbaldehyde;

6-(2-((1-acetylpiperidin-4-yl)oxy)pyridin-4-yl)-1-(2-(difluoromethoxy)benzyl)-2-methyl-1H-indazol-3(2H)-one;

1-(2-(difluoromethoxy)-5-morpholinobenzyl)-6-(2-(2-hydroxypropan-2-yl)pyrimidin-5-yl)-2-methyl-1H-indazol-3(2H)-one;

1-(2-(difluoromethoxy)benzyl)-6-(2-(3-hydroxy-1-(2-hydroxyacetyl)azetidin-3-yl)pyrimidin-5-yl)-2-methyl-1H-indazol-3(2H)-one;

(R)-2-(3-((6-(2-(4-acetyl-3-methylpiperazin-1-yl)pyrimidin-5-yl)-2-methyl-3-oxo-2,3-dihydro-1H-indazol-1-yl)methyl)-4-(difluoromethoxy)phenyl)acetonitrile;

(R)-6-(2-(4-acetyl-2-methylpiperazin-1-yl)-4-methylpyrimidin-5-yl)-1-(2-(difluoromethoxy)-5-methylbenzyl)-2-methyl-1H-indazol-3(2H)-one;

(R)-1-(2-(difluoromethoxy)benzyl)-5,7-difluoro-6-(2-(4-(2-hydroxyacetyl)-2-methylpiperazin-1-yl)pyrimidin-5-yl)-2-methyl-1H-indazol-3(2H)-one; or (R)-6-(2-(4-acetyl-2-methylpiperazin-1-yl)-4-methylpyrimidin-5-yl)-1-(2-(difluoromethoxy)-5-methylbenzyl)-2-methyl-1H-indazol-3(2H)-one.

In a twenty-sixth embodiment, the disclosure provides a pharmaceutical composition comprising a compound according to any of the foregoing embodiments and one or more pharmaceutically acceptable excipients.

In a twenty-seventh embodiment, the disclosure provides a method of treating a disease comprising administering a therapeutically effective amount of a compound or pharmaceutical composition according to any of the foregoing embodiments.

In a twenty-eighth embodiment, the disclosure provides a method of the twenty-seventh embodiment, wherein the disease is rheumatoid arthritis, juvenile rheumatoid arthritis, psoriasis, psoriatic arthritis, Crohn's disease, inflammatory bowel disease, ulcerative colitis, psoriatic arthritis, psoriasis, ankylosing spondylitis, systemic lupus erythematosus, lupus nephritis, multiple sclerosis, uveitis or hidraenitis suppurativa.

In a twenty-ninth embodiment, the disclosure provides a kit comprising a packaged product comprising components with which to administer a compound or composition of any of the foregoing embodiments for the treatment of an autoimmune disorder.

In a thirtieth embodiment, the disclosure provides a kit according to the twenty-ninth embodiment, wherein the packaged product comprises a compound or pharmaceutical composition of any of the foregoing embodiments and instructions for use.

DETAILED DESCRIPTION OF THE DISCLOSURE

Definitions

In this disclosure, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g., (+) or (−)-tartaric acid or mixtures thereof), amino acids (e.g., (+) or (−)-amino acids or mixtures thereof), and the like. These salts can be prepared by methods known to those skilled in the art.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present disclosure wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

The term "heterocycle," "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this disclosure, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this disclosure: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]

pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b;2'3'-d]pyridinyl, 6H-3-thia-2,5,6-triaza-as-indacenyl, 4,5-dihydro-1H-benzo[b]azepin-2(3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b]pyridine.

As used herein, "alkyl," "alkylene" or notations such as "($C_1$-$C_8$)" include straight chained or branched hydrocarbons which are completely saturated. An alkyl is a monovalent radical while an alkylene is a bivalent radical. Examples of alkyls are methyl, ethyl, propyl, isopropyl, butyl, pentyl, hexyl and isomers thereof. Examples of alkylenes include methylene (—$CH_2$—), ethylene (—$CH_2CH_2$—), propylene (—$CH_2CH_2CH_2$—), isopropylene (—$CH(CH_3)CH_2$—) and the like. As used herein, "alkenyl," "alkenylene," "alkynylene" and "alkynyl" means $C_2$-$C_8$ and includes straight chained or branched hydrocarbons which contain one or more units of unsaturation, one or more double bonds for alkenyl and one or more triple bonds for alkynyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkoxyalkyl" as used herein, refers to an alkoxy group, as defined herein, appended to the parent molecular moiety through an alkyl group, as defined herein. Representative examples of alkoxyalkyl include, but are not limited to, methoxymethyl, methoxyethyl, and methoxypropyl.

As used herein, "aromatic" groups (or "aryl" or "arylene" groups) include aromatic carbocyclic ring systems (e.g., phenyl) and fused polycyclic aromatic ring systems (e.g., naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that are completely saturated. Examples of cycloalkyl groups are cyclopropyl, cyclobutyl, cyclopentyl, bicyclo[1.1.1]pentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of cycloalkenyl groups are cyclopentenyl and cyclohexenyl.

As used herein, many moieties or substituents are termed as being either "substituted" or "optionally substituted." When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this disclosure, some examples of groups that are substituents are: ($C_1$-$C_8$)alkyl groups optionally substituted with —OH, ($C_2$-$C_8$)alkenyl groups, ($C_2$-$C_8$)alkynyl groups, ($C_3$-$C_{10}$)cycloalkyl groups optionally substituted with —CN, halogen (F, Cl, Br or I), halogenated ($C_1$-$C_8$)alkyl groups (for example but not limited to —$CF_3$), —O—($C_1$-$C_8$)alkyl groups, —($C_1$-$C_6$)alkyl-C(O)OH, =O, =$CH_2$, —OH, —$CH_2$OH, —$CH_2NH_2$, ($C_1$-$C_4$)alkyl-OH, —$CH_2CH_2OCH_2CH_3$, —S—($C_1$-$C_8$)alkyl groups, —SH, —NH($C_1$-$C_8$)alkyl groups, —N(($C_1$-$C_8$)alkyl)$_2$ groups, —$NH_2$, —C(O)$NH_2$, —C(O)$CH_2NH_2$, —C(O)CH($CH_3$)$NH_2$, —C(O)CH(OH)$CH_2NH_2$, —C(O)CH(OH)$CH_2$C(O)OH, —C(O)$CH_2$OC(O)CH($NH_2$)($C_1$-$C_6$)alkyl, —C(O)($C_1$-$C_6$)alkyl($C_1$-$C_6$)alkoxy, —($C_1$-$C_6$)alkyl($C_1$-$C_6$)alkoxy, —C(O)($C_1$-$C_6$)alkyl-CN, —($C_1$-$C_6$)alkyl-CN, —C(O)CH(OH)$CH_2$OH, —C(O)($C_1$-$C_6$)alkyl-P(O)$_4$, —$CH_2$NHC(O)($C_1$-$C_4$)alkyl optionally substituted with ($C_1$-$C_4$)alkyl), —$CH_2$NHC(O)($C_1$-$C_4$)alkoxy, —$CH_2$NHC(O)$CH_2$Cl, —$CH_2$NHC(O)$CH_2$CN, —$CH_2$NHC(O)$CH_2CH_2$N($CH_3$)$_2$, —$CH_2$OC(O)N($CH_3$)$_2$, —$CH_2$OC(O)($C_1$-$C_6$)alkyl optionally substituted with $NH_2$, —$CH_2$NHC(O)C(=$CH_2$)$CH_3$, —$CH_2$NHC(O)($C_2$-$C_4$)alkynyl, —$CH_2$NHC(O)$CH_2CH_2$-piperidinyl, —($C_1$-$C_4$)alkyl-morpholinyl, —$CH_2$NHC(O)$CH_2$O-phenyl wherein the phenyl is optionally substituted with halogen, ($C_1$-$C_4$)alkoxy, —C(O)($C_1$-$C_4$)alkyl, —C(O)($C_1$-$C_4$)alkyl-OH, —C(O)N(H)$_2$, —C(O)N($CH_3$)$_2$, —C(O)($C_1$-$C_6$)heteroaryl, —N($CH_3$)$_2$, —NHC(O)($C_1$-$C_4$)alkyl, —NHC(O)($C_2$-$C_4$)alkenyl, —NHC(O)$CH_2$CN, —S(O)$_2$($C_1$-$C_4$)alkyl, —S(O)$_2$($C_1$-$C_6$)heteroaryl, —S(O)$_2$($C_1$-$C_6$)heterocyclyl, 4-methylpiperazinecarbonyl, —($C_1$-$C_4$)alkyl-C(O)$NH_2$, —C(O)NH($C_1$-$C_8$)alkyl groups, —C(O)N(($C_1$-$C_8$)alkyl)$_2$, —C(O)N(H)($C_3$-$C_8$)cycloalkyl groups, —C(O)($C_1$-$C_4$)alkoxy, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)$NH_2$, —NHC(O)NH($C_1$-$C_8$)alkyl groups, —N(($C_1$-$C_8$)alkyl)C(O)$NH_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —NH($C_1$-$C_6$)alkyl optionally substituted with —OH, —$NHCH_2$-heteroaryl, benzyl, —$OCH_2$-heteroaryl, —C(O)H, —C(O)($C_1$-$C_8$)alkyl groups, —CN, —$NO_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$$NH_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$)alkyl groups (for example but not limited to —S(O)$_2$$CF_3$), —S-halogenated ($C_1$-$C_8$)alkyl groups (for example but not limited to —$SCF_3$), -(substituted or unsubstituted)($C_1$-$C_6$)heterocyclyl (for example but not limited to pyrrolidine, tetrahydrofuran, pyran or morpholine), —NH-heterocyclyl, —C(O)-(substituted or unsubstituted)($C_1$-$C_6$)heterocyclyl —($C_1$-$C_6$)alkyl-(substituted or unsubstituted)heterocyclyl, -(substituted or unsubstituted)($C_1$-$C_6$)heteroaryl (for example but not limited to tetrazole, imidazole, furan, pyrazine or pyrazole), —($C_1$-$C_6$)alkyl-(substituted or unsubstituted)heteroaryl, —($C_1$-$C_6$)alkyl-O-(substituted or unsubstituted)heteroaryl, -phenyl, optionally substituted benzyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$)alkyl groups, or —C(=N—O—($C_1$-$C_6$)alkyl)-($C_1$-$C_6$)alkyl groups.

The term "kit" as used herein refers to a packaged product comprising components with which to administer a compound of Formula (I) of the disclosure for treatment of an autoimmune disorder. The kit preferably comprises a box or container that holds the components of the kit. The box or container is affixed with a label or a Food and Drug Administration approved protocol. The box or container holds components of the disclosure which are preferably contained within plastic, polyethylene, polypropylene, ethylene, or propylene vessels. The vessels can be capped-tubes or bottles. The kit can also include instructions for administering a compound of Formula (I).

Compounds

Compounds of this disclosure include compounds of Formula (I), which include compounds of Formula (Ia), (Ib), (Ic), (Id) and (Ie) as described herein.

For example, compounds of the disclosure include compounds of Formula (I),

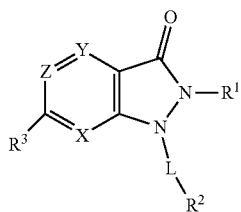

Formula (I)

or a pharmaceutically acceptable salt, prodrug or stereoisomer thereof, wherein

X, Y and Z are independently $CR^4$ or N;

provided that Y and Z are not both N;

L is a bond, optionally substituted $(C_1-C_3)$alkylene or —C(O)—;

$R^1$ is H, $CD_3$, optionally substituted $(C_1-C_3)$alkyl or optionally substituted $(C_3-C_6)$cycloalkyl;

$R^2$ is optionally substituted aryl or optionally substituted heteroaryl;

$R^3$ is —$R^{3a}$—$R^{3b}$, wherein:

$R^a$ is an optionally substituted saturated, unsaturated or partially saturated heterocyclyl or optionally substituted heteroaryl;

$R^{3b}$ is —$N(R^a)(R^b)$, —$O(R^a)$, optionally substituted $(C_1-C_5)$alkyl, optionally substituted $(C_3-C_6)$cycloalkyl, or —$(CH_2)_p$-optionally substituted heterocyclyl; wherein $R^a$ and $R^b$ are independently selected from H, optionally substituted $(C_1-C_5)$alkyl, and —$(CH_2)_n$-optionally substituted heterocyclyl;

$R^4$ is independently H, Cl, CN, F, $CF_3$, or optionally substituted $(C_1-C_3)$alkyl; and p is 0, 1 or 2.

The compound of Formula (I) may be a compound of Formula (Ia), Formula (Ib), Formula (Ic), Formula (Id) or Formula (Ie):

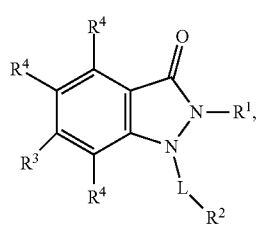

Formula (Ia)

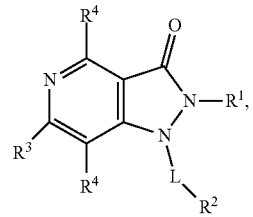

Formula (Ib)

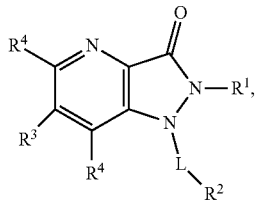

Formula (Ic)

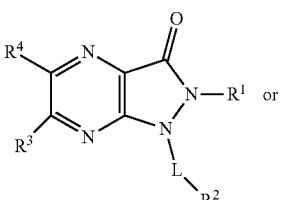

Formula (Id)

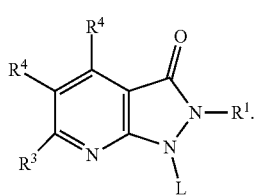

Formula (Ie)

It is to be understood that throughout this disclosure, any reference to a compound of Formula (I) includes references to compounds of Formula (Ia), Formula (Ib), Formula (Ic), Formula (Id) and Formula (Ie).

In some embodiments, $R^1$ is optionally substituted $(C_1-C_3)$alkyl (e.g., —$CH_3$) or optionally substituted cyclopropyl (e.g., unsubstituted cyclopropyl).

In some embodiments, $R^2$ is optionally substituted heteroaryl, or optionally substituted phenyl. For example, in some embodiments $R^2$ is unsubstituted phenyl, unsubstituted pyridinyl, or unsubstituted pyrimidinyl. In some embodiments, $R^2$ is phenyl, pyridinyl or pyrimidinyl that is substituted by one or more substituents (e.g., one substituent or two substituents) independently selected from halogen (e.g., F or Cl), CN, haloalkoxy (e.g., —$OCHF_2$), $CF_3$, an optionally substituted $(C_1-C_3)$alkyl (e.g., —$CH_3$ or —$CH_2OH$).

In some embodiments, $R^{3a}$ is optionally substituted 1,2,4-oxadiazolyl, optionally substituted pyrazolyl, optionally substituted pyridinyl, optionally substituted pyrimidinyl, optionally substituted pyrazinyl, or optionally substituted 1,2,4-thiadiazolyl. For example, $R^{3a}$ may be 1,2,4-oxadiazolyl, pyrazolyl, pyridinyl, pyrimidinyl, pyrazinyl, or 1,2,4-thiadiazolyl. In some embodiments, $R^{3a}$ may be substituted 1,2,4-oxadiazolyl, substituted pyrazolyl, substituted pyridinyl, substituted pyrimidinyl, substituted pyrazinyl, or substituted 1,2,4-thiadiazolyl; for example, $R^{3a}$ may be substituted with one or more substituents (e.g., one substituent or two substituents) such as halogen (e.g., Cl).

In some embodiments, $R^{3b}$ is —N($R^a$)($R^b$), —O($R^a$), optionally substituted ($C_1$-$C_3$)alkyl, —(CH$_2$)$_p$-optionally substituted 2-oxa-6-azaspiro[3.3]heptanyl, —(CH$_2$)$_p$-optionally substituted 2-azaspiro[3.3]heptanyl, —(CH$_2$)$_p$-optionally substituted 5-azaspiro[2.3]hexanyl, —(CH$_2$)$_p$-optionally substituted azetidinyl, —(CH$_2$)$_p$-optionally substituted morpholinyl, —(CH$_2$)-optionally substituted oxetanyl, —(CH$_2$)$_p$-optionally substituted piperazinyl, —(CH$_2$)$_p$-optionally substituted piperidinyl, —(CH$_2$)$_p$-optionally substituted pyrrolidinyl, —(CH$_2$)$_p$-optionally substituted tetrahydropyranyl, —(CH$_2$)$_p$-optionally substituted 6-oxohexahydropyrrolo[1,2-a]pyrazinyl, —(CH$_2$)$_p$-optionally substituted tetrahydro-1H-oxazolo[3,4-a]pyrazin-3(5H)-one or —(CH$_2$)$_p$-optionally substituted hexahydroimidazo[1,5-a]pyrazin-3(2H)-one;

wherein $R^a$ and $R^b$ are independently selected from H, optionally substituted ($C_1$-$C_3$)alkyl, —(CH$_2$)$_n$-oxoazepanyl, —(CH$_2$)$_n$-optionally substituted tetrahydrofuranyl, —(CH$_2$)$_n$-optionally substituted oxetanyl, —(CH$_2$)$_n$-optionally substituted tetrahydropyranyl, and —(CH$_2$)$_n$-optionally substituted pyrrolidinyl.

For example, $R^{3b}$ may be —N(H)CH$_2$-optionally substituted pyrrolidinyl, —O($R^a$), —N(H)-optionally substituted oxetanyl, optionally substituted ($C_1$-$C_3$)alkyl, optionally substituted 2-oxa-6-azaspiro[3.3]heptanyl, optionally substituted 5-azaspiro[2.3]hexanyl, optionally substituted azetidinyl, optionally substituted morpholinyl, —(CH$_2$)$_p$-optionally substituted oxetanyl, optionally substituted piperazinyl, optionally substituted piperidinyl, —(CH$_2$)$_p$-optionally substituted pyrrolidinyl, or optionally substituted tetrahydropyranyl. In some embodiments, $R^{3b}$ may be optionally substituted by one or more substituents independently selected from halogen, CN, —C(O)OH, —C(O)CH$_3$, —C(O)NH$_2$, NH$_2$, =O, —OH, optionally substituted ($C_1$-$C_3$)alkyl, optionally substituted ($C_1$-$C_3$)alkoxy and optionally substituted oxetanyl.

In some embodiments, L is a bond or optionally substituted ($C_1$-$C_2$)alkylene (e.g., —CH$_2$—, —CH$_2$CH$_2$—, —CH(CH$_3$)—, —C(O)—).

In some embodiments, X is CR$^4$. In some embodiments, Y is CR$^4$. In some embodiments, Z is CR$^4$.

Exemplary compounds of Formula (I) include:
1-(2-(difluoromethoxy)benzyl)-2-methyl-6-(2-(((1-methyl-5-oxopyrrolidin-3-yl)methyl)amino)pyrimidin-5-yl)-1H-indazol-3(2H)-one;
(R)-1-(5-(1-(2-(difluoromethoxy)benzyl)-2-methyl-3-oxo-2,3-dihydro-1H-indazol-6-yl)pyrimidin-2-yl)pyrrolidine-3-carboxylic acid;
(S)-1-(5-(1-(2-(difluoromethoxy)benzyl)-2-methyl-3-oxo-2,3-dihydro-1H-indazol-6-yl)pyrimidin-2-yl)pyrrolidine-3-carboxylic acid;
1-((4-chloropyridin-3-yl)methyl)-2-methyl-6-(2-morpholinopyrimidin-5-yl)-1H-indazol-3(2H)-one;
(R)-1-(2-(difluoromethoxy)benzyl)-6-(2-(3-hydroxypyrrolidin-1-yl)pyrimidin-5-yl)-2-methyl-1H-indazol-3(2H)-one;
2-(5-(1-(2-(difluoromethoxy)benzyl)-2-methyl-3-oxo-2,3-dihydro-1H-indazol-6-yl)pyrimidin-2-yl)-2-azaspiro[3.3]heptane-6-carboxylic acid;
5-(5-(1-(2-(difluoromethoxy)benzyl)-2-methyl-3-oxo-2,3-dihydro-1H-indazol-6-yl)pyrimidin-2-yl)-5-azaspiro[2.3]hexane-1-carboxylic acid;
1-(2-(difluoromethoxy)benzyl)-2-ethyl-6-(2-morpholinopyrimidin-5-yl)-1H-indazol-3(2H)-one;
1-(2-(difluoromethoxy)-5-fluorobenzyl)-2-methyl-6-(2-morpholinopyrimidin-5-yl)-1H-indazol-3(2H)-one;
6-(2-(2-oxa-6-azaspiro[3.3]heptan-6-yl)pyrimidin-5-yl)-1-(2-(difluoromethoxy)benzyl)-2-methyl-1H-indazol-3(2H)-one;
1-(5-(1(2-(difluoromethoxy)benzyl)-2,5-dimethyl-3-oxo-2,3-dihydro-1H-indazol-6-yl)pyrimidin-2-yl)piperidine-4-carboxylic acid;
1-(2-(difluoromethoxy)benzyl)-2,5-dimethyl-6-(2-morpholinopyrimidin-5-yl)-1H-indazol-3(2H)-one;
1-(2-(difluoromethoxy)benzyl)-2,5-dimethyl-6-(2-(3-oxopiperazin-1-yl)pyrimidin-5-yl)-1H-indazol-3(2H)-one;
1-((3,6-dichloropyridin-2-yl)methyl)-2-methyl-6-(2-morpholinopyrimidin-5-yl)-1H-indazol-3(2H)-one;
6-(2-((1-acetylpyrrolidin-3-yl)amino)pyrimidin-5-yl)-1-(2-(difluoromethoxy)benzyl)-2-methyl-1H-indazol-3(2H)-one;
1-(5-(1-(2-(difluoromethoxy)benzyl)-2-methyl-3-oxo-2,3-dihydro-1H-indazol-6-yl)pyrimidin-2-yl)azetidine-3-carboxylic acid;
1-(2-(difluoromethoxy)benzyl)-6-(2-(2,2-dimethylmorpholino)pyrimidin-5-yl)-2-methyl-1H-indazol-3(2H)-one;
1-(2-(difluoromethoxy)benzyl)-6-(2-(3-(hydroxymethyl)azetidin-1-yl)pyrimidin-5-yl)-2-methyl-1H-indazol-3(2H)-one;
1-(2-(difluoromethoxy)benzyl)-6-(2-(3-hydroxyazetidin-1-yl)pyrimidin-5-yl)-2-methyl-1H-indazol-3(2H)-one;
1-(5-(1-(2,5-dichlorobenzyl)-2-methyl-3-oxo-2,3-dihydro-1H-indazol-6-yl)pyrimidin-2-yl)piperidine-4-carboxylic acid:
6-(5-chloro-2-morpholinopyridin-4-yl)-1-(2-(difluoromethoxy)benzyl)-2-methyl-1H-indazol-3(2H)-one;
1-(2-(difluoromethoxy)benzyl)-2-methyl-6-(2-(oxetan-3-ylamino)pyrimidin-5-yl)-1H-indazol-3(2H)-one;
1-benzoyl-2-methyl-6-(2-morpholinopyrimidin-5-yl)-1H-indazol-3(2H)-one;
6-(5-chloro-2-morpholinopyridin-4-yl)-1-(3-fluorobenzyl)-2-methyl-1H-indazol-3(2H)-one;
1-(2-(difluoromethoxy)benzoyl)-2-methyl-6-(2-morpholinopyrimidin-5-yl)-1H-indazol-3(2H)-one;
1-(2-(difluoromethoxy)benzyl)-6-(2-((2-hydroxyethyl)amino)pyrimidin-5-yl)-2-methyl-1H-indazol-3(2H)-one;
2-(1-(5-(1-(2-(difluoromethoxy)benzyl)-2-methyl-3-oxo-2,3-dihydro-1H-indazol-6-yl)pyrimidin-2-yl)azetidin-3-yl) acetic acid;
1-(2-(difluoromethoxy)benzyl)-2-methyl-6-(1-(tetrahydro-2H-pyran-4-yl)-1H-pyrazol-4-yl)-1H-indazol-3(2H)-one;
1-(2-(difluoromethoxy)benzyl)-2-methyl-6-(2-morpholinopyridin-4-yl)-1H-indazol-3(2H)-one;
1-(3-fluorobenzyl)-2-methyl-6-(1-(tetrahydro-2H-pyran-4-yl)-1H-pyrazol-4-yl)-1H-indazol-3(2H)-one;
1-(3-fluorobenzyl)-2-methyl-6-(2-morpholinopyridin-4-yl)-1H-indazol-3(2H)-one;
1-(2-(difluoromethoxy)-6-fluorobenzyl)-2-methyl-6-(2-morpholinopyrimidin-5-yl)-1H-indazol-3(2H)-one;
1-(1-(2-(difluoromethoxy)phenyl)ethyl)-2-methyl-6-(2-morpholinopyrimidin-5-yl)-1H-indazol-3(2H)-one;
2-methyl-6-(2-morpholinopyrimidin-5-yl)-1-phenethyl-1H-indazol-3(2H)-one;
2-methyl-1-(2-methylbenzyl)-6-(2-morpholinopyrimidin-5-yl)-1H-indazol-3(2H)-one;
1-(2,6-dichlorobenzyl)-2-methyl-6-(2-morpholinopyrimidin-5-yl)-1H-indazol-3(2H)-one;
1-(3-(difluoromethoxy)benzyl)-2-methyl-6-(2-morpholinopyrimidin-5-yl)-1H-indazol-3(2H)-one;
1-(3-fluorobenzyl)-2-methyl-6-(2-morpholinopyrimidin-5-yl)-1H-indazol-3(2H)-one;

1-(2-fluorophenethyl)-2-methyl-6-(2-morpholinopyrimidin-5-yl)-1H-indazol-3(2H)-one;
1-(2-fluorobenzyl)-2-methyl-6-(2-morpholinopyrimidin-5-yl)-1H-indazol-3(2H)-one;
2-((2-methyl-6-(2-morpholinopyrimidin-5-yl)-3-oxo-2,3-dihydro-1H-indazol-1-yl)methyl)benzonitrile;
2-methyl-1-(3-methylbenzyl)-6-(2-morpholinopyrimidin-5-yl)-1H-indazol-3(2H)-one;
1-(4-fluorobenzyl)-2-methyl-6-(2-morpholinopyrimidin-5-yl)-1H-indazol-3(2H)-one;
1-benzyl-2-methyl-6-(2-morpholinopyrimidin-5-yl)-1H-indazol-3(2H)-one;
1-(2,6-dichlorobenzyl)-2-methyl-6-(2-(3-oxopiperazin-1-yl)pyrimidin-5-yl)-1H-indazol-3(2H)-one;
1-(5-(1-(2-(difluoromethoxy)benzyl)-2-methyl-3-oxo-2,3-dihydro-1H-indazol-6-yl)pyrimidin-2-yl)piperidine-4-carboxylic acid;
1-(2-(difluoromethoxy)benzyl)-6-(2-methoxypyrimidin-5-yl)-2-methyl-1H-indazol-3(2H)-one;
1-(2-(difluoromethoxy)benzyl)-2-methyl-6-(2-(3-oxopiperazin-1-yl)pyrimidin-5-yl)-1H-indazol-3(2H)-one;
1-(2-(difluoromethoxy)benzyl)-6-(2-morpholinopyrimidin-5-yl)-1H-indazol-3(2H)-one;
1-(2,5-dichlorobenzyl)-2-methyl-6-(2-(piperazin-1-yl)pyrimidin-5-yl)-1H-indazol-3(2H)-one;
1-(2,5-dichlorobenzyl)-2-methyl-6-(2-morpholinopyrimidin-5-yl)-1H-indazol-3(2H)-one;
1-(2-(difluoromethoxy)benzyl)-2-methyl-6-(2-morpholinopyrimidin-5-yl)-1H-indazol-3(2H)-one;
1-(2-(difluoromethoxy)benzyl)-2-methyl-6-(6-(3-oxopiperazin-1-yl)pyridin-3-yl)-1H-indazol-3(2H)-one;
1-(2-(difluoromethoxy)benzyl)-2-methyl-6-(6-(piperazin-1-yl)pyridin-3-yl)-1H-indazol-3(2H)-one;
1-(2-(difluoromethoxy)benzyl)-2-methyl-6-(6-morpholinopyridin-3-yl)-1H-indazol-3(2H)-one;
1-(2-(difluoromethoxy)benzyl)-6-(2-(2-hydroxypropan-2-yl)pyrimidin-5-yl)-2-methyl-1H-indazol-3(2H)-one;
1-(2-(difluoromethoxy)benzyl)-2-methyl-6-(2-(3-(oxetan-3-yl)azetidin-1-yl)pyrimidin-5-yl)-1H-indazol-3(2H)-one;
2-((5-(1-(2-(difluoromethoxy)benzyl)-2-methyl-3-oxo-2,3-dihydro-1H-indazol-6-yl)pyrimidin-2-yl)amino)propanamide;
1-(2-(difluoromethoxy)benzyl)-2-methyl-6-(5-morpholinopyrazin-2-yl)-1H-indazol-3(2H)-one;
1-((5-(1-(2-(difluoromethoxy)benzyl)-2-methyl-3-oxo-2,3-dihydro-1H-indazol-6-yl)pyrimidin-2-yl)methyl)azetidine-3-carboxylic acid;
1-(2-(difluoromethoxy)benzyl)-2-methyl-6-(2-(((5-oxopyrrolidin-3-yl)methyl)amino)pyrimidin-5-yl)-1H-indazol-3(2H)-one;
1-((3-chloropyridin-2-yl)methyl)-2-methyl-6-(2-morpholinopyrimidin-5-yl)-1H-indazol-3(2H)-one;
2-cyclopropyl-1-(2-(difluoromethoxy)benzyl)-6-(2-morpholinopyrimidin-5-yl)-1H-indazol-3(2H)-one;
1-(2,5-dichlorophenyl)-2-methyl-6-(2-morpholinopyrimidin-5-yl)-1H-indazol-3(2H)-one;
1-(2-(difluoromethoxy)-6-fluorobenzyl)-2-methyl-6-(2-morpholinopyrimidin-5-yl)-1H-indazol-3(2H)-one;
4-(5-(1-(2-(difluoromethoxy)benzyl)-2-methyl-3-oxo-2,3-dihydro-1H-indazol-6-yl)pyrimidin-2-yl)piperazine-1-carboxamide;
1-(1-(2-(difluoromethoxy)phenyl)ethyl)-6-(2-((R)-2-(methoxymethyl)pyrrolidin-1-yl)pyrimidin-5-yl)-2-methyl-1H-indazol-3(2H)-one;
6-(2-(4-acetylpiperazin-1-yl)pyrimidin-5-yl)-1-(2-(difluoromethoxy)benzyl)-2-methyl-1H-indazol-3(2H)-one;
1-(2-(difluoromethoxy)benzyl)-2-methyl-6-(2-((2-oxoazepan-3-yl)amino)pyrimidin-5-yl)-1H-indazol-3(2H)-one;
1-(3-(difluoromethoxy)benzyl)-2-methyl-6-(2-((tetrahydrofuran-3-yl)amino)pyrimidin-5-yl)-1H-indazol-3(2H)-one;
1-(2-(difluoromethoxy)benzyl)-2-methyl-6-(2-((tetrahydro-2H-pyran-3-yl)amino)pyrimidin-5-yl)-1H-indazol-3(2H)-one;
1-(2-(difluoromethoxy)benzyl)-6-(2-((3-methoxypropyl)amino)pyrimidin-5-yl)-2-methyl-1H-indazol-3(2H)-one;
1-(2,5-dichlorobenzyl)-2-methyl-6-(2-morpholinopyrimidin-5-yl)-1H-indazol-3(2H)-one;
1-(5-(1-(2-(difluoromethoxy)benzyl)-2-methyl-3-oxo-2,3-dihydro-1H-indazol-6-yl)pyrazin-2-yl)piperidine-4-carboxylic acid;
1-(2-(difluoromethoxy)benzyl)-2-methyl-6-(5-morpholino-1,2,4-thiadiazol-3-yl)-1H-indazol-3(2H)-one;
1-(2-(difluoromethoxy)benzyl)-2-methyl-6-(2-morpholinopyrimidin-5-yl)-1H-pyrazolo[4,3-b]pyridin-3(2H)-one;
1-(2-(difluoromethoxy)benzyl)-2-methyl-6-(2-((3-methyloxetan-3-yl)methyl)pyrimidin-5-yl)-1H-indazol-3(2H)-one;
1-(2-(difluoromethoxy)benzyl)-2-methyl-6-(3-morpholino-1,2,4-oxadiazol-5-yl)-1H-indazol-3(2H)-one;
1-(2-(difluoromethoxy)benzyl)-2-methyl-6-(2-morpholinopyrimidin-5-yl)-1H-pyrazolo[3,4-b]pyridin-3(2H)-one;
1-(2-(difluoromethoxy)benzyl)-6-(2-(2-hydroxypropan-2-yl)pyrimidin-5-yl)-2-methyl-1H-pyrazolo[3,4-b]pyridin-3(2H)-one;
1-(2-(difluoromethoxy)benzyl)-2-methyl-6-(2-morpholinopyrimidin-5-yl)-1H-pyrazolo[4,3-c]pyridin-3(2H)-one;
1-(2-(difluoromethoxy)benzyl)-2-methyl-6-(2-(6-oxohexahydropyrrolo[1,2-a]pyrazin-2(1H)-yl)pyrimidin-5-yl)-1H-indazol-3(2H)-one;
(R)-1-(2-(difluoromethoxy)benzyl)-2-methyl-6-(2-((tetrahydrofuran-3-yl)amino)pyrimidin-5-yl)-1H-indazol-3(2H)-one;
(R)-7-(5-(1-(2-(difluoromethoxy)benzyl)-2-methyl-3-oxo-2,3-dihydro-1H-indazol-6-yl)pyrimidin-2-yl)tetrahydro-1H-oxazolo[3,4-a]pyrazin-3(5H)-one;
(S)-7-(5-(1-(2-(difluoromethoxy)benzyl)-2-methyl-3-oxo-2,3-dihydro-1H-indazol-6-yl)pyrimidin-2-yl)tetrahydro-1H-oxazolo[3,4-a]pyrazin-3(5H)-one;
7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;
(R)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;
(S)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one;
1-(2-(difluoromethoxy)-5-methylbenzyl)-2-methyl-6-(2-morpholinopyrimidin-5-yl)-1H-indazol-3(2H)-one;
1-(2-(difluoromethoxy)-5-(hydroxymethyl)benzyl)-2-methyl-6-(2-morpholinopyrimidin-5-yl)-1H-indazol-3(2H)-one;
(R)-7-(5-(1-(2-(difluoromethoxy)-5-methylbenzyl)-2-methyl-3-oxo-2,3-dihydro-1H-indazol-6-yl)pyrimidin-2-yl)hexahydroimidazo[1,5-a]pyrazin-3(2H)-one;
(S)-7-(5-(1-(2-(difluoromethoxy)-5-methylbenzyl)-2-methyl-3-oxo-2,3-dihydro-1H-indazol-6-yl)pyrimidin-2-yl)hexahydroimidazo[1,5-a]pyrazin-3(2H)-one;
(S)-7-(5-(1-(2-(Difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one; or 7-(5-(1-(2-(difluoromethoxy)-5-(hydroxymethyl)benzyl)-2-methyl-3-oxo-2,3-dihydro-1H-indazol-6-yl)pyrimidin-2-yl)-5,6,7,8-tetrahydroimidazo[1,5-a]pyrazin-3(2H)-one.

As another example, compounds of the disclosure include compounds of Formula (I), wherein X, Y and Z are independently $CR^4$ or N;
provided that Y and Z are not both N;
L is a bond, optionally substituted $(C_1-C_3)$alkylene or —C(O)—;
$R^1$ is H, $CD_3$, CN, optionally substituted $(C_1-C_3)$alkyl, —$(CH_2)_n$-optionally substituted phenyl, —$(CH_2)_n$-optionally substituted heteroaryl or —$(CH_2)_n$-optionally substituted heterocyclyl;
$R^2$ is optionally substituted aryl, optionally substituted heteroaryl, optionally substituted heterocyclyl or optionally substituted cycloalkyl;
$R^3$ is —$R^{3a}$—$R^{3b}$, wherein:
  $R^{3a}$ is an optionally substituted saturated, unsaturated or partially saturated heterocyclyl or optionally substituted heteroaryl;
  $R^{3b}$ is —$N(R^a)(R^b)$, —$O(R^a)$, optionally substituted $(C_1-C_5)$alkyl, optionally substituted $(C_3-C_6)$cycloalkyl, or —$(CH_2)_p$-optionally substituted heterocyclyl; wherein $R^a$ and $R^b$ are independently selected from H, optionally substituted $(C_1-C_5)$alkyl, and —$(CH_2)_n$-optionally substituted heterocyclyl;
$R^4$ is independently H, Cl, CN, F, $CF_3$, optionally substituted $(C_1-C_3)$alkyl or optionally substituted $(C_1-C_3)$ alkoxy; and
n is 0 or 1;
p is 0, 1 or 2.

Certain compounds of Formula (I) which have acidic substituents may exist as salts with pharmaceutically acceptable bases. The present disclosure includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present disclosure includes each crystal form and mixtures thereof.

Certain compounds of Formula (I) and their salts may also exist in the form of solvates, for example hydrates, and the present disclosure includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present disclosure includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present disclosure includes each diastereoisomer of compounds of Formula (I) (and mixtures thereof.

Certain compounds of Formula (I) may exist in different tautomeric forms or as different geometric isomers, and the present disclosure includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present disclosure includes each conformational isomer of compounds of Formula (1) and mixtures thereof.

Certain compounds of Formula (I) may exist in zwitterionic form and the present disclosure includes each zwitterionic form of compounds of Formula (1) (and mixtures thereof.

Certain compounds of Formula (1) may further be in the form of a pro-drug. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this disclosure include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as 3-dimethylamino-ethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($(C_1-C_6)$alkanoyloxy)ethyl, 1-methyl-1-(($(C_1-C_6)$alkanoyloxy)ethyl, $(C_1-C_{12})$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylacyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

Compounds of Formula (1) also include compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Methods of Treatment

Many autoimmune diseases and disease associated with chronic inflammation, as well as acute responses, have been linked to excessive or unregulated production or activity of one or more cytokines.

The compounds of the disclosure are also useful in the treatment of rheumatoid arthritis, asthma, allergic asthma, osteoarthritis, juvenile arthritis, ankylosing spondylitis, hidradenitis supportive, ulcerative colitis. Crohn's disease, and inflammatory bowel disease.

Combination Therapies

Compounds of Formula (I) of the disclosure can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present disclosure. The additional agent also can be an agent that imparts a beneficial attribute to the therapeutic composition e.g., an agent that affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the compounds of the present disclosure and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDs which include drugs like ibuprofen. Other preferred combinations are corticosteroids including prednisolone; the well-known side-effects of steroid use can be reduced or even eliminated by tapering the steroid dose required when treating patients in combination with the compounds of this disclosure. Non-limiting examples of therapeutic agents for rheumatoid arthritis with which a compound of Formula (I) of the disclosure can be combined include the following: cytokine suppressive anti-inflammatory drug(s) (CSAIDs); antibodies to or antagonists of other human cytokines or growth factors, for example, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the disclosure can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade, preferred examples include IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the disclosure may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as IL-1 (e.g., NIK, IKK, JAK1, JAK2, JAK3, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g., sIL-1RI, sIL-1RII, sIL-6R), anti-inflammatory cytokines (e.g., IL-4, IL-10, IL-11, IL-13), celecoxib, folic acid, hydroxychloroquine sulfate, rofecoxib, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, tofacitinib. IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, and cyclosporine.

Non-limiting examples of therapeutic agents for inflammatory bowel disease with which a compound of Formula (I) of the disclosure can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide;

NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as IL-1 (e.g., NIK, IKK, p38 or MAP kinase inhibitors); IL-13 converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g., sIL-1RI, sIL-1RII, sIL-6R) and anti-inflammatory cytokines (e.g., IL-4, IL-10, IL-11, IL-13). Preferred examples of therapeutic agents for Crohn's disease with which a compound of Formula (I) can be combined include PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atropine sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenososine agonists, antithrombotic agents, complement inhibitors, adrenergic agents, agents which interfere with signaling by proinflammatory cytokines such as IL-1 (e.g., NIK, IKK, p38 or MAP kinase inhibitors), IL-10 converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., sIL-1RI, sIL-1RII, sIL-6R) and anti-inflammatory cytokines (e.g., IL-4. IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor). MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, and prednisone Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol. TgAAT, cilomilast and roflumilast.

Non-limiting examples of therapeutic agents for Idiopathic Pulmonary Fibrosis with which a compound of Formula (I) (can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone dipropionate augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emollient, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone dipropionate augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, and alefacept.

Non-limiting examples of therapeutic agents for restenosis with which a compound of Formula (I) can be combined include the following: sirolimus, paclitaxel, everolimus, tacrolimus, ABT-578, and acetaminophen.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) (can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), and lymphostat-B (anti-BlyS antibody).

Compositions and Routes of Administration

One or more compounds of this disclosure can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eye drop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present disclosure may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the disclosure may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the disclosure is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the disclosure may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present disclosure include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present disclosure, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the disclosure formulated in a compatible pharmaceutical carrier may also be prepared, placed in an appropriate container, and labeled for treatment of an indicated condition.

In some formulations it may be beneficial to use the compounds of the present disclosure in the form of particles of very small size, for example as obtained by fluid energy milling.

The use of compounds of the present disclosure in the manufacture of pharmaceutical compositions is illustrated by the following description. In this description the term "active compound" denotes any compound of the disclosure but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present disclosure the active compound may, if desired, be associated with other compatible pharmacologically active ingredients. For example, the compounds of this disclosure can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the disclosure can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the disclosure and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present disclosure.

The present disclosure also comprises the use of a compound of Formula (I) as a medicament.

A further aspect of the present disclosure provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present disclosure also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

EXAMPLES

| Abbreviations | |
|---|---|
| Ac | Acetyl |
| AcOH | Glacial acetic acid |
| aq. | Aqueous |
| Boc | t-Butoxycarbonyl |
| Bu | Butyl |
| d | Doublet |
| dba | Dibenzylideneacetone |
| dd | Doublet of doublets |
| DCM | Dichloromethane (methylene chloride) |
| DIEA | N,N-Diisopropylethylamine |
| DMAP | 4-Dimethylaminopyridine |
| DMF | N,N-Dimethylformamide |
| DMSO | Dimethyl sulfoxide |
| dppf | 1,1'-Bis(diphenylphosphino)ferrocene |
| EDTA | Ethylene diamine tetraacetic acid |
| Et | Ethyl |
| EtOAc | Ethyl acetate |
| EtOH | Ethanol |
| Et$_2$O | Diethyl ether |
| g | Gram(s) |
| h | Hour(s) |
| HEPES | N-2-Hydroxyethylpiperazine-N'-2-ethanesulfonic acid |
| HPLC | High-pressure liquid chromatography |
| IPA | Isopropyl alcohol |
| KOAc | Potassium acetate |
| LC/MS | Liquid chromatography/mass spectrometry |
| LiHMDS | Lithium bis(trimethylsilyl)amide |
| m | Multiplet |
| M | Molar |
| Me | Methyl |
| MeCN | Acetonitrile |
| MeI | Iodomethane |
| MeOH | Methyl alcohol |
| min | Minute(s) |
| MS | Mass spectrometry |
| MsCl | Methanesulfonyl chloride |
| n- | Normal (nonbranched) |
| mmol | Millimole |
| N | Normal |
| N$_2$ | Nitrogen |
| NaBH(OAc)$_3$ | Sodium triacetoxyborohydride |
| NBS | N-Bromosuccinimide |
| NH$_4$OAc | Ammonium acetate |
| NMP | 1-Methyl-2-pyrrolidinone |
| NMR | Nuclear magnetic resonance |
| Pd(OAc)$_2$ | Palladium(II) acetate |
| pH | −log[H$^+$] |
| Pd(dppf)Cl$_2$ | [1,1'-Bis(diphenylphosphino)ferrocene]dichloropalladium(II) |
| Pd$_2$(dba)$_3$ | Tris(dibenzylideneacetone)dipalladium(0) |
| Pd(PPh$_3$)$_4$ | Tetrakis(triphenylphosphine)palladium(0) |
| PPh$_3$ | Triphenylphosphine |
| PBr$_3$ | Phosphorus tribromide |
| ppm | Parts per million |
| R$_t$ | Retention time |
| rt | Room temperature |
| s | Singlet |
| sat. | Saturated |
| SEM | 2-(Trimethylsilyl)ethoxymethyl |
| SPE | Solid phase extraction |
| Soln | Solution |
| SM | Small molecule |
| t | Triplet |
| TBS | tert-Butyldimethylsilyl |
| TBDPS | tert-Butyldiphenylsilyl |
| TEA | Triethylamine |
| tert- | Tertiary |
| TNFα | Tumor necrosis factor alpha |
| TFA | Trifluoroacetic acid |
| THF | Tetrahydrofuran |
| THP | Tetrahydro-2H-pyran-2-yl |
| trt | Trityl |
| UV | Ultraviolet |
| q | Quartet |

TNFα FP Competitive Binding Assay

Solution Preparation

1. Assay Buffer: Prepare 1× Assay Buffer (Water with 47 mM HEPES, 47 mM NaCl, 0.9 mM EDTA, 0.0071% Triton X-100) by adding 25 mL of 1 M HEPES, 5 mL of 5 M NaCl, 1 mL of 0.5 M EDTA, and 375 µL of a 10% Triton X-100 stock to a fresh 500 mL bottle of water.

2. Assay Mixture: Prepare fresh Assay Mixture containing 20 nM TNFα trimer (60 nM protein) and 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide probe in 1× Assay Buffer.

Compound Plate Preparation

Manual 12-Point 1:3 Dilution Plates: (384 Well Polypropylene Plates)

Top concentration of compounds, 10 mM in DMSO, dispensed in rows A-O in columns 1 and 13. Compounds are serially diluted 1:3 with DMSO in columns 2-12 or 14-24 using a 16-channel Matrix pipettor. Plates stored at −20° C.

Discovery Preps 12-Point 1:3 Dilution Plates: (384 Well Assay Plates)

Top concentration, 5 mM in DMSO, of compounds placed in rows A-O in columns 1 and 13. Compounds are serially diluted 1:3 with DMSO in columns 2-12 or 14-24. Compound solutions are dispensed into replicate assay plates at 410 nL per well. Plates stored at 4° C.

TNFα FP Competitive Binding Assay Protocol

1. Compound plates warmed to rt.
2. Fresh Assay Mixture is prepared.
3. Assay Mixture (20 µL) is dispensed each well of 384 assay plates using a Thermo Multidrop Combi or 16-channel Matrix pipettor. If Manual 12-point 1:3 Dilution Plates are to be tested, Assay Mix is dispensed into empty plates. Discovery Preps 12-point 1:3 Dilution Plates already contain 410 nL compound solution in DMSO.
4. For Manual 12-point 1:3 Dilution Plates, 0.7 µL is manually transferred using a 16-channel Matrix pipettor to replicate assay plates containing 20 µL Assay Mixture for a final top compound concentration of 338 µM (3.4% DMSO).
5. For Discovery Preps 12-point 1:3 Dilution Plates, 20 µL Assay Mixture added the 410 nL compound solution already in the plates yields a final top compound concentration of 100 µM (2.0% DMSO).
6. Background subtraction controls are wells P1-P8 containing only Assay Buffer. The low % inhibition controls are wells P9-P16 containing only Assay Mix. The high % inhibition are wells P17-P24 containing only 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide probe in 1× Assay Buffer.
7. Plates are incubated at rt for 18-24 h in 37° C. incubator ($CO_2$ is off).
8. Prior to reading the assay, the plates are placed in a dark cabinet to equilibrate at rt for one hour.
9. Background-subtracted fluorescence polarization (mP) is measured using a PerkinElmer Envision plate reader.
10. Raw data is entered into Assay Explorer and dose-response curves are generated using a variable slope curve.

Supplies, Materials, and Reagents

| Item | Vendor | Catalog # |
|---|---|---|
| HEPES (1M) | Invitrogen | 15630-080 |
| EDTA (0.5M) | Invitrogen | 15575-038 |
| NaCl (5M) | Sigma | S5150 |
| Triton X-100 | Sigma | T8787 |
| Water | Invitrogen | 10977-015 |

| Item | Vendor | Catalog # |
|---|---|---|
| SM-antiTNFα OregonGreen488 probe | Abbvie | 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethyl)-3-oxo-3H-spiro[isobenzofuran-1,9'-xanthene]-5-carboxamide |
| Corning 3676 Compound Plate: 384 Well Low Volume Black Round Bottom Polystyrene NBS | Corning | 3676 |

For the purpose of the Tables and Examples below, the FP binding assay $IC_{50}$ of each compound is expressed as follows: A=a compound with $IC_{50}$ less than 1 µM, B=a compound with $IC_{50}$ within the range of 1 µM to 10 µM, and C=a compound with a TNFα $IC_{50}$ greater than 10 µM.

Preparation A: SM-antiTNFα OregonGreen488 Probe

Preparation of 2-(4-(isoquinolin-8-yl)phenyl)ethanol

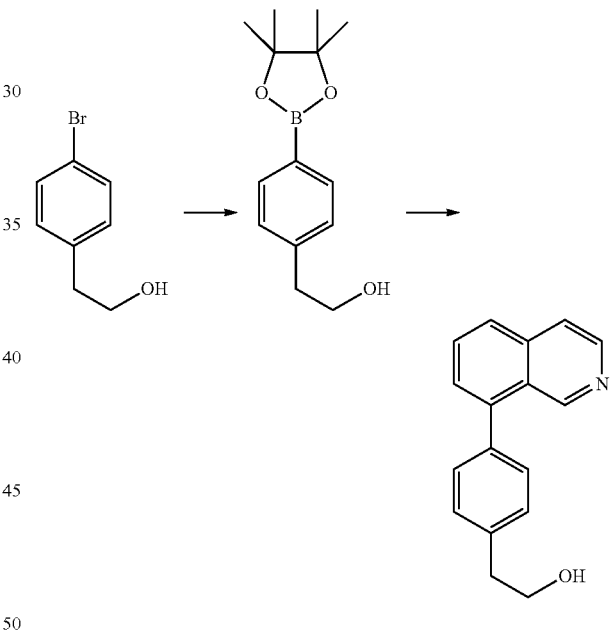

Step 1: 2-(4-(4,4,5,5-Tetramethyl-1,3,2-dioxaborolan-2-yl)phenyl)ethanol

KOAc (4.88 g, 49.7 mmol), 4,4,4',4',5,5,5',5'-octamethyl-2,2'-bi(1,3,2-dioxaborolane) (7.6 g, 30 mmol) and $PdCl_2$(dppf) (0.91 g, 1.2 mmol) were added to a solution of 2-(4-bromophenyl)ethanol (5.0 g, 25 mmol) in 1,4-dioxane (100 mL) under $N_2$. The mixture was purged with $N_2$ then stirred under $N_2$ at about 85° C. for about 12 h. After cooling to rt, water (100 mL) was added and the mixture was extracted with EtOAc (2×100 mL). The combined organic layers were washed with sat. aq.NaCl (100 mL) and dried over $Na_2SO_4$, filtered and concentrated under reduced pressure. The residue was purified by flash chromatography on silica gel (17% EtOAc/petroleum ether). The appropriate fractions were collected and concentrated under reduced pressure to afford the title product (6.2 g, 100%). $^1$H NMR (400 MHz, CDCl$_3$) δ 7.78 (d, J=7.9 Hz, 2H), 7.29-7.23(m, 2H), 3.87 (t, J=6.6 Hz, 2H), 2.90 (t, J=6.6 Hz, 2H), 1.36 (s, 12H).

Step 2: 2-(4-(Isoquinolin-yl)phenyl)ethanol

A vigorously stirred mixture of 2-(4-(4,4,5,5-tetramethyl-1,3,2-dioxaborolan-2-yl)phenyl)ethanol (2.0 g, 8.1 mmol), 8-bromoisoquinoline (1.7 g, 8.1 mmol), cesium carbonate (5.3 g, 16 mmol), and 1,4-dioxane (80 mL) was degassed with N$_2$. PdCl$_2$(dppf) (0.30 g, 0.40 mmol) was added. The mixture was purged with N$_2$ and then stirred at about 100° C. for about 2 h. After cooling to rt, the reaction mixture was partitioned between water (50 mL) and EtOAc (3×50 mL). The combined organic layers were dried over Na$_2$SO$_4$, filtered, and concentrated under reduced pressure. The residue was purified by flash chromatography on silica gel (0-5% MeOH/DCM). The appropriate fractions were collected and concentrated under reduced pressure to afford the title product (169 mg, 88%). MS m/z: 250 (M+H)$^+$.

Preparation B: Methyl 3-hydroxy-4-(isoquinolin-8-yl)benzoate

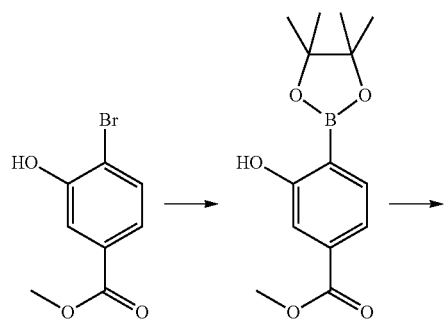

Step 1: Methyl 3-hydroxy-4-(4,4,5,5-tetramethyl-1,3,2-dioxaborolan-2-yl)benzoate KOAc (1.27 g, 13.0 mmol) was added to a solution of methyl 4-bromo-3-hydroxybenzoate (1.0 g, 4.3 mmol) in 1,4-dioxane (20 mL) under N$_2$ followed by addition of 4,4,4',4',5,5,5',5'-octamethyl-2,2'-bi(1,3,2-dioxaborolane) (2.2 g, 8.7 mmol) and PdCl$_2$(dppf) (0.18 g, 0.22 mmol). The mixture was purged with N$_2$ then stirred at about 80° C. for about 3 h. The reaction mixture was cooled to rt and water (50 mL) was added. The mixture was extracted with EtOAc (3×50 mL). The combined organics were dried over Na$_2$SO$_4$, filtered, and concentrated under reduced pressure. The residue was purified by flash chromatography on silica gel (0-10% MeOH/DCM). The appropriate fractions were combined and concentrated under reduced pressure to afford the title product (1.13 g, 94%). $^1$H NMR (400 MHz, CDCl$_3$) δ 7.81 (s, 1H), 7.60 (d, J=8.1 Hz, 1H), 7.50-7.40 (m, 2H), 3.84 (s, 3H), 1.31 (s, 12H).

Step 2: Methyl 3-hydroxy-4-(isoquinolin-8-yl)benzoate

EtOH (100 mL) was added to a mixture of sodium carbonate (2.04 g, 19.2 mmol), Pd(OAc)$_2$ (0.022 g, 0.096 mmol), 8-bromoisoquinoline (2.00 g, 9.61 mmol), methyl 3-hydroxy-4-(4,4,5,5-tetramethyl-1,3,2-dioxaborolan-2-yl)benzoate (2.67 g, 9.61 mmol), and dicyclohexyl(2',6'-dimethoxy-[1,1'-biphenyl]-2-yl)phosphine (0.079 g, 0.19 mmol) under N$_2$. The mixture was degassed with N$_2$ and then heated to about 80° C. for about 16 h. Water (200 mL) was added and the resulting solid was collected by filtration then dried to afford the title product (1.27 g, 47%). MS m/z: 280 (M+H)$^+$.

Preparation #C: 2',7'-Difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide

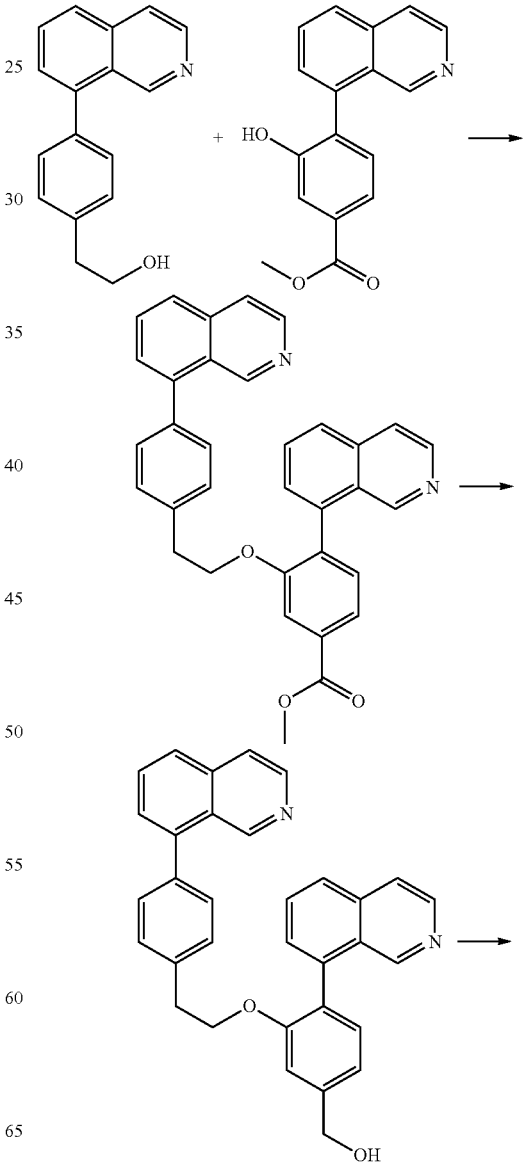

-continued

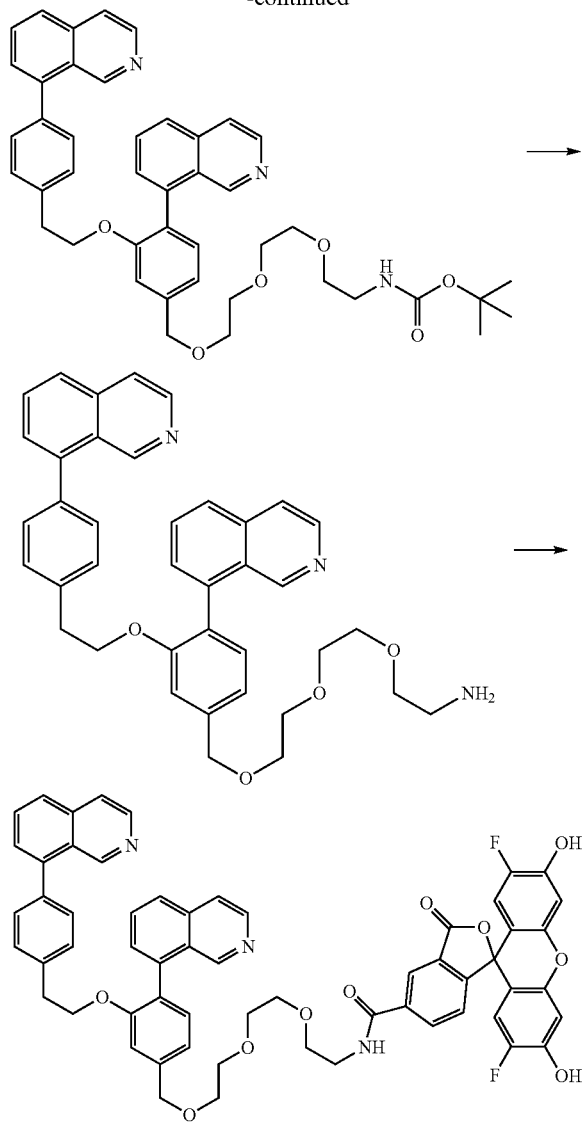

Step 1: Methyl 4-(isoquinolin-8-yl)-3-(4-(isoquinolin-8-yl)phenethoxy)benzoate Cyanomethylenetributylphosphorane (0.90 mL, 3.4 mmol) was added to a mixture of methyl 3-hydroxy-4-(isoquinolin-8-yl)benzoate (800 mg, 2.86 mmol), 2-(4-(isoquinolin-8-yl)phenyl)ethanol (714 mg, 2.86 mmol), and toluene (30 mL). After stirring for about 4 h at about 100° C., the reaction mixture was allowed to cool to rt. Tri-n-butylphosphine (0.71 mL, 2.9 mmol) and (E)-N1,N1,N2,N2-tetramethyldiazene-1,2-dicarboxamide (493 mg, 2.86 mmol) were added respectively. After stirring at rt for about 18 h, the organic volatiles were removed under reduced pressure. The residue was purified by flash chromatography on silica gel (20% acetone/hexanes). The appropriate fractions were collected and concentrated under reduced pressure to afford the title product (1.07 g, 73%). MS m/z: 511 (M+H)+.

Step 2: (4-(Isoquinolin-8-yl)-3-(4-(isoquinolin-8-yl)phenethoxy)phenyl)methanol Lithium aluminum hydride (1 M solution in THF, 0.4 mL, 0.4 mmol) was added to a solution of methyl 4-(isoquinolin-8-yl)phenethoxy)benzoate (204 mg, 0.400 mmol) and THF (3.6 mL) under $N_2$ at about 0° C. After about 1 h, 10% aqueous sodium potassium tartrate (6 mL) was added. The reaction was allowed to warm to rt. After about 10 min at rt, EtOAc (10 mL) was added. The layers were separated and the aqueous layer was extracted with EtOAc (10 mL). The combined organics were washed with sat. aq. NaCl (10 mL), dried over $MgSO_4$, filtered and concentrated under reduced pressure. The residue was purified by flash chromatography on silica gel (0-5% MeOH/$CHCl_3$). The appropriate fractions were collected and concentrated under reduced pressure to afford the title product (169 mg, 88%). MS m/z: 483 (M+H)+.

Step 3: 2-(2-(2-((4-(Isoquinolin-8-yl)-3-(4-(isoquinolin-8-yl)phenethoxy)benzyl)oxy)ethoxy)ethoxy)ethanamine (4-(Isoquinolin-8-yl)-3-(4-(isoquinolin-8-yl)phenethoxy)phenyl)methanol (31 mg, 0.064 mmol) and 2,2-dimethyl-4-oxo-3,8,11-trioxa-5-azatridecan-13-yl methanesulfonate (32 mg, 0.096 mmol) were combined in DMF (1 mL). Sodium hydride (10 mg, 0.26 mmol) was added in one portion. The reaction was stirred at rt for about 16 h, 50% MeCN/water (1 mL) was added and the resulting mixture was lyophilized to dryness. The residue was diluted with 90% DMSO/water (3 mL) and purified in one injection using RP-HPLC (Waters Deltapak C18 200×25 mm column) with time collection. The appropriate peak was collected and lyophilized. The residue was dissolved in TFA (2 mL) and shaken at rt for about 1 min. The volatiles were evaporated under a stream of dry nitrogen gas. The film was dissolved in 50% MeCN/water (1 mL) and lyophilized to afford a trifluoroacetate salt of the title compound (10 mg, 19%). MS m/z: 614 (M+H)+.

Step 4: 2',7'-difluoro-3',6'-dihydroxy-N-(2-(2-(2-(4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide 2-(2-(2-((4-(Isoquinolin-8-yl)-3-(4-(isoquinolin-8-yl)phenethoxy)benzyl)oxy)ethoxy)ethoxy)ethanamine (9.38 mg, 9.82 μmol) and 2,5-dioxopyrrolidin-1-yl 2',7'-difluoro-3',6'-dihydroxy-3-oxo-3H-spiro[isobenzofuran-1,9'-xanthene]-5-carboxylate (5 mg, 10 μmol) were combined in 1% DIEA/DMF (1 mL) and shaken at rt. After completion, the reaction was diluted with 90% DMSO/water (2 mL) and purified in one injection using RP-HPLC (Waters Deltapak C18 200×25 mm column) with slope collection. The appropriate peak was collected and lyophilized to afford the title product (4.1 mg, 41%). MS m/z: 1008 (M+H)+.

Analytical Methods

Analytical data was included within the procedures below or in the tables of examples. Unless otherwise stated, all $^1$H NMR data were collected on a Varian 400 MHz Mercury Plus, Inova, or 400-MR instrument and chemical shifts are quoted in parts per million (ppm). LC/MS and HPLC data are referenced to the table of LC/MS and HPLC conditions using the lower case method letter provided in Table A.

TABLE A

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| b | LC/MS: The gradient was 10% B for 0.1 min, 10-100% from 0.1 to 1.1 min, hold till 1.3 min, and then back to 10% till over 0.1 min (1.0 mL/min flow rate). Mobile phase A was 0.1% TFA in water, mobile phase B was HPLC grade MeCN. The column used for the chromatography was a 2.1 × 30 mm Waters BEH C8 (1.7 μm particles). Detection methods were diode array (DAD) and evaporative light scattering (ELSD) detection as well as positive/negative electrospray ionization |
| c | HPLC: The gradient was 10-100% B over 25 min (21 mL/min flow rate). Mobile phase A was 0.05N $NH_4OAc$ buffer (pH = 4.5), mobile phase B was HPLC grade MeCN. The column used for the chromatography is 250 × 21.1 mm Hypersil HS C18 (8 μm particles). Detection method is UV (245 nm) |
| d | HPLC: The gradient was 20-100% B over 25 min (21 mL/min flow rate). Mobile phase A was 0.05N $NH_4OAc$ buffer (pH = 4.5), mobile phase B was HPLC grade MeCN. The column used for the chromatography is 250 × 21.1 mm Hypersil HS C18 (8 μm particles). Detection method is UV (360 nm) |
| e | LC/MS: The gradient was 5-60% B in 1.50 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| f | HPLC: The gradient was 5-45% B in 9.5 min then 45-95% B to 10 min with a hold at 95% B for 2 min (25 mL/min flow rate). Mobile phase A was 0.1% formic acid in water, mobile phase B was HPLC grade MeCN. The column used for the chromatography is a 19 × 50 mm Waters Atlantis C18 column (5 μm particles). Detection methods are diode array (DAD) and positive/negative APCI ionization. |
| g | HPLC: The gradient was 10-100% B over 25 min (21 mL/min flow rate). Mobile phase A was 0.05N $NH_4OAc$ buffer (pH = 4.5), mobile phase B was HPLC grade MeCN. The column used for the chromatography is 250 × 21.1 mm Hypersil HS C18 (8 μm particles). Detection method is UV (280 nm). |
| h | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| i | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization.) |
| j | LC/MS: Halo-2 C8 monitoring method: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Halo-2 C8 column (2 μm particles). Detection methods are diode array (DAD) and evaporative light scattering (ELSD) detection as well as positive/negative electrospray ionization.) |
| k | LC/MS: The gradient was 25-95% B in 1.6 min then a hold at 95% B for 1.2 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| l | HPLC: The gradient was a hold at 5% B for 1.4 min, then 5-95% B over 8.5 min, then a hold at 95% B for 1.1 min (83 mL/min flow rate). Mobile phase A was 10 mM $NH_4OAc$ buffer (pH = 4.2), mobile phase B was HPLC grade MeCN. The column used for the chromatography is a 100 × 50 mm Atlantis Prep T3 OBD C18 column (5 μm particles). Detection method is UV (254 nm). |
| m | HPLC: Step gradient separation method wherein mobile phase B was MeCN, mobile phase A was 0.10% formic acid in water. Flow rate was 25 mL/min. Gradient was held at 15% B for 2.5 min, then ramp to 40% B in 28.5 min, then ramp to 95% B in 0.1 min and hold for 8.4 min. The column used for the chromatography was a Phenomenex: Kinetek EVO Prep (21.2 × 150 mm, 5 μm particles). |

TABLE B

Chiral HPLC methods

| Method | conditions |
|---|---|
| a | Step gradient separation method wherein mobile phase B was EtOH (200 proof), mobile phase A was HPLC grade heptane with 0.20% diethylamine. Flow rate was 20 mL/min. Gradient was held at 30% B for 12.4 min, then ramp to 60% B in 0.2 min, hold for 5.4 min. The column used for the chromatography was a YMC-SA column (20 × 250 mm, 5 μm particles). |
| b | Isocratic - 20% B for 36 min (20 mL/min flow rate). Mobile phase B was EtOH (200 proof), mobile phase A was HPLC grade heptane with 0.2% diethylamine added. The column used for the chromatography used a Daicel ADH column (20 × 250 mm, 5 μm particles). |
| c | Gradient separation method wherein mobile phase B was 50% EtOH (200 proof)/MeOH, mobile phase A was HPLC grade heptane with 0.2% diethylamine added. Flow rate was 20 mL/min. Gradient was 10-35% B in 0.5 min then 35-70% B over 24.5 min then hold at 70% for 10 min. The column used for the chromatography was a Daicel ID column (20 × 250 mm, 5 μm particles). |
| d | Step gradient separation method wherein mobile phase B was 80:20 HPLC grade isopropanol:MeCN, mobile phase A was HPLC grade heptane with 0.2% diethylamine added. Flow rate was 20 mL/min. Gradient was 60% B for 12 min then step to 80% B in 0.5 min and hold at 80% B for 5 min. The column used for the chromatography was a YMC-SA (20 × 250 mm, 5 μm particles). |
| e | Step gradient separation method wherein mobile phase B was HPLC grade isopropanol, mobile phase A was HPLC grade heptane with 0.2% diethylamine added. Flow rate was 20 mL/min. Gradient was 20% B for 2 min then 20-70% B in 1 min, hold at 70% B for 10 min then step to 80% B for 4 min. The column used for the chromatography was a YMC-SB (20 × 250 mm, 5 μm particles). |
| f | Step gradient separation method wherein mobile phase B was IPA, mobile phase A was HPLC grade heptane with 0.10% DEA. Flow rate was 4 mL/min. Gradient was held at 10% B for 1.0 min, then ramp to 55% B in 6.0 min, hold for 1.0 min. The column used for the chromatography was a YMC-SB column (4.6 × 250 mm, 5 μm particles). |

TABLE C

SFC methods

| Method | Conditions |
|---|---|
| a | 30% ethanol in $CO_2$ (60 mL/min, 130 bar, 35° C.). Cycle time was 4.8 min, with single run time of 10 min. 200 proof ethanol was used with SFC grade $CO_2$. The chromatography used a YMC-SA, 21 × 250 mm column (5 μm particles). |
| b | A gradient of (10% ethanol for 0.7 min, then 10-55% ethanol over 5.3 min then hold at 55% ethanol for 1.5 min) in $CO_2$ (3.5 mL/min, 110 bar, 340° C.). Run time was 9 min. 200 proof ethanol was used with SFC grade $CO_2$. The chromatography used a YMC-SB, 4.6 × 100 mm column (3 μm particles). |
| c | 30% methanol in $CO_2$ (56 mL/min, 226 bar, 39° C.). Cycle time was 4.1 min, with single run time of 10 min. HPLC grade methanol was used with SFC grade $CO_2$. The chromatography used a YMC Amylose-C, 30 × 250 mm column (5 μm particles). |
| d | 25% (80:20) isopropanol:MeCN (0.2% diethylamine modifier) in $CO_2$ (45 mL/min, 140 bar, 35° C.). Cycle time was 10.5 min, with single run time of 22 min. HPLC grade isopropanol and MeCN were used with SFC grade $CO_2$. The chromatography used a YMC-SA, 20 × 250 mm column (5 μm particles). |
| e | 27% 80:20 isopropanol:MeCN (0.2% diethylamine modifier) in $CO_2$ (65 mL/min, 140 bar, 35° C.). Cycle time was 6 min, with single run time of 12 min. HPLC grade isopropanol and MeCN were used with SFC grade $CO_2$. The chromatography used a YMC-SA, 20 × 250 mm column (5 μm particles). |
| f | Gradient 15-28% methanol in $CO_2$ (55 mL/min, 140 bar, 35° C.). Cycle time and run times were 16.9 min. HPLC grade methanol was used with SFC grade $CO_2$. The chromatography used a YMC-SA, 20 × 250 mm column (5 μm particles). |

Compound Syntheses

Starting materials are commercially available, may be prepared by the procedures described herein, by literature procedures, or by procedures that would be well known to one skilled in the art of organic chemistry. Reagent/reactant names given are as named on the commercial bottle or as generated by IUPAC conventions, CambridgeSoft® ChemDraw Ultra 12.0, CambridgeSoft® ChemDraw Professional 15.0, CambridgeSoft® Chemistry E-Notebook 11, or AutoNom 2000. None of the specific conditions and reagents noted herein are to be construed as limiting the scope of the disclosure and are provided for illustrative purposes only. Compounds designated as salts (e.g., hydrochloride, trifluoroacetate) may contain more than one molar equivalent of the salt or may contain the acid as an excipient. Compounds of the disclosure where the absolute stereochemistry has been determined by the use of a commercially available enantiomerically pure starting material or a stereochemically defined intermediate or by X-ray diffraction are denoted by an asterisk after the example number. Otherwise the absolute stereochemistry is unknown and assigned randomly as drawn.

Compounds of the disclosure may be prepared using synthetic transformations shown herein. For groups of compounds that have been prepared in a similar fashion, a representative example is given followed by a table of these similarly prepared compounds. It should be appreciated by one skilled in the art that minor modifications to the representative example may be necessary to successfully execute these syntheses. Prepared compounds may be purified by any technique or combination of techniques known to one skilled in the art. Some examples that are not limiting include column chromatography with a solid phase (i.e. silica gel, alumina, etc.) and a solvent (or combination of solvents) that elutes the desired compounds (i.e. hexanes, heptane, EtOAc, DCM, MeOH, EtOH, MeCN, water, etc.); preparatory TLC with a solid phase (i.e. silica gel, alumina etc.) and a solvent (or combination of solvents) that elutes the desired compounds (i.e. hexanes, heptane, EtOAc, DCM, MeOH, EtOH, MeCN, water, etc.); reverse phase HPLC (see Table 1 for some non-limiting conditions); recrystallization from an appropriate solvent (i.e. MeOH, EtOH, IPA, EtOAc, toluene, etc.) or combination of solvents (i.e. EtOAc/heptane, EtOAc/MeOH, etc.); chiral LC with a solid phase and an appropriate solvent (i.e. EtOH/heptane, MeOH/heptane, IPA/heptane, etc. with or without a modifier such as diethylamine, TFA, etc.) to elute the desired compound; chiral SFC with a solid phase and $CO_2$ with an appropriate modifier (i.e. MeOH, EtOH, IPA with or without additional modifier such as diethylamine, TFA, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, IPA, n-PrOH, etc.); extractions by dissolving a compound in a liquid and washing with an appropriately immiscible liquid (i.e. DCM/water, EtOAc/water, DCM/sat. aq. $NaHCO_3$, EtOAc/sat. aq. $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. *J. Org. Chem.* 1978, 43, 2923: Yan. B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, $4^{th}$ Edition", 1993; Skoog, D. A. and Leary, J. J. "Principles of Instrumental Analysis, $4^{th}$ Edition" 1992; Subramanian, G. "Chiral Separation Techniques $3^{rd}$ Edition" 2007; Kazakevich, Y. and Lobrutto, R. "HPLC for Pharmaceutical Scientists" 2007.

PREPARATIONS

Preparation #1:
6-Bromo-2-methyl-1H-indazol-3(2H)-one

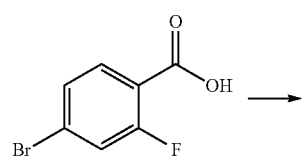

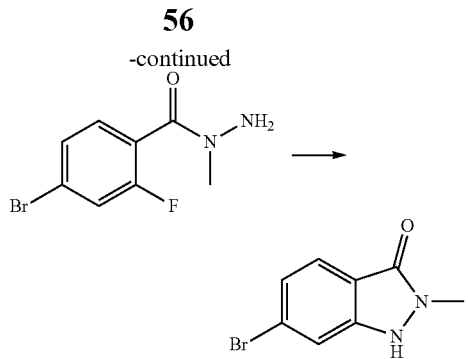

Step 1: 4-Bromo-2-fluoro-N-methylbenzohydrazide

A flask was charged with 4-bromo-2-fluorobenzoic acid (5.00 g, 22.8 mmol) and DCM (125 mL). The suspension was treated with DIEA (4.20 mL, 24.1 mmol) and stirred for about 10 min. The reaction mixture was cooled to about −45° C., MsCl (1.88 mL, 24.1 mmol) was added and the mixture was allowed to warm to rt. After about 10 min, the mixture was added to a solution of methylhydrazine (3.16 g, 68.5 mmol) in DCM (100 mL) at about −40° C. After the addition was complete, the mixture was warmed to rt, concentrated and then partitioned between water (100 mL) and EtOAc (100 mL). The aqueous layer was extracted with EtOAc (50 mL) and the combined organics were washed with water (50 mL) and sat. aq. NaCl (30 mL), dried over $MgSO_4$, filtered and evaporated under reduced pressure to yield the title product (4.66 g, 83%); LC/MS (Table A, Method e) $R_t$=1.56 min; MS m/z: 247, 249 (M+H)$^+$.

Step 2: 6-Bromo-2-methyl-1H-indazol-3(2H)-one

4-Bromo-2-fluoro-N-methylbenzohydrazide (4.50 g, 18.2 mmol) in DMF (90 mL) was treated with potassium 2-methylpropan-2-olate (4.29 g, 38.2 mmol) and stirred for about 5 min at rt then heated to about 85° C. for about 1 h. The reaction mixture was then cooled, concentrated under reduced pressure and then dissolved in water (30 mL). The pH was adjusted to about 4 with AcOH and the mixture was diluted with EtOAc (50 mL) then filtered. The precipitate was washed with EtOAc (10 mL) to give the first crop of the desired product. The layers were separated and the aqueous layer was further extracted with EtOAc (3×50 mL). The combined organics were washed with sat. aq. NaCl (25 mL), dried over $MgSO_4$, filtered and concentrated under reduced pressure. EtOAc (20 mL) was added and the mixture was stirred at rt for about 16 h. The precipitate was collected via filtration rinsing with EtOAc (5 mL) and then combined with the first crop to give the title product (1.77 g, 43%); LC/MS (Table A, Method e) $R_t$=1.43 min; MS m/z: 227 and 229 (M+H)$^+$.

Preparation #2: 2-Methyl-6-(2-morpholinopyrimidin-5-yl)-1H-indazol-3(2H)-one

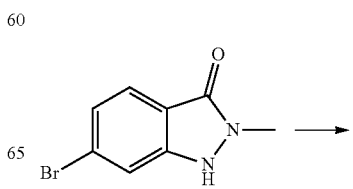

-continued

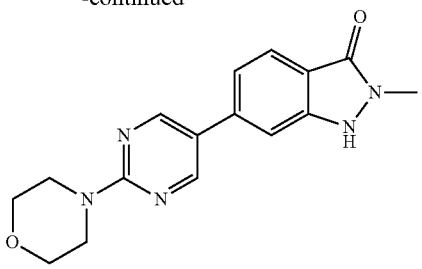

Pd(PPh₃)₄ (0.6 g, 0.5 mmol) was added to a suspension of 6-bromo-2-methyl-1H-indazol-3(2H)-one (1.67 g, 7.35 mmol) (Preparation #1), 4-(5-(4,4,5,5-tetramethyl-1,3,2-dioxaborolan-2-yl)pyrimidin-2-yl)morpholine (2.57 g, 8.83 mmol) and Cs₂CO₃ (5.99 g, 18.4 mmol) in 1,4-dioxane (20 mL) and water (5.0 mL) under N₂. The mixture purged with N₂ and then heated to about 90° C. for about 2 h. The reaction mixture was allowed to cool to it. DCM (30 mL) with a few drops of MeOH and water (20 mL) were added. The solid was collected by filtration then dried to give the title product (1.88 g, 82%); LC/MS (Table A, Method e) R$_t$=1.41 min; MS m/z: 312 (M+H)⁺

Preparation #3:
1-(1-Bromoethyl)-2-(difluoromethoxy)benzene

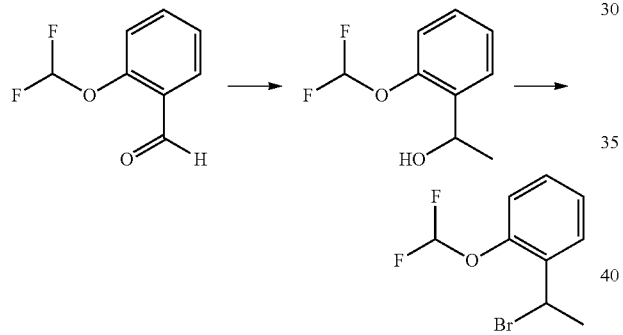

Step 1: 1-(2-(Difluoromethoxy)phenyl)ethanol

A solution of 2-(difluoromethoxy)benzaldehyde (0.39 mL, 2.9 mmol) in THF (15 mL) was cooled to about −10° C. Methylmagnesium bromide (3 M in ether, 1.5 mL, 4.5 mmol) was added dropwise over about 10 min. The resulting solution was left in the cooling bath which was allowed to warm to rt and then the reaction was left to stir for about 16 h. The reaction mixture was cooled to about 0° C. and then quenched by careful addition of sat. aq. NH₄Cl (10 mL). After separating the layers, the aqueous phase was extracted with EtOAc (3×10 mL). The combined organic phases were washed with sat. aq. NaCl (25 mL), dried over Na₂SO₄, filtered, and concentrated under reduced pressure to give the title product (0.54 g, 99%); ¹H NMR (400 MHz, CDCl₃) δ 7.56 (dd, J=7.3, 2.1 Hz, 1H), 7.33-7.20 (m, 2H), 7.10-7.05 (m, 1H), 6.55 (t, J=74.2 Hz, 1H), 5.24 (q. J=6.5 Hz, 1H), 1.50 (d, J=6.4 Hz, 3H).

Step 2: 6-Bromo-2-methyl-1H-indazol-3(2H)-one

PBr₃ (1 M in DCM, 2.9 mL, 2.9 mmol) was added to a solution of 1-(2-(difluoromethoxy)phenyl)ethanol (0.50 g, 2.7 mmol) and DCM (13.3 mL) at about −10° C. under N₂. The reaction was allowed to warm to rt over about 1 h by thawing of the bath and then stirred at rt for about 16 h. The reaction mixture was quenched at rt by careful addition of sat. aq. NaHCO₃ (2 mL) and partitioned between DCM (10 mL) and water (5 mL). After separating the layers, the organic phase was washed with sat. aq. NaCl (10 mL), dried over Na₂SO₄, filtered, and concentrated under reduced pressure to give the title product (0.55 g, 82%); ¹H NMR (400 MHz, CDCl₃) δ 7.69-7.57 (m, 1H), 7.38-7.19 (m, 2H), 7.16-7.07 (m, 1H), 6.55 (dd, J=76.0, 72.0 Hz, 1H), 5.59 (q, J=7.0 Hz, 1H), 2.03(d, J=7.3 Hz, 3H).

Preparation #4: 6-(2-Chloropyrimidin-5-yl)-1-(2-(difluoromethoxy)benzyl)-2-methyl-1H-indazol-3(2H)-one

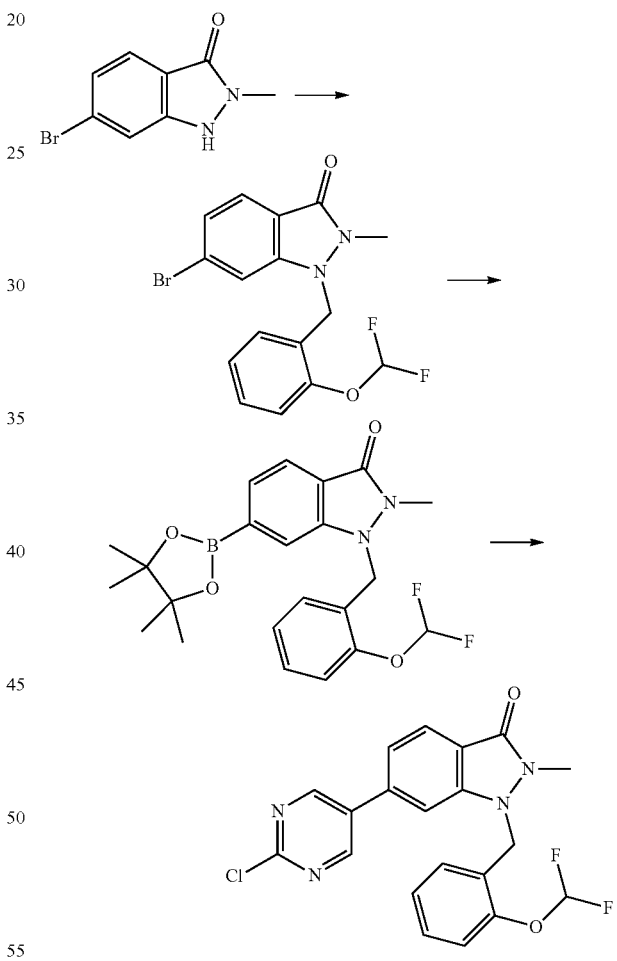

Step 1: 6-Bromo-1-(2-(difluoromethoxy)benzyl)-2-methyl-1H-indazol-3(2H)-one

6-Bromo-2-methyl-1H-indazol-3(2H)-one (1.25 g, 5.51 mmol) (Preparation #1) in DMF (25 mL) with potassium carbonate (0.89 g, 6.4 mmol) was treated with 1-(bromomethyl)-2-(difluoromethoxy)benzene (1.38 g, 5.83 mmol). After about 90 min, 1-(bromomethyl)-2-(difluoromethoxy)benzene (0.090 g, 0.38 mmol) was added. After about 15 min, the organic volatiles were removed under reduced pressure. Water (15 mL) and ether (10 mL) were added. After stirring for about 15 min, the solid was collected by filtration and then dried under reduced pressure at about 65° C. to give the title product (1.66 g, 79%); (Table A, Method e) $R_t$=2.20 min; MS m/z: 383 and 385 (M+H)$^+$ Step 2: 1-(2-(Difluoromethoxy)benzyl)-2-methyl-6-(4,4,5,5-tetramethyl-1,3,2-dioxaborolan-2-yl)-1H-indazol-3(2H)-one A flask was charged with 6-bromo-1-(2-(difluoromethoxy)benzyl)-2-methyl-1H-indazol-3(2H)-one (1.66 g, 4.33 mmol) and DMF (20 mL). Nitrogen was bubbled through the solution for about 15 min then the flask was charged with KOAc (1.49 g, 15.2 mmol), 4,4,4',4',5,5,5',5'-octamethyl-2,2'-bi(1,3,2-dioxaborolane) (1.54 g, 6.06 mmol) and PdCl$_2$(dppf) (0.19 g, 0.26 mmol). The reaction mixture was heated to about 90° C. for about 1 h then cooled, concentrated under reduced pressure, triturated with DCM (30 mL) and filtered rinsing with DCM (10 mL). The filtrate was concentrated under reduced pressure and the residue was purified via flash chromatography on silica gel (0-50% EtOAc/DCM). The appropriate fractions were collected and concentrated under reduced pressure to yield the title product (1.64 g, 68%); (Table A, Method e) $R_t$=2.41 min; MS m/z: 431 (M+H)$^+$.

Step 3: 6-(2-Chloropyrimidin-5-yl)-1-(2-(difluoromethoxy)benzyl)-2-methyl-1H-indazol-3(2H)-one The reaction was performed using 1-(2-(difluoromethoxy)benzyl)-2-methyl-6-(4,4,5,5-tetramethyl-1,3,2-dioxaborolan-2-yl)-1H-indazol-3(2H)-one and 5-bromo-2-chloropyrimidine in a similar fashion to Preparation #2 to give the title product (62%); (Table A, Method e) $R_t$=2.08 min; MS m/z: 417 (M+H)$^+$.

Preparation #5: 6-Bromo-1-(2,6-dichlorobenzyl)-2-methylethyl-H-indazol-3(2H)-one

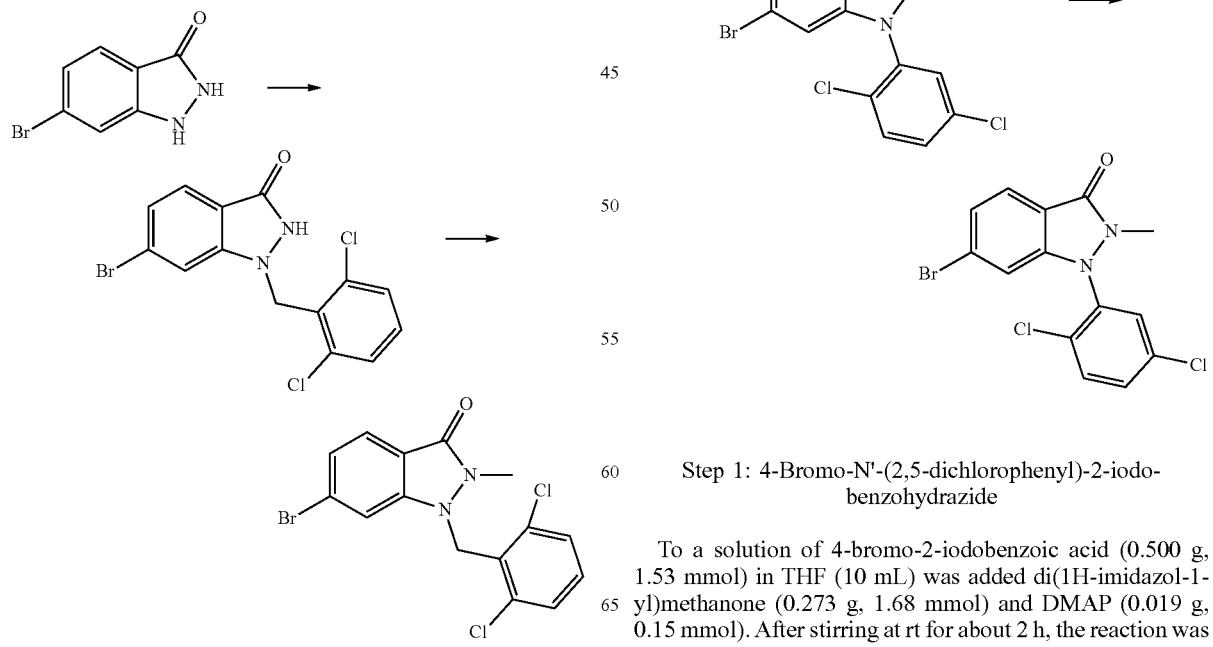

Step 1: 6-Bromo-1-(2,6-dichlorobenzyl)-1H-indazol-3(2H)-one

The reaction was performed using 6-bromo-1H-indazol-3(2H)-one and 2-(bromomethyl)-1,3-dichlorobenzene in a similar fashion to Example #1 to give the title product (69%); (Table A, Method e) $R_t$=2.47 min; MS m/z: 371 and 373(M+H)$^+$.

Step 2: 6-Bromo-1-(2,6-dichlorobenzyl)-2-methyl-1H-indazol-3(2H)-one

The reaction was performed using 6-bromo-1-(2,6-dichlorobenzyl)-1H-indazol-3(2H)-one and MeI in a similar fashion to Example #14, step 3 to give the title product (34%); (Table A, Method e) $R_t$=2.41 min; MS m/z: 385 and 387 (M+H)$^+$.

Preparation #6: 6-Bromo-1-(2,5-dichlorophenyl)-2-methyl-1H-indazol-3(2H)-one

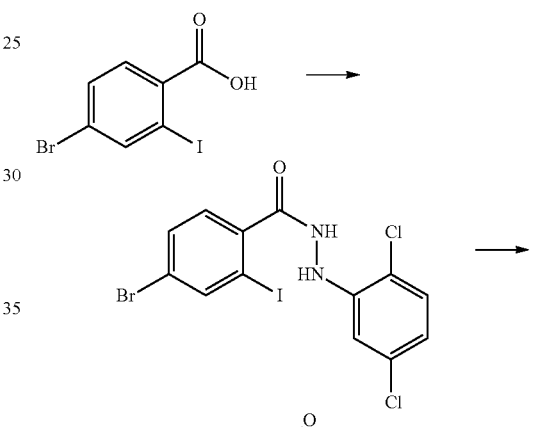

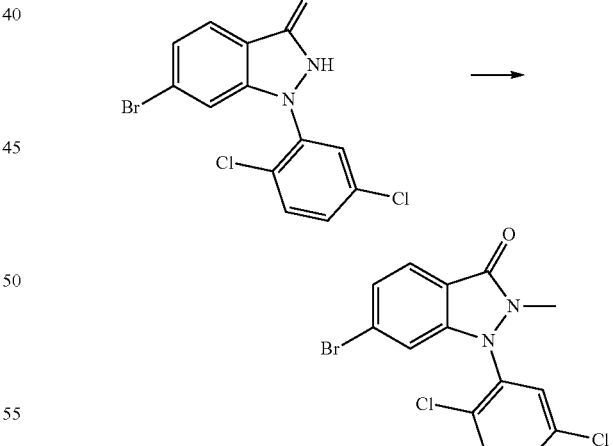

Step 1: 4-Bromo-N'-(2,5-dichlorophenyl)-2-iodobenzohydrazide

To a solution of 4-bromo-2-iodobenzoic acid (0.500 g, 1.53 mmol) in THF (10 mL) was added di(1H-imidazol-1-yl)methanone (0.273 g, 1.68 mmol) and DMAP (0.019 g, 0.15 mmol). After stirring at rt for about 2 h, the reaction was added dropwise to a solution of (2,5-dichlorophenyl)hydrazine (0.298 g, 1.68 mmol) in THF (10 mL). After about 1 h, the reaction was partitioned between DCM (30 mL) and sat. aq. NaHCO$_3$(30 mL). The organic layer was washed with sat. aq. NaCl (30 mL), dried over Na$_2$SO$_4$, filtered and concentrated under reduced pressure. The residue was triturated in DCM (20 mL), filtered and washed with DCM (10 mL) to give the title product (0.51 g, 69%); LC/MS (Table A, Method e) R$_t$=2.57 min; MS m/z: 483 and 485 (M−H)$^-$.

Step 2: 6-Bromo-1-(2,5-dichlorophenyl)-1H-indazol-3(2H)-one

A degassed solution of 4-bromo-N'-(2,5-dichlorophenyl)-2-iodobenzohydrazide (0.500 g, 1.03 mmol), L-proline (0.024 g, 0.21 mmol), K$_2$CO$_3$(0.284 g, 2.06 mmol) and CuI (0.020 g, 0.10 mmol) in DMSO (10 mL) was stirred under N$_2$ at rt for about 1 h. The reaction was partitioned between EtOAc (50 mL) and sat. aq. NaHCO$_3$(50 mL). The organic layer was washed with sat. aq. NaCl (50 mL), dried over Na$_2$SO$_4$, filtered, concentrated under reduced pressure. The residue was purified by flash chromatography on silica gel (0-20% EtOAc/heptane) to afford the title product (0.24 g, 64%); LC/MS (Table A, Method e) R$_t$=2.56 min; MS m/z: 357 and 359 (M+H)$^+$.

Step 3: 6-Bromo-1-(2,5-dichlorophenyl)-2-methyl-1H-indazol-3(2H)-one

6-Bromo-1-(2,5-dichlorophenyl)-1H-indazol-3(2H)-one was alkylated with MeI in a similar fashion to Example #14, step 3 to give the title product (35%); LC/MS (Table A, Method e) R$_t$=2.44 min; MS m/z: 371 and 373(M+H)$^+$.

Preparation #7:
1-(5-bromopyrazin-2-yl)piperidine-4-carboxylic acid

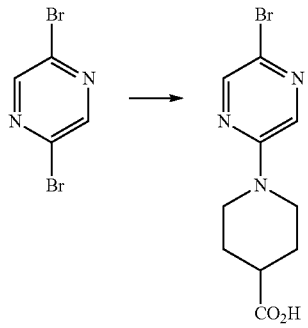 [SMILES: Brc1cnc(Br)cn1 ; O=C(O)C1CCN(c2cnc(Br)cn2)CC1]

A suspension of piperidine-4-carboxylic acid (0.500 g, 3.87 mmol) in THF (10 mL) was added to a suspension of sodium hydride (60 wt % in mineral oil, 0.325 g, 8.13 mmol) in THF (5 mL) at about 0° C. After about 15 min, a solution of 2,5-dibromopyrazine (0.921 g, 3.87 mmol) and THF (5 mL) was added. The mixture was warmed to about 60° C. After about 3 h, the reaction was allowed to cool to rt. Sat. aq. NH$_4$Cl (50 mL) was added. The mixture was adjusted to ~pH 2 with 1 N aqueous HCl and then extracted with EtOAc (100 mL). The organics were dried over MgSO$_4$, filtered, and concentrated under reduced pressure. The residue was purified by flash chromatography on silica gel (0-80% EtOAc/DCM) to give the title product (0.130 g, 12%); LC/MS (Table A, Method e) R$_t$=1.75 min; MS m/z: 286 and 288 (M+H)$^+$.

Preparation #8: 4-(5-(4,4,5,5-Tetramethyl-1,3,2-dioxaborolan-2-yl)pyridin-2-yl)piperazin-2-one

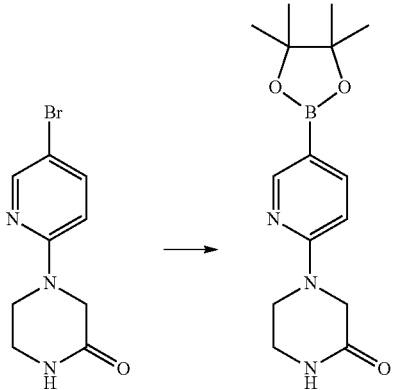 [SMILES: O=C1CN(c2ccc(Br)cn2)CCN1 ; CC1(C)OB(c2ccc(N3CCNC(=O)C3)nc2)OC1(C)C]

4-(5-Bromopyridin-2-yl)piperazin-2-one (1.00 g, 3.90 mmol), 4,4,4',4',5,5,5',5'-octamethyl-2,2'-bi(1,3,2-dioxaborolane) (2.97 g, 11.7 mmol), and KOAc (1.15 g, 11.7 mmol) were added to 1,4-dioxane (10 mL) and the mixture was purged with N$_2$. 2-(Dicyclohexylphosphino)-2',4',6'-triisopropylbiphenyl (0.074 g, 0.16 mmol) and Pd$_2$(dba)$_3$ (0.286 g, 0.312 mmol) were added. The mixture and was purged with N$_2$ and then heated to about 100° C. After about 2 h, the mixture was allowed to cool to rt. EtOAc (10 mL) and MeOH (1 mL) were added and the mixture was filtered through a pad of Celite®, rinsing with EtOAc. The organic volatiles were partially removed under reduced pressure. The solid was collected by filtration, slurried in MeOH (~5 mL) and then sonicated. The solid was collected by filtration to give the title product (0.570 g, 48%); LC/MS (Table A, Method e) R$_t$=1.75 min; MS m/z: 304 (M+H)$^+$.

Preparation #9:
(2-(Difluoromethoxy)-6-fluorophenyl)methanol

Sodium borohydride (0.149 g, 3.94 mmol) was added to a solution of 2-(difluoromethoxy)-6-fluorobenzaldehyde (0.250 g, 1.32 mmol) and MeOH (6.6 mL) at about −10° C. After about 1 h, water (5 mL) was added and the volatiles were removed under reduced pressure. The residue was partitioned between EtOAc (10 mL) and sat. aq. NaHCO$_3$ (10 mL). The organic phase was washed with sat. aq. NaCl (10 mL), dried over Na$_2$SO$_4$, filtered, and concentrated under reduced pressure to give the title product (0.219 g, 87%); $^1$H NMR (400 MHz, CDCl$_3$) δ 7.35-7.24 (m, 1H), 7.05-6.93(m, 2H), 6.59 (t, J=73.3 Hz, 1H), 4.79 (d, J=1.5 Hz, 2H).

Preparation #10: (2-(Difluoromethoxy)-5-fluorophenyl)methanol

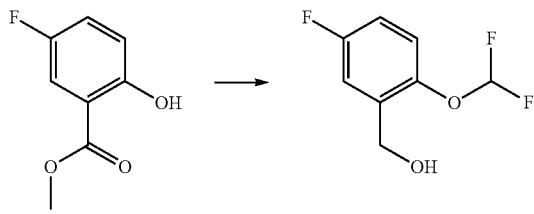

Sodium chlorodifluoroacetate (1.80 g, 11.8 mmol) was added in one portion to a mixture of methyl 5-fluoro-2-hydroxybenzoate (1.00 g, 5.88 mmol), $K_2CO_3$ (3.25 g, 23.5 mmol), and DMF (10.0 mL) under $N_2$. The mixture was warmed to about 80° C. After about 5 h, water (1.0 mL) was added. The mixture was warmed to about 100° C. After about 15 h, the mixture was allowed to cool rt. 2 M aqueous HCl (20 mL) was added portionwise over about 30 min to adjust the reaction mixture to about pH 1. The reaction mixture was extracted with $Et_2O$ (2×25 mL). The combined organics were washed with sat. aq. NaCl (20 mL), dried over $Na_2SO_4$, filtered, and concentrated under reduced pressure. The residue was dissolved in $Et_2O$ (20 mL) under $N_2$ and then $LiAlH_4$ (0.168 g, 4.42 mmol) was added in one portion. After about 1 h, THF (10 mL) was added. After about 16 h, the mixture was cooled to about 0° C. Sodium sulfate decahydrate was slowly added. The cold bath was removed and the mixture was left to vigorously stir for about 43 h. The mixture was filtered rinsing with $Et_2O$ (50 mL). The organics were washed with 2 M aqueous NaOH (2×20 mL) and sat. aq. NaCl (10 mL). The aqueous layers were extracted with $Et_2O$ (20 mL). The combined organics were dried over $Na_2SO_4$, filtered and concentrated under reduced pressure. The residue was purified via flash chromatography on silica gel (0-20% EtOAc/heptane). The appropriate fractions were collected and concentrated under reduced pressure to give the title product (0.178 g, 16%); $^1$H NMR (400 MHz, CDCl$_3$) δ 7.23(dd, J=8.8, 3.1 Hz, 1H), 7.14-7.07 (m, 1H), 7.02-6.94 (m, 1H), 6.49 (t, J=73.8 Hz, 1H), 4.74 (s, 2H).

Preparation #11: (2-(Difluoromethoxy)-5-methylphenyl)methanol

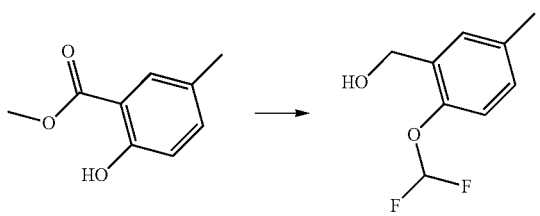

Potassium carbonate (8.38 g, 60.7 mmol) was added to a solution of methyl 2-hydroxy-5-methylbenzoate (2.52 g, 15.2 mmol) and DMF (30.0 mL) under $N_2$. Sodium chlorodifluoroacetate (4.62 g, 30.3 mmol) was added. The mixture was warmed to about 80° C. After about 2.5 h, water (3.00 mL) was added and the mixture was warmed to about 100° C. After about 14 h, the mixture was cooled to rt and was then slowly acidified to about pH 1 using 2 N aqueous HCl (50 mL). $Et_2O$ (100 mL) was added. The layers were separated and the organics were dried over $Na_2SO_4$, filtered and concentrated under reduced pressure. The residue was dissolved in $Et_2O$ (50 mL) then washed with water (2×25 mL). The organic layer was dried over $Na_2SO_4$, filtered and concentrated under reduced pressure. The residue was dissolved in THF (60.0 mL) under $N_2$ and $LiAlH_4$ (0.557 g, 14.7 mmol) was added portionwise over 15 min. After about 15 min, the ice bath was removed. After about 3 h, $LiAlH_4$ (0.557 g, 14.7 mmol) was added portionwise. After about 2 h, the mixture was cooled to about 0° C. then $Et_2O$ (50 mL) was added. Sodium sulfate decahydrate was slowly added until reaction was not observed during addition. The ice bath was removed and the mixture was left to vigorously stir for about 17 h. The solids were removed by filtration rinsing with $Et_2O$ (200 mL). The volatiles were removed under reduced pressure. The residue was dissolved in $Et_2O$ (10 mL) and DCM (20 mL). The solution was dried over $Na_2SO_4$, filtered, and concentrated under reduced pressure. The residue was purified using flash chromatography on silica gel (DCM) to give the title product (0.217 g, 8%); $^1$H NMR (400 MHz, CDCl$_3$) δ 7.31-7.23(m, 1H), 7.14-7.07 (m, 1H), 7.04-6.98 (m, 1H), 6.51 (t, J=74.3 Hz, 1H), 4.71 (s, 2H), 2.34 (s, 3H).

Preparation #12: (5-Bromo-2-(Difluoromethoxy)phenyl)methanol

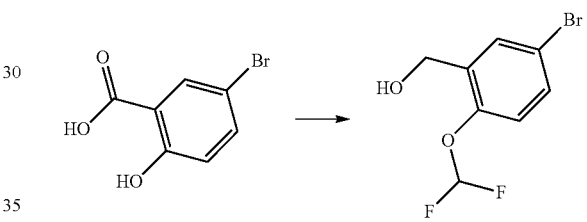

Ethyl bromodifluoroacetate (7.00 mL, 54.6 mmol) was added in one portion to a mixture of methyl 5-bromosalicylate (10.0 g, 43.3 mmol), $K_2CO_3$ (8.97 g, 64.9 mmol) and DMF (120 mL) under $N_2$. The mixture was warmed to about 80° C. for about 4 h. After stirring at rt for about 20 h, ethyl 2-bromo-2,2-difluoroacetate (3.50 mL, 27.3 mmol) and $K_2CO_3$ (3.01 g, 21.78 mmol) were added. The mixture was warmed to about 80° C. for about 90 min. A solution of water (100 mL) and potassium hydroxide (7.26 g, 129 mmol) was added and the reaction was warmed to about 100° C. After about 3 h, the mixture was cooled to rt. The reaction mixture was acidified to ~pH 1 by slowly adding 2 M aqueous HCl (250 mL). $Et_2O$ (200 mL) was added. The layers were separated and the organics were washed with water (100 mL). The aqueous layers were extracted with $Et_2O$ (100 mL). The combined organics were dried over $Na_2SO_4$, filtered, and concentrated under reduced pressure. The residue was dissolved in $Et_2O$ (100 mL) then washed with water (2×50 mL). The organics were dried over $Na_2SO_4$, filtered, and concentrated under reduced pressure. The residue was dried under high vacuum for about 24 h then dissolved in THF (20.0 mL). The solution was placed under $N_2$ then cooled to about 0° C. Borane-THF complex (1 M solution in THF, 9.00 mL, 9.00 mmol) was added dropwise. After about 45 min, the ice bath was removed. After stirring at rt for about 1 h, borane-THF complex (1 M solution in THF, 9.00 mL, 9.00 mmol) was added. The solution was warmed to about 60° C. After about 1 h, the solution was cooled to about 0° C. MeOH (5.00 mL, 124 mmol) was added dropwise. After completion of addition, the ice bath was removed. The solution was stirred for about 30 min and then the volatiles were removed under reduced pressure. The residue was dissolved in EtOAc (50 mL) and then washed with 1 M aqueous HCl (2×50 mL) and 50 mL sat. aq. NaCl (50 mL). The organics were dried over $Na_2SO_4$, filtered, and concentrated under reduced pressure. The residue was purified using flash chromatography on silica gel (0-25% EtOAc/heptane) to give the title product (0.865 g, 8%); $^1H$ NMR (400 MHz, $CDCl_3$) δ 7.67-7.62 (m, 1H), 7.44-7.39 (m, 1H), 7.03-6.98 (m, 1H), 6.52 (t, J=73.5 Hz, 1H), 4.73(s, 2H).

Preparation #13: (S)-7-(5-Bromopyrimidin-2-yl)hexahydroimidazo[1,5-a]pyrazin-3(2H)-one and (R)-7-(5-bromopyrimidin-2-yl)hexahydroimidazo[1,5-a]pyrazin-3(2H)-one

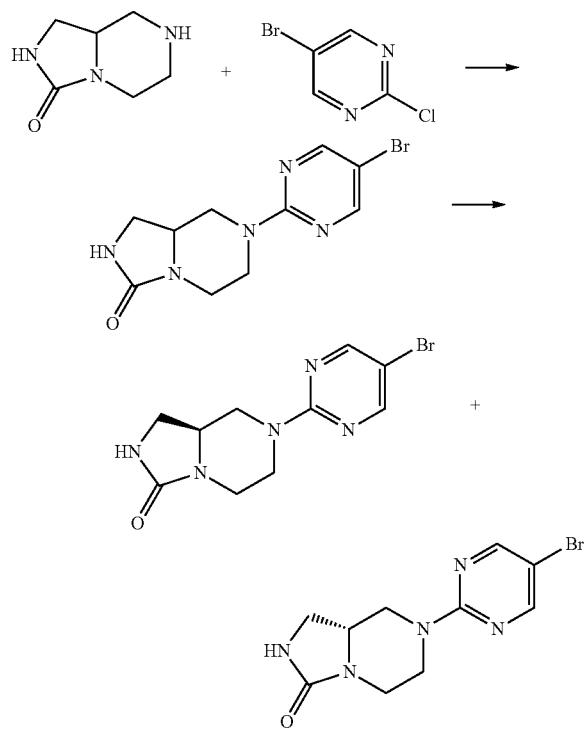

Step 1: 7-(5-Bromopyrimidin-2-yl)hexahydroimidazo[1,5-a]pyrazin-3(2H)-one

A mixture of hexahydroimidazo[1,5-a]pyrazin-3(2H)-one hydrochloride (1.50 g, 8.44 mmol), 5-bromo-2-chloropyrimidine (1.87 g, 9.67 mmol), TEA (4.19 mL, 30.0 mmol), and EtOH (70 mL) was warmed to about 78° C. After about 5 h, the mixture was allowed to cool to rt. After stirring about 1 h, the solids were collected by filtration rinsing with EtOH (10 mL). The mother liquor was concentrated under reduced pressure. Diethyl ether (25 mL) and water (25 mL) were added to the residue. After about 10 min, the solids were collected by filtration rinsing with diethyl ether (10 mL). The two crops of solids were combined then dried in a vacuum oven at about 60° C. for about 16 h to afford the title product as a white solid (2.32 g, 92%); LC/MS (Table A, Method e) $R_t$=1.63 min; MS m/z: 298 and 300 (M+H)$^+$.

Step 2: (S)-7-(5-Bromopyrimidin-2-yl)hexahydroimidazo[1,5-a]pyrazin-3(2H)-one and (R)-7-(5-bromopyrimidin-2-yl)hexahydroimidazo[1,5-a]pyrazin-3(2H)-one 7-(5-Bromopyrimidin-2-yl)hexahydroimidazo[1,5-a]pyrazin-3(2H)-one (2.32 g, 7.79 mmol) was submitted for chiral purification (Table B, Method a). Fractions from the first eluting component were combined and concentrated under reduced pressure then dried in a vacuum oven at about 60° C. for about 16 h to afford (S)-7-(5-bromopyrimidin-2-yl)hexahydroimidazo[1,5-a]pyrazin-3(2H)-one (1.02 g, 41%) with positive optical rotation. (Table A, Method e) $R_t$=1.63 min; MS m/z: 298 and 300 (M+H)$^+$. Fractions from the second eluting component were combined and concentrated under reduced pressure then dried in a vacuum oven at about 60° C. for about 16 h to afford (R)-7-(5-bromopyrimidin-2-yl)hexahydroimidazo[1,5-a]pyrazin-3(2H)-one (1.03 g, 41%) with negative optical rotation. (Table A, Method e) $R_t$=1.63 min; MS m/z: 298 and 300 (M+H)$^+$.

Preparation #14: (((3-(Bromomethyl)-4-(difluoromethoxy)benzyl)oxy)methanetriyl)tribenzene

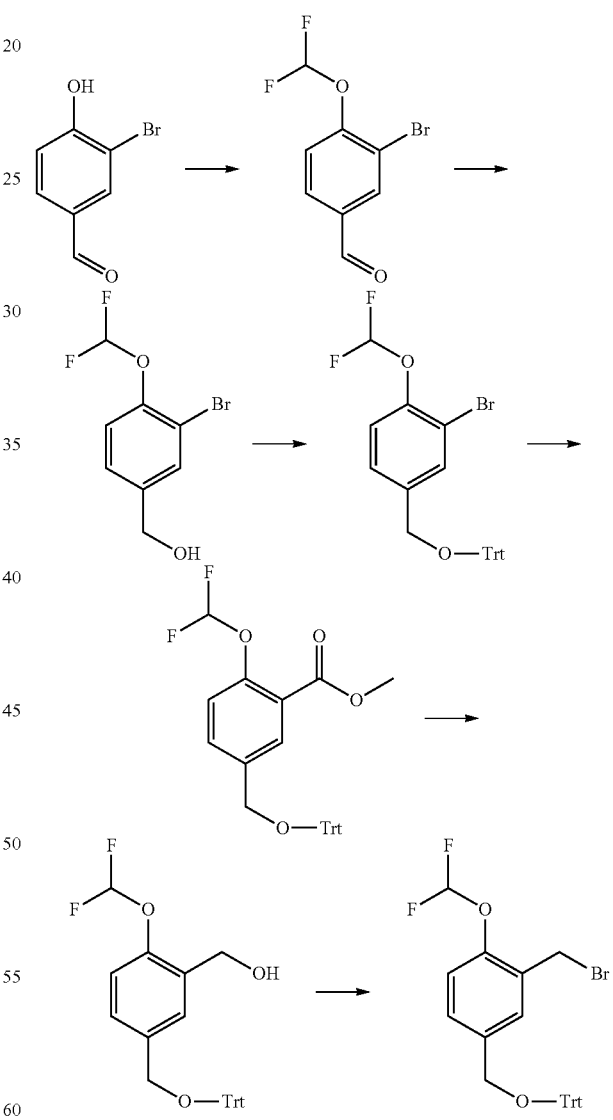

Step 1: 3-Bromo-4-(difluoromethoxy)benzaldehyde

DMF (50 mL) was added to a 250 mL flask charged with 3-bromo-4-hydroxybenzaldehyde (5.0 g, 25 mmol), sodium chlorodifluoroacetate (9.48 g, 62.2 mmol), and cesium carbonate (12.2 g, 37.3 mmol). The mixture was warmed to about 65° C. for about 1 h. After cooling to about 35° C., the reaction mixture was poured slowly into ice water (600 mL). The mixture was extracted with EtOAc (2×200 mL). The combined organic layers were washed with sat. aq. NaCl (100 mL), dried over Na$_2$SO$_4$, filtered and concentrated under reduced pressure. The residue was purified on silica gel (220 g) using a gradient of 10-25% EtOAc in heptane. Product fractions were combined and concentrated to yield the title compound (3.50 g, 56%). $^1$H NMR (400 MHz, DMSO-d$_6$) δ 9.94 (d, J=0.5 Hz, 1H), 8.24 (d, J=2.0 Hz, 1H), 7.98 (dd, J=8.5, 2.0 Hz, 1H), 7.54-7.49 (m, 1H), 7.46 (t, J=72.5 Hz, 1H).

Step 2: (3-Bromo-4-(difluoromethoxy)phenyl)methanol

Sodium borohydride (0.63 g, 17 mmol) was added to a solution of 3-bromo-4-(difluoromethoxy)benzaldehyde (3.5 g, 14 mmol) in ethanol (70 mL) at rt. After about 90 min, the reaction was quenched by slow addition of 2 N aqueous HCl (30 mL) with cooling. The reaction mixture was concentrated to about 30 mL and then extracted with EtOAc (2×50 mL). The combined organics were dried over Na$_2$SO$_4$, filtered and concentrated under reduced pressure to yield the title compound (3.53 g, 100%). $^1$H NMR (400 MHz, DMSO-d$_6$) δ 7.63(dd, J=1.9, 0.9 Hz, 1H), 7.37-7.32 (m, 1H), 7.27 (dt, J=8.4, 0.9 Hz, 1H), 7.21 (t, J=73.5 Hz, 1H), 5.55-5.09 (bs, 1H), 4.47 (s, 2H).

Step 3: (((3-Bromo-4-(difluoromethoxy)benzyl)oxy)methanetriyl)tribenzene

N,N-Dimethylpyridin-4-amine (0.077 g, 0.63 mmol) was added to a solution of (3-bromo-4-(difluoromethoxy)phenyl)methanol (1.60 g, 6.32 mmol) and (chloromethanetriyl)tribenzene (1.76 g, 6.32 mmol) in pyridine (20 mL) at rt. The reaction mixture was warmed to about 80° C. After about 2 h, the reaction was concentrated. The residue was dissolved in DCM (100 mL) and washed with sat. aq. NH$_4$Cl (2×100 mL). The organic layer was dried over Na$_2$SO$_4$, filtered, and concentrated under reduced pressure onto silica gel (15 g). The residue was purified on silica gel (120 g) using a gradient of 50-100% DCM in heptane. Product fractions were combined and concentrated to yield the title compound (1.44 g, 46%). $^1$H NMR (400 MHz, DMSO-d$_6$) δ 7.58 (d, J=2.1 Hz, 1H), 7.44-7.38 (m, 7H), 7.38-7.32 (m, 6H), 7.31-7.24 (m, 4H), 7.23(t, J=74.5 Hz, 1H), 4.12 (s, 2H).

Step 4: Methyl 2-(difluoromethoxy)-5-((trityloxy)methyl)benzoate

A solution of (((3-bromo-4-(difluoromethoxy)benzyl)oxy)methanetriyl)tribenzene (4.41 g, 8.90 mmol), Pd$_2$(dba)$_3$(0.326 g, 0.356 mmol) and (9,9-dimethyl-9H-xanthene-4,5-diyl)bis(diphenylphosphine) (0.618 g, 1.07 mmol) in DMF (40 mL) was degassed with a stream of nitrogen, evacuated, then an atmosphere of carbon monoxide was introduced. TEA (2.50 mL, 17.8 mmol) and methanol (0.72 mL, 18 mmol) were added and the reaction was warmed to about 105° C. MeOH (2.2 mL, 53 mmol) was added while maintaining the reaction temperature at about 105° C. After about 3 h, the reaction mixture was cooled to rt and concentrated under reduced pressure. The residue was dissolved with 40% DCM/heptane (50 mL) and filtered. The filtrate was purified on silica gel (120 g) using a gradient of 40-80% DCM in heptane. Product fractions were combined and concentrated under reduced pressure to yield the title compound (2.1 g, 50%). $^1$H NMR (400 MHz, DMSO-d$_6$) δ 7.73(d, J=2.3 Hz, 1H), 7.62 (dd, J=8.5, 2.3 Hz, 1H), 7.44-7.39 (m, 6H), 7.38-7.31 (m, 6H), 7.31-7.24 (m, 4H), 7.14 (t, J=74.1 Hz, 1H), 4.14 (s, 2H), 3.81 (s, 3H).

Step 5: (2-(Difluoromethoxy)-5-((trityloxy)methyl)phenyl)methanol

A solution of ethyl 2-(difluoromethoxy)-5-((trityloxy)methyl)benzoate (1.64 g, 3.36 mmol) and lithium borohydride (0.18 g, 8.1 mmol) in THF (32 mL) was warmed at about 60° C. under nitrogen for about 16 h. The reaction was cooled to rt and concentrated under reduced pressure. The residue was dissolved in DCM (50 mL) and washed with sat. aq. NaHCO$_3$(2×30 mL) and sat. aq. NaCl (30 mL). The organic layer was dried over Na$_2$SO$_4$ and passed through a pad of silica gel (4 cm), rinsing with EtOAc (50 mL). The filtrate was concentrated under reduced pressure and the resulting solid was dried to yield the title compound (1.44 g, 96%). $^1$H NMR (400 MHz, DMSO-d$_6$) δ 7.49 (d, J=2.2 Hz, 1H), 7.45-7.39 (m, 6H), 7.39-7.32 (m, 6H), 7.30-7.23(m, 4H), 7.13(t, J=74.4 Hz, 1H), 7.13-7.10 (m, 1H), 5.22 (t, J=5.7 Hz, 1H), 4.52 (d, J=5.7 Hz, 2H), 4.04 (s, 2H).

Step 6: (((3-(Bromomethyl)-4-(difluoromethoxy)benzyl)oxy)methanetriyl)tribenzene A solution of (2-(difluoromethoxy)-5-((trityloxy)methyl)phenyl)methanol (1.25 g, 2.45 mmol) and PPh$_3$ (0.987 g, 3.76 mmol) in DCM (50 mL) was cooled to about 0° C. and 1-bromopyrrolidine-2,5-dione (0.670 g, 3.76 mmol) was added in portions, maintaining the reaction temperature between about 2-4° C. After about 90 min at about 0° C., sat. aq. NaHCO$_3$(50 mL) was added. The layers were separated and the organic layer was dried over Na$_2$SO$_4$, filtered, and concentrated onto silica gel (about 10 g). The residue was purified on silica gel (40 g) using a gradient of 30-100% DCM in heptane to afford the target compound (1.25 g, 78%). $^1$H NMR (400 MHz, CDCl$_3$) δ 7.56-7.46 (m, 6H), 7.37 (t, J=0.9 Hz, 1H), 7.36-7.21 (m, 10H), 7.12 (dt, J=8.7, 1.1 Hz, 1H), 6.47 (d, J=73.9 Hz, 1H), 4.53(s, 2H), 4.16 (t, J=0.8 Hz, 2H).

Preparation #15: (R)-1-(4-(5-Bromopyrimidin-2-yl)-2-methylpiperazin-1-yl)-2-hydroxyethanone

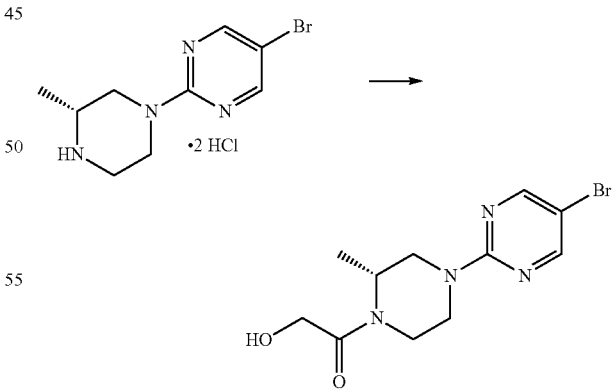

Trethylamine (20.0 mL, 143 mmol) was added to a slurry of (R)-5-bromo-2-(3-methylpiperazin-1-yl)pyrimidine dihydrochloride (10.0 g, 30.3 mmol) (synthesized in a similar fashion to Example #3, step 1 from (R)-tert-butyl 4-(5-bromopyrimidin-2-yl)-2-methylpiperazine-1-carboxylate (synthesized in a similar fashion to Preparation #13, step 1 from (R)-1-N-Boc-2-methylpiperazine)), glycolic acid (3.52 g, 46.3 mmol) and DMF (150 mL). After stirring for about 5 min, 1-[bis(dimethylamino)methylene]-1H-1,2,3-triazolo[4,5-B]pyridinium 3-oxide hexafluorophosphate (13.8 g, 36.4 mmol) was added. After about 2 h, 1-[bis(dimethylamino)methylene]-1H-1,2,3-triazolo[4,5-B]pyridinium 3-oxide hexafluorophosphate (1.73 g, 4.54 mmol) was added. After about 2 h, the volatiles were removed under reduced pressure. EtOAc (300 mL), water (300 mL) and sat. aq. NaHCO$_3$(100 mL) were added. The layers were separated and the aqueous layer was extracted with EtOAc (2×100 mL). The combined organic layers were dried over Na$_2$SO$_4$, filtered, and concentrated under reduced pressure. The residue was purified on silica gel (0-100% EtOAc/heptane) to afford the title product (8.29 g, 87%); LC/MS (Table A, Method h) R$_t$=0.96 min; MS m/z: 315 and 317 (M+H)$^+$ Preparation #16: (R)-1-(4-(5-bromopyrimidin-2-yl)-2-methylpiperazin-1-yl)ethanone

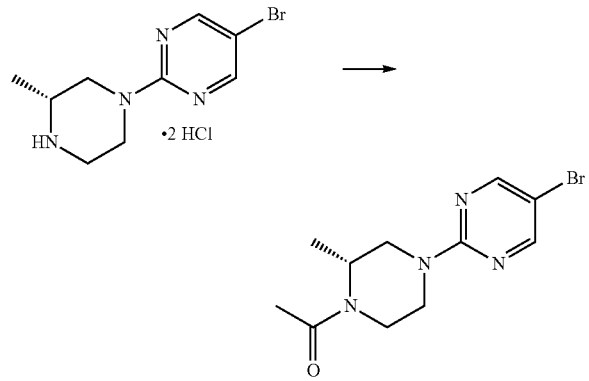

A suspension of (R)-5-bromo-2-(3-methylpiperazin-1-yl)pyrimidine dihydrochloride (3.75 g, 11.4 mmol) (synthesized in a similar fashion to Example #3, step 1 from (R)-tert-butyl 4-(5-bromopyrimidin-2-yl)-2-methylpiperazine-1-carboxylate (synthesized in a similar fashion to Preparation #13, step 1 from (R)-1-N-Boc-2-methylpiperazine) in DCM (114 mL) under N$_2$ was treated with TEA (5.23 mL, 37.5 mmol) and stirred for about 15 min. The reaction mixture was cooled to about 0° C. for about 15 min and acetyl chloride (0.880 mL, 12.5 mmol) was added dropwise via syringe. The resulting suspension was allowed to stir at about 0° C. for about 10 min. Water (20 mL) was added. The organic layer was separated and washed with sat. aq. NaHCO$_3$(20 mL) and sat. aq. NaCl (30 mL), dried over MgSO$_4$, filtered and concentrated under reduced pressure to afford the title product (3.43 g, 100%); LC/MS (Table A, Method i) R$_t$=1.07 min.; MS m/z: 299, 301 (M+H)$^+$.

Preparation #17: (6-Methyl-3-(trifluoromethyl)pyridin-2-yl)methanol

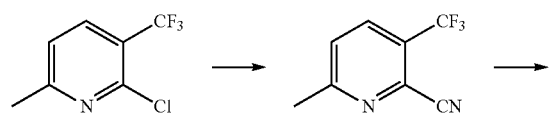

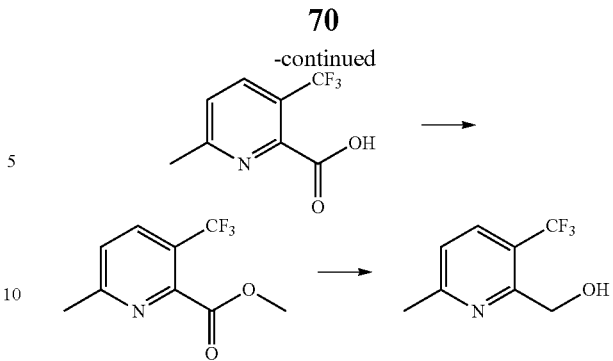

Step 1: 6-Methyl-3-(trifluoromethyl)picolinonitrile

A flask was charged with 2-chloro-6-methyl-3-(trifluoromethyl)pyridine (1.95 g, 9.97 mmol), dicyanozinc (1.41 g, 11.9 mmol), zinc (0.078 g, 1.2 mmol) then evacuated and back-filled with N$_2$ three times. Dimethylacetamide (39.7 mL) and PdCl$_2$(dppf) (0.292 g, 0.399 mmol) were added and the mixture was purged with N$_2$ for about 25 min at rt. The mixture was placed on a preheated mantle at about 140° C. and the temperature was adjusted until an internal temperature of about 140° C. was reached. After about 90 min, the reaction mixture was cooled to about room temperature and filtered through a pad of Celite® rinsing with EtOAc (350 mL). The solution was washed with a sat. aq. 5% NH$_4$OH solution (100 mL) and sat. aq. NaCl (2×100 mL). The organic layer was dried over MgSO$_4$, filtered and concentrated under reduced pressure. The material was purified via flash chromatography on silica gel (0-20% EtOAc/DCM). The appropriate fractions were collected and concentrated under reduced pressure to yield the title product (1.70 g, 92%); $^1$H NMR (400 MHz, DMSO-d$_6$) δ 8.38 (d, J=8.4 Hz, 1H), 7.86 (d, J=8.3 Hz, 1H), 2.65 (s, 3H).

Step 2: 6-Methyl-3-(trifluoromethyl)picolinic acid

A mixture of 6-methyl-3-(trifluoromethyl)picolinonitrile (1.70 g, 9.13 mmol) and 5 N NaOH (10.9 mL, 54.8 mmol) in EtOH (12.6 mL) was heated to about 85° C. for about 7 h. The reaction was cooled to ambient temperature and stirred for about 16 h at room temperature. The ethanol was removed under reduced pressure and the aqueous layer was acidified with 5 N aq. HCl (10.9 mL, 54.8 mmol). DCM (100 mL) was added and layers were separated. The aqueous layer was extracted with DCM (100 mL). The combined organic layers were dried over MgSO$_4$, filtered, concentrated under reduced pressure. The residue was dried under vacuum oven at about 65° C. for about 3 h to yield the title product (1.73 g, 92%); $^1$H NMR (400 MHz, DMSO-d$_6$) δ 13.93(s, 1H), 8.18 (d, J=8.3 Hz, 1H), 7.60 (d, J=8.2 Hz, 1H), 2.58 (s, 3H).

Step 3: Methyl 6-methyl-3-(trifluoromethyl)picolinate

Sulfuric acid (4.50 mL, 84.0 mmol) was added dropwise to a mixture of 6-methyl-3-(trifluoromethyl)picolinic acid (1.73 g, 8.43 mmol) in MeOH (17.3 mL). The reaction mixture was refluxed for about 20 h and then cooled to ambient temperature. Sat. aq. NaHCO$_3$(110 mL) was added slowly. EtOAc (100 mL) was added and the layers were separated. The aqueous layer was extracted with EtOAc (100 mL). The combined organic layers were washed with sat. aq. NaCl (50 mL), dried over MgSO$_4$, filtered and concentrated under reduced pressure to afford the title product (1.56 g, 84%); $^1$H NMR (400 MHz, DMSO-d$_6$) δ 8.24 (d, J=8.3 Hz, 1H), 7.67 (d, J=8.3 Hz, 1H), 3.91 (s, 3H), 2.60 (s, 3H).

Step 4:
(6-Methyl-3-(trifluoromethyl)pyridin-2-yl)methanol

NaBH$_4$ (0.93 g, 24.6 mmol) was added portionwise to a mixture of methyl 6-methyl-3-(trifluoromethyl)picolinate (0.912 g, 4.16 mmol)) in EtOH (40 mL) under N$_2$. The mixture was heated to about 50° C. for about 4 h. Additional NaBH$_4$ (0.35 g, 9.25 mmol) was added. After about 16 h, additional NaBH$_4$ (0.35 g, 9.25 mmol) and EtOH (3 mL) were added. After about 4 h. NaBH$_4$ (0.40 g, 10.6 mmol) was added. Additional NaBH$_4$ (0.945 g, 24.9 mmol) and EtOH (10 mL) were added after about 16 h. After about 8 h, the reaction mixture was cooled to ambient temperature and partially concentrated under reduced pressure. To the mixture was added sat. aq. NH$_4$Cl (100 mL) then EtOAc (150 mL) and stirred for about 20 min. The layers were separated and the aqueous layer was extracted with EtOAc (3×150 mL). The combined organic layers were dried over MgSO$_4$, filtered and concentrated under reduced pressure. The material was purified via flash chromatography on silica gel (0-20% EtOAc/heptane). The appropriate fractions were collected and concentrated under reduced pressure to yield the title product (0.307 g, 26%, 67% purity); LC/MS (Table A, Method i) R$_t$=0.80 min.; MS m/z: 192 (M+H)$^+$.

Preparation #18:
(2-((Difluoromethyl)thio)-5-methylphenyl)methanol

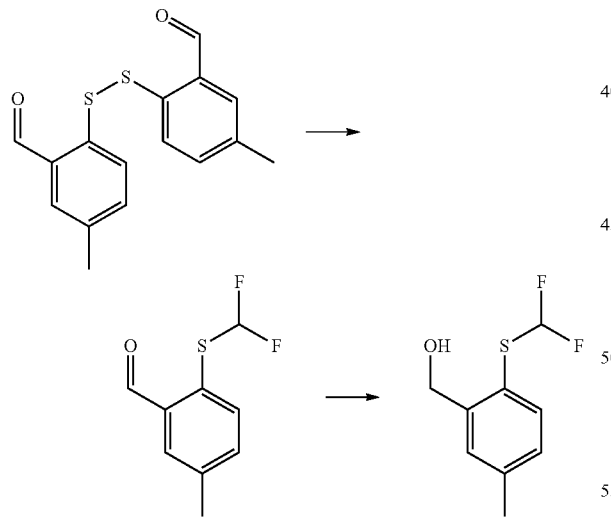

Step 1:
2-((Difluoromethyl)thio)-5-methylbenzaldehyde 6,6'-Disulfanediylbis(3-methylbenzaldehyde) (688 mg, 2.28 mmol) and TEA (0.698 mL, 5.01 mmol) was dissolved in a degassed mixture of DMF (11 mL) and water (0.5 mL). The reaction was purged with argon, then tris(2-carboxyethyl)phosphine hydrochloride (1.30 g, 4.55 mmol) was added and the reaction was stirred for about 30 min at room temperature. Degassed water (2 mL) was added while maintaining inert atmosphere, then extracted with degassed Et$_2$O (2×10 mL). The organic layer was transferred via syringe to an argon-filled flask. The solvent was removed in vacuo, and the resulting residue was dissolved in MeCN (1.7 mL) and cooled to about −78° C. Degassed 4 M aq. potassium hydroxide (23 mL, 91 mmol) was added, followed by diethyl (bromodifluoromethyl)phosphonate (1.62 mL, 9.10 mmol) in one portion. The frozen mixture was placed in an ice bath for about 30 min, then warmed to rt for about 60 min. The reaction mixture was extracted into Et$_2$O (2×40 mL). The organic layer was washed with water and sat. aq. NaCl (40 mL each), then dried over MgSO$_4$ filtered, and concentrated in vacuo. Purification via flash chromatography on silica gel (0-40% DCM in heptane) yielded the title compound (520 mg, 57%); $^1$H NMR (400 MHz, CDCl$_3$) δ 10.56 (s, 1H), 7.84 (d, J=2.1 Hz, 1H), 7.60 (d, J=7.9 Hz, 1H), 7.44 (dd, J=7.9, 2.1 Hz, 1H), 6.84 (t, J=56.3 Hz, 1H), 2.45 (s, 3H).

Step 2:
(2-((Difluoromethyl)thio)-5-methylphenyl)methanol 2-((Difluoromethyl)thio)-5-methylbenzaldehyde (296 mg, 1.46 mmol) in dry methanol (7 mL) under nitrogen atmosphere was cooled to about 0° C. Sodium borohydride (111 mg, 2.93 mmol) was added and the reaction stirred at about 0° C. for about 15 min, then allowed to warm to room temperature for about 30 min. The solvent was removed in vacuo and the resulting residue was partitioned between EtOAc (20 mL) and water (20 mL). The aqueous layer was extracted with additional EtOAc (20 mL), then the combined organic layers were dried over MgSO$_4$, filtered, and concentrated to yield the title compound (289 mg, 97%), used without further purification. $^1$H NMR (400 MHz, CDCl$_3$) δ 7.51 (d, J=7.8 Hz, 1H), 7.38 (s, 1H), 7.15 (d, J=7.8 Hz, 1H), 6.80 (t, J=57.1 Hz, 1H), 4.86 (s, 2H), 2.39 (s, 3H), 1.75 (s, 1H).

Preparation #19: 6-(2-(2-Hydroxypropan-2-yl)pyrimidin-5-yl)-2-methyl-1H-indazol-3(2H)-one

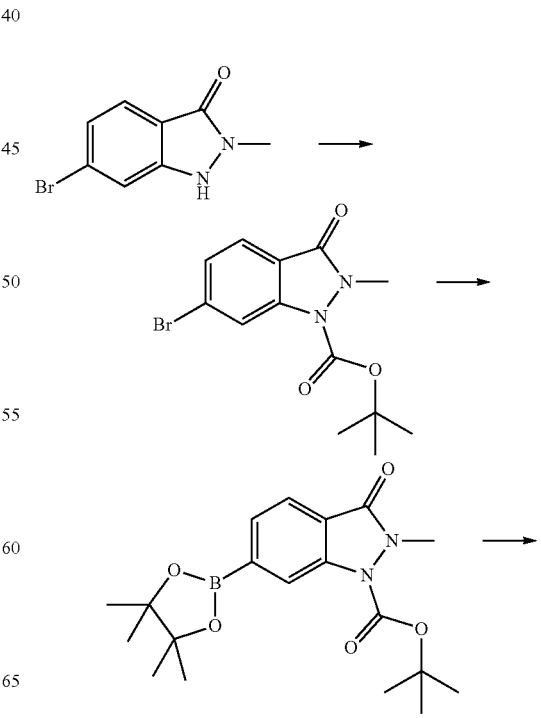

-continued

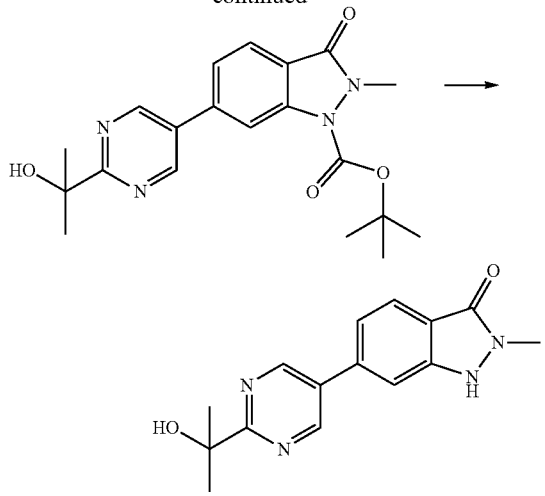

Step 1: tert-Butyl 6-bromo-2-methyl-3-oxo-2,3-dihydro-1H-indazole-1-carboxylate To a suspension of 6-bromo-2-methyl-1H-indazol-3(2H)-one (5.00 g, 22.0 mmol) (Preparation #1) in DCM (60 mL) was added TEA (4.00 mL, 28.6 mmol) and N,N-dimethylpyridin-4-amine (0.27 g, 2.2 mmol). The mixture was stirred under nitrogen and cooled to about 0° C. A mixture of di-tert-butyl dicarbonate (5.89 g, 24.2 mmol) in DCM (25.0 mL) was added and the mixture was stirred an additional 5 min at about 0° C. The reaction was allowed to warm to rt, diluted with DCM (150 mL) and washed with water (150 mL). The organic layer was dried over $Na_2SO_4$ and concentrated. The residue was purified on silica gel using a gradient of 5-30% EtOAc in heptane. The product fractions were concentrated to dryness to provide the title product (5.65 g, 78%); $^1$H NMR (400 MHz, DMSO-$d_6$) δ 8.00 (dd, J=1.6, 0.5 Hz, 1H), 7.72 (dd, J=8.2, 0.5 Hz, 1H), 7.55 (dd, J=8.2, 1.6 Hz, 1H), 3.48 (s, 3H), 1.58 (s, 91H).

Step 2: tert-Butyl 2-methyl-3-oxo-6-(4,4,5,5-tetramethyl-1,3,2-dioxaborolan-2-yl)-2,3-dihydro-1H-indazole-1-carboxylate tert-Butyl 2-methyl-3-oxo-6-(4,4,5,5-tetramethyl-1,3,2-dioxaborolan-2-yl)-2,3-dihydro-1H-indazole-1-carboxylate was prepared in a similar fashion to Preparation #4, step 2 using tert-butyl 6-bromo-2-methyl-3-oxo-2,3-dihydro-1H-indazole-1-carboxylate to give the title compound (1.38 g, 23%); LC/MS (Table A, Method e) $R_t$=2.63 min; MS m/z: 375 (M+H)$^+$.

Step 3: tert-Butyl 6-(2-(2-hydroxypropan-2-yl)pyrimidin-5-yl)-2-methyl-3-oxo-2,3-dihydro-1H-indazole-1-carboxylate tert-Butyl 6-(2-(2-hydroxypropan-2-yl)pyrimidin-5-yl)-2-methyl-3-oxo-2,3-dihydro-1H-indazole-1-carboxylate was prepared in a similar fashion to Example #14, step 4 using tert-butyl 2-methyl-3-oxo-6-(4,4,5,5-tetramethyl-1,3,2-dioxaborolan-2-yl)-2,3-dihydro-1H-indazole-1-carboxylate and 2-(5-bromopyrimidin-2-yl)propan-2-ol to give the title compound (0.138 g, 90%); LC/MS (Table A, Method e) $R_t$=1.97 min; MS m/z: 385 (M+H)$^+$.

Step 4: 6-(2-(2-Hydroxypropan-2-yl)pyrimidin-5-yl)-2-methyl-1H-indazol-3(2H)-one TFA (0.270 mL, 3.51 mmol) was added to a solution of tert-butyl 6-(2-(2-hydroxypropan-2-yl)pyrimidin-5-yl)-2-methyl-3-oxo-2,3-dihydro-1H-indazole-1-carboxylate (0.135 g, 0.351 mmol) in DCM (3 mL). The reaction was stirred at rt for about 1 h. TFA (0.271 mL, 3.51 mmol) was added to the reaction which continued to stir at rt for about 5 h. The reaction was concentrated under reduced pressure. DCM (2×10 mL) was added to the residue and was concentrated under reduced pressure to give an off-white solid. The residue was triturated with $Et_2O$ (10 mL), filtered and washed with $Et_2O$ (10 mL) to give the title compound (0.065 g, 65%); LC/MS (Table A, Method e) $R_t$=1.18 min; MS m/z: 285 (M+H)$^+$.

Preparation #20: 2-(3-((6-Bromo-2-methyl-3-oxo-2,3-dihydro-1H-indazol-1-yl)methyl)-4-(difluoromethoxy)phenyl)acetonitrile

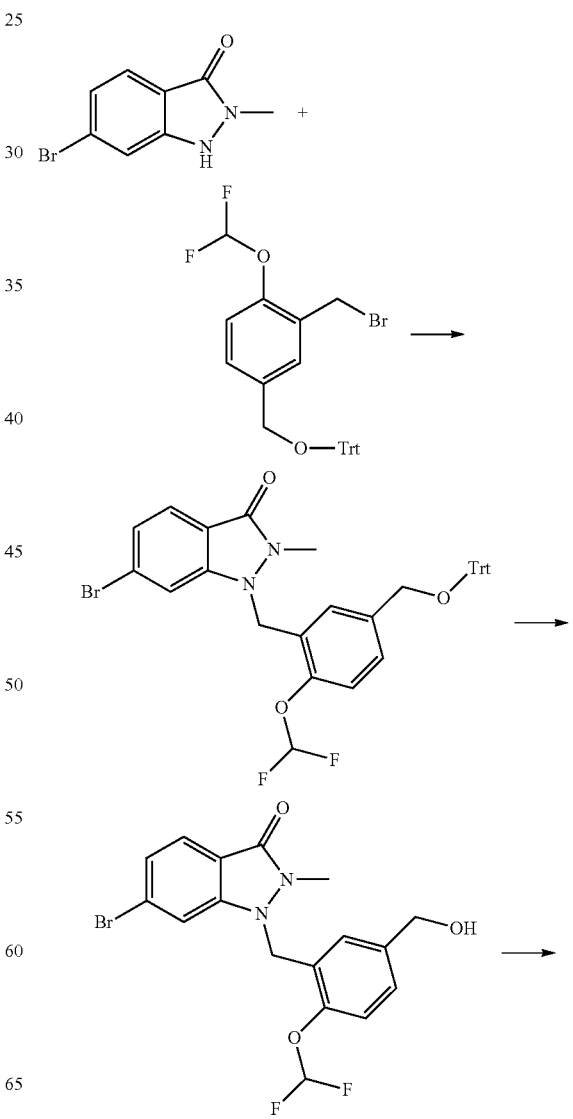

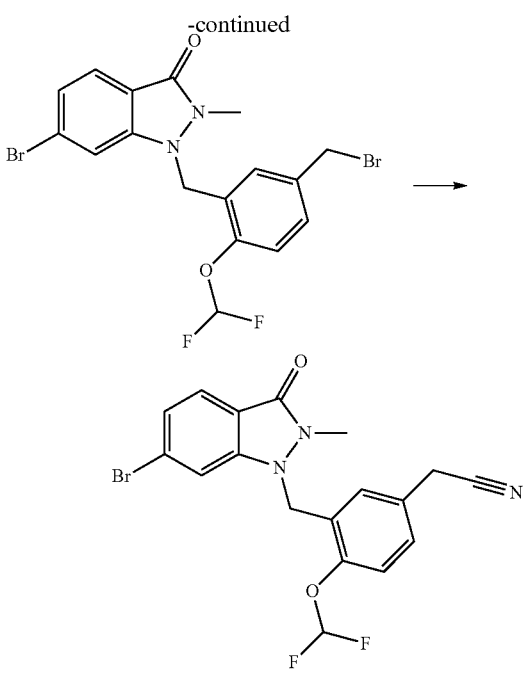

Step 1: 6-Bromo-1-(2-(difluoromethoxy)-5-((trityloxy)methyl)benzyl)-2-methyl-1,2-dihydro-3H-indazol-3-one A suspension of (((3-(bromomethyl)-4-(difluoromethoxy)benzyl)oxy)methanetriyl)tribenzene (12.5 g, 24.5 mmol) (Preparation #14), 6-bromo-2-methyl-1H-indazol-3(2H)-one (5.70 g, 25.1 mmol) (Preparation #1), and potassium carbonate (4.00 g, 28.9 mmol) in DMF (100 mL) was stirred at ambient temperature for about 45 min. The mixture was partitioned between water (500 mL) and EtOAc (250 mL), and after separating the layers the aqueous phase was extracted with EtOAc (2×125 mL). The combined organic phases were washed with sat. aq. NaCl (500 mL), dried over $Na_2SO_4$, filtered, and concentrated. The residue was purified on silica gel using a gradient of 0-100% EtOAc in heptane to afford the target compound (11.3 g, 70%). $^1$H NMR (400 MHz, DMSO-$d_6$) δ 7.95 (d, J=1.5 Hz, 1H), 7.50 (d, J=8.3 Hz, 1H), 7.43-7.04 (m, 19H), 6.99-6.96 (m, 1H), 5.24 (s, 2H), 3.87 (s, 2H), 3.31 (s, 3H).

Step 2: 6-Bromo-1-(2-(difluoromethoxy-(hydroxymethyl)benzyl)-2-methyl-1,2-dihydro-3H-indazol-3-one A solution of 6-bromo-1-(2-(difluoromethoxy)-5-((trityloxy)methyl)benzyl)-2-methyl-1,2-dihydro-3H-indazol-3-one (11.3 g, 17.2 mmol) and triisopropylsilane (5.30 mL, 25.9 mmol) in DCM (100 mL) was treated with TFA (25.0 mL, 324 mmol) and the mixture was stirred at ambient temperature for about 30 min. The reaction mixture was cooled in an ice water bath before addition of sat. aq. $NaHCO_3$ (200 mL). The organic phase was dried over $Na_2SO_4$, filtered, and concentrated under reduced pressure. The material was purified on silica gel using 5% MeOH in DCM to afford the target compound (5.66 g, 79%); LC/MS (Table A, Method i) $R_f$=1.23 min; MS m/z: 413 and 415 (M+H)$^+$.

Step 3: 6-bromo-1-(5-(bromomethyl)-2-(difluoromethoxy)benzyl)-2-methyl-1,2-dihydro-3H-indazol-3-one A solution of 6-bromo-1-(2-(difluoromethoxy)-5-(hydroxymethyl)benzyl)-2-methyl-1,2-dihydro-3H-indazol-3-one (5.64 g, 13.6 mmol) and $PPh_3$ (3.60 g, 13.7 mmol) in DCM (180 mL) at about 0° C. was treated with NBS (2.43 g, 13.7 mmol) and was then stirred at about 0° C. for about 20 min. Additional portions of $PPh_3$ (0.358 g, 1.37 mmol) and NBS (0.243 g, 1.37 mmol) were added and stirring was continued for about 5 min; final portions of $PPh_3$ (0.358 g, 1.37 mmol) and NBS (0.243 g, 1.37 mmol) were added followed by about an additional 5 min of stirring. Sat. aq. $NaHCO_3$ (150 mL) was added to the reaction mixture and after separating the layers the aqueous phase was extracted with DCM (2×20 mL). The combined organics were dried over $Na_2SO_4$, filtered, and concentrated under reduced pressure. The material was purified on silica gel using 5% MeOH in DCM to afford the target compound (5.95 g, 92%); LC/MS (Table A, Method i) $R_f$=1.55 min; MS m/z: 477 (M+H)$^+$.

Step 4: 2-(3-((6-Bromo-2-methyl-3-oxo-2,3-dihydro-1H-indazol-1-yl)methyl)-4-(difluoromethoxy)phenyl)acetonitrile A suspension of 6-bromo-1-(5-(bromomethyl)-2-(difluoromethoxy)benzyl)-2-methyl-1,2-dihydro-3H-indazol-3-one (0.12 g, 0.25 mmol) and sodium cyanide (0.037 g, 0.76 mmol) in DMF (2 mL) was stirred at ambient temperature for about 1 h. The reaction mixture was partitioned between water (5 mL) and EtOAc (5 mL) and after separating the layers the aqueous phase was extracted with EtOAc (2×5 mL). The combined organic phases were washed with sat. aq. NaCl (10 mL), dried over $Na_2SO_4$, filtered, and concentrated under reduced pressure to give the title compound (0.102 g, 96%); LC/MS (Table A, Method i) $R_f$=1.31 min; MS m/z: 422 and 424 (M+H)$^+$.

Preparation #21:
1-(1-Bromopropyl)-3-methylbenzene

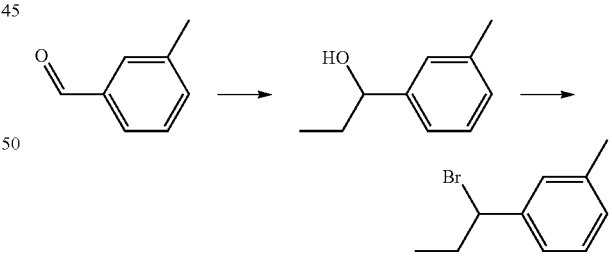

Step 1: 1-(m-Tolyl)propan-1-ol

To a solution of ethylmagnesium bromide (3.0 M in diethyl ether) (8.30 mL, 24.9 mmol) in THF (8.5 mL) under $N_2$ at about 0° C. was added dropwise a solution of 3-methylbenzaldehyde (1.47 mL, 12.5 mmol) in THF (8.5 mL). The mixture was allowed to stir at about 0° C. for about 10 min. The ice bath was removed and the reaction mixture stirred for about 1 h at ambient temperature. The reaction mixture was cooled to about 0° C. and quenched slowly by dropwise addition of sat. aq. NH₄Cl. The solvent was partially removed under reduced pressure. EtOAc (30 mL) and water (15 mL) were added. The organic layer was separated and the aqueous layer was back extracted with EtOAc (20 mL). The combined organic layers were washed with sat. aq. NaCl (15 mL), dried over MgSO₄, filtered and concentrated under reduced pressure to give the title product (1.87 g, 99%); ¹H NMR (400 MHz, DMSO-d₆) δ 7.40-6.72 (m, 4H), 5.01 (dd, J=4.4, 0.8 Hz, 1H), 4.42-4.34 (m, 1H), 2.29 (s, 3H), 1.67-1.50 (m, 2H), 0.81 (t, J=7.4 Hz, 3H).

Step 2: 1-(1-Bromopropyl)-3-methylbenzene

To a solution of 1-(m-tolyl)propan-1-ol (1.87, 12.5 mmol) in DCM (41 mL) under N₂ was added PPh₃ (3.27 g, 12.4 mmol) and perbromomethane (4.13 g, 12.4 mmol). After about 4 h, the solvent was removed under reduced pressure. The residue was triturated with heptane (3×20 mL). The filtrate was concentrated under reduced pressure to provide the title compound (1.14 g, 43.0%, 50% purity); ¹H NMR (400 MHz, DMSO-d₆) δ 7.30-7.22 (m, 4H), 5.16-5.11 (m, 1H), 2.30 (s, 3H), 1.83(dd, J=6.4, 1.4 Hz, 1H), 1.64-1.54 (m, 1H), 0.92 (s, 3H).

Preparation #22: (R)-1-(4-(5-Bromopyrimidin-2-yl)-3-methylpiperazin-1-yl)-2-hydroxyethanone

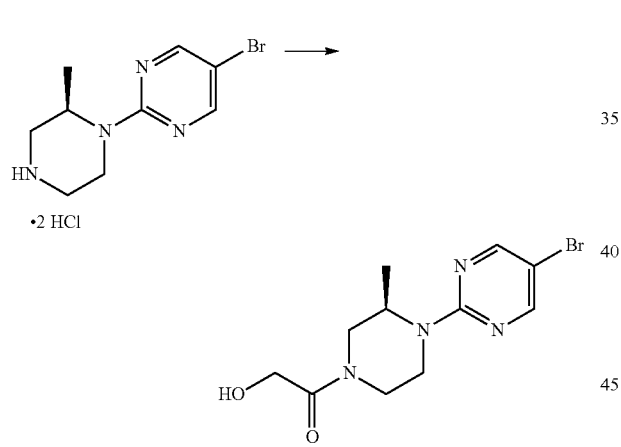

To a mixture of glycolic acid (0.11 g, 1.45 mmol), (R)-5-bromo-2-(2-methylpiperazin-1-yl)pyrimidine dihydrochloride (0.40 g, 1.21 mmol) (synthesized in a similar fashion to Example #3, step 1 from (R)-tert-butyl 4-(5-bromopyrimidin-2-yl)-3-methylpiperazine-1-carboxylate (synthesized in a similar fashion to Preparation #13, step 1 from (R)-tert-butyl 3-methylpiperazine-1-carboxylate)), and 1-[bis(dimethylamino)methylene]-1H-1,2,3-triazolo[4,5-b]pyridinium 3-oxid hexafluorophosphate (0.55 g, 1.45 mmol) under N₂ was added DCM (6.89 mL) then TEA (0.45 mL, 3.23 mmol). After stirring for 90 min at ambient temperature, DCM (20 mL) and sat. aq. NaHCO₃ (10 mL) were added. The organic layer was separated, washed with sat. aq. NaCl (10 mL), dried over MgSO₄, filtered and concentrated under reduced pressure. The material was purified via flash chromatography on silica gel (20-40% EtOAc/heptane). The appropriate fractions were concentrated under reduced pressure. The solid was sonicated in ether (10 mL) for about 5 min, filtered and rinsed with ether (2×10 mL) then dried in a vacuum oven at about 65° C. for about 15 min to provide the title product (0.178 g, 46%); LC/MS (Table A, Method i) R_t=0.96 min.; MS m/z: 315 and 317 (M+H)⁺.

Preparation #23: 6-(2-Chloropyrimidin-5-yl)-2-methyl-1H-indazol-3(2H)-one

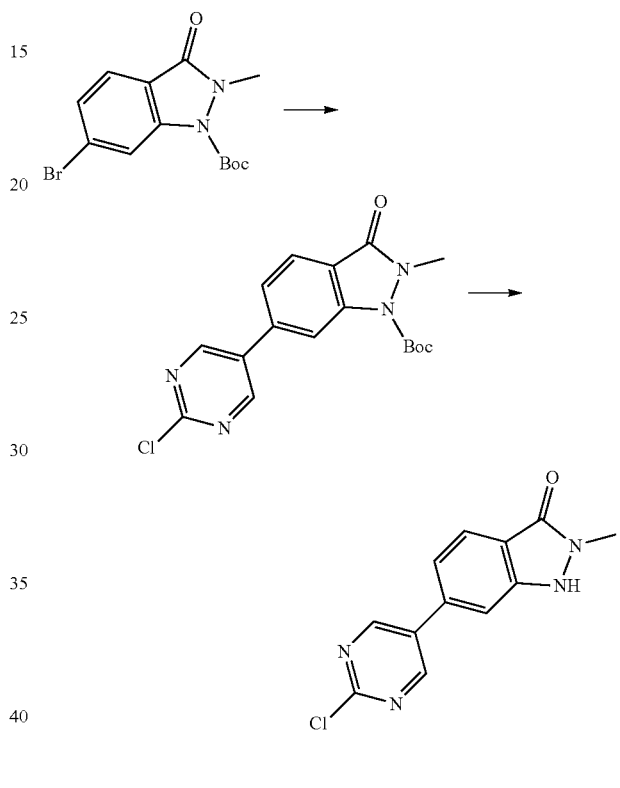

Step 1: tert-Butyl 6-(2-chloropyrimidin-5-yl)-2-methyl-3-oxo-2,3-dihydro-1H-indazole-1-carboxylate The reaction was performed using tert-butyl 6-bromo-2-methyl-3-oxo-2,3-dihydro-1H-indazole-1-carboxylate (Preparation #19, step 1) and 2-chloro-5-(4,4,5,5-tetramethyl-1,3,2-dioxaborolan-2-yl)pyrimidine in a similar fashion to Example #5 to afford the title product (0.70 g, 62%); LC/MS (Table A, Method e) R_t=2.18 min; MS m/z: 361 (M+H)⁺

Step 2: 6-(2-Chloropyrimidin-5-yl)-2-methyl-1H-indazol-3(2H)-one

The reaction was performed using tert-butyl 6-(2-chloropyrimidin-5-yl)-2-methyl-3-oxo-2,3-dihydro-1H-indazole-1-carboxylate in a similar fashion to Preparation #19, step 4 to give the title compound (485 mg, 100%); LC/MS (Table A, Method e) R_t. 1.33 min; MS m/z: 261 (M+H)⁺.

Preparation #24: 6-(2-Chloropyrimidin-5-yl)-1-(2-(difluoromethoxy)-5-((trityloxy)methyl)benzyl)-2-methyl-1H-indazol-3(2H)-one

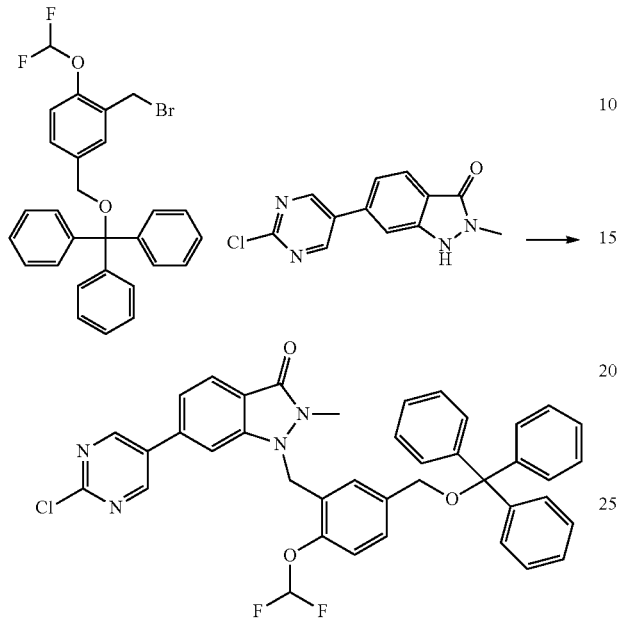

6-(2-Chloropyrimidin-5-yl)-1-(2-(difluoromethoxy)-5-((trityloxy)methyl)benzyl)-2-methyl-1H-indazol-3(2H)-one was prepared in a similar fashion to Preparation #4, step 1 using (((3-(bromomethyl)-4-(difluoromethoxy)benzyl)oxy)methanetriyl)tribenzene (Preparation #14) and 6-(2-chloropyrimidin-5-yl)-2-methyl-1H-indazol-3(2H)-one (Preparation #23) to give the title compound (1.09 g, 76%); LC/MS (Table A, Method e) $R_t$=2.83 min; MS m/z: 689 and 691 (M+H)$^+$.

Preparation #25: 6-Bromo-5,7-difluoro-2-methyl-1H-indazol-3(2H)-one

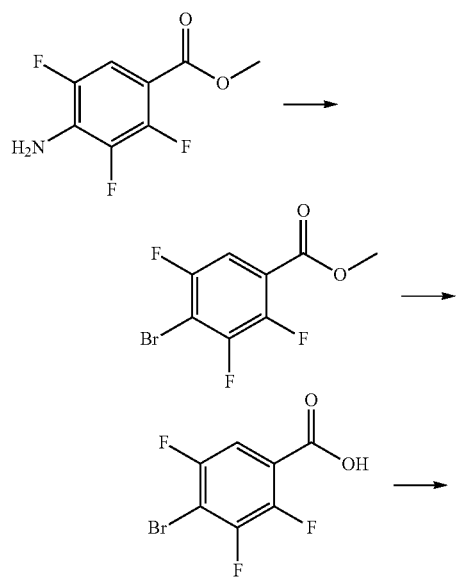

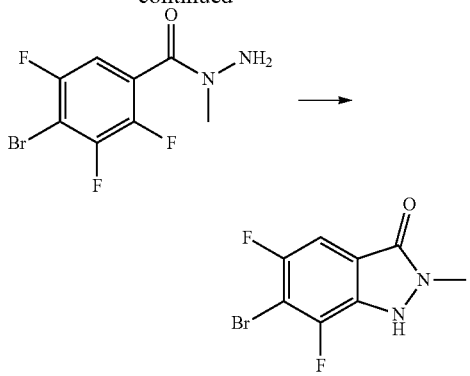

Step 1: Methyl 4-bromo-2,3,5-trifluorobenzoate

A solution of methyl 4-amino-2,3,5-trifluorobenzoate (2.00 g, 9.75 mmol) (prepared according to Sui XiongCai, et. al. *J. Org. Chem.* 1992, 57, 1299-1304) in MeCN (40 mL) was cooled to about 0° C. under $N_2$ and copper(II) bromide (3.27 g, 14.6 mmol) was added. After stirring for about 2 min, tert-butyl nitrite (1.51 g, 14.6 mmol) was added dropwise over about 2 min. The cooling bath was removed and the reaction was allowed to warm to rt for about 1 h. The reaction was poured into water (200 mL) and extracted with EtOAc (400 mL). The organic layer was washed with sat. aq. $NH_4Cl$ (2×200 mL), dried over $Na_2SO_4$, filtered and concentrated to yield the title product (2.50 g, 95%); LC/MS (Table A, Method h) $R_t$=1.56 min; MS m/z: not detected; $^1$H NMR (400 MHz, CDCl$_3$) δ 7.75-7.67 (m, 1H), 3.88 (s, 3H).

Step 2: 4-Bromo-2,3,5-trifluorobenzoic acid

To a solution of methyl 4-bromo-2,3,5-trifluorobenzoate (2.50 g, 9.29 mmol) in MeOH (20 mL) was added lithium hydroxide monohydrate (0.780 g, 18.6 mmol) and water (2 mL). The mixture was stirred at rt for about 30 min. The reaction was diluted with water (100 mL) and washed with ether (2×50 mL). The mixture was acidified with 2 N aq. HCl (10 mL) and extracted with EtOAc (100 mL). The organic extracts were washed with sat. aq. NaCl (50 mL), dried over $Na_2SO_4$, filtered, concentrated to solids and dried under vacuum to yield the title product (2.30 g, 97%); LC/MS (Table A, Method h) $R_t$=0.55 min; MS m/z: 253/255 (M−H)$^-$.

Step 3: 4-Bromo-2,3,5-trifluoro-N-methylbenzohydrazide

The reaction was performed using 4-bromo-2,3,5-trifluorobenzoic acid in a similar fashion to Preparation #1, step 1 to give the title product (84%); (Table A, Method h) $R_t$=0.88 min; MS m/z: 371 and 283/285 (M+H)$^+$.

Step 4: 6-Bromo-5,7-difluoro-2-methyl-1H-indazol-3(2H)-one

A solution of 4-bromo-2,3,5-trifluoro-N-methylbenzohydrazide (450 mg, 1.59 mmol) in DMF (150 mL) was added dropwise to a solution of potassium tert-butoxide (803 mg, 7.15 mmol) and DMF (150 mL) under nitrogen at about 0° C. over about 40 min. AcOH (1.0 mL, 18 mmol) was added and the volatiles were removed under reduced pressure.

Water (15 mL) was added and the mixture was extracted with DCM (2×25 mL). The crude product was concentrated onto silica gel and purified on silica gel using a gradient of 0-10% MeOH in DCM. Product containing fractions were combined and concentrate to yield the title product (0.33 g, 80%, about 50% purity); LC/MS (Table A, Method j) $R_t$=0.83 min; MS m/z: 263 and 265 (M+H)$^+$, which was used without further purification.

Preparation #26: (R)-6-(2-(4-(2-(tert-Butoxy) acetyl)-2-methylpiperazin-1-yl)pyrimidin-5-yl)-1-(2-(difluoromethoxy)benzyl)-5,7-difluoro-2-methyl-1H-indazol-3(2H)-one

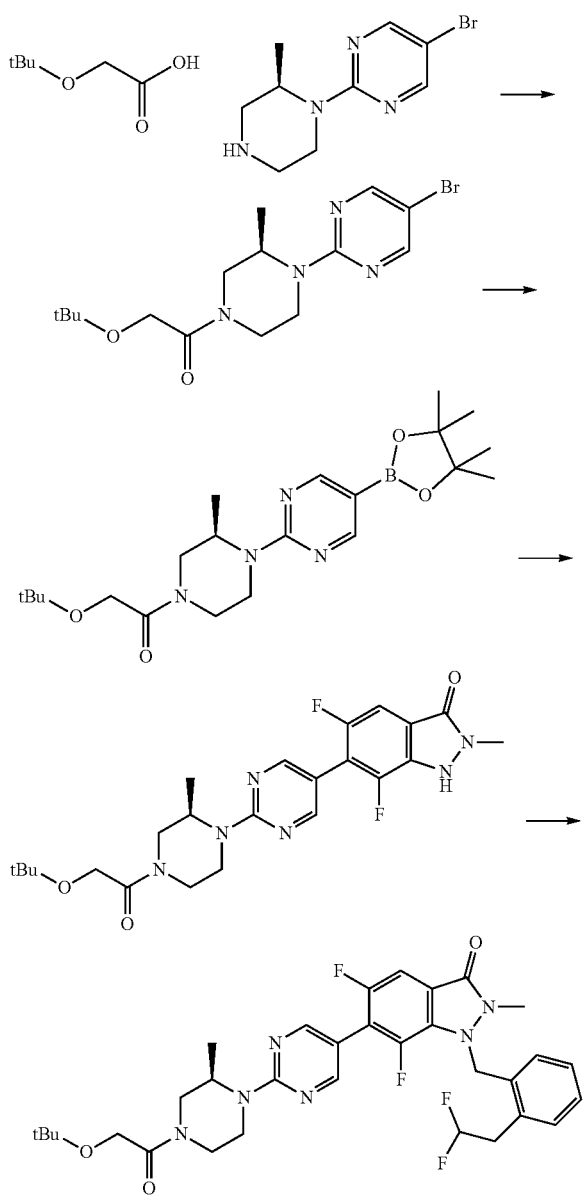

Step 1: (R)-1-(4-(5-Bromopyrimidin-2-yl)-3-methylpiperazin-1-yl)-2-(tert-butoxy)ethanone DIEA (6.61 mL, 37.9 mmol) was added to a slurry of (R)-5-bromo-2-(2-methylpiperazin-1-yl)pyrimidine dihydrochloride (2.50 g, 7.57 mmol) (synthesized in a similar fashion to Example #3, step 1 from (R)-tert-butyl 4-(5-bromopyrimidin-2-yl)-3-methylpiperazine-1-carboxylate (synthesized in a similar fashion to Preparation #13, step 1 from (R)-tert-butyl 3-methylpiperazine-1-carboxylate)), 2-(tert-butoxy)acetic acid (1.00 g, 7.57 mmol), 1H-benzo[d][1,2,3]triazol-1-ol hydrate (1.22 g, 7.95 mmol), and DCM (30 mL). After stirring for about 5 min, 1(3-dimethylaminopropyl)-3-ethylcarbodiimide hydrochloride (1.53 g, 7.95 mmol) was added. The reaction was stirred for about 72 h, then transferred to a separatory funnel and washed with sat. aq. NaHCO$_3$ solution (2×10 mL) and with sat. aq. NH$_4$Cl (2×10 mL). The organic layer was dried over Na$_2$SO$_4$, filtered and concentrated. The residue was purified on silica gel using a gradient of 30-60% EtOAc/heptane. Product fractions were combined and concentrated to yield the title product (2.44 g, 87%); LC/MS (Table A, Method i) $R_t$=1.47 min; MS m/z: 371 and 373(M+H)$^+$.

Step 2: (R)-2-(tert-Butoxy)-1-(3-methyl-4-(5-(4,4,5,5-tetramethyl-1,3,2-dioxaborolan-2-yl)pyrimidin-2-yl)piperazin-1-yl)ethanone A mixture of (R)-1-(4-(5-bromopyrimidin-2-yl)-3-methylpiperazin-1-yl)-2-(tert-butoxy)ethanone (2.44 g, 6.57 mmol), KOAc (2.06 g, 21.0 mmol), and bis(pinacolato)diboron (2.17 g, 8.54 mmol) in 1,4-dioxane (30 mL) was degassed with a stream of nitrogen. PdCl$_2$(dppf) (0.337 g, 0.460 mmol) was added and the reaction was further degassed for about 5 min. The reaction was heated at about 95° C. for about 5 h and then cooled to rt. The mixture was filtered rinsing with EtOAc. The filtrate was concentrated and the residue was purified on silica gel using a gradient of 0-100% EtOAc in DCM. Product fractions were combined and concentrated to yield the title product (2.17 g, 79%); LC/MS (Table A, Method i) $R_t$=1.63 min; MS m/z: 419 (M+H)$^+$.

Step 3: (R)-6-(2-(4-(2-(tert-Butoxy)acetyl)-2-methylpiperazin-1-yl)pyrimidin-5-yl-5,7-difluoro-2-methyl-1H-indazol-3(2H)-one A mixture of (R)-2-(tert-butoxy)-1-(3-methyl-4-(5-(4,4,5,5-tetramethyl-1,3,2-dioxaborolan-2-yl)pyrimidin-2-yl)piperazin-1-yl)ethanone (91 mg, 0.28 mmol), 6-bromo-5,7-difluoro-2-methyl-1H-indazol-3(2H)-one (95 mg, 0.14 mmol) (Preparation #25) and Cs$_2$CO$_3$(94 mg, 0.29 mmol) was diluted with toluene (2 mL) and water (2 mL). The mixture was degassed with a stream of nitrogen and 2$^{nd}$ Generation XPhos precatalyst (5 mg, 6 μmol) was added. The mixture was further degassed with nitrogen for about 5 min, then the reaction was heated to about 110° C. under nitrogen for about 6 h. The reaction was cooled to rt and diluted with water (5 mL) and EtOAc (10 mL). The organic layer was extracted again with 1 N aq. NaOH (5 mL). The combined aqueous extracts were washed once with EtOAc (10 mL), then acidified with HOAc to about pH 4. The aqueous layer was extracted with EtOAc (2×10 mL). The combined organics were dried over Na$_2$SO$_4$, filtered and concentrated. The material was purified on silica gel using a gradient of 0-10% MeOH in DCM. Product fractions were combined and concentrated to yield the title product (25 mg, 36%); LC/MS (Table A, Method i) $R_t$=1.11 min; MS m/z: 475 (M+H)$^+$.

Step 4: (R)-6-(2-(4-(2-(tert-Butoxy)acetyl)-2-methylpiperazin-1-yl)pyrimidin-5-yl)-1-(2-(difluoromethoxy)benzyl)-5,7-difluoro-2-methyl-1H-indazol-3(2H)-one To a mixture of (R)-6-(2-(4-(2-(tert-butoxy)acetyl)-2-methylpiperazin-1-yl)pyrimidin-5-yl)-5,7-difluoro-2- methyl-1H-indazol-3(2H)-one (51 mg, 0.11 mmol) and K₂CO₃ (18 mg, 0.13 mmol) in DMF (1.0 mL) was added 1-(bromomethyl)-2-(difluoromethoxy)benzene (28.0 mg, 0.118 mmol) and the mixture was stirred at rt for about 1 h. The reaction was quenched with AcOH (0.012 mL, 0.22 mmol), diluted with water (10 mL) and extracted with EtOAc (2×10 mL). The extracts were washed with sat. aq. NaCl (10 mL), dried over Na₂SO₄, filtered and concentrated. The residue was purified on silica gel using EtOAc. The product fractions were combined and concentrated to yield the title product (44 mg, 65%); LC/MS (Table A, Method i) R$_t$=1.63 min; MS m/z: 631 (M+H)⁺.

Preparation #27: 4-Bromo-2-((tetrahydro-2H-pyran-3-yl)oxy)pyridine

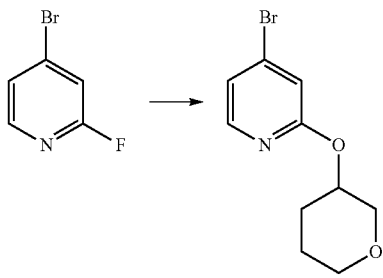 [SMILES: Fc1cc(Br)ccn1 ; Brc1ccnc(OC2CCCOC2)c1]

To a solution of tetrahydro-2H-pyran-3-ol (0.10 g, 0.97 mmol) in THF (2.5 mL) was added sodium hydride (60% dispersion in mineral oil, 0.065 g, 1.6 mmol) and stirred at ambient temperature for about 2 h. To the reaction mixture was added 4-bromo-2-fluoropyridine (0.144 g, 0.816 mmol) in THF (2.5 mL). After about 16 h, water (5 mL) and EtOAc (10 mL) were added. The organic layer was separated and the aqueous layer was back extracted with EtOAc (10 mL). The combined organic layers were dried over MgSO₄, filtered and concentrated under reduced pressure. The material was purified via flash chromatography on silica gel (0-50% EtOAc/heptane). The appropriate fractions were collected and concentrated under reduced pressure to provide the title product (0.117 g, 55%); LC/MS (Table A, Method i) R$_t$=1.33 min.; MS m/z: 258 and 260 (M+H)⁺.

Preparation #28: (R)-6-(2-(4-Acetyl-3-methylpiperazin-1-yl)pyrimidin-5-yl)-2-methyl-1H-indazol-3(2H)-one

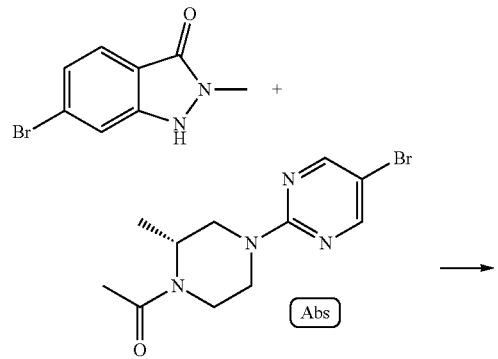

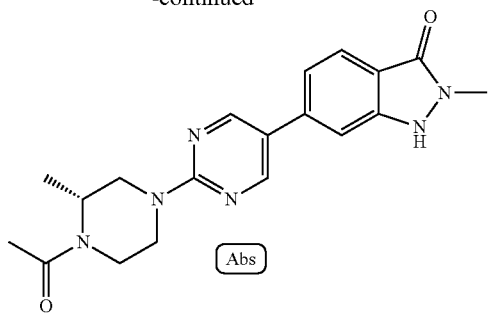

A mixture of bis(pinacolato)diboron (0.239 g, 0.942 mmol), (R)-1-(4-(5-bromopyrimidin-2-yl)-2-methylpiperazin-1-yl)ethanone (0.174 g, 0.581 mmol) (Preparation #16), KOAc (0.144 g, 1.47 mmol), PdCl₂(dppf) (0.026 g, 0.035 mmol), and 1,4-dioxane (5.03 mL) was purged with N₂ for about 10 min. then warmed to about 95° C. After about 2 h, the mixture was allowed to cool to ambient temperature and 6-bromo-2-methyl-1H-indazol-3(2H)-one (0.11 g, 0.48 mmol) (Preparation #1), Cs₂CO₃ (0.432 g, 1.33 mmol), and PdCl₂(PPh₃)₂ (0.026 g, 0.036 mmol) and water (1.3 mL) were added. The reaction mixture was purged with N₂ for about 10 min then heated to about 85° C. for about 1 h. The mixture was cooled to ambient temperature and water (5 mL) and EtOAc (10 mL) were added. The organic layer was separated and the aqueous layer was extracted with EtOAc (10 mL). The aqueous layer was acidified to about pH 4 with 1 N aq. HCl and EtOAc (5 mL) was added and the organic layer was separated. The organic layers were combined, dried over MgSO₄, filtered and concentrated under reduced pressure. The material was purified by flash chromatography on silica gel (0-10% MeOH/DCM) to afford the title product (0.135 g, 76%); LC/MS (Table A, Method i) R$_t$=0.75 min; MS m/z: 367 (M+H)⁺.

Preparation #29: 6-Chloro-2-methyl-1H-indazol-3(2H)-one

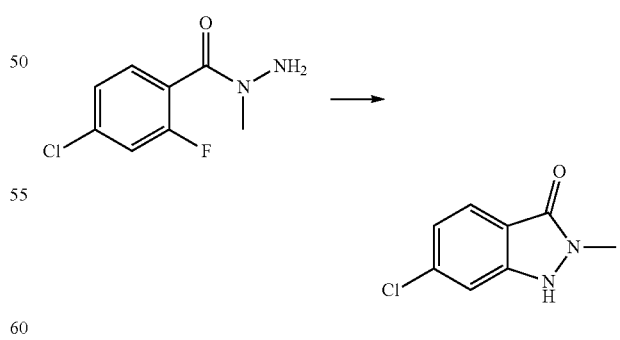

The reaction was performed using 4-chloro-2-fluoro-N-methylbenzohydrazide (prepared in a similar fashion to Example #1, step 1 using 4-chloro-2-fluorobenzoic acid) in a similar fashion to Example #1, step 2 to give the title product (57%); LC/MS (Table A, Method j) R$_t$=0.63 min; MS m/z: 183(M+H)⁺.

Preparation #30: (R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone

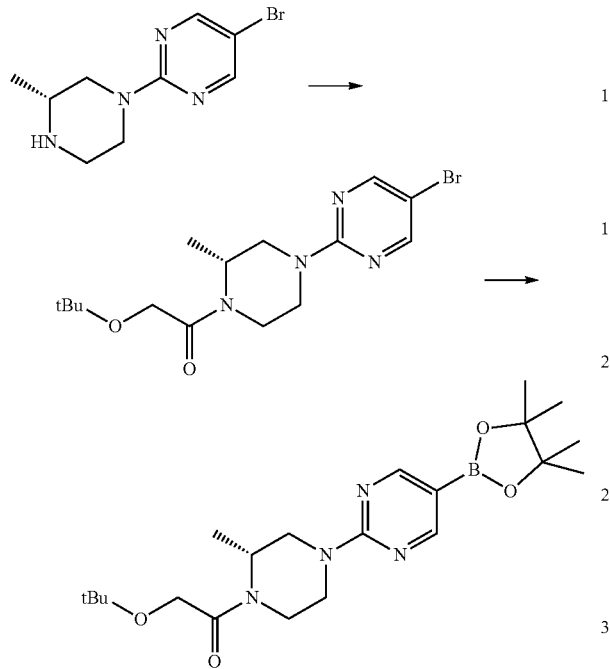

Step 1: (R)-1-(4-(5-Bromopyrimidin-2-yl)-2-methylpiperazin-1-yl)-2-(tert-butoxy)ethanone To a mixture of 2-(tert-butoxy)acetic acid (0.50 g, 3.8 mmol), (R)-5-bromo-2-(3-methylpiperazin-1-yl)pyrimidine, 2 hydrochloric acid (1.25 g, 3.78 mmol) (synthesized in a similar fashion to Example #3, step 1 from (R)-tert-butyl 4-(5-bromopyrimidin-2-yl)-3-methylpiperazine-1-carboxylate (synthesized in a similar fashion to Preparation #13, step 1 from (R)-ter-butyl 3-methylpiperazine-1-carboxylate)), 1H-benzo[d][1,2,3]triazol-1-ol hydrate (0.61 g, 3.97 mmol), and DIEA (3.3 mL, 19 mmol) in DCM (15 mL) was added 1-(3-dimethylaminopropyl)-3-ethylcarbodiimide hydrochloride (0.76 g, 4.0 mmol) and the mixture was stirred at rt for about 72 h. The mixture was washed with sat. aq. NaHCO$_3$ (2×10 mL), then with sat. aq. NH$_4$Cl (2×10 mL) and with water (10 mL). The organic layer was dried over sodium sulfate, filtered and concentrated. The residue was purified on silica gel using a gradient of 30-60% EtOAc/heptane. Product fractions were combined and concentrated to yield the title compound (1.27 g, 90%); LC/MS (Table A, Method i) R$_t$=1.45 min; MS m/z: 371/373(M+H)$^+$.

Step 2: (R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone The reaction was performed using (R)-1-(4-(5-bromopyrimidin-2-yl)-2-methylpiperazin-1-yl)-2-(tert-butoxy)ethanone in a similar fashion to Preparation #26, step 2 to give the title product (70%); LC/MS (Table A, Method i) R$_t$=1.63 min; MS m/z: 419 (M+H)$^+$.

Preparation #31: 6-Chloro-5-methoxy-2-methyl-1H-indazol-3(2H)-one

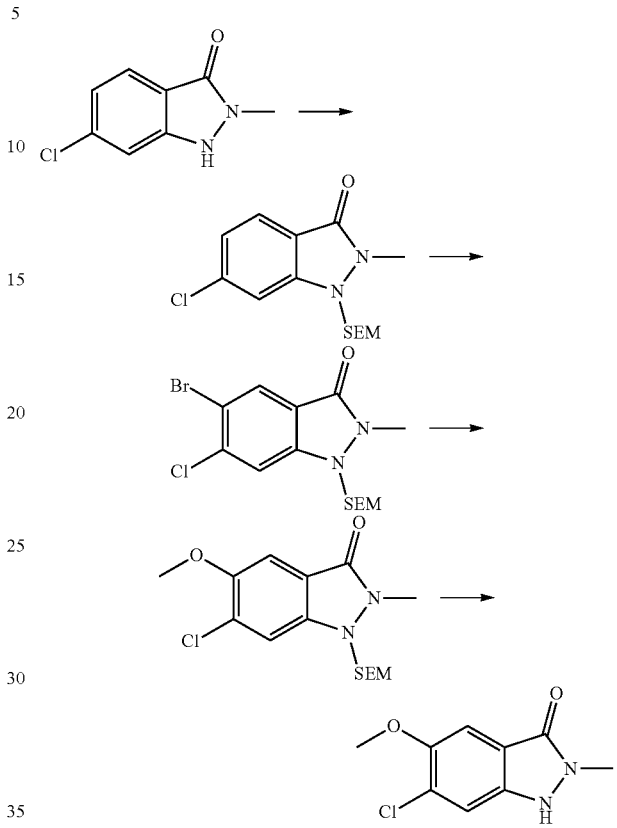

Step 1: 6-Chloro-2-methyl-1-((2-(trimethylsilyl)ethoxy)methyl)-1H-indazol-3(2H)-one A suspension of 6-chloro-2-methyl-1H-indazol-3(2H)-one (5.00 g, 27.4 mmol) (Preparation #29) in THF (100 mL) was treated with NaH (60% dispersion in mineral oil, 1.31 g, 32.9 mmol) under nitrogen. The reaction stirred until reaction subsided, then SEM-Cl (7.28 mL, 41.1 mmol) was added dropwise over about 5 min. The reaction was stirred for about 2.5 h. The mixture was partitioned between EtOAc (400 mL) and water (200 mL). The organic layer was washed with water (200 mL) and sat. aq. NaCl (200 mL). The organic layer was dried over Na$_2$SO$_4$, filtered and concentrated under reduced pressure. The residue was purified on silica gel using a gradient of 30-100% EtOAc in heptane. Product fractions were combined and concentrated to yield the title compound (7.32 g, 85%); LC/MS (Table A, Method i) R$_t$=1.61 min; MS m/z: 313(M+H)$^+$.

Step 2: 5-Bromo-6-chloro-2-methyl-1-((2-(trimethylsilyl)ethoxy)methyl)-1H-indazol-3(2H)-one A solution of 6-chloro-2-methyl-1-((2-(trimethylsilyl)ethoxy)methyl)-1H-indazol-3(2H)-one (0.90 g, 2.9 mmol) in DCM (15 mL) was treated with NBS (0.563 g, 3.16 mmol) and the suspension was stirred at rt for about 24 h. NBS (0.256 g, 1.44 mmol) was added in one portion and the mixture stirred about 18 h. The reaction mixture was partitioned between DCM (100 mL) and sat. aq. NaHCO$_3$ (75 mL). The aqueous phase was extracted with DCM (25 mL) and the combined organic layers were washed with sat. Aq. NaCl (50 mL), dried over Na$_2$SO$_4$, filtered, and concentrated under reduced pressure. The residue was purified on silica gel using a gradient of 0-50% EtOAc in heptane. Product fractions were combined and concentrated under reduced pressure to yield the title compound (0.74 g, 66%); LC/MS (Table A, Method k) R$_t$=0.89 min; MS m/z: 391 and 393(M+H)$^+$.

Step 3: 6-Chloro-5-methoxy-2-methyl-1-((2-(trimethylsilyl)ethoxy)methyl)-1H-indazol-3(2H)-one A mixture of 5-bromo-6-chloro-2-methyl-1-((2-(trimethylsilyl)ethoxy)methyl)-1H-indazol-3(2H)-one (0.74 g, 1.9 mmol), cesium carbonate (0.923 g, 2.83 mmol), Pd$_2$(dba)$_3$ (0.035 g, 0.038 mmol) and di-tert-butyl(2',4',6'-triisopropyl-[1,1'-biphenyl]-2-yl)phosphine (0.048 g, 0.11 mmol) was diluted with toluene (12 mL) and degassed with a stream of nitrogen. Methanol (0.400 mL, 9.89 mmol) was added and the mixture was heated at reflux under a balloon. After about 5 h, the reaction was cooled to rt, methanol (0.400 mL, 9.89 mmol) and di-tert-butyl(2',4',6'-triisopropyl-[1,1'-biphenyl]-2-yl)phosphine (0.048 g, 0.11 mmol) were added and the mixture was heated at reflux for about 3 h. The reaction was cooled to rt, diluted with EtOAc (30 mL) and filtered, rinsing with EtOAc (20 mL). Solvents were removed under reduced pressure and the residue was purified on silica gel using a gradient of 30-80% EtOAc in heptane. Product fractions were combined and concentrated to yield the title compound (0.176 g, 27%); LC/MS (Table A, Method i) R$_t$=1.62 min; MS m/z: 343(M+H)$^+$.

Step 4: 6-Chloro-5-methoxy-2-methyl-1H-indazol-3(2H)-one

To a solution of 6-chloro-5-methoxy-2-methyl-1-((2-(trimethylsilyl)ethoxy)methyl)-1H-indazol-3(2H)-one (170 mg, 0.496 mmol) in EtOH (3 mL) was added concentrated HCl (2 mL) and the mixture was heated to about 80° C. for about 10 min. The reaction was cooled to rt and concentrated under reduced pressure. The residue was treated with water (5 mL) and the product was collected by filtration rinsing with diethyl ether (3×5 mL). The solid was dried under vacuum to yield the title compound (0.095 g, 90%); LC/MS (Table A, Method i) R$_t$=0.65 min; MS m/z: 213(M+H)$^+$.

Preparation #32: 9-(Bromomethyl)-4,5-dihydrobenzo[f][1,4]thiazepin-3(2H)-one

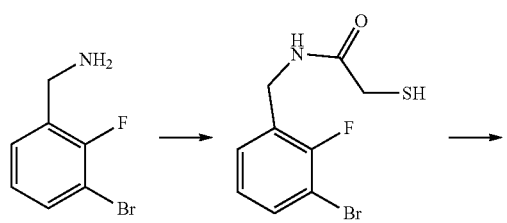

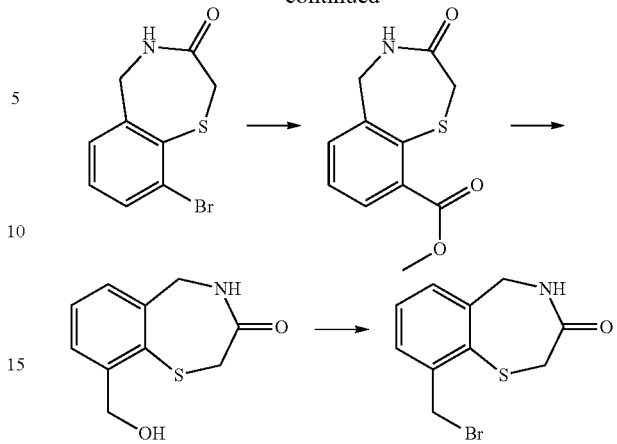

Step 1:
N-(3-Bromo-2-fluorobenzyl)-2-mercaptoacetamide (3-Bromo-2-fluorophenyl)methanamine (1.50 g, 7.35 mmol) was added to mercaptoacetic acid (0.613 mL, 8.82 mmol) under nitrogen. The mixture was heated to reflux using a Dean-Stark apparatus for about 18 h. The volatiles were evaporated in vacuo and the residue was purified on silica gel using a gradient of 10-50% EtOAc/heptane to afford the title product (1.53 g, 75%). $^1$H NMR (500 MHz, DMSO-d$_6$) δ 8.56 (t, J=5.8 Hz, 1H), 7.60 (ddd, J=8.2, 6.7, 1.7 Hz, 1H), 7.34 (dddd, J=7.7, 6.9, 1.7, 0.8 Hz, 1H), 7.14 (td, J=7.8, 0.9 Hz, 1H), 4.42-4.29 (m, 2H), 3.16 (s, 2H), 2.80 (s, 1H).

Step 2: 9-Bromo-4,5-dihydrobenzo[f][1,4]thiazepin-3(2H)-one

N-(3-Bromo-2-fluorobenzyl)-2-mercaptoacetamide (1.52 g, 5.46 mmol) was flushed with nitrogen and DMF (25 mL) was added. The reaction was cooled to about 0° C. before addition of potassium tert-butoxide (0.613 g, 5.46 mmol). After about 10 min, the mixture was warmed to ambient temperature and then to about 100° C. After about 16 h, the mixture was cooled to ambient temperature. Water (50 mL), 1 M aq. KHSO$_4$ (10 mL), and EtOAc (300 mL) were added. The organic layer was washed with water (2×50 mL), sat. aq. NaCl (20 mL), dried over MgSO$_4$ and evaporated in vacuo. The residue was purified on silica gel using a gradient of 20-50% (75% EtOAc/EtOH)/heptane. The appropriate fractions were combined and concentrated. The resulting solid was dissolved in a minimum amount of refluxing ethanol (~100 mL) and left to cool and crystallize. The solid was isolated by filtration and a second crop was obtained from the liquors in a same fashion affording the title product (366 mg, 26%). $^1$H NMR (400 MHz, DMSO-d$_6$) δ 8.20 (t, J=6.5 Hz, 1H), 7.52 (dd, J=8.0, 1.4 Hz, 1H), 7.17 (dd, J=7.6, 1.3 Hz, 1H), 6.99 (t, J=7.8 Hz, 1H), 4.43(d, J=6.6 Hz, 2H), 3.94 (s, 2H).

Step 3: Methyl 3-oxo-2,3,4,5-tetrahydrobenzo[f][1,4]thiazepine-9-carboxylate

9-Bromo-4,5-dihydrobenzo[f][1,4]thiazepin-3(2H)-one (100 mg, 0.387 mmol), Pd(dppf)Cl$_2$ (10 mg, 0.014 mmol), MeOH (10 mL), and TEA (0.108 mL, 0.775 mmol) were added to a 50 mL pressure vessel. The reactor was degassed with argon several times followed by carbon monoxide. The mixture was heated at about 100° C. for about 16 h at about 60 psi. The volatiles were evaporated in vacuo and the residue was purified on silica gel eluting with a gradient of 0-100% (75% EtOAc/EtOH)/heptane to afford the title product (49.7 mg, 54%). $^1$H NMR (500 MHz, DMSO-d$_6$) δ 8.14 (t, J=6.4 Hz, 1H), 7.67 (dd, J=7.8, 1.6 Hz, 1H), 7.34 (dd, J=7.5, 1.6 Hz, 1H), 7.15 (t, J=7.6 Hz, 1H), 4.45 (d, J=6.4 Hz, 2H), 3.83(s, 2H), 3.80 (s, 3H).

Step 4: 9-(Hydroxymethyl)-4,5-dihydrobenzo[f][1,4]thiazepin-3(2H)-one

A solution of methyl 3-oxo-2,3,4,5-tetrahydrobenzo[f][1,4]thiazepine-9-carboxylate (45 mg, 0.19 mmol) in THF (5 mL) was cooled to about −78° C. under nitrogen and LiAlH$_4$ (1 M in diethyl ether, 0.379 mL, 0.379 mmol) was added. The cold bath was allowed to warm to ambient temperature. After about 16 h, 10% aq. HCl (5 mL) was added dropwise and the mixture was extracted with EtOAc (2×25 mL). The organic layer was dried over sodium sulfate, filtered, and evaporated in vacuo. The residue was purified on silica gel (0.5-25% MeOH/DCM) to afford the title product (12 mg, 30%, 90% purity). $^1$H NMR (400 MHz, DMSO-d$_6$) δ 8.14 (t, J=6.2 Hz, 1H), 7.39 (dd, J=7.3, 1.8 Hz, 1H), 7.18-7.00 (m, 2H), 5.28 (t, J=5.5 Hz, 1H), 4.42 (dd, J=22.3, 6.0 Hz, 4H), 3.84 (s, 2H).

Step 5: 9-(Bromomethyl)-4,5-dihydrobenzo[f][1,4]thiazepin-3(2H)-one 9-(Hydroxymethyl)-4,5-dihydrobenzo[f][1,4]thiazepin-3(2H)-one (100 mg, 0.478 mmol), AcOH (1 mL) and hydrobromic acid (33% in AcOH, 1.17 g, 4.78 mmol) were stirred at ambient temperature under nitrogen for about 1 h. The reaction was diluted with toluene (10 mL) and evaporated in vacuo. EtOAc (30 mL) was added. The solution was washed with sat. aq. sodium bicarbonate (2×10 mL), water (5 mL), dried over MgSO$_4$ and evaporated in vacuo to give the title compound (80 mg, 62%); LC/MS (Table A, Method j) R$_t$=0.99 min; MS m/z: 272 and 274 (M+H)$^+$ Preparation #33: (R)-1-(2-(Difluoromethoxy)benzyl)-2-methyl-6-(2-(3-methylpiperazin-1-yl)pyrimidin-5-yl)-1H-indazol-3(2H)-one The reaction was performed using (R)-5-bromo-2-(2-methylpiperazin-1-yl)pyrimidine dihydrochloride (synthesized in a similar fashion to Example #3, step 1 from (R)-tert-butyl 4-(5-bromopyrimidin-2-yl)-3-methylpiperazine-1-carboxylate (synthesized in a similar fashion to Preparation #13, step 1 from (R)-tert-butyl 3-methylpiperazine-1-carboxylate)) and 1-(2-(difluoromethoxy)benzyl)-2-methyl-6-(4,4,5,5-tetramethyl-1,3,2-dioxaborolan-2-yl)-1H-indazol-3(2H)-one (Preparation #4, step 2) in a similar fashion to Example #14, step 4 to afford the title product (0.62 g, 67%); LC/MS (Table A, Method i) R$_t$=0.83 min; MS m/z: 481 (M+H)$^+$.

Preparation #34: 1-(4-(5-Bromopyrimidin-2-yl)piperazin-1-yl)-2-hydroxyethanone

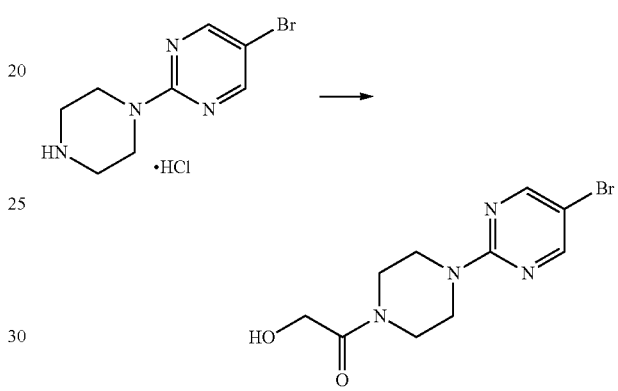

The reaction was performed using 5-bromo-2-(piperazin-1-yl)pyrimidine, hydrochloric acid (synthesized in a similar fashion to Example #3, step 1 from 1-(4-(5-bromopyrimidin-2-yl)piperazin-1-yl)-3,3-dimethylbutan-1-one and glycolic acid) in a similar fashion to Preparation #15 to afford the title product (0.20 g, 52%); LC/MS (Table A, Method i) R$_t$=0.79 min; MS m/z: 301 and 303(M+H)$^+$.

Preparation #35: (1-Methyl-4-(trifluoromethyl)-1H-pyrazol-3-yl)methanol

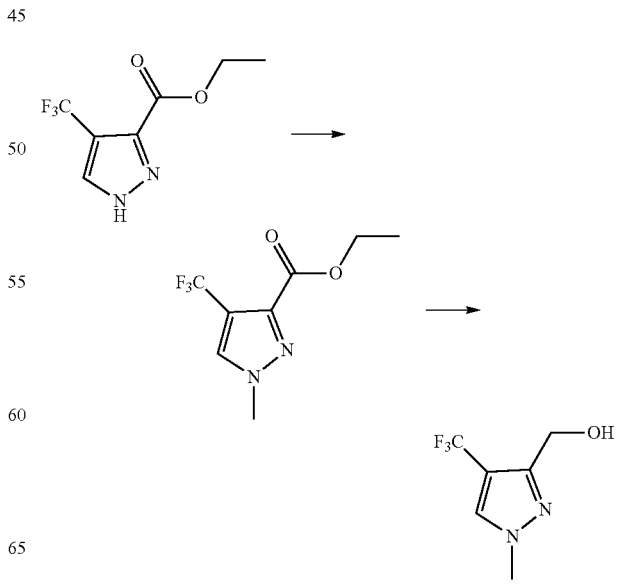

Step 1: Ethyl 1-methyl-4-(trifluoromethyl)-1H-pyrazole-3-carboxylate

To a solution of ethyl 4-(trifluoromethyl)-1H-pyrazole-3-carboxylate (0.77 mg, 3.7 mmol) (WO2007/045868) in THF (23 mL) under $N_2$ was added sodium hydride (60% dispersion in mineral oil) (0.178 g, 4.44 mmol) and stirred for about 10 min at ambient temperature. MeI (0.463 mL, 7.40 mmol) was added. After about 1 h, sat. aq. $NH_4Cl$ (5 mL) and EtOAc (20 mL) was added. The organic layer was separated and the aqueous layer was back extracted with EtOAc (10 mL). The combined organic layers were dried over $MgSO_4$, filtered and concentrated under reduced pressure. The material was purified via flash chromatography on silica gel (0-60% EtOAc/heptane). The appropriate fractions were collected and concentrated under reduced pressure to provide the title product (0.695 g, 85%); LC/MS (Table A, Method i) $R_t$=1.02 min.; MS m/z: 223(M+H)$^+$.

Step 2: (1-Methyl-4-(trifluoromethyl)-1H-pyrazol-3-yl)methanol

The reaction was performed with ethyl 1-methyl-4-(trifluoromethyl)-1H-pyrazole-3-carboxylate (0.695 g, 3.13 mmol) in a similar fashion to Preparation #32, step 4 to give the title compound (0.453 g, 76%); $^1$H NMR (400 MHz, DMSO-d$_6$) δ 8.21 (s, 1H), 5.12 (t, J=5.6 Hz, 1H), 4.44 (d, J=5.5 Hz, 2H), 3.83(s, 3H).

Preparation #36: (S)-1-(4-(5-Bromopyrimidin-2-yl)-3-methylpiperazin-1-yl)ethanone

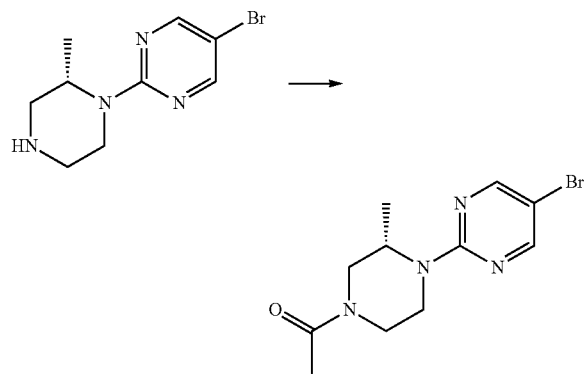

The title compound was prepared in a manner similar to Example #3, Steps 1 and 2 from (S)-tert-butyl 4-(5-bromopyrimidin-2-yl)-3-methylpiperazine-1-carboxylate (prepared in a similar manner Example #2 from 5-bromo-2-chloropyrimidine and (S)-tert-butyl 3-methylpiperazine-1-carboxylate); LC/MS (Table A, Method i) $R_t$=2.34 min; MS m/z: 299 and 301 (M+H)$^+$.

Preparation #37: 6-Bromo-1-(2-(difluoromethoxy)benzyl)-2-(difluoromethyl)-1H-indazol-3(2H)-one

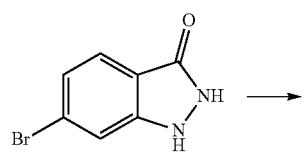

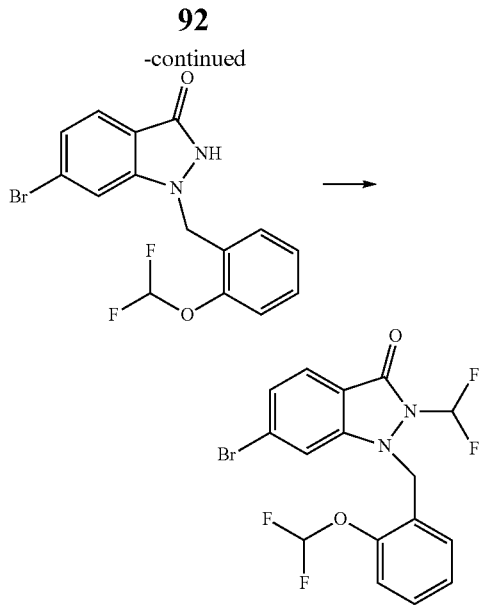

Step 1: 6-Bromo-1-(2-(difluoromethoxy)benzyl)-1H-indazol-3(2H)-one

6-Bromo-1-(2-(difluoromethoxy)benzyl)-1H-indazol-3(2H)-one was prepared in a similar fashion to Preparation #4, step 1 using 6-bromo-1H-indazol-3(2H)-one and 1-(bromomethyl)-2-(difluoromethoxy)benzene to give the title compound (1.10 g, 32%); LC/MS (Table A, Method e) $R_t$=2.34 min; MS m/z: 369 and 371 (M+H)$^+$.

Step 2: 6-Bromo-1-(2-(difluoromethoxy)benzyl)-2-(difluoromethyl)-1H-indazol-3(2H)-one A solution of 6-bromo-1-(2-(difluoromethoxy)benzyl)-1H-indazol-3(2H)-one (0.750 g, 2.03 mmol) and cesium carbonate (6.62 g, 20.3 mmol) in DMF (6 mL) at about 0° C. was added diethyl (bromodifluoromethyl)phosphonate (1.09 g, 4.06 mmol) dropwise. The ice bath was allowed to melt and the reaction was stirred at rt for about 2 days. The reaction was partitioned between EtOAc (50 mL) and sat. aq. NaCl (100 mL). The organic layer was dried over $Na_2SO_4$, filtered and concentrated under reduced pressure. The residue was purified on silica gel using 0-10% EtOAc in heptanes to give the title compound (0.105 g, 12%); LC/MS (Table A, Method e) $R_t$=1.82 min; MS m/z: 219 and 221 (M+H)$^+$.

Preparation #38: 6-Bromo-7-fluoro-2-methyl-1H-indazol-3(2H)-one

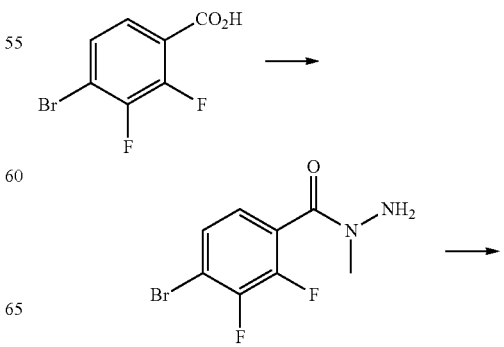

93

-continued

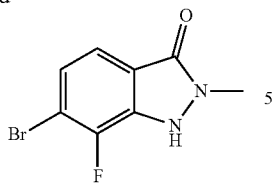

Step 1: 4-Bromo-2,3-difluoro-N-methylbenzohydrazide

4-Bromo-2,3-difluoro-N-methylbenzohydrazide was prepared in a similar fashion to Preparation #1, step 1 using 4-bromo-2,3-difluorobenzoic acid to give the title compound (4.29 g, 77%); LC/MS (Table A, Method i) $R_t$=0.85 min; MS m/z: 265 and 267 (M+H)$^+$.

Step 2: 6-Bromo-7-fluoro-2-methyl-1H-indazol-3(2H)-one

6-Bromo-7-fluoro-2-methyl-1H-indazol-3(2H)-one was prepared in a similar fashion to Preparation #1, step 2 using 4-bromo-2,3-difluoro-N-methylbenzohydrazide to give the title compound (3.20 g, 81%); LC/MS (Table A, Method e) $R_t$=1.49 min; MS m/z: 245 and 247 (M+H)$^+$.

Preparation #39: Methyl 3-((6-bromo-2-methyl-3-oxo-2,3-dihydro-1H-indazol-1-yl)methyl)-4-(difluoromethoxy)benzylcarbamate

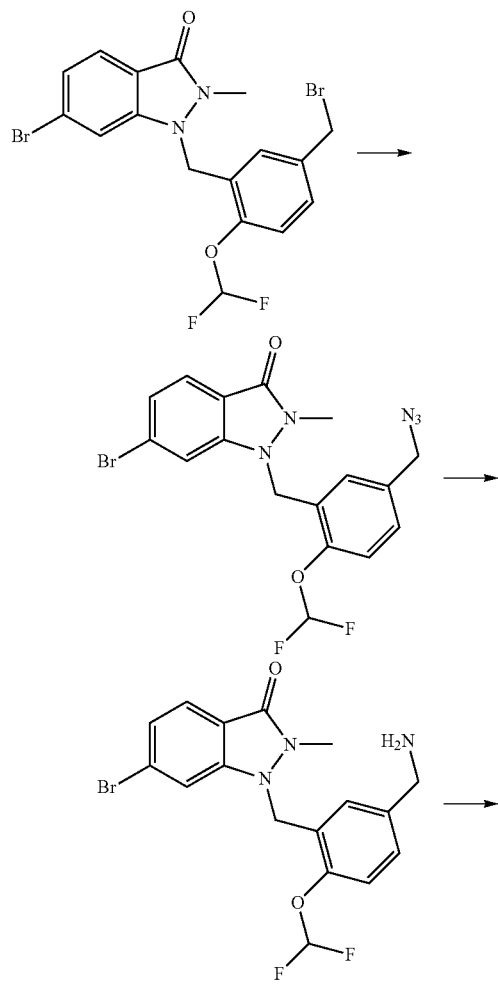

94

-continued

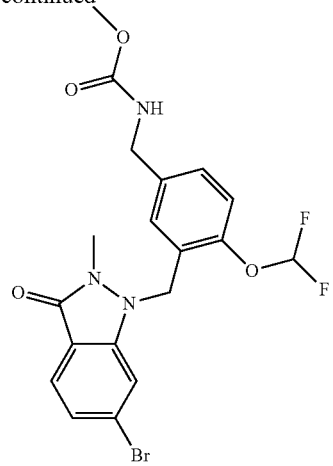

Step 1: 1-(5-(Azidomethyl)-2-(difluoromethoxy)benzyl)-6-bromo-2-methyl-1H-indazol-3(2H)-one A flask was charged with sodium azide (30 mg, 0.5 mmol), 6-bromo-1-(5-(bromomethyl)-2-(difluoromethoxy)benzyl)-2-methyl-1H-indazol-3(2H)-one (192 mg, 0.403 mmol) (Preparation #20, step 3) and DMF (2 mL) at room temperature. After about 1 h, the mixture was diluted with H$_2$O (100 mL) and extracted with 10% MeOH in CH$_2$Cl$_2$ (3×20 mL). The organic layer was dried over Na$_2$SO$_4$, filtered, and concentrated under reduced pressure to afford the title product (155 mg, 88%); LC/MS (Table A, Method i) $R_t$=1.55 min; MS m/z: 438 and 440 (M+H)$^+$.

Step 2: 1-(5-(Aminomethyl)-2-(difluoromethoxy)benzyl)-6-bromo-2-methyl-1H-indazol-3(2H)-one A flask was charged with 1-(5-(azidomethyl)-2-(difluoromethoxy)benzyl)-6-bromo-2-methyl-1H-indazol-3(2H)-one (155 mg, 0.354 mmol), THF (2 mL), H$_2$O (0.2 mL) and trimethylphosphine (1M in toluene, 0.4 mL, 0.4 mmol) at room temperature. After about 1 h, the solution was diluted with 10% MeOH in CH$_2$Cl$_2$ (20 mL), dried over Na$_2$SO$_4$, filtered, and concentrated under reduced pressure to afford the title product (140 mg, 96%); LC/MS (Table A, Method i) $R_t$=0.88 min; MS m/z: 412 and 414 (M+H)$^+$.

Step 3: Methyl 3-((6-bromo-2-methyl-3-oxo-2,3-dihydro-1H-indazol-1-yl)methyl)-4-(difluoromethoxy)benzylcarbamate A flask was charged with 1-(5-(aminomethyl)-2-(difluoromethoxy)benzyl)-6-bromo-2-methyl-1H-indazol-3(2H)-one (140 mg, 0.34 mmol), CH$_2$Cl$_2$ (2 mL), TEA (0.1 mL, 0.7 mmol) followed by triphosgene (111 mg, 0.374 mmol) at room temperature. After about 1 h, MeOH (0.5 mL) was added. After about 2 h, the volatiles were removed under reduced pressure. The residue was purified by flash chromatography on silica gel (0-10% MeOH/CH$_2$Cl$_2$) to afford the title product (107 mg, 67%); LC/MS (Table A, Method i) $R_t$=1.27 min; MS m/z: 470 and 472 (M+H)$^+$.

Preparation #40: 6-Bromo-1-(2-(difluoromethoxy)benzyl)-5-fluoro-2-methyl-1H-indazol-3(2H)-one

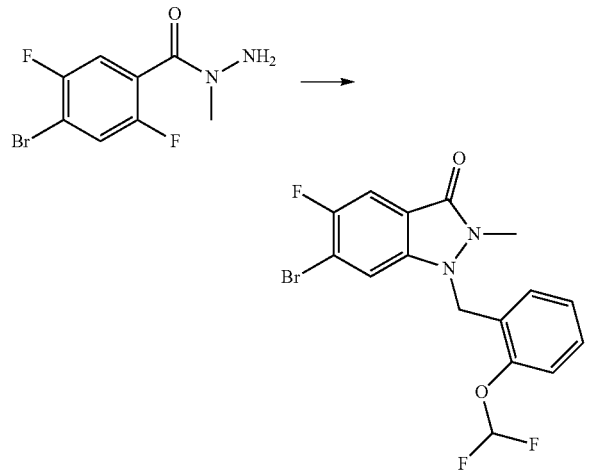

Potassium tert-butoxide (10.3 g, 92 mmol) was added in one portion to a solution of 4-bromo-2,5-difluoro-N-methylbenzohydrazide (11.0 g, 41.5 mmol) (prepared in a similar fashion to Example #17, step 1 using 4-bromo-2,5-difluorobenzoic acid) and DMF (220 mL). The mixture was warmed to about 85° C. After about 10 min, the reaction vessel was transferred to an ice bath. After about 15 min, 2-(difluoromethoxy)benzyl bromide (7.50 mL, 49.2 mmol) was added dropwise over about 4 min. The ice bath was removed. After about 90 min, AcOH (0.600 mL, 10.5 mmol) was added to adjust the pH to about 5. The volatiles were mostly removed under reduced pressure at about 60° C. Water (250 mL) and DCM (250 mL) were added. The layers were separated and the aqueous layer was extracted with DCM (2×100 mL). The combined organic layers were dried over Na$_2$SO$_4$, filtered, and concentrated. The residue was purified by flash chromatography on silica gel eluding with a gradient of 0-25% EtOAc/DCM The appropriate fractions were collected and concentrated under reduced pressure to afford the title compound (8.75 g, 53%); LC/MS (Table A, Method i) R$_t$=1.45 min; MS m/z: 401 and 403(M+H)$^+$.

Preparation #41: (S)-2-((R)-4-(5-(1-(2-(Difluoromethoxy)benzyl)-2-methyl-1-oxo-2,3-dihydro-1H-indazol-6-yl)pyrimidin-2-yl)-2-methylpiperazin-1-yl)-2-oxoethyl 2-((tert-butoxycarbonyl)amino)-3-methylbutanoate

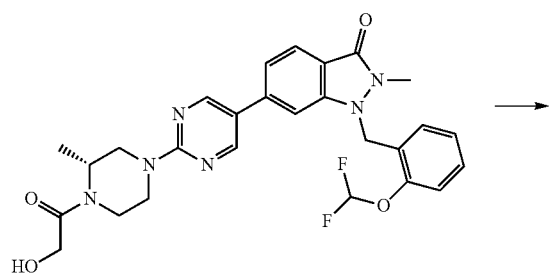

(R)-1-(2-(Difluoromethoxy)benzyl)-6-(2-(4-(2-hydroxyacetyl)-3-methylpiperazin-1-yl)pyrimidin-5-yl)-2-methyl-1H-indazol-3(2H)-one (150 mg, 0.279 mmol), (S)-2-((tert-butoxycarbonyl)amino)-3-methylbutanoic acid (73 mg, 0.33 mmol), DMAP (17 mg, 0.139 mmol), and 1-(3-dimethylaminopropyl)-3-ethylcarbodiimide hydrochloride (80 mg, 0.42 mmol) were combined in DMF (2.8 mL). TEA (97 µL, 0.70 mmol) was added, and the reaction was allowed to stir for about 20 h. Additional 1-(3-dimethylaminopropyl)-3-ethylcarbodiimide hydrochloride (80 mg, 0.42 mmol) and (S)-2-((tert-butoxycarbonyl)amino)-3-methylbutanoic acid (73 mg, 0.33 mmol) were added and the reaction mixture was allowed to stir for about 28 h. The reaction was partitioned between EtOAc (15 mL) and water (15 mL). The aqueous layer was back-extracted with additional EtOAc (15 mL), then the combined organic layers were washed sequentially with sat. aq. NH$_4$Cl (20 mL), sat. aq. NaHCO$_3$ (20 mL), and sat. aq. NaCl (20 mL). The organic layer was dried over MgSO$_4$, filtered, and concentrated in vacuo. The residue was purified via flash chromatography (0-5% MeOH in DCM). Concentration of the relevant fractions yielded the title compound (132 mg, 64%); LC/MS (Table A, Method i) R$_t$=1.75 min; MS m/z: 738 (M+H)$^+$.

Preparation #42: 3-Iodo-1-methylpiperidin-2-one

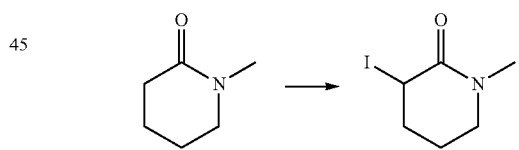

1-Methylpiperidin-2-one (0.97 mL, 8.8 mmol) was dissolved in anhydrous toluene (33 mL) and cooled to about 0° C. Tetramethylethylenediamine (4.00 mL, 26.5 mmol) was added and the solution was stirred for about 5 min, then chlorotrimethylsilane (2.26 mL, 17.7 mmol) was added dropwise. The solution was allowed to stir about 30 min at about 0° C., then iodine (2.47 g, 9.72 mmol) was added in one portion. The flask was removed from the ice bath and allowed to stir while warming to rt for about 2 h. The reaction was partitioned between sat. aq. sodium thiosulfate (50 mL) and EtOAc (30 mL). The organic layer was washed with sat. aq. sodium thiosulfate (20 mL) and sat. aq. NaCl (20 mL). The organic layer was dried over MgSO$_4$, vacuum filtered, and concentrated in vacuo. Further purification via silica gel chromatography (30-100% EtOAc in heptane) isolated the title compound (1.31 g, 62%); LC/MS (Table A, Method i) R$_t$=0.45 min; MS m/z: 240 (M+H)$^+$.

Preparation #43: 3-((4-Chloro-3-(hydroxymethyl)phenyl)amino)-1-methylpiperidin-2-one

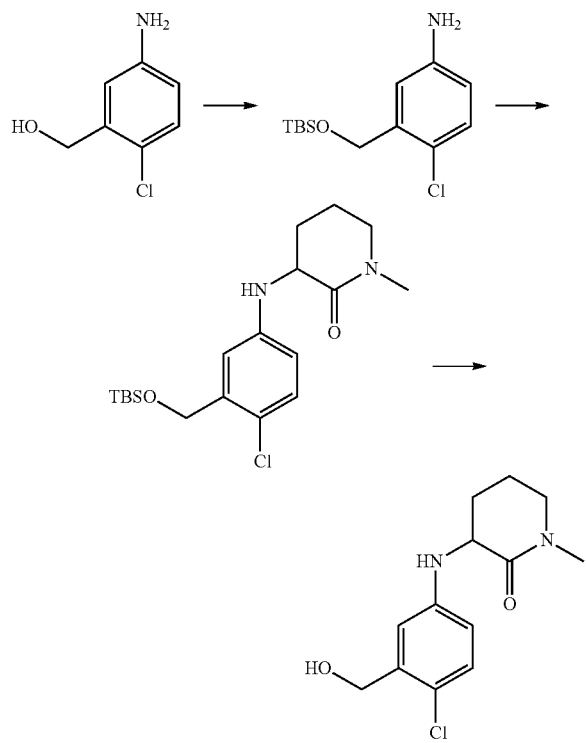

Step 1: (3-(((tert-Butyldimethylsilyl)oxy)methyl)-4-chloroaniline)

(5-Amino-2-chlorophenyl)methanol (1.50 g, 9.52 mmol), imidazole (0.97 g, 14 mmol) and tert-butyldimethylsilyl chloride (1.58 g, 10.5 mmol) were combined in anhydrous DMF (15.9 mL) and cooled to about 0° C. The reaction was allowed to stir for about 16 h while warming to rt. Additional tert-butyldimethylsilyl chloride (0.70 g, 4.6 mmol) was added in two equal portions over about 3 h, then stirred for about an additional 3 h at rt. The reaction was quenched via the addition of sat. aq. NH$_4$Cl (45 mL) then extracted with EtOAc (3×20 mL). The organic layer was washed with water (2×50 mL) and sat. aq. NaCl (50 mL), then dried over MgSO$_4$, filtered, and concentrated in vacuo. Further purification via flash chromatography (0-30% EtOAc in heptane) isolated the title compound (2.37 g, 92%); LC/MS (Table A, Method k) R$_t$=1.34 min; MS m/z: 272 (M+H)$^+$.

Step 2: (3-((3-(((tert-Butyldimethylsilyl)oxy)methyl)-4-chlorophenyl)amino)-1-methylpiperidin-2-one)

A solution of 3-(((tert-butyldimethylsilyl)oxy)methyl)-4-chloroaniline (682 mg, 2.51 mmol) in anhydrous THF (2 mL) was added to an oven-dried vial and cooled to about 0° C. A solution of LiHMDS (1 M in THF, 4.18 mL, 4.18 mmol) was added dropwise, then the reaction was stirred for approximately 20 min at about 0° C. A solution of 3-iodo-1-methylpiperidin-2-one (500 mg, 2.09 mmol) (Preparation #42) in anhydrous THF (2 mL) was added dropwise. The reaction was diluted with additional anhydrous THF (3 mL) and allowed to stir about 30 min while warming to rt. The reaction was quenched by the addition of cold sat. aq. NH$_4$Cl solution (20 mL) and extracted into EtOAc (2×10 mL). The organic layer was washed with water (20 mL) and sat. aq. NaCl (20 mL), then dried over MgSO$_4$, filtered, and concentrated in vacuo. The residue was further purified via flash chromatography (0-70% EtOAc in heptane) to isolate the title compound (609 mg, 76%); LC/MS (Table A, Method k) R$_t$=1.40 min; MS m/z 383(M+H)$^+$.

Step 3: (3-((4-Chloro-3-(hydroxymethyl)phenyl)amino)-1-methylpiperidin-2-one)

3-((3-(((tert-Butyldimethylsilyl)oxy)methyl)-4-chlorophenyl)amino)-1-methylpiperidin-2-one (694 mg, 1.81 mmol) was dissolved in anhydrous THF (9 mL) and cooled to about 0° C. Tetrabutylammonium fluoride (1.0 M in THF, 3.63 mL, 3.63 mmol) was added and the reaction was stirred for about 2 h at about 0° C. The reaction mixture was concentrated in vacuo and partitioned between EtOAc (20 mL) and sat. aq. NaCl (20 mL). The organic layer was washed with sat. aq. NaCl (20 mL), dried over MgSO$_4$, filtered, and concentrated in vacuo. Purification via silica gel chromatography (50-100% EtOAc in heptane) isolated the title compound (450 mg, 92%); LC/MS (Table A, Method i) R$_t$=0.83 min; MS m/z: 269 (M+H)$^+$.

Preparation #44: 3-((4-Chloro-3-(hydroxymethyl)phenyl)amino)-1-methylpyrrolidin-2-one

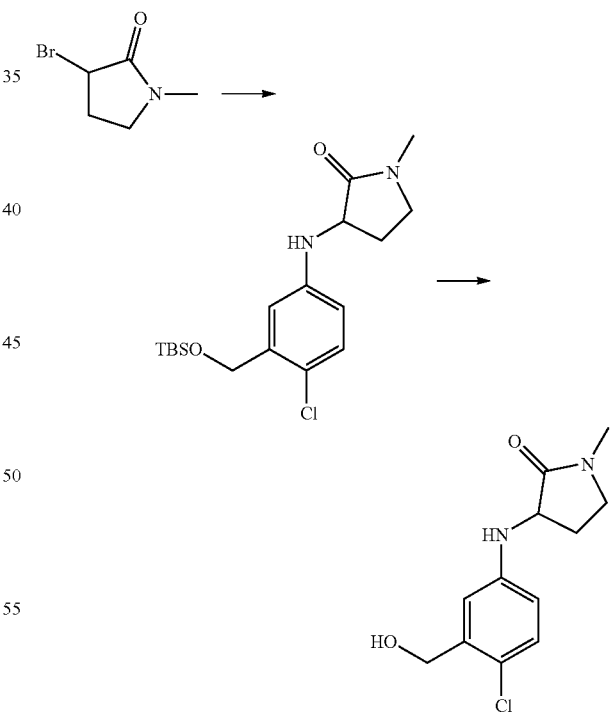

Step 1: 3-((3-(((tert-Butyldimethylsilyl)oxy)methyl)-4-chlorophenyl)amino)-1-methylpyrrolidin-2-one The title compound was prepared in a manner similar to Preparation #43, step 2, from 3-bromo-1-methylpyrrolidin-2-one (synthesized in a manner similar to preparation found in WO2008050101 A2) and 3-(((tert-butyldimethylsilyl)oxy)methyl)-4-chloroaniline (Preparation #43, step 1) (67%); LC/MS (Table A, Method i) $R_t$=2.05 min; MS m/z: 369 (M+H)$^+$.

Step 2: 3-((4-Chloro-3-(hydroxymethyl)phenyl)amino)-1-methylpyrrolidin-2-one

The title compound was synthesized in a manner similar to Preparation #43, step 3, from 3-((3-(((tert-butyldimethylsilyl)oxy)methyl)-4-chlorophenyl)amino)-1-methylpyrrolidin-2-one (90%); LC/MS (Table A, Method i) $R_t$=0.74 min; MS m/z: 255 (M+H)$^+$.

Preparation #45: 1-(7-Chloroimidazo[1,2-b]pyridazin-3-yl)ethanol

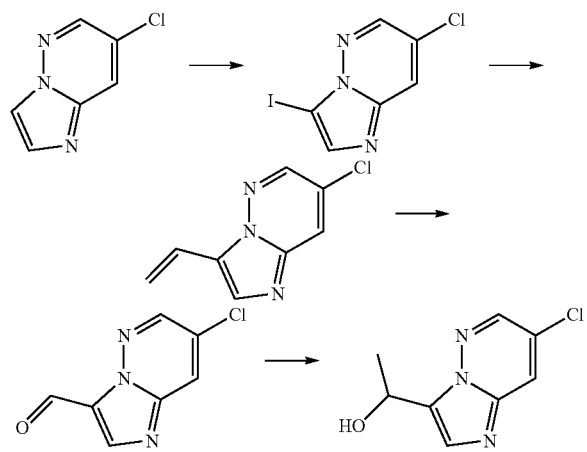

Step 1: 7-Chloro-3-iodoimidazo[1,2-b]pyridazine

A mixture of 7-chloroimidazo[1,2-b]pyridazine (900 mg, 5.86 mmol) and N-iodosuccinimide (1.58 g, 7.03 mmol) in MeCN (25 mL) was heated to about 60° C. for approximately 16 h. The reaction was cooled to rt and partitioned between DCM (200 mL) and sat. aq. sodium thiosulfate (100 mL). The organic layer was washed with sat. aq. NaHCO$_3$ (100 mL) and sat. aq. NaCl (50 mL), dried over Na$_2$SO$_4$, filtered, and concentrated under reduced pressure to give the title compound (1.63 g, 100%); LC/MS (Table A, Method i) $R_t$=0.95 min; MS m/z=280 (M+H)$^+$.

Step 2: 7-Chloro-3-vinylimidazo[1,2-b]pyridazine

The compound was synthesized in a manner similar to Example #14, step 4 from 7-chloro-3-iodoimidazo[1,2-b]pyridazine (79%); LC/MS (Table A, Method h) $R_t$=1.02 min; MS m/z=180 (M+H)$^+$.

Step 3: 7-Chloroimidazo[1,2-b]pyridazine-3-carbaldehyde

The compound was synthesized in a manner similar to Example #4, step 1 from 7-chloro-3-vinylimidazo[1,2-b]pyridazine (76%); LC/MS (Table A, Method j) $R_t$=0.32 min; MS m/z=182 (M+H)$^+$.

Step 4: 1-(7-Chloroimidazo[1,2-b]pyridazin-3-yl)ethanol

7-Chloroimidazo[1,2-b]pyridazine-3-carbaldehyde (640 mg, 3.52 mmol) was dissolved in anhydrous THF (20 mL) and cooled to about −25 to −30° C., then methylmagnesium bromide (3.0 M in diethyl ether, 2.70 mL, 8.11 mmol) was added dropwise while maintaining a temperature below about −10° C. The reaction was allowed to stir while warming to rt over about 30 min, then the reaction was quenched with a combination of ice water (20 mL), sat. aq. NH$_4$Cl (20 mL), and sat. aq. NaCl (20 mL). The resulting suspension was extracted with EtOAc (2×30 mL). The aqueous layer was saturated with NaCl and extracted with additional EtOAc (2×30 mL). The combined organic layers were dried over MgSO$_4$, filtered, and concentrated under reduced pressure. Further purification via flash chromatography (0-10% MeOH in DCM) isolated the title compound (218 mg, 31%); LC/MS (Table A, Method j) $R_t$=0.52 min; MS m/z=198 (M+H)$^+$.

Preparation #46: (R)-Hexahydroimidazo[1,5-a]pyrazin-3(2H)-one and (S)-hexahydroimidazo[1,5-a]pyrazin-3(2H)-one

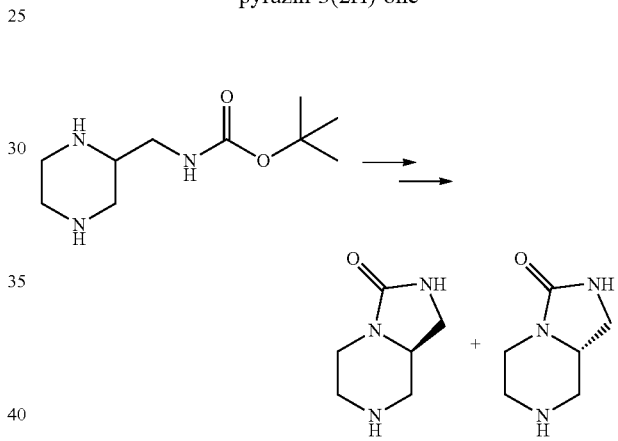

A solution of tert-butyl (piperazin-2-ylmethyl)carbamate (WO2006014580A1) (21 g, 98 mmol) and DIEA (85 mL, 490 mmol) in DCM (420 mL) was cooled to about 0° C. before benzyl chloroformate (41.8 mL, 293 mmol) was added drop-wise over about 50 min. The mixture was allowed to warm to rt and then was added to sat. aq. NH$_4$Cl (150 mL). The layers were separated and the aqueous layer was extracted with DCM (100 mL). The combined organic layers were dried over Na$_2$SO$_4$, filtered and concentrated under reduced pressure to give dibenzyl 2-(((tert-butoxycarbonyl)amino)methyl)piperazine-1,4-dicarboxylate (56.5 g, 96.0 mmol) which was used without further purification. This product was taken up in 1,4-dioxane (250 mL) and the resulting suspension was filtered through a frit funnel and washed with 1,4-dioxane (~25 mL). The combined filtrate was stirred and then treated with HCl (4 M in 1,4-dioxane) (120 mL, 479 mmol) and subsequently heated to about 70° C. for about 45 min. The slurry was allowed to cool to ambient temperature and the mixture was quenched with sat. aq. NaHCO$_3$ (500 mL). The mixture was extracted with EtOAc (500 mL). The aqueous layer was then neutralized with 1 M aq. NaOH (500 mL) and extracted with EtOAc (500 mL). The combined organic layers were dried over Na$_2$SO$_4$, filtered and concentrated under reduced pressure. The crude mixture was purified on silica gel (0-20% MeOH in DCM) to give dibenzyl 2-(aminomethyl)piperazine-1,4-dicarboxylate (7.1 g, 18%) which was used directly in the next step. To a suspension of dibenzyl 2-(aminomethyl)piperazine-1,4-dicarboxylate (4.70 g, 12.3 mmol) in THF (120 mL) at about ambient temperature was added sodium tert-butoxide (2 M in THF) (9.19 mL, 18.4 mmol) and the resulting solution was stirred for about 2 h. A solution of sat. aq. NH$_4$Cl and water (1:1) was added, and the aqueous layer was extracted twice with EtOAc. The combined organic layers were dried over Na$_2$SO$_4$, filtered and concentrated under reduced pressure. The resulting material was dissolved in EtOAc and the product precipitated by adding heptane. The solid was collected by filtration and dried under vacuum to give benzyl 3-oxohexahydroimidazo[1,5-a]pyrazine-7(1H)-carboxylate (2.9 g, 76%). Chiral separation according to Table B, method f gave, in order of elution, benzyl (S)-3-oxohexahydroimidazo[1,5-a]pyrazine-7(1H)-carboxylate (1.60 g) and benzyl (R)-3-oxohexahydroimidazo[1,5-a]pyrazine-7(1H)-carboxylate (1.51 g). A 50 mL Parr reactor was charged with benzyl (S)-3-oxohexahydroimidazo[1,5-a]pyrazine-7(1H)-carboxylate (1.50 g, 5.45 mmol), 10% Pd(OH)$_2$/C (42.6 weight % in water) (0.352 g) and THF (16.5 mL). The mixture was stirred at about 50° C. under about 50 psi of hydrogen for about 6 h, after which the suspension was filtered and the filter cake washed with THF and MeOH. The combined filtrates were concentrated to give (R)-hexahydroimidazo[1,5-a]pyrazin-3(2H)-one (0.75 g); SFC/MS (Table C, Method c) R$_t$=4.66 min; MS m/z: 140 (M−H)$^−$. Benzyl (S)-3-oxohexahydroimidazo[1,5-a]pyrazine-7(1H)-carboxylate (1.40 g, 5.09 mmol) was used in the same fashion to prepare (S)-hexahydroimidazo[1,5-a]pyrazin-3(2H)-one (0.60 g); SFC/MS (Table C, Method c) R$_t$=4.83 min; MS m/z: 140 (M−H)$^−$.

Preparation #47: 6-(2-Chloropyrimidin-5-yl)-2-methyl-1-((5-methyl-2-(trifluoromethyl)pyridin-3-yl)methyl)-1,2-dihydro-3H-indazol-3-one Step 1: (5-Methyl-2-(trifluoromethyl)pyridin-3-yl)methanol Ethyl 5-methyl-2-(trifluoromethyl)nicotinate (0.495 g, 2.12 mmol) (prepared as described in European Journal of Organic Chemistry, 2013(19), 4131-4145) in EtOH (10 mL) was heated to about 50° C. and treated with NaBH$_4$ (0.360 g, 9.54 mmol) added in three equal portions over about 90 min. The reaction was concentrated under reduced pressure and the residue was partitioned between EtOAc (15 mL) and water (10 mL). After separating the layers, the aqueous phase was extracted with EtOAc (2×5 mL). The combined organic phases were washed with sat. aq. NaCl (25 mL), dried over Na$_2$SO$_4$, filtered, and concentrated via rotary evaporation. The residue was purified on silica gel using a gradient of 0-100% EtOAc in heptane to give the title product (0.290 g, 71%). (Table A, Method e) R$_t$=1.55 min; MS m/z: 192 (M+H)$^+$.

Step 2: 3-(Bromomethyl)-5-methyl-2-(trifluoromethyl)pyridine

The reaction was performed using (5-methyl-2-(trifluoromethyl)pyridin-3-yl)methanol and PBr$_3$ in a similar fashion to Preparation #3, step 2 to give the title product (63%); $^1$H NMR (400 MHz, CDCl$_3$) δ 8.44 (s, 1H), 7.74 (s, 1H), 4.59 (s, 2H), 2.44 (s, 3H).

Step 3: 6-(2-Chloropyrimidin-5-yl)-2-methyl-1-((5-methyl-2-(trifluoromethyl)pyridin-3-yl)methyl)-1,2-dihydro-3H-indazol-3-one The reaction was performed using 3-(bromomethyl)-5-methyl-2-(trifluoromethyl)pyridine and potassium carbonate with 6-(2-chloropyrimidin-5-yl)-2-methyl-1-H-indazol-3(2H)-one (Preparation #23) in a similar fashion to Example #1 to give the title product (35%); (Table A, Method e) R$_t$=2.02 min; MS m/z: 434 (M+H)$^+$.

Preparation #48: 6-(2-Chloropyrimidin-5-yl)-2-methyl-1-((2-(trifluoromethyl)pyridin-3-yl)methyl)-1,2-dihydro-3H-indazol-3-one

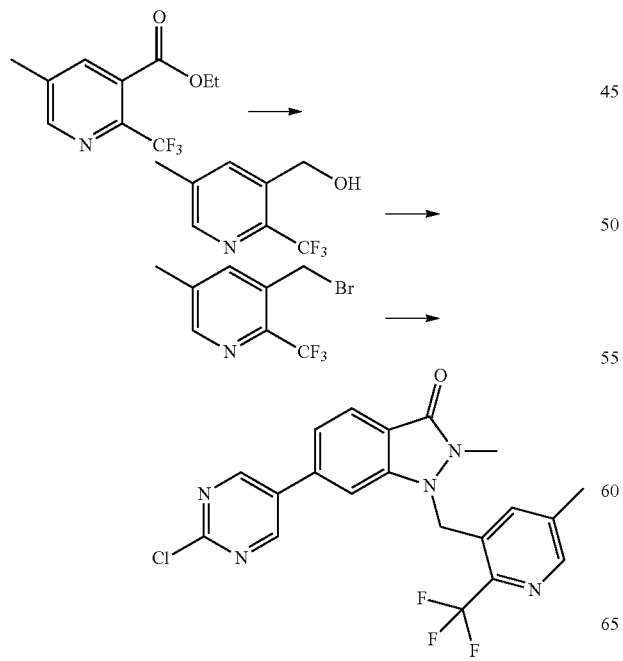

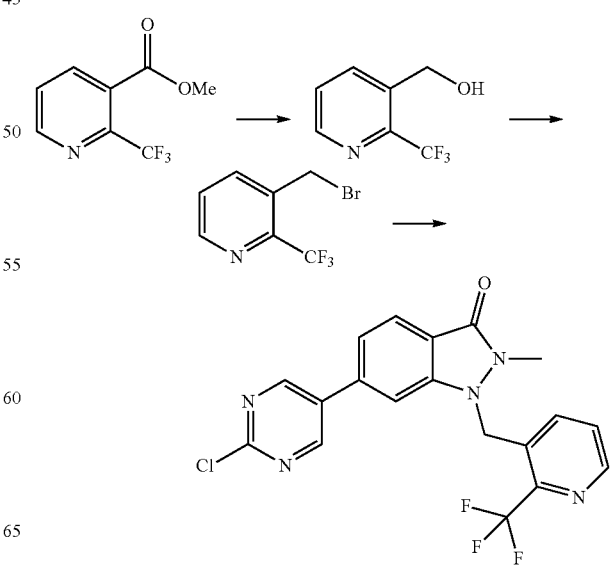

Step 1: (5-Methyl-2-(trifluoromethyl)pyridin-3-yl)methanol

Methyl 2-(trifluoromethyl)nicotinate was treated with sodium borohydride in a fashion similar to Preparation #14, step 2 to give the title product (34%); $^1$H NMR (400 MHz, CDCl$_3$) δ 8.62 (d. J=4.7 Hz, 1H), 8.16 (d, J=7.9 Hz, 1H), 7.55 (dd, J=7.9, 4.7 Hz, 1H), 4.95 (s, 2H).

Step 2: 3-(Bromomethyl)-2-(trifluoromethyl)pyridine

The reaction was performed using (5-methyl-2-(trifluoromethyl)pyridin-3-yl)methanol and PBr$_3$ in a similar fashion to Preparation #3, step 2 to give the title product (63%); $^1$H NMR (400 MHz, CDCl$_3$) δ 8.73-8.60 (m, 1H), 8.06-7.93(m, 1H), 7.59-7.47 (m, 1H), 5.42-5.28 (m, 2H).

Step 3: 6-(2-Chloropyrimidin-5-yl)-2-methyl-1-((5-methyl-2-(trifluoromethyl)pyridin-3-yl)methyl)-1,2-dihydro-3H-indazol-3-one The reaction was performed using 3-(bromomethyl)-2-(trifluoromethyl)pyridine and potassium carbonate with 6-(2-chloropyrimidin-5-yl)-2-methyl-1H-indazol-3(2H)-one (Preparation #23) in a similar fashion to Example #1 to give the title product (25%); (Table A, Method e) R$_t$=1.93 min; MS m/z: 420 (M+H)$^+$.

Preparation #49: 6-(2-Chloropyrimidin-5-yl)-2-methyl-1-(5-methyl-2-(trifluoromethyl)benzyl)-1,2-dihydro-3H-indazol-3-one borane THF complex (1.0 M in THF) (4.90 mL, 4.90 mmol) and the reaction mixture was heated at about reflux for about 1.5 h. The reaction was cooled to rt and then MeOH (5 mL) was added slowly and the mixture refluxed for 1 h. The mixture was concentrated under reduced pressure and the crude material was purified on silica gel (25 g, using 0 to 50% EtOAc in heptane) to give the title product (0.414 g, 89%); $^1$H NMR (400 MHz, CDCl$_3$) δ 7.58-7.46 (m, 2H), 7.18 (d, J=7.8 Hz, 1H), 4.85 (s, 2H), 2.42 (s, 3H).

Step 2: 2-(Bromomethyl)-4-methyl-1-(trifluoromethyl)benzene

The reaction was performed using (5-methyl-2-(trifluoromethyl)phenyl)methanol and PBr$_3$ in a similar fashion to Preparation #3, step 2 to give the title product (59%); $^1$H NMR (400 MHz, CDCl$_3$) δ 7.52 (d, J=8.1 Hz, 1H), 7.39 (s, 1H), 7.20 (d, J=8.0 Hz, 1H), 4.60 (s, 2H), 2.41 (s, 3H).

Step 3: 6-(2-Chloropyrimidin-5-yl)-2-methyl-1-(5-methyl-2-(trifluoromethyl)benzyl)-1,2-dihydro-3H-indazol-3-one The reaction was performed using 2-(bromomethyl)-4-methyl-1-(trifluoromethyl)benzene and potassium carbonate with 6-(2-chloropyrimidin-5-yl)-2-methyl-1H-indazol-3(2H)-one (Preparation #23) in a similar fashion to Example #1 to give the title product (25%); (Table A, Method e) R$_t$=2.35 min; MS m/z: 435 (M+H)$^+$.

Preparation #50: 1-((5-Chloro-1,3-dihydroisobenzofuran-4-yl)methyl)-6-(2-chloropyrimidin-5-yl)-2-methyl-1,2-dihydro-3H-indazol-3-one

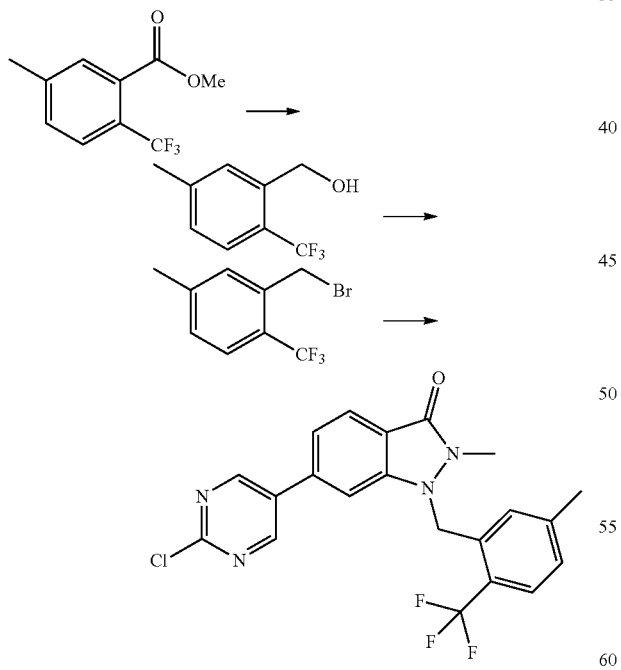

Step 1: (5-Methyl-2-(trifluoromethyl)phenyl)methanol

A solution of 5-methyl-2-(trifluoromethyl)benzoic acid (0.500 g, 2.45 mmol) in THF (10 mL) was treated with

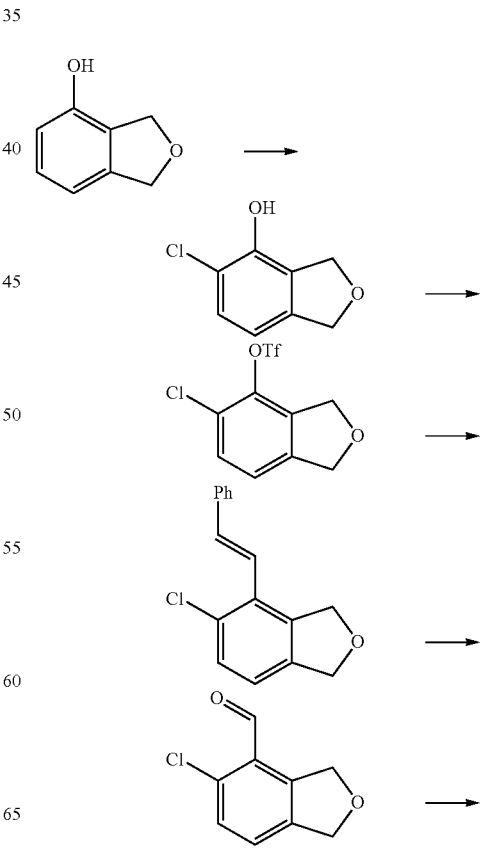

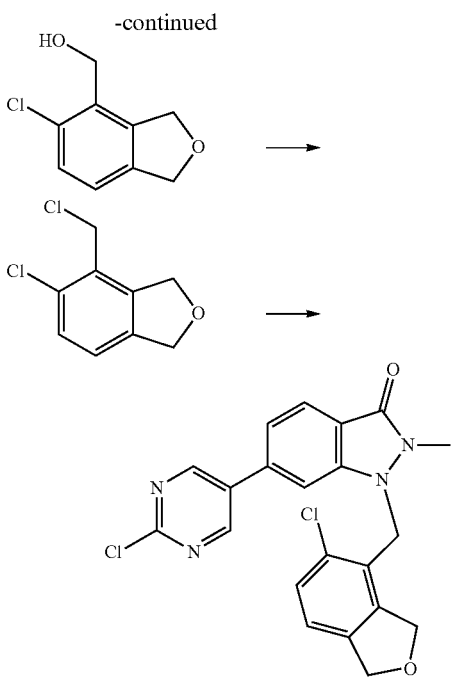

Step 1: 5-Chloro-1,3-dihydroisobenzofuran-4-ol

A solution of 1,3-dihydroisobenzofuran-4-ol (2.60 g, 12.6 mmol) (prepared as described in Journal of the American Chemical Society, 125(19), 5757-5766; 2003) and diisopropylamine (0.180 mL, 1.26 mmol) in toluene (80 mL) was treated with sulfuryl chloride (1.03 mL, 12.6 mmol) added dropwise. Water (50 mL) was added and the reaction was stirred for about 5 min. The mixture was extracted with EtOAc (3×50 mL) and the combined organic phases were washed with sat. aq. NaCl (75 mL), dried over $Na_2SO_4$, filtered, and concentrated under reduced pressure to give a mixture of regioisomers. The mixture was purified by reverse phase chromatography (Atlantis-, Prep T3 OBD™ 5 μm 50×100 mm column in 25-40% MeCN/water over 12 min) to give the title compound (1.29 g, 60%); (Table A, Method e) $R_t$=1.75 min; MS m/z: 169 (M−H)⁻.

Step 2: 5-Chloro-1,3-dihydroisobenzofuran-4-yl trifluoromethanesulfonate

A suspension of 5-chloro-1,3-dihydroisobenzofuran-4-ol (1.45 g, 8.52 mmol) and N,N-bis(trifluoromethylsulfonyl)aniline (3.35 g, 9.38 mmol) in DCM (40 mL) was treated with TEA (3.56 mL, 25.6 mmol) and the mixture was stirred at about rt. After about 1.5 h, additional N,N-bis(trifluoromethylsulfonyl)aniline (0.457 g, 1.28 mmol) was added and stirring was continued for about 30 min. The reaction mixture was partitioned between DCM (25 mL) and water (25 mL), the aqueous phase was extracted with DCM (10 mL). The combined organic phases were washed with 1N aq. NaOH (25 mL) and sat. aq. NaCl (50 mL), dried over $Na_2SO_4$, filtered, and concentrated under reduced pressure. The sample was purified on silica gel using a gradient of 0-50% EtOAc in heptane to afford the title compound (2.23 g, 86%); ¹H NMR (400 MHz, CDCl₃) δ 7.44 (d, J=8.2 Hz, 1H), 7.18 (d, J=7.9 Hz, 1H), 5.24-5.19 (m, 2H), 5.14-5.10 (m, 2H).

Step 3: (E)-5-Chloro-4-styryl-1,3-dihydroisobenzofuran

The reaction was performed using 5-chloro-1,3-dihydroisobenzofuran-4-yl trifluoromethanesulfonate with (E)-phenylethenylboronic acid in a similar fashion to Example #14, step 4 to give the title product (53%); ¹H NMR (400 MHz, CDCl₃) δ 7.57-7.49 (m, 2H), 7.48-7.27 (m, 5H), 7.06 (d, J=8.0 Hz, 1H), 6.71 (d, J=16.7 Hz, 1H), 5.33-5.28 (m, 2H), 5.15-5.06 (m, 2H).

Step 4: 5-Chloro-1,3-dihydroisobenzofuran-4-carbaldehyde

The reaction was performed using (E)-5-chloro-4-styryl-1,3-dihydroisobenzofuran in a similar fashion to Example #4, step 1 to give the title product (69%); ¹H NMR (400 MHz, CDCl₃) δ 10.56 (d, J=0.5 Hz, 1H), 7.45-7.33(m, 2H), 5.41-5.36 (m, 2H), 5.10-5.02 (m, 2H).

Step 5: (5-Chloro-1,3-dihydroisobenzofuran-4-yl)methanol

The reaction was performed using 5-chloro-1,3-dihydroisobenzofuran-4-carbaldehyde in a similar fashion to Preparation #9 to give the title product (87%); ¹H NMR (400 MHz, CDCl₃) δ 7.29 (d, J=8.0 Hz, 1H), 7.10 (d, J=8.0 Hz, 1H), 5.25 (s, 2H), 5.07 (s, 2H), 4.78 (s, 2H).

Step 6: 5-Chloro-4-(chloromethyl)-1,3-dihydroisobenzofuran

A solution of (5-chloro-1,3-dihydroisobenzofuran-4-yl)methanol (0.118 g, 0.639 mmol) in DCM (5 mL) cooled to about 0° C. was treated with thionyl chloride (0.070 mL, 0.96 mmol). The ice bath was removed. After stirring at rt for about 4 h, additional thionyl chloride (0.030 mL, 0.41 mmol) was added and stirring was continued for about 3 days. The reaction mixture was partitioned between DCM (5 mL) and sat aq. NaHCO₃(5 mL). After separating the layers, the aqueous phase was extracted with DCM (5 mL). The combined organic phases were dried using a phase separator, and concentrated under reduced pressure to give the title product (0.120 g, 92%); ¹H NMR (400 MHz, CDCl₃) δ 7.33(d, J=8.0 Hz, 1H), 7.14 (d, J=8.0 Hz, 1H), 5.24-5.04 (m, 4H), 4.64 (s, 2H).

Step 7: 1-((5-chloro-1,3-dihydroisobenzofuran-4-yl)methyl)-6-(2-chloropyrimidin-5-yl)-2-methyl-1,2-dihydro-3H-indazol-3-one The reaction was performed using 5-chloro-4-(chloromethyl)-1,3-dihydroisobenzofuran with 6-(2-chloropyrimidin-5-yl)-2-methyl-1,2-dihydro-3H-indazol-3-one in a similar fashion to Example #1 to give the title product (58%); (Table A, Method e) $R_t$=2.08 min; MS m/z: 427 (M+H)⁺.

Preparation #51: 6-Bromo-2-methyl-1-(1-(6-methylpyridin-2-yl)ethyl)-H-indazol-3(2H)-one

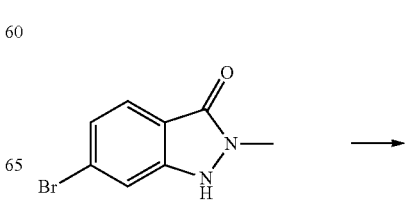

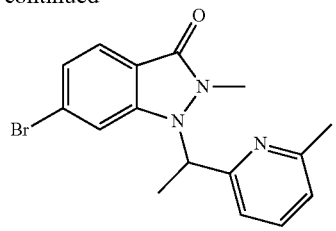

The reaction was performed using 2-(1-bromoethyl)-6-methylpyridine (synthesized in a similar fashion to Preparation #21, step 2 from 1-(6-methylpyridin-2-yl)ethanol (synthesized in a similar fashion to Preparation #21, step 1 from 6-methyl-2-pyridinecarboxaldehyde)) and 6-bromo-2-methyl-1H-indazol-3(2H)-one (Preparation #1, step 2) in a similar fashion to Preparation #4, step 1 to afford the title product (0.40 g, 63%); LC/MS (Table A, Method j) $R_f$=1.26 min; MS m/z: 346 and 348 (M+H)$^+$ Preparation #52:
2-(5-Bromopyrimidin-2-yl)-2-methylpropan-1-ol

Step 1: Ethyl 2-(5-bromopyrimidin-2-yl)-2-methylpropanoate

LiHMDS (1 M solution in hexanes, 4.80 mL, 4.80 mmol) was added over about 10 min to a solution of ethyl 2-(5-bromopyrimidin-2-yl)acetate (1.06 g, 4.33 mmol) and THF (15.0 mL) under N$_2$ at about −78° C. After stirring for about 15 min, MeI (0.300 mL, 4.80 mmol) was added. The reaction was allowed to warm to rt over about 1 h. The solution was cooled to about −78° C. LiHMDS (1 M solution in hexanes) (4.80 mL, 4.80 mmol) was added over about 10 min. After about 15 min, MeI (0.300 mL, 4.80 mmol) was added in one portion. The solution was allowed to warm to rt over about 1 h. After about 30 min, the solution was cooled to about 0° C. Sat. aq. NH$_4$Cl (40 mL), water (10 mL) and EtOAc (50 mL) were added. The layers were separated and the aqueous layer was extracted with EtOAc (20 mL). The combined organic layers were dried over Na$_2$SO$_4$, filtered, and concentrated. The residue was purified on silica gel using a gradient of 0-10% EtOAc/heptane to afford the title product (1.00 g, 85%). LC/MS (Table A, Method i) $R_f$=1.37 min; MS m/z: 273 and 275 (M+H)$^+$.

Step 2: 2-(5-Bromopyrimidin-2-yl)-2-methylpropan-1-ol

Diisobutylaluminum hydride (1 M solution in toluene, 11 mL, 11 mmol) was added dropwise to a solution of ethyl 2-(5-bromopyrimidin-2-yl)-2-methylpropanoate (2.0 g, 7.3 mmol) and DCM (50 mL) under N$_2$ at about 0° C. over about 50 min. After about 1 h, diisobutylaluminum hydride (1 M solution in toluene, 3.5 mL, 3.5 mmol) was added over about 10 min. After about 1 h, 5% aq. potassium sodium tartrate (50 mL) and DCM (50 mL) were added at rt and the mixture was stirred for about 1 h, 10% Aq. potassium sodium tartrate (25 mL) was added and the mixture was stirred vigorously for about 16 h. The layers were separated and the aqueous layer was extracted with DCM (2×10 mL). The combined organic layers were dried over MgSO$_4$, filtered, concentrated and purified on silica gel using a gradient of 0-30% EtOAc/DCM to afford the title product (1.3 g, 77%); LC/MS (Table A, Method j) $R_f$=0.75 min; MS m/z: 231 and 233 (M+H)$^+$ Preparation #53: 6-Chloro-1-(2-(difluoromethoxy)benzyl)-2-methyl-3-oxo-2,3-dihydro-1H-indazole-5-carbonitrile

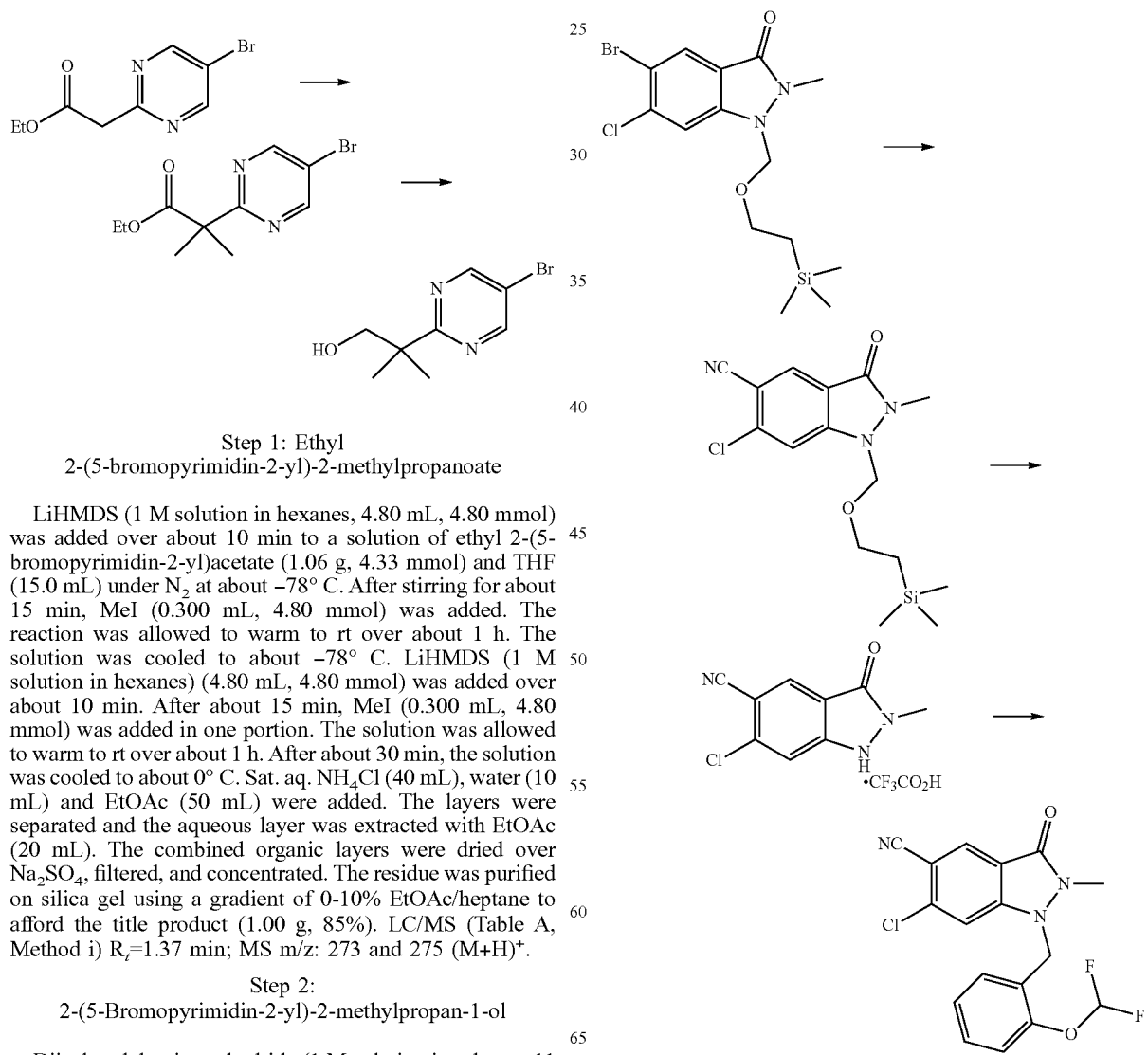

Step 1: 6-Chloro-2-methyl-3-oxo-1-((2-(trimethylsilyl)ethoxy)methyl)-2,3-dihydro-1H-indazole-5-carbonitrile The reaction was performed using 5-bromo-6-chloro-2-methyl-1-((2-(trimethylsilyl)ethoxy)methyl)-1H-indazol-3(2H)-one (Preparation #31, step 2) in a similar fashion to Preparation #17, step 1 to afford the title product (1.43 g, 73%); LC/MS (Table A, Method k) $R_t$=0.89 min; MS m/z: 338 (M+H)$^+$.

Step 2: 6-Chloro-2-methyl-3-oxo-2,3-dihydro-1H-indazole-5-carbonitrile trifluoroacetic acid TFA (0.300 mL, 3.89 mmol) was added to a solution of 6-chloro-2-methyl-3-oxo-1-((2-(trimethylsilyl)ethoxy)methyl)-2,3-dihydro-1H-indazole-5-carbonitrile (0.50 g, 1.34 mmol) at about 0° C. under N$_2$. The reaction was warmed to rt and stirred for about 4 h then concentrated under reduced pressure. EtOAc (3×10 mL) was added and concentrated under reduced pressure. To the solid was added MeOH (5×10 mL) and concentrated under reduced pressure each time to provide the title product (0.31 g, 72%); LC/MS (Table A, Method i) $R_t$=0.58 min; MS m/z: 208 (M+H)$^+$.

Step 3: 6-Chloro-1-(2-(difluoromethoxy)benzyl)-2-methyl-3-oxo-2,3-dihydro-1H-indazole-5-carbonitrile Potassium carbonate (0.180 g, 1.27 mmol) was added to a solution of 6-chloro-2-methyl-3-oxo-2,3-dihydro-1H-indazole-5-carbonitrile trifluoroacetic acid (0.15 g, 0.42 mmol) in DMF (4 mL) under N$_2$. After stirring for about 2 min at rt, 1-(bromomethyl)-2-(difluoromethoxy)benzene (0.100 mL, 0.656 mmol) was added and stirring was continued for about 20 min. EtOAc (30 mL) and water (10 mL) were added to the reaction mixture. The layers were separated and the aqueous layer was back extracted with EtOAc (2×10 mL). The combined organic layers were dried over MgSO$_4$, filtered and concentrated under reduced pressure. The material was purified via flash chromatography on silica gel (0-100% EtOAc/heptane). The appropriate fractions were collected and concentrated under reduced pressure to yield the title product (0.15 g, 51%); LC/MS (Table A, Method i) $R_t$=1.32 min; MS m/z: 364 (M+H)$^+$.

Preparation #54: (S)-1-(4-(5-bromopyrimidin-2-yl)-3-methylpiperazin-1-yl)-2-hydroxyethanone

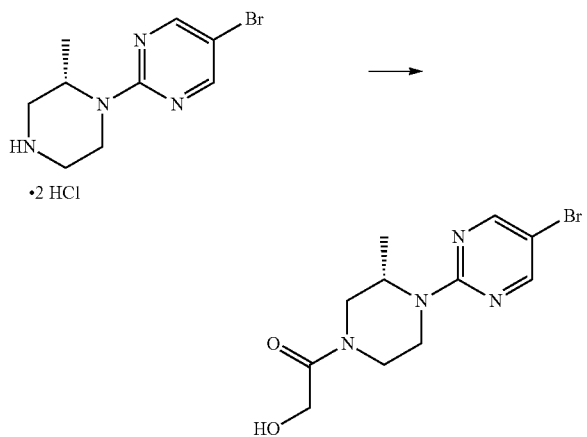

(S)-5-Bromo-2-(2-methylpiperazin-1-yl)pyrimidine dihydrochloride (1.0 g, 3.0 mmol) (synthesized in a similar fashion to Example #3, step 1 from (S)-tert-butyl 4-(5-bromopyrimidin-2-yl)-3-methylpiperazine-1-carboxylate (synthesized in a similar fashion to Preparation #13, step 1 from (S)-tert-butyl 3-methylpiperazine-1-carboxylate)) in DMF (15 mL) was treated with 2-hydroxyacetic acid (0.35 g, 4.5 mmol), 2-(3H-[1,2,3]triazolo[4,5-b]pyridin-3-yl)-1,1,3,3-tetramethylisouronium hexafluorophosphate(V) (1.38 g, 3.64 mmol) and TEA (1.7 mL, 12 mmol). After about 30 min, the volatiles were removed under reduced pressure and water (20 mL) and EtOAc (20 mL) were added. The organic layer was separated and the aqueous layer was back extracted with EtOAc (3×10 mL). The combined organic layers were dried over MgSO$_4$, filtered and concentrated under reduced pressure. The material was purified via flash chromatography on silica gel (0-100% EtOAc/heptane). The appropriate fractions were collected and concentrated under reduced pressure to yield the title product (0.76 g, 80%); LC/MS (Table A, Method i) $R_t$=0.93 min.; MS m/z: 315 and 317 (M+H)$^+$.

Preparation #55: (R)-1-(4-(5-Bromopyridin-2-yl)-2-methylpiperazin-1-yl)-2-hydroxyethanone

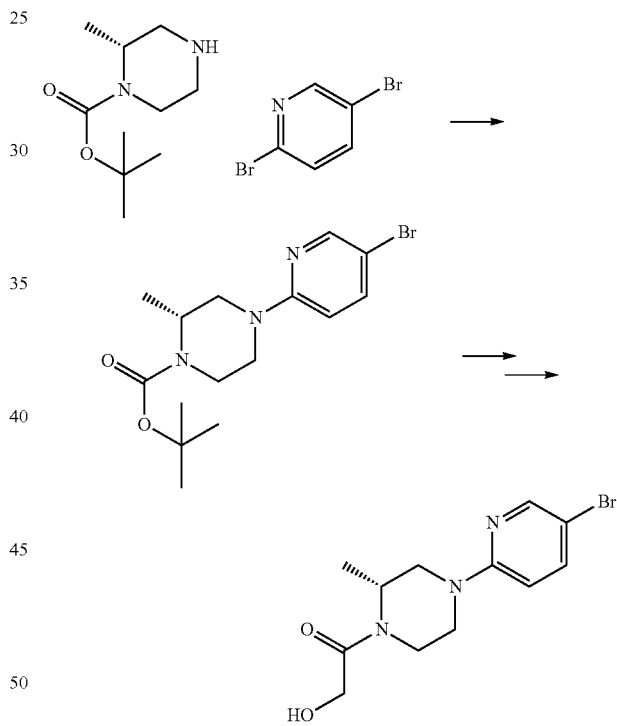

Step 1: (R)-tert-Butyl 4-(5-bromopyridin-2-yl)-2-methylpiperazine-1-carboxylate Toluene (215 ml) was degassed under vacuum then placed under an atmosphere of nitrogen then Pd$_2$(dba)$_3$ (0.394 g, 0.430 mmol), (9,9-dimethyl-9H-xanthene-4,5-diyl)bis(diphenylphosphine) (0.746 g, 1.290 mmol), (R)-tert-butyl 2-methylpiperazine-1-carboxylate (4.31 g, 21.5 mmol) and 2,5-dibromopyridine (6.6 g, 27.9 mmol) were added. The mixture was stirred about 10 min then sodium tert-butoxide (3.10 g, 32.3 mmol) was added and the mixture was heated to about 100° C. for about 3 h. The mixture was cooled to rt then washed with water, dried over magnesium sulfate, filtered and concentrated. The material was purified via flash chromatography on silica gel (0-50% EtOAc/Heptane) to give the title compound (5.6 g, 73%); LC/MS (Table A, Method i) R$_t$=1.91 min; MS m/z: 356, 358 (M+H)$^+$.

Step 2: (R)-1-(4-(5-Bromopyridin-2-yl)-2-methyl-piperazin-1-yl)-2-hydroxyethanone The title compound was synthesized in a manner similar to Preparation #15 from glycolic acid and (R)-1-(5-bromopyridin-2-yl)-3-methylpiperazine dihydrochloride (synthesized in a manner similar to Example #3, step 1 from (R)-tert-butyl 4-(5-bromopyridin-2-yl)-2-methylpiperazine-1-carboxylate); LC/MS (Table A, Method i) R$_t$=1.00 min; MS m/z: 314, 316 (M+H)$^+$.

Preparation #56: 3-(3-((6-Bromo-2-methyl-3-oxo-2,3-dihydro-1H-indazol-1-yl)methyl)-4-(difluoromethoxy)phenyl)-2-methylpropanenitrile

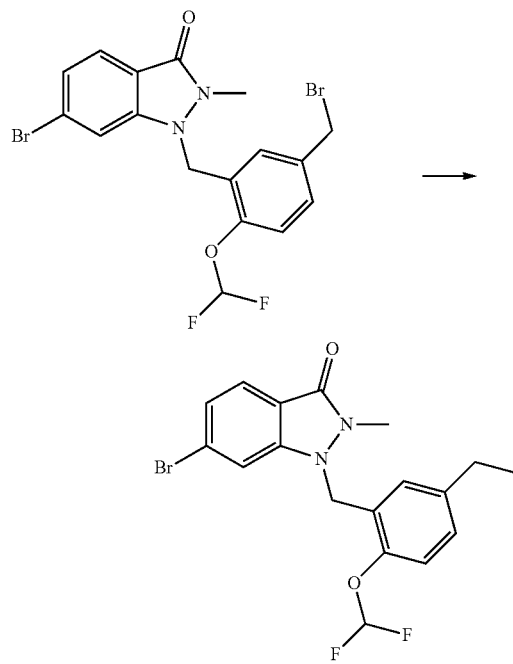

A flask, purged with nitrogen, was charged with diisopropylamine (0.14 mL, 0.98 mmol), then cooled on an ice-water bath for 10 min. Following cooling, n-butyllithium (2.5M in hexanes) (0.40 mL, 1.0 mmol) was added, followed by THF (5 mL). The solution was then cooled to about −78° C., then propiononitrile (51 mg, 0.93 mmol) was added, and the solution was stirred for about 10 min. After stirring, this solution was added to a separate flask containing 6-bromo-1-(5-(bromomethyl)-2-(difluoromethoxy)benzyl)-2-methyl-1H-indazol-3(2H)-one (417 mg, 0.876 mmol) (Preparation #20, step 3) and THF (5 mL) that was pre-cooled to about −78° C. The mixture was stirred for about 3 h, then quenched with sat. aq. NH$_4$Cl (20 mL). The mixture was extracted with EtOAc (4×10 mL). The combined organic layers were dried over Na$_2$SO$_4$, filtered and concentrated. The residue was purified by flash chromatography on silica gel (0-7% MeOH/CH$_2$Cl$_2$) to afford the title product (121 mg, 31%); LC/MS (Table A, Method i) R$_t$=1.44 min; MS m/z: 450 and 452 (M+H)$^+$.

Preparation #57: 6-(2-Chloropyrimidin-5-yl)-1-((3-(difluoromethoxy)-6-methylpyridin-2-yl)methyl)-2-methyl-1H-indazol-3(2H)-one

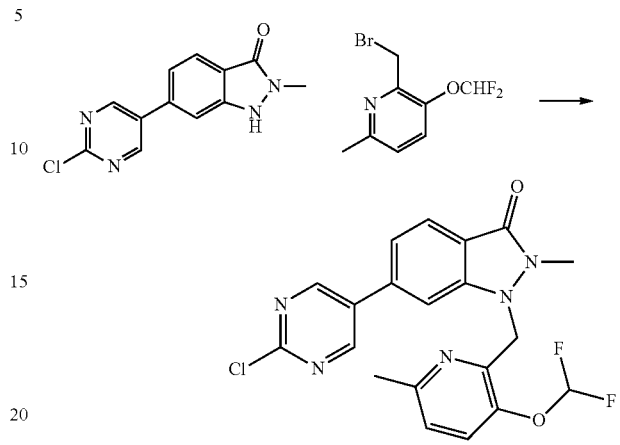

6-(2-Chloropyrimidin-5-yl)-1-((3-(difluoromethoxy)-6-methylpyridin-2-yl)methyl)-2-methyl-1H-indazol-3(2H)-one was prepared in a similar fashion to Example #1, from 6-(2-chloropyrimidin-5-yl)-2-methyl-1H-indazol-3(2H)-one (Preparation #23) and 2-(bromomethyl)-3-(difluoromethoxy)-6-methylpyridine (prepared from (3-(difluoromethoxy)-6-methylpyridin-2-yl)methanol (prepared from 3-(difluoromethoxy)-6-methylpicolinaldehyde (prepared from (E)-3-(difluoromethoxy)-6-methyl-2-styrylpyridine (prepared from 2-bromo-3-(difluoromethoxy)-6-methyl-pyridine (prepared from 2-bromo-6-methylpyridin-3-ol in a similar fashion to Preparation #14, step 1) in a similar fashion to Example #14, step 4) in a similar fashion to Example #4, step 1) in a similar fashion to Preparation of #14, step 2) in a similar fashion to Preparation #14, step 6) to afford the title product (79%); LC/MS (Table A, Method i) R$_t$=1.31 min; MS m/z: 432 (M+H)$^+$.

Preparation #58: 6-(2-(4-Acetyl-3-methylpiperazin-1-yl)pyrimidin-5-yl)-1-(2-(difluoromethoxy)-5-methylbenzyl)-2-methyl-1H-indazol-3(2H)-one

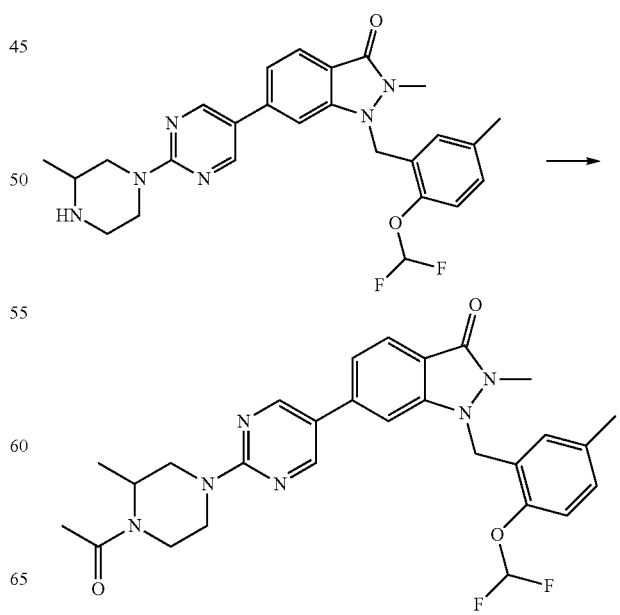

6-(2-(4-Acetyl-3-methylpiperazin-1-yl)pyrimidin-5-yl)-1-(2-(difluoromethoxy)-5-methylbenzyl)-2-methyl-1H-indazol-3(2H)-one was prepared in a similar fashion to Preparation #16 using 1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (prepared in a similar fashion to Example #3, step 1 using tert-butyl 4-(5-(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate (prepared in a similar fashion to Example #2 using 1-Boc-2-methylpiperazine and 6-(2-chloropyrimidin-5-yl)-1-(2-(difluoromethoxy)-5-methylbenzyl)-2-methyl-1H-indazol-3(2H)-one (Example #22, step 3))) to give the title compound (100%); LC/MS (Table A, Method i) $R_t$=1.28 min; MS m/z: 537 (M+H)$^+$.

Preparation #59: 1-(2-(Difluoromethoxy)-5-methylbenzyl)-2-(methyl-d$_3$)-6-(4,4,5,5-tetramethyl-1,3,2-dioxaborolan-2-yl)-1H-indazol-3(2H)-one

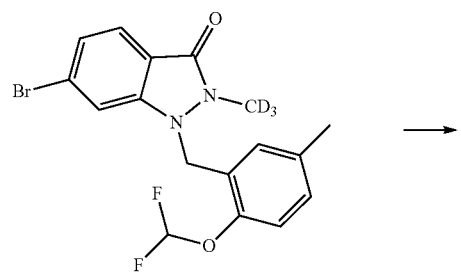

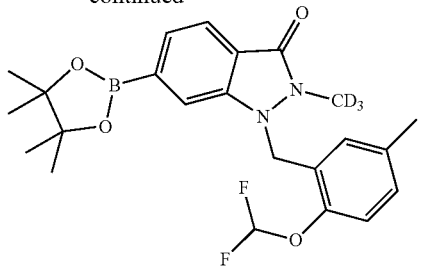

1-(2-(Difluoromethoxy)-5-methylbenzyl)-2-(methyl-d$_3$)-6-(4,4,5,5-tetramethyl-1,3,2-dioxaborolan-2-yl)-1H-indazol-3(2H)-one was prepared in a similar fashion to Preparation #4, step 2 using 6-bromo-1-(2-(difluoromethoxy)-5-methylbenzyl)-2-(methyl-d$_3$)-1H-indazol-3(2H)-one (prepared in a similar fashion to Example #14, step 3 from iodomethane-d$_3$ and 6-bromo-1-(2-(difluoromethoxy)-5-methylbenzyl)-1H-indazol-3(2H)-one (prepared in a similar fashion to Example #1 using 6-bromo-1H-indazol-3(2H)-one and 2-(bromomethyl)-1-(difluoromethoxy)-4-methylbenzene (prepared in a similar fashion to Preparation #3, step 2 using (2-(difluoromethoxy)-5-methylphenyl)methanol (Preparation #11)))) to give the title compound (81%); LC/MS (Table A, Method i) $R_t$=1.78 min; MS m/z; 448 (M+H)$^+$.

Preparation #60: (R)-6-(2-(4-(2-(tert-Butoxy)acetyl)-3-methylpiperazin-1-yl)pyrimidin-5-yl)-2-methyl-1H-indazol-3(2H)-one

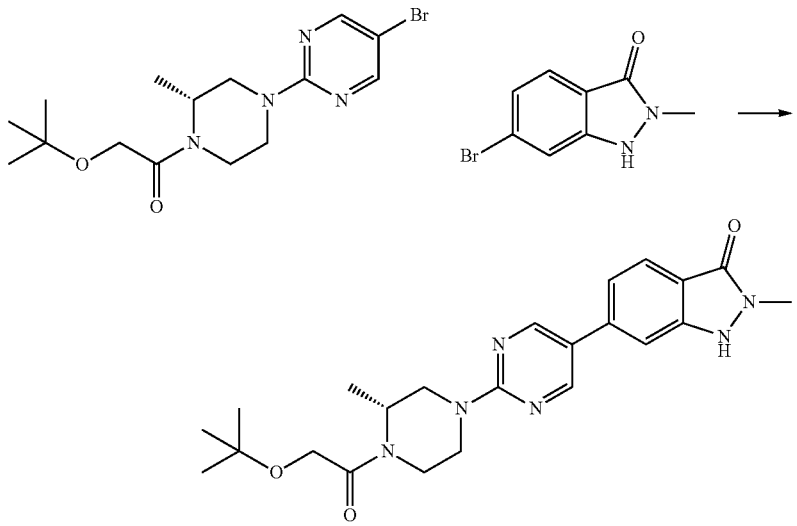

(R)-6-(2-(4-(2-(tert-Butoxy)acetyl)-3-methylpiperazin-1-yl)pyrimidin-5-yl)-2-methyl-1H-indazol-3(2H)-one was prepared in a similar fashion to Example #8 using 6-bromo-2-methyl-1H-indazol-3(2H)-one (Preparation #1) and (R)-1-(4-(5-bromopyrimidin-2-yl)-2-methylpiperazin-1-yl)-2-(tert-butoxy)ethanone (Preparation #30, step 1) to give the title compound to give the title compound (46%); LC/MS (Table A, Method j) $R_t$=0.98 min; MS m/z: 439 (M+H)$^+$.

115

Preparation #61: 2-(Bromomethyl)-3-(trifluoromethyl)-6-((trityloxy)methyl)pyridine

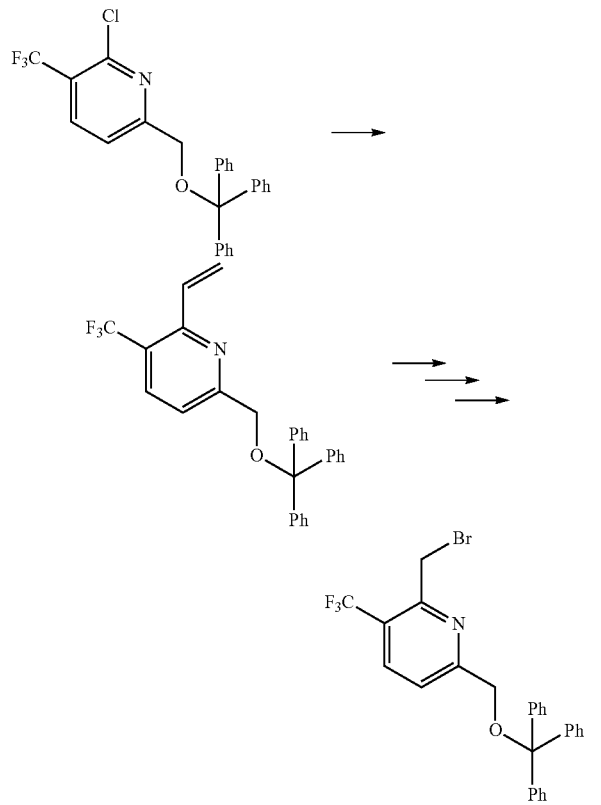

Step 1: 3-(Trifluoromethyl)-6-((trityloxy)methyl)-2-vinylpyridine

2-Chloro-3-(trifluoromethyl)-6-((trityloxy)methyl)pyridine (1.54 g, 3.39 mmol) (synthesized in a manner similar to Preparation #14, step 3 from (6-chloro-5-(trifluoromethyl)pyridin-2-yl)methanol (synthesized in a manner similar to Preparation #9 from methyl 6-chloro-5-(trifluoromethyl)picolinate)) and tributyl(vinyl)stannane (1.10 mL, 3.73 mmol) in 1,4-dioxane (15 mL) was treated with Pd(Ph$_3$P)$_4$ (0.196 g, 0.170 mmol) then the mixture was heated at about 95° C. for about 14 h. Additional portions of tributyl(vinyl)stannane (0.299 mL, 1.02 mmol) and Pd(Ph$_3$P)$_4$ (0.196 g, 0.170 mmol) were added then the mixture was heated at about 95° C. for about 7 h. The mixture was cooled and concentrated under reduced pressure then the material was purified via flash chromatography on silica gel (0-20% EtOAc/Heptane) to give the title compound (2.14 g, 142%). The material was used without further manipulation; LC/MS (Table A, Method i) R$_t$=2.45 min; MS m/z: 446 (M+H)$^+$.

Step 2: 2-(Bromomethyl)-3-(trifluoromethyl)-6-((trityloxy)methyl)pyridine

The title compound was synthesized in a manner similar to Preparation #3, step 2 from (3-(trifluoromethyl)-6-((trityloxy)methyl)pyridin-2-yl)methanol (synthesized in a manner similar to Preparation #9 from 3-(trifluoromethyl)-6-((trityloxy)methyl)picolinaldehyde (synthesized in a manner similar to Example #4, step 1 from 3-(trifluoromethyl)-6-((trityloxy)methyl)-2-vinylpyridine)); LC/MS (Table A, Method i) R$_4$=2.31 min; MS m/z: 243(M+H)$^+$.

Preparation #62: 1-(5-((1H-1,2,4-Triazol-1-yl)methyl)-2-(difluoromethoxy)benzyl)-6-bromo-5-fluoro-2-methyl-1H-indazol-3(2H)-one and 1-(5-((4H-1,2,4-triazol-4-yl)methyl)-2-(difluoromethoxy)benzyl)-6-bromo-5-fluoro-2-methyl-1H-indazol-3(2H)-one

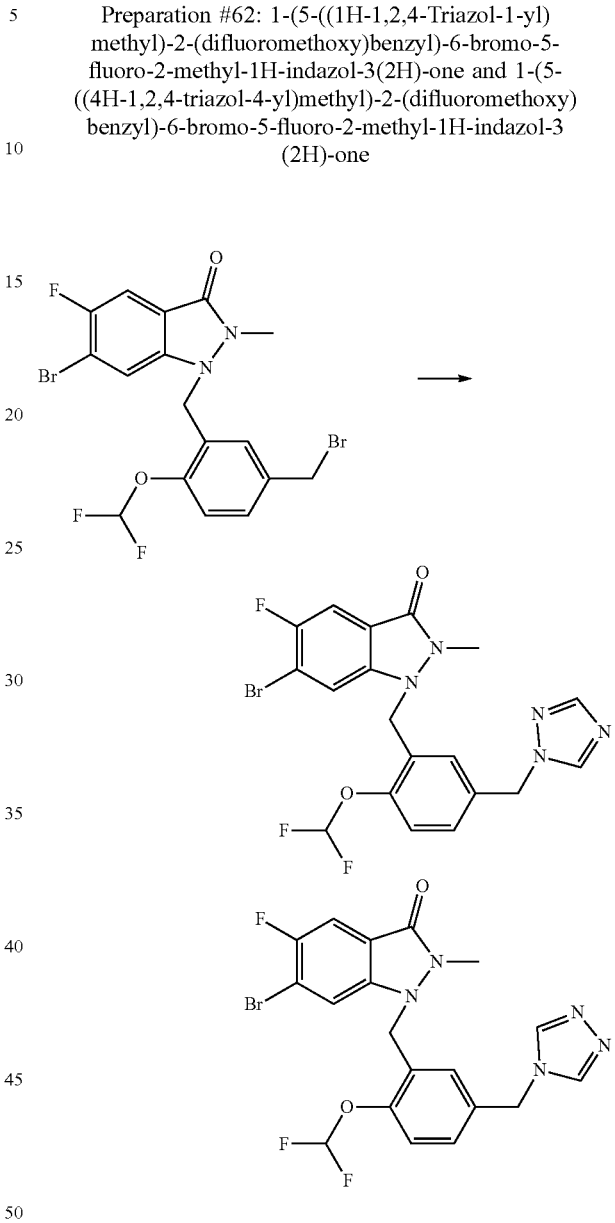

A mixture of 6-bromo-1-(5-(bromomethyl)-2-(difluoromethoxy) benzyl)-5-fluoro-2-methyl-1H-indazol-3(2H)-one (200 mg, 0.405 mmol) (synthesized in a manner similar to Preparation #14, step 6 from 6-bromo-1-(2-(difluoromethoxy)-5-(hydroxymethyl)benzyl)-5-fluoro-2-methyl-1H-indazol-3(2H)-one (synthesized in a manner similar to Example #18 from 6-bromo-1-(2-(difluoromethoxy)-5-((trityloxy)methyl)benzyl)-5-fluoro-2-methyl-1H-indazol-3(2H)-one (synthesized in a manner similar to Preparation #4, step 1 from 6-bromo-5-fluoro-2-methyl-1H-indazol-3(2H)-one (synthesized in a manner similar to Preparation #1 from 4-bromo-2,5-difluorobenzoic acid) and (((3-(bromomethyl)-4-(difluoromethoxy)benzyl)oxy)methanetriyl)tribenzene (Preparation #14)))), 1H-1,2,4-triazole (61.5 mg, 0.891 mmol), and potassium carbonate (67.1 mg, 0.486 mmol) in MeCN (4 mL) was stirred at about 50° C. for about 1 h. The reaction was cooled to rt and partitioned between EtOAc (20 mL) and water (5 mL). The organic layer was dried over MgSO₄, filtered, concentrated and the residue was purified on silica gel (0-10% MeOH/DCM then 10% MeOH/DCM spiked with 1% 7 N NH₃ in MeOH) to afford 1-(5-(((1H-1,2,4-triazol-1-yl)methyl)-2-(difluoromethoxy)benzyl)-6-bromo-5-fluoro-2-methyl-1H-indazol-3(2H)-one (160 mg, 82%); LC/MS (Table A, Method i) $R_t$=1.17 min; MS m/z: 482 and 484 (M+H)⁺ and 1-(5-((4H-1,2,4-triazol-4-yl)methyl)-2-(difluoromethoxy)benzyl)-6-bromo-5-fluoro-2-methyl-1H-indazol-3(2H)-one (30 mg, 15%); LC/MS (Table A, Method i) $R_t$=1.08 min; MS m/z: 482 and 484 (M+H)⁺.

Preparation #63: 1-(5-(((1-Acetylazetidin-3-yl)methyl)-2-(difluoromethoxy)benzyl)-6-bromo-5-fluoro-2-methyl-1H-indazol-3(2H)-one

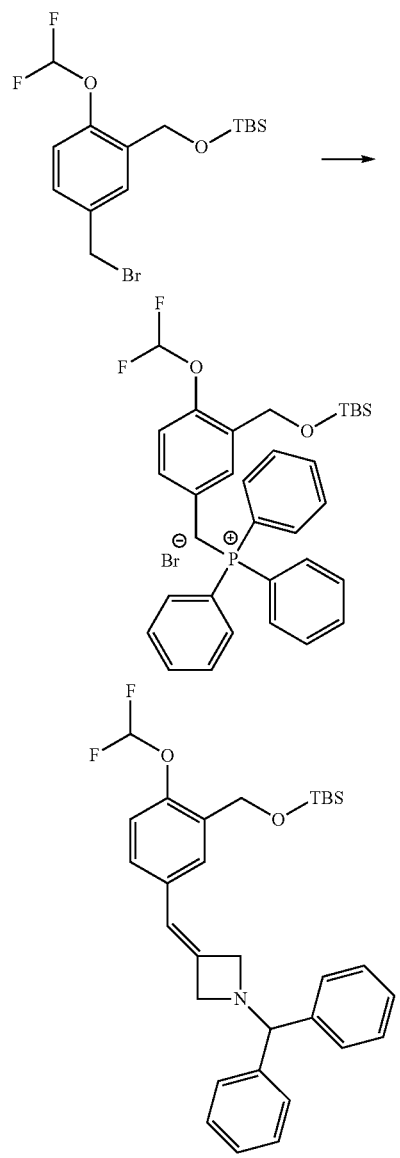

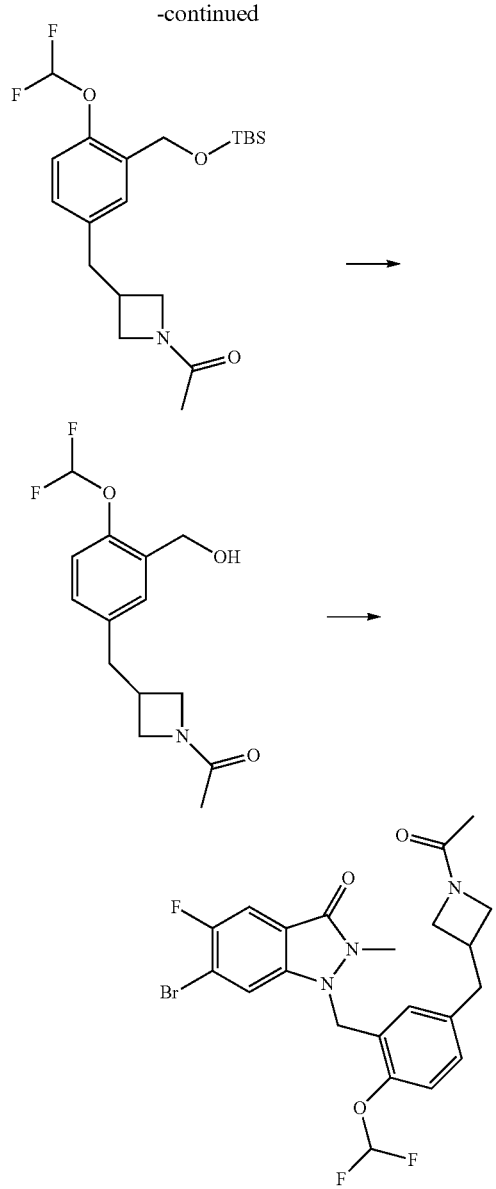

Step 1: (3-(((tert-Butyldimethylsilyl)oxy)methyl)-4-(difluoromethoxy)benzyl)triphenylphosphonium bromide A mixture of ((5-(bromomethyl)-2-(difluoromethoxy)benzyl)oxy)(tert-butyl)dimethylsilane (prepared in a similar fashion to Preparation #14, step 6 using (3-(((tert-butyldimethylsilyl)oxy)methyl)-4-(difluoromethoxy)phenyl)methanol) (prepared in a similar fashion to Preparation #14, step 5 using methyl 3-(((tert-butyldimethylsilyl)oxy)methyl)-4-(difluoromethoxy)benzoate (prepared in a similar fashion to Example #9, step 1 using ((5-bromo-2-(difluoromethoxy)benzyl)oxy)(tert-butyl)dimethylsilane (prepared in a similar fashion to Preparation #43, step 1 using (5-bromo-2-(difluoromethoxy)phenyl)methanol (Preparation #12)))) and PPh₃ (1.57 g, 6.01 mmol) in toluene (40 mL) was refluxed for about 5 h. The reaction was allowed to cool to rt. Et₂O (30 mL) was added and the precipitate was triturated, filtered and washed with Et$_2$O (30 mL) to give the title compound (2.92 g, 76%); LC/MS (Table A, Method i) R$_t$=1.98 min; MS m/z: 563(M+H)$^+$.

Step 2: 1-Benzhydryl-3-(3-(((tert-butyldimethylsilyl)oxy)methyl)-4-(difluoromethoxy)benzylidene)azetidine 60% Sodium hydride in mineral oil (0.186 g, 4.66 mmol) was added to a mixture of (3-(((tert-butyldimethylsilyl)oxy)methyl)-4-(difluoromethoxy)benzyl)triphenylphosphonium bromide (2.72 g, 4.23 mmol) and THF (40 mL). The reaction was stirred at rt for about 1 h then the reaction temperature was gradually raised to about 60° C. over about 1 h, 1-Benzhydrylazetidin-3-one (1.00 g, 4.23 mmol) was added. After about 2 h, the reaction was allowed to cool to rt. The reaction was partitioned between EtOAc (200 mL) and 20% aq. NH$_4$Cl (200 mL). The organic layer was washed with sat. aq. NaCl (200 mL), dried over Na$_2$SO$_4$, filtered and was concentrated under reduced pressure. The residue was purified on silica gel using 2-5% EtOAc in heptanes to give the title compound (0.950 g, 43%); LC/MS (Table A, Method k) R$_t$=1.92 min; MS m/z: 522 (M+H)$^+$.

Step 3: 1-(3-(3-(((tert-Butyldimethylsilyl)oxy)methyl)-4-(difluoromethoxy)benzyl)azetidin-1-yl)ethanone A mixture of 1-benzhydryl-3-(3-(((tert-butyldimethylsilyl)oxy)methyl)-4-(difluoromethoxy)benzylidene)azetidine (0.950 g, 1.82 mmol) and palladium hydroxide on carbon (0.256 g, 0.182 mmol) in MeOH (30 mL)/THF (10 mL) at about 60° C. was shaken under 50 psi hydrogen for about 3 h. The reaction was allowed to cool to rt and filtered through Celite®. The filtrate was concentrated under reduced pressure. The residue was dissolved in DCM (20 mL) then TEA (0.507 mL, 3.64 mmol), acetic anhydride (0.206 mL, 2.18 mmol) and DMAP (0.022 g, 0.18 mmol) were added. The reaction was stirred at rt for about 2 h. The reaction was diluted with DCM (20 mL) and washed with a sat. aq. NaHCO$_3$(20 mL) and sat. aq. NaCl (20 mL). The organic layer was dried over Na$_2$SO$_4$, filtered and concentrated under reduced pressure. The residue was purified on silica gel using 30-100% EtOAc in heptanes to give the title compound (0.460 g, 63%); LC/MS (Table A, Method i) R$_t$=1.95 min; MS m/z: 400 (M+H)$^+$.

Step 4: 1-(3-(4-(Difluoromethoxy)-3-(hydroxymethyl)benzyl)azetidin-1-yl)ethanone 1-(3-(4-(Difluoromethoxy)-3-(hydroxymethyl)benzyl)azetidin-1-yl)ethanone was prepared in a similar fashion to Example #35, step 3 using 1-(3-(3-(((tert-butyldimethylsilyl)oxy)methyl)-4-(difluoromethoxy)benzyl)azetidin-1-yl)ethanone to give the title compound (0.223 g, 80%); LC/MS (Table A, Method i) R$_t$=0.82 min; MS m/z: 286 (M+H)$^+$.

Step 5: 1-(5-((1-Acetylazetidin-3-yl)methyl)-2-(difluoromethoxy)benzyl)-6-bromo-5-fluoro-2-methyl-1H-indazol-3(2H)-one 1-(5-((1-Acetylazetidin-3-yl)methyl)-2-(difluoromethoxy)benzyl)-6-bromo-5-fluoro-2-methyl-1H-indazol-3(2H)-one was prepared in a similar fashion to Example #42, step 1 using 1-(3-(4-(difluoromethoxy)-3-(hydroxymethyl)benzyl)azetidin-1-yl)ethanone to prepare the solution of 1-(3-(3-(bromomethyl)-4-(difluoromethoxy)benzyl)azetidin-1-yl)ethanone to react with 6-bromo-5-fluoro-2-methyl-1H-indazol-3(2H)-one ((synthesized in a similar fashion to Preparation #1 from 4-bromo-2,5-difluorobenzoic acid)) to give the title compound (0.349 g, 88%); LC/MS (Table A, Method i) R$_t$=1.28 min; MS m/z: 512 and 514 (M+H)$^+$.

Preparation #64: 3-(Piperidin-4-yl)-1,2,4-thiadiazol-5(4H)-one hydrochloride

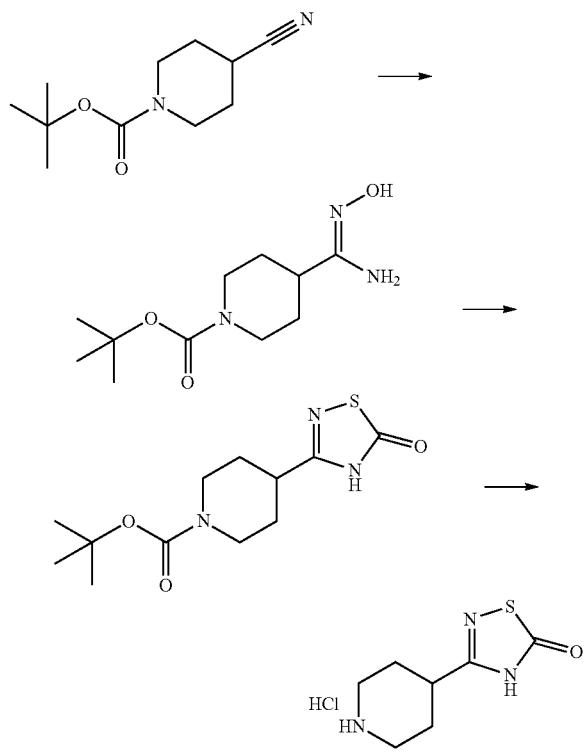

Step 1: (Z)-tert-Butyl 4-(N'-hydroxycarbamimidoyl)piperidine-1-carboxylate

A mixture of tert-butyl 4-cyanopiperidine-1-carboxylate (0.500 g, 2.38 mmol), hydroxylamine hydrochloride (0.330 g, 4.76 mmol), and DIEA (0.831 mL, 4.76 mmol) in EtOH (10 mL) was heated at about 80° C. for about 15 h. The reaction mixture was concentrated under reduced pressure and the residue was partitioned between EtOAc (25 mL) and water (25 mL). After separating the layers, the aqueous phase was extracted with EtOAc (3×10 mL). The combined organic phases were washed with sat. aq. NaCl (50 mL), dried over Na$_2$SO$_4$, filtered, and concentrated under reduced pressure to give the title product (0.45 g, 78%); LC/MS (Table A, Method e) R$_t$=1.33 min; MS m/z: 244 (M+H)$^+$.

Step 2: tert-Butyl 4-(5-oxo-4,5-dihydro-1,2,4-thiadiazol-3-yl)piperidine-1-carboxylate A mixture of (Z)-tert-butyl 4-(N'-hydroxycarbamimidoyl)piperidine-1-carboxylate (0.454 g, 1.87 mmol), 1,8-diazabicyclo[5.4.0]undec-7-ene (0.422 mL, 2.80 mmol), and 1,1'-thiocarbonyldiimidazole (0.499 g, 2.80 mmol) in 1,4-dioxane (10 mL) was heated at about 80° C. for about 75 min. The reaction was concentrated under reduced pressure and the resulting solid was triturated with diethyl ether (10 mL) and isolated by vacuum filtration to give the title product (0.33 g, 62%); LC/MS (Table A, Method i)$_R$=0.93 min; MS m/z: 284 (M−H)⁻.

Step 3: 3-(Piperidin-4-yl)-1,2,4-thiadiazol-5(4H)-one hydrochloride

The reaction was performed using tert-butyl 4-(5-oxo-4,5-dihydro-1,2,4-thiadiazol-3-yl)piperidine-1-carboxylate in a similar fashion to Example #3, step 1 to give the title product (90%); LC/MS (Table A, Method e) R$_t$=0.42 min; MS m/z: 186 (M+H)⁺.

Preparation #65: 6-Bromo-1-(2-chlorobenzyl)-7-methoxy-2-methyl-1H-indazol-3(2H)-one

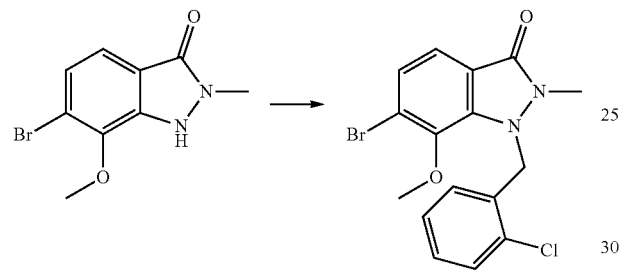

6-Bromo-1-(2-chlorobenzyl)-7-methoxy-2-methyl-1H-indazol-3(2H)-one was prepared in a similar manner to Example #1 using 2-chlorobenzyl bromide and 6-bromo-7-methoxy-2-methyl-1H-indazol-3(2H)-one (prepared in a similar manner to Preparation #1 using 4-bromo-2-fluoro-3-methoxybenzoic acid); LC/MS (Table A, Method i) R$_t$=1.59 min; MS m/z: 381 and 383(M+H)⁺.

Preparation #66: 6-Bromo-1-(2-(difluoromethoxy)benzyl)-7-methoxy-2-methyl-1H-indazol-3(2H)-one

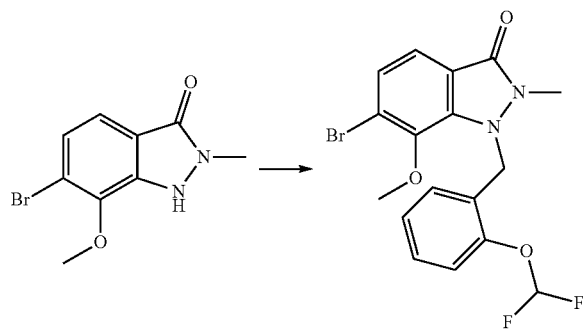 [SMILES: COc1c(Br)ccc2c(=O)n(C)[nH]c12 ; COc1c(Br)ccc2c(=O)n(C)n(Cc3ccccc3OC(F)F)c12]

6-Bromo-1-(2-(difluoromethoxy)benzyl)-7-methoxy-2-methyl-1H-indazol-3(2H)-one was prepared in a similar manner to Example #1 using 1-(bromomethyl)-2-(difluoromethoxy)benzene and 6-bromo-7-methoxy-2-methyl-1H-indazol-3(2H)-one (prepared in a similar manner to Preparation #1 using 4-bromo-2-fluoro-3-methoxybenzoic acid); LC/MS (Table A, Method i) R$_t$=1.53 min; MS m/z: 413 and 415 (M+H)⁺.

Preparation #67: 6-Chloro-2-methyl-3-oxo-2,3-dihydro-1H-indazole-7-carbonitrile

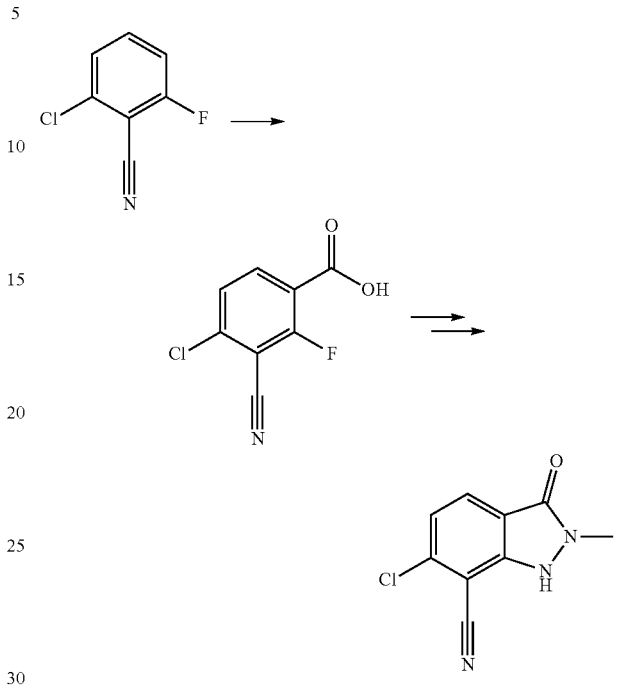

Step 1: 4-Chloro-3-cyano-2-fluorobenzoic acid

A solution of 2-chloro-6-fluorobenzonitrile (10 g, 64 mmol) and THF (200 mL) under N$_2$ was cooled to about −65° C. A freshly prepared solution of lithium diisopropylamide (0.5 M in THF, 130 mL, 66 mmol) was added over about 15 min. Immediately after completion of addition, carbon dioxide was bubbled through the resulting solution. The reaction was maintained at about −50° C. for 15 min then allowed to thaw to rt over about 90 min. Water (200 mL) and Et$_2$O (200 mL) were added. The layers were separated. The organic layer was extracted with 1 M aq. NaOH (50 mL). The aqueous layers were combined then washed with Et$_2$O (200 mL). The aqueous layer was acidified with 2 M aq. HCl (85 mL). EtOAc (300 mL) was added. The layers were separated. The organic layer was washed with sat. aq. NaCl (200 mL). The aqueous layers were extracted with EtOAc (200 mL). The combined organic layers were dried over Na$_2$SO$_4$, filtered, and concentrated under reduced pressure to afford the title compound (5.96 g, 42%); ¹H NMR (400 MHz, DMSO-d$_6$) δ 13.86 (broad s, 1H), 8.17 (dd, J=8.5, 7.3 Hz, 1H), 7.70 (dd, J=8.6, 1.0 Hz, 1H).

Step 2: 6-Chloro-2-methyl-3-oxo-2,3-dihydro-1H-indazole-7-carbonitrile

6-Chloro-2-methyl-3-oxo-2,3-dihydro-1H-indazole-7-carbonitrile was prepared in a similar manner to Preparation 1 using 4-chloro-3-cyano-2-fluorobenzoic acid to afford the title compound (77%); LC/MS (Table A, Method i) R$_t$=0.68 min; MS m/z: 208 (M+H)⁺.

123

Preparation #68: tert-Butyl 2-(5-bromopyridin-2-yl)propan-2-ylcarbamate

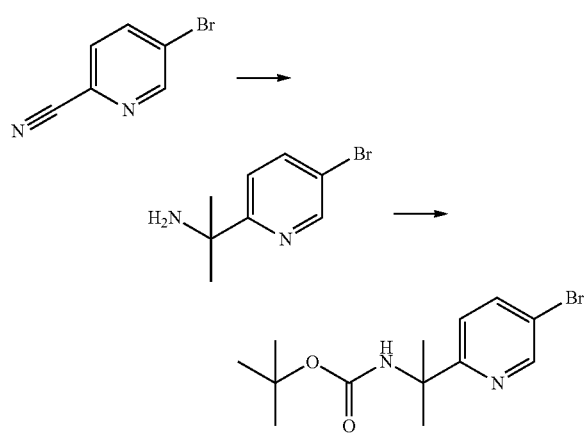

Step 1: 2-(5-Bromopyridin-2-yl)propan-2-amine

Methyl magnesium bromide (3 M in Et$_2$O) (4.00 mL, 12.0 mmol) was slowly added to a solution of 5-bromopicolinonitrile (1.00 g, 5.46 mmol) in toluene (13 mL) at about 0° C. After completion of addition, the ice bath was removed and the reaction was heated at about 100° C. for about 16 h. The reaction was cooled to rt then 2-methyl tetrahydrofuran (6 mL) was added and heating was continued at about 100° C. for about 1 h. The reaction was cooled to rt then methyl magnesium bromide (3 M in Et$_2$O) (4.00 mL, 12.0 mmol) was added. The reaction was heated at 100° C. for about 12 h. The reaction was allowed to cool to rt then was added carefully to ice cold stirring 2 N aq. HCl (50 mL, 100 mmol). The aqueous solution was extracted with EtOAc (2×50 mL) then the aqueous layer was basified with 5 N aq. sodium hydroxide (25.0 mL, 125 mmol). The aqueous layer was extracted with EtOAc (2×50 mL). The combined organic extracts were washed with sat. aq. NaCl (25 mL), dried over Na$_2$SO$_4$, filtered and concentrated under reduced pressure to give the title compound (0.53 g, 45%); LC/MS (Table A, Method i) R$_t$=0.21 min; MS m/z: 215 and 217 (M+H)$^+$.

Step 2: tert-Butyl (2-(5-bromopyridin-2-yl)propan-2-yl)carbamate

A solution of sodium carbonate (0.197 g, 1.86 mmol) in water (3.0 mL) was added to a mixture of 2-(5-bromopyridin-2-yl)propan-2-amine (0.400 g, 1.86 mmol) in 1,4-dioxane (5.0 mL) and water (5.0 mL). The mixture was cooled in an ice bath then di-tert-butyl dicarbonate (0.406 g, 1.86 mmol) was added in one portion. About 5 min after the addition, the ice bath was removed and the reaction was stirred at rt for about 16 h. The reaction was extracted with EtOAc (2×20 mL). The combined organic layers were dried over Na$_2$SO$_4$, filtered and concentrated under reduced pressure. The residue was purified on silica gel using a gradient of 5-20% EtOAc in heptane to give the title compound (0.136 g, 23%); LC/MS (Table A, Method i) R$_t$=1.52 min; MS m/z: 315 and 317 (M+H)$^+$.

124

Preparation #69: 2-(1-Benzyl-3-methylpyrrolidin-3-yl)-5-bromopyrimidine

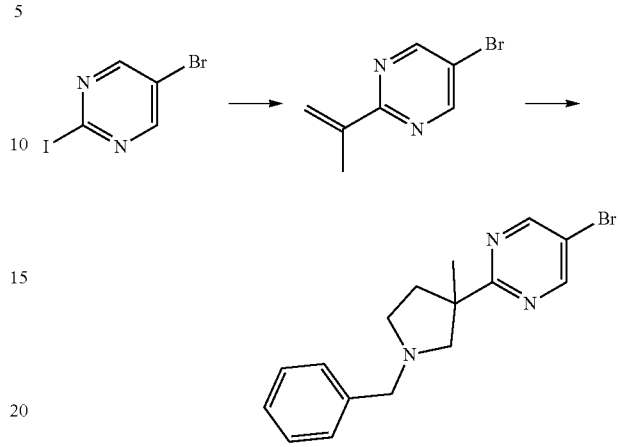

Step 1: 5-Bromo-2-(prop-1-en-2-yl)pyrimidine

5-Bromo-2-iodopyrimidine (2.00 g, 7.02 mmol), cesium carbonate (5.72 g, 17.6 mmol), 4,4,5,5-tetramethyl-2-(prop-1-en-2-yl)-1,3,2-dioxaborolane (1.36 g, 8.07 mmol), 1,4-dioxane (40 mL) and water (10 mL) were stirred under an atmosphere of nitrogen then PdCl$_2$(PPh$_3$)$_2$ (0.246 g, 0.351 mmol) was added. The mixture was heated to about 90° C. for about 1.5 h then XPhos Pd G2 catalyst (0.100 g, 0.127 mmol) was added. The mixture was stirred at about 90° C. for about 3 h then cooled and diluted with EtOAc (30 mL). The organic layer was separated from the aqueous layer then washed with sat. aq. NaCl (25 mL). The organic solution was dried over magnesium sulfate, filtered and concentrated under reduced pressure. The residue was purified via flash chromatography on silica gel (0-20% EtOAc/heptane) to give the title compound (1.32 g, 94%); LC/MS (Table A, Method i) R$_t$=1.20 min; MS m/z: 199, 201 (M+H)$^+$.

Step 2: 2-(1-Benzyl-3-methylpyrrolidin-3-yl)-5-bromopyrimidine

To 5-bromo-2-(prop-1-en-2-yl)pyrimidine (1.32 g, 6.63 mmol) in DCM (8 mL) was added TFA (0.19 mL, 2.5 mmol) then N-benzyl-1-methoxy-N-((trimethylsilyl)methyl)methanamine (2.05 g, 8.62 mmol) in DCM (8 mL) over about 10 min. The mixture was stirred at rt for about 12 h then a second portion of TFA (0.72 mL, 9.3 mmol) and N-benzyl-1-methoxy-N-((trimethylsilyl)methyl)methanamine (2.05 g, 8.62 mmol) were added. The mixture was stirred for about 1.5 h then diluted with DCM and washed with sat. aq. sodium bicarbonate. The organic solution was dried over magnesium sulfate, filtered then concentrated under reduced pressure. The residue was purified via flash chromatography on silica gel (0-10% DCM/MeOH) to give the title compound (0.335 g, 15%); LC/MS (Table A, Method i) R$_t$=0.79 min; MS m/z: 332, 334 (M+H)$^+$.

Preparation #70: (2-(Difluoromethoxy)-5-((1-((2-(trimethylsilyl)ethoxy)methyl)-1H-pyrazol-4-yl)methyl)phenyl)methanol

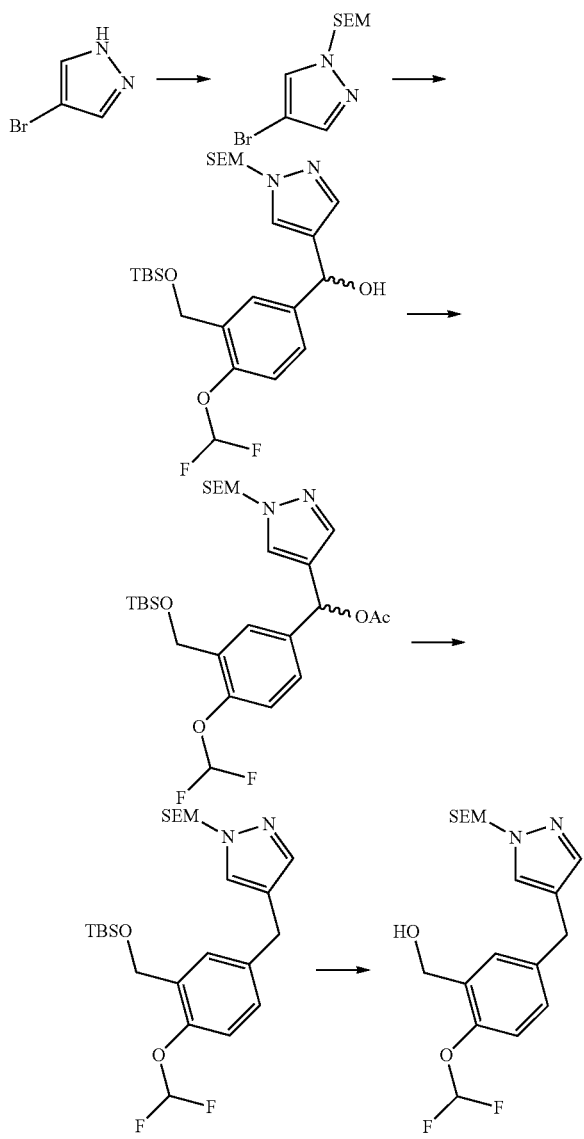

Step 1: 4-Bromo-1-((2-(trimethylsilyl)ethoxy)methyl)-1H-pyrazole

Sodium hydride (60 wt % in mineral oil, 327 mg, 8.16 mmol) was added to a dry reaction vessel, followed by anhydrous THF (30 mL). The reaction was cooled to about 0° C., then 4-bromo-1H-pyrazole (1.00 g, 6.80 mmol) in anhydrous THF (4 mL) was added dropwise over about 5 min. The reaction was allowed to warm to rt for about 30 min before re-cooling to about 0° C. 2-(Trimethylsilyl)ethoxymethyl chloride (1.57 mL, 8.85 mmol) was added dropwise over about 5 min, and the reaction was allowed to stir for about 16 h while warming to rt. The reaction was quenched with sat. aq. NH$_4$Cl (30 mL). EtOAc (50 mL) and water (50 mL) were added and the layers were separated. The aqueous layer was extracted with additional EtOAc (30 mL), then the combined organic layers were washed with water (50 mL) and sat. aq. NaCl (50 mL), dried over MgSO$_4$, filtered, and concentrated in vacuo. The resulting residue was further purified via flash chromatography (0-40% EtOAc in heptane) to afford the title compound (1.72 g, 91%); LC/MS (Table A, Method i) R$_t$=1.78 min; MS m/z: 277 (M+H)$^+$.

Step 2: (3-(((tert-Butyldimethylsilyl)oxy)methyl)-4-(difluoromethoxy)phenyl)(1-((2-(trimethylsilyl)ethoxy)methyl)-1H-pyrazol-4-yl)methanol 4-Bromo-1-((2-(trimethylsilyl)ethoxy)methyl)-1H-pyrazole (550 mg, 1.99 mmol) in anhydrous THF (3.0 mL) was added to an oven-dried reaction vial and cooled to about −78° C. for about 5 min, then n-butyllithium (2.5 M solution in hexane, 0.794 mL, 1.99 mmol) was added dropwise over about 5 min. The reaction was stirred at about −78° C. for about 5 min, then an anhydrous solution of 3-(((tert-butyldimethylsilyl)oxy)methyl)-4-(difluoromethoxy)benzaldehyde (synthesized in a manner similar to Example #4, step 1 from tert-butyl((2-(difluoromethoxy)-5-vinylbenzyl)oxy)dimethylsilane (synthesized in a manner similar to Example #14, step 4 from ((5-bromo-2-(difluoromethoxy)benzyl)oxy)(tert-butyl)dimethylsilane (synthesized in a manner similar to Preparation #43, step 1 from (5-bromo-2-(difluoromethoxy)phenyl)methanol (Preparation #12)))) (571 mg, 1.81 mmol) in anhydrous THF (3 mL) was added slowly dropwise over about 5 min. The reaction was stirred for about 5 additional min at about −78° C., then allowed to stir about 15 min while warming to rt. The reaction was quenched via dropwise addition of water (2 mL) and diethyl ether (2 mL). The aqueous layer was extracted with additional diethyl ether (5 mL), then the combined organic layers were washed with water (5 mL) and sat. aq. NaCl (5 mL). The organic extract was dried over MgSO$_4$, filtered, and concentrated in vacuo. Further purification via flash chromatography (0-80% EtOAc in heptane) isolated the title compound (654 mg, 70%); LC/MS (Table A, Method k) R$_t$=1.51 min; MS m/z: 515 (M+H)$^+$.

Step 3: (3-(((tert-Butyldimethylsilyl)oxy)methyl)-4-(difluoromethoxy)phenyl)(1-((2-(trimethylsilyl)ethoxy)methyl)-1H-pyrazol-4-yl)methyl acetate The compound was synthesized in a manner similar to Example #3, step 1 from (3-(((tert-butyldimethylsilyl)oxy)methyl)-4-(difluoromethoxy)phenyl)(1-((2-(trimethylsilyl)ethoxy)methyl)-1H-pyrazol-4-yl)methanol (92%); LC/MS (Table A, Method k) R$_t$=1.69 min; MS m/z: 557 (M+H)$^+$.

Step 4: 4-(3-(((tert-Butyldimethylsilyl)oxy)methyl)-4-(difluoromethoxy)benzyl)-1-((2-(trimethylsilyl)ethoxy)methyl)-1H-pyrazole (3-(((tert-Butyldimethylsilyl)oxy)methyl)-4-(difluoromethoxy)phenyl)(1-((2-(trimethylsilyl)ethoxy)methyl)-1H-pyrazol-4-yl)methyl acetate (526 mg, 0.945 mmol) and palladium on carbon (10 wt %, 50 mg) were added to EtOH (29 mL) in a 3-neck flask. The atmosphere was evacuated and replaced with H$_2$ from a balloon. The reaction was warmed to about 55° C. and stirred for about 30 min, then cooled and filtered through Celite®. The filter was washed with EtOH (75 mL), then the combined filtrates were concentrated and used without further purification (437 mg, 93%); LC/MS (Table A, Method k) R$_t$=1.76 min; MS m/z: 499 (M+H)$^+$.

Step 5: (2-(Difluoromethoxy)-5-((1-((2-(trimethylsilyl)ethoxy)methyl)-1H-pyrazol-4-yl)methyl)phenyl)methanol The compound was synthesized in a manner similar to Example #35, step 3 from 4-(3-(((tert-butyldimethylsilyl)oxy)methyl)-4-(difluoromethoxy)benzyl)-1-((2-(trimethylsilyl)ethoxy)methyl)-1H-pyrazole (74%); LC/MS (Table A, Method k) $R_t$=0.98 min; MS m/z: 385 (M+H)$^+$.

Preparation #71: 6-Bromo-1-(2-(difluoromethoxy)benzyl)-2,7-dimethyl-1H-indazol-3(2H)-one

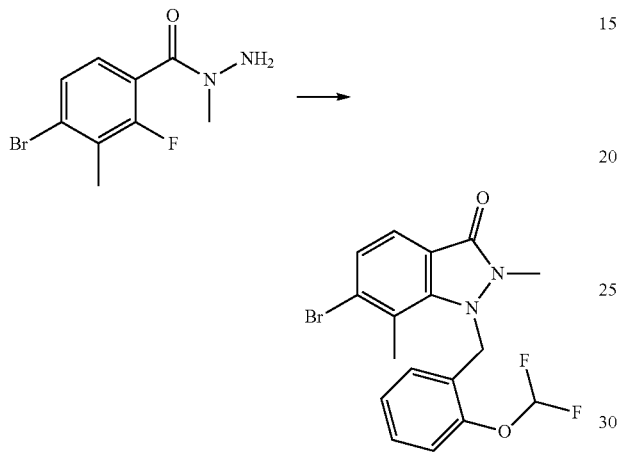

Potassium tert-butoxide (0.29 g, 2.63 mmol) was added in one portion to a solution of 4-bromo-2-fluoro-N,3-dimethylbenzohydrazide (0.310 g, 1.19 mmol) (prepared in a similar fashion to Example #17, step 1 using 4-bromo-2-fluoro-3-methylbenzoic acid) and DMF (2.8 mL). The mixture was warmed to about 85° C. After about 10 min, the reaction vessel was transferred to an ice bath. After about 10 min, 1-(bromomethyl)-2-(difluoromethoxy)benzene (0.20 mL, 1.3 mmol) in DMF (0.28 mL) was added dropwise over about 1 min and the ice bath was removed. After about 30 min, the volatiles were mostly removed under reduced pressure and water (5 mL) and EtOAc (10 mL) were added. The layers were separated and the aqueous layer was extracted with EtOAc (2×5 mL). The combined organic layers were dried over MgSO$_4$, filtered and concentrated under reduced pressure. The material was purified via flash chromatography on silica gel (0-40% EtOAc/DCM). The appropriate fractions were collected and concentrated under reduced pressure to provide the title product (0.29 g, 61%); LC/MS (Table A, Method i) $R_t$=1.54 min.; MS m/z: 397 and 399 (M+H)$^+$.

Preparation #72: 6-Bromo-2-methyl-1-((4-(trifluoromethyl)-1H-pyrrol-3-yl)methyl)-1H-indazol-3(2H)-one

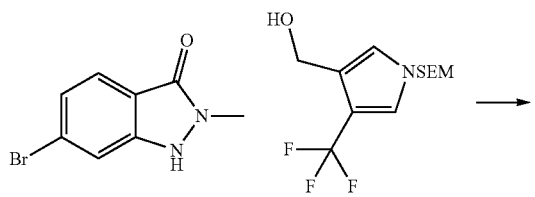

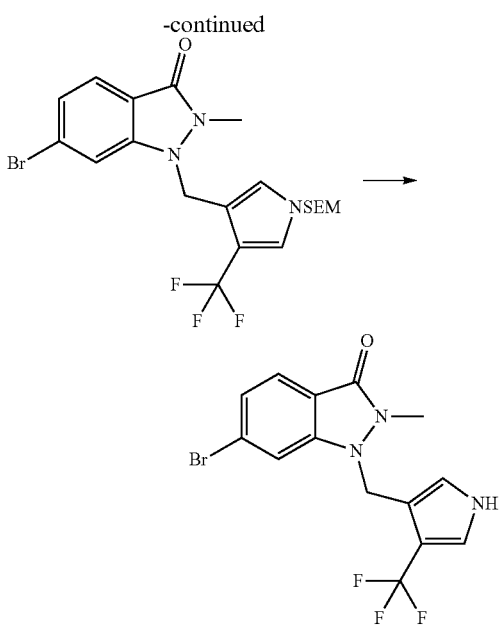

Step 1: 6-Bromo-2-methyl-1-((4-(trifluoromethyl)-1-((2-(trimethylsilyl)ethoxy)methyl)-1H-pyrrol-3-yl)methyl)-1H-indazol-3(2H)-one CBr$_4$ (3.67 g, 11.1 mmol) was added in one portion to a solution of (4-(trifluoromethyl)-1-((2-(trimethylsilyl)ethoxy)methyl)-1H-pyrrol-3-yl)methanol (2.95 g, 9.99 mmol) (prepared in a similar manner to Preparation #52, step 2 using ethyl 4-(trifluoromethyl)-1-((2-(trimethylsilyl)ethoxy)methyl)-1H-pyrrole-3-carboxylate (prepared in a similar manner to Preparation #31, step 1 using ethyl 4-(trifluoromethyl)-1H-pyrrole-3-carboxylate (WO 2009147167 A1))) and DMF (50.0 mL) under N$_2$. After about 5 min, the solution was cooled to about 0° C. PPh$_3$(3.41 g, 13.0 mmol) was added in one portion. After about 30 min, 6-bromo-2-methyl-1H-indazol-3(2H)-one (2.27 g, 10.00 mmol) (Preparation #1) and K$_2$CO$_3$(2.76 g, 20.0 mmol) were added respectively, each in one portion. The reaction vessel was evacuated and back-filled with N$_2$. The ice bath was removed. After about 90 min, DCM (200 mL) and water (200 mL) were added. The layers were separated and the aqueous layer was extracted with DCM (100 mL). The combined organic layers were dried over Na$_2$SO$_4$, filtered, and concentrated under reduced pressure. The residue was purified via flash chromatography on silica gel (0-75% EtOAc/heptane). The appropriate fractions were combined and concentrated to afford the title compound (47%); LC/MS (Table A, Method i) $R_t$=2.04 min; MS m/z: 504 and 506 (M+H)$^+$.

Step 2: 6-Bromo-2-methyl-1-((4-(trifluoromethyl)-1H-pyrrol-3-yl)methyl)-H-indazol-3(2H)-one TFA (4.80 mL, 62.3 mmol) was added over about 5 min to a solution of 6-bromo-2-methyl-1-((4-(trifluoromethyl)-1-((2-(trimethylsilyl)ethoxy)methyl)-1H-pyrrol-3-yl)methyl)-1H-indazol-3(2H)-one (1.60 g, 3.17 mmol) and DCM (30.0 mL) under N$_2$ at about 0° C. The ice bath was removed. After about 17 h, heptane (20 mL) was added and the volatiles were removed under reduced pressure. The residue was dissolved in DCM (about 20 mL), heptane (about 20 mL) was added and the volatiles were removed under reduced pressure. A solution of ammonium hydroxide (1.20 mL, 30.8 mmol) and MeOH (30.0 mL) was added. After about 5 min, the solution was warmed to about 40° C. After about 12 h, the solution was allowed to cool to rt. The volatiles were removed under reduced pressure. The material was dissolved in about 10% MeOH/DCM (80 mL), silica gel (12 g) was added and the volatiles were removed under reduced pressure. The resulting solid was purified via flash chromatography on silica gel (0-100% EtOAc/heptane then EtOAc). The appropriate fractions were combined and concentrated under reduced pressure to afford the title compound (61%); LC/MS (Table A, Method i) R$_t$=1.35 min; MS m/z: 374 and 376 (M+H)$^+$.

Preparation #73: 6-Bromo-2-(pyridin-4-ylmethyl)-1H-indazol-3(2H)-one

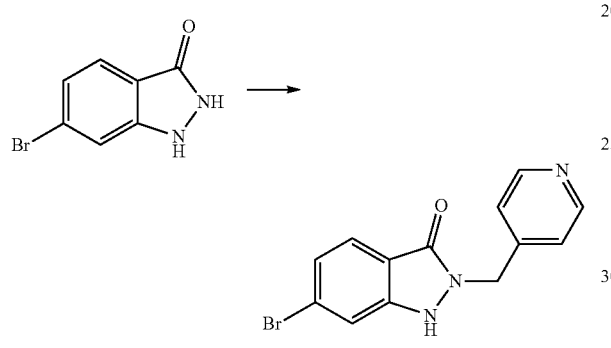

4-(Bromomethyl)pyridine hydrobromide (1.78 g, 7.04 mmol) was added to 6-bromo-1H-indazol-3(2H)-one (1.5 g, 7.0 mmol) in NMP (25 mL). The mixture was warmed to about 100° C. for about 12 h then cooled to it. Ice water was added and the mixture was filtered. The aqueous layer was then washed with EtOAc and DCM/MeOH. The aqueous layer was concentrated under reduced pressure to afford the title product (0.400 g, 19%); LC/MS (Table A, Method i) R$_t$=0.73 min; MS m/z: 304 and 306 (M+H)$^+$.

Preparation #74: 6-Bromo-1-(2-(difluoromethoxy)-5-methylbenzyl)-1H-indazol-3(2H)-one

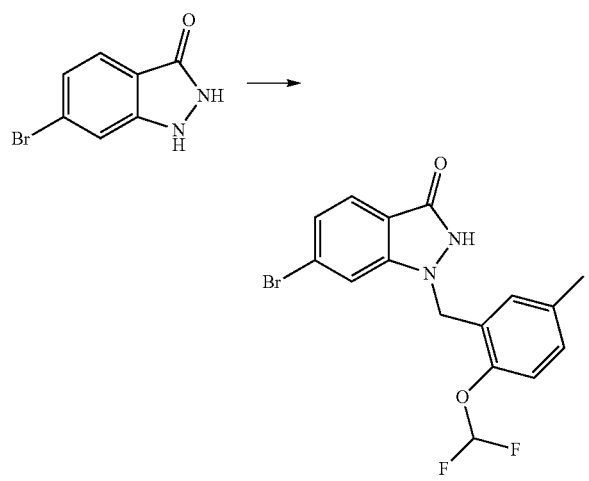

A solution of 2-(bromomethyl)-1-(difluoromethoxy)-4-methylbenzene (2.67 g, 10.6 mmol) (prepared in a similar manner to Preparation #3, step 2 using (2-(difluoromethoxy)-5-methylphenyl)methanol (Preparation #11)) in DMF (6.00 mL) was added over about 5 min to a mixture of 6-bromo-1H-indazol-3(2H)-one (2.27 g, 10.6 mmol) and potassium carbonate (1.62 g, 11.7 mmol) in DMF (30.0 mL) under N$_2$ at about 0° C. The ice bath was allowed to thaw to rt over about 2 h. Water (60 mL) was added. After stirring for about 5 min, the mixture was cooled to about 0° C. After about 5 min, the solid was collected by filtration rinsing with water (2×10 mL). The aqueous layer was extracted with EtOAc (2×25 mL). The aqueous layer was acidified with sat. aq. NH$_4$Cl then extracted with EtOAc (50 mL). The solid from the filtration was combined with the organic layers and the volatiles were removed under reduced pressure. The residue was slurried in Et$_2$O (20 mL). The solid was collected by filtration rinsing with Et$_2$O (2×15 mL) and dried in a vacuum oven at about 50° C. for about 30 min to afford the title compound (2.22 g, 55%); LC/MS (Table A, Method i) R$_t$=1.70 min; MS m/z: 383 and 385 (M+H)$^+$.

Example #1: 1-(2-(Difluoromethoxy)-6-fluorobenzyl)-2-methyl-6-(2-morpholinopyrimidin-5-yl)-1H-indazol-3(2H)-one

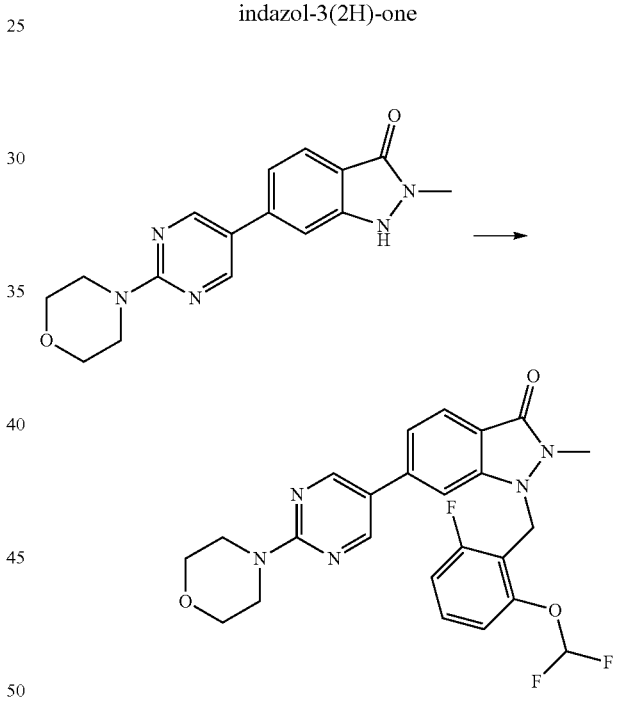

A flask was charged with 2-methyl-6-(2-morpholinopyrimidin-5-yl)-1H-indazol-3(2H)-one (0.060 g, 0.19 mmol) (Preparation #2), K$_2$CO$_3$ (0.027 g, 0.19 mmol) and 2-(bromomethyl)-1-(difluoromethoxy)-3-fluorobenzene (0.079 g, 0.31 mmol) (prepared in a similar fashion to Preparation #3, step 2 from (2-(difluoromethoxy)-6-fluorophenyl)methanol (Preparation #9)) and DMF (1 mL). After about 2 h, the reaction mixture was partitioned between water (5 mL) and EtOAc (5 mL). The aqueous phase was extracted with EtOAc (2×5 mL). The combined organic phases were washed with sat. aq. NaCl (10 mL), dried over Na$_2$SO$_4$, filtered, and concentrated under reduced pressure. The residue was purified using flash chromatography on silica gel (0-100% EtOAc/DCM) to give the title product (0.073 g, 78%); LC/MS (Table A, Method a) R$_t$=2.05 min; MS m/z: 486 (M+H)$^+$; (TNF IC$_{50}$=A).

The compounds shown in Table 1 were synthesized in a manner similar to Example #1 from 2-methyl-6-(2-morpholinopyrimidin-5-yl)-1H-indazol-3(2H)-one (Preparation #2) and the corresponding halides or acid halides.

TABLE 1

| Halide/acid halide | Product | Example # | R_t min (Table A, Method) | m/z ESI+ (M + H)+ | TNF IC_{50} |
|---|---|---|---|---|---|
| 3-Fluorobenzyl bromide | | 1.1 | 2.01 (a) | 420 | B |
| 3-(Difluoromethoxy)benzyl bromide | | 1.2 | 2.07 (a) | 468 | B |
| 1-(Bromomethyl)-2-methylbenzene | | 1.3 | 2.10 (a) | 416 | B |
| (2-Bromoethyl)benzene | | 1.4 | 2.07 (a) | 416 | C |
| 1-(1-Bromoethyl)-2-(difluoromethoxy)benzene (Preparation #3, step 2) | | 1.5 | 2.20 (a) | 482 | B |

TABLE 1-continued

| Halide/acid halide | Product | Example # | R, min (Table A, Method) | m/z ESI+ (M + H)+ | TNF IC50 |
|---|---|---|---|---|---|
| 2-(Bromomethyl)-1-(difluoromethoxy)-4-fluorobenzene (synthesized in a similar fashion to Preparation #3, step 2 from 2-(difluoromethoxy)-5-fluorophenyl)methanol (Preparation #10) | 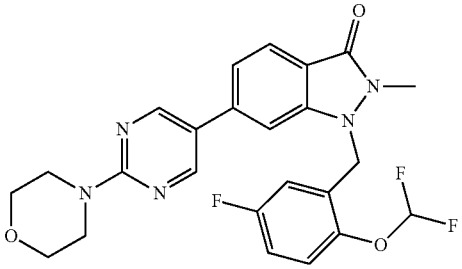 [SMILES: Cn1c(=O)c2ccc(-c3cnc(N4CCOCC4)nc3)cc2n1Cc1cc(F)ccc1OC(F)F] | 1.6 | 2.12 (a) | 486 | B |
| 2-(Difluoromethoxy)benzoyl chloride | 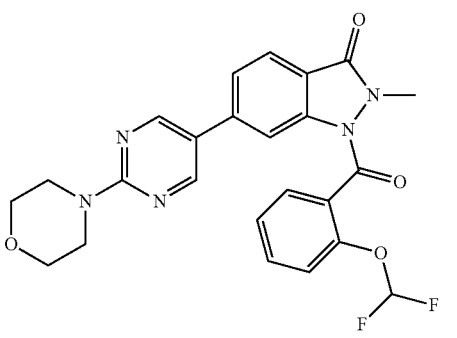 [SMILES: Cn1c(=O)c2ccc(-c3cnc(N4CCOCC4)nc3)cc2n1C(=O)c1ccccc1OC(F)F] | 1.7 | 2.17 (a) | 482 | C |
| Benzoyl chloride | 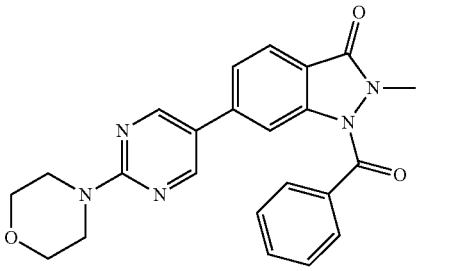 [SMILES: Cn1c(=O)c2ccc(-c3cnc(N4CCOCC4)nc3)cc2n1C(=O)c1ccccc1] | 1.8 | 2.07 (a) | 416 | C |
| 1-(Bromomethyl)-3-methylbenzene | 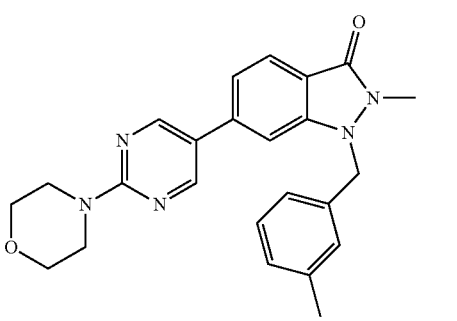 [SMILES: Cc1cccc(Cn2c3cc(-c4cnc(N5CCOCC5)nc4)ccc3c(=O)n2C)c1] | 1.9 | 1.99 (e) | 416 | B |
| (Bromomethyl)benzene | 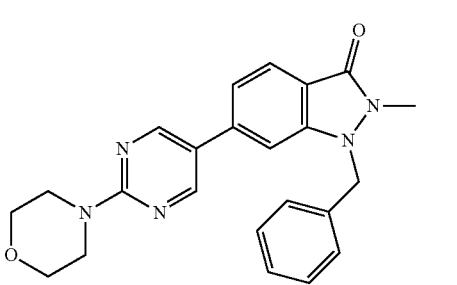 [SMILES: Cn1c(=O)c2ccc(-c3cnc(N4CCOCC4)nc3)cc2n1Cc1ccccc1] | 1.10 | 1.89 (e) | 402 | B |

TABLE 1-continued

| Halide/acid halide | Product | Example # | R$_t$ min (Table A, Method) | m/z ESI+ (M + H)$^+$ | TNF IC$_{50}$ |
|---|---|---|---|---|---|
| 1-(Bromomethyl)-4-fluorobenzene | | 1.11 | 1.92 (e) | 420 | C |
| 2-(Bromomethyl)benzonitrile | | 1.12 | 1.83 (e) | 427 | B |
| 1-(2-bromoethyl)-2-fluorobenzene | | 1.13 | 2.05 (e) | 434 | C |
| 2-(Bromomethyl)-3-chloropyridine (synthesized in a similar fashion to Preparation #3, step 2 from (3-chloropyridin-2-yl)methanol) | | 1.14 | 1.83 (e) | 437, 438 | B |
| 1-(Bromomethyl)-2-fluorobenzene | | 1.15 | 2.03 (a) | 420 | B |

TABLE 1-continued

| Halide/acid halide | Product | Example # | $R_t$ min (Table A, Method) | m/z ESI+ $(M + H)^+$ | TNF $IC_{50}$ |
|---|---|---|---|---|---|
| 2-(Bromomethyl)-3,6-dichloropyridine (synthesized in a similar fashion to Preparation #3, step 2 from (3,6-dichloropyridin-2-yl)methanol) | | 1.16 | 2.04 (a) | 471 | B |
| 3-(Bromomethyl)-4-chloropyridine (synthesized in a similar fashion to Preparation #3, step 2 from (4-chloropyridin-3-yl)methanol) | | 1.17 | 1.68 (a) | 437 | C |
| 2-(Bromomethyl)-1-(difluoromethoxy)-4-methylbenzene (synthesized in a similar fashion to Preparation #3, step 2 from (2-(difluoromethoxy)-5-methylphenyl)methanol (Preparation #11)) | | 1.18 | 2.18 (a) | 482 | A |
| 2-(Bromomethyl)-1,4-dimethylbenzene methylbenzene (synthesized in a similar fashion to Preparation #21, step 2 from (2,5-dimethylphenyl)methanol) | | 1.19 | 2.24 (a) | 430 | A |

Example #2: 1-(2-(Difluoromethoxy)benzyl)-6-(2-(2,2-dimethylmorpholino)pyrimidin-5-yl)-2-methyl-1H-indazol-3(2H)-one

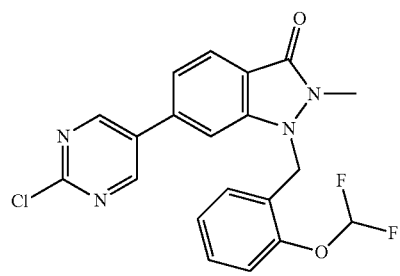

→

-continued

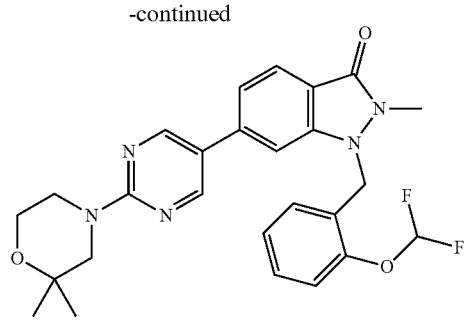

A flask was charged with 6-(2-chloropyrimidin-5-yl)-1-(2-(difluoromethoxy)benzyl)-2-methyl-1H-indazol-3(2H)- one (50 mg, 0.12 mmol) (Preparation #4), 2,2-dimethylmorpholine (28 mg, 0.24 mmol), EtOH (1.5 mL) and TEA (0.033 mL, 0.24 mmol). The reaction mixture was heated at about 80° C. for about 20 h. The reaction mixture was cooled to rt and then purified via reverse phase HPLC (Table 1, Method g) to give the title product (36 mg, 61%); LC/MS (Table A, Method a) $R_t$=2.31 min; MS m/z: 496 (M+H)$^+$ (TNF IC$_{50}$=A).

The compounds shown in Table 2 were synthesized in a manner similar to Example #2 from 6-(2-chloropyrimidin-5-yl)-1-(2-(difluoromethoxy)benzyl)-2-methyl-1H-indazol-3(2H)-one (Preparation #4) and the corresponding amines.

TABLE 2

| Amine | Product | Example # | $R_t$ min (Table A, Method) | m/z ESI+ (M + H)$^+$ | TNF IC$_{50}$ |
|---|---|---|---|---|---|
| Piperazine-1-carboxamide | | 2.1 | 0.63 (b) | 510 | A |
| (R)-2-(Methoxymethyl)pyrrolidine | | 2.2* | 0.75 (b) | 496 | A |
| 1-(Piperazin-1-yl)ethanone | | 2.3 | 0.68 (b) | 509 | A |
| 2-Oxa-6-azaspiro[3.3]heptane | | 2.4 | 1.78 (a) | 480 | B |

TABLE 2-continued

| Amine | Product | Example # | R, min (Table A, Method) | m/z ESI+ (M + H)+ | TNF IC50 |
|---|---|---|---|---|---|
| (R)-3-Hydroxypyrrolidine hydrochloride | | 2.5* | 1.65 (a) | 468 | C |
| (R)-Pyrrolidine-3-carboxylic acid | | 2.6* | 1.70 (e) | 496 | C |
| 4-(Aminomethyl)pyrrolidin-2-one | | 2.7 | 1.60 (e) | 495 | B |
| 3-(Oxetan-3-yl)azetidine | | 2.8 | 1.80 (e) | 494 | B |
| Azetidin-3-ol hydrochloride | | 2.9 | 1.64 (e) | 454 | B |

TABLE 2-continued

| Amine | Product | Example # | R, min (Table A, Method) | m/z ESI+ (M + H)+ | TNF IC50 |
|---|---|---|---|---|---|
| Oxetan-3-amine | | 2.10 | 1.69 (a) | 454 | B |
| Azetidin-3-ylmethanol hydrochloride | | 2.11 | 1.66 (a) | 468 | B |
| Ethanolamine | | 2.12 | 1.62 (a) | 442 | B |
| Azetidine-3-carboxylic acid | | 2.13 | 1.53 (a) | 482 | C |
| 5-Azaspiro[2.3]hexane-1-carboxylic acid (synthesized from 5-(tert-butoxycarbonyl)-5-azaspiro[2.3]hexane-1-carboxylic acid via Boc cleavage using methods similar to Example #3, step 1) | | 2.14 | 1.68 (a) | 508 | C |

TABLE 2-continued

| Amine | Product | Example # | R$_t$ min (Table A, Method) | m/z ESI+ (M + H)$^+$ | TNF IC$_{50}$ |
|---|---|---|---|---|---|
| (S)-Pyrrolidine-3-carboxylic acid | 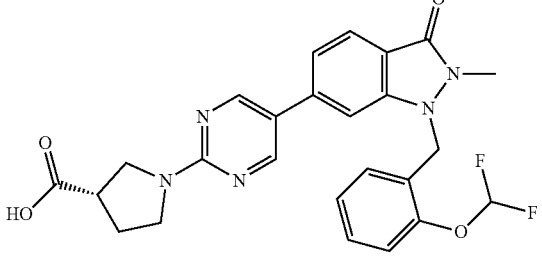 | 2.15* | 1.64 (a) | 496 | C |
| 4-(Aminomethyl)-1-methylpyrrolidin-2-one | 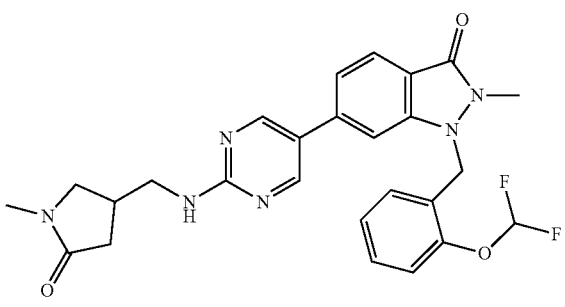 [SMILES: CN1CC(CNc2ncc(-c3ccc4c(=O)n(C)n(Cc5ccccc5OC(F)F)c4c3)cn2)CC1=O] | 2.16 | 1.61 (a) | 509 | B |
| 2-Azaspiro[3.3]heptane-6-carboxylic acid, hydrochloric acid (synthesized from 2-(tert-butoxycarbonyl)-2-azaspiro[3.3]heptane-6-carboxylic acid via Boc cleavage using methods similar to Example #3, step 1) | 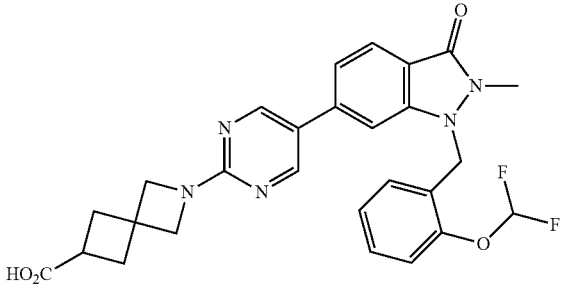 [SMILES: Cn1c(=O)c2ccc(-c3cnc(N4CC5(CC(C(=O)O)C5)C4)nc3)cc2n1Cc1ccccc1OC(F)F] | 2.17 | 1.70 (a) | 522 | B |
| 2-(Azetidin-3-yl)acetic acid hydrochloride | 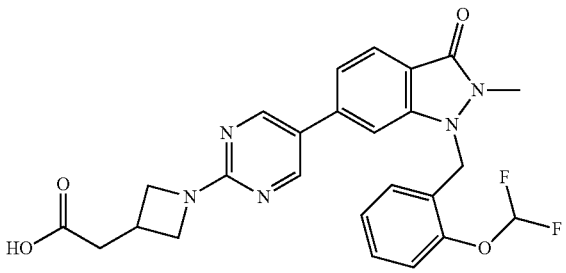 [SMILES: Cn1c(=O)c2ccc(-c3cnc(N4CC(CC(=O)O)C4)nc3)cc2n1Cc1ccccc1OC(F)F] | 2.18 | 1.60 (a) | 496 | C |
| 3-Aminoazepan-2-one | 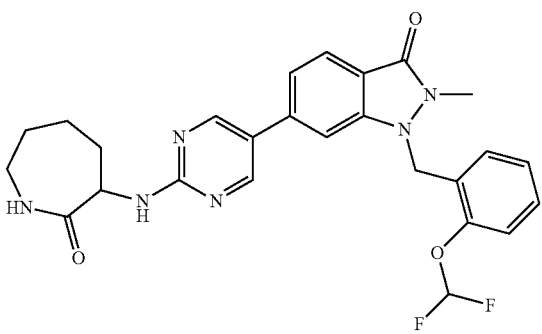 [SMILES: Cn1c(=O)c2ccc(-c3cnc(NC4CCCCNC4=O)nc3)cc2n1Cc1ccccc1OC(F)F] | 2.19 | 0.67 (b) | 509 | B |

TABLE 2-continued
| Amine | Product | Example # | R$_t$ min (Table A, Method) | m/z ESI+ (M + H)$^+$ | TNF IC$_{50}$ |
|---|---|---|---|---|---|
| Tetrahydrofuran-3-amine | 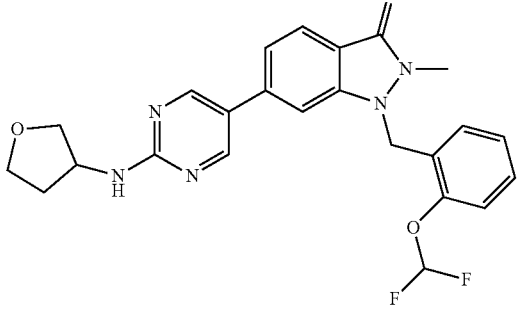 | 2.20 | 0.65 (b) | 468 | B |
| Tetrahydro-2H-pyran-3-amine | 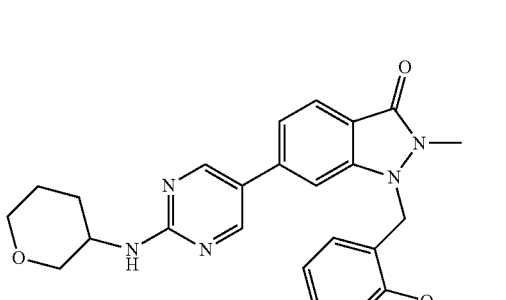 | 2.21 | 0.54 (b) | 482 | B |
| 3-Methoxypropan-1-amine | 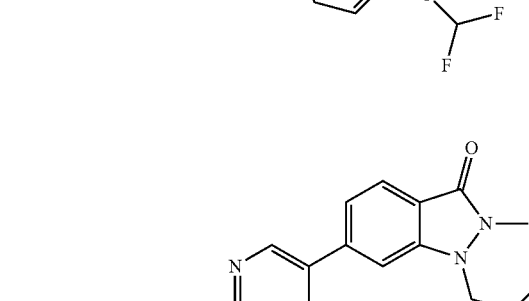 | 2.22 | 0.66 (b) | 470 | B |
| Hexahydropyrrolo[1,2-a]pyrazin-6-one | 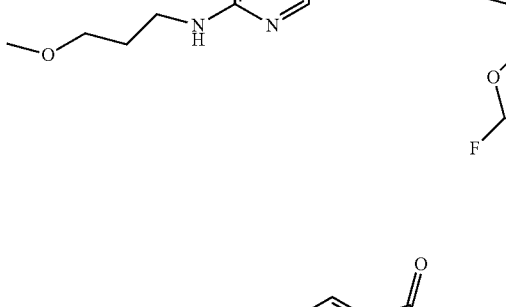 | 2.23 | 1.83 (a) | 521 | A |

TABLE 2-continued

| Amine | Product | Example # | R$_t$ min (Table A, Method) | m/z ESI+ (M + H)+ | TNF IC$_{50}$ |
|---|---|---|---|---|---|
| (R)-Tetrahydrofuran-3-amine | | 2.24* | 1.81 (a) | 468 | B |
| (R)-Hexahydrooxazolo[3,4-a]pyrazin-3-one hydrochloride | | 2.25* | 1.91 (a) | 523 | A |
| (S)-Hexahydrooxazolo[3,4-a]pyrazin-3-one hydrochloride | | 2.26* | 1.91 (a) | 523 | A |
| Octahydroimidazolidino[1,5-a]piperazin-3-one hydrochloride | | 2.27 | 1.74 (a) | 572 | A |

TABLE 2-continued

| Amine | Product | Example # | R$_t$ min (Table A, Method) | m/z ESI+ (M + H)$^+$ | TNF IC$_{50}$ |
|---|---|---|---|---|---|
| 3-(Piperidin-4-yl)-1,2,4-thiadiazol-5(4H)-one hydrochloride (Preparation #64) | 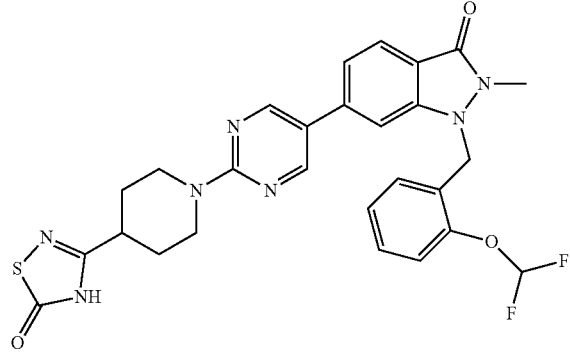 [SMILES: Cn1c(=O)c2ccc(-c3cnc(N4CCC(c5nsc(=O)[nH]5)CC4)nc3)cc2n1Cc1ccccc1OC(F)F] | 2.28 | 1.83 (a) | 566 | B |

The compound shown in Table 3 was synthesized in a manner similar to Example #2 from 6-(2,5-dichloropyridin-4-yl)-1-(3-fluorobenzyl)-2-methyl-1H-indazol-3(2H)-one (synthesized from 6-bromo-1H-indazol-3(2H)-one and 1-(bromomethyl)-3-fluorobenzene in a similar fashion to Example 1, alkylation with MeI in a similar fashion to Example #14, step 3, Suzuki reaction with 2,5-dichloro-4-(4,4,5,5-tetramethyl-1,3,2-dioxaborolan-2-yl)pyridine in a similar fashion to Example #5) and the corresponding amine.

TABLE 3

| Amine | Product | Example # | R$_t$ min (Table A, Method) | m/z ESI+ (M + H)$^+$ | TNF IC$_{50}$ |
|---|---|---|---|---|---|
| Morpholine | 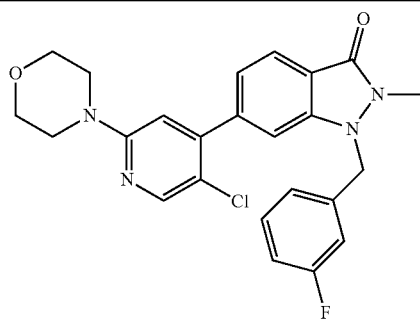 | 3.1 | 2.14 (e) | 453 | C |

The compound shown in Table 4 was synthesized in a manner similar to Example #2 from 6-(2,5-dichloropyridin-4-yl)-1-(2-(difluoromethoxy)benzyl)-2-methyl-1H-indazol-3(2H)-one (synthesized from 6-bromo-1-(2-(difluoromethoxy)benzyl)-2-methyl-1H-indazol-3(2H)-one (Preparation #4, step 1) and 2,5-dichloro-4-(4,4,5,5-tetramethyl-1,3,2-dioxaborolan-2-yl)pyridine in a similar fashion to Example #5) and the corresponding amine.

TABLE 4

| Amine | Product | Example # | R, min (Table A, Method) | m/z ESI+ (M + H)+ | TNF IC50 |
|---|---|---|---|---|---|
| Morpholine | (structure) | 4.1 | 2.20 (e) | 501 | C |

Example #3*: (S)-6-(2-((1-Acetylpyrrolidin-3-yl)amino)pyrimidin-5-yl)-1-(2-(difluoromethoxy)benzyl)-2-methyl-1H-indazol-3(2H)-one

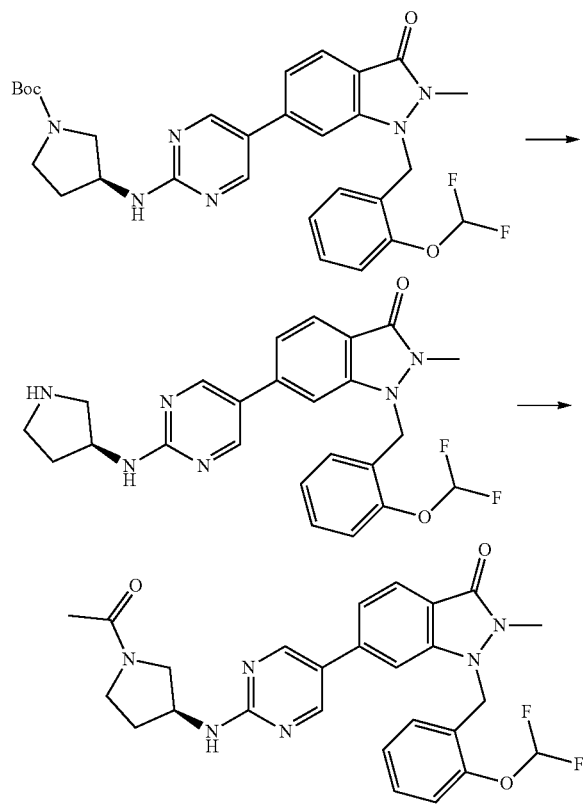

Step 1: (S)-1-(2-(Difluoromethoxy)benzyl)-2-methyl-6-(2-(pyrrolidin-3-ylamino)pyrimidin-5-yl)-1H-indazol-3(2H)-one HCl (4 M solution in 1,4-dioxane, 1.20 mL, 4.80 mmol) was added to a solution of(S)-tert-butyl 3-((5-(1-(2-(difluoromethoxy)benzyl)-2-methyl-3-oxo-2,3-dihydro-1H-indazol-6-yl)pyrimidin-2-yl)amino)pyrrolidine-1-carboxylate (0.134 g, 0.236 mmol) (synthesized from 6-(2-chloropyrimidin-5-yl)-1-(2-(difluoromethoxy)benzyl)-2-methyl-1H-indazol-3(2H)-one (Preparation 4) and (S)-tert-butyl 3-aminopyrrolidine-1-carboxylate in a similar fashion to Example #2) and 1,4-dioxane (1.0 mL). After about 90 min, MeOH (5 mL) was added. The reaction mixture was concentrated under reduced pressure and the residue was dried under high vacuum for about 18 h to afford a HCl salt of the title product (0.119 g, 96%); LC/MS (Table A, Method e) R$_t$=1.47 min; MS m/z: 467 (M+H)+.

Step 2: (S)-6-(2-((1-Acetylpyrrolidin-3-yl)amino)pyrimidin-5-yl)-1-(2-(difluoromethoxy)benzyl)-2-methyl-1H-indazol-3(2H)-one TEA (0.30 mL, 2.2 mmol) was added to a slurry of (S)-1-(2-(difluoromethoxy)benzyl)-2-methyl-6-(2-(pyrrolidin-3-ylamino)pyrimidin-5-yl)-1H-indazol-3(2H)-one, hydrochloric acid (0.098 g, 0.20 mmol) and DCM (1.30 mL). A solution of acetic anhydride (0.022 mL, 0.24 mmol) and DCM (0.650 mL) was added. After about 30 min, the reaction mixture was concentrated under reduced pressure. The residue was dissolved in EtOAc (20 mL) and the resulting solution was washed with sat. aq. NH$_4$Cl (5 mL), sat. aq. NaHCO$_3$(5 mL), and sat. aq. NaCl (5 mL). The aqueous layers were extracted with EtOAc (5 mL). The combined organics were dried over Na$_2$SO$_4$, filtered, concentrated under reduced pressure. The residue was purified using flash chromatography on silica gel (2-10% MeOH/DCM) to afford the title product (72 mg, 72%); LC/MS (Table A, Method a) R$_t$=1.63 min; MS m/z: 509 (M+H)+ (TNF IC$_{50}$=B).

Example #4: 1-((5-(1-(2-(Difluoromethoxy)benzyl)-2-methyl-3-oxo-2,3-dihydro-1H-indazol-6-yl)pyrimidin-2-yl)methyl)azetidine-3-carboxylic acid

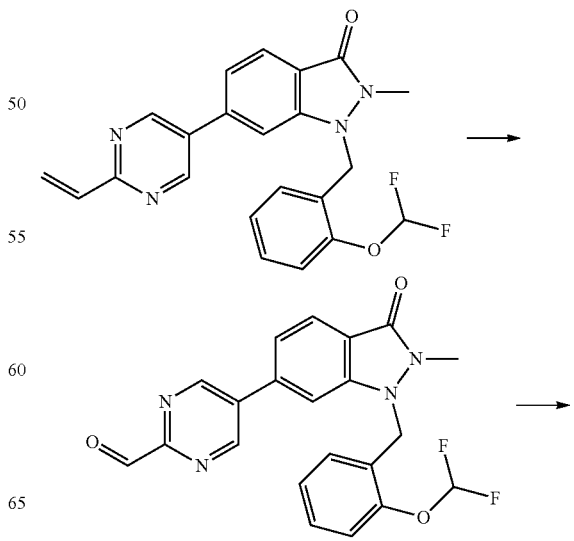

-continued

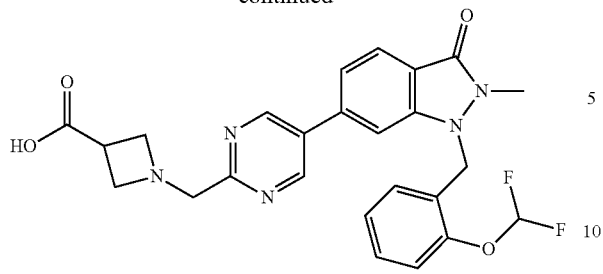

Step 1: 5-(1(2-(Difluoromethoxy)benzyl)-2-methyl-3-oxo-2,3-dihydro-1H-indazol-6-yl)pyrimidine-2-carbaldehyde Sodium periodate (0.306 g, 1.43 mmol) was added to a mixture of 1-(2-(difluoromethoxy)benzyl)-2-methyl-6-(2-vinylpyrimidin-5-yl)-1H-indazol-3(2H)-one (0.195 g, 0.477 mmol) (prepared using 6-(2-chloropyrimidin-5-yl)-1-(2-(difluoromethoxy)benzyl)-2-methyl-1H-indazol-3(2H)-one (Preparation #4) and 4,4,5,5-tetramethyl-2-vinyl-1,3,2-dioxaborolane in a similar fashion to Preparation #2), 4% osmium tetroxide in water (0.060 mL, 9.6 mmol), 2,6-dimethylpyridine (0.11 mL, 0.96 mmol) in 1,4-dioxane (3 mL) and water (2 mL). The reaction was stirred at rt for about 1 h, 4% osmium tetroxide in H$_2$O (0.120 mL, 19 μmol) was added and the mixture was stirred at rt for about 1 h, 10% aqueous sodium thiosulfate (20 mL) was added. The solution was stirred for about 30 min and then extracted with EtOAc (2×20 mL). The combined organic layers were dried over Na$_2$SO$_4$, filtered, and concentrated under reduced pressure. The residue was purified on silica gel (10-100% EtOAc/heptane) to afford the title product (0.051 g, 26%); LC/MS (Table A, Method e) R$_t$=1.82 min; MS m/z: 411 (M+H)$^+$

Step 2: 1-((5-(1(2-(Difluoromethoxy)benzyl)-2-methyl-3-oxo-2,3-dihydro-1H-indazol-6-yl)pyrimidin-2-yl)methyl)azetidine-3-carboxylic acid A solution of azetidine-3-carboxylic acid (0.014 g, 0.14 mmol) in AcOH (0.3 mL) was added to a suspension of 5-(1-(2-(difluoromethoxy)benzyl)-2-methyl-3-oxo-2,3-dihydro-1H-indazol-6-yl)pyrimidine-2-carbaldehyde (0.048 g, 0.12 mmol) in DMF (1 mL). NaBH(OAc)$_3$ (0.037 g, 0.18 mmol) was added. The reaction was stirred at rt for about 2 h. Water (0.5 mL) was added and the reaction mixture was concentrated under reduced pressure. The residue was purified via HPLC (Table A, Method f). Product containing fractions were combined and concentrated under reduced pressure to remove the organic volatiles. The aqueous solution was lyophilized to give the formic acid salt of the title product (14 mg, 23%); LC/MS (Table A, Method e) R$_t$=1.34 min; MS m/z: 496 (M+H)$^+$ (TNF IC$_{50}$=C).

Example #5: 1-(2-(Difluoromethoxy)benzyl)-2-methyl-6-(2-morpholinopyrimidin-5-yl)-1H-indazol-3(2H)-one

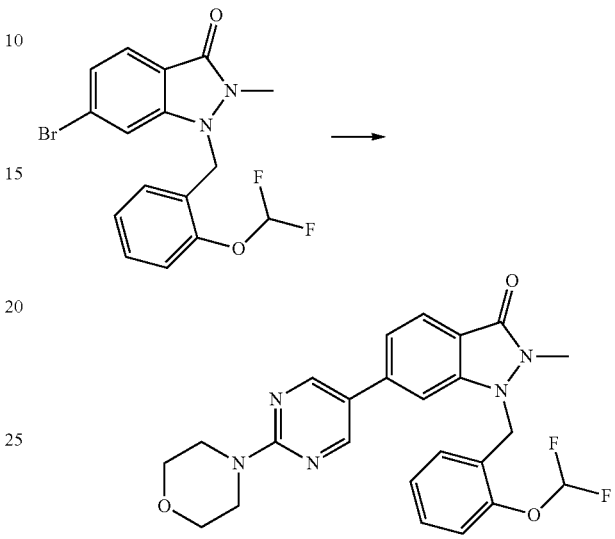

1,4-Dioxane (2 mL) and water (0.5 mL) were added to 6-bromo-1-(2-(difluoromethoxy)benzyl)-2-methyl-1H-indazol-3(2H)-one (0.060 g, 0.16 mmol) (Preparation #4, step 1), 4-(5-(4,4,5,5-tetramethyl-1,3,2-dioxaborolan-2-yl)pyrimidin-2-yl)morpholine (0.059 g, 0.20 mmol) and Cs$_2$CO$_3$ (0.128 g, 0.391 mmol). The mixture was placed under N$_2$. Pd(PPh$_3$)$_4$ (0.013 g, 11 μmol) was added. The mixture was purged with N$_2$ and then heated to about 100° C. After about 2 h, the reaction mixture was allowed to cool to rt. Water (5 mL) was added and then the mixture was extracted with 5% MeOH/DCM (2×10 mL). The combined organics were dried over MgSO$_4$, filtered and concentrated under reduced pressure. The residue was purified via chromatography on silica gel (10-100% EtOAc/DCM) to give the title product (60 mg, 82%); LC/MS (Table A, Method a) R$_t$=2.07 min; MS m/z: 468 (M+H)$^+$ (TNF IC$_{50}$=A).

The compounds shown in Table 5 were synthesized in a manner similar to Example #5 from 6-bromo-1-(2-(difluoromethoxy)benzyl)-2-methyl-1H-indazol-3(2H)-one (Preparation #4, step 1) and the corresponding boronic acid/boronate.

TABLE 5

| Boronic acid/boronate | Product | Example # | R$_t$ min (Table A, Method) | m/z ESI+ (M + H)$^+$ | TNF IC$_{50}$ |
|---|---|---|---|---|---|
| (2-(3-Oxopiperazin-1-yl)pyrimidin-5-yl)boronic acid (synthesized as described in WO 2014/009296) | | 5.1 | 1.67 (a) | 481 | B |

TABLE 5-continued

| Boronic acid/boronate | Product | Example # | R, min (Table A, Method) | m/z ESI+ (M + H)+ | TNF IC50 |
|---|---|---|---|---|---|
| (6-Morpholinopyridin-3-yl)boronic acid | | 5.2 | 2.07 (a) | 467 | B |
| 4-(5-(4,4,5,5-Tetramethyl-1,3,2-dioxaborolan-2-yl)pyridin-2-yl)piperazin-2-one (Preparation #8) | | 5.3 | 1.69 (a) | 480 | B |
| (2-Methoxypyrimidin-5-yl)boronic acid | | 5.4 | 1.94 (a) | 413 | B |
| 1-(5-Boronopyrimidin-2-yl)piperidine-4-carboxylic acid (synthesized as described in WO2014009295A1) | | 5.5 | 1.90 (a) | 510 | B |
| 4-(4-(4,4,5,5-Tetramethyl-1,3,2-dioxaborolan-2-yl)pyridin-2-yl)morpholine | | 5.6 | 1.97 (e) | 467 | C |

TABLE 5-continued

| Boronic acid/boronate | Product | Example # | R, min (Table A, Method) | m/z ESI+ (M + H)+ | TNF IC50 |
|---|---|---|---|---|---|
| 1-(Tetrahydro-2H-pyran-4-yl)-4-(4,4,5,5-tetramethyl-1,3,2-dioxaborolan-2-yl)-1H-pyrazole | | 5.7 | 1.84 (e) | 455 | C |

The compound shown in Table 6 was synthesized in a manner similar to Example #5 from 6-bromo-1-(2-(difluoromethoxy)benzyl)-1H-indazol-3(2H)-one (prepared from 6-bromo-1H-indazol-3(2H)-one (Preparation #1) and 1-(bromomethyl)-2-(difluoromethoxy)benzene using methods similar to those described for Example #1) and the corresponding boronic acid/boronate.

TABLE 6

| Boronic acid/boronate | Product | Example # | R, min (Table A, Method) | m/z ESI+ (M + H)+ | TNF IC50 |
|---|---|---|---|---|---|
| 4-(5-(4,4,5,5-Tetramethyl-1,3,2-dioxaborolan-2-yl)pyrimidin-2-yl)morpholine | | 6.1 | 2.15 (a) | 454 | C |

The compounds shown in Table 7 were synthesized in a manner similar to Example #5 from 6-bromo-1-(2,5-dichlorobenzyl)-2-methyl-1H-indazol-3(2H)-one (synthesized from 6-bromo-2-methyl-1H-indazol-3(2H)-one (Preparation #1) and 2-(bromomethyl)-1,4-dichlorobenzene in a similar fashion to Example #1) and the corresponding boronic acid/boronate.

TABLE 7

| Boronic acid/boronate | Product | Example # | R, min (Table A, Method) | m/z ESI+ (M + H)+ | TNF IC50 |
|---|---|---|---|---|---|
| 4-(5-(4,4,5,5-Tetramethyl-1,3,2-dioxaborolan-2-yl)pyrimidin-2-yl)morpholine | | 7.1 | 2.31 (a) | 470 | A |

TABLE 7-continued

| Boronic acid/boronate | Product | Example # | R, min (Table A, Method) | m/z ESI+ (M + H)+ | TNF IC50 |
|---|---|---|---|---|---|
| 1-(5-Boronopyrimidin-2-yl)piperidine-4-carboxylic acid (synthesized as described in WO2014009295A1) | | 7.2 | 2.05 (e) | 512 | B |

The compounds shown in Table 8 were synthesized in a manner similar to Example #5 from 6-bromo-1-(2,6-dichlorobenzyl)-2-methyl-1H-indazol-3(2H)-one (Preparation #5) and the corresponding boronic acid/boronate.

TABLE 8

| Boronic acid/boronate | Product | Example # | R, min (Table A, Method) | m/z ESI+ (M + H)+ | TNF IC50 |
|---|---|---|---|---|---|
| (2-Morpholinopyrimidin-5-yl)boronic acid | | 8.1 | 2.34 (a) | 470 | B |
| (2-(3-Oxopiperazin-1-yl)pyrimidin-5-yl)boronic acid (synthesized as described in WO 2014/009296) | | 8.2 | 1.80 (a) | 483 | B |

The compound shown in Table 9 was synthesized in a manner similar to Example #5 from 6-bromo-1-(2,5-dichlorobenzyl)-1H-indazol-3(2H)-one (synthesized in a similar fashion to Preparation #5, step 1, from 6-bromo-1H-indazol-3(2H)-one and 2-(bromomethyl)-1,4-dichlorobenzene) and the corresponding boronic acid/boronate.

TABLE 9

| Boronic acid/boronate | Product | Example # | R$_t$ min (Table A, Method) | m/z ESI+ (M + H)$^+$ | TNF IC$_{50}$ |
|---|---|---|---|---|---|
| 4-(5-(4,4,5,5-Tetramethyl-1,3,2-dioxaborolan-2-yl)pyrimidin-2-yl)morpholine | | 9.1 | 2.26 (e) | 456 | C |

The compounds shown in Table 10 were synthesized in a manner similar to Example #5 from 1-(2-(difluoromethoxy)benzyl)-2-methyl-6-(4,4,5,5-tetramethyl-1,3,2-dioxaborolan-2-yl)-1H-indazol-3(2H)-one (Preparation #4, step 2) and the corresponding bromide.

TABLE 10

| Bromide | Product | Example # | R$_t$ min (Table A, Method) | m/z ESI+ (M + H)$^+$ | TNF IC$_{50}$ |
|---|---|---|---|---|---|
| 2-(5-Bromopyrimidin-2-yl)propan-2-ol | | 10.1 | 1.87 (a) | 441 | B |
| 4-(5-Bromopyrazin-2-yl)morpholine (synthesized from 2,5-dibromopyrazine and morpholine using methods similar to Preparation #7) | | 10.2 | 2.04 (a) | 468 | B |
| 1-(5-Bromopyrazin-2-yl)piperidine-4-carboxylic acid (Preparation #7) | | 10.3 | 1.86 (a) | 510 | C |

TABLE 10-continued

| Bromide | Product | Example # | R$_t$ min (Table A, Method) | m/z ESI+ (M + H)+ | TNF IC$_{50}$ |
|---|---|---|---|---|---|
| 2-((5-Bromopyrimidin-2-yl)amino)propanamide (synthesized from 5-bromo-2-chloropyrimidine and 2-aminopropanamide using methods similar to Example #2) | | 10.4 | 1.57 (a) | 469 | B |
| 4-(3-Bromo-1,2,4-thiadiazol-5-yl)morpholine (synthesized from 3-bromo-5-chloro-1,2,4-thiadiazole and morpholine using methods similar to Example #2) | | 10.5 | 2.14 (a) | 474 | C |
| (R)-1-(4-(5-Bromopyrimidin-2-yl)-2-methylpiperazin-1-yl)-2-hydroxyethanone (Preparation #15) | | 10.6* | 1.80 (a) | 539 | A |
| (S)-1-(4-(5-Bromo-4-methylpyrimidin-2-yl)-3-methylpiperazin-1-yl)-2-hydroxyethanone (synthesized in a method similar to Preparation 13, step 1 using (S)-5-bromo-4-methyl-2-(2-methylpiperazin-1-yl)pyrimidine (synthesized in a method similar to Example 3, step 1 using (S)-tert-butyl 4-(5-bromo-4-methylpyrimidin-2-yl)-3-methylpiperazine-1-carboxylate (prepared in a method similar to Example 2 using (S)-tert-butyl 3-methylpiperazine-1-carboxylate and 5-bromo-2-chloro-4-methylpyrimidine))) | | 10.7* | 1.87 (a) | 553 | A |

TABLE 10-continued

| Bromide | Product | Example # | $R_t$ min (Table A, Method) | m/z ESI+ $(M + H)^+$ | TNF $IC_{50}$ |
|---|---|---|---|---|---|
| (R)-1-(4-(5-Bromo-4-methylpyrimidin-2-yl)-2-methylpiperazin-1-yl)-2-hydroxyethanone (synthesized in a method similar to Preparation 13 using (R)-5-bromo-4-methyl-2-(3-methylpiperazin-1-yl)pyrimidine (synthesized in a method similar to Example 3, step 1 using (R)-tert-butyl 4-(5-bromo-4-methylpyrimidin-2-yl)-2-methylpiperazine-1-carboxylate (prepared in a method similar to Example 2 using (R)-tert-butyl 2-methylpiperazine-1-carboxylate and 5-bromo-2-chloro-4-methylpyrimidine))) | 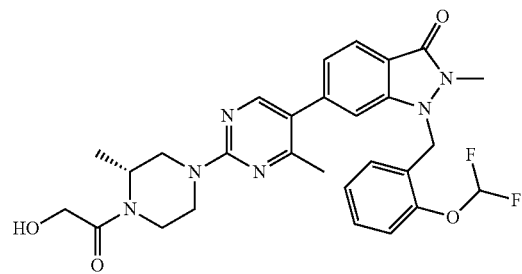 [SMILES: Cc1nc(N2CCN(C(=O)CO)[C@H](C)C2)ncc1-c1ccc2c(=O)n(C)n(Cc3ccccc3OC(F)F)c2c1] | 10.8* | 1.87 (a) | 553 | A |
| (2R,4R)-1-(5-Bromopyrimidin-2-yl)-2-methylpiperidin-4-ol (prepared in a similar fashion to Preparation 13, step 1) | 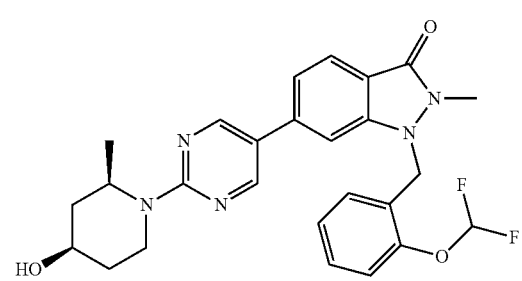 [SMILES: C[C@@H]1C[C@H](O)CCN1c1ncc(-c2ccc3c(=O)n(C)n(Cc4ccccc4OC(F)F)c3c2)cn1] | 10.9* | 1.97 (a) | 496 | A |
| (R)-1-(4-(5-Bromo-4-methylpyrimidin-2-yl)-3-methylpiperazin-1-yl)-2-hydroxyethanone (prepared in a similar fashion to Preparation #15 using glycolic acid and (R)-5-bromo-4-methyl-2-(2-methylpiperazin-1-yl)pyrimidine dihydrochloride (prepared in a similar fashion to Example #3, step1 from (R)-tert-butyl 4-(5-bromo-4-methylpyrimidin-2-yl)-3-methylpiperazine-1-carboxylate (prepared in a similar fashion to Preparation #13, step 1 using (R)-tert-butyl 3-methylpiperazine-1-carboxylate and 5-bromo-2-chloro-4-methylpyrimidine))). | 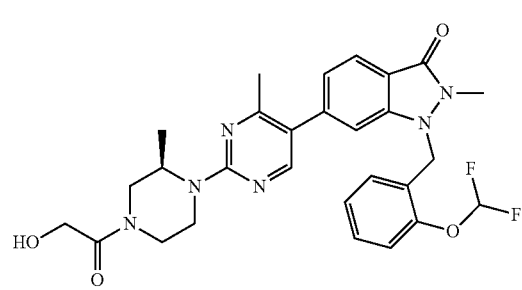 [SMILES: Cc1nc(N2CCN(C(=O)CO)C[C@H]2C)ncc1-c1ccc2c(=O)n(C)n(Cc3ccccc3OC(F)F)c2c1] | 10.10* | 1.24 (i) | 553 | A |
| 4-Bromo-2-((tetrahydro-2H-pyran-4-yl)oxy)pyridine (synthesized in a similar fashion to Preparation #27, from tetrahydro-2H-pyran-4-ol) | 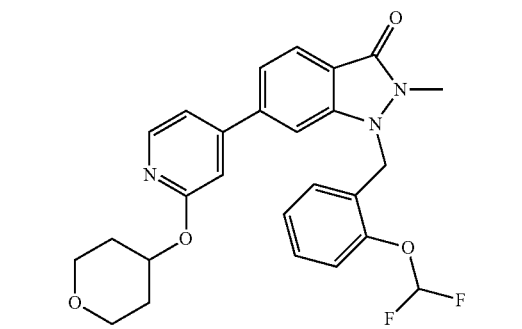 [SMILES: Cn1c(=O)c2ccc(-c3ccnc(OC4CCOCC4)c3)cc2n1Cc1ccccc1OC(F)F] | 10.11 | 2.19 (a) | 482 | A |

TABLE 10-continued

| Bromide | Product | Example # | R$_t$ min (Table A, Method) | m/z ESI+ (M + H)+ | TNF IC$_{50}$ |
|---|---|---|---|---|---|
| 1-(4-((4-Bromopyridin-2-yl)oxy)piperidin-1-yl)ethanone (synthesized in a similar fashion to Preparation #27, from 1-acetyl-4-hydroxy-piperidine). | | 10.12 | 1.91 (a) | 523 | B |
| 4-Bromo-2-((tetrahydro-2H-pyran-3-yl)oxy)pyridine (Preparation #27) | | 10.13 | 2.27 (a) | 482 | B |
| (R)-1-(4-(5-Bromopyrimidin-2-yl)-3-methylpiperazin-1-yl)-2-hydroxyethanone (Preparation #22) | | 10.14* | 1.79 (a) | 539 | A |
| 5-Bromo-2-(dimethylamino)pyrimidine | | 10.15 | 2.12 (a) | 426 | B |

TABLE 10-continued

| Bromide | Product | Example # | R$_t$ min (Table A, Method) | m/z ESI+ (M + H)+ | TNF IC$_{50}$ |
|---|---|---|---|---|---|
| (R)-1-(4-(5-Bromopyrimidin-2-yl)-3-methylpiperazin-1-yl)ethanone (synthesized a manner similar to Preparation #13 from 5-bromo-2-chloropyrimidine and (R)-1-(3-methylpiperazin-1-yl)ethanone (synthesized in a manner similar to Preparation #19, step 4 from (R)-tert-butyl 4-acetyl-2-methylpiperazine-1-carboxylate (synthesized in a manner similar to Preparation #16 from (R)-tert-butyl 2-methylpiperazine-1-carboxylate))) | | 10.16* | 1.93 (a) | 523 | A |
| (S)-1-(4-(5-bromopyrimidin-2-yl)-3-methylpiperazin-1-yl)-2-hydroxyethanone (Preparation #54) | | 10.17* | 1.79 (a) | 539 | A |
| 1-(4-(5-Bromopyrimidin-2-yl)piperazin-1-yl)-2-hydroxyethanone (synthesized in a manner similar to Preparation #15 from glycolic acid and 5-bromo-2-(piperazin-1-yl)pyrimidine (synthesized in a manner similar to Example #3, Step 1 from tert-butyl 4-(5-bromopyrimidin-2-yl)piperazine-1-carboxylate)) | | 10.7 | 1.75 (e) | 525 | A |
| (R)-1-(4-(5-Bromopyrimidin-2-yl)-2-methylpiperazin-1-yl)ethanone (Preparation #16) | | 10.8* | 1.89 (e) | 523 | A |

The compounds shown in Table 11 were synthesized in a manner similar to Example #5 from 6-bromo-1-(3-fluorobenzyl)-2-methyl-1H-indazol-3(2H)-one (synthesized from 6-bromo-1H-indazol-3(2H)-one (Preparation #1) and 1-(bromomethyl)-3-fluorobenzene using a similar method to Preparation #5, step 1, alkylation with MeI using a similar method to Example #14, step 3) and the corresponding boronic acid/boronate.

TABLE 11

| Boronic acid/boronate | Product | Example # | R$_t$ min (Table A, Method) | m/z ESI+ (M + H)$^+$ | TNF IC$_{50}$ |
|---|---|---|---|---|---|
| 4-(4-(4,4,5,5-Tetramethyl-1,3,2-dioxaborolan-2-yl)pyridin-2-yl)morpholine | 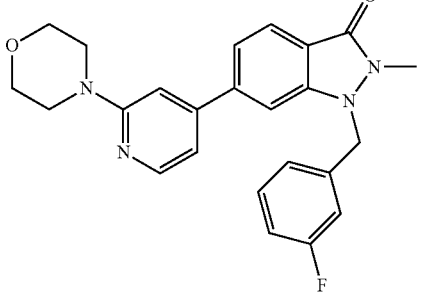 | 11.1 | 1.89 (e) | 419 | C |
| 1-(Tetrahydro-2H-pyran-4-yl)-4-(4,4,5,5-tetramethyl-1,3,2-dioxaborolan-2-yl)-1H-pyrazole | 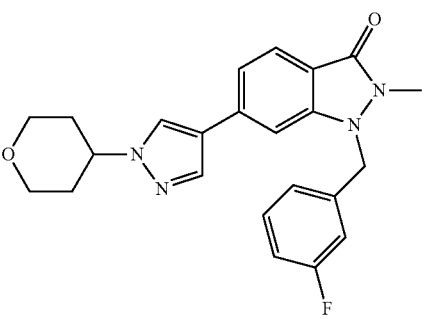 [SMILES: Cn1c(=O)c2ccc(-c3cnn(C4CCOCC4)c3)cc2n1Cc1cccc(F)c1] | 11.2 | 1.74 (e) | 407 | C |

The compound shown in Table 12 was synthesized in a manner similar to Example #5 from 6-bromo-1-(2,5-dichlorophenyl)-2-methyl-1H-indazol-3(2H)-one (Preparation #6) and the corresponding boronic acid/boronate.

TABLE 12

| Boronic acid/boronate | Product | Example # | R$_t$ min (Table A, Method) | m/z ESI+ (M + H)$^+$ | TNF IC$_{50}$ |
|---|---|---|---|---|---|
| 4-(5-(4,4,5,5-Tetramethyl-1,3,2-dioxaborolan-2-yl)pyrimidin-2-yl)morpholine | 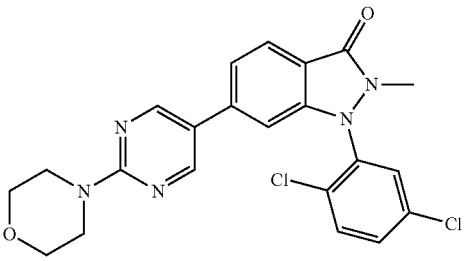 [SMILES: Cn1c(=O)c2ccc(-c3cnc(N4CCOCC4)nc3)cc2n1-c1cc(Cl)ccc1Cl] | 12.1 | 2.23 (e) | 456, 458 | B |

The compounds shown in Table 13 were synthesized in a manner similar to Example #5 from 6-bromo-1-(2-(difluoromethoxy)benzyl)-2,5-dimethyl-1H-indazol-3(2H)-one (synthesized from 4-bromo-2-fluoro-5-methylbenzoic acid in a similar fashion to Preparation #1, alkylation with 1-(bromomethyl)-2-(difluoromethoxy)benzene in a similar fashion to Preparation #4, step 1) and the corresponding boronic acid/boronate.

TABLE 13

| Boronic acid/boronate | Product | Example # | R$_t$ min (Table A, Method) | m/z ESI+ (M + H)+ | TNF IC$_{50}$ |
|---|---|---|---|---|---|
| 4-(5-(4,4,5,5-Tetramethyl-1,3,2-dioxaborolan-2-yl)pyrimidin-2-yl)morpholine | | 13.1 | 2.11 (a) | 482 | A |
| (2-(3-Oxopiperazin-1-yl)pyrimidin-5-yl)boronic acid (synthesized from 2-chloropyrimidine-5-boronic acid and piperazin-2-one using a similar method to Example #2) | | 13.2 | 1.67 (a) | 495 | B |
| 1-(5-Boronopyrimidin-2-yl)piperidine-4-carboxylic acid (synthesized as described in WO2014009295A1) | | 13.3 | 1.89 (a) | 524 | B |

The compounds shown in Table 14 were synthesized in a manner similar to Example #3, step 1 from the corresponding Boc-protected amine.

TABLE 14

| Boc-protected amine | Product | Example # | R$_t$ min (Table A, Method) | m/z ESI+ (M + H)+ | TNF IC$_{50}$ |
|---|---|---|---|---|---|
| tert-Butyl 4-(5-(1-(2-(difluoromethoxy)benzyl)-2-methyl-3-oxo-2,3-dihydro-1H-indazol-6-yl)pyridin-2-yl)piperazine-1-carboxylate (synthesized from 6-bromo-1-(2-(difluoromethoxy)benzyl)-2-methyl-1H-indazol-3(2H)-one [Preparation #4, step 1] and tert-butyl 4-(5-(4,4,5,5-tetramethyl-1,3,2-dioxaborolan-2-yl)pyridin-2-yl)piperazine-1-carboxylate using a similar method to Example #5) | | 14.1 | 1.46 (a) | 466 | B |

TABLE 14-continued

| Boc-protected amine | Product | Example # | R$_t$ min (Table A, Method) | m/z ESI+ (M + H)+ | TNF IC$_{50}$ |
|---|---|---|---|---|---|
| tert-Butyl 4-(5-(1-(2,5-dichlorobenzyl)-2-methyl-3-oxo-2,3-dihydro-1H-indazol-6-yl)pyrimidin-2-yl)piperazine-1-carboxylate (synthesized from 6-bromo-1-(2,5-dichlorobenzyl)-2-methyl-1H-indazol-3(2H)-one (synthesized from 6-bromo-1H-indazol-3(2H)-one using a similar method to Preparation #5) and tert-butyl 4-(5-(4,4,5,5-tetramethyl-1,3,2-dioxaborolan-2-yl)pyrimidin-2-yl)piperazine-1-carboxylate using a similar method to Example #5) | | 14.2 | 1.51 (a) | 469 | B |
| tert-Butyl (2-(4-(5-(1-(2-(difluoromethoxy)benzyl)-2-methyl-3-oxo-2,3-dihydro-1H-indazol-6-yl)pyrimidin-2-yl)-4-hydroxypiperidin-1-yl)-2-oxoethyl)carbamate (synthesized from 1-(2-(difluoromethoxy)benzyl)-6-(2-(4-hydroxypiperidin-4-yl)pyrimidin-5-yl)-2-methyl-1H-indazol-3(2H)-one, hydrochloric acid (Example #20, step 3) with 2-((tert-butoxycarbonyl)amino)acetic acid using methods similar to Preparation #15) | | 14.3 | 1.34 (a) | 539 | B |
| (S)-4-(Difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-((tert-butoxycarbonyl)amino)-3-methylbutanoate (synthesized in a similar fashion to Example #21, step 1 from (S)-7-(5-(1-(2-(difluoromethoxy)-5-(hydroxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one (Example #16.3) and N-tert-butoxycarbonyl)-L-valine) | | 14.4* | 1.52 (a) | 653 | B |
| (R)-tert-Butyl 4-(5-(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate (synthesized in a similar manner to Example #15, step 4 from 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, step 2) and (R)-tert-butyl 4-(5-bromopyrimidin-2-yl)-2-methylpiperazine-1-carboxylate (synthesized in a similar fashion to Preparation #13, step 1 from (R)-1-N-Boc-2-methylpiperazine)) | | 14.5* | 1.51 (a) | 495 | B |

TABLE 14-continued

| Boc-protected amine | Product | Example # | R$_t$ min (Table A, Method) | m/z ESI+ (M + H)+ | TNF IC$_{50}$ |
|---|---|---|---|---|---|
| tert-Butyl ((S)-1-((S)-4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-1-oxopropan-2-yl)carbamate (synthesized in a similar fashion to Preparation #15 from (S)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (Example #36, step 2) and N-(tert-butoxycarbonyl)-L-alanine) | 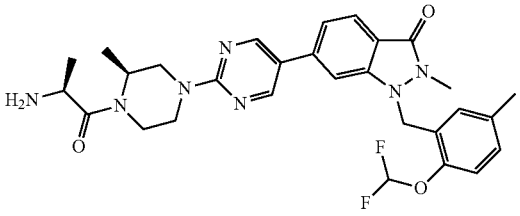 [SMILES: Cc1ccc(OC(F)F)c(Cn2c3cc(-c4cnc(N5CCN(C(=O)[C@H](C)N)[C@@H](C)C5)nc4)ccc3c(=O)n2C)c1] | 14.6* | 1.54 (a) | 566 | A |
| (S)-tert-Butyl (2-(4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-2-oxoethyl)carbamate (synthesized in a similar fashion to Preparation #15 from (S)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (Example #36, step 2) and N-tert-butoxycarbonyl)glycine) | 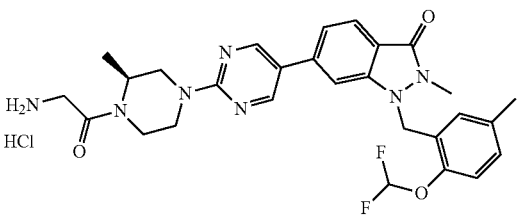 [SMILES: Cc1ccc(OC(F)F)c(Cn2c3cc(-c4cnc(N5CCN(C(=O)CN)[C@@H](C)C5)nc4)ccc3c(=O)n2C)c1 ; Cl] | 14.7* | 1.54 (a) | 552 | A |
| tert-Butyl (3-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-2-hydroxy-3-oxopropyl)carbamate (synthesized in a manner similar to Preparation #30, step 1 from 3-((tert-butoxycarbonyl)amino)-2-hydroxypropanoic acid (WO 2011146354 A1) and (R)-1-(2-(difluoromethoxy)benzyl)-2-methyl-6-(2-(3-methylpiperazin-1-yl)pyrimidin-5-yl)-1H-indazol-3(2H)-one (Preparation #33)) | 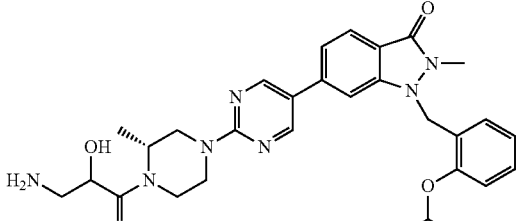 | 14.8 | 1.46 (a) | 568 | A |
| tert-Butyl (3-((R)-4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-2-hydroxy-3-oxopropyl)carbamate (synthesized in a manner similar to Preparation #30, step 1 from 3-((tert-butoxycarbonyl)amino)-2-hydroxypropanoic acid (WO 2011146354 A1) and (R)-1-(2-(difluoromethoxy)-5-methylbenzyl)-2-methyl-6-(2-(3-methylpiperazin-1-yl)pyrimidin-5-yl)-1H-indazol-3(2H)-one (Example #14.5)) | 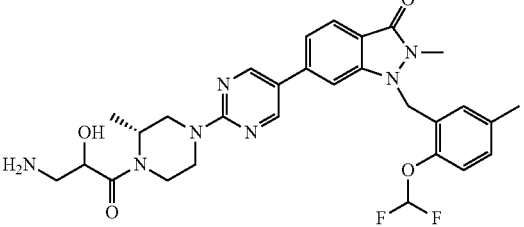 | 14.9 | 1.52 (a) | 582 | A |

TABLE 14-continued

| Boc-protected amine | Product | Example # | R$_t$ min (Table A, Method) | m/z ESI+ (M + H)+ | TNF IC$_{50}$ |
|---|---|---|---|---|---|
| (R)-tert-Butyl (2-(4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-2-oxoethyl)carbamate (prepared in a similar fashion to Preparation #15 using N-(tert-butoxycarbonyl)glycine and (R)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (Example #14.5)) | | 14.10* | 1.53 (a) | 552 | A |
| tert-Butyl ((S)-1-((R)-4-(5-(1-(2-(difluoromethoxy)-5-methylbenzyl)-2-methyl-3-oxo-2,3-dihydro-1H-indazol-6-yl)pyrimidin-2-yl)-2-methylpiperazin-1-yl)-1-oxopropan-2-yl)carbamate (prepared in a similar fashion to Preparation #15 using N-(tert-butoxycarbonyl)-L-alanine and (R)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (Example #14.5)) | | 14.11* | 1.56 (a) | 566 | A |
| (S)-2-((R)-4-(5-(1-(2-(Difluoromethoxy)benzyl)-2-methyl-3-oxo-2,3-dihydro-1H-indazol-6-yl)pyrimidin-2-yl)-2-methylpiperazin-1-yl)-2-oxoethyl 2-((tert-butoxycarbonyl)amino)-3-methylbutanoate (Preparation #41) | | 14.12* | 1.62 (e) | 639 | A |
| (R)-2-((R)-4-(5-(1-(2-(Difluoromethoxy)benzyl)-2-methyl-3-oxo-2,3-dihydro-1H-indazol-6-yl)pyrimidin-2-yl)-2-methylpiperazin-1-yl)-2-oxoethyl 2-((tert-butoxycarbonyl)amino)-3-methylbutanoate (prepared in a manner similar to Preparation #41 from (R)-1-(2-(difluoromethoxy)benzyl)-6-(2-(4-(2-hydroxyacetyl)-3-methylpiperazin-1-yl)pyrimidin-5-yl)-2-methyl-1H-indazol-3(2H)-one (Example #10.6) and (R)-2-((tert-butoxycarbonyl)amino)-3-methylbutanoic acid) | | 14.13* | 1.62 (e) | 639 | A |

TABLE 14-continued

| Boc-protected amine | Product | Example # | R$_t$ min (Table A, Method) | m/z ESI+ (M + H)+ | TNF IC$_{50}$ |
|---|---|---|---|---|---|
| (S)-2-((R)-4-(5-(1-(2-(Difluoromethoxy)-5-methylbenzyl)-2-methyl-3-oxo-2,3-dihydro-1H-indazol-6-yl)pyrimidin-2-yl)-2-methylpiperazin-1-yl)-2-oxoethyl 2-((tertbutoxycarbonyl)amino)-3-methylbutanoate (prepared in a similar manner to Preparation #41 using (R)-1-(2-(difluoromethoxy)-5-methylbenzyl)-6-(2-(4-(2-hydroxyacetyl)-3-methylpiperazin-1-yl)pyrimidin-5-yl)-2-methyl-1H-indazol-3(2H)-one (Example #22.1) and N-tert-butoxycarbonyl)-L-valine) | | 14.14* | 1.70 (a) | 653 | A |
| (S)-4-(Difluoromethoxy)-3-((2-methyl-3-oxo-6-(2-((R)-3-oxohexahydroimidazo[1,5-a]pyrazin-7(1H)-yl)pyrimidin-5-yl)-2,3-dihydro-1H-indazol-1-yl)methyl)benzyl 2-((tert-butoxycarbonyl)amino)propanoate (prepared in a similar manner to Preparation #41 using (R)-7-(5-(1-(2-(difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one (Example #16.1) and N-(tert-butoxycarbonyl)-L-alanine) | | 14.15 | 1.41 (a) | 623 | A |
| (S)-4-(Difluoromethoxy)-3-((2-methyl-3-oxo-6-(2-((R)-3-oxohexahydroimidazo[1,5-a]pyrazin-7(1H)-yl)pyrimidin-5-yl)-2,3-dihydro-1H-indazol-1-yl)methyl)benzyl 2-((tert-butoxycarbonyl)amino)-3-methylbutanoate(prepared in a similar manner to Preparation #41 using (R)-7-(5-(1-(2-(difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one (Example #16.1) and N-tert-butoxycarbonyl)-L-valine) | | 14.16 | 1.47 (a) | 651 | A |

Example #6: (R)-7-(5-(1-(2-(Difluoromethoxy)benzyl)-2-methyl-3-oxo-2,3-dihydro-1H-indazol-6-yl)pyrimidin-2-yl)hexahydroimidazo[1,5-a]pyrazin-3(2H)-one

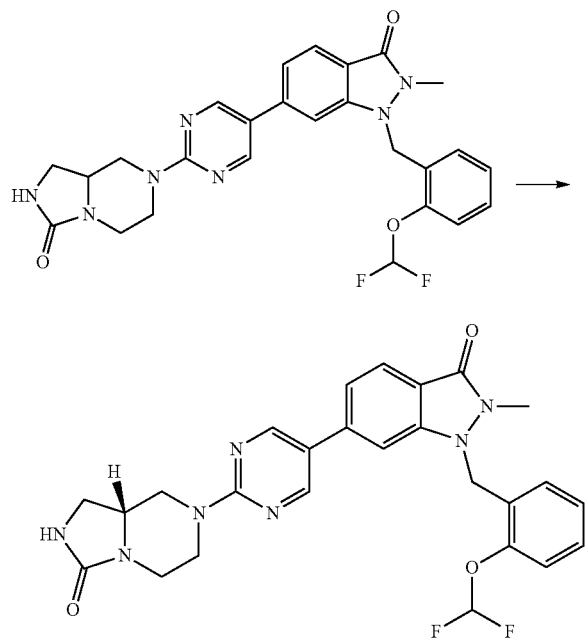

7-(5-(1-(2-(Difluoromethoxy)benzyl)-2-methyl-3-oxo-2,3-dihydro-1H-indazol-6-yl)pyrimidin-2-yl)hexahydroimidazo[1,5-a]pyrazin-3(2H)-one (0.100 g, 0.192 mmol) (Example #2.27) was submitted for chiral separation (Table B, Method b). Fractions from the first eluting component were combined and concentrated under reduced pressure then dried in a vacuum oven at about 60° C. for about 16 h to afford the title product (0.033 g, 33%) with undetermined optical rotation. LC/MS (Table A, Method a) $R_t$=1.76 min; MS m/z: 522 (M+H)$^+$ (TNF IC$_{50}$=A).

Example #7: (S)-7-(5-(1-(2-(Difluoromethoxy)benzyl)-2-methyl-3-oxo-2,3-dihydro-1H-indazol-6-yl)pyrimidin-2-yl)hexahydroimidazo[1,5-a]pyrazin-3(2H)-one

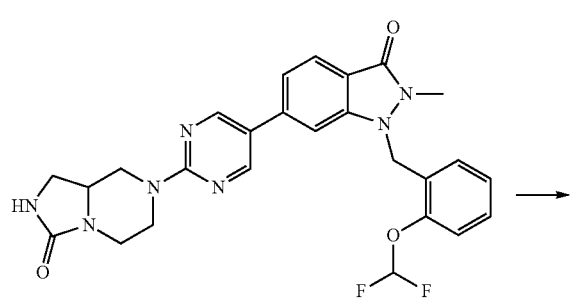

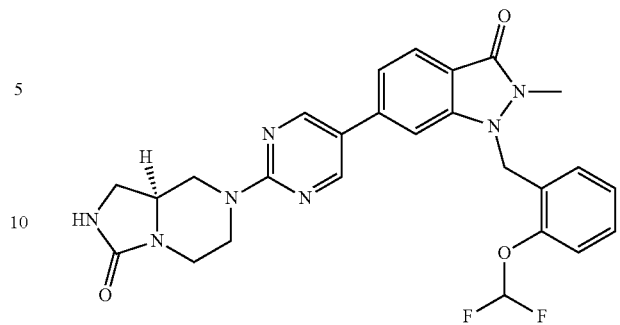

7-(5-(1-(2-(Difluoromethoxy)benzyl)-2-methyl-3-oxo-2,3-dihydro-1H-indazol-6-yl)pyrimidin-2-yl)hexahydroimidazo[1,5-a]pyrazin-3(2H)-one (0.100 g, 0.192 mmol) (Example #2.27) was submitted for chiral separation (Table B, Method b). Fractions from the first eluting component were combined and concentrated under reduced pressure then dried in a vacuum oven at about 60° C. for about 16 h to afford the title product (0.033 g, 33%) with undetermined optical rotation. LC/MS (Table A, Method a) $R_t$1.76 min; MS m/z: 522 (M+H)$^+$ (TNF IC$_{50}$=A).

Example #8: (R)-7-(5-(1-(2-(Difluoromethoxy)-5-methylbenzyl)-2-methyl-3-oxo-2,3-dihydro-1H-indazol-6-yl)pyrimidin-2-yl)hexahydroimidazo[1,5-a]pyrazin-3(2H)-one

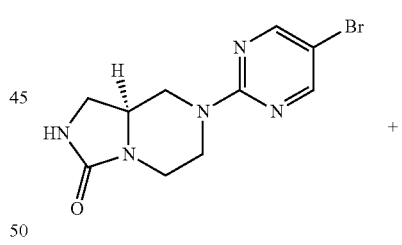 +

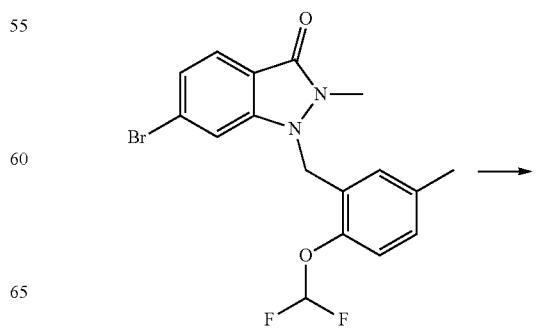

187
-continued

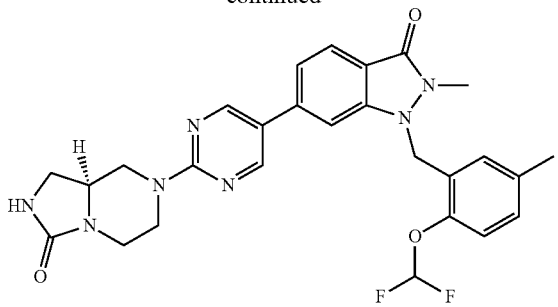

A mixture of bis(pinacolato)diboron (0.0445 g, 0.175 mmol), (R)-7-(5-bromopyrimidin-2-yl)hexahydroimidazo[1,5-a]pyrazin-3(2H)-one (0.0350 g, 0.117 mmol) (Preparation #13), KOAc (0.0282 g, 0.287 mmol), PdCl$_2$(dppf) (0.0061 g, 8.3 μmol), and dioxane (1.0 mL) was evacuated then back-filled with N$_2$ three times then purged with N$_2$ for about 15 min. The mixture was warmed to about 95° C. After about 90 min, the mixture was allowed to cool to rt. 6-bromo-1-(2-(difluoromethoxy)-5-methylbenzyl)-2-methyl-1H-indazol-3(2H)-one (0.0393 g, 0.099 mmol) (synthesized from 6-bromo-1H-indazol-3(2H)-one (Preparation #1) and 2-(bromomethyl)-1-(difluoromethoxy)-4-methylbenzene (synthesized in a similar fashion to Preparation #3, step 2 from (2-(difluoromethoxy)-5-methylphenyl)methanol (Preparation #11), Cs$_2$CO$_3$(0.102 g, 0.313 mmol), and bis(triphenylphosphine)palladium(II) dichloride were added in one portion. Water (0.25 mL) was added. The reaction was evacuated then back-filled with N$_2$ three times then purged with N$_2$ for about 15 min. The mixture was warmed to about 80° C. After about 2 h, the mixture was allowed to cool to rt. Water (5 mL), DCM (10 mL), and MeOH (0.5 mL) were added. The mixture was filtered then the layers were separated. The aqueous layer was extracted with 5% MeOH/DCM (2×10 mL). The combined organics were dried over Na$_2$SO$_4$, filtered and concentrated under reduced pressure. The residue was purified using flash chromatography on silica gel (1-5% MeOH/DCM) to give the title product (0.0431 g, 81%). (Table A, Method a) R$_t$=1.82 min; MS m/z: 536 (M+H)$^+$ (TNF IC$_{50}$=A).

The compounds shown in Table 15 were synthesized in a manner similar to Example #8 from 6-bromo-1-(2-(difluoromethoxy)-5-methylbenzyl)-2-methyl-1H-indazol-3(2H)-one (synthesized from 6-bromo-1H-indazol-3(2H)-one (Preparation #1) and 2-(bromomethyl)-1-(difluoromethoxy)-4-methylbenzene (synthesized in a similar fashion to Preparation #3, step 2 from (2-(difluoromethoxy)-5-methylphenyl)methanol (Preparation #11)) and the corresponding halide.

188

Example #9: 1-(2-(Difluoromethoxy)-5-(hydroxymethyl)benzyl)-2-methyl-6-(2-morpholinopyrimidin-5-yl)-1H-indazol-3(2H)-one

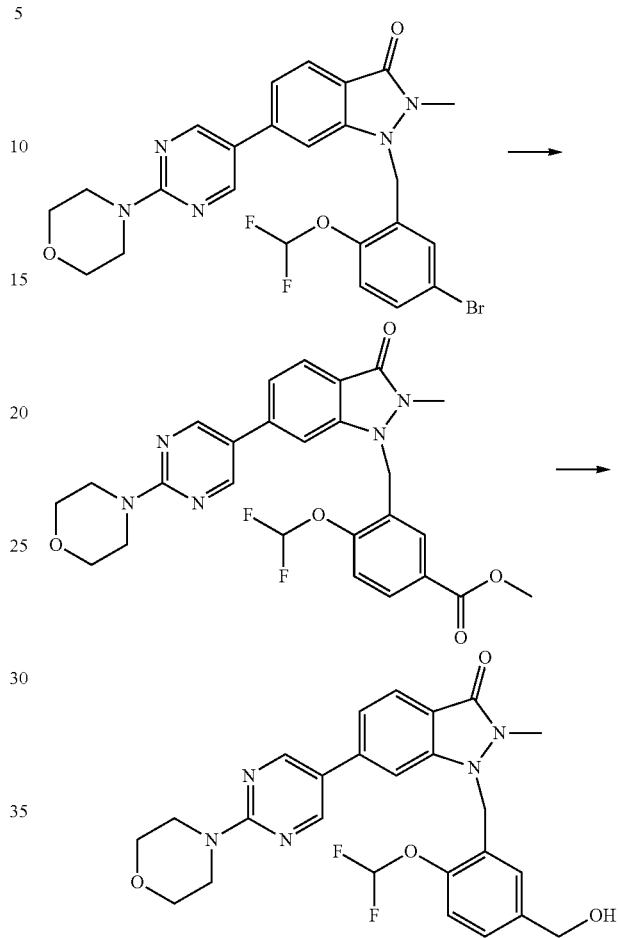

Step 1: Methyl 4-(difluoromethoxy)-3-((2-methyl-6-(2-morpholinopyrimidin-5-yl)-3-oxo-2,3-dihydro-1H-indazol-1-yl)methyl)benzoate PdCl$_2$(dppf) complex with DCM (0.070 g, 0.086 mmol) was added to a solution of 1-(5-bromo-2-(difluoromethoxy)benzyl)-2-methyl-6-(2-morpholinopyrimidin-5-yl)-1H-indazol-3(2H)-one (0.459 g, 0.580 mmol) (prepared using 2-methyl-6-(2-morpholinopyrimidin-5-yl)-1H-indazol-3(2H)-one (Preparation #2) and 4-bromo-2-(bromomethyl)-

TABLE 15

| Halide | Product | Example # | R$_t$ min (Table A, Method) | m/z ESI+ (M + H)$^+$ | TNF IC$_{50}$ |
|---|---|---|---|---|---|
| (S)-7-(5-Bromopyrimidin-2-yl)hexahydroimidazo[1,5-a]pyrazin-3(2H)-one (Preparation #13) | | 15.1 | 1.82 (a) | 536 | A |

1-(difluoromethoxy)benzene (prepared using (5-bromo-2-(difluoromethoxy)phenyl)methanol (Preparation #12) in a similar fashion to Preparation #3, step 2) in a similar fashion to Example #1) and DMF (4.00 mL) under N₂. MeOH (2.00 mL, 49.4 mmol) and TEA (0.250 mL, 1.79 mmol) were added respectively. The reaction vessel was evacuated then back-filled with N₂ three times then evacuated and back-filled with carbon monoxide twice. The reaction was warmed to about 80° C. After about 3 h, the reaction was allowed to cool to rt. The organic volatiles were removed under reduced pressure. The residue was slurried in water (25 mL) and EtOAc (25 mL). The solids were removed by filtration rinsing with EtOAc. The layers were separated and the aqueous layer was extracted with EtOAc (25 mL). The combined organics were dried over Na₂SO₄, filtered, and concentrated under reduced pressure. The residue was purified using flash chromatography on silica gel (75-100% EtOAc/heptane) to give the title product (0.244 g, 80%). (Table A, Method e) $R_f$=2.03 min; MS m/z: 526 (M+H)⁺.

Step 2: 1-(2-(Difluoromethoxy)-5-(hydroxymethyl)benzyl)-2-methyl-6-(2-morpholinopyrimidin-5-yl)-1H-indazol-3(2H)-one Lithium borohydride (0.0152 g, 0.698 mmol) was added in one portion to a mixture of methyl 4-(difluoromethoxy)-3-((2-methyl-6-(2-morpholinopyrimidin-5-yl)-3-oxo-2,3-dihydro-1H-indazol-1-yl)methyl)benzoate (0.119 g, 0.226 mmol) and THF (2.20 mL) under N₂. After about 90 min, MeOH (5 mL) was added. The solution was left to vigorously stir for about 25 h, 5% MeOH/DCM (10 mL), sat. aq. NH₄Cl (5 mL), and water (2 mL) were added. The biphasic solution was left to vigorously stir for about 16 h. The layers were separated and the aqueous layer was extracted with DCM (2×5 mL). The combined organics were dried over Na₂SO₄, filtered, and concentrated under reduced pressure. The residue was purified using flash chromatography on silica gel (0-7.5% MeOH/DCM) to give the title product (0.0756 g, 66%). (Table A, Method a) $R_f$=1.79 min; MS m/z: 498 (M+H)⁺ (TNF IC₅₀=A).

Example #10: 1-(2-(Difluoromethoxy)benzyl)-2-ethyl-6-(2-morpholinopyrimidin-5-yl)-1H-indazol-3(2H)-one

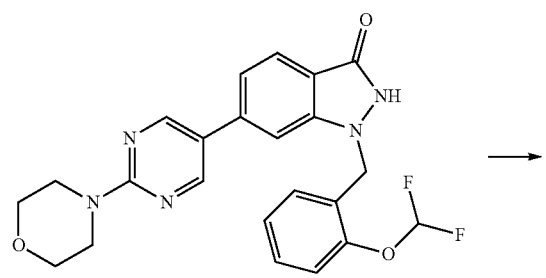

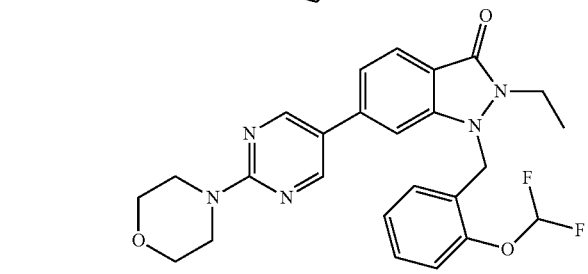

Iodoethane (0.017 mL, 0.21 mmol) was added to a solution of 1-(2-(difluoromethoxy)benzyl)-6-(2-morpholin-opyrimidin-5-yl)-1H-indazol-3(2H)-one (Example #6.1) (0.080 g, 0.18 mmol), LiOH hydrate (10 mg, 0.25 mmol), and DMF (1.8 mL). The reaction mixture was heated to about 100° C. for about 1 h. After cooling to rt, the reaction was partitioned between EtOAc (15 mL) and water (2 mL). The aqueous layer was extracted with EtOAc (15 mL) and the combined organic layers were dried over MgSO₄, filtered, and concentrated under reduced pressure. The residue was purified via flash chromatography on silica gel (0-100% EtOAc/heptane) to provide the title product (4.8 mg, 6%); LC/MS (Table A, Method e) $R_f$=2.15 min; MS m/z: 482 (M+H)⁺ (TNF IC₅₀=B).

Example #11: 2-Cyclopropyl-1-(2-(difluoromethoxy)benzyl)-6-(2-morpholinopyrimidin-5-yl)-1H-indazol-3(2H)-one

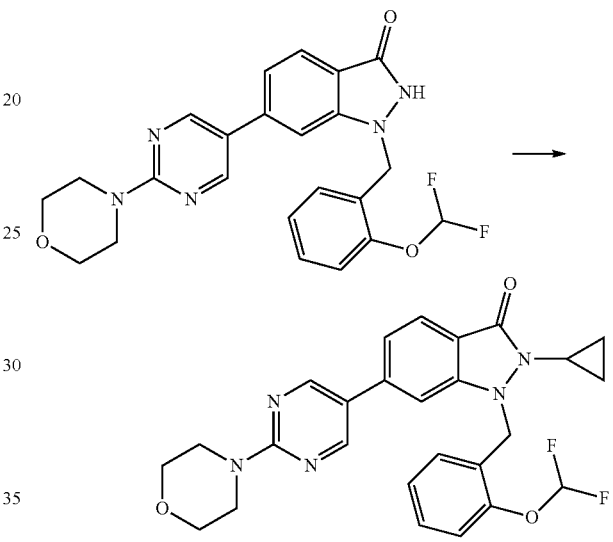

A mixture of 1-(2-(difluoromethoxy)benzyl)-6-(2-morpholinopyrimidin-5-yl)-1H-indazol-3(2H)-one (0.050 g, 0.11 mmol) (Example #6.1), cyclopropylboronic acid (0.019 g, 0.22 mmol), Cs₂CO₃ (0.018 g, 0.055 mmol), pyridine (0.027 mL, 0.33 mmol), diacetoxycopper (0.020 g, 0.11 mmol) in toluene (0.22 mL) was heated to about 110° C. under dry air. After about 1 h, the reaction was allowed to cool to rt and then partitioned between EtOAc (10 mL) and water (10 mL). The organic layer was separated and the aqueous layer was extracted with EtOAc (10 mL). The combined organics were dried over MgSO₄, filtered and concentrated under reduced pressure. The residue was purified on silica gel (0-100% EtOAc/heptane) to provide the title product (23.4 mg, 42%); LC/MS (Table A, Method e) $R_f$=2.14 min; MS m/z: 494 (M+H)⁺ (TNF IC₅₀=B).

Example #12: 1-(2-(Difluoromethoxy)benzyl)-2-methyl-6-(2-((3-methyloxetan-3-yl)methyl)pyrimidin-5-yl)-1H-indazol-3(2H)-one

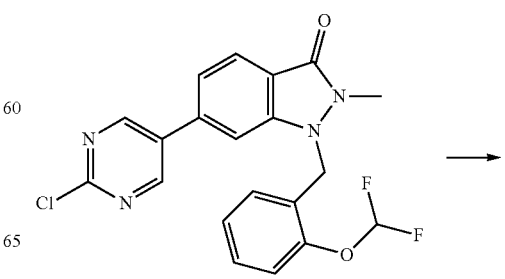

-continued

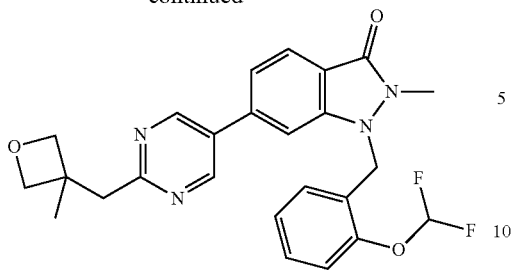

A solution of 3-(bromomethyl)-3-methyloxetane (0.495 g, 3.00 mmol), THF (6 mL) and 1,2-dibromoethane (0.020 g, 0.11 mmol) was added to acid-washed and oven-dried magnesium turnings (0.109 g, 4.50 mmol) under $N_2$. The reaction mixture was heated unstirred to about 55° C. When bubbling began, the mixture was gently stirred to maintain the magnesium below the reaction surface. The reaction was then warmed to about 65° C. for about 45 min until the bubbling ceased. The mixture was allowed to cool, stirring was ceased, and the solids were allowed to settle to the bottom of the reaction vessel. A portion of the (((3-methyl-oxetan-3-yl)methyl)magnesium bromide solution (0.48 mL) was removed via syringe and then added dropwise over about 15 min to a flask containing a mixture of 6-(2-chloropyrimidin-5-yl)-1-(2-(difluoromethoxy)benzyl)-2-methyl-1H-indazol-3(2H)-one (0.100 g, 0.240 mmol) (Preparation #4), $PPh_3$ (0.025 g, 0.096 mmol) and nickel acetylacetonate (7.4 mg, 0.029 mmol) in THF (1 mL) at about 0° C. After about 1 h, the reaction was removed from the ice bath and stirred at rt for about 1 h. ((3-methyloxetan-3-yl)methyl)magnesium bromide solution (0.480 mL) and nickel acetylacetonate (7.4 mg, 0.029 mmol) were added and the reaction was stirred at rt for about 1 h. The reaction was heated at about 60° C. for about 1 h. The reaction was allowed to cool to rt and nickel acetylacetonate (62 mg, 0.24 mmol) and ((3-methyloxetan-3-yl)methyl)magnesium bromide solution (0.48 mL) were added. The reaction was stirred at rt for about 50 h. The reaction mixture was partitioned between EtOAc (10 mL) and sat. aq. $NH_4Cl$ (10 mL). The organic layer was washed with sat. aq. NaCl (10 mL) and concentrated under reduced pressure. The residue was purified on silica gel (20-80% EtOAc/heptane) to give the title product (10 mg, 8%); LC/MS (Table A, Method e) $R_t$=2.13 min; MS m/z: 467 $(M+H)^+$ (TNF $IC_{50}$=B).

Example #13: 1-(2-(Difluoromethoxy)benzyl)-2-methyl-6-(3-morpholino-1,2,4-oxadiazol-5-yl)-1H-indazol-3(2H)-one

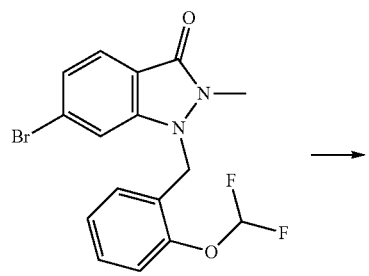

-continued

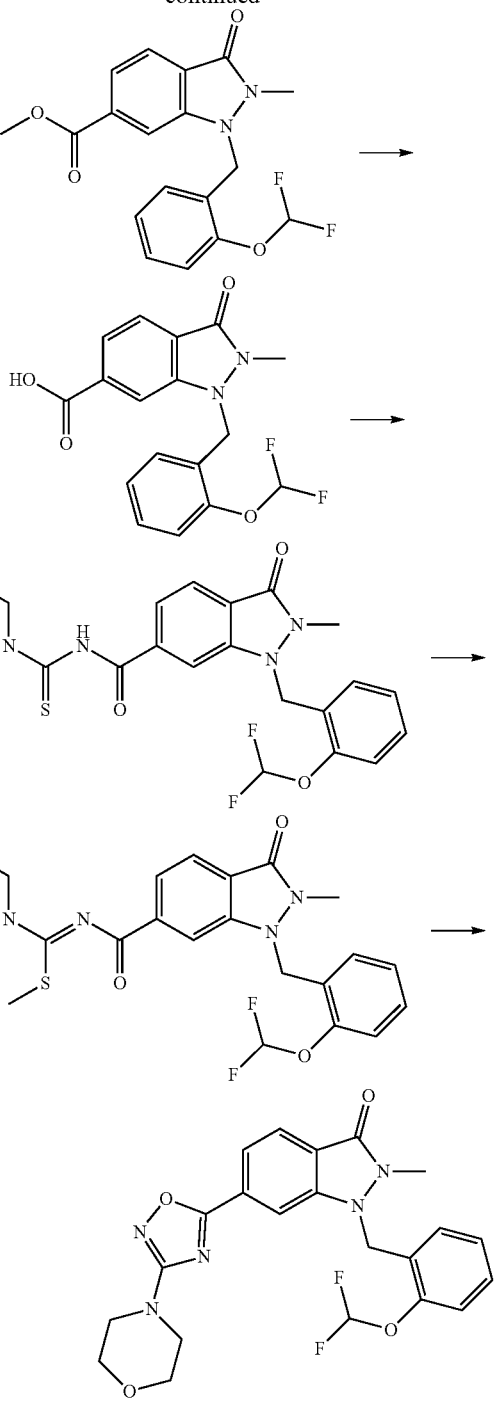

Step 1: Methyl 1-(2-(difluoromethoxy)benzyl)-2-methyl-3-oxo-2,3-dihydro-1H-indazole-6-carboxylate A flask was charged with 6-bromo-1-(2-(difluoromethoxy)benzyl)-2-methyl-1H-indazol-3(2H)-one (400 mg, 1.04 mmol) (Preparation #4, step 1), $Pd(OAc)_2$ (0.023 g, 0.10 mmol) and dppf (0.116 g, 0.209 mmol) under $N_2$. DMF (6.1 mL) was added and the mixture was evacuated and back-filled with CO. MeOH (2.1 mL, 52 mmol) and TEA (0.78 mL, 5.2 mmol) were added. The mixture was warmed to about 85° C. for about 18 h. The reaction mixture was allowed to cool to rt. EtOAc (40 mL) and water (40 mL) were added. The organic layer was separated and washed with water (2×40 mL), dried over MgSO$_4$, filtered and concentrated under reduced pressure. The residue was purified on silica gel (0-100% EtOAc/heptane) to provide the title product (319 mg, 84%); LC/MS (Table A, Method e) R$_t$=2.03 min; MS m/z: 363 (M+H)$^+$ Step 2: 1-(2-(Difluoromethoxy)benzyl)-2-methyl-3-oxo-2,3-dihydro-H-indazole-6-carboxylic acid LiOH (42 mg, 1.8 mmol) was added to a solution of methyl 1-(2-(difluoromethoxy)benzyl)-2-methyl-3-oxo-2,3-dihydro-1H-indazole-6-carboxylate (319 mg, 0.880 mmol) in THF (5.5 mL), water (2.8 mL) and MeOH (2.8 mL) was added LiOH (42 mg, 1.8 mmol). The reaction was warmed to about 55° C. for about 4 h then allowed to cool to rt. The organic volatiles were removed under reduced pressure. The reaction mixture was acidified with 1 N aqueous HCl. The solid was collected by filtration and washed with EtOAc (10 mL). The filtrate was partially concentrated under reduced pressure and the resulting solid was collected by filtration. The solids were collected and blended to provide the title product (253 mg, 83%); LC/MS (Table A, Method e) R$_t$=1.50 min; MS m/z: 349 (M+H)$^+$ Step 3: 1-(2-(Difluoromethoxy)benzyl)-2-methyl-N-(morpholine-4-carbonothioyl)-3-oxo-2,3-dihydro-1H-indazole-6-carboxamide Oxalyl dichloride (2 M solution in DCM, 0.73 mL, 1.5 mmol) was added to a solution of 1-(2-(difluoromethoxy)benzyl)-2-methyl-3-oxo-2,3-dihydro-1H-indazole-6-carboxylic acid (253 mg, 0.726 mmol) in DCM (1.7 mL) at about 0° C. A drop of DMF was added. The ice bath was removed and reaction was allowed to warm to rt. After about 3 h, the volatiles were removed under reduced pressure. The residue was dissolved in MeCN (2.2 mL). The resulting solution was added dropwise to a solution of potassium thiocyanate (0.076 g, 0.78 mmol) in MeCN (2.2 mL). After about 16 h, the reaction mixture was concentrated under reduced pressure. DCM (2.2 mL) was added. The solid was removed by filtration and then the filtrate was added dropwise to a solution of morpholine (0.062 mL, 0.71 mmol), TEA (0.18 mL, 1.3 mmol) and DCM (2.2 mL). After about 1 h, water (20 mL) was added and the organic layer was separated, dried over MgSO$_4$, filtered, and concentrated under reduced pressure. The residue was purified on silica gel (0-100% EtOAc/heptane) to provide the title product (82 mg, 26%); LC/MS (Table A, Method e) R$_t$=1.88 min; MS m/z: 477 (M+H)$^+$ Step 4: (Z)-Methyl N-(1-(2-(difluoromethoxy)benzyl)-2-methyl-3-oxo-2,3-dihydro-1H-indazole-6-carbonyl)morpholine-4-carbimidothioate MeI (11 µL, 0.17 mmol) was added to a solution of 1-(2-(difluoromethoxy)benzyl)-2-methyl-N-(morpholine-4-carbonothioyl)-3-oxo-2,3-dihydro-1H-indazole-6-carboxamide (82 mg, 0.17 mmol) in DMF (1 mL). After about 1 h, EtOAc (30 mL) and water (10 mL) were added. The organic layer was separated and then washed with water (2×10 mL), dried over MgSO$_4$, filtered and concentrated under reduced pressure to provide the title compound (84 mg, 100%); LC/MS (Table A, Method e) R$_t$=1.78 min; MS m/z: 491 (M+H)$^+$ Step 5: 1-(2-(Difluoromethoxy)benzyl)-2-methyl-6-(3-morpholino-1,2,4-oxadiazol-5-yl)-1H-indazol-3(2H)-one Sodium acetate (45.2 mg, 0.550 mmol) was added to hydroxylamine hydrochloride (38.3 mg, 0.55 mmol) in MeOH (0.180 mL) at about 0° C. After about 30 min, (Z)-methyl N-(1-(2-(difluoromethoxy)benzyl)-2-methyl-3-oxo-2,3-dihydro-1H-indazole-6-carbonyl)morpholine-4-carbimidothioate (90 mg, 0.18 mmol) in MeOH (0.180 mL) was added. After about 2 h, the ice bath was removed and the reaction was allowed to warm to rt. Additional MeOH (3 mL) was added and the reaction mixture was stirred at rt for about 2 h. The reaction mixture was concentrated under reduced pressure. EtOAc (10 mL) and water (5 mL) were added. The layers were separated and the aqueous layer was extracted with EtOAc (10 mL). The combined organic layers were washed with sat. aq. NaCl (5 mL), dried over MgSO$_4$, filtered, and concentrated under reduced pressure. The residue was purified on silica gel (0-60% EtOAc/DCM) to provide the title product (18.3 mg, 22%); LC/MS (Table A, Method e) R$_t$=2.06 min; MS m/z: 458 (M+H)$^+$ (TNF IC$_{50}$=B).

Example #14: 1-(2-(Difluoromethoxy)benzyl)-2-methyl-6-(2-morpholinopyrimidin-5-yl)-1H-pyrazolo[4,3-b]pyridin-3(2H)-one

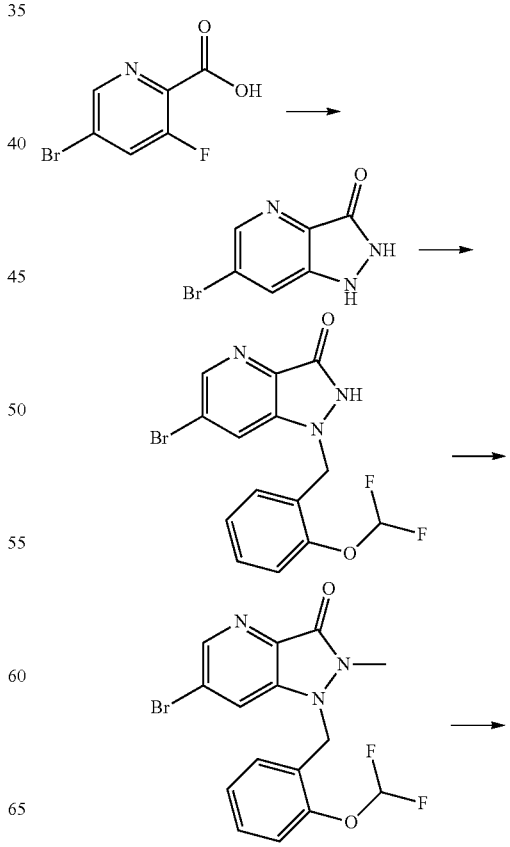

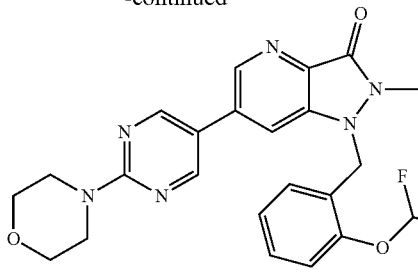

Step 1: 6-Bromo-1H-pyrazolo[4,3-b]pyridin-3(2H)-one

A mixture of 5-bromo-3-fluoropicolinic acid hydrochloride (2.0 g, 7.8 mmol) in MeCN (50 mL) was treated with DIEA (4.1 mL, 23 mmol). After stirring for about 10 min, 2-(3H-[1,2,3]triazolo[4,5-b]pyridin-3-yl)-1,1,3,3-tetramethylisouronium hexafluorophosphate(V) (3.56 g, 9.36 mmol) was added. After stirring for about 15 min, a solution of hydrazine hydrate (1.88 g, 37.6 mmol) in MeCN (25 mL) was added to the mixture. After stirring for about 1 h, the mixture was diluted with water (150 mL) then extracted with DCM (3×100 mL). The combined organic layers were concentrated under reduced pressure. The residue was dissolved in n-butanol (50 mL) and hydrazine hydrate (1.5 g, 30 mmol) then the mixture was heated to about 100° C. After about 12 h, the reaction mixture was cooled to rt then diluted with ethyl ether (50 mL). After stirring for about 15 min, the solids were collected by filtration rinsing with ethyl ether (25 mL). The material was dried under reduced pressure at about 60° C. to yield the title compound (0.485 g, 29%); LC/MS (Table A, Method e) R$_t$=1.21 min; MS m/z: 214 and 216 (M+H)$^+$.

Step 2: 6-Bromo-1-(2-(difluoromethoxy)benzyl)-1H-pyrazolo[4,3-b]pyridin-3(2H)-one A solution of 6-bromo-1H-pyrazolo[4,3-b]pyridin-3(2H)-one (0.30 g, 1.4 mmol) in DMF (7 mL) was treated with potassium carbonate (0.194 g, 1.40 mmol). After stirring for about 10 min, the mixture was treated with 1-(bromomethyl)-2-(difluoromethoxy)benzene (0.34 g, 1.4 mmol). After stirring for about 2 days, the mixture was concentrated under reduced pressure and the residue was partitioned between EtOAc (20 mL) and water (10 mL). The aqueous layer was extracted with EtOAc (10 mL) then neutralized with AcOH. EtOAc (20 mL) was added. The mixture was stirred and filtered. The filtrate layers were separated and the aqueous layer was extracted with EtOAc (10 mL). The organic solutions were combined, dried over sodium sulfate, filtered and concentrated under reduced pressure. The residue was triturated with EtOAc (5 mL) then the solids were collected by filtration rinsing with EtOAc (1 mL). The solid was dried to yield the title compound (0.23 g, 44%); LC/MS (Table A, Method e) R$_t$=2.14 min; MS m/z: 370 and 372 (M+H)$^+$.

Step 3: 6-Bromo-1-(2-(difluoromethoxy)benzyl)-2-methyl-1H-pyrazolo[4,3-b]pyridin-3(2H)-one A solution of 6-bromo-1-(2-(difluoromethoxy)benzyl)-1H-pyrazolo[4,3-b]pyridin-3(2H)-one (0.23 g, 0.62 mmol) in acetone (6 mL) was treated with potassium carbonate (0.094 g, 0.68 mmol) and MeI (0.31 mL, 4.9 mmol). The mixture was heated to about 50° C. for about 10 h then concentrated under reduced pressure. The residue was partitioned between water (10 mL) and EtOAc (20 mL). The aqueous layer was extracted with EtOAc (10 mL). The combined organic solutions were dried over sodium sulfate, filtered, and concentrated under reduced pressure. The material was purified via flash chromatography on silica gel (0-50% EtOAc/DCM) to yield the title compound (0.026 g, 11%); LC/MS (Table A, Method e) R$_t$=2.14 min; MS m/z: 384 and 386 (M+H)$^+$ Step 4: 1-(2-(Difluoromethoxy)benzyl)-2-methyl-6-(2-morpholinopyrimidin-5-yl)-1H-pyrazolo[4,3-b]pyridin-3(2H)-one A mixture of 6-bromo-1-(2-(difluoromethoxy)benzyl)-2-methyl-1H-pyrazolo[4,3-b]pyridin-3(2H)-one (0.025 g, 0.065 mmol, 4-(5-(4,4,5,5-tetramethyl-1,3,2-dioxaborolan-2-yl)pyrimidin-2-yl)morpholine (0.023 g, 0.078 mmol), cesium carbonate (0.045 g, 0.14 mmol) and PdCl$_2$(PPh$_3$)$_2$ (0.004 g, 0.006 mmol) in 1,4-dioxane (1 mL) and water (0.25 mL) was degassed with N$_2$ then heated to about 85° C. for about 45 min. The reaction mixture was cooled, filtered through a 0.45 μM filter then purified by preparative reverse phase HPLC (Table A, Method c). Lyophilization of the appropriate fractions yielded the title compound (0.012 g, 40%); LC/MS (Table A, Method a) R$_t$=1.88 min; MS m/z: 469 (M+H)$^+$ (TNF IC$_{50}$=C).

Example #15: 1-(2-(Difluoromethoxy)benzyl)-2-methyl-6-(2-morpholinopyrimidin-5-yl)-1H-pyrazolo[3,4-b]pyridin-3(2H)-one

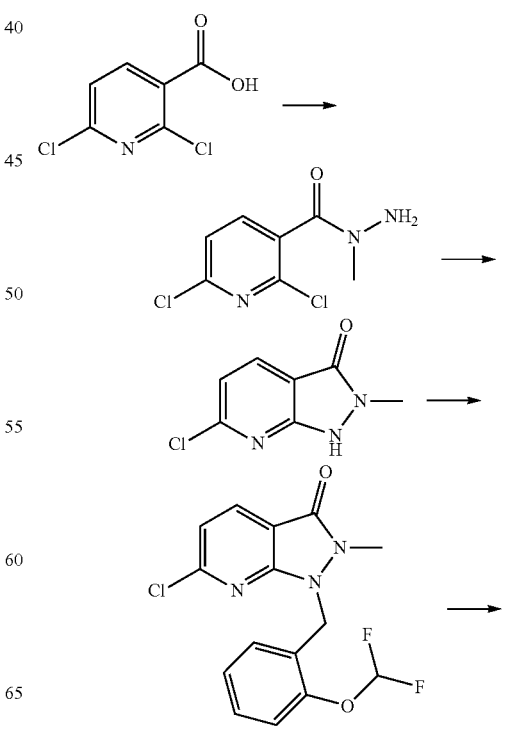

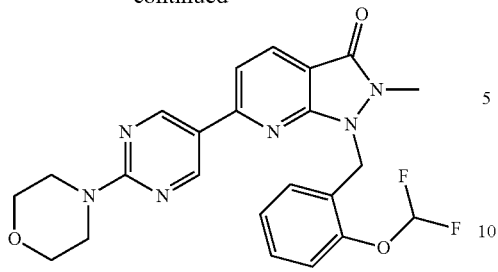

Step 1: 2,6-Dichloro-N-methylnicotinohydrazide 2,6-Dichloronicotinic acid (tech ~90%) (1.5 g, 7.8 mmol) in DCM (35 mL) was treated with oxalyl dichloride (0.84 mL, 9.6 mmol) and a few drops of DMF then stirred at rt for about 14 h. The mixture was concentrated under reduced pressure then dissolved in DCM (35 mL). The solution was added to methylhydrazine (1.1 g, 24 mmol) in DCM (35 mL) cooled to about −50° C. keeping the reaction temp between −40° C. and −45° C. during the addition. After completion of addition, the mixture was allowed to warm slowly to rt. The solvent was removed under reduced pressure then the residue was partitioned between EtOAc (50 mL) and water (50 mL). The aqueous layer was extracted with EtOAc (2×25 mL) then the combined organics were washed with sat. aq. NaCl (20 mL), dried over magnesium sulfate, filtered, and concentrated under reduced pressure to yield the title compound which was used without further manipulation (1.78 g, 104%); LC/MS (Table A, Method e) $R_t$=1.26 min; MS m/z; 220 (M+H)$^+$.

Step 2: 6-Chloro-2-methyl-H-pyrazolo[3,4-b]pyridin-3(2H)-one

A mixture of 2,6-dichloro-N-methylnicotinohydrazide (1.78 g, 8.09 mmol), n-butanol (60 mL) and sodium carbonate (0.88 g, 8.3 mmol) was heated to reflux with stirring for about 23 h. The mixture was concentrated under reduced pressure then the material was dissolved in water (25 mL). The pH of the solution was adjusted to about 6 with AcOH. EtOAc (50 mL) was added to the mixture then the solids were collected by filtration rinsing with EtOAc (10 mL). The filtrate layers were separated then the organic layer was dried over magnesium sulfate, filtered, concentrated under reduced pressure. The material was triturated with EtOAc (10 mL) then the solids were collected by filtration and washed with EtOAc (2 mL). The collected solids were combined and dried under reduced pressure to yield the title compound (0.90 g, 61%); LC/MS (Table A, Method e) $R_t$=1.12 min; MS m/z: 184 (M+H)$^+$

Step 3: 6-Chloro-1-(2-(difluoromethoxy)benzyl)-2-methyl-1H-pyrazolo[3,4-b]pyridin-3(2H)-one 6-Chloro-2-methyl-1H-pyrazolo[3,4-b]pyridin-3(2H)-one (0.250 g, 1.36 mmol) in DMF (7 mL) was treated with potassium carbonate (0.230 g, 1.66 mmol). After stirring for about 10 min, 1-(bromomethyl)-2-(difluoromethoxy)benzene (0.365 g, 1.54 mmol) was added over about 5 min. After stirring for about 30 min at rt the reaction mixture was concentrated under reduced pressure then the residue was partitioned between EtOAc (20 mL) and water (5 mL). The layers were separated then the organic layer was washed with water (10 mL) and sat. aq. NaCl (10 mL), dried over magnesium sulfate, filtered and concentrated under reduced pressure. The material was stirred with 10:1 heptane/EtOAc (5.5 mL) until a solid formed. The mixture was diluted with heptane (5 mL). The solids were collected by filtration rinsing with heptane (2 mL) and then dried under reduced pressure at about 60° C. to provide the title compound (0.384 g, 83%); LC/MS (Table A, Method e) $R_t$=2.11 min; MS m/z: 340 (M+H)$^+$.

Step 4: 1-(2-(Difluoromethoxy)benzyl)-2-methyl-6-(2-morpholinopyrimidin-5-yl)-1H-pyrazolo[3,4-b]pyridin-3(2H)-one A mixture of 6-chloro-1-(2-(difluoromethoxy)benzyl)-2-methyl-1H-pyrazolo[3,4-b]pyridin-3(2H)-one (0.075 g, 0.22 mmol), 4-(5-(4,4,5,5-tetramethyl-1,3,2-dioxaborolan-2-yl)pyrimidin-2-yl)morpholine (0.081 g, 0.28 mmol) and cesium carbonate (0.18 g, 0.55 mmol) in 1,4-dioxane (2 mL) and water (0.5 mL) under $N_2$ was treated with PdCl$_2$(PPh$_3$)$_2$ (0.011 g, 0.015 mmol). The mixture was purged with $N_2$ and then heated to about 100° C. for about 30 min. The reaction mixture was cooled, filtered through a 0.45 μM filter then purified by preparative reverse phase HPLC (Table A, Method d). Lyophilization of the appropriate fractions yielded the title compound (0.086 g, 83%); LC/MS (Table A, Method a) $R_t$=2.15 min; MS m/z: 469 (M+H)$^+$ (TNF IC$_{50}$=B).

Example #16: 1-(2-(Difluoromethoxy)benzyl)-6-(2-(2-hydroxypropan-2-yl)pyrimidin-5-yl)-2-methyl-1H-pyrazolo[3,4-b]pyridin-3(2H)-one

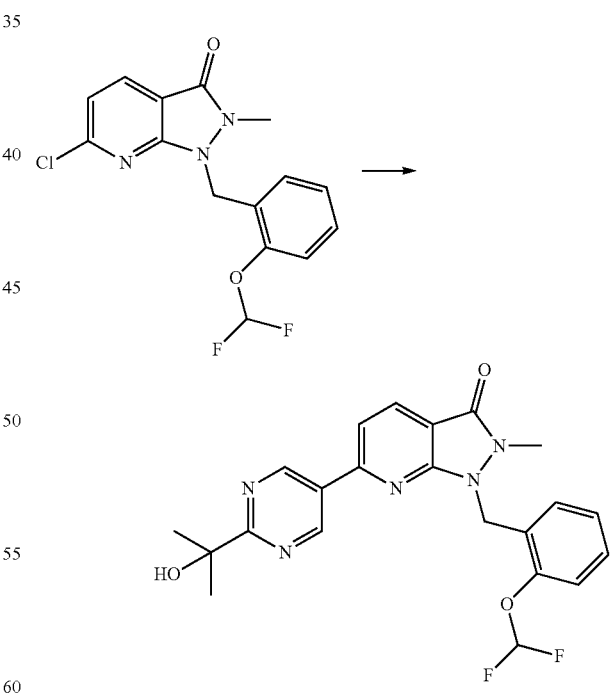

A mixture of 2-(5-bromopyrimidin-2-yl)propan-2-ol (0.065 g, 0.30 mmol), 4,4,4',4',5,5,5',5'-octamethyl-2,2'-bi(1,3,2-dioxaborolane) (0.15 g, 0.60 mmol), KOAc (0.072 g, 0.73 mmol) and PdCl$_2$(dppf) (0.011 g, 0.015 mmol in 1,4-dioxane (2 mL) under $N_2$ was heated to about 95° C. for about 90 min. The mixture was cooled to rt then 6-chloro- 1-(2-(difluoromethoxy)benzyl)-2-methyl-1H-pyrazolo[3,4-b]pyridin-3(2H)-one (0.075 g, 0.221 mmol) (Example #15, step 3), water (0.500 mL), cesium carbonate (0.18 g, 0.55 mmol) and PdCl$_2$(PPh$_3$)$_2$ (0.08 g, 0.01 mmol) were added. The mixture was placed under N$_2$ and then heated at about 100° C. for about 30 min. The reaction mixture was cooled, filtered through a 0.45 µM filter then purified by preparative reverse phase HPLC (Table A, Method d). Lyophilization of the appropriate fractions yielded the title compound (0.070 g, 72%); LC/MS (Table A, Method a) R$_t$=1.93 min; MS m/z: 442 (M+H)$^+$ (TNF IC$_{50}$=B).

Example #17: 1-(2-(Difluoromethoxy)benzyl)-2-methyl-6-(2-morpholinopyrimidin-5-yl)-1H-pyrazolo[4,3-c]pyridin-3(2H)-one

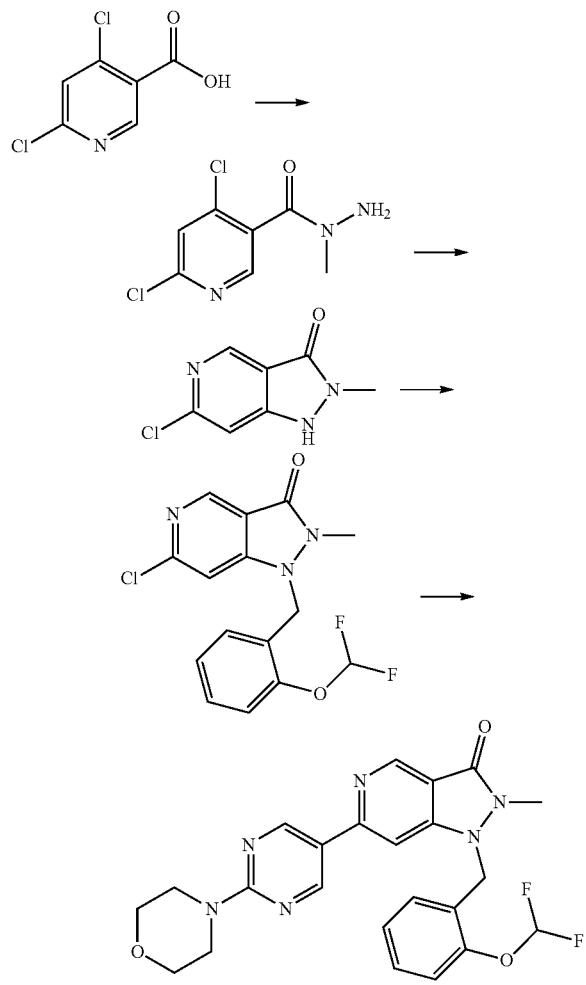

Step 1: 4,6-Dichloro-N-methylnicotinohydrazide

Oxalyl dichloride (5.5 mL, 63 mmol) was added to a suspension of 4,6-dichloronicotinic acid (10.0 g, 52.1 mmol) in DCM (240 mL). DMF (0.10 mL, 1.3 mmol) was added to the reaction dropwise and the reaction was stirred at rt for about 16 h. The reaction was concentrated under reduced pressure. The residue was dissolved in DCM (240 mL). The solution was added to a solution of methylhydrazine (8.2 mL, 160 mmol) in DCM (240 mL) cooled to about −50° C. at a rate to maintain the reaction temp between about −40° C. and −45° C. After the complete addition, the reaction was allowed to slowly warm to about 0° C. The reaction was quenched with sat. aq. NaHCO$_3$(200 mL) and the layers were separated. The aqueous layer was extracted with DCM (2×200 mL). The combined organic layers were dried over Na$_2$SO$_4$, filtered and concentrated under reduced pressure to give the title compound (11.2 g, 83%); LC/MS (Table A, Method e) R$_t$=1.22 min; MS m/z: 220 (M+H)$^+$.

Step 2: 5-Chloro-2-methyl-2,3-dihydro-1H-pyrazolo[4,3-c]pyridin-1-one

A mixture of 4,6-dichloro-N-methylnicotinohydrazide (0.50 g, 2.3 mmol) and sodium carbonate (0.250 g, 2.36 mmol) in cyclopentanol (20 mL) was gently refluxed for about 8 h. The reaction was allowed to cool to rt. AcOH (0.130 mL, 2.27 mmol) was added. The reaction mixture was concentrated under reduced pressure. The residue was triturated in DCM (25 mL) washing with DCM (25 mL) to give the title compound (0.420 g, 70%); LC/MS (Table A, Method e) R$_t$=0.87 min; MS m/z; 184 (M+H)$^+$.

Step 3: 6-Chloro-1-(2-(difluoromethoxy)benzyl)-2-methyl-1H-pyrazolo[3,4-c]pyridin-3(2H)-one 6-Chloro-2-methyl-1H-pyrazolo[4,3-c]pyridin-3(2H)-one (0.420 g, 2.29 mmol) in DMF (10 mL) was treated with potassium carbonate (0.632 g, 4.58 mmol). After stirring for about 10 min, 1-(bromomethyl)-2-(difluoromethoxy)benzene (0.596 g, 2.52 mmol) was added dropwise. The reaction was stirred at rt for about 30 min. The reaction was partitioned between EtOAc (100 mL) and sat. aq. NaCl (100 mL). The organic layer was washed with sat. aq. NaCl (100 mL), dried over Na$_2$SO$_4$, filtered, and concentrated under reduced pressure. The material was purified via flash chromatography on silica gel (0-3% MeOH/DCM) to yield the title compound (0.273 g, 35%); LC/MS (Table A, Method e) R$_t$=1.85 min; MS m/z: 340 (M+H)$^+$.

Step 4: 1-(2-(Difluoromethoxy)benzyl)-2-methyl-6-(2-morpholinopyrimidin-5-yl)-1H-pyrazolo[4,3-c]pyridin-3(2H)-one A mixture of 6-chloro-1-(2-(difluoromethoxy)benzyl)-2-methyl-H-pyrazolo[4,3-c]pyridin-3(2H)-one (0.270 g, 0.795 mmol), 4-(5-(4,4,5,5-tetramethyl-1,3,2-dioxaborolan-2-yl)pyrimidin-2-yl)morpholine (0.301 g, 1.03 mmol), cesium carbonate (0.647 g, 1.99 mmol), 1,4-dioxane (6.0 mL) and water (1.5 mL) was degassed with N$_2$. PdCl$_2$(PPh$_3$)$_2$(0.056 g, 0.079 mmol) was added to the mixture. The reaction was degassed under N$_2$ and heated at about 100° C. for about 1 h then allowed to cool to rt. The reaction mixture was partitioned between EtOAc (30 mL) and sat. aq. NaCl (30 mL). The organic layer was dried over Na$_2$SO$_4$, filtered and concentrated under reduced pressure. The material was purified via flash chromatography on silica gel (0-3% MeOH/DCM) to yield the title compound (0.280 g, 71%); LC/MS (Table A, Method e) R$_t$=1.88 min; MS m/z: 469 (M+H)$^+$. (TNF IC$_{50}$=C).

Example #18: (S)-7-(5-(1-(2-(Difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one

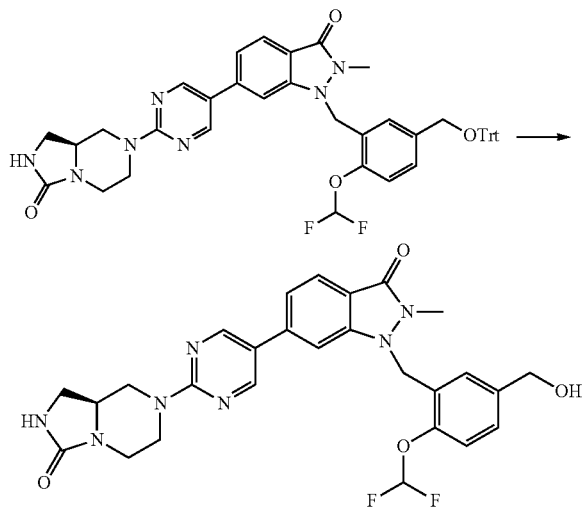

Triisopropylsilane (12 µL, 0.059 mmol) and TFA (2 mL) were added to a solution of (S)-7-(5-(1-(2-(difluoromethoxy)-5-((trityloxy)methyl)benzyl)-2-methyl-3-oxo-2,3-dihydro-1H-indazol-6-yl)pyrimidin-2-yl)hexahydroimidazo[1,5-a]pyrazin-3(2H)-one (47 mg, 0.059 mmol) (synthesized from 1-(2-(difluoromethoxy)-5-((trityloxy)methyl)benzyl)-2-methyl-6-(4,4,5,5-tetramethyl-1,3,2-dioxaborolan-2-yl)-1H-indazol-3(2H)-one (synthesized using 6-bromo-2-methyl-1H-indazol-3(2H)-one (Preparation #1) and (((3-(bromomethyl)-4-(difluoromethoxy)benzyl)oxy)methanetriyl)tribenzene (Preparation #14) in a method similar to Preparation #4, steps 1 and 2) and (S)-2-(5-bromopyrimidin-2-yl)hexahydroimidazo[1,5-a]pyrazin-3(2H)-one (Preparation #13) using a similar method to Example #5) in DCM (2 mL). After about 10 min, the reaction mixture was concentrated under reduced pressure. The residue was triturated twice with diethyl ether (5 mL), decanting the diethyl ether layer each time. MeCN (5 mL) and water (3 mL) were added and the resulting solution was made basic with sat. aq. NaHCO$_3$(0.2 mL). The solution was concentrated under reduced pressure to about 2 mL. The product was collected by filtration rinsing with water (1 mL). The material was air dried on the funnel then dried in the vacuum oven to yield the title compound (25 mg, 77%). LC/MS (Table A, Method a) R$_t$=1.56 min; MS m/z: 552 (M+H)$^+$. (TNF IC$_{50}$=A).

The compounds shown in Table 16 were synthesized in a manner similar to Example #18 from the corresponding Trt-protected alcohol.

TABLE 16

| Trt-protected alcohol | Product | Ex # | R$_t$ min (Table A, Method) | m/z ESI+ (M + H)$^+$ | TNF IC$_{50}$ |
|---|---|---|---|---|---|
| (R)-7-(5-(1-(2-(Difluoromethoxy)-5-((trityloxy)methyl)benzyl)-2-methyl-3-oxo-2,3-dihydro-1H-indazol-6-yl)pyrimidin-2-yl)hexahydroimidazo[1,5-a]pyrazin-3(2H)-one (synthesized using 6-bromo-2-methyl-1H-indazol-3(2H)-one (Preparation #1) and (((3-(bromomethyl)-4-(difluoromethoxy)benzyl)oxy)methanetriyl)tribenzene (Preparation #14) in a method similar to Preparation #4, steps 1 and 2) and (R)-2-(5-bromopyrimidin-2-yl)hexahydroimidazo[1,5-a]pyrazin-3(2H)-one (Preparation #13) using a similar method to Example #5) |  | 16.1 | 1.56 (a) | 552 | A |
| 1-(2-(Difluoromethoxy)-5-(trityloxymethyl)benzyl)-2-methyl-6-(2-((1-methyl-2-oxopyrrolidin-3-yl)amino)pyrimidin-5-yl)-1H-indazol-3(2H)-one (synthesized using 6-bromo-2-methyl-1H-indazol-3(2H)-one (Preparation #1) and (((3-(bromomethyl)-4-(difluoromethoxy)benzyl)oxy)methanetriyl)tribenzene (Preparation #14) in a method similar to Preparation #4, steps 1 and 2) and 3-((5-bromopyrimidin-2-yl)amino)-1-methylpyrrolidin-2-one(synthesized in a method similar to Preparation #13, step 1 using 3-amino-1-methylpyrrolidin-2-one) using a similar method to Example #5) |  | 16.2 | 1.47 (a) | 525 | B |

TABLE 16-continued

| Trt-protected alcohol | Product | Ex # | R, min (Table A, Method) | m/z ESI+ (M + H)+ | TNF IC50 |
|---|---|---|---|---|---|
| (S)-7-(5-(1-(2-(Difluoromethoxy)-5-(trityloxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one (synthesized using 6-bromo-2-methyl-1H-indazol-3(2H)-one (Preparation #1) and (((3-(bromomethyl)-4-(difluoromethoxy)benzyl)oxy)methanetriyl)tribenzene (Preparation #14) in a method similar to Preparation #4, steps 1 and 2) and (S)-7-(5-bromopyrimidin-2-yl)tetrahydro-1H-oxazolo[3,4-a]pyrazin-3(5H)-one (synthesized in a method similar to Preparation #13, step 1 using (S)-tetrahydro-1H-oxazolo[3,4-a]pyrazin-3(5H)-one) using a similar method to Example #5 | 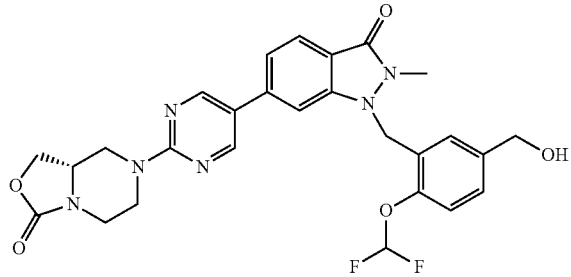 [SMILES: Cn1c(=O)c2ccc(-c3cnc(N4CCN5C(=O)OC[C@@H]5C4)nc3)cc2n1Cc1cc(CO)ccc1OC(F)F] | 16.3* | 1.66 (a) | 553 | A |
| (R)-7-(5-(1-(2-(Difluoromethoxy)-5-(trityloxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one (synthesized using 6-bromo-2-methyl-1H-indazol-3(2H)-one (Preparation #1) and (((3-(bromomethyl)-4-(difluoromethoxy)benzyl)oxy)methanetriyl)tribenzene (Preparation #14) in a method similar to Preparation #4, steps 1 and 2) and (R)-7-(5-bromopyrimidin-2-yl)tetrahydro-1H-oxazolo[3,4-a]pyrazin-3(5H)-one (synthesized in a method similar to Preparation #13, step 1 using (R)-tetrahydro-1H-oxazolo[3,4-a]pyrazin-3(5H)-one) using a similar method to Example #5 | 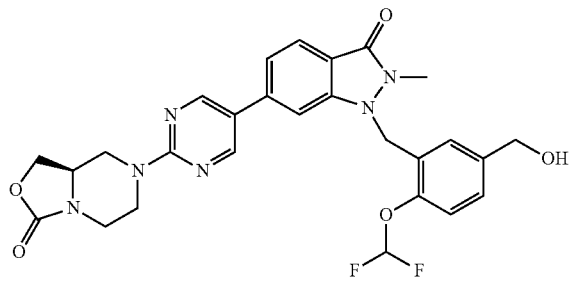 [SMILES: Cn1c(=O)c2ccc(-c3cnc(N4CCN5C(=O)OC[C@H]5C4)nc3)cc2n1Cc1cc(CO)ccc1OC(F)F] | 16.4* | 1.66 (a) | 553 | A |
| 1-(2-(Difluoromethoxy)-5-((trityloxy)methyl)benzyl)-2-methyl-6-(2-((2-oxopiperidin-4-yl)amino)pyrimidin-5-yl)-1H-indazol-3(2H)-one (prepared in a similar fashion to Example #2, from 6-(2-chloropyrimidin-5-yl)-1-(2-(difluoromethoxy)-5-((trityloxy)methyl)benzyl)-2-methyl-1H-indazol-3(2H)-one (Preparation #24) and 4-aminopiperidin-2-one hydrochloride) | 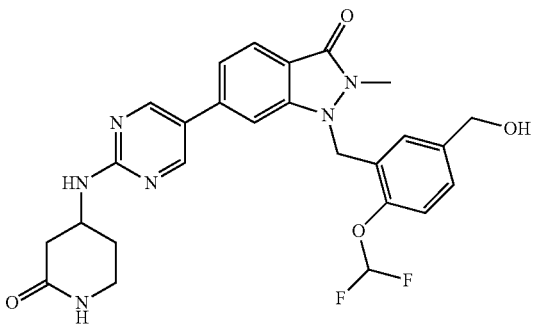 [SMILES: Cn1c(=O)c2ccc(-c3cnc(NC4CCNC(=O)C4)nc3)cc2n1Cc1cc(CO)ccc1OC(F)F] | 16.5 | 1.42 (e) | 525 | A |

TABLE 16-continued

| Trt-protected alcohol | Product | Ex # | R$_t$ min (Table A, Method) | m/z ESI+ (M + H)+ | TNF IC$_{50}$ |
|---|---|---|---|---|---|
| 1-(2-(Difluoromethoxy)-5-((trityloxy)methyl)benzyl)-2-methyl-6-(2-((2-oxopyrrolidin-3-yl)amino)pyrimidin-5-yl)-1H-indazol-3(2H)-one (prepared in a similar fashion to Example #2, from 6-(2-chloropyrimidin-5-yl)-1-(2-(difluoromethoxy)-5-((trityloxy)methyl)benzyl)-2-methyl-1H-indazol-3(2H)-one (Preparation #24) and 3-aminopyrrolidin-2-one) | | 16.6 | 1.42 (e) | 511 | B |
| 1-(2-(Difluoromethoxy)-5-((trityloxy)methyl)benzyl)-6-(2-(2-hydroxypropan-2-yl)pyrimidin-5-yl)-2-methyl-1H-indazol-3(2H)-one (prepared in a similar fashion to Preparation #4, step 1 from 6-(2-(2-hydroxypropan-2-yl)pyrimidin-5-yl)-2-methyl-1H-indazol-3(2H)-one (Preparation #19) and (((3-(bromomethyl)-4-(difluoromethoxy)benzyl)oxy)methanetriyl)tribenzene (Preparation #14)) | | 16.7 | 1.61 (e) | 471 | A |
| 6-(2-(4-Acetylpiperazin-1-yl)pyrimidin-5-yl)-1-(2-(difluoromethoxy)-5-((trityloxy)methyl)benzyl)-2-methyl-1H-indazol-3(2H)-one (prepared in a similar fashion to Example #2, from 6-(2-chloropyrimidin-5-yl)-1-(2-(difluoromethoxy)-5-((trityloxy)methyl)benzyl)-2-methyl-1H-indazol-3(2H)-one (Preparation #24) and 1-(piperazin-1-yl)ethanone) | | 16.8 | 1.63 (e) | 539 | A |
| 1-(2-(Difluoromethoxy)-5-((trityloxy)methyl)benzyl)-2-methyl-6-(2-((1-methyl-2-oxopiperidin-4-yl)amino)pyrimidin-5-yl)-1H-indazol-3(2H)-one (prepared in a similar fashion to Example #2, from 6-(2-chloropyrimidin-5-yl)-1-(2-(difluoromethoxy)-5-((trityloxy)methyl)benzyl)-2-methyl-1H-indazol-3(2H)-one (Preparation #24) and 4-amino-1-methylpiperidin-2-one hydrochloride) | | 16.9 | 1.50 (e) | 539 | A |

TABLE 16-continued

| Trt-protected alcohol | Product | Ex # | R, min (Table A, Method) | m/z ESI+ (M + H)+ | TNF IC50 |
|---|---|---|---|---|---|
| (R)-7-(5-(2-Methyl-3-oxo-1-((3-(trifluoromethyl)-6-((trityloxy)methyl)pyridin-2-yl)methyl)-2,3-dihydro-1H-indazol-6-yl)pyrimidin-2-yl)hexahydroimidazo[1,5-a]pyrazin-3(2H)-one (synthesized in a manner similar to Preparation #13 from (S)-hexahydroimidazo[1,5-a]pyrazin-3(2H)-one hydrochloride (Preparation #46) and 6-(2-chloropyrimidin-5-yl)-2-methyl-1-((3-(trifluoromethyl)-6-((trityloxy)methyl)pyridin-2-yl)methyl)-1H-indazol-3(2H)-one (synthesized a manner similar to Preparation #4, step 1 from 6-(2-chloropyrimidin-5-yl)-2-methyl-1H-indazol-3(2H)-one (Preparation #23) and 2-(bromomethyl)-3-(trifluoromethyl)-6-((trityloxy)methyl)pyridine (Preparation #61))) | (structure) | 16.10 | 1.56 (a) | 555 | A |

The compounds shown in Table 17 were synthesized in a manner similar to Example #8 from 6-bromo-1-(2-(difluoromethoxy)benzyl)-5-fluoro-2-methyl-1H-indazol-3(2H)-one (synthesized in a similar fashion to Preparation #4, step 1 from 6-bromo-5-fluoro-2-methyl-1H-indazol-3(2H)-one (synthesized in a similar fashion to Preparation #1 from 4-bromo-2,5-difluorobenzoic acid) and 2-(bromomethyl)-1-(difluoromethoxy)-4-methylbenzene (synthesized in a similar fashion to Preparation #3, step 2 from (2-(difluoromethoxy)-5-methylphenyl)methanol (Preparation #11))) and the corresponding halide.

TABLE 17

| Halide | Product | Example # | R, min (Table A, Method) | m/z ESI+ (M + H)+ | TNF IC50 |
|---|---|---|---|---|---|
| 2-(5-Bromopyrimidin-2-yl)propan-2-ol | (structure) | 17.1 | 2.05 (a) | 473 | A |
| 2-(5-Bromo-4-methylpyrimidin-2-yl)propan-2-ol (synthesized as described in WO2015/86506 A1) | (structure) | 17.2 | 2.15 (a) | 487 | A |

TABLE 17-continued

| Halide | Product | Example # | R_t min (Table A, Method) | m/z ESI+ (M + H)+ | TNF IC_{50} |
|---|---|---|---|---|---|
| (R)-1-(4-(5-Bromopyrimidin-2-yl)-3-methylpiperazin-1-yl)-2-hydroxyethanone (Preparation #22) | | 17.3* | 1.94 (a) | 571 | A |
| 2-(5-Bromopyrimidin-2-yl)-2-methylpropan-1-ol (Preparation #52) | | 17.4 | 2.09 (a) | 487 | A |

The compounds shown in Table 18 were synthesized in a manner similar to Example #17, step 3 from (R)-6-(2-(4-acetyl-3-methylpiperazin-1-yl)pyrimidin-5-yl)-2-methyl-1H-pyrazolo[3,4-b]pyridin-3(2H)-one (synthesized in a similar manner to Example #8 using 6-chloro-2-methyl-1H-pyrazolo[3,4-b]pyridin-3(2H)-one (Example #15, step 2) and (R)-1-(4-(5-bromopyrimidin-2-yl)-2-methylpiperazin-1-yl)ethanone (Preparation #ft 16)) and the corresponding halides.

TABLE 18

| Halide | Product | Example # | R_t min (Table A, Method) | m/z ESI+ (M + H)+ | TNF IC_{50} |
|---|---|---|---|---|---|
| (2-(Bromomethyl)-4-methylphenyl)(difluoromethyl)sulfane (synthesized in a manner similar to Preparation #14, step 6, from (2-((difluoromethyl)thio)-5-methylphenyl)methanol (Preparation #18) | | 18.1* | 2.13 (e) | 554 | A |
| 2-(Bromomethyl)-1-(difluoromethoxy)-4-methylbenzene (synthesized in a similar fashion to Preparation #3, step 2 from (2-(difluoromethoxy)-5-methylphenyl)methanol (Preparation #11)) | | 18.2* | 2.01 (a) | 538 | A |

TABLE 18-continued

| Halide | Product | Example # | R_t min (Table A, Method) | m/z ESI+ (M + H)+ | TNF IC_{50} |
|---|---|---|---|---|---|
| 2-(Bromomethyl)-1-chloro-4-methylbenzene (synthesized in a similar fashion to Preparation #3, step 2 from (2-chloro-5-methylphenyl)methanol (prepared in a similar fashion to Preparation #14, step 2 from methyl 2-chloro-5-methylbenzoate)) | | 18.3* | 2.15 (a) | 506 | A |

The compounds shown in Table 19 were synthesized in a manner similar to Example #8 from 6-bromo-2-methyl-1-((6-methyl-3-(trifluoromethyl)pyridin-2-yl)methyl)-1H-indazol-3(2H)-one (synthesized in a similar fashion to Preparation #4, step 1 from 6-bromo-2-methyl-1H-indazol-3(2H)-one (Preparation #1) and 2-(bromomethyl)-6-methyl-3-(trifluoromethyl)pyridine (synthesized in a similar fashion to Preparation #14, step 6 from (6-methyl-3-(trifluoromethyl)pyridin-2-yl)methanol (Preparation #17)) and the corresponding halide.

TABLE 19

| Halide | Product | Example # | R_t min (Table A, Method) | m/z ESI+ (M + H)+ | TNF IC_{50} |
|---|---|---|---|---|---|
| (R)-1-(4-(5-bromopyrimidin-2-yl)-2-methylpiperazin-1-yl)ethanone (Preparation #16) | | 19.1* | 1.96 (e) | 540 | A |
| (S)-7-(5-bromopyrimidin-2-yl)hexahydroimidazo[1,5-a]pyrazin-3(2H)-one (Preparation #13) | | 19.2 | 1.81 (e) | 539 | A |
| (R)-1-(4-(5-Bromopyrimidin-2-yl)-2-methylpiperazin-1-yl)-2-hydroxyethanone (Preparation #15) | | 19.3* | 1.79 (a) | 556 | A |

TABLE 19-continued

| Halide | Product | Example # | R, min (Table A, Method) | m/z ESI+ (M + H)+ | TNF IC50 |
|---|---|---|---|---|---|
| (R)-7-(5-bromopyrimidin-2-yl)tetrahydro-1H-oxazolo[3,4-a]pyrazin-3(5H)-one (synthesized in a similar fashion to Preparation #13, step 1 using (R)-hexahydro-oxazolo[3,4-A]pyrazine-3-one HCl | 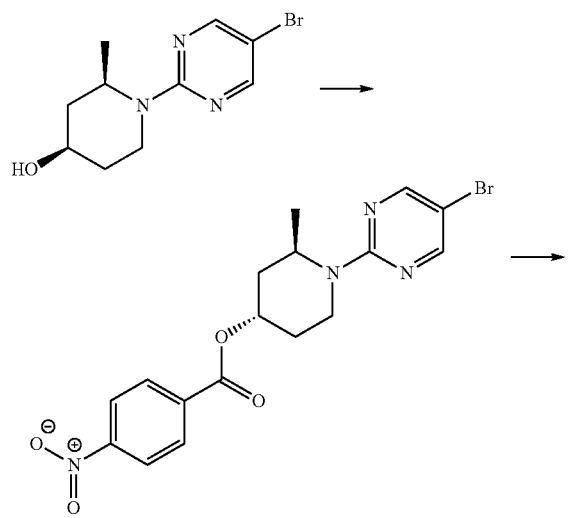 | 19.4* | 1.91 (a) | 540 | A |
| (R)-1-(4-(5-bromopyrimidin-2-yl)-3-methylpiperazin-1-yl)-2-hydroxyethanone (Preparation #22) | 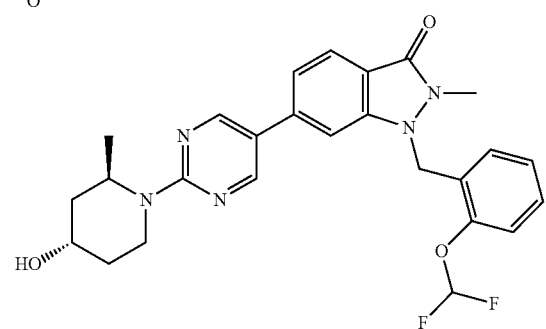 | 19.5* | 1.79 (a) | 556 | A |

Example #19: 1-(2-(Difluoromethoxy)benzyl)-6-(2-((2R,4S)-4-hydroxy-2-methylpiperidin-1-yl)pyrimidin-5-yl)-2-methyl-1H-indazol-3(2H)-one Step 1: (2R,4S)-1-(5-Bromopyrimidin-2-yl)-2-methylpiperidin-4-yl 4-nitrobenzoate To a solution of (2R,4R)-1-(5-bromopyrimidin-2-yl)-2-methylpiperidin-4-ol (265 mg, 0.974 mmol) (prepared in a similar fashion to Preparation 13, step 1), Ph₃P (255 mg, 0.970 mmol) and 4-nitrobenzoic acid (163 mg, 0.97 mmol) was added di-tert-butyl azodicarboxylate (224 mg, 0.970 mmol) in THF (1 mL) dropwise. The mixture was stirred for about 3 h and then Ph₃P (255 mg, 0.970 mmol) and di-tert-butyl azodicarboxylate (224 mg, 0.970 mmol) in THF (1 mL) were added. The mixture was stirred for about 72 h at rt. The mixture was dried onto silica gel (3 g) and purified on silica gel using a gradient of 0-30% EtOAc in heptane. Product fractions were combined and concentrated to yield the title product (90 mg, 22%); LC/MS (Table A, Method j) $R_f$=2.17 min; MS m/z: 421/423(M+H)⁺.

Step 2: 1-(2-(Difluoromethoxy)benzyl)-6-(2-((2R,4S)-4-hydroxy-2-methylpiperidin-1-yl)pyrimidin-5-yl)-2-methyl-1H-indazol-3(2H)-one A mixture of (2R,4S)-1-(5-bromopyrimidin-2-yl)-2-methylpiperidin-4-yl 4-nitrobenzoate (87 mg, 0.21 mmol), 1-(2-(difluoromethoxy)benzyl)-2-methyl-6-(4,4,5,5-tetramethyl-1,3,2-dioxaborolan-2-yl)-1H-indazol-3(2H)-one (89 mg, 0.21 mmol) (Preparation 4, step 2), and cesium carbonate (236 mg, 0.723 mmol) under nitrogen was diluted with 1,4-dioxane (2 mL) and water (0.5 mL). The mixture was degassed with a stream of nitrogen for about 5 min. PdCl₂(PPh₃)₂ (11 mg, 0.016 mmol) was added and the reaction was further degassed for an additional 5 min. The reaction was heated to about 80° C. for about 1 h. The mixture was cooled to rt and the layers were separated. The organic layer was dried over $Na_2SO_4$, filtered, and concentrated onto silica gel (2 g). The residue was purified on silica gel using a gradient of 0-70% EtOAc/DCM. The appropriate fractions were combined and concentrated. The residue was dissolved in dioxane (2 mL) and a solution of lithium hydroxide (25 mg, 1.0 mmol) and water (0.5 mL) was added. After about 1 h, AcOH (0.5 mL) was added and the reaction was concentrated. The residue was dissolved in EtOAc (5 mL) and washed with sat. aq. $NaHCO_3$ (3 mL). The organic layer was dried over $Na_2SO_4$, filtered and concentrated to yield the title product (65 mg, 63%); LC/MS (Table A, Method a) $R_t$=1.98 min; MS m/z: 496 (M+H)$^+$. (TNF $IC_{50}$=A).

Example #20: 4-(5-(1-(2-(Difluoromethoxy)benzyl)-2-methyl-3-oxo-2,3-dihydro-1H-indazol-6-yl)pyrimidin-2-yl)-4-hydroxypiperidine-1-carbaldehyde

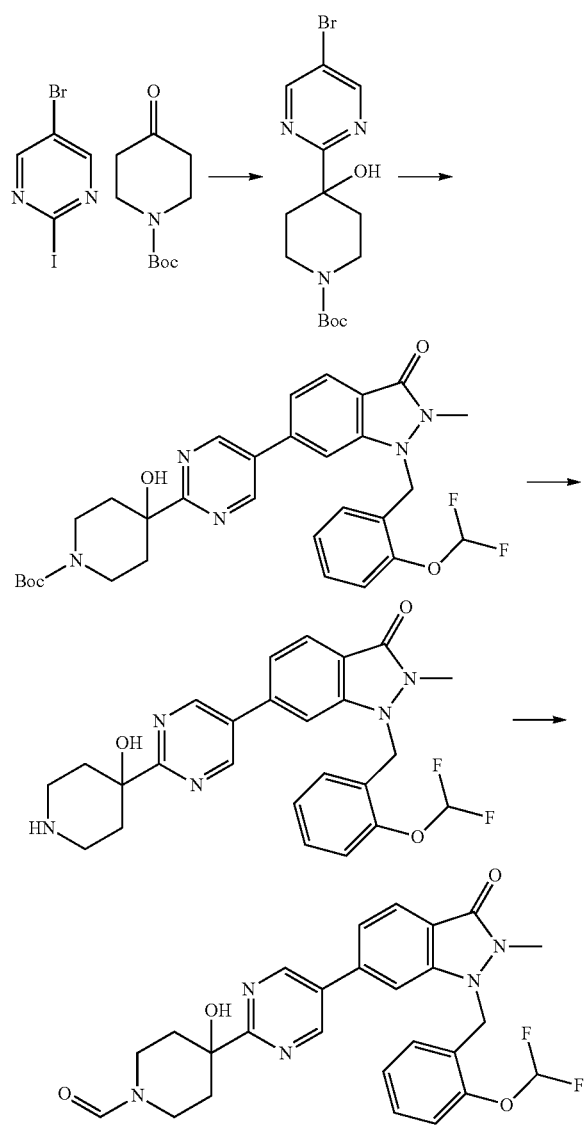

Step 1: tert-Butyl 4-(5-bromopyrimidin-2-yl)-4-hydroxypiperidine-1-carboxylate

Toluene (80 mL) was added to 5-bromo-2-iodopyrimidine (4.00 g, 14.0 mmol). The solution was cooled to about −78° C. n-Butyllithium (2.5 M in hexane, 5.90 mL, 14.7 mmol) was added dropwise via syringe to the suspension. The reaction was mixed at about −78° C. for about 30 min. A solution of tert-butyl 4-oxopiperidine-1-carboxylate (3.08 g, 15.5 mmol) in toluene (20 mL) was added dropwise via syringe. The reaction was stirred for about 30 min at about −78° C. The dry ice/acetone bath was removed. The reaction was quenched with water (100 mL), extracted with EtOAc (150 mL). The aqueous layer was extracted with EtOAc (2×25 mL). The organic layer was dried over $MgSO_4$, filtered, concentrated. The residue was purified on silica gel (0-50% EtOAc/DCM) to afford the title product (1.86 g, 37%); LC/MS (Table A, Method e) $R_t$=2.16 min; MS m/z: 258 and 260 (M+H)$^+$.

Step 2: tert-Butyl 4-(5-(1-(2-(difluoromethoxy)benzyl)-2-methyl-3-oxo-2,3-dihydro-1H-indazol-6-yl)pyrimidin-2-yl)-4-hydroxypiperidine-1-carboxylate The reaction was performed using tert-butyl 4-(5-bromopyrimidin-2-yl)-4-hydroxypiperidine-1-carboxylate and 1-(2-(difluoromethoxy)benzyl)-2-methyl-6-(4,4,5,5-tetramethyl-1,3,2-dioxaborolan-2-yl)-1H-indazol-3(2H)-one (Preparation #4, step 2) in a similar fashion to Example #15, step 4 to give the title compound (1.30 g, 97%); LC/MS (Table A, Method e) $R_t$=2.27 min; MS m/z: 582 (M+H)$^+$ Step 3: 1-(2-(Difluoromethoxy)benzyl)-6-(2-(4-hydroxypiperidin-4-yl)pyrimidin-5-yl)-2-methyl-1H-indazol-3(2H)-one, hydrochloric acid The reaction was performed using tert-butyl 4-(5-(1-(2-(difluoromethoxy)benzyl)-2-methyl-3-oxo-2,3-dihydro-1H-indazol-6-yl)pyrimidin-2-yl)-4-hydroxypiperidine-1-carboxylate in a similar fashion to Example #3 step 1 to give the title compound (1.20 g, 100%); LC/MS (Table A, Method i) $R_t$=0.77 min; MS m/z: 482 (M+H)$^+$.

Step 4: 4-(5-(1-(2-(Difluoromethoxy)benzyl)-2-methyl-3-oxo-2,3-dihydro-1H-indazol-6-yl)pyrimidin-2-yl)-4-hydroxypiperidine-1-carbaldehyde Ethyl formate (2.60 mL, 32.4 mmol) and TEA (0.045 mL, 0.32 mmol) were added to 1-(2-(difluoromethoxy)benzyl)-6-(2-(4-hydroxypiperidin-4-yl)pyrimidin-5-yl)-2-methyl-1H-indazol-3(2H)-one, hydrochloric acid (84.0 mg, 0.162 mmol) to give a white suspension. The reaction was warmed to about 58° C. THF (1 mL) was added. After about 24 h, the reaction was quenched with water (10 mL) and extracted with EtOAc (30 mL). The organic layer was dried over $MgSO_4$, filtered, and concentrated. The residue was purified on silica gel (0-8% MeOH/DCM) to afford the title product (33 mg, 39%); LC/MS (Table A, Method a) $R_t$=1.61 min; MS m/z: 510 (M+H)$^+$. (TNF $IC_{50}$=B).

Example #21*: (S)-4-(Difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-aminopropanoate

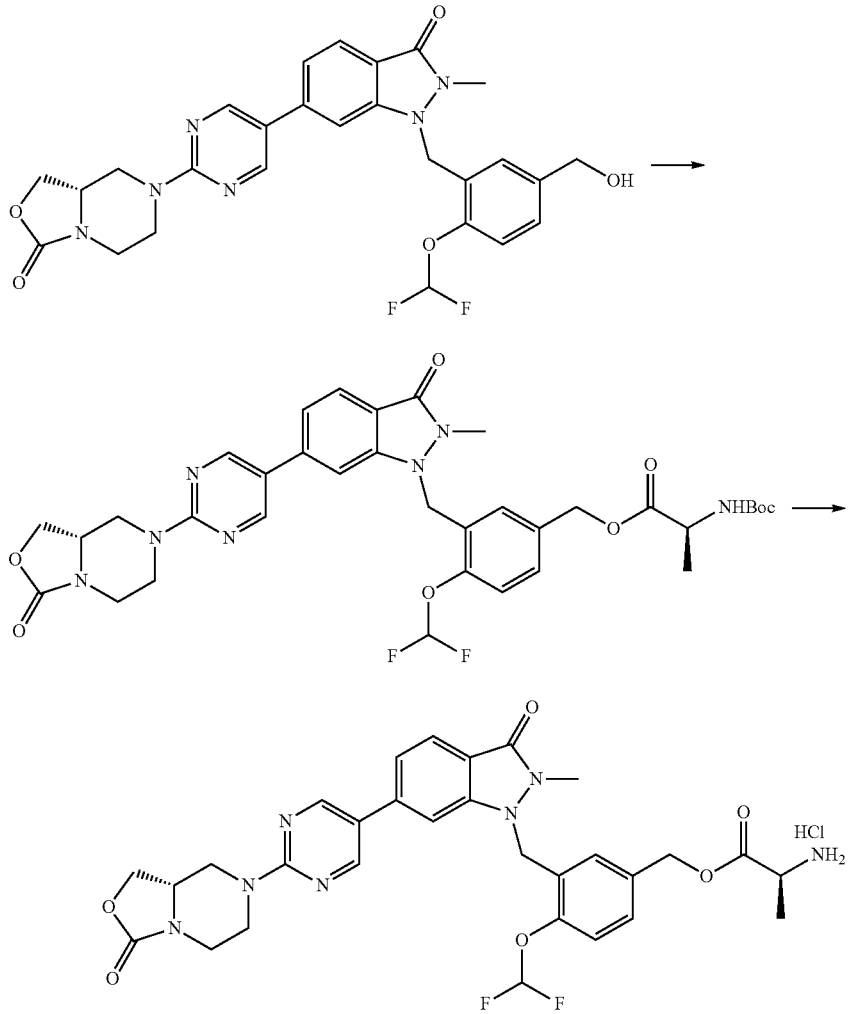

Step 1: (S)-4-(Difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-((tert-butoxycarbonyl)amino)propanoate A flask was charged with N-(tert-butoxycarbonyl)-L-alanine (70.0 mg, 0.400 mmol), DMAP (11 mg, 0.090 mmol), N,N'-dicyclohexylcarbodiimide (96 mg, 0.50 mmol). (S)-7-(5-(1-(2-(difluoromethoxy)-5-(hydroxymethyl)benzyl)-2-methyl-3-oxo-2,3-dihydro-1H-indazol-6-yl)pyrimidin-2-yl)tetrahydro-1H-oxazolo[3,4-a]pyrazin-3(5H)-one (170 mg, 0.31 mmol) (Example #16.3), and CH$_2$Cl$_2$ (2 mL) at room temperature. After stirring for 15 h, the solution was diluted with CH$_2$Cl$_2$ (5 mL), and filtered off solid. The filtrate was concentrated under reduced pressure. The residue was purified on silica gel (0-10% MeOH/CH$_2$Cl$_2$) to afford the title product (113 mg, 51%); LC/MS (Table A, Method i) R$_t$=1.49 min; MS m/z: 723.72 and 724.62 (M+H)$^+$ Step 2: (S)-4-(Difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-aminopropanoate (S)-4-(Difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-aminopropanoate was synthesized in a manner similar to Example #3(step 1) from (S)-4-(difluoromethoxy)-3-((2-methyl-3-oxo-6-(2-((S)-3-oxotetrahydro-1H-oxazolo[3,4-a]pyrazin-7(3H)-yl)pyrimidin-5-yl)-2,3-dihydro-1H-indazol-1-yl)methyl)benzyl 2-((tert-butoxycarbonyl)amino)propanoate. LC/MS (Table A, Method a) R$_t$=1.46 min; MS m/z: 623.61 and 624.50 (M+H)$^+$. (TNF IC$_{50}$=A).

219

Example #22: 1-(2-(Difluoromethoxy)-5-methylbenzyl)-6-(2-(4-hydroxypiperidin-1-yl)pyrimidin-5-yl)-2-methyl-1H-indazol-3(2H)-one

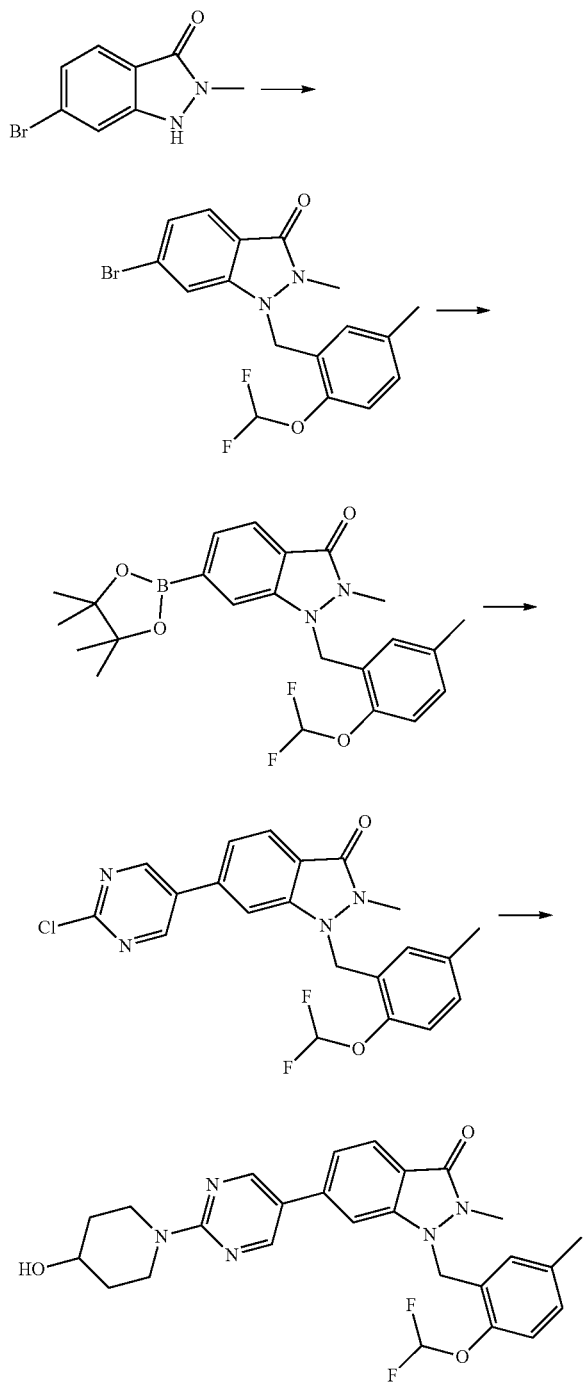

Step 1: 6-Bromo-1-(2-(difluoromethoxy)-5-methylbenzyl)-2-methyl-1H-indazol-3(2H)-one The reaction was performed using 6-bromo-2-methyl-1H-indazol-3(2H)-one (Preparation #1) and 2-(bromomethyl)-1-(difluoromethoxy)-4-methylbenzene (synthesized in a similar fashion to Preparation #3, step 2 from (2-(difluoromethoxy)-5-methylphenyl)methanol (Preparation #11)) in a similar fashion to Preparation #4, step 1 to give the title product (62%); (Table A, Method e) $R_t$=2.28 min; MS m/z: 397 and 399 (M+H)$^+$.

Step 2: 1-(2-(Difluoromethoxy)-5-methylbenzyl)-2-methyl-6-(4,4,5,5-tetramethyl-1,3,2-dioxaborolan-2-yl)-1H-indazol-3(2H)-one The reaction was performed using 6-bromo-1-(2-(difluoromethoxy)-5-methylbenzyl)-2-methyl-1H-indazol-3(2H)-one in a similar fashion to Preparation #4, step 2 to give the title product (90%); (Table A, Method e) $R_t$=2.48 min; MS m/z: 445 (M+H)$^+$.

Step 3: 6-(2-Chloropyrimidin-5-yl)-1-(2-(difluoromethoxy)-5-methylbenzyl)-2-methyl-1H-indazol-3(2H)-one Dimethyl acetamide (8.00 mL) and water (2.00 mL) were add to a mixture of PdCl$_2$(dppf) complex with DCM (0.0876 g, 0.107 mmol), 1-(2-(difluoromethoxy)-5-methylbenzyl)-2-methyl-6-(4,4,5,5-tetramethyl-1,3,2-dioxaborolan-2-yl)-1H-indazol-3(2H)-one (0.471 g, 1.06 mmol), 5-bromo-2-chloropyrimidine (0.369 g, 1.91 mmol), and Na$_2$CO$_3$ (0.295 g, 2.78 mmol). The reaction vessel was evacuated then back-filled with N$_2$ three times then purged with N$_2$ for about 10 min. The mixture was warmed to about 70° C. After about 45 min, the mixture was allowed to cool to rt. DCM (20 mL) and water (20 mL) were added. The layers were separated and the aqueous layer was extracted with DCM (2×10 mL). The combined organic layers were dried over Na$_2$SO$_4$, filtered and concentrated. The residue was purified by flash chromatography on silica gel (0-50% EtOAc/DCM). The appropriate fractions were collected and concentrated under reduced pressure to afford the title product (0.293 g, 64%); (Table A, Method e) $R_t$=2.14 min; MS m/z: 431 (M+H)$^+$.

Step 4: 1-(2-(Difluoromethoxy)-5-methylbenzyl)-6-(2-(4-hydroxypiperidin-1-yl)pyrimidin-5-yl)-2-methyl-1H-indazol-3(2H)-one The reaction was performed using 6-(2-chloropyrimidin-5-yl)-1-(2-(difluoromethoxy)-5-methylbenzyl)-2-methyl-1H-indazol-3(2H)-one and 4-hydroxypiperidine in a similar fashion to Example #2 to give the title product (83%); (Table A, Method a) $R_t$=1.88 min; MS m/z: 496 (M+H)$^+$. (TNF IC$_{50}$=A).

The compounds shown in Table 20 were synthesized in a manner similar to Example #2 from 6-(2-chloropyrimidin-5-yl)-1-(2-(difluoromethoxy)-5-methylbenzyl)-2-methyl-1H-indazol-3(2H)-one

TABLE 20

| Amine | Product | Example # | R, min (Table A, Method) | m/z ESI+ (M + H)+ | TNF IC50 |
|---|---|---|---|---|---|
| Pyrrolidine-3-carboxamide | 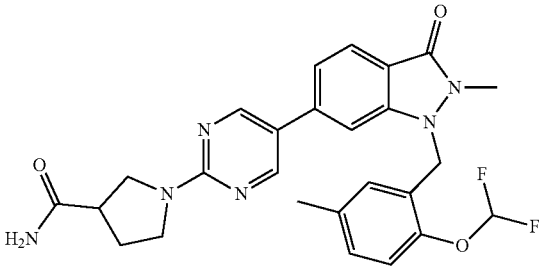 [SMILES: Cc1ccc(OC(F)F)c(Cn2c3cc(-c4cnc(N5CCC(C(N)=O)C5)nc4)ccc3c(=O)n2C)c1] | 20.1 | 1.67 (a) | 509 | B |
| (S)-Tetrahydro-1H-oxazolo[3,4-a]pyrazin-3(5H)-one, hydrochloric acid | 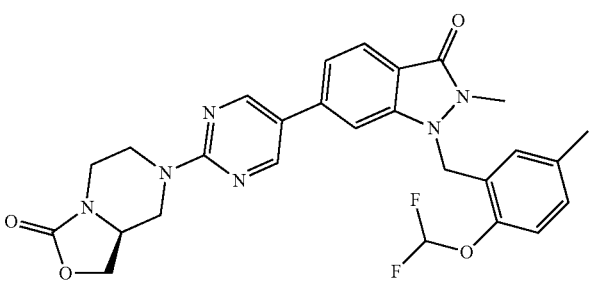 [SMILES: Cc1ccc(OC(F)F)c(Cn2c3cc(-c4cnc(N5CCN6C(=O)OC[C@@H]6C5)nc4)ccc3c(=O)n2C)c1] | 20.2* | 1.97 (a) | 537 | A |
| rac-(3aR,6aS)-Hexahydropyrrollo[3,4-c]pyrrol-1(2H)-one hydrochloride | 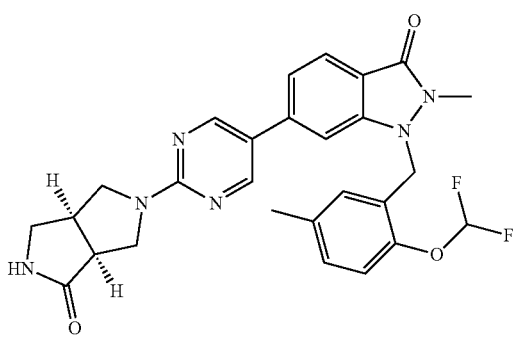 [SMILES: Cc1ccc(OC(F)F)c(Cn2c3cc(-c4cnc(N5C[C@@H]6CNC(=O)[C@@H]6C5)nc4)ccc3c(=O)n2C)c1] | 20.3 | 1.69 (a) | 521 | B |
| (R)-1-(3-Methylpiperazin-1-yl)ethanone hydrochloride (Prepared in a similar fashion to Example#3, step 1 from (R)-tert-butyl 4-acetyl-2-methylpiperazine-1-carboxylate (Prepared in similar fashion to Preparation #16, from (R)-tert-butyl 2-methylpiperazine-1-carboxylate)) | 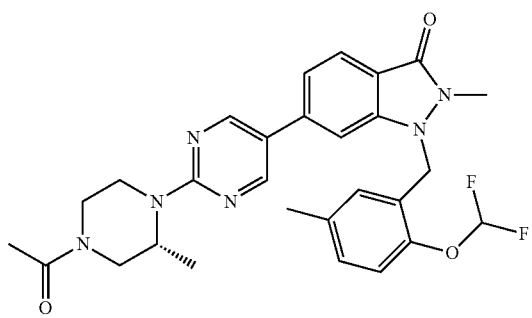 [SMILES: CC(=O)N1CCN(c2ncc(-c3ccc4c(=O)n(C)n(Cc5cc(C)ccc5OC(F)F)c4c3)cn2)[C@H](C)C1] | 20.4* | 1.99 (a) | 537 | A |
| (R)-1-(3-Ethylpiperazin-1-yl)ethanone hydrochloride (Prepared in a similar fashion to Example#3, step 1 from (R)-tert-butyl 4-acetyl-2-ethylpiperazine-1-carboxylate (Prepared in similar fashion to Preparation #16, from (R)-tert-butyl 2-ethylpiperazine-1-carboxylate)) | 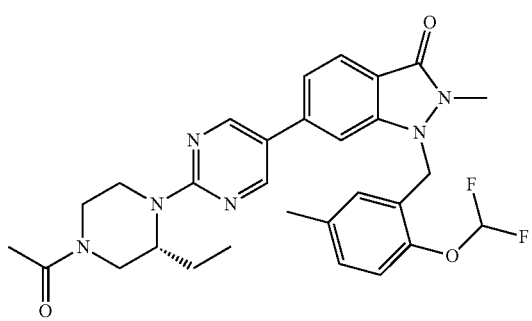 [SMILES: CC[C@@H]1CN(C(C)=O)CCN1c1ncc(-c2ccc3c(=O)n(C)n(Cc4cc(C)ccc4OC(F)F)c3c2)cn1] | 20.5* | 2.09 (a) | 552 | A |

Example #23*: (R)-Methyl 4-(5-(1-(2-(difluoromethoxy)-5-methylbenzyl)-2-methyl-3-oxo-2,3-dihydro-1H-indazol-6-yl)pyrimidin-2-yl)-2-methyl-piperazine-1-carboxylate

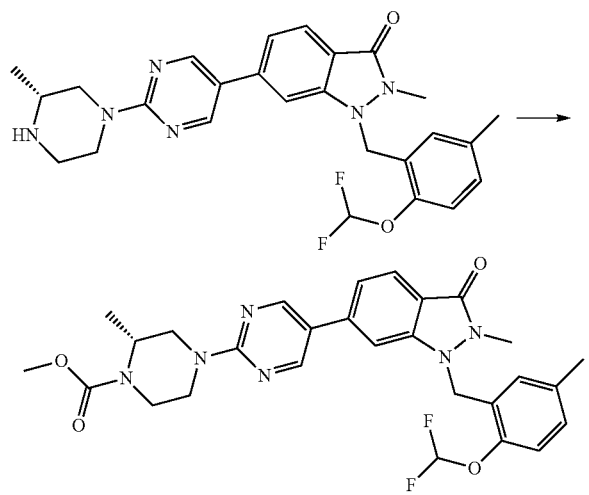

(R)-1-(2-(Difluoromethoxy)-5-methylbenzyl)-2-methyl-6-(2-(3-methylpiperazin-1-yl)pyrimidin-5-yl)-1H-indazol-3(2H)-one, hydrochloric acid (96.0 mg, 0.181 mmol) (Example #14.5) and TEA (0.100 mL, 0.723 mmol) in THF (3.00 mL) were added to give a yellow solution. The reaction was cooled to about 0° C. A solution of methyl carbonochloridate (18.8 mg, 0.199 mmol) in THF (1.00 mL) was added dropwise via syringe. After about 1 h, the reaction mixture was filtered rinsing with EtOAc (30 mL). The filtrate was washed with sat. aq. NaCl (10 mL). The organic layer was dried over MgSO$_4$, filtered, and concentrated. The residue was purified on silica gel (0-100% EtOAc/DCM then 10% MeOH/DCM) to afford the title product (58 mg, 55%); LC/MS (Table A, Method a) R$_t$=2.28 min; MS m/z: 553 (M+H)$^+$. (TNF IC$_{50}$=A).

The compounds shown in Table 21 were synthesized in a manner similar to Preparation #15 from (R)-1-(2-(difluoromethoxy)-5-methylbenzyl)-2-methyl-6-(2-(3-methylpiperazin-1-yl)pyrimidin-5-yl)-1H-indazol-3(2H)-one (Example #14.5) and the corresponding carboxylic acid.

TABLE 21

| Carboxylic Acid | Product | Example # | R$_t$ min (Table A, Method) | m/z ESI+ (M + H)$^+$ | TNF IC$_{50}$ |
|---|---|---|---|---|---|
| 2-Methoxyacetic acid | | 21.1* | 1.96 (a) | 567 | A |
| Oxetane-3-carboxylic acid | | 21.2* | 1.93 (a) | 579 | A |
| Oxetane-2-carboxylic acid | | 21.3* | 1.94 (a) | 579 | A |

TABLE 21-continued

| Carboxylic Acid | Product | Example # | R$_t$ min (Table A, Method) | m/z ESI+ (M + H)+ | TNF IC$_{50}$ |
|---|---|---|---|---|---|
| 2-Cyanoacetic acid | 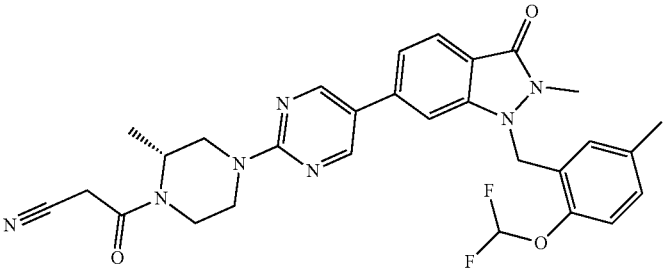 [SMILES: Cc1ccc(OC(F)F)c(Cn2c3cc(-c4cnc(N5CCN(C(=O)CC#N)[C@H](C)C5)nc4)ccc3c(=O)n2C)c1] | 21.4* | 2.02 (a) | 562 | A |

Example #24*: (R)-1-(2-(Difluoromethoxy)-5-methylbenzyl)-2-methyl-6-(2-(3-methyl-4-(methylsulfonyl)piperazin-1-yl)pyrimidin-5-yl)-1H-indazol-3(2H)-one

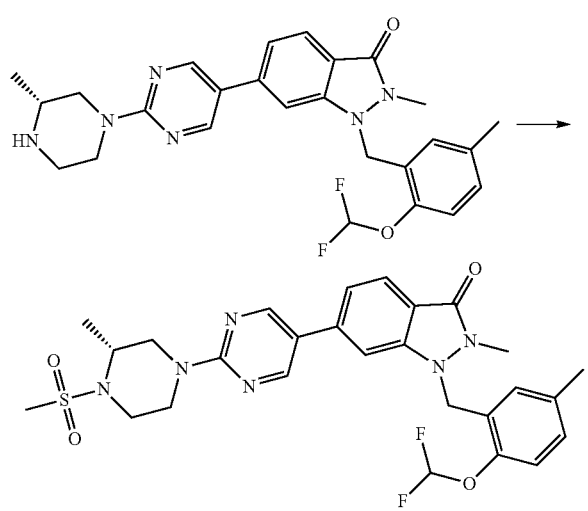

MsCl (0.012 mL, 0.16 mmol) and TEA (0.092 mL, 0.66 mmol) in DCM (1.00 mL) were added to (R)-1-(2-(difluoromethoxy)-5-methylbenzyl)-2-methyl-6-(2-(3-methylpiperazin-1-yl)pyrimidin-5-yl)-1H-indazol-3(2H)-one (65.0 mg, 0.131 mmol) (Example #14.5). After about 1 h, MsCl (0.040 mL, 0.52 mmol) and TEA (180 mL, 1.3 mmol) were added. After about 1 h, the reaction was quenched with water (5 mL) and extracted with DCM (10 mL). The organic layer was washed with NaHCO$_3$(5 mL), dried over MgSO$_4$, filtered, and concentrated. The residue was purified on silica gel (0-87% EtOAc/DCM) to afford the title product (50 mg, 64%); LC/MS (Table A, Method a) R$_t$=2.15 min; MS m/z: 573(M+H)+. (TNF IC$_{50}$=A).

The compounds shown in Table 22 were synthesized in a manner similar to Example #14, step 4 from 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, step 2) and the corresponding halide.

TABLE 22

| Halide | Product | Example # | R$_t$ min (Table A, Method) | m/z ESI+ (M + H)+ | TNF IC$_{50}$ |
|---|---|---|---|---|---|
| 1-(4-(5-Bromopyrimidin-2-yl)piperazin-1-yl)-2-hydroxyethanone (Preparation #34) | 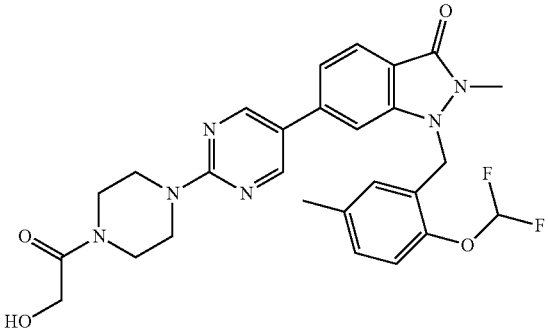 [SMILES: Cc1ccc(OC(F)F)c(Cn2c3cc(-c4cnc(N5CCN(C(=O)CO)CC5)nc4)ccc3c(=O)n2C)c1] | 22.1 | 1.80 (a) | 539 | A |

TABLE 22-continued

| Halide | Product | Example # | R$_t$ min (Table A, Method) | m/z ESI+ (M + H)+ | TNF IC$_{50}$ |
|---|---|---|---|---|---|
| (S)-1-(4-(5-Bromopyrimidin-2-yl)-3-methylpiperazin-1-yl)ethanone (Preparation #36) | | 22.2* | 1.99 (a) | 537 | A |
| (R)-1-(4-(5-Bromopyrimidin-2-yl)-2-methylpiperazin-1-yl)-2-hydroxyethanone (Preparation #15) | | 22.3* | 1.90 (a) | 553 | A |
| (R)-1-(4-(5-Bromopyrimidin-2-yl)-3-methylpiperazin-1-yl)-2-hydroxyethanone (Preparation #22) | | 22.4* | 1.89 (a) | 553 | A |
| 2-(5-Bromo-4-methylpyrimidin-2-yl)propan-2-ol (synthesized as described in WO2015/86506 A1) | | 22.5 | 2.09 (a) | 469 | A |

TABLE 22-continued

| Halide | Product | Example # | R$_t$ min (Table A, Method) | m/z ESI+ (M + H)$^+$ | TNF IC$_{50}$ |
|---|---|---|---|---|---|
| 1-(4-(5-Bromopyrimidin-2-yl)piperazin-1-yl)ethanone (prepared in a similar fashion to Preparation #13, step 1 using 1-(piperazin-1-yl)ethanone) | | 22.6 | 1.93 (a) | 523 | A |
| (S)-(1-(5-Bromopyrimidin-2-yl)pyrrolidin-2-yl)methanol (synthesized in a similar fashion to Preparation #13, step 1 using (S)-pyrrolidin-2-ylmethanol) | | 22.7* | 2.06 (a) | 496 | B |
| (R)-(1-(5-Bromopyrimidin-2-yl)pyrrolidin-2-yl)methanol (synthesized in a similar fashion to Preparation #13, step 1 using (R)-pyrrolidin-2-ylmethanol) | | 22.8* | 2.03 (a) | 496 | B |
| 2-(5-bromopyrimidin-2-yl)-2-methylpropan-1-ol (Preparation #52, step 2) | | 22.9 | 2.00 (a) | 469 | B |
| (S)-1-(4-(5-Bromopyrimidin-2-yl)-2-(hydroxymethyl)piperazin-1-yl)ethanone (synthesized in a manner similar to Example #3, step 2 from (S)-(4-(5-bromopyrimidin-2-yl)piperazin-2-yl)methanol, Hydrochloric Acid (synthesized in a manner similar to Example #3, step 1 from (S)-tert-butyl 4-(5-bromopyrimidin-2-yl)-2-(hydroxymethyl)piperazine-1-carboxylate (synthesized in a manner similar to Preparation #13, step 1 from (S)-tert-butyl 2-(hydroxymethyl)piperazine-1-carboxylate))) | | 22.10* | 1.74 (a) | 553 | A |

TABLE 22-continued

| Halide | Product | Example # | $R_t$ min (Table A, Method) | m/z ESI+ $(M + H)^+$ | TNF $IC_{50}$ |
|---|---|---|---|---|---|
| (R)-1-(4-(5-Bromopyrimidin-2-yl)-2-(hydroxymethyl)piperazin-1-yl)ethanone (synthesized in a similar manner to Example #3, step 2 from (R)-(4-5-bromopyrimidin-2-yl)piperazin-2-yl)methanol hydrochloride (synthesized in a similar manner to Example #3, step 1 from (R)-tert-buty) 4-(5-bromopyrimidin-2-yl)-2-(hydroxymethyl)piperazine-1-carboxylate (synthesized in a similar manner to Preparation #13, step 1 from (R)-tert-butyl 2-(hydroxymethyl)piperazine-1-carboxylate | 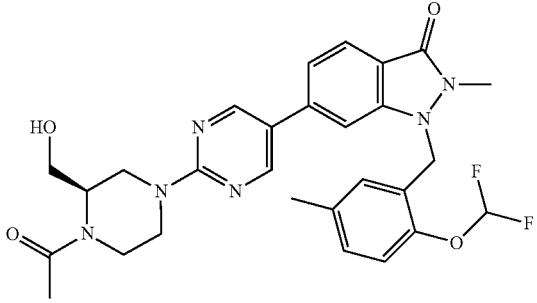 [SMILES: CC(=O)N1CCN(c2ncc(-c3ccc4c(=O)n(C)n(Cc5cc(C)ccc5OC(F)F)c4c3)cn2)C[C@@H]1CO] | 22.11* | 1.78 (a) | 553 | A |
| (R)-7-(5-Bromopyrimidin-2-yl)tetrahydro-1H-oxazolo[3,4-a]pyrazin-3(5H)-one (prepared in a similar fashion to Example #2 using (R)-hexahydro-oxazolo[3,4-a]pyrazine-3-one HCl and 5-bromo-2-chloropyrimidine) | 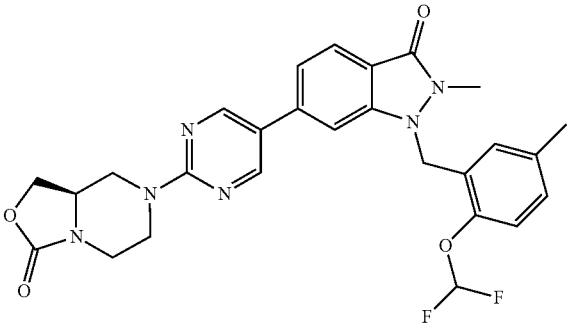 [SMILES: Cc1ccc(OC(F)F)c(Cn2c3cc(-c4cnc(N5CCN6C(=O)OC[C@H]6C5)nc4)ccc3c(=O)n2C)c1] | 22.12* | 2.00 (a) | 537 | A |
| 4-Bromo-2-((tetrahydro-2H-pyran-4-yl)oxy)pyridine (prepared in a similar fashion to Preparation #27 using tetrahydro-2H-pyran-4-ol) | 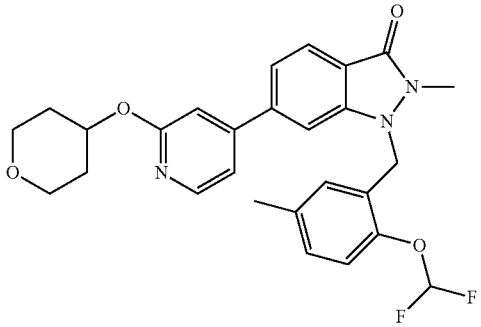 [SMILES: Cc1ccc(OC(F)F)c(Cn2c3cc(-c4ccnc(OC5CCOCC5)c4)ccc3c(=O)n2C)c1] | 22.13 | 2.33 (a) | 496 | A |
| (R)-1-(4-(5-Bromo-4-methylpyrimidin-2-yl)-3-methylpiperazin-1-yl)ethanone (synthesized in a manner similar to Example #3, step 2 from (R)-5-bromo-4-methyl-2-(2-methylpiperazin-1-yl)pyrimidine dihydrochloride (synthesized in a manner similar to Example #3, step 1 from (R)-tert-butyl 4-(5-bromo-4-methylpyrimidin-2-yl)-3-methylpiperazine-1-carboxylate (synthesized in a manner similar to Preparation #13 from 5-bromo-2-chloro-4-methylpyrimidine and (R)-tert-butyl 3-methylpiperazine-1-carboxylate))) | 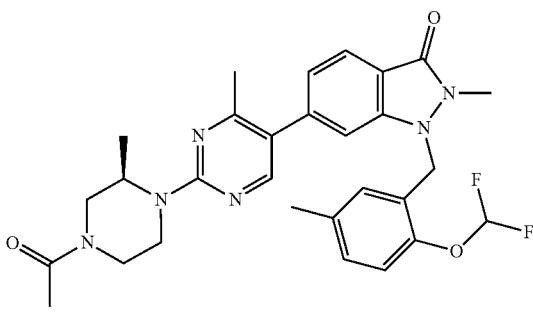 [SMILES: CC(=O)N1CCN(c2ncc(-c3ccc4c(=O)n(C)n(Cc5cc(C)ccc5OC(F)F)c4c3)c(C)n2)[C@H](C)C1] | 22.14* | 2.08 (h) | 551 | A |

TABLE 22-continued

| Halide | Product | Example # | R$_t$ min (Table A, Method) | m/z ESI+ (M + H)$^+$ | TNF IC$_{50}$ |
|---|---|---|---|---|---|
| (S)-1-(4-(5-Bromopyrimidin-2-yl)-3-methylpiperazin-1-yl)-2-hydroxyethanone (Preparation #54) | | 22.15* | 1.87 (a) | 553 | A |

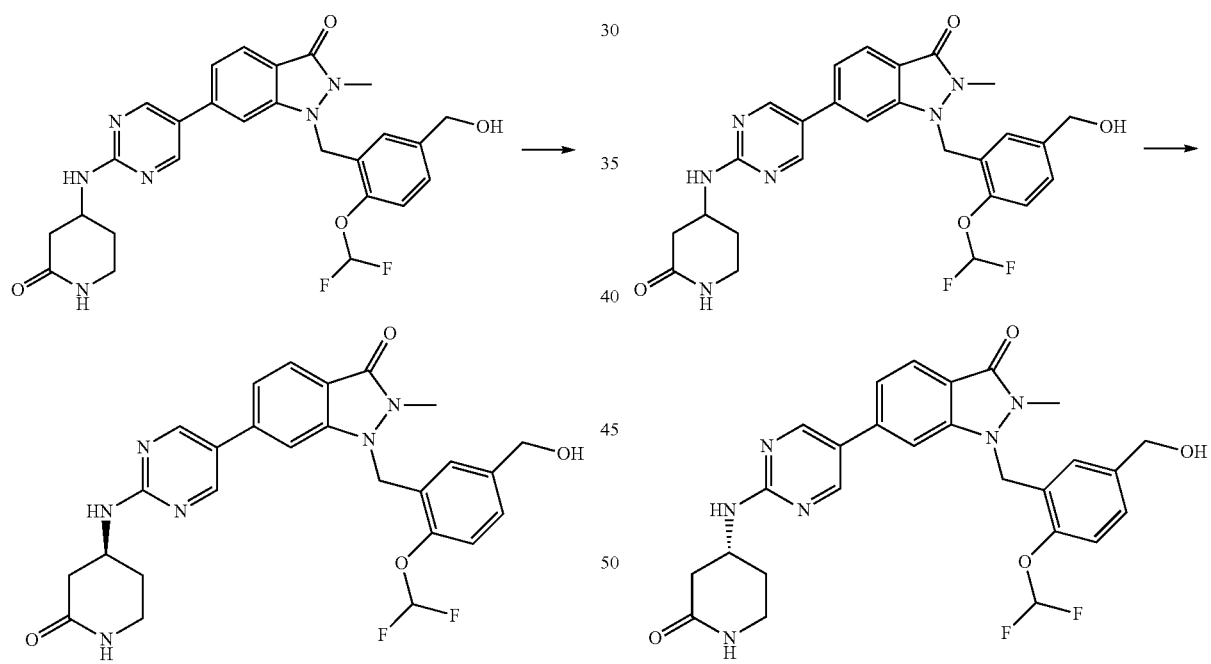

Example #25: (S)-1-(2-(Difluoromethoxy)-5-(hydroxymethyl)benzyl)-2-methyl-6-(2-((2-oxopiperidin-4-yl)amino)pyrimidin-5-yl)-1H-indazol-3(2H)-one Example #26: (R)-1-(2-(Difluoromethoxy)-5-(hydroxymethyl)benzyl)-2-methyl-6-(2-((2-oxopiperidin-4-yl)amino)pyrimidin-5-yl)-1H-indazol-3(2H)-one 1-(2-(Difluoromethoxy)-5-(hydroxymethyl)benzyl)-2-methyl-6-(2-((2-oxopiperidin-4-yl)amino)pyrimidin-5-yl)-1H-indazol-3(2H)-one (0.238 g, 0.454 mmol) (Example #16.5) was submitted for chiral separation (Table B, Method d). Fractions from the first eluting component were concentrated under reduced pressure to afford the title product (0.060 g, 25%) with undetermined optical rotation. LC/MS (Table A, Method e) R$_t$=1.42 min; MS m/z: 525 (M+H)$^+$. (TNF IC$_{50}$=A).

1-(2-(Difluoromethoxy)-5-(hydroxymethyl)benzyl)-2-methyl-6-(2-((2-oxopiperidin-4-yl)amino)pyrimidin-5-yl)-1H-indazol-3(2H)-one (0.238 g, 0.454 mmol) (Example #16.5) was submitted for chiral separation (Table B, Method d). Fractions from the second eluting component were concentrated under reduced pressure to afford the title product (0.053 g, 22%) with undetermined optical rotation. LC/MS (Table A, Method e) R$_t$=1.42 min; MS m/z: 525 (M+H)$^+$. (TNF IC$_{50}$=A).

Example #27: (S)-1-(2-(Difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one Example #28: (R)-1-(2-(Difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one

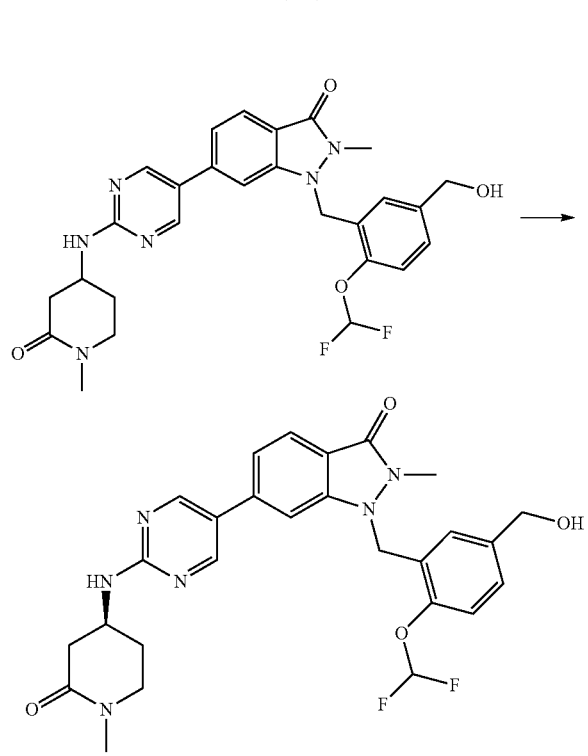

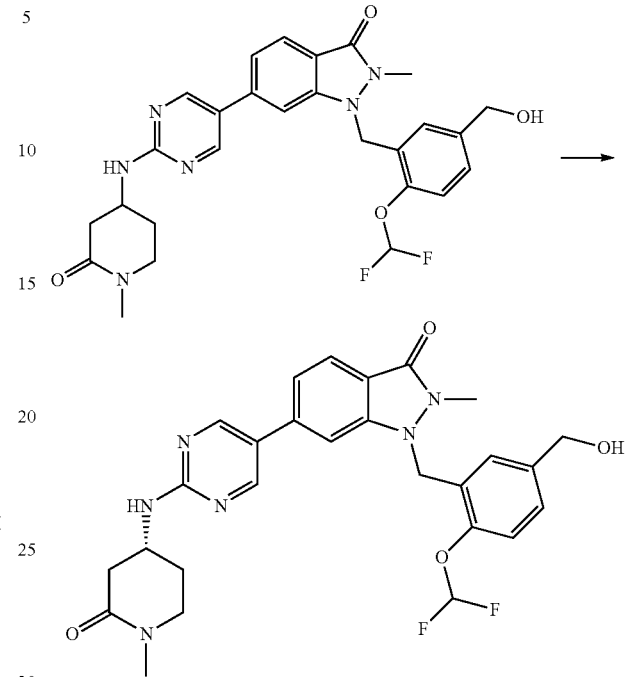

1-(2-(Difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one (0.159 g, 0.295 mmol) (Example #16.9) was submitted for chiral separation (Table B, Method e). Fractions from the first eluting component were concentrated under reduced pressure to afford the title product (0.051 g, 32%) with undetermined optical rotation. LC/MS (Table A, Method e) $R_t$=1.50 min; MS m/z: 539 (M+H)$^+$. (TNF IC$_{50}$=B).

1-(2-(Difluoromethoxy)-5-(hydroxymethyl)benzyl)-2-methyl-6-(2-((1-methyl-2-oxopiperidin-4-yl)amino)pyrimidin-5-yl)-1H-indazol-3(2H)-one (0.159 g, 0.295 mmol) (Example #16.9) was submitted for chiral separation (Table B, Method e). Fractions from the second eluting component were concentrated under reduced pressure to afford the title product (0.052 g, 32%) with undetermined optical rotation. LC/MS (Table A, Method e) $R_t$=1.50 min; MS m/z: 539 (M+H)$^+$. (TNF IC$_{50}$=A).

Example #29: 4-(5-(1-(2-(Difluoromethoxy)-5-(hydroxymethyl)benzyl)-2-methyl-3-oxo-2,3-dihydro-1H-indazol-6-yl)pyrimidin-2-yl)piperazine-1-carbaldehyde

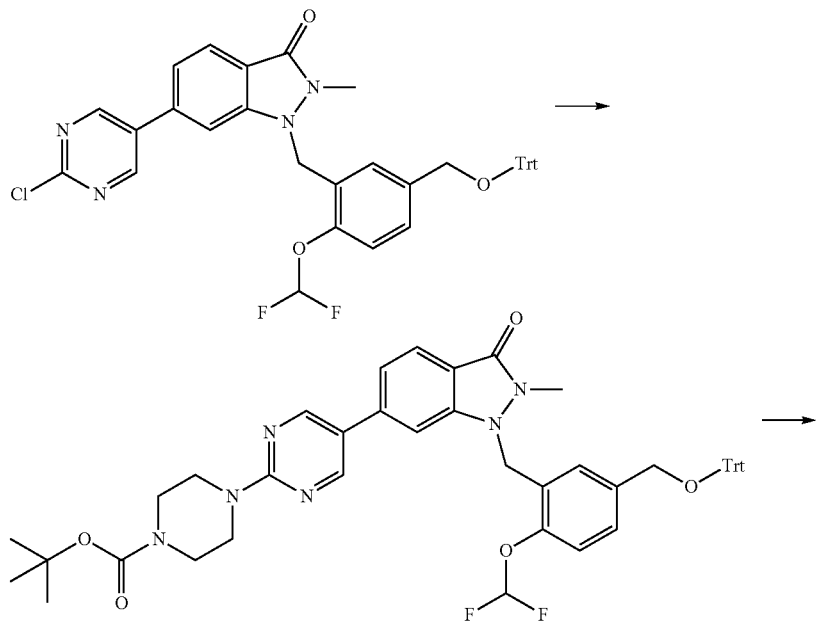

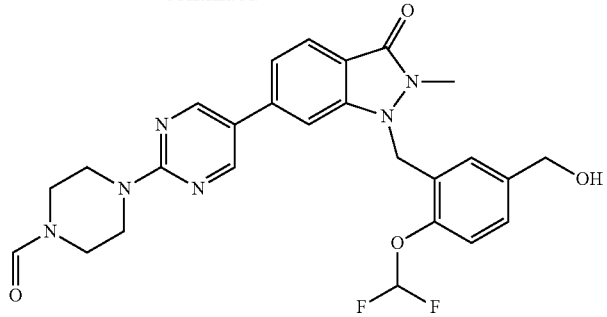

Step 1: tert-Butyl 4-(5-(1-(2-(difluoromethoxy)methyl)benzyl)-2-methyl-3-oxo-2,3-dihydro-1H-indazol-6-yl)pyrimidin-2-yl)piperazine-1-carboxylate A solution of 6-(2-chloropyrimidin-5-yl)-1-(2-(difluoromethoxy)-5-(((trityloxy)methyl)benzyl)-2-methyl-1H-indazol-3(2H)-one (100 mg, 0.133 mmol) (Preparation #24), 1-Boc-piperazine (50 mg, 0.27 mmol) and TEA (56 μL, 0.40 mmol) in ethanol (1 mL) was sealed and heated at about 80° C. for about 2 h. The reaction was cooled to rt and concentrated. DCM (5 mL) and water (5 mL) were added. The organic layer was dried over Na$_2$SO$_4$, filtered and concentrated to yield the title product; LC/MS (Table A, Method e) R$_t$=3.00 min; MS m/z: 839 (M+H)$^+$.

Step 2: 4-(5-(1-(2-(Difluoromethoxy)-5-(hydroxymethyl)benzyl)-2-methyl-3-oxo-2,3-dihydro-H-indazol-6-yl)pyrimidin-2-yl)piperazine-1-carbaldehyde To a mixture of tert-butyl 4-(5-(1-(2-(difluoromethoxy)-5-((trityloxy)methyl)benzyl)-2-methyl-3-oxo-2,3-dihydro-1H-indazol-6-yl)pyrimidin-2-yl)piperazine-1-carboxylate (112 mg, 0.134 mmol) and triisopropylsilane (43 mg, 0.27 mmol) in DCM (1 mL) was added TFA (1 mL) at rt. The mixture was stirred for about 10 min at rt and then concentrated under reduced pressure. The residue was triturated with ether (2×10 mL), decanting the ether layers. The residue was dissolved in ethyl formate (3 mL) and heated at reflux with TEA (0.065 mL, 0.47 mmol) for about 16 h. The reaction was cooled and concentrated under reduced pressure. The residue was purified on silica gel using a gradient of 0-10% MeOH in DCM. Product fractions were combined and concentrated. The residue was dissolved in MeCN (5 mL) and water (5 mL) and concentrated to water. Product was collected by filtration and dried overnight in the vacuum oven to yield the title compound (30 mg, 41%); LC/MS (Table A, Method e) R$_t$=1.60 min; MS m/z: 525 (M+H)$^+$. (TNF IC$_{50}$=A).

Example #30*: 1-(2-(Difluoromethoxy)benzyl)-5,7-difluoro-6-(2-(4-(2-hydroxyacetyl)piperazin-1-yl)pyrimidin-5-yl)-2-methyl-1H-indazol-3(2H)-one

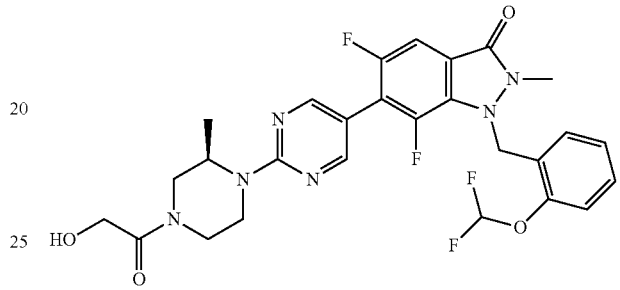

To a solution of (R)-6-(2-(4-(2-(tert-butoxy)acetyl)-2-methylpiperazin-1-yl)pyrimidin-5-yl)-1-(2-(difluoromethoxy)benzyl)-5,7-difluoro-2-methyl-1H-indazol-3(2H)-one (Preparation #26) (44 mg, 0.070 mmol) in DCM (3 mL) was added TFA (3 mL) and the mixture was stirred at rt for about 45 min. The reaction was concentrated under reduced pressure. The residue was dissolved with DCM (5 mL) and washed with aq. sat. NaHCO$_3$ (5 mL). The organic layer was dried over Na$_2$SO$_4$, filtered and concentrated to yield the title product (37 mg, 92%); LC/MS (Table A, Method a) R$_t$=1.92 min; MS m/z: 575 (M+H)$^+$. (TNF IC$_{50}$=A).

Example #31*: (R)-2-(4-(5-(1-(2-(Difluoromethoxy)benzyl)-2-methyl-3-oxo-2,3-dihydro-1H-indazol-6-yl)pyrimidin-2-yl)-2-methylpiperazin-1-yl)-2-oxoethyl phosphate

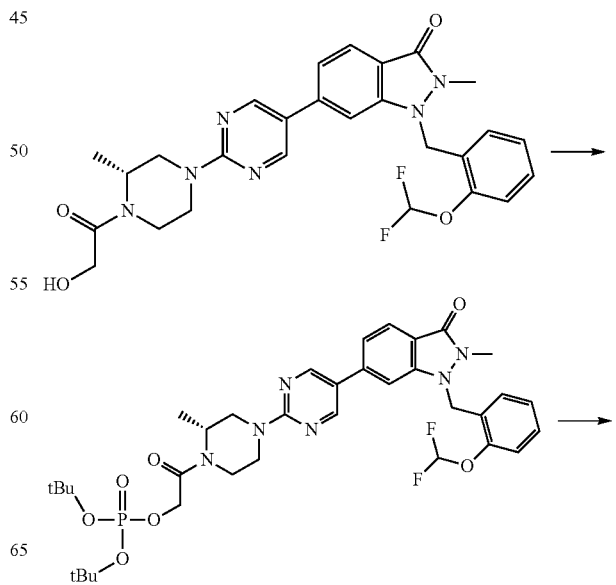

239
-continued

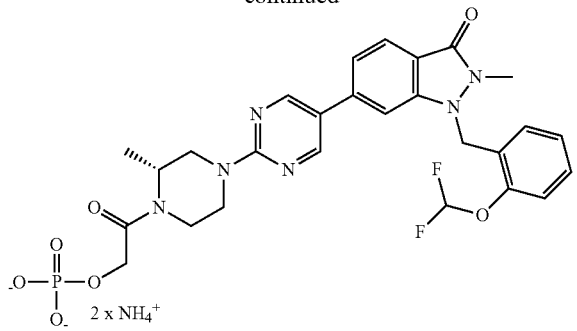

Step 1: (R)-D-tert-butyl (2-(4-(5-(1(2-(difluoromethoxy)benzyl)-2-methyl-3-oxo-2,3-dihydro-1H-indazol-6-yl)pyrimidin-2-yl)-2-methylpiperazin-1-yl)-2-oxoethyl)phosphate (R)-1-(2-(Difluoromethoxy)benzyl)-6-(2-(4-(2-hydroxyacetyl)-3-methylpiperazin-1-yl)pyrimidin-5-yl)-2-methyl-1H-indazol-3(2H)-one (130 mg, 0.24 mmol) (Example #10.6), imidazole (25 mg, 0.36 mmol), and imidazole hydrochloride (57 mg, 0.54 mmol) were added to anhydrous DMF (2.4 mL) in a dry reaction vessel. The atmosphere was removed and replaced with $N_2$. Di-tert-butyl N,N-diisopropylphosphoramidite (114 μL, 0.360 mmol) was added dropwise, and the reaction was stirred for about 16 h at rt. Additional di-tert-butyl N,N-diisopropylphosphoramidite (38 μL, 0.12 mmol) was added to the reaction mixture. After about 4 h, the reaction mixture was cooled to about 0° C., then hydrogen peroxide (30 wt % in water, 222 μL, 2.17 mmol) was added and the reaction was stirred while warming to rt for about 1 h. The reaction was quenched with a cold sat. aq. sodium thiosulfate (10 mL), then extracted with EtOAc (2×10 mL). The combined organic layers were washed with water (2×20 mL) and sat. aq. NaCl (20 mL), dried over $MgSO_4$, filtered, and concentrated in vacuo. Purification via silica gel chromatography (0-5% MeOH in DCM) afforded the title compound (93 mg, 53%); LC/MS (Table A, Method i) $R_t$=1.57 min; MS m/z: 731 (M+H)$^+$.

Step 2: (R)-2-(4(5-(1-(2-(Difluoromethoxy)benzyl)-2-methyl-3-oxo-2,3-dihydro-1H-indazol-6-yl)pyrimidin-2-yl)-2-methylpiperazin-1-yl)-2-oxoethyl phosphate (R)-Di-tert-butyl (2-(4-(5-(1-(2-(difluoromethoxy)benzyl)-2-methyl-3-oxo-2,3-dihydro-1H-indazol-6-yl)pyrimidin-2-yl)-2-methylpiperazin-1-yl)-2-oxoethyl)phosphate (160 mg, 0.22 mmol) was dissolved in anhydrous dioxane (2.3 mL). A solution of HCl in dioxane (4 M, 2.3 mL, 9.20 mmol) was added, and the reaction was allowed to stir for about 30 min at rt. The solvent was removed in vacuo, and the resulting residue was purified by preparative reverse phase HPLC (Table A, Method l). The relevant fractions were collected and lyophilized to yield the title compound as the diammonium salt (90 mg, 64%); LC/MS (Table A, Method e) $R_t$=1.45 min; MS m/z: 619 (M+H)$^+$.

240

Example #32: 6-(2-(1-Acetyl-4-hydroxypiperidin-4-yl)pyrimidin-5-yl)-1-(2-(difluoromethoxy)benzyl)-2-methyl-1H-indazol-3(2H)-one

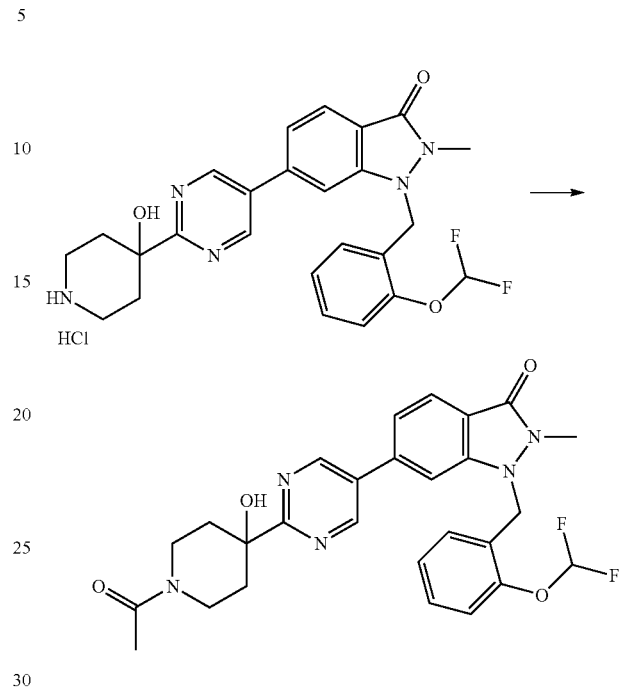

A mixture of 1-(2-(difluoromethoxy)benzyl)-6-(2-(4-hydroxypiperidin-4-yl)pyrimidin-5-yl)-2-methyl-1H-indazol-3(2H)-one, hydrochloric acid (0.10 g, 0.193 mmol) (Example #20, step 3) and TEA (0.160 mL, 1.16 mmol) in MeCN (3 mL) and water (0.5 mL) was cooled to 0° C. and a dropwise solution of acetyl chloride (0.014 mL, 0.19 mmol) in MeCN (3 mL) was added. The ice bath was removed and stirring was continued at ambient temperature for about 1 h. Methanol (1 mL) was added to the mixture and the volatiles were removed under reduced pressure. To the residue was added DCM (10 mL) and sat. aq. $NaHCO_3$ (5 mL). The organic layer was removed and washed with sat. aq. $NaHCO_3$ (5 mL). The combined organic layers were dried over $MgSO_4$, filtered and concentrated under reduced pressure. The material was purified by flash chromatography on silica gel (0-10% MeOH/DCM) to afford the title product (0.062 g, 62%); LC/MS (Table A, Method a) $R_t$=1.64 min; MS m/z: 524 (M+H)$^+$. (TNF IC$_{50}$=B).

Example #33: (R)-7-(5-(1-(2-(Difluoromethoxy)-6-(methoxymethyl)benzyl)-2-methyl-3-oxo-2,3-dihydro-1H-indazol-6-yl)pyrimidin-2-yl)hexahydroimidazo[1,5-a]pyrazin-3(2H)-one

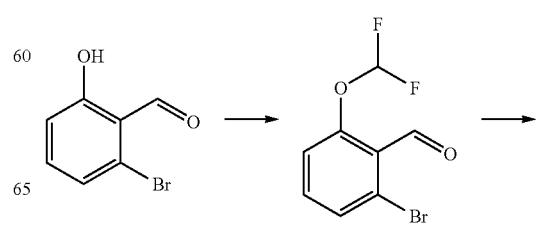

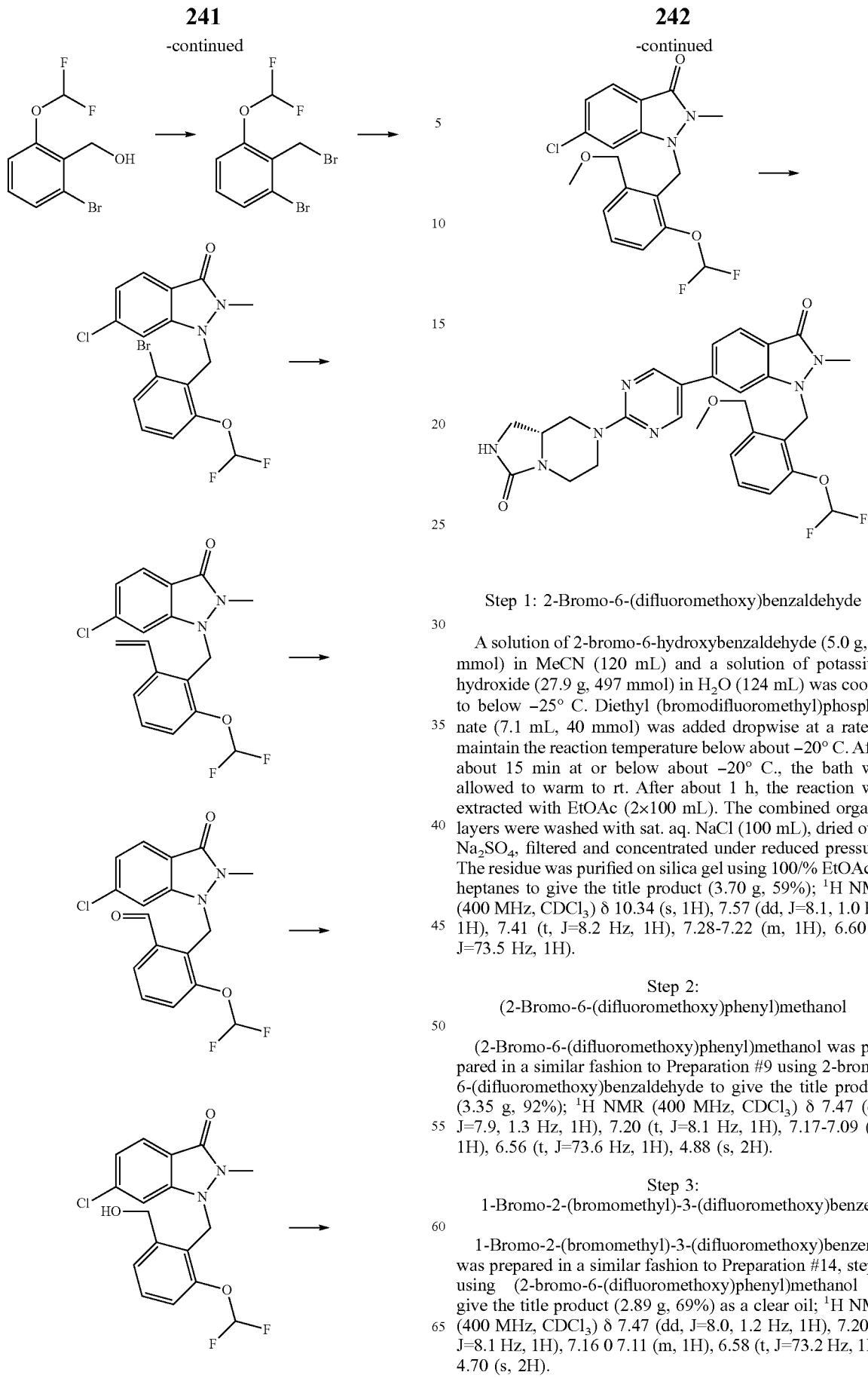

Step 1: 2-Bromo-6-(difluoromethoxy)benzaldehyde

A solution of 2-bromo-6-hydroxybenzaldehyde (5.0 g, 25 mmol) in MeCN (120 mL) and a solution of potassium hydroxide (27.9 g, 497 mmol) in $H_2O$ (124 mL) was cooled to below −25° C. Diethyl (bromodifluoromethyl)phosphonate (7.1 mL, 40 mmol) was added dropwise at a rate to maintain the reaction temperature below about −20° C. After about 15 min at or below about −20° C., the bath was allowed to warm to rt. After about 1 h, the reaction was extracted with EtOAc (2×100 mL). The combined organic layers were washed with sat. aq. NaCl (100 mL), dried over $Na_2SO_4$, filtered and concentrated under reduced pressure. The residue was purified on silica gel using 100/% EtOAc in heptanes to give the title product (3.70 g, 59%); $^1$H NMR (400 MHz, $CDCl_3$) δ 10.34 (s, 1H), 7.57 (dd, J=8.1, 1.0 Hz, 1H), 7.41 (t, J=8.2 Hz, 1H), 7.28-7.22 (m, 1H), 6.60 (t, J=73.5 Hz, 1H).

Step 2: (2-Bromo-6-(difluoromethoxy)phenyl)methanol (2-Bromo-6-(difluoromethoxy)phenyl)methanol was prepared in a similar fashion to Preparation #9 using 2-bromo-6-(difluoromethoxy)benzaldehyde to give the title product (3.35 g, 92%); $^1$H NMR (400 MHz, $CDCl_3$) δ 7.47 (dd, J=7.9, 1.3 Hz, 1H), 7.20 (t, J=8.1 Hz, 1H), 7.17-7.09 (m, 1H), 6.56 (t, J=73.6 Hz, 1H), 4.88 (s, 2H).

Step 3: 1-Bromo-2-(bromomethyl)-3-(difluoromethoxy)benzene

1-Bromo-2-(bromomethyl)-3-(difluoromethoxy)benzene was prepared in a similar fashion to Preparation #14, step 6 using (2-bromo-6-(difluoromethoxy)phenyl)methanol to give the title product (2.89 g, 69%) as a clear oil; $^1$H NMR (400 MHz, $CDCl_3$) δ 7.47 (dd, J=8.0, 1.2 Hz, 1H), 7.20 (t, J=8.1 Hz, 1H), 7.16 0 7.11 (m, 1H), 6.58 (t, J=73.2 Hz, 1H), 4.70 (s, 2H).

Step 4: 1-(2-Bromo-6-(difluoromethoxy)benzyl)-6-chloro-2-methyl-1H-indazol-3(2H)-one 1-(2-Bromo-6-(difluoromethoxy)benzyl)-6-chloro-2-methyl-1H-indazol-3(2H)-one was prepared in a similar fashion to Preparation #4, step 1 using 1-bromo-2-(bromomethyl)-3-(difluoromethoxy)benzene and 6-chloro-2-methyl-1H-indazol-3(2H)-one (Preparation #29) to give the title compound (3.60 g, 55%); LC/MS (Table A, Method e) $R_f$=2.36 min; MS m/z: 417 and 419 (M+H)$^+$.

Step 5: 6-Chloro-1-(2-(difluoromethoxy)-6-vinylbenzyl)-2-methyl-1H-indazol-3(2H)-one 6-Chloro-1-(2-(difluoromethoxy)-6-vinylbenzyl)-2-methyl-1H-indazol-3(2H)-one was prepared in a similar fashion to Example #14, step 4 using 1-(2-bromo-6-(difluoromethoxy)benzyl)-6-chloro-2-methyl-1H-indazol-3(2H)-one and 4,4,5,5-tetramethyl-2-vinyl-1,3,2-dioxaborolane to give the title compound (1.46 g, 84%) as a yellow solid; LC/MS (Table A, Method e) $R_f$=2.35 min; MS m/z: 365 (M+H)$^+$.

Step 6: 2-((6-Chloro-2-methyl-3-oxo-2,3-dihydro-1H-indazol-1-yl)methyl)-3-(difluoromethoxy)benzaldehyde 2-((6-Chloro-2-methyl-3-oxo-2,3-dihydro-1H-indazol-1-yl)methyl)-3-(difluoromethoxy)benzaldehyde was prepared in a similar fashion to Example #4, step 1 using 6-chloro-1-(2-(difluoromethoxy)-6-vinylbenzyl)-2-methyl-1H-indazol-3(2H)-one to give the title compound (1.33 g, 91%); LC/MS (Table A, Method e) $R_f$=2.10 min; MS m/z: 367 (M+H)$^+$.

Step 7: 6-Chloro-1-(2-(difluoromethoxy)-6-(hydroxymethyl)benzyl)-2-methyl-1H-indazol-3(2H)-one 6-Chloro-1-(2-(difluoromethoxy)-6-(hydroxymethyl)benzyl)-2-methyl-1H-indazol-3(2H)-one was prepared in a similar fashion to Preparation #9 using 2-((6-chloro-2-methyl-3-oxo-2,3-dihydro-1H-indazol-1-yl)methyl)-3-(difluoromethoxy)benzaldehyde to give the title compound (1.14 g, 85%) as a yellow solid LC/MS (Table A, Method e) $R_f$=1.91 min; MS m/z: 369 (M+H)$^+$.

Step 8: 6-Chloro-1-(2-(difluoromethoxy)-6-(methoxymethyl)benzyl)-2-methyl-1H-indazol-3(2H)-one Sodium hydride (60% in mineral oil, 0.065 g, 1.6 mmol) was added to a mixture of 6-chloro-1-(2-(difluoromethoxy)-6-(hydroxymethyl)benzyl)-2-methyl-1H-indazol-3(2H)-one (0.300 g, 0.814 mmol) and MeI (0.51 mL, 8.1 mmol) in THF (6 mL) was at about 0° C. The reaction was stirred at about 0° C. for about 2 h then was quenched with 20% aq. NH$_4$Cl (20 mL) and extracted with EtOAc (20 mL). The organic layer was washed with sat. aq. NaCl (20 mL), dried over Na$_2$SO$_4$, filtered and concentrated under reduced pressure. The residue was purified on silica gel using 5-40% EtOAc in heptanes to give the title compound (0.271 g, 87%); LC/MS (Table A, Method e) Rt=2.24 min; MS m/z: 383 (M+H)$^+$.

Step 9: (R)-7-(5-(1-(2 Difluoromethoxy)-6-(methoxymethyl)benzyl)-2-methyl-3-oxo-2,3-dihydro-1H-indazol-6-yl)pyrimidin-2-yl)hexahydroimidazo[1,5-a]pyrazin-3(2H)-one A mixture of bis(pinacolato)diboron (0.119 g, 0.470 mmol), (R)-7-(5-bromopyrimidin-2-yl)hexahydroimidazo[1,5-a]pyrazin-3(2H)-one (0.078 g, 0.261 mmol) (Preparation #13), KOAc (0.083 g, 0.84 mmol), PdCl$_2$(dppf) (0.015 g, 0.021 mmol), and 1,4-dioxane (2 mL) was purged with N$_2$ three times and degassed for about 5 min. The mixture was placed in a preheated oil bath at about 95° C. and stirred for about 2 h. The reaction was cooled to ambient temperature, 6-Chloro-1-(2-(difluoromethoxy)-6-(methoxymethyl)benzyl)-2-methyl-1H-indazol-3(2H)-one (0.100 g, 0.261 mmol), Cs$_2$CO$_3$(0.213 g, 0.653 mmol), H$_2$O (0.500 mL) and 2$^{ND}$ generation XPHOS precatalyst (0.021 g, 0.026 mmol) were added to the above mixture. The reaction mixture was purged with N$_2$ for about 10 min and placed in a preheated oil bath at about 85° C. After about 16 h, the reaction was cooled to ambient temperature. The reaction was partitioned between DCM (50 mL) and H$_2$O (30 mL). The organic layer was washed with sat. aq. NaCl (30 mL), dried over Na$_2$SO$_4$, filtered and concentrated under reduced pressure. The residue was purified on silica gel using 1-4% MeOH in DCM to give the title compound (0.066 g, 42%); LC/MS (Table A, Method e) $R_f$=1.84 min; MS m/z: 566 (M+H)$^+$. (TNF IC$_{50}$=A).

The compounds shown in Table 23 were synthesized in a manner similar to Example #33, step 9 from (R)-1-(4-(5-bromopyrimidin-2-yl)-2-methylpiperazin-1-yl)-2-hydroxyethanone (Preparation #15) and the corresponding halide.

TABLE 23

| Halide | Product | Example # | $R_t$ min (Table A, Method) | m/z ESI+ (M + H)$^+$ | TNF IC$_{50}$ |
|---|---|---|---|---|---|
| 6-Chloro-1-(2-chlorobenzyl)-2-methyl-1H-pyrazolo[3,4-b]pyridin-3(2H)-one (synthesized in a similar fashion to Example #1, from 1-(bromomethyl)-2-chlorobenzene and 6-chloro-2-methyl-1H-pyrazolo[3,4-b]pyridin-3(2H)one (Example #15, step 2)) | | 23.1* | 1.89 (a) | 508 | A |

TABLE 23-continued

| Halide | Product | Example # | R$_t$ min (Table A, Method) | m/z ESI+ (M + H)$^+$ | TNF IC$_{50}$ |
|---|---|---|---|---|---|
| 6-Chloro-1-(2-(difluoromethoxy)benzyl)-2-methyl-3-oxo-2,3-dihydro-1H-indazole-5-carbonitrile (Preparation #53) | | 23.2* | 1.79 (a) | 564 | B |
| 6-Chloro-1-(2-(difluoromethoxy)benzyl)-2-methyl-3-oxo-2,3-dihydro-1H-indazole-7-carbonitrile (prepared in a similar manner to Example #1 using 6-chloro-2-methyl-3-oxo-2,3-dihydro-1H-indazole-7-carbonitrile (Preparation #67) and 1-(bromomethyl)-2-(difluoromethoxy)benzene) | | 23.3* | 1.81 (a) | 564 | A |

The compounds shown in Table 24 were synthesized in a manner similar to Example #8 from (R)-1-(4-(5-bromopyrimidin-2-yl)-2-methylpiperazin-1-yl)-2-hydroxyethanone (Preparation #15) and the corresponding halide.

TABLE 24

| Halide | Product | Example # | R$_t$ min (Table A, Method) | m/z ESI+ (M + H)$^+$ | TNF IC$_{50}$ |
|---|---|---|---|---|---|
| 2-(3-((6-Bromo-2-methyl-3-oxo-2,3-dihydro-1H-indazol-1-yl)methyl)-4-(difluoromethoxy)phenyl acetonitrile (Preparation #20) | | 24.1* | 1.74 (a) | 578 | A |
| 6-bromo-2-methyl-1-(1-(6-methylpyridin-2-yl)ethyl)-1H-indazol-3(2H)-one (Preparation #51) | | 24.2 | 0.99 (h) | 502 | B |

TABLE 24-continued

| Halide | Product | Example # | R$_t$ min (Table A, Method) | m/z ESI+ (M + H)+ | TNF IC$_{50}$ |
|---|---|---|---|---|---|
| 6-Bromo-2-methyl-1-(1-(m-tolyl)propyl)-1H-indazol-3(2H)-one (synthesized in a similar fashion to Preparation #4, step 1 from 6-bromo-2-methyl-1H-indazol-3(2H)-one (Preparation #1) and 1-(1-bromopropyl)-3-methylbenzene (Preparation #21)) | | 24.3 | 1.31 (h) | 515 | A |
| 6-Bromo-1-(2-(difluoromethoxy)benzyl)-2-(difluoromethyl)-1H-indazol-3(2H)-one (Preparation #37) | | 24.4* | 1.51 (e) | 575 | A |
| 6-Bromo-1-(2-chlorobenzyl)-7-fluoro-2-methyl-1H-indazol-3(2H)-one (prepared in a similar fashion to Preparation #4, step 1 using 6-bromo-7-fluoro-2-methyl-1H indazol-3(2H)-one (Preparation #38) and 1-(bromomethyl)-2-chlorobenzene) | | 24.5* | 1.31 (e) | 525 | A |
| 6-Bromo-1-(2-(difluoromethoxy)benzyl)-7-fluoro-2-methyl-1H-indazol-3(2H)-one (prepared in a similar fashion to Preparation #4, step 1 using 6-bromo-7-fluoro-2-methyl-1H indazol-3(2H)-one (Preparation #38) and 1-(bromomethyl)-2-(difluoromethoxy)benzene) | | 24.6* | 1.25 (e) | 557 | A |
| 6-Bromo-1-(1-(2,5-difluorophenyl)ethyl)-2-methyl-1H-indazol-3(2H)-one (synthesized in a manner similar to Preparation #4, step 1 from 6-bromo-2-methyl-1H-indazol-3(2H)-one and 2-(1-bromoethyl)-1,4-difluorobenzene (synthesized in a manner similar to Preparation #21, step 2 from 1-(2,5-difluorophenyl)ethanol)) | | 24.7 | 1.17 (h) | 523 | A |

TABLE 24-continued

| Halide | Product | Example # | R, min (Table A, Method) | m/z ESI+ (M + H)+ | TNF IC50 |
|---|---|---|---|---|---|
| 1-(2-Chlorobenzyl)-2-methyl-6-(4,4,5,5-tetramethyl-1,3,2-dioxaborolan-2-yl)-1H-indazol-3(2H)-one (prepared in a similar fashion to Preparation #4, step 2 using 6-bromo-1-(2-chlorobenzyl)-2-methyl-1H-indazol-3(2H)-one (prepared in a similar fashion to Preparation #4, step 1 using 2-chlorobenzyl bromide)) | | 24.8* | 1.82 (a) | 507 | A |
| 6-Bromo-1-(2-chlorobenzyl)-7-methoxy-2-methyl-1H-indazol-3(2H)-one (Preparation #65) | | 24.9* | 1.92 (a) | 537 | A |
| 6-Bromo-2-methyl-1-(1-(4-methylpyridin-2-yl)ethyl)-1H-indazol-3(2H)-one (prepared in a manner similar to Example #1 from 6-bromo-2-methyl-1H-indazol-3(2H)-one (Preparation #1) and 2-(1-bromoethyl)-4-methylpyridine (prepared in a manner similar to Preparation #21 step 2 from 1-(4-methylpyridin-21 yl)ethanol (prepared in a manner similar to Preparation #9 from 1-(4-methylpyridin-2-yl)ethanone))) | | 24.10 | 0.98 (h) | 502 | B |
| 6-Chloro-1-(2-(difluoromethoxy)benzyl)-5-fluoro-2-methyl-1H-pyrazolo[3,4-6]pyridin-3(2H)-one (prepared in a manner similar to Example #15, step 3 from 6-chloro-5-fluoro-2-methyl-1H-pyrazolo[3,4-b]pyridin-3(2H)-one (Example #98, step 1) and 1-(bromomethyl)-2-(difluoromethoxy)benzene) | | 24.11* | 1.91 (e) | 558 | A |
| 6-Bromo-1-(2-(difluoromethoxy)benzyl)-2,7-dimethyl-1H-indazol-3(2H)-one (Preparation #71) | | 24.12* | 1.85 (a) | 553 | A |

TABLE 24-continued

| Halide | Product | Example # | $R_t$ min (Table A, Method) | m/z ESI+ (M + H)+ | TNF IC$_{50}$ |
|---|---|---|---|---|---|
| 6-Bromo-1-(2-chlorobenzyl)-2,7-dimethyl-1H-indazol-3(2H)-one (prepared in a similar fashion to Preparation #71 from 1-(bromomethyl)-2-chlorobenzene and 4-bromo-2-fluoro-N,3-dimethylbenzohydrazide (prepared in a similar fashion to Example #17, step 1 using 4-bromo-2-fluoro-3-methylbenzoic acid) | 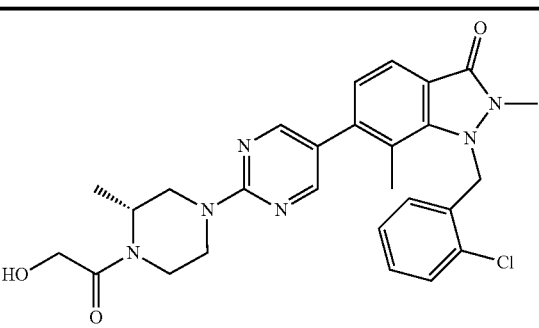 | 24.13* | 1.91 (a) | 521 | A |

The compound shown in Table 25 was synthesized in a manner similar to Preparation #15 from (S)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid (Example #36, step 2) and the corresponding carboxylic acid.

TABLE 25

| Carboxylic Acid | Product | Example # | $R_t$ min (Table A, Method) | m/z ESI+ (M + H)+ | TNF IC$_{50}$ |
|---|---|---|---|---|---|
| 2-Cyanoacetic acid | 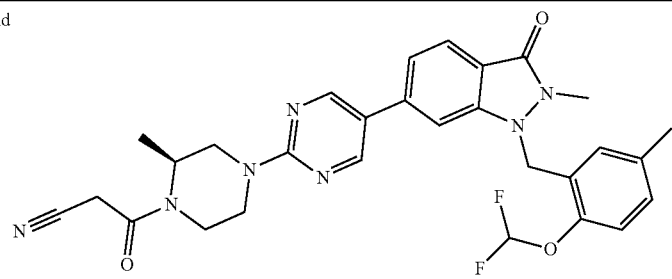 | 25.1* | 2.02 (a) | 562 | A |

Example #34: (R)-7-(5-(1-(2-(Difluoromethoxy)benzyl)-2-methyl-3-oxo-2,3-dihydro-1H-indazol-6-yl)pyrimidin-2-yl)-2-methylhexahydroimidazo[1,5-a]pyrazin-3(2H)-one

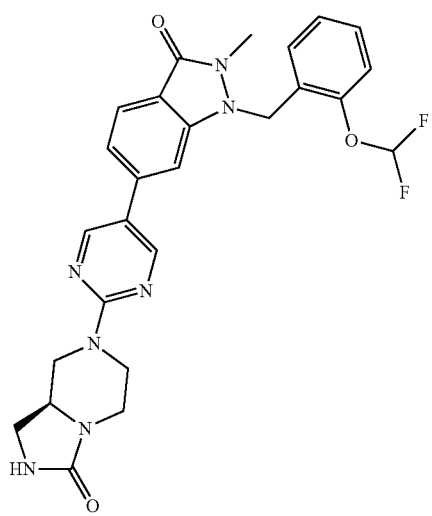

→

-continued

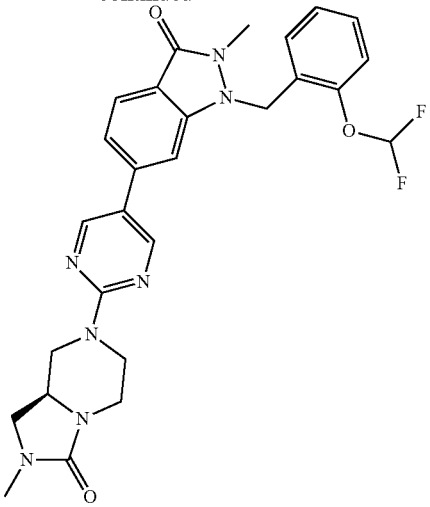

A flask was charged with (S)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one (89 mg, 0.17 mmol) (Example #7), DMF (1.5 mL), MeI (0.015 mL, 0.25 mmol) followed by cesium carbonate (67 mg, 0.21 mmol) at room temperature and stirred for about 9 h. MeI (0.033 mL, 0.53 mmol) was added. After about 15 h, MeI (0.11 mL, 1.7 mmol) was added. The reaction vessel was sealed and stirred at about 50° C. for about 24 h. The mixture was cooled to room temperature, diluted with water (10 mL) and extracted with 10% MeOH in $CH_2Cl_2$ (2×10 mL). The organic layer was dried over $Na_2SO_4$, filtered and concentrated. The residue was purified by flash chromatography on silica gel (0-10% MeOH/$CH_2Cl_2$) to afford the title product (51 mg, 56%); LC/MS (Table A, Method a) $R_t$=1.88 min; MS m/z: 536 (M+H)$^+$. (TNF IC$_{50}$=A).

Example #35: (R)-7-(5-Bromopyrimidin-2-yl)-2-(2-((tert-butyldimethylsilyl)oxy)ethyl)hexahydroimidazo[1,5-a]pyrazin-3(2H)-one

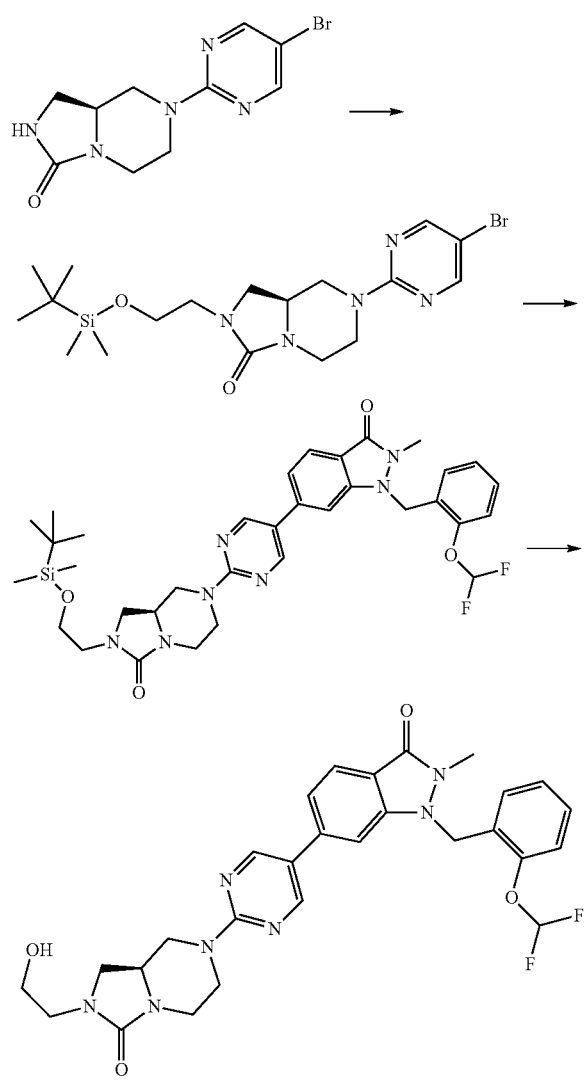

Step 1: (R)-7-(5-Bromopyrimidin-2-yl)-2-(2-((tert-butyldimethylsilyl)oxy)ethyl)hexahydroimidazo[1,5-a]pyrazin-3(2H)-one A flask, purged with nitrogen, was charged with cesium carbonate (5.6 g, 17 mmol), (S)-7-(5-bromopyrimidin-2-yl) hexahydroimidazo[1,5-a]pyrazin-3(2H)-one (450 mg, 1.51 mmol) (Preparation #13), DMF (10 mL) then (2-bromomethoxy)-tert-butyldimethylsilane (410 mg, 1.71 mmol) at rt. After stirring at about 70° C. for about 26 h, additional (2-bromomethoxy)-tert-butyldimethylsilane (408 mg, 1.71 mmol) was added. After stirring at about 70° C. for about 27 h, the reaction mixture was cooled to rt and concentrated under reduced pressure. To the resulting residue was added $H_2O$ (15 mL) and 10% MeOH in $CH_2Cl_2$ (10 mL). The organic layer was separated, and the aqueous layer was extracted with 10% MeOH in $CH_2Cl_2$ (2×10 mL). The combined organic layers were dried over $Na_2SO_4$, filtered and concentrated under reduced pressure. The residue was purified by flash chromatography on silica gel (0-10% MeOH/$CH_2Cl_2$) to afford the title product (511 mg, 74%); LC/MS (Table A, Method i) $R_t$=1.90 min; MS m/z: 456 and 458 (M+H)$^+$.

Step 2: (R)-2-(2-((tert-Butyldimethylsilyl)oxy) ethyl)-7-(5-(1-(2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one The reaction was performed using (R)-2-(2-((tert-butyldimethylsilyl)oxy)ethyl)-7-(5-(1-(2-(difluoromethoxy) benzyl)-2-methyl-3-oxo-2,3-dihydro-1H-indazol-6-yl)pyrimidin-2-yl)hexahydroimidazo[1,5-a]pyrazin-3(2H)-one and 6-bromo-1-(2-(difluoromethoxy)benzyl)-2-methyl-1H-indazol-3(2H)-one (Preparation #4, step 1) in a similar fashion to Example #8, to give the title compound (170 mg, 66%); LC/MS (Table A, Method i) $R_t$=1.76 min; MS m/z: 680 (M+H)$^+$.

Step 3: (R)-7-(5-(1-(2-(Difluoromethoxy)benzyl)-2-methyl-3-oxo-2,3-dihydro-1H-indazol-6-yl)pyrimidin-2-yl)-2-(2-hydroxyethyl)hexahydroimidazo[1,5-a]pyrazin-3(2H)-one A round-bottomed flask was charged with (R)-2-(2-((tert-butyldimethylsilyl)oxy)ethyl)-7-(5-(1-(2-(difluoromethoxy) benzyl)-2-methyl-3-oxo-2,3-dihydro-1H-indazol-6-yl)pyrimidin-2-yl)hexahydroimidazo[1,5-a]pyrazin-3(2H)-one (170 mg, 0.25 mmol), THF (1 mL) and TBAF (1 M in THF, 0.8 mL, 0.8 mmol). The solution was stirred at rt for about 90 min, then concentrated under reduced pressure. The residue was purified by flash chromatography on silica gel (0-10% MeOH/$CH_2Cl_2$) to afford the title product (98 mg, 67%); LC/MS (Table A, Method a) $R_t$=1.70 min; MS m/z: 567 (M+H)$^+$. (TNF IC$_{50}$=A).

Example #36*: (S)-1-(2-Difluoromethoxy)-5-methylbenzyl)-6-(2-(4-(2-hydroxyacetyl)-3-methylpiperazin-1-yl)pyrimidin-5-yl)-2-methyl-1H-indazol-3 (2H)-one

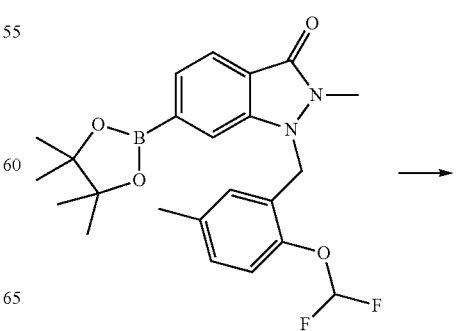

255

-continued

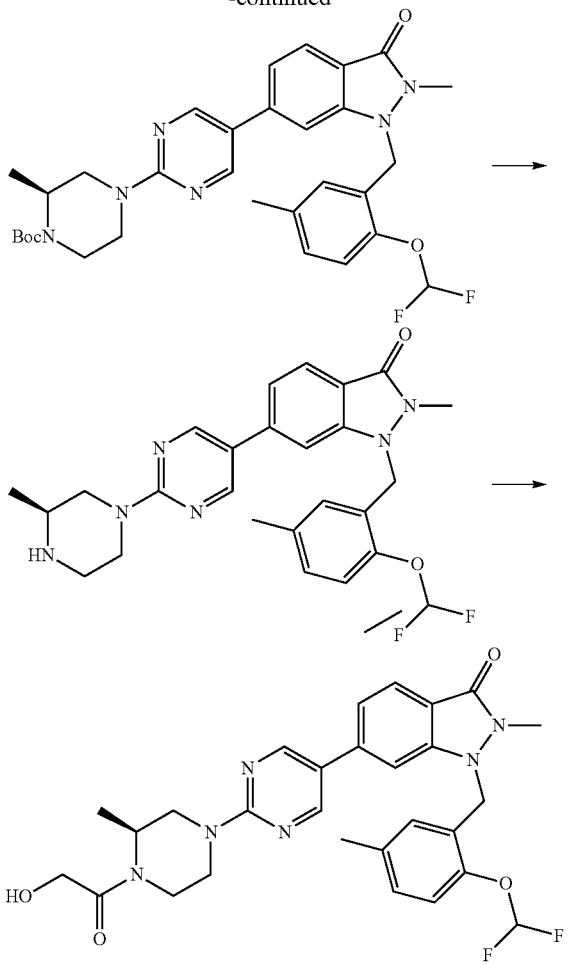

Step 1: (S)-tert-Butyl 4-(5(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate The reaction was performed using 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, step 2) and (S)-tert-butyl 4-(5-bromopyrimidin-2-yl)-2-methylpiperazine-1-carboxylate (synthesized in a similar fashion to Preparation #13, step 1 using (S)-1-N-Boc-2-methylpiperazine) in a similar fashion to Example #14, step 4 to afford the title product (62%); LC/MS (Table A, Method i) $R_t$=1.87 min; MS m/z: 595 (M+H)$^+$.

Step 2: (S)-1-(2-(Difluoromethoxy)-5-methylbenzyl)-2-methyl-6-(2-(3-methylpiperazin-1-yl)pyrimidin-5-yl)-1H-indazol-3(2H)-one, hydrochloric acid The reaction was performed using (S)-tert-butyl 4-(5-(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate in a similar fashion to Example #3, step 1 to afford the title product (98%); LC/MS (Table A, Method i) $R_t$=0.97 min; MS m/z: 495 (M+H)$^+$.

256

Step 3: (S)-1-(2-(Difluoromethoxy)-5-methylbenzyl)-6-(2-(4-(2-hydroxyacetyl)-3-methylpiperazin-1-yl)pyrimidin-5-yl)-2-methyl-1H-indazol-3(2H)-one The reaction was performed using (S)-1-(2-(difluoromethoxy)-5-methylbenzyl)-2-methyl-6-(2-(3-methylpiperazin-1-yl)pyrimidin-5-yl)-1H-indazol-3(2H)-one, hydrochloric acid in a similar fashion to Preparation #15 to afford the title product (35%); LC/MS (Table A, Method a) $R_t$=1.89 min; MS m/z: 553(M+H)$^+$. (TNF IC$_{50}$=A).

Example #37: (S)-4-Methyl-2-((2-methyl-3-oxo-6-(2-(3-oxohexahydromidazo[1,5-a]pyrazin-7(1H)-yl)pyrimidin-5-yl)-2,3-dihydro-1H-indazol-1-yl)methyl)benzonitrile

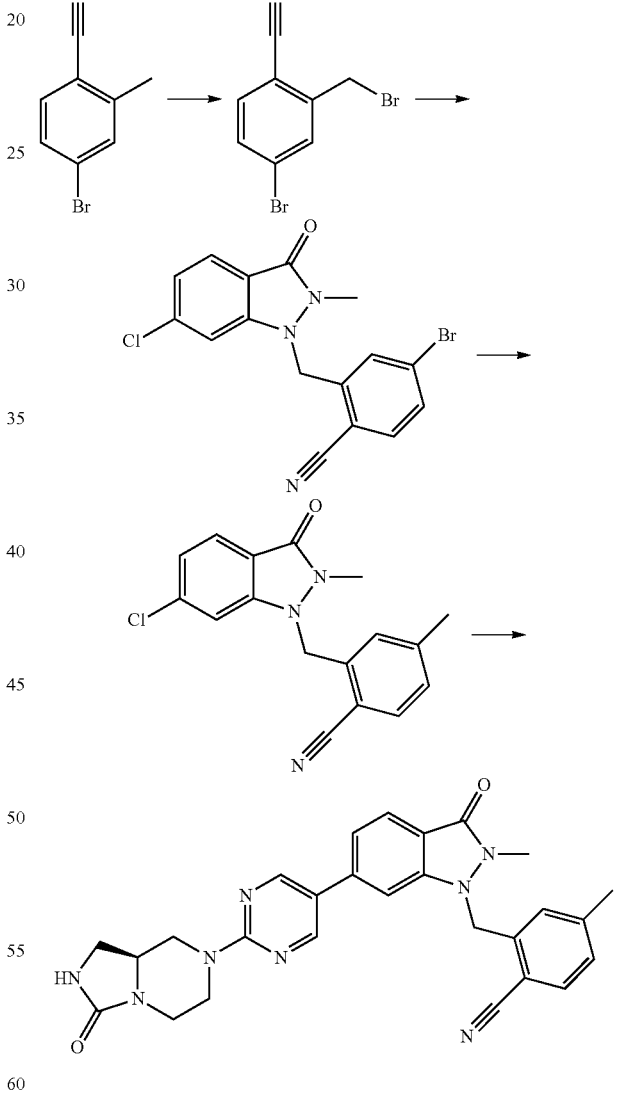

Step 1: 4-Bromo-2-(bromomethyl)benzonitrile

A mixture of 4-bromo-2-methylbenzonitrile (2.0 g, 10 mmol), 1-bromopyrrolidine-2,5-dione (1.82 g, 10.2 mmol) and benzoic peroxyanhydride (0.124 g, 0.510 mmol) in CCl$_4$ (10 mL) was heated at reflux under nitrogen for about 18 h.

The reaction was cooled to rt, diluted with DCM (25 mL) and washed with sat. aq. NaHCO₃ (20 mL) and water (20 mL). The organic layer was dried over Na₂SO₄ and filtered. The residue was dried onto silica gel and purified on silica gel using a gradient of 0-20% EtOAc in heptane. The product fractions were combined and concentrated to yield the title compound (1.57 g, 56%); ¹H NMR (400 MHz, CDCl₃) δ 7.73(d, J=1.8 Hz, 1H), 7.57 (dd, J=8.3, 1.8 Hz, 1H), 7.52 (d, J=8.3 Hz, 1H), 4.57 (s, 2H).

Step 2: 4-Bromo-2-((6-chloro-2-methyl-3-oxo-2,3-dihydro-1H-indazol-1-yl)methyl)benzonitrile The reaction was performed using 4-bromo-2-(bromomethyl)benzonitrile and 6-chloro-2-methyl-1H-indazol-3(2H)-one (Preparation #29) in a similar fashion to Preparation #4, step 1 to give the title product (90%); (Table A, Method j) R$_t$=1.34 min; MS m/z: 376 and 378 (M+H)⁺.

Step 3: 2-((6-Chloro-2-methyl-3-oxo-2,3-dihydro-1H-indazol-1-yl)methyl)-4-methylbenzonitrile The reaction was performed using 2,4,6-trimethyl-1,3,5,2,4,6-trioxatriborinane in a similar fashion to Preparation #14, step 4 to give the title product (56%); (Table A, Method j) R$_t$=1.27 min; MS m/z: 312 (M+H)⁺.

Step 4: (S)-4-Methyl-2-((2-methyl-3-oxo-6-(2-(3-oxohexahydroimidazo[1,5-a]pyrazin-7(1H)-yl)pyrimidin-5-yl)-2,3-dihydro-1H-indazol-1-yl)methyl)benzonitrile The reaction was performed using (S)-7-(5-bromopyrimidin-2-yl)hexahydroimidazo[1,5-a]pyrazin-3(2H)-one (Preparation #13) in a similar fashion to Example #8 to give the title product (32%); (Table A, Method j) R$_t$=1.66 min; MS m/z: 495 (M+H)⁺. (TNF IC₅₀=B).

Example #38*: 1-(2-(Difluoromethoxy)benzyl)-6-(2-((R)-4-((S)-3-hydroxy-2-methylpropanoyl)-3-methylpiperazin-1-yl)pyrimidin-5-yl)-2-methyl-1H-indazol-3(2H)-one

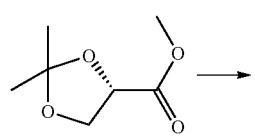

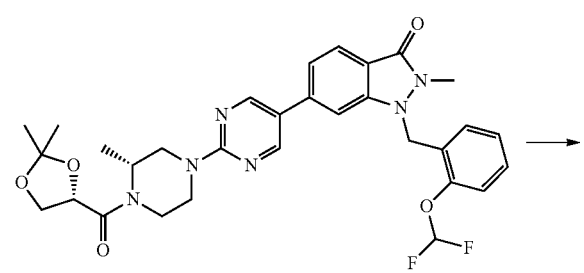

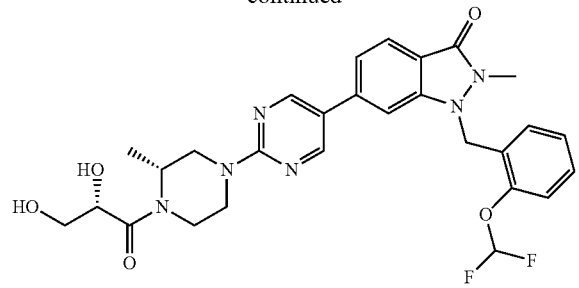

Step 1: 1-(2-(Difluoromethoxy)benzyl)-6-(2-((R)-4-((S)-2,2-dimethyl-1,3-dioxolane-4-carbonyl)-3-methylpiperazin-1-yl)pyrimidin-5-yl)-2-methyl-1H-indazol-3(2H)-one To a solution of (S)-methyl 2,2-dimethyl-1,3-dioxolane-4-carboxylate (0.45 g, 2.8 mmol) in THF (5 mL) at 0° C. was added a solution of lithium hydroxide monohydrate (0.218 g, 5.20 mmol) in water (5 mL) at about 6° C. dropwise over about 10 min. After about 1 h, the mixture was diluted with water (15 mL) and extracted with EtOAc (15 mL). The aqueous layer was acidified with 1H₃PO₄ to about pH=2. The product was extracted with EtOAc (4×15 mL). The combined organic layers were washed with water (15 mL) and sat. aq. NaCl (15 mL), dried over Na₂SO₄, filtered and concentrated under reduced pressure. The residue (57 mg, 0.39 mmol) was dissolved in TEA (0.109 mL, 0.780 mmol) and DCM (2 mL). Bis(tetramethylene)fluoroformamidiniumhexafluorophosphate (0.082 g, 0.26 mmol) was added and the mixture was stirred for about 5 min. (R)-1-(2-(Difluoromethoxy)benzyl)-2-methyl-6-(2-(3-methylpiperazin-1-yl)pyrimidin-5-yl)-1H-indazol-3(2H)-one (0.125 g, 0.260 mmol) was added. The mixture was stirred for about 1 h. The mixture was purified on silica gel using a gradient of 0-100% EtOAc in DCM. Product fractions were combined and concentrated under reduced pressure to yield the title product (68 mg, 43%); (Table A, Method j) R$_t$=1.47 min; MS m/z: 609 (M+H)⁺. (TNF IC₅₀=A).

Step 2: 1-(2-(Difluoromethoxy)benzyl)-6-(2-((R)-4-((S)-2,3-dihydroxypropanoyl)-3-methylpiperazin-1-yl)pyrimidin-5-yl)-2-methyl-1H-indazol-3(2H)-one A solution containing 1-(2-(difluoromethoxy)benzyl)-6-(2-((R)-4-((S)-2,2-dimethyl-1,3-dioxolane-4-carbonyl)-3-methylpiperazin-1-yl)pyrimidin-5-yl)-2-methyl-1H-indazol-3(2H)-one (68 mg, 0.11 mmol) in AcOH (3 mL) and water (0.75 mL) was heated at 70° C. for about 90 min. The reaction was cooled and concentrated under reduced pressure to yield the title product (56 mg, 88%); (Table A, Method a) R$_t$=1.64 min; MS m/z: 569 (M+H)⁺. (TNF IC₅₀=A).

Example #39*: 1-(2-(Difluoromethoxy)benzyl)-6-(2-((R)-4-((R)-3-hydroxy-2-methylpropanoyl)-3-methylpiperazin-1-yl)pyrimidin-5-yl)-2-methyl-1H-indazol-3(2H)-one

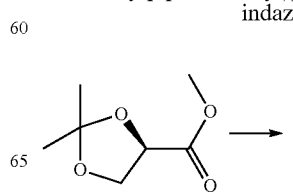

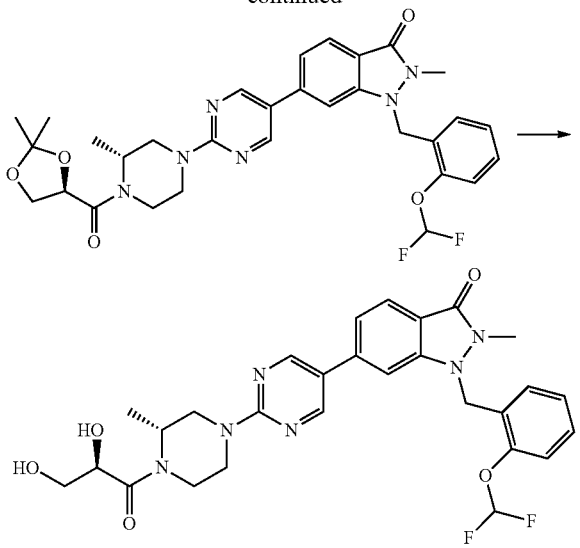

Step 1: 1-(2-(Difluoromethoxy)benzyl)-6-(2-((R)-4-((R)-2,2-dimethyl-1,3-dioxolane-4-carbonyl)-3-methylpiperazin-1-yl)pyrimidin-5-yl)-2-methyl-1H-indazol-3(2H)-one The reaction was performed using (R)-methyl 2,2-dimethyl-1,3-dioxolane-4-carboxylate in a similar fashion to Example #38, step 1 to yield the title product (80 mg, 50%); (Table A, Method j) $R_t$=1.47 min; MS m/z: 609 (M+H)$^+$.

Step 2: 1-(2-(Difluoromethoxy)benzyl)-6-(2-((R)-4-((R)-2,3-dihydroxypropanoyl)-3-methylpiperazin-1-yl)pyrimidin-5-yl)-2-methyl-1H-indazol-3(2H)-one The reaction was performed in a similar fashion to Example #38, step 2 to yield the title product (71 mg, 95%); (Table A, Method a) $R_t$=1.65 min; MS m/z: 569 (M+H)$^+$. (TNF IC$_{50}$=A).

Example #40: 1-(2-(Difluoromethoxy)benzyl)-5-fluoro-6-(2-(2-hydroxypropan-2-yl)pyrimidin-5-yl)-2-methyl-1H-indazol-3(2H)-one

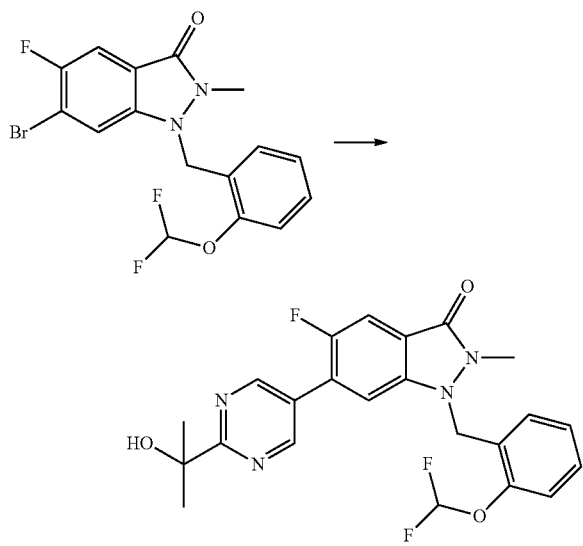

DMF (7 mL) was added to a mixture of 6-bromo-1-(2-(difluoromethoxy)benzyl)-5-fluoro-2-methyl-1H-indazol-3(2H)-one (0.31 g, 0.77 mmol) (synthesized in a manner similar to Preparation #4, step 1 from 6-bromo-5-fluoro-2-methyl-1H-indazol-3(2H)-one (synthesized in a manner similar to Preparation #1 from 4-bromo-2,5-difluorobenzoic acid)), bis(pinacolato)diboron (0.334 g, 1.31 mmol), KOAc (0.228 g, 2.32 mmol), and PdCl$_2$(dppf) DCM complex (0.050 g, 0.062 mmol). The reaction vessel was evacuated then back-filled with N$_2$ three times then purged with N$_2$ for about 5 min. The mixture was warmed to about 90° C. for about 90 min. The mixture was allowed to cool to rt. The volatiles were removed under reduced pressure at about 70° C. 2-(5-bromopyrimidin-2-yl)propan-2-ol (139 mg, 0.639 mmol), cesium carbonate (481 mg, 1.48 mmol), dioxane (4 mL), and water (1 mL) were added. The reaction vessel was evacuated then back-filled with N$_2$ three times. PdCl$_2$(PPh$_3$)$_2$(27.6 mg, 0.039 mmol) was added. The reaction vessel was evacuated then back-filled with N, three times. The reaction was stirred at about 80° C. for about 1 h then cooled to rt. EtOAc (20 mL) was added to the reaction and the solids were removed by filtration. The organic layer was washed with water (10 mL). The combined organic layers were dried over MgSO$_4$, filtered, concentrated and purified on silica gel (0-73% EtOAc/DCM) then preparative reverse phase HPLC (The gradient was a hold at 10% B for 1.5 min, 10%-95% B to 12.5 min and then a hold at 95% B for 3 min. Mobile phase A was 0.1% formic acid in water, mobile phase B was HPLC grade MeCN. The column used for the chromatography is a 21.2×150 mm Phenomenex Kinetex Biphenyl (5 µm particles). Detection methods are diode array (DAD) and positive/negative ESI ionization.). The fractions were concentrated, partitioned between DCM (20 mL) and sat. aq. NaHCO$_3$ (10 mL), washed with sat. aq. NaCl (10 mL), dried over MgSO$_4$, filtered, concentrated. The residue was chased with EtOAc/heptane then ACN/water and dried in a 70° C. vacuum oven to afford the title product (26 mg, 11%). LC/MS (Table A, Method a) $R_t$=1.92 min; MS m/z: 459 (M+H)$^+$. (TNF IC$_{50}$=B).

Example #41*: (S)-1-(2-(Difluoromethoxy)-5-methylbenzyl)-2-methyl-6-(2-(3-methyl-4-(methylsulfonyl)piperazin-1-yl)pyrimidin-5-yl)-1H-indazol-3(2H)-one

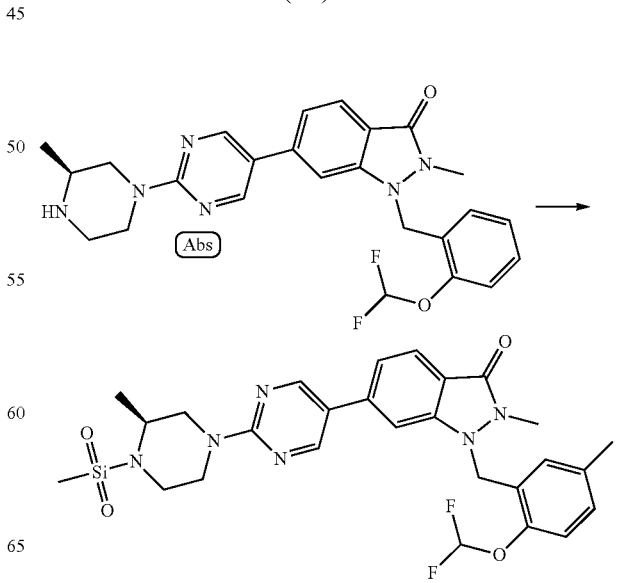

(S)-1-(2-(Difluoromethoxy)-5-methylbenzyl)-2-methyl-6-(2-(3-methyl-4-(methylsulfonyl)piperazin-1-yl)pyrimidin-5-yl)-1H-indazol-3(2H)-one was prepared in a similar fashion to Example #24 using (S)-1-(2-(difluoromethoxy)-5-methylbenzyl)-2-methyl-6-(2-(3-methylpiperazin-1-yl)pyrimidin-5-yl)-1H-indazol-3(2H)-one (Example #36, step 2) and MsCl to give the title compound (0.041 g, 48%); LC/MS (Table A, Method e) R$_t$=2.17 min; MS m/z: 573(M+H)$^+$. (TNF IC$_{50}$=A).

The compounds shown in Table 26 were synthesized in a manner similar to Example #8 from 2-(5-bromopyrimidin-2-yl)propan-2-ol and the corresponding halide.

TABLE 26

| Halide | Product | Example # | R$_t$ min (Table A, Method) | m/z ESI+ (M + H)$^+$ | TNF IC$_{50}$ |
|---|---|---|---|---|---|
| 6-Bromo-1-(2-(difluoromethoxy)-5-methylbenzyl)-7-fluoro-2-methyl-1H-indazol-3(2H)-one (prepared in a similar fashion to Preparation #4, step 1 using 6-bromo-7-fluoro-2-methyl-1H indazol-3(2H)-one (Preparation #38) and 2-(bromomethyl)-1-(difluoromethoxy)-4-methylbenzene(prepared in a similar fashion to Preparation #3, step 2 using (2-(difluoromethoxy)-5-methylphenyl)methanol (Preparation #11))) | | 26.1 | 2.09 (e) | 473 | B |
| 6-Bromo-1-(2-(difluoromethoxy)-5-methylbenzyl)-2-(difluoromethyl)-1H-indazol-3(2H)-one (prepared in a similar fashion to Preparation #37, step 2 using 6-bromo-1-(2-(difluoromethoxy)-5-methylbenzyl)-1H-indazol-3(2H)-one (Preparation #74) | | 26.2 | 2.40 (e) | 491 | B |
| Methyl 3-((6-bromo-2-methyl-3-oxo-2,3-dihydro-1H-indazol-1-yl)methyl)-4-(difluoromethoxy) benzylcarbamate (Preparation #39) | | 26.3 | 1.72 (a) | 528 | B |
| 1-(5-((1H-1,2,4-Triazoi-1-yl)methyl)-2-(difluoromethoxy)benzyl)-6-bromo-5-fluoro-2-methyl-1H-indazol-3(2H)-one (Preparation #62) | | 26.4 | 1.64 (a) | 540 | A |

TABLE 26-continued

| Halide | Product | Example # | $R_t$ min (Table A, Method) | m/z ESI+ $(M + H)^+$ | TNF $IC_{50}$ |
|---|---|---|---|---|---|
| 1-(5-((4H-1,2,4-Triazol-4-yl)methyl)-2-(difluoromethoxy)benzyl)-6-bromo-5-fluoro-2-methyl-1H-indazol-3(2H)-one (Preparation #62) | | 26.5 | 1.54 (a) | 540 | B |
| 1-(5-((1-Acetylazetidin-3-yl)methyl)-2-(difluoromethoxy)benzyl)-6-bromo-5-fluoro-2-methyl-1H-indazol-3(2H)-one (Preparation #63) | | 26.6 | 1.71 (e) | 570 | B |
| 6-Chloro-1-(2-(difluorometboxy)-5-methylbenzyl)-5-fluoro-2-methyl-1,2-dihydro-3H-pyrazolo[3,4-b]pyridin-3-one (Example #98, step 2) | | 26.7 | 2.14 (a) | 474 | B |
| 2-(3-((6-Bromo-2-methyl-3-oxo-2,3-dihydro-1H-indazol-1-yl)methyl)-4-(difluoromethoxy)phenyl)acetonitrile (Preparation #20) | | 26.8 | 1.78 (a) | 480 | B |

Example #42: 1-(2-Chloro-5-((pyridin-2-ylmethyl)amino)benzyl)-6-(2-(2-hydroxypropan-2-yl)pyrimidin-5-yl)-2-methyl-1H-indazol-3(2H)-one

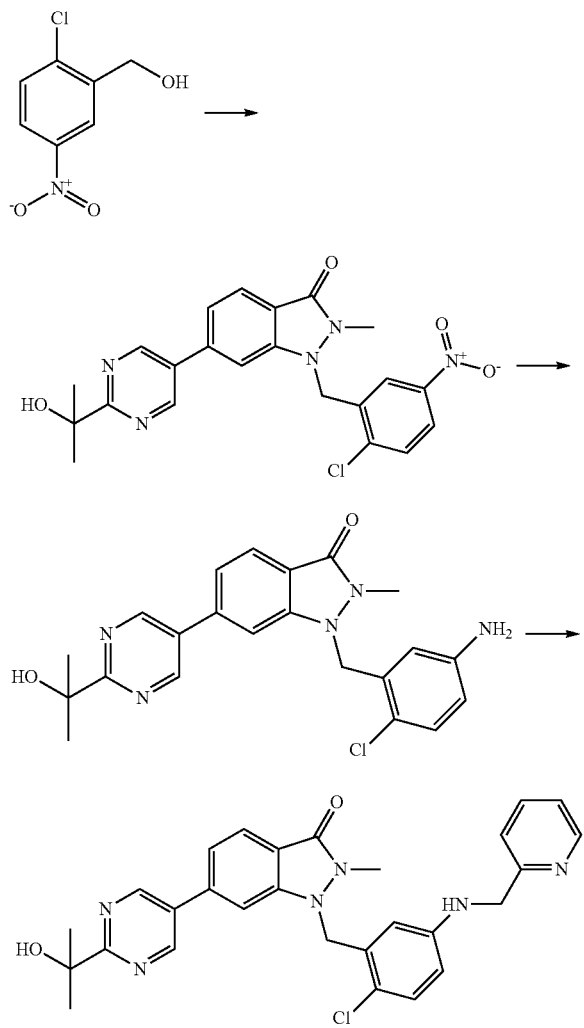

Step 1: 1-(2-Chloro-5-nitrobenzyl)-6-(2-(2-hydroxypropan-2-yl)pyrimidin-5-yl)-2-methyl-1H-indazol-3(2H)-one Carbon tetrabromide (0.389 g, 1.17 mmol) was added to a mixture of (2-Chloro-5-nitrophenyl)methanol (0.200 g, 1.07 mmol) and PPh$_3$(0.308 g, 1.17 mmol) in THF (3.00 mL). The mixture was stirred at rt for about 1 h. Immediately after adding the CBr$_4$, in a separate vial, DMF (5.00 mL) was added to a mixture of 6-(2-(2-hydroxypropan-2-yl)pyrimidin-5-yl)-2-methyl-1H-indazol-3(2H)-one (0.303 g, 1.066 mmol) (Preparation #19) and potassium carbonate (0.295 g, 2.132 mmol). The crude DCM solution containing the bromide was added to the reaction which was stirred at rt for about 16 h. The reaction was partitioned between EtOAc (50 mL) and 20% aq, NH$_4$Cl (50 mL). The organic layer was washed with sat. aq. NaCl (50 mL), dried over Na$_2$SO$_4$, filtered and was concentrated under reduced pressure. The residue was purified on silica gel using 40-100% EtOAc in heptanes to give the title compound (0.39 g, 81%); LC/MS (Table A, Method e) R$_t$=1.84 min; MS m/z: 454 (M+H)$^+$.

Step 2: 1-(5-Amino-2-chlorobenzyl)-6-(2-(2-hydroxypropan-2-yl)pyrimidin-5-yl)-2-methyl-1H-indazol-3(2H)-one A mixture of 1-(2-chloro-5-nitrobenzyl)-6-(2-(2-hydroxypropan-2-yl)pyrimidin-5-yl)-2-methyl-1H-indazol-3(2H)-one (1.39 g, 3.06 mmol) and 10% palladium on carbon (0.326 g, 0.306 mmol) was rapidly stirred under a hydrogen balloon for about 8 h. The reaction was filtered through Celite® and concentrated under reduced pressure. The residue was triturated in MeOH and filtered. The precipitate from the filtrate was also triturated the filtered. The combined filtrates were concentrated under reduced pressure. The residue was purified on silica gel using 0-5% MeOH in DCM then further purified by mass-triggered reverse-phase purification (The gradient was a hold at 10% B for 1.5 min, 10%-75% B to 12.5 min, 75%-95% in 0.1 min and then a hold at 95% B for 3 min. Mobile phase A was 0.1% formic acid in water and mobile phase B was HPLC grade MeCN. The column used for the chromatography is a 21.2×150 mm Mac-Mod ACE C18 (5 μm particles). Detection methods are diode array (DAD) and positive/negative ESI ionization.). The product-containing fractions were concentrated under reduced pressure to remove the volatiles then filtered to give the title compound (0.473 g, 36%); LC/MS (Table A, Method i) R$_t$=1.03 min; MS m/z: 424 (M+H)$^+$.

Step 3: 1-(2-Chloro-5-((pyridin-2-ylmethyl)amino)benzyl)-6-(2-(2-hydroxypropan-2-yl)pyrimidin-5-yl)-2-methyl-1H-indazol-3(2H)-one A mixture of 1-(5-amino-2-chlorobenzyl)-6-(2-(2-hydroxypropan-2-yl)pyrimidin-5-yl)-2-methyl-1H-indazol-3(2H)-one (0.075 g, 0.18 mmol), picolinaldehyde (0.017 mL, 0.18 mmol) and AcOH (0.030 ml, 0.53 mmol) in DMF (0.500 mL) was stirred at rt for about 1 h then sodium cyanoborohydride (0.056 g, 0.89 mmol) was added. The reaction was stirred at rt for about 2 h. The reaction was partitioned between EtOAc (5 mL) and sat. aq. NaHCO$_3$(5 mL). The organic layer was washed with sat. aq. NaCl (5 mL), dried over Na$_2$SO$_4$, filtered and concentrated under reduced pressure. The residue was purified by mass triggered reverse-phase purification (The gradient was a hold at 10% B for 1.5 min, 10%-75% B to 12.5 min, 75%-95% in 0.1 min and then a hold at 95% B for 3 min. Mobile phase A was 0.1% formic acid in water and mobile phase B was HPLC grade MeCN. The column used for the chromatography is a 21.2×150 mm Phenomenex Kinetex C18 (5 μm particles). Detection methods are diode array (DAD) and positive/negative ESI ionization.). The product-containing fractions were concentrated under reduced pressure to remove the volatiles then freeze-dried to give the title compound (0.029 g, 30%); LC/MS (Table A, Method e) R$_t$=1.81 min; MS m/z: 515 (M+H)$^+$. (TNF IC$_{50}$=B).

Example #43: (R)-1-(4-(5-Bromopyridin-2-yl)-2-methylpiperazin-1-yl)-2-hydroxyethanone

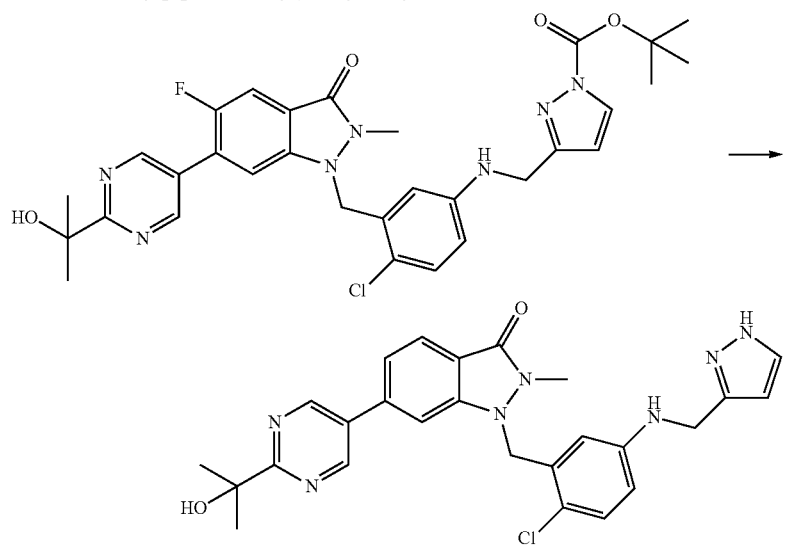

The title compound was synthesized in a manner similar to Preparation #19, step 4 from (tert-butyl 3-(((4-chloro-3-((6-(2-(2-hydroxypropan-2-yl)pyrimidin-5-yl)-2-methyl-3-oxo-2,3-dihydro-1H-indazol-1-yl)methyl)phenyl)amino) methyl)-1H-pyrazole-1-carboxylate (synthesized in a manner similar to Preparation #21, step 2 then Preparation #4, step 1 from 6-(2-(2-hydroxypropan-2-yl)pyrimidin-5-yl)-2-methyl-1H-indazol-3(2H)-one (Preparation #19) and tert-butyl 3-(((4-chloro-3-(hydroxymethyl)phenyl)amino) methyl)-1H-pyrazole-1-carboxylate (synthesized in a manner similar to Example #4, step 2 from tert-butyl 3-formyl-1H-pyrazole-1-carboxylate and (5-amino-2-chlorophenyl) methanol)); LC/MS (Table A, Method i) $R_t$=1.73 min; MS m/z: 504 (M+H)$^+$. (TNF IC$_{50}$=B).

Example #44: 1-(2-Chloro-5-((4,5,6,7-tetrahydro-1H-indazol-7-yl)amino)benzyl)-6-(2-(2-hydroxypropan-2-yl)pyrimidin-5-yl)-2-methyl-1H-indazol-3 (2H)-one

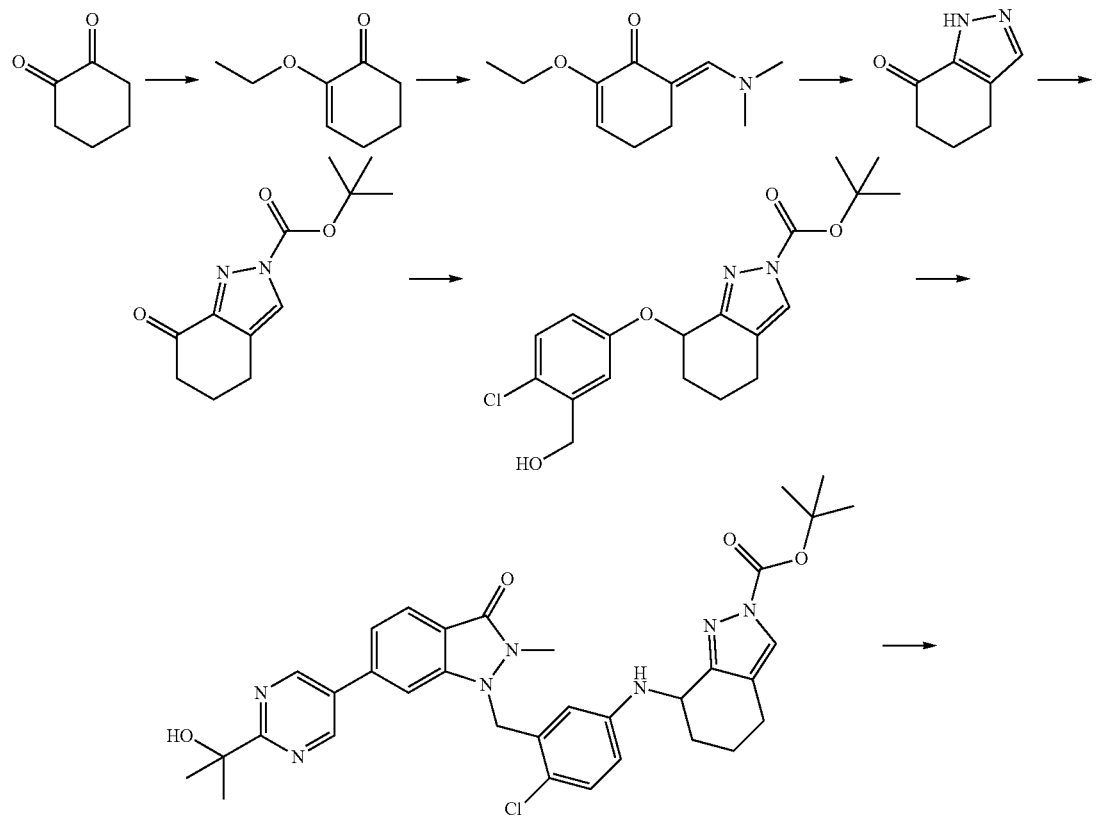

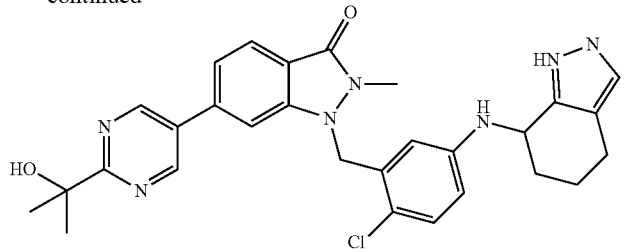

Step 1: 2-Ethoxycyclohex-2-enone

A flask with stir bar and distillation apparatus was charged with cyclohexane-1,2-dione (5.00 g, 44.6 mmol), EtOH (75 mL) and 4-methylbenzenesulfonic acid hydrate (0.848 g, 4.46 mmol). The mixture was heated to reflux until about 30 mL of solvent was distilled off. The flask was charged with EtOH (50 mL) then reheated to reflux until about 50 mL of solvent was distilled off. The flask was charged with EtOH (100 mL) then reheated to reflux until about 100 mL of solvent was distilled off. The mixture was cooled then concentrated under reduce pressure. The material was purified via flash chromatography on silica gel (0-100% EtOAc/heptane) to give the title compound (6.14 g, 98%); LC/MS (Table A, Method i) $R_t$=0.53 min; MS m/z: 141 (M+H)$^+$.

Step 2: (E)-6-((Dimethylamino)methylene)-2-ethoxycyclohex-2-enone

2-Ethoxycyclohex-2-enone (6.14 g, 43.8 mmol) in DMF (30 mL) with 1,1-dimethoxy-N,N-dimethylmethanamine (60 mL, 450 mmol) was heated to about 130° C. for about 3 h. The flask was charged with 1,1-dimethoxy-N,N-dimethylmethanamine (15 mL, 110 mmol) then the mixture was heated at about 130° C. for about 18 h. The mixture was cooled then concentrated under reduced pressure to give the title compound (8.1 g, 95%); LC/MS (Table A, Method i) $R_t$=0.77 min; MS m/z: 196 (M+H)$^+$.

Step 3: 5,6-Dihydro-1H-indazol-7(4H)-one (E)-6-((Dimethylamino)methylene)-2-ethoxycyclohex-2-enone (8.10 g, 41.5 mmol) in EtOH (200 mL) was treated with hydrazine hydrate (4.15 g, 830 mmol) then stirred for about 10 min. AcOH (1.2 mL, 21 mmol) was added then the mixture was warmed to about 70° C. for about 18 h. The mixture was cooled then concentrated under reduced pressure. The material was dissolved in MeOH (200 mL) then treated with 3 M aq. sulfuric acid (70 mL, 210 mmol). The mixture was stirred for about 3 h. Water (50 mL) was added to the mixture then it was concentrated under reduced pressure to remove most of the volatile organic solvents. The mixture was filtered. The filtrate was extracted with EtOAc (7×100 mL). The combined organic extracts were dried over magnesium sulfate, filtered and concentrated. The material was purified via flash chromatography on silica gel (EtOAc) to give the title compound (3.23 g, 57%); LC/MS (Table A, Method i) $R_t$=0.24 min; MS m/z: 137 (M+H)$^+$.

Step 4: tert-Butyl 7-oxo-4,5,6,7-tetrahydro-2H-indazole-2-carboxylate

The title compound was synthesized in a manner similar to Preparation #19, step 1 from 5,6-dihydro-1H-indazol-7 (4H)-one; $^1$H NMR (400 MHz, CDCl$_3$) δ 8.00 (s, 1H), 2.82-2.74 (m, 2H), 2.71-2.61 (m, 2H), 2.19-2.07 (m, 2H), 1.65 (s, 9H).

Step 5: tert-Butyl 7-((4-chloro-3-(hydroxymethyl)phenyl)amino)-4,5,6,7-tetrahydro-2H-indazole-2-carboxylate A flask with stir bar, Dean Stark apparatus and nitrogen line charged with tert-butyl 7-oxo-4,5,6,7-tetrahydro-2H-indazole-2-carboxylate (1.11 g, 4.70 mmol), (5-amino-2-chlorophenyl)methanol (0.890 g, 5.65 mmol), 4-methylbenzenesulfonic acid hydrate (0.040 g, 0.21 mmol) and toluene (75 mL). The mixture was heated to reflux for about 45 min. The mixture was cooled and concentrated under reduced pressure then dissolved in MeOH (25 mL). The mixture was cooled in an ice/water bath then sodium tetrahydroborate (0.485 g, 12.8 mmol) was added. The mixture was stirred for about 15 min then concentrated under reduced pressure. The residue was partitioned between EtOAc (30 mL) and water (30 mL). The aqueous layer was extracted with EtOAc (20 mL) then the combined organic solutions were dried over magnesium sulfate, filtered and concentrated. The mixture was stirred with EtOAc (20 mL) for about 1 h then filtered. The filtrate was concentrated under reduced pressure then the material was purified via flash chromatography on silica gel (0-100% EtOAc/heptane) to give the title compound (0.42 g, 24%); $^1$H NMR (400 MHz, DMSO-d$_6$) δ 7.95 (s, 1H), 7.03(d, J=8.6 Hz, 1H), 6.88 (d, J=2.8 Hz, 1H), 6.58 (dd, J=8.7, 2.9 Hz, 1H), 6.02 (d, J=7.8 Hz, 1H), 5.16 (t, J=5.6 Hz, 1H), 4.61-4.50 (m, 1H), 4.43(d, J=5.6 Hz, 2H), 2.55-2.49 (m, 2H), 1.96-1.89 (m, 1H), 1.80-1.84 (m, 1H), 1.67-1.70 (m, 2H), 1.53(s, 9H).

Step 6: tert-Butyl 7-((4-chloro-3-((6-(2-(2-hydroxypropan-2-yl)pyrimidin-5-yl)-2-methyl-3-oxo-2,3-dihydro-1H-indazol-1-yl)methyl)phenyl)amino)-4,5,6,7-tetrahydro-2H-indazole-2-carboxylate The title compound was synthesized in a manner similar to Preparation #21, step 2 then Preparation #4, step 1 from 6-(2-(2-hydroxypropan-2-yl)pyrimidin-5-yl)-2-methyl-1H-indazol-3(2H)-one (Preparation #19) and tert-butyl 7-((4-chloro-3-(hydroxymethyl)phenyl)amino)-4,5,6,7-tetrahydro-2H-indazole-2-carboxylate; LC/MS (Table A, Method i) $R_t$=1.65 min; MS m/z: 644 (M+H)$^+$.

Step 7: 1-(2-Chloro-5-((4,5,6,7-tetrahydro-1H-indazol-7-yl)amino)benzyl)-6-(2-(2-hydroxypropan-2-yl)pyrimidin-5-yl)-2-methyl-1H-indazol-3(2H)-one The title compound was synthesized in a manner similar to Preparation #19, step 4 from tert-butyl 7-((4-chloro-3-((6-(2-(2-hydroxypropan-2-yl)pyrimidin-5-yl)-2-methyl-3-oxo-2,3-dihydro-1H-indazol-1-yl)methyl)phenyl)amino)-4, 5,6,7-tetrahydro-2H-indazole-2-carboxylate; LC/MS (Table A, Method a) $R_t$=1.95 min; MS m/z: 544 (M+H)$^+$. (TNF IC$_{50}$=A).

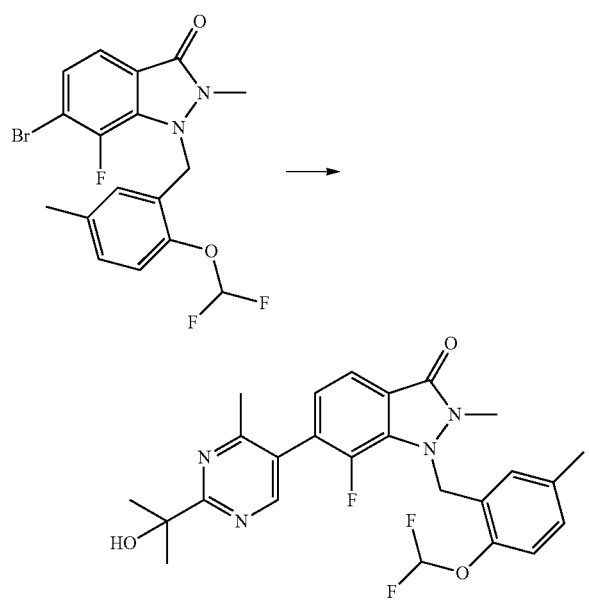

Example #45: 1-(2-(Difluoromethoxy)-5-methylbenzyl)-7-fluoro-6-(2-(2-hydroxypropan-2-yl)-4-methylpyrimidin-5-yl)-2-methyl-1H-indazol-3(2H)-one The title compound was synthesized in a manner similar to Example #8 from 2-(5-bromo-4-methylpyrimidin-2-yl)propan-2-ol (synthesized as described in WO2015/86506 A1) and 6-bromo-1-(2-(difluoromethoxy)-5-methylbenzyl)-7-fluoro-2-methyl-1H-indazol-3(2H)-one (synthesized in a manner similar to Preparation #21, step 2 then Preparation #4, step 1 from 6-bromo-7-fluoro-2-methyl-1H-indazol-3(2H)-one (Preparation #38) and (2-(difluoromethoxy)-5-methylphenyl)methanol (Preparation #11); LC/MS (Table A, Method a) $R_t$=2.19 min; MS m/z: 487 (M+H)$^+$. (TNF IC$_{50}$=A).

The compounds shown in Table 27 were synthesized in a manner similar to Example #8 from (R)-1-(4-(5-bromopyrimidin-2-yl)-2-methylpiperazin-1-yl)ethanone (Preparation #16) and the corresponding halide.

TABLE 27

| Halide | Product | Example # | $R_t$ min (Table A, Method) | m/z ESI+ (M + H)$^+$ | TNF IC$_{50}$ |
|---|---|---|---|---|---|
| N-(3-((6-Bromo-2-methyl-3-oxo-2,3-dihydro-1H-indazol-1-yl)methyl)-4-(difluoromethoxy)benzyl)acetamide (synthesized from 1-(5-(aminomethyl)-2-(difluoromethoxy)benzyl)-6-bromo-2-methyl-1H-indazol-3(2H)-one (Preparation #39, step 2) in a similar fashion to Preparation #16) | | 27.1* | 1.61 (a) | 594 | B |
| Methyl 3-((6-bromo-2-methyl-3-oxo-2,3-dihydro-1H-indazol-1-yl)methyl)-4-(difluoromethoxy)benzylcarbamate (Preparation #39) | | 27.2* | 1.78 (a) | 610 | A |
| 2-(3-((6-Bromo-2-methyl-3-oxo-2,3-dihydro-1H-indazol-1-yl)methyl)-4-(difluoromethoxy)phenyl)acetonitrile (Preparation #20) | | 27.3* | 1.82 (a) | 562 | A |

TABLE 27-continued

| Halide | Product | Example # | R_f min (Table A, Method) | m/z ESI+ (M + H)+ | TNF IC_{50} |
|---|---|---|---|---|---|
| 3-(3-((6-Bromo-2-methyl-3-oxo-2,3-dihydro-1H-indazol-1-yl)methyl)-4-(difluoromethoxy)phenyl)-2-methylpropanenitrile (Preparation #56) | | 27.4 | 1.92 (a) | 590 | B |
| 6-Bromo-2-methyl-1-((4-(trifluoromethyl)-1H-pyrrol-3-yl)methyl)-1H-indazol-3(2H)-one (Preparation #72) | | 27.5* | 1.77 (a) | 514 | A |
| 6-Bromo-1-(2-(difluoromethoxy)benzyl)-2-(pyridin-4-ylmethyl)-1H-indazol-3(2H)-one (prepared in a similar manner to Example #1 using 6-bromo-2-(pyridin-4-ylmethyl)-1H-indazol-3(2H)-one (Preparation #73) and 1-(bromomethyl)-2-(difluoromethoxy)benzene) | | 27.6* | 1.85 (a) | 600 | B |
| 6-Bromo-1-(2-chlorobenzyl)-2-(pyridin-4-ylmethyl)-1H-indazol-3(2H)-one (prepared in a similar manner to Example #1 using 6-bromo-2-(pyridin-4-ylmethyl)-1H-indazol-3(2H)-one (Preparation #73) and 1-(bromomethyl)-2-chlorobenzene) | | 27.7* | 1.88 (a) | 568 | B |

Example #46*: (R)-1-(2-(Difluoromethoxy)benzyl)-6-(2-(4-(2-hydroxyacetyl)-3-methylpiperazin-1-yl)pyrimidin-5-yl)-2-methyl-1H-indazol-3(2H)-one

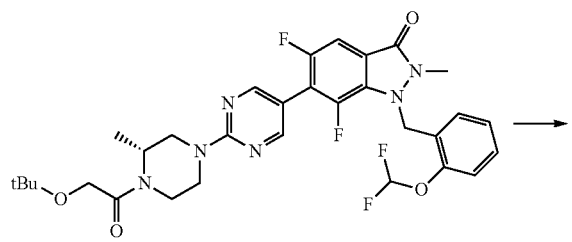

The reaction was performed in a similar fashion to Example #30 using (R)-6-(2-(4-(2-(tert-butoxy)acetyl)-3-methylpiperazin-1-yl)pyrimidin-5-yl)-1-(2-(difluoromethoxy)benzyl)-2-methyl-1H-indazol-3(2H)-one (prepared in a similar fashion to Preparation #26, step 4 from (R)-6-(2-(4-(2-(tert-butoxy)acetyl)-3-methylpiperazin-1-yl)pyrimidin-5-yl)-5,7-difluoro-2-methyl-1H-indazol-3(2H)-one), prepared in a similar fashion to as Preparation #26, step 3 from (R)-2-(tert-butoxy)-1-(2-methyl-4-(5-(4,4,5,5-tetramethyl-1,3,2-dioxaborolan-2-yl)pyrimidin-2-yl)piperazin-1-yl)ethanone (Preparation #30) and 6-bromo-5,7-difluoro-2-methyl-1H-indazol-3(2H)-one (Preparation #25) to yield the title product (93%); (Table A, Method j) $R_t$=1.25 min; MS m/z: 575 (M+H)$^+$. (TNF IC$_{50}$=A).

Example #47*: (R)-1-(2-(Difluoromethoxy)benzyl)-6-(2-(4-(2-hydroxyacetyl)-3-methylpiperazin-1-yl)pyrimidin-5-yl)-5-methoxy-2-methyl-1H-indazol-3(2H)-one

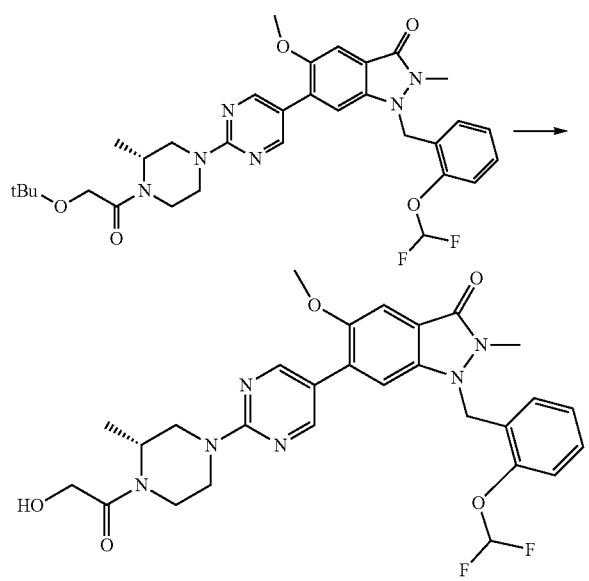

The reaction was prepared in a similar fashion to Example #30 using (R)-6-(2-(4-(2-(tert-butoxy)acetyl)-3-methylpiperazin-1-yl)pyrimidin-5-yl)-1-(2-(difluoromethoxy)benzyl)-5-methoxy-2-methyl-1H-indazol-3(2H)-one (prepared in a fashion similar to Preparation #26, step 3 using (R)-2-(tert-butoxy)-1-(2-methyl-4-(5-(4,4,5,5-tetramethyl-1,3,2-dioxaborolan-2-yl)pyrimidin-2-yl)piperazin-1-yl)ethanone (Preparation #30) and 6-chloro-1-(2-(difluoromethoxy)benzyl)-5-methoxy-2-methyl-1H-indazol-3(2H)-one), prepared in a fashion similar to Example #1 using 6-chloro-5-methoxy-2-methyl-1H-indazol-3(2H)-one (Preparation #31) to yield the title product (82%); (Table A, Method i) $R_t$=1.17 min; MS m/z: 569 (M+H)$^+$. (TNF IC$_{50}$=B).

Example #48*: (R)-6-(2-(4-Acetyl-3-methylpiperazin-1-yl)pyrimidin-5-yl)-1-(2-(difluoromethoxy)-6-(hydroxymethyl)benzyl)-2-methyl-1H-indazol-3(2H)-one

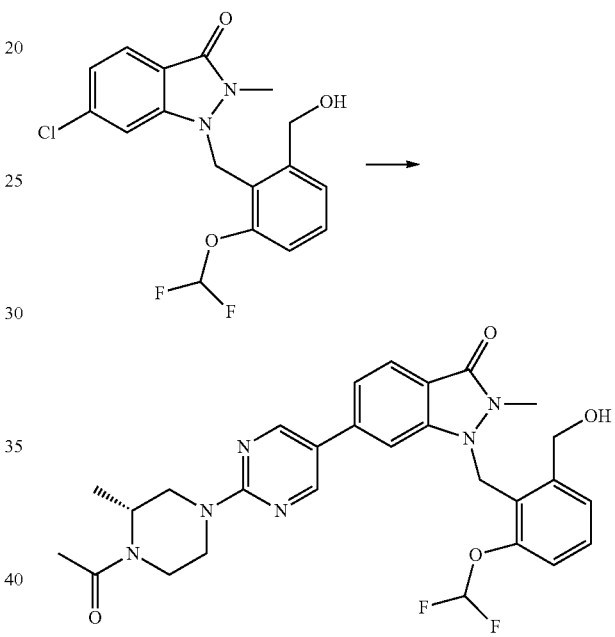

The reaction was performed in a similar fashion to Example #33, step 9 using (R)-1-(4-(5-bromopyrimidin-2-yl)-2-methylpiperazin-1-yl)ethanone (Preparation #16) and 6-chloro-1-(2-(difluoromethoxy)-6-(hydroxymethyl)benzyl)-2-methyl-1H-indazol-3(2H)-one (Example #33, step 7) to yield the title product (72%); (Table A, Method i) $R_t$=1.10 min; MS m/z: 553(M+H)$^+$. (TNF IC$_{50}$=A).

Example #49*: (R)-2-(2-((6-(2-(4-Acetyl-3-methylpiperazin-1-yl)pyrimidin-5-yl)-2-methyl-3-oxo-2,3-dihydro-1H-indazol-1-yl)methyl)-3-(difluoromethoxy)phenyl)acetonitrile

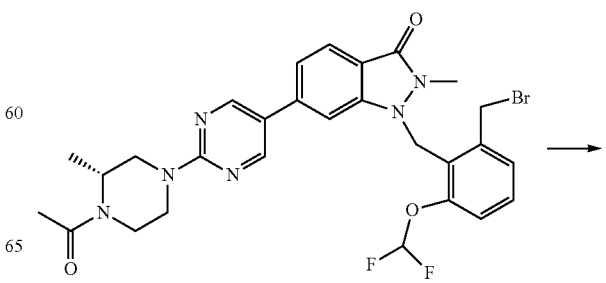

-continued

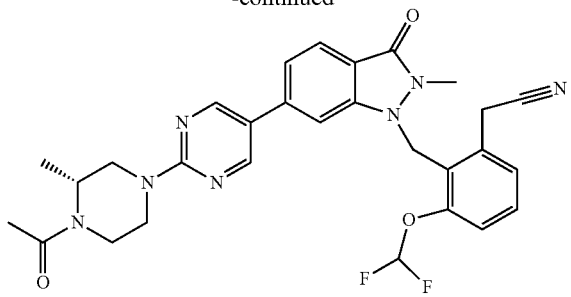

The reaction was performed in a similar fashion to Preparation #20, step 4 using (R)-6-(2-(4-acetyl-3-methyl-piperazin-1-yl)pyrimidin-5-yl)-1-(2-(bromomethyl)-6-(difluoromethoxy)benzyl)-2-methyl-1H-indazol-3(2H)-one (prepared in a similar fashion to Preparation #20, step 3 from (R)-6-(2-(4-acetyl-3-methylpiperazin-1-yl)pyrimidin-5-yl)-1-(2-(difluoromethoxy)-6-(hydroxymethyl)benzyl)-2-methyl-1H-indazol-3(2H)-one (Example #48)) to yield the title product (44% over 2 steps); (Table A, Method i) $R_t$=1.93 min; MS m/z: 562 (M+H)$^+$. (TNF IC$_{50}$=A).

Example #50*: (R)-4-((R)-4-(5-(1-(2-(Difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoic acid

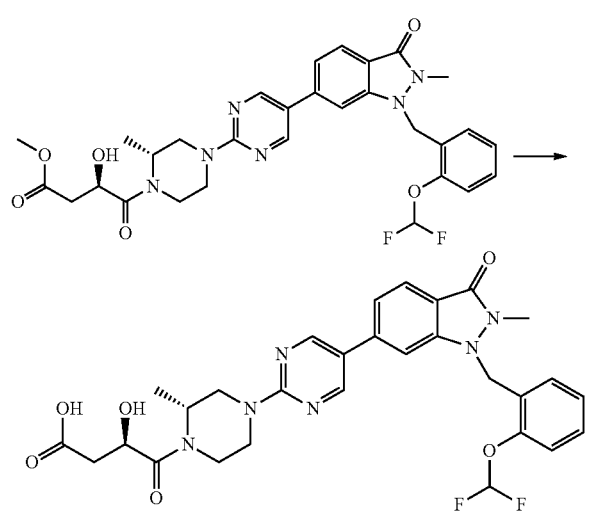

10% Aq. sodium carbonate (20 mL) was added to (R)-methyl 4-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoate (0.145 g, 0.237 mmol) (synthesized in a manner similar to Preparation #15 from (R)-2-hydroxy-4-methoxy-4-oxobutanoic acid (US 20090312342 A1) and (R)-1-(2-(difluoromethoxy)benzyl)-2-methyl-6-(2-(3-methylpiperazin-1-yl)pyrimidin-5-yl)-1H-indazol-3(2H)-one (Preparation #33)) in MeOH (2.6 mL). After about 16 h, the pH was adjusted to 3 with 2 N aq. HCl. The MeOH was removed under reduced pressure. The residue was partitioned between EtOAc (40 mL) and water (10 mL). The aqueous layer was extracted with EtOAc (2×5 mL). The combined organic layers were washed with water (5 mL) and sat. aq. NaCl (5 mL), dried over MgSO$_4$, filtered, and concentrated. The residue was purified on silica gel (0-6% MeOH/DCM) to afford the title product (47 mg, 32%); LC/MS (Table A, Method a) $R_t$=1.62 min; MS m/z: 597 (M+H)$^+$. (TNF IC$_{50}$=A).

Example #51*: (S)-4-((R)-4-(5-(1-(2-(Difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoic acid

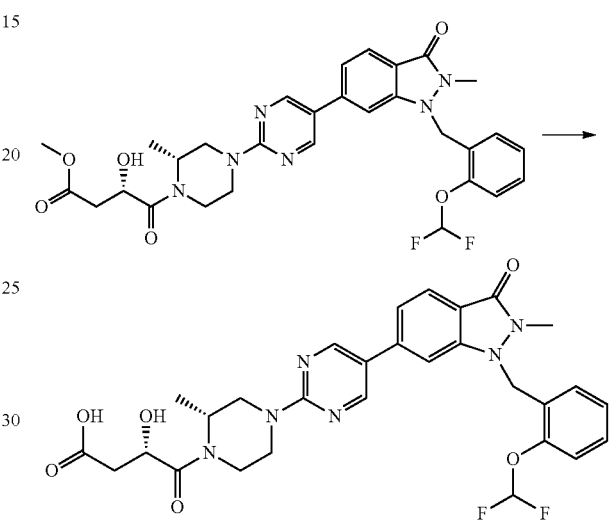

The reaction was performed using (S)-methyl 4-((R)-4-(5-(1-(2-(difluoromethoxy)benzyl)-2-methyl-3-oxo-2,3-dihydro-1H-indazol-6-yl)pyrimidin-2-yl)-2-methylpiperazin-1-yl)-3-hydroxy-4-oxobutanoate (synthesized in a manner similar to Preparation #15 from (S)-2-hydroxy-4-methoxy-4-oxobutanoic acid (US 20090312342 A1) and (R)-1-(2-(difluoromethoxy)benzyl)-2-methyl-6-(2-(3-methylpiperazin-1-yl)pyrimidin-5-yl)-1H-indazol-3(2H)-one (Preparation #33)) in a similar fashion to Example #51 to afford the title product (20 mg, 23%); LC/MS (Table A, Method a) $R_t$=1.62 min; MS m/z: 597 (M+H)$^+$. (TNF IC$_{50}$=A).

Example #52*: (R)-9-((6-(2-(4-Acetyl-3-methylpiperazin-1-yl)pyrimidin-5-yl)-2-methyl-3-oxo-2,3-dihydro-1H-indazol-1-yl)methyl)-4,5-dihydrobenzo[f][1,4]thiazepin-3(2H)-one

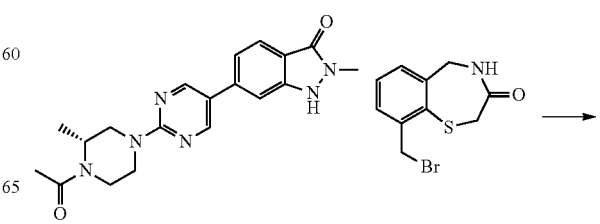

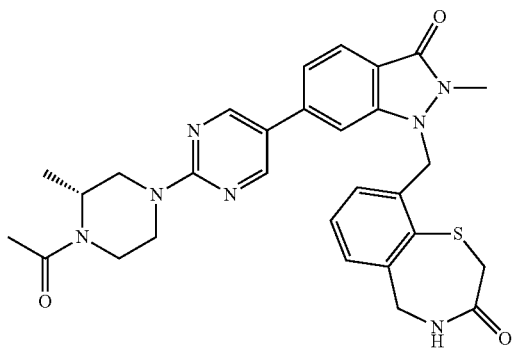

The reaction was performed using (R)-6-(2-(4-acetyl-3-methylpiperazin-1-yl)pyrimidin-5-yl)-2-methyl-1H-indazol-3(2H)-one (Preparation #28) and 9-(bromomethyl)-4,5-dihydrobenzo[f][1,4]thiazepin-3(2H)-one (Preparation #32) in a similar fashion to Preparation #4, step 1 to afford the title product (90 mg, 52%); LC/MS (Table A, Method h) $R_t$=0.94 min; MS m/z: 558 (M+H)$^+$. (TNF IC$_{50}$=B).

Example #53: 1-(2-Chloro-5-((pyridin-3-ylmethyl)amino)benzyl)-6-(2-(2-hydroxypropan-2-yl)pyrimidin-5-yl)-2-methyl-1H-indazol-3(2H)-one

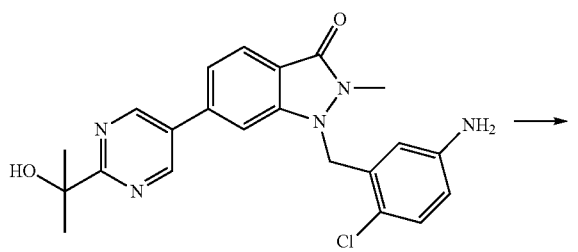

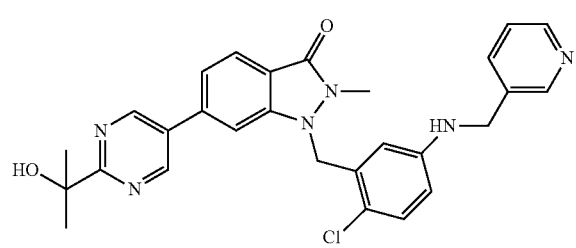

1-(2-Chloro-5-((pyridin-3-ylmethyl)amino)benzyl)-6-(2-(2-hydroxypropan-2-yl)pyrimidin-5-yl)-2-methyl-1H-indazol-3(2H)-one was prepared in a similar fashion to Example #42, step 3 using 1-(5-amino-2-chlorobenzyl)-6-(2-(2-hydroxypropan-2-yl)pyrimidin-5-yl)-2-methyl-1H-indazol-3(2H)-one (Example #42, step 2 and nicotinaldehyde to give the title compound (0.020 g, 20%); LC/MS (Table A, Method i) $R_t$ =1.10 min; MS m/z: 515 (M+H)$^+$. (TNF IC$_{50}$=B).

Example #54: (R)-6-(2-(4-Acetyl-3-methylpiperazin-1-yl)pyrimidin-5-yl)-1-(2-(difluoromethoxy)-5-methylbenzyl)-2-methyl-1H-indazol-3(2H)-one

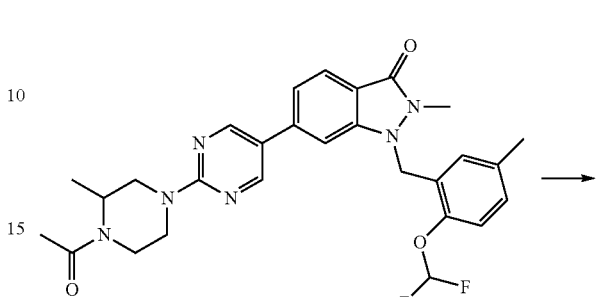

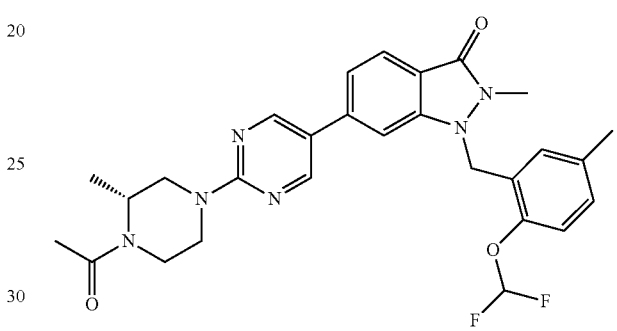

6-(2-(4-Acetyl-3-methylpiperazin-1-yl)pyrimidin-5-yl)-1-(2-(difluoromethoxy)-5-methylbenzyl)-2-methyl-1H-indazol-3(2H)-one (0.173 g, 0.323 mmol) (Preparation #58) was submitted for chiral separation (Table B, Method c). Fractions from the first eluting component were combined and concentrated. The residue was dissolved in MeCN (0.5 mL) then water (5 mL) was added. The mixture was sonicated then frozen. The resulting solid was lyophilized to afford the title product (0.055 g, 32%) with undetermined optical rotation. LC/MS (Table A, Method a) $R_t$=1.97 min; MS m/z: 537 (M+H)$^+$. (TNF IC$_{50}$=A).

Example #55: (S)-6-(2-(4-Acetyl-3-methylpiperazin-1-yl)pyrimidin-5-yl)-1-(2-(difluoromethoxy)-5-methylbenzyl)-2-methyl-1H-indazol-3(2H)-one

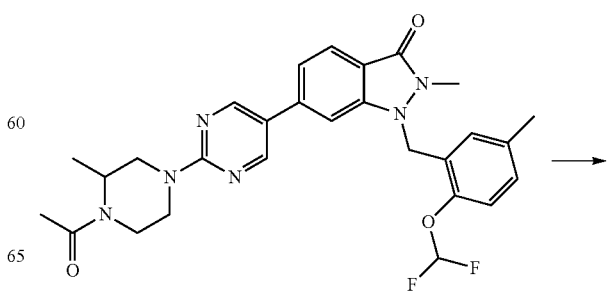

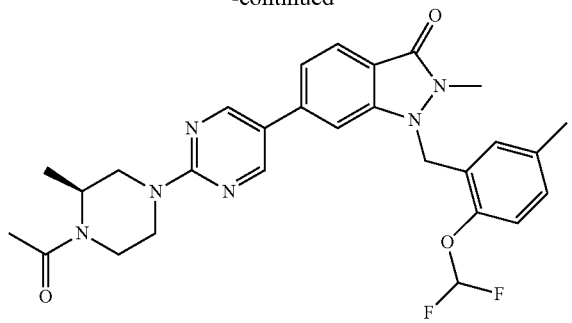

6-(2-(4-Acetyl-3-methylpiperazin-1-yl)pyrimidin-5-yl)-1-(2-(difluoromethoxy)-5-methylbenzyl)-2-methyl-1H-indazol-3(2H)-one (0.173 g, 0.323 mmol) (Preparation #58) was submitted for chiral separation (Table B, Method c). Fractions from the second eluting component were combined and concentrated. The residue was dissolved in MeCN (0.5 mL) then water (5 mL) was added. The mixture was sonicated then frozen. The resulting solid was lyophilized to afford the title product (0.062 g, 34%) with undetermined optical rotation. LC/MS (Table A, Method a) $R_t$=1.97 min; MS m/z: 537 (M+H)$^+$. (TNF IC$_{50}$=A).

Example #56: 1-(5-(Hydroxymethyl)-2-methylbenzyl)-2-methyl-6-(2-morpholinopyrimidin-5-yl)-1H-indazol-3(2H)-one

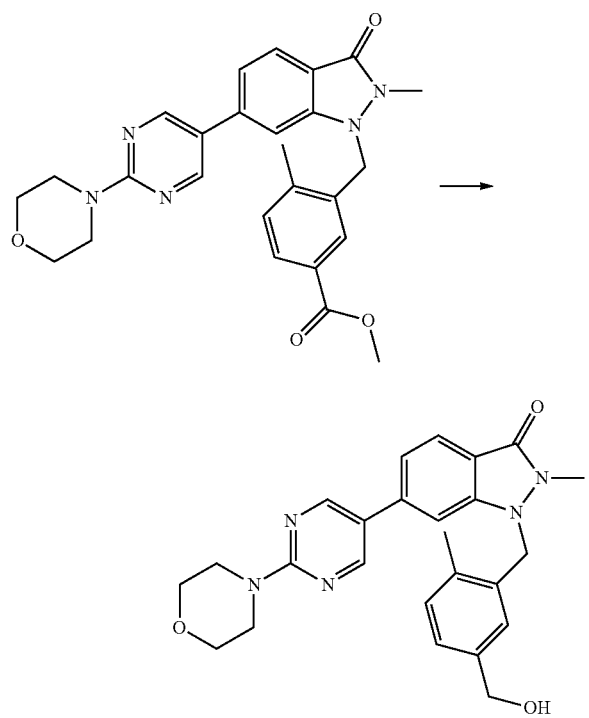

The reaction was prepared in a similar fashion to Preparation #14, step 5 using methyl 4-methyl-3-((2-methyl-6-(2-morpholinopyrimidin-5-yl)-3-oxo-2,3-dihydro-1H-indazol-1-yl)methyl)benzoate (prepared in a fashion similar to Example #1 using 2-methyl-6-(2-morpholinopyrimidin-5-yl)-1H-indazol-3(2H)-one (Preparation #2) and methyl 3-(bromomethyl)-4-methylbenzoate (prepared in a fashion similar to Preparation #3, step 2 using methyl 3-(hydroxymethyl)-4-methylbenzoate (prepared in a fashion similar to Example #9, step 1 using (5-bromo-2-methylphenyl)methanol (prepared in a fashion similar to Preparation #49, step 1 using 5-bromo-2-methylbenzoic acid)))) to yield the title product (13%); LC/MS (Table A, Method a) $R_t$=1.72 min; MS m/z: 446 (M+H)$^+$. (TNF IC$_{50}$=B).

Example #57*: (R)-7-(5-(1-(2-(Difluoromethoxy)-5-methylbenzyl)-2-(methyl-d$_3$)-3-oxo-2,3-dihydro-1H-indazol-6-yl)pyrimidin-2-yl)hexahydro-3H-oxazolo[3,4-a]pyrazin-3-one

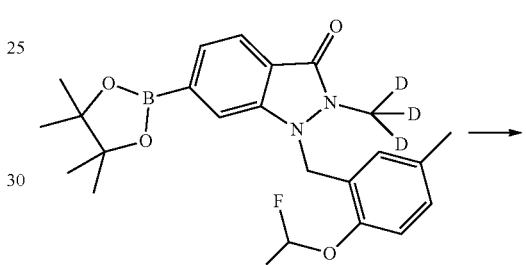

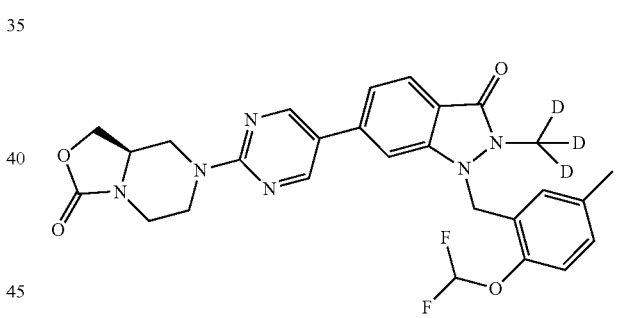

(R)-7-(5-(1-(2-(Difluoromethoxy)-5-methylbenzyl)-2-(methyl-d$_3$)-3-oxo-2,3-dihydro-1H-indazol-6-yl)pyrimidin-2-yl)hexahydro-3H-oxazolo[3,4-a]pyrazin-3-one was prepared in a similar fashion to Example #14, step 4 using 1-(2-(difluoromethoxy)-5-methylbenzyl)-2-(methyl-d$_3$)-6-(4,4,5,5-tetramethyl-1,3,2-dioxaborolan-2-yl)-1H-indazol-3(2H)-one (Preparation #59) and (R)-7-(5-bromopyrimidin-2-yl)tetrahydro-1H-oxazolo[3,4-a]pyrazin-3(5H)-one (prepared in a similar fashion to Example #2 using 5-bromo-2-chlorpyrimidine and (R)-hexahydro-oxazolo[pyrazine-3-one HCl) to give the title compound (74%); LC/MS (Table A, Method a) $R_t$=1.98 min; MS m/z: 540 (M+H)$^+$. (TNF IC$_{50}$=A).

The compounds shown in Table 28 were synthesized in a manner similar to Example #30 from the corresponding tert-butyl ether.

TABLE 28

| tert-Butyl Ether | Product | Example # | R$_t$ min (Table A, Method) | m/z ESI+ (M + H)$^+$ | TNF IC$_{50}$ |
|---|---|---|---|---|---|
| 6-(2-((R)-4-(2-(tert-Butoxy)acetyl)-3-methylpiperazin-1-yl)pyrimidin-5-yl)-1-(1-(2,6-difluorophenyl)ethyl)-2-methyl-1H-indazol-3(2H)-one (prepared in a manner similar to Example #18 from (R)-6-(2-(4-(2-(tert-butoxy)acetyl)-3-methylpiperazin-1-yl)pyrimidin-5-yl)-2-methyl-1H-indazol-3(2H)-one (Preparation #60) and 2-(1-bromoethyl)-1,3-dimethylbenzene (prepared from 1-(2,6-dimethylphenyl)ethanol in a similar manner to Preparation #21, step 2)) | | 28.1 | 1.17 (j) | 523 | A |
| 6-(2-((R)-4-(2-(tert-Butoxy)acetyl)-3-methylpiperazin-1-yl)pyrimidin-5-yl)-2-methyl-1-(1-phenylethyl)-1H-indazol-3(2H)-one (prepared in a similar manner to Example #1 using (R)-6-(2-(4-(2-(tert-butoxy)acetyl)-3-methylpiperazin-1-yl)pyrimidin-5-yl)-2-methyl-1H-indazol-3(2H)-one (Preparation #60) and (1-bromoethyl)benzene | | 28.2 | 1.19 (j) | 487 | A |
| 6-(2-((R)-4-(2-(tert-Butoxy)acetyl)-3-methylpiperazin-1-yl)pyrimidin-5-yl)-1-(1-(2-fluorophenyl)ethyl)-2-methyl-1H-indazol-3(2H)-one (prepared in a similar fashion to Preparation #4, step 1 using (R)-6-(2-(4-(2-((tert-butoxy)acetyl)-3-methylpiperazin-1-yl)pyrimidin-5-yl)-2-methyl-1H-indazol-3(2H)-one (Preparation #60) and 1-(1-bromoethyl)-2-fluorobenzene (prepared in a similar fashion to Preparation #21, step 2 using 1-(2-fluorophenyl)ethanol)) | | 28.3 | 1.16 (i) | 505 | A |
| 6-(2-((R)-4-(2-(tert-Butoxy)acetyl)-3-methylpiperazin-1-yl)pyrimidin-5-yl)-1-(1-(2-chlorophenyl)ethyl)-2-methyl-1H-indazol-3(2H)-one (prepared in a similar fashion to Preparation #4, step 1 using (R)-6-(2-(4-(2-(tert-butoxy)acetyl)-3-methylpiperazin-1-yl)pyrimidin-5-yl)-2-methyl-1H-indazol-3(2H)-one (Preparation #60) and 1-(1-bromoethyl)-2-chlorobenzene (prepared in a similar fashion to Preparation #21, step 2 using 1-(2-chlorophenyl)ethanol)) | | 28.4 | 1.24 (i) | 521 | B |

Example #58: 1-((S)-1-(2,6-Difluorophenyl)ethyl)-6-(2-((R)-4-(2-hydroxyacetyl)-3-methylpiperazin-1-yl)pyrimidin-5-yl)-2-methyl-1H-indazol-3(2H)-one

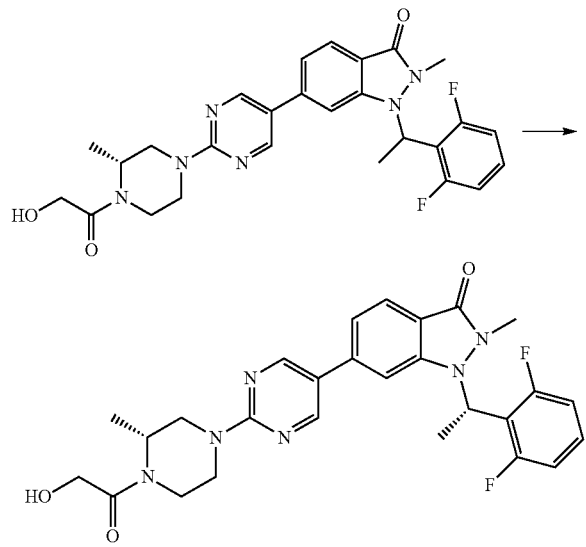

1-(1-(2,6-Difluorophenyl)ethyl)-6-(2-((R)-4-(2-hydroxyacetyl)-3-methylpiperazin-1-yl)pyrimidin-5-yl)-2-methyl-1H-indazol-3(2H)-one (250 mg) (Example #28.1) was submitted for chiral separation (Table C, Method b). The product fractions from the second eluting component were concentrated under reduced pressure. The residue was concentrated from methanol (25 mL), and then concentrated from ether (25 mL) to yield the title product (0.083 g, 33%) with negative optical rotation. LC/MS (Table A, Method j) $R_t$=1.17 min; MS m/z: 523(M+H)$^+$. (TNF IC$_{50}$=A).

Example #59*: (R)-1-(2-(Difluoromethoxy)benzyl)-5-fluoro-6-(2-(4-(2-hydroxyacetyl)-3-methylpiperazin-1-yl)pyrimidin-5-yl)-2-methyl-1H-indazol-3(2H)-one

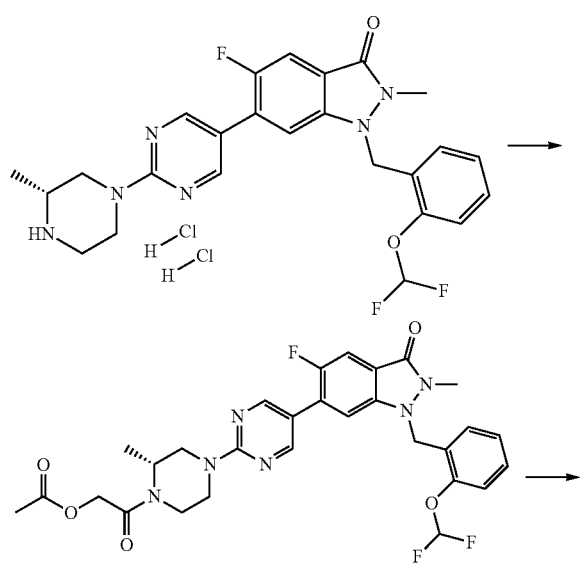

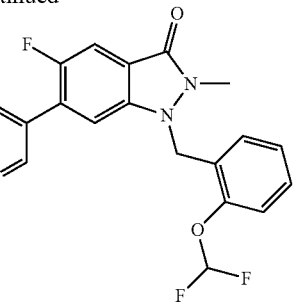

Step 1: (R)-2-(4-(5-(1-(2-(Difluoromethoxy)benzyl)-5-fluoro-2-methyl-3-oxo-2,3-dihydro-H-indazol-6-yl)pyrimidin-2-yl)-2-methylpiperazin-1-yl)-2-oxoethyl acetate (R)-1-(2-(Difluoromethoxy)benzyl)-5-fluoro-2-methyl-6-(2-(3-methylpiperazin-1-yl)pyrimidin-5-yl)-1H-indazol-3(2H)-one dihydrochloride (0.5 g, 0.875 mmol) (synthesized in a manner similar to Example #3, step 1 from (R)-tert-butyl 4-(5-(1-(2-(difluoromethoxy)benzyl)-5-fluoro-2-methyl-3-oxo-2,3-dihydro-1H-indazol-6-yl)pyrimidin-2-yl)-2-methylpiperazine-1-carboxylate (synthesized in a manner similar to Example #8 from 6-bromo-1-(2-(difluoromethoxy)benzyl)-5-fluoro-2-methyl-1H-indazol-3(2H)-one (Preparation #40) and (R)-tert-butyl 4-(5-bromopyrimidin-2-yl)-2-methylpiperazine-1-carboxylate (synthesized in a manner similar to Preparation #13 from (R)-tert-butyl 2-methylpiperazine-1-carboxylate and 5-bromo-2-chloropyrimidine))) in DCM (8 mL) with TEA (0.46 mL, 3.3 mmol) was cooled in an ice/water bath then treated with 2-chloro-2-oxoethyl acetate (0.179 g, 1.31 mmol). The mixture was stirred for about 15 min then washed twice with water (10 mL), dried over magnesium sulfate, filtered and concentrated to give the title compound (0.498 g, 95%); LC/MS (Table A, Method i) $R_t$=1.33 min; MS m/z: 599 (M+H)$^+$.

Step 2: (R)-1-(2-(Difluoromethoxy)benzyl)-5-fluoro-6-(2-(4-(2-hydroxyacetyl)-3-methylpiperazin-1-yl)pyrimidin-5-yl)-2-methyl-1H-indazol-3(2H)-one (R)-2-(4-(5-(1-(2-(Difluoromethoxy)benzyl)-5-fluoro-2-methyl-3-oxo-2,3-dihydro-1H-indazol-6-yl)pyrimidin-2-yl)-2-methylpiperazin-1-yl)-2-oxoethyl acetate (10.0 g, 16.7 mmol) in ethanol (150 mL) with 4-methylbenzenesulfonic acid hydrate (0.186 g, 0.978 mmol) was heated at about 77° C. for about 30 h. The mixture was cooled and concentrated under reduced pressure then dissolved in EtOAc (250 mL). The organic solution was washed with water (50 mL) then with sat. aq. sodium bicarbonate (30 mL), dried over magnesium sulfate, filtered and concentrated. The material was purified by supercritical fluid chromatography (Table C, Method a) to give the title compound (R)-1-(2-(difluoromethoxy)benzyl)-5-fluoro-6-(2-(4-(2-hydroxyacetyl)-3-methylpiperazin-1-yl)pyrimidin-5-yl)-2-methyl-1H-indazol-3(2H)-one (7.88 g, 81%); LC/MS (Table A, Method a) $R_t$=1.86 min; MS m/z: 557 (M+H)$^+$. (TNF IC$_{50}$=A).

287

Example #60*: (R)-1-(2-(Difluoromethoxy)benzyl)-5-fluoro-6-(6-(4-(2-hydroxyacetyl)-3-methylpiperazin-1-yl)pyridin-3-yl)-2-methyl-1H-indazol-3(2H)-one

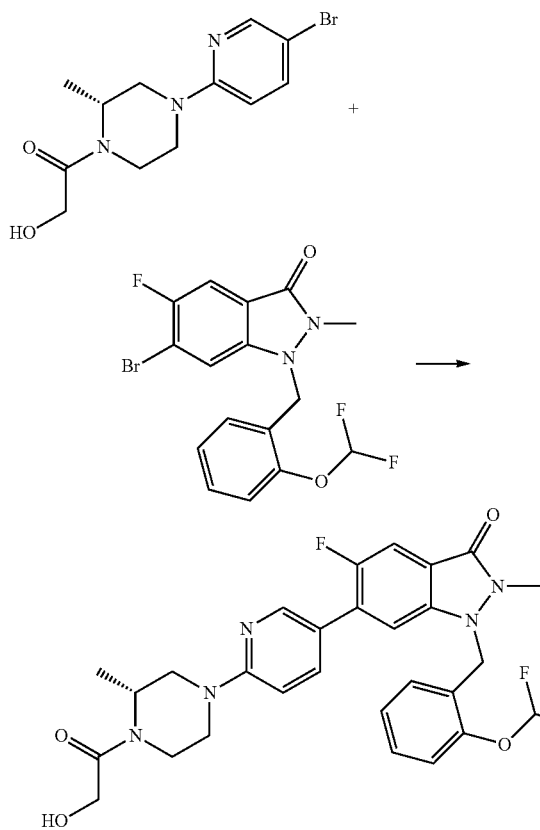

The title compound was synthesized in a manner similar to Example #8 from 6-bromo-1-(2-(difluoromethoxy)benzyl)-5-fluoro-2-methyl-1H-indazol-3(2H)-one (Preparation #40) and (R)-1-(4-(5-bromopyridin-2-yl)-2-methylpiperazin-1-yl)-2-hydroxyethanone (Preparation #55); LC/MS (Table A, Method a) $R_t$=1.88 min; MS m/z: 556 (M+H)$^+$. (TNF IC$_{50}$=A).

Example #61*: (R)-2-(6-((6-(2-(4-Acetyl-3-methylpiperazin-1-yl)pyrimidin-5-yl)-2-methyl-3-oxo-2,3-dihydro-1H-indazol-1-yl)methyl)-5-(trifluoromethyl)pyridin-2-yl)acetonitrile

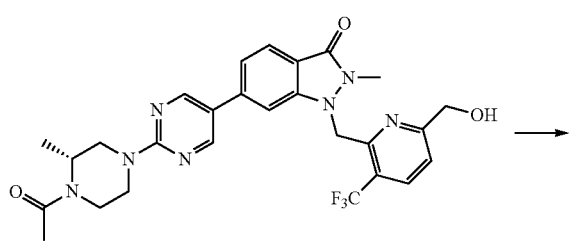

288

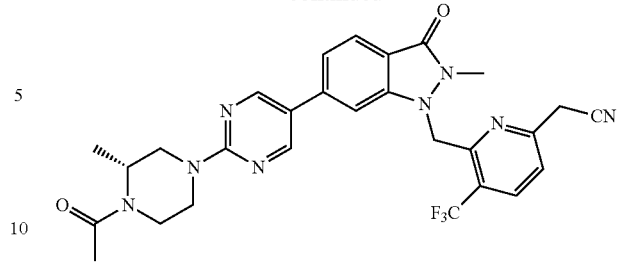

(R)-6-(2-(4-Acetyl-3-methylpiperazin-1-yl)pyrimidin-5-yl)-1-((6-(hydroxymethyl)-3-(trifluoromethyl)pyridin-2-yl)methyl)-2-methyl-1H-indazol-3(2H)-one (55 mg, 0.099 mmol) (synthesized in a manner similar to Example #18 from (R)-6-(2-(4-acetyl-3-methylpiperazin-1-yl)pyrimidin-5-yl)-2-methyl-1-((3-(trifluoromethyl)-6-((trityloxy)methyl)pyridin-2-yl)methyl)-1H-indazol-3(2H)-one (synthesized in a manner similar to Preparation #4, step 1 from 2-(bromomethyl)-3-(trifluoromethyl)-6-((trityloxy)methyl)pyridine (Preparation #61) and (R)-6-(2-(4-acetyl-3-methyl-piperazin-1-yl)pyrimidin-5-yl)-2-methyl-1H-indazol-3(2H)-one (Preparation #28))) in DCM (2 mL) with DIEA (0.026 mL, 0.15 mmol) was cooled in an ice/water bath then MsCl (0.012 mL, 0.16 mmol) was added. The mixture was warmed to rt then stirred for about 15 min. A second portion of DIEA (0.026 mL, 0.15 mmol) and MsCl (0.012 mL, 0.16 mmol) were added. After about 5 min, the mixture was concentrated under reduced pressure then DMF (2 mL) and NaCN (28 mg, 0.57 mmol) were added. The mixture was stirred for about 90 min then a second portion of NaCN (30 mg, 0.61 mmol) was added. The mixture was stirred for about 90 min then purified directly by preparative reverse phase HPLC (Hypersil HS C18 column, 250 mm×21.2 mm, 8 μm particle size, flow rate 21 mL/min, detection 254 nm, A=0.05 N NH$_4$OAc pH 4.5 buffer, B=MeCN, 10 to 100% over 25 min) to afford the title compound; LC/MS (Table A, Method i) $R_t$=2.31 min; MS m/z: 243(M+H)$^+$. (TNF IC$_{50}$=A).

Example #62*: (R)-1-(2-(Difluoromethoxy)-5-methylbenzyl)-6-(2-(4-(2-hydroxyacetyl)-3-methylpiperazin-1-yl)pyrimidin-5-yl)-2-(methyl-d$_3$)-1H-indazol-3(2H)-one

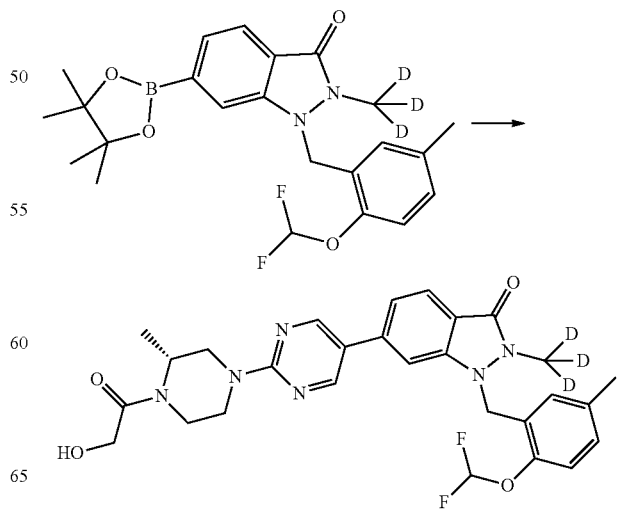

(R)-1-(2-(Difluoromethoxy)-5-methylbenzyl)-6-(2-(4-(2-hydroxyacetyl)-3-methylpiperazin-1-yl)pyrimidin-5-yl)-2-(methyl-$d_3$)-1H-indazol-3(2H)-one was prepared in a similar fashion to Example #14, step 4 using 1-(2-(difluoromethoxy)-5-methylbenzyl)-2-(methyl-$d_3$)-6-(4,4,5,5-tetramethyl-1,3,2-dioxaborolan-2-yl)-1H-indazol-3(2H)-one (Preparation #59) and (R)-1-(4-(5-bromopyrimidin-2-yl)-2-methylpiperazin-1-yl)-2-hydroxyethanone (Preparation #15) to give the title compound (41%); LC/MS (Table A, Method a) $R_t$=1.88 min; MS m/z: 556 (M+H)$^+$. (TNF IC$_{50}$=A).

Example #63*: (R)-6-(2-(4-Acetyl-3-methylpiperazin-1-yl)pyrimidin-5-yl)-1-(2-(difluoromethoxy)-5-methylbenzyl)-2-methyl-$d_3$-1H-indazol-3(2H)-one

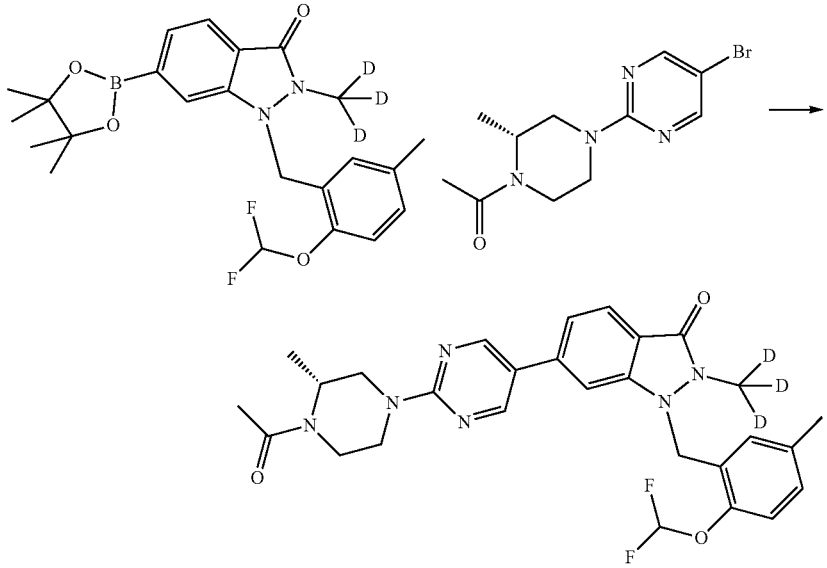

The reaction was performed using 1-(2-(difluoromethoxy)-5-methylbenzyl)-2-methyl-$d_3$-6-(4,4,5,5-tetramethyl-1,3,2-dioxaborolan-2-yl)-1H-indazol-3(2H)-one (Preparation #59) and (R)-1-(4-(5-bromopyrimidin-2-yl)-2-methylpiperazin-1-yl)ethanone (Preparation #16) in a similar fashion to Example #15, step 4 to afford the title product (48 mg, 49%); LC/MS (Table A, Method a) $R_t$=1.97 min; MS m/z: 540 (M+H)$^+$. (TNF IC$_{50}$=A).

Example #64*: (R)-6-(2-(4-Acetyl-3-methylpiperazin-1-yl)pyrimidin-5-yl)-1-((1-(2-hydroxyethyl)-4-(trifluoromethyl)-1H-pyrrol-3-yl)methyl)-2-methyl-1H-indazol-3(2H)-one

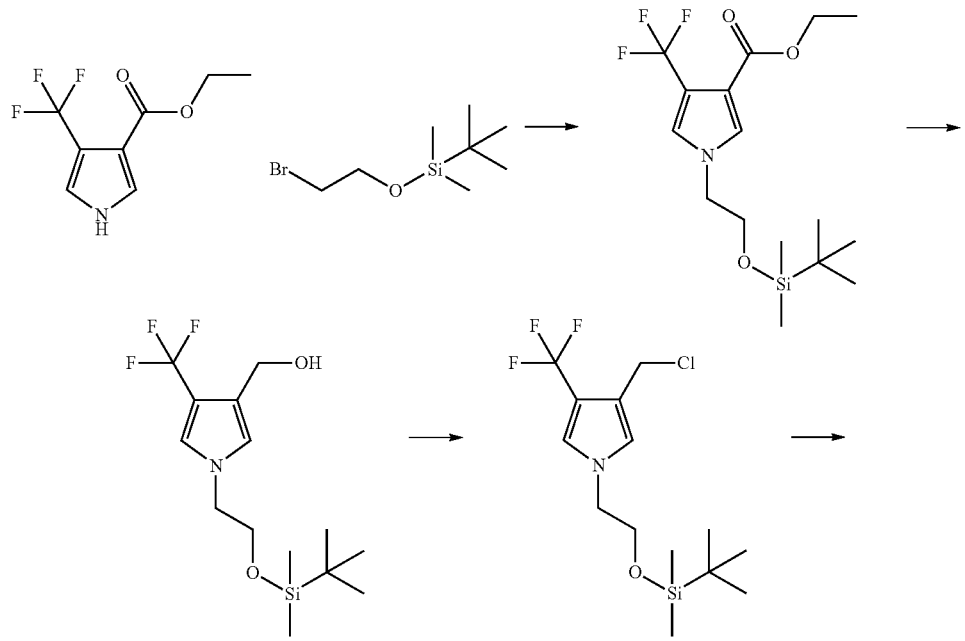

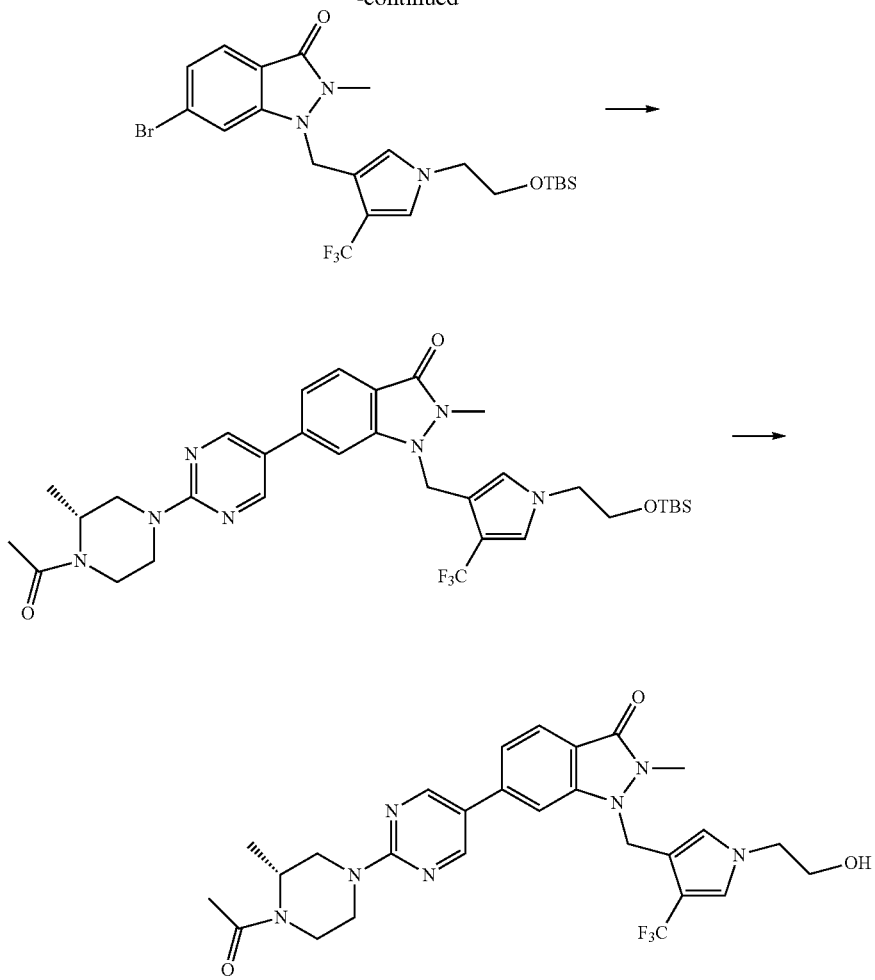

Step 1: Ethyl 1-(2-((tert-butyldimethylsilyl)oxy)ethyl)-4-(trifluoromethyl)-1H-pyrrole-3-carboxylate To a solution of ethyl 4-(trifluoromethyl)-1H-pyrrole-3-carboxylate (1.00 g, 4.83 mmol)(synthesized according to WO 2009147167 A1) and THF (10 mL) under $N_2$ at about 0° C. was added NaH (60% dispersion in mineral oil) (0.212 g, 5.31 mmol) in one portion. After about 5 min, (2-bromoethoxy)(tert-butyl)dimethylsilane (1.50 g, 6.28 mmol) was added and the mixture was stirred at rt for about 72 h. The reaction was quenched with $NaHCO_3$(20 mL), extracted with EtOAc (2×50 mL). The organic layer was dried over $MgSO_4$, filtered, and concentrated. The residue was purified on silica gel (0-5% EtOAc/DCM) to afford the title product (1.16 g, 66%); LC/MS (Table A, Method i) $R_t$=2.21 min; MS m/z: 366 (M+H)$^+$.

Step 2: (1-(2-((tert-Butyldimethylsilyl)oxy)ethyl)-4-(trifluoromethyl)-1H-pyrrol-3-yl)methanol The reaction was performed using ethyl 1-(2-((tert-butyldimethylsilyl)oxy)ethyl)-4-(trifluoromethyl)-1H-pyrrole-3-carboxylate in a similar fashion to Preparation #52, step 2 to afford the title product (1.00 g, 70%); LC/MS (Table A, Method i) $R_t$=1.41 min; MS m/z: 324 (M+H)$^+$.

Step 3: 1-(2-((tert-Butyldimethylsilyl)oxy)ethyl)-3-(chloromethyl)-4-(trifluoromethyl)-1H-pyrrole A solution of thionyl chloride (368 mg, 3.09 mmol) in DCM (5.00 mL) was added portionwise to a solution of (1-(2-((tert-butyldimethylsilyl)oxy)ethyl)-4-(trifluoromethyl)-1H-pyrrol-3-yl)methanol (500 mg, 1.55 mmol) and 2,6-dimethylpyridine (994 mg, 9.28 mmol) in DCM (10 mL). The reaction was stirred at rt for about 10 min. The volatiles were removed at rt under reduced pressure to afford the title product (529 mg, 100%). For analytical purposes, a sample of the title product was quenched with MeOH; LC/MS (Table A, Method i) $R_t$=2.22 min; MS m/z: 338 (M+H-Cl+MeO)$^+$.

Step 4: 6-Bromo-1-((1-(2-((tert-butyldimethylsilyl)oxy)ethyl)-4-(trifluormethyl)-H-pyrrol-3-yl)methyl)-2-methyl-1H-indazol-3(2H)-one The reaction was performed using 1-(2-((tert-butyldimethylsilyl)oxy)ethyl)-3-(chloromethyl)-4-(trifluoromethyl)-1H-pyrrole and 6-bromo-2-methyl-1H-indazol-3(2H)-one (Preparation #1) in a similar fashion to Preparation #4, step 1 to afford the title product (0.48 g, 85%); LC/MS (Table A, Method i) $R_t$=2.19 min; MS m/z: 532 and 534 (M+H)$^+$.

Step 5: (R)-6-(2-(4-Acetyl-3-methylpiperazin-1-yl) pyrimidin-5-yl)-1-((1-(2-((tert-butyldimethylsilyl) oxy)ethyl)-4-(trifluoromethyl)-1H-pyrrol-3-yl) methyl)-2-methyl-1H-indazol-3(2H)-one The reaction was performed using 6-bromo-1-((1-(2-((tert-butyldimethylsilyl)oxy)ethyl)-4-(trifluoromethyl)-1H-pyrrol-3-yl)methyl)-2-methyl-1H-indazol-3(2H)-one and (R)-1-(4-(5-bromopyrimidin-2-yl)-2-methylpiperazin-1-yl) ethanone (Preparation #16) in a similar fashion to Example #8 to afford the title product (0.157 g, 69%); LC/MS (Table A, Method i) $R_t$=1.89 min; MS m/z: 672 (M+H)$^+$.

Step 6: (R)-6-(2-(4-Acetyl-3-methylpiperazin-1-yl) pyrimidin-5-yl)-1-((1-(2-hydroxyethyl)-4-(trifluoromethyl)-1H-pyrrol-3-yl)methyl)-2-methyl-1H-indazol-3(2H)-one The reaction was performed using (R)-6-(2-(4-acetyl-3-methylpiperazin-1-yl)pyrimidin-5-yl)-1-((1-(2-((tert-butyldimethylsilyl)oxy)ethyl)-4-(trifluoromethyl)-1H-pyrrol-3-yl)methyl)-2-methyl-1H-indazol-3(2H)-one in a similar fashion to Example #35, step 3 to afford the title product (0.102 g, 77%); LC/MS (Table A, Method a) $R_t$=1.70 min; MS m/z: 558 (M+H)$^+$. (TNF IC$_{50}$=A).

Example #65*: (R)-6-(2-(4-acetyl-2-methylpiperazin-1-yl)pyrimidin-5-yl)-1-(2-(difluoromethoxy)-6-(hydroxymethyl)benzyl)-2-methyl-1H-indazol-3 (2H)-one

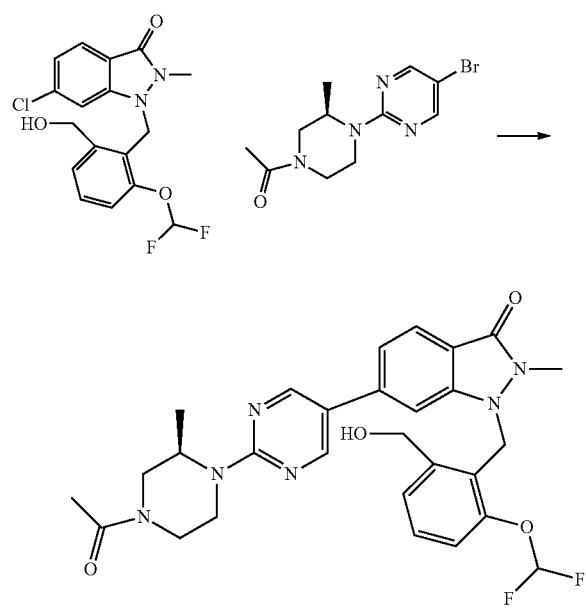

(R)-6-(2-(4-Acetyl-2-methylpiperazin-1-yl)pyrimidin-5-yl)-1-(2-(difluoromethoxy)-6-(hydroxymethyl)benzyl)-2-methyl-1H-indazol-3(2H)-one was prepared in a similar fashion to Example #33, step 9 using 6-chloro-1-(2-(difluoromethoxy)-6-(hydroxymethyl)benzyl)-2-methyl-1H-indazol-3(2H)-one (Example #33, step 7) and (R)-1-(4-(5-bromopyrimidin-2-yl)-3-methylpiperazin-1-yl)ethanone (prepared in a similar fashion to Preparation #13 using 5-bromo-2-chloropyrimidine and (R)-1-(3-methylpiperazin-1-yl)ethanone, trifluoroacetic acid salt (prepared in a similar fashion to Preparation #19, step 4 using (R)-tert-butyl 4-acetyl-2-methylpiperazine-1-carboxylate (prepared in a similar fashion to Preparation #16 using (R)-tert-butyl 2-methylpiperazine-1-carboxylate))) to give the title compound (0.060 g, 38%); LC/MS (Table A, Method e) $R_t$=1.68 min; MS m/z: 553(M+H)$^+$. (TNF IC$_{50}$=A).

Example #66: (R)-7-(5-(1-(2-(difluoromethoxy)-6-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one

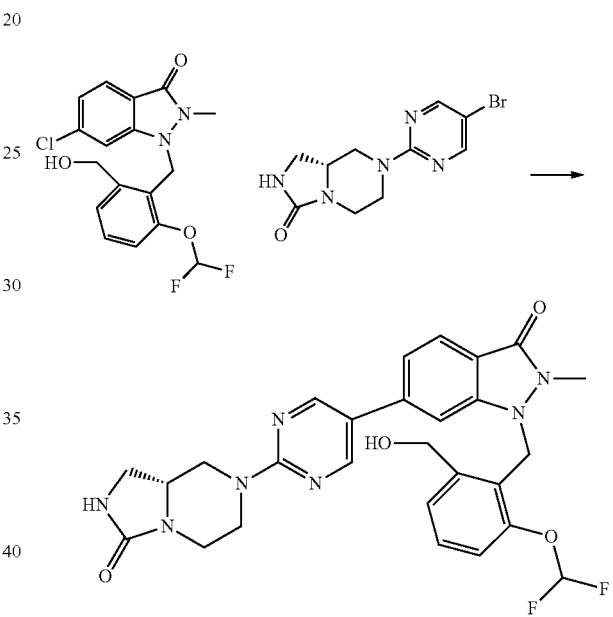

(R)-6-(2-(4-Acetyl-2-methylpiperazin-1-yl)pyrimidin-5-yl)-1-(2-(difluoromethoxy)-6-(hydroxymethyl)benzyl)-2-methyl-1H-indazol-3(2H)-one was prepared in a similar fashion to Example #33, step 9 using 6-chloro-1-(2-(difluoromethoxy)-6-(hydroxymethyl)benzyl)-2-methyl-1H-indazol-3(2H)-one (Example #33, step 7) and (R)-1-(4-(5-bromopyrimidin-2-yl)-3-methylpiperazin-1-yl)ethanone (prepared in a similar fashion to Preparation #13 using 5-bromo-2-chloropyrimidine and (R)-1-(3-methylpiperazin-1-yl)ethanone, trifluoroacetic acid salt (prepared in a similar fashion to Preparation #19, step 4 using (R)-tert-butyl 4-acetyl-2-methylpiperazine-1-carboxylate (prepared in a similar fashion to Preparation #16 using (R)-tert-butyl 2-methylpiperazine-1-carboxylate))) to give the title compound (0.060 g, 38%); LC/MS (Table A, Method e) $R_t$=1.68 min; MS m/z: 553(M+H)$^+$. (TNF IC$_{50}$=A).

The compounds shown in Table 29 were synthesized in a manner similar to Example #2 from (R)-hexahydroimidazo[1,5-a]pyrazin-3(2H)-one (Preparation #46) and the corresponding 2-chloropyrimidines.

TABLE 29

| 2-Chloropyrimidine | Product | Example # | R_f min (Table A, Method) | m/z ESI+ (M + H)+ | TNF IC_{50} |
|---|---|---|---|---|---|
| 6-(2-Chloropyrimidin-5-yl)-2-methyl-1-((5-methyl-2-(trifluoromethyl)pyridin-3-yl)methyl)-1,2-dihydro-3H-indazol-3-one (Preparation #47) | | 29.1 | 1.68 (a) | 539 | B |
| 6-(2-Chloropyrimidin-5-yl)-2-methyl-1-((2-(trifluoromethyl)pyridin-3-yl)methyl)-1,2-dihydro-3H-indazol-3-one (Preparation #48) | | 29.2 | 1.61 (a) | 525 | B |
| 6-(2-Chloropyrimidin-5-yl)-2-methyl-1-(5-methyl-2-(trifluoromethyl)benzyl)-1,2-dihydro-3H-indazol-3-one (Preparation #49) | | 29.3 | 1.96 (a) | 538 | A |
| 1-((5-Chloro-1,3-dihydroisobenzofuran-4-yl)methyl)-6-(2-chloropyrimidin-5-yl)-2-methyl-1,2-dihydro-3H-indazol-3-one (Preparation #50) | | 29.4 | 1.81 (a) | 532 | A |
| 1-(5-Chloro-2-(trifluoromethyl)benzyl)-6-(2-chloropyrimidin-5-yl)-2-methyl-1H-indazol-3(2H)-one (prepared in a similar manner to Example #1 using 6-(2-chloropyrimidin-5-yl)-2-methyl-1H-indazol-3(2H)-one (Preparation #23) and 2-(bromomethyl)-4-chloro-1-(trifluoromethyl)benzene | | 29.5 | 2.02 (a) | 558 | A |

TABLE 29-continued

| 2-Chloropyrimidine | Product | Example # | R, min (Table A, Method) | m/z ESI+ (M + H)+ | TNF IC50 |
|---|---|---|---|---|---|
| 6-(2-Chloropyrimidin-5-yl)-1-((3-(difluoromethoxy)-6-methylpyridin-2-yl)methyl)-2-methyl-1H-indazol-3(2H)-one (Preparation #57) | | 29.6 | 1.66 (a) | 537 | B |

Example #67: (R)-4-(Difluoromethoxy)-3-((2-methyl-3-oxo-6-(2-(3-oxohexahydroimidazo[1,5-a]pyrazin-7(1H)-yl)pyrimidin-5-yl)-2,3-dihydro-1H-indazol-1-yl)methyl)benzyldimethylcarbamate

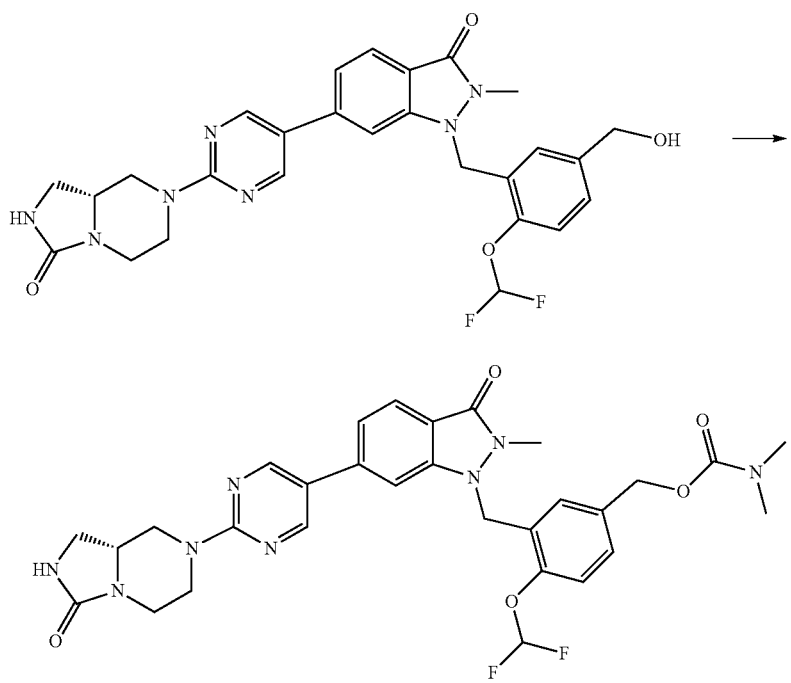

A solution of 4-nitrophenyl chloroformate (0.058 g, 0.29 mmol) and DIEA (0.076 mL, 0.44 mmol) in DCM (0.725 mL) was treated with a solution of (R)-7-(5-(1-(2-(difluoromethoxy)-5-(hydroxymethyl)benzyl)-2-methyl-3-oxo-2,3-dihydro-1H-indazol-6-yl)pyrimidin-2-yl)hexahydroimidazo[1,5-a]pyrazin-3(2H)-one (0.080 g, 0.14 mmol) (Example #16.1) in DMF (0.725 mL) and the resulting solution was allowed to stir at ambient temperature for about 45 min. Additional 4-nitrophenyl chloroformate (0.058 g, 0.29 mmol) and DIEA (0.076 mL, 0.44 mmol) were each added and stirring was continued for about 16 h. Dimethylamine (2 M in THF) (1.0 mL, 2.0 mmol) was added dropwise via syringe and stirring was continued for about 10 min. The reaction mixture was partitioned between EtOAc (10 mL) and water (10 mL). The organic phase was washed with sat. aq. NaCl (5 mL), dried over $Na_2SO_4$, filtered, and concentrated under reduced pressure. The sample was purified on silica gel using a gradient of 0-5% MeOH in DCM to give the title product (0.052 g, 58%); LC/MS (Table A, Method a) $R_f$=1.73 min; MS m/z: 623(M+H)+. (TNF IC50=A).

Example #68: (R)-2-(4-(Difluoromethoxy)-3-((2-methyl-3-oxo-6-(2-(3-oxohexahydromidazo[1,5-a]pyrazin-7(1H)-yl)pyrimidin-5-yl)-2,3-dihydro-1H-indazol-1-yl)methyl)phenyl)acetonitrile

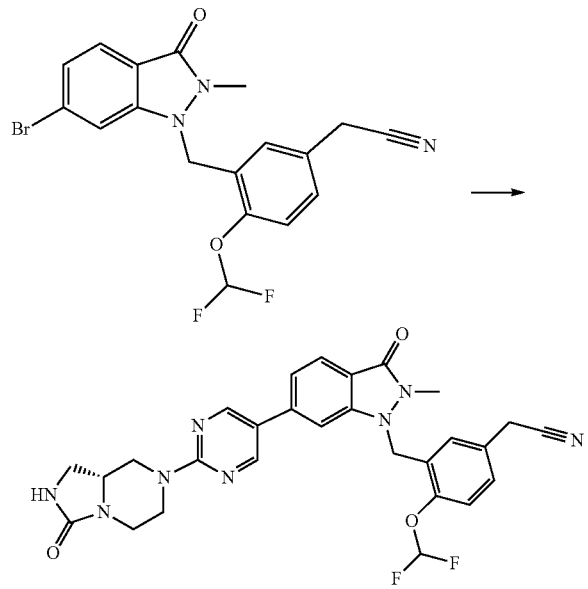

The reaction was performed using 2-(3-((6-bromo-2-methyl-3-oxo-2,3-dihydro-1H-indazol-1-yl)methyl)-4-(difluoromethoxy)phenyl)acetonitrile (Preparation #20) and (R)-7-(5-bromopyrimidin-2-yl)hexahydroimidazo[1,5-a]pyrazin-3(2H)-one (Preparation #13) in a similar fashion to Example #8 to give the title product (46%); LC/MS (Table A, Method a) R$_t$=1.68 min; MS m/z: 561 (M+H)$^+$. (TNF IC$_{50}$=A).

Example #69*: (R)-2-(4-(5-(1-(2-(Difluoromethoxy)-5-methylbenzyl)-2-methyl-3-oxo-2,3-dihydro-1H-indazol-6-yl)pyrimidin-2-yl)-2-methyl dihydrogen phosphate

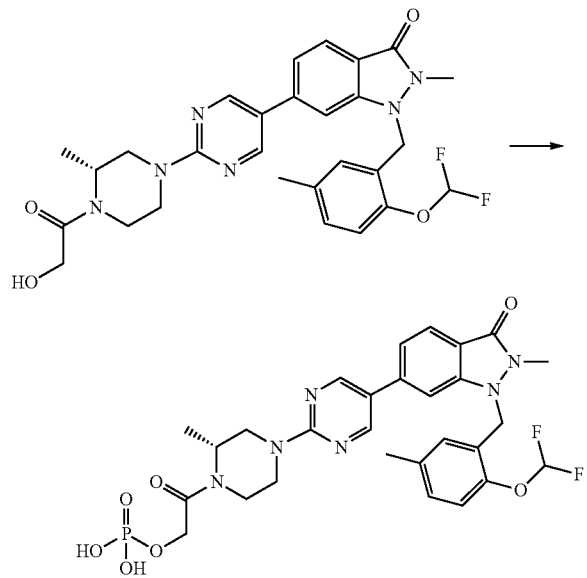

The reaction was performed using (R)-1-(2-(difluoromethoxy)-5-methylbenzyl)-6-(2-(4-(2-hydroxyacetyl)-3-methylpiperazin-1-yl)pyrimidin-5-yl)-2-methyl-1,2-dihydro-3H-indazol-3-one (Example #22.1) in a similar fashion to Example #31 to give the title product (37%); LC/MS (Table A, Method a) R$_t$=1.57 min; MS m/z: 633(M+H)$^+$. (TNF IC$_{50}$=A).

Example #70*: (R)-1-(2-(Difluoromethoxy)benzyl)-6-(2-(4-(2-hydroxyacetyl)-3-methylpiperazin-1-yl)pyrimidin-5-yl)-7-methoxy-2-methyl-1H-indazol-3(2H)-one

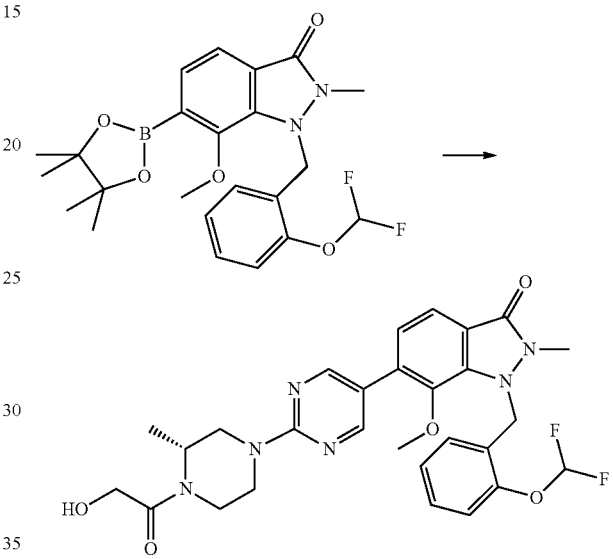

(R)-1-(2-(Difluoromethoxy)benzyl)-6-(2-(4-(2-hydroxyacetyl)-3-methylpiperazin-1-yl)pyrimidin-5-yl)-7-methoxy-2-methyl-1H-indazol-3(2H)-one was prepared in a similar fashion to Example #14, step 4 using (R)-1-(4-(5-bromopyrimidin-2-yl)-2-methylpiperazin-1-yl)-2-hydroxyethanone (Preparation #15) and 1-(2-(difluoromethoxy)benzyl)-7-methoxy-2-methyl-6-(4,4,5,5-tetramethyl-1,3,2-dioxaborolan-2-yl)-1H-indazol-3(2H)-one (prepared in a similar fashion to Preparation #4, step 2 using 6-bromo-1-(2-(difluoromethoxy)benzyl)-7-methoxy-2-methyl-1H-indazol-3(2H)-one (Preparation #66)) to afford the title compound (52%); LC/MS (Table A, Method a) R$_t$=1.86 min; MS m/z: 569 (M+H)$^+$. (TNF IC$_{50}$=A).

Example #71*: (R)-1-(2-Chlorobenzyl)-6-(2-(4-(2-hydroxyacetyl)-3-methylpiperazin-1-yl)pyrimidin-5-yl)-2-methyl-3-oxo-2,3-dihydro-1H-indazole-7-carbonitrile

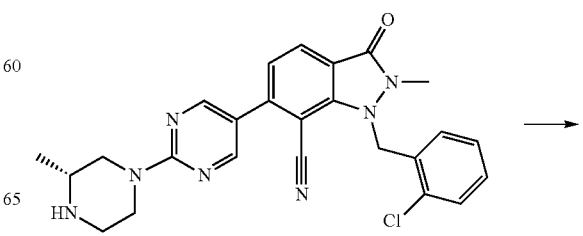

-continued

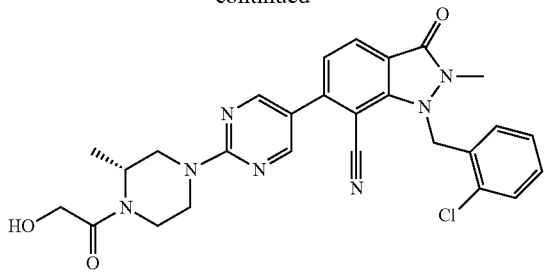

(R)-1-(2-Chlorobenzyl)-6-(2-(4-(2-hydroxyacetyl)-3-methylpiperazin-1-yl)pyrimidin-5-yl)-2-methyl-3-oxo-2,3-dihydro-1H-indazole-7-carbonitrile was prepared in a similar manner to Preparation #15 using (R)-1-(2-chlorobenzyl)-2-methyl-6-(2-(3-methylpiperazin-1-yl)pyrimidin-5-yl)-3-oxo-2,3-dihydro-1H-indazole-7-carbonitrile, 2 hydrochloric acid (prepared in a similar manner to Example #3, step 1 using (R)-tert-butyl 4-(5-(1-(2-chlorobenzyl)-7-cyano-2-methyl-3-oxo-2,3-dihydro-1H-indazol-6-yl)pyrimidin-2-yl)-2-methylpiperazine-1-carboxylate (prepared in a similar manner to Example #1 using 2-chlorobenzyl bromide and (R)-tert-butyl 4-(5-(7-cyano-2-methyl-3-oxo-2,3-dihydro-1H-indazol-6-yl)pyrimidin-2-yl)-2-methylpiperazine-1-carboxylate (prepared in a similar manner to Example #33, step 9 using 6-chloro-2-methyl-3-oxo-2,3-dihydro-1H-indazole-7-carbonitrile (Preparation #67) and (R)-tert-butyl 4-(5-bromopyrimidin-2-yl)-2-methylpiperazine-1-carboxylate (prepared in a similar manner to Preparation #13, step 1 using (R)-1-N-Boc-2-methylpiperazine)))) to afford the title compound (66%); LC/MS (Table A, Method a) $R_t$=1.84 min; MS m/z: 532 (M+H)$^+$. (TNF IC$_{50}$=B).

Example #72: (S)-7-(5-(2-methyl-1-((1-methyl-4-(trifluoromethyl)-1H-pyrazol-3-yl)methyl)-3-oxo-2,3-dihydro-1H-indazol-6-yl)pyrimidin-2-yl)hexahydroimidazo[1,5-a]pyrazin-3(2H)-one

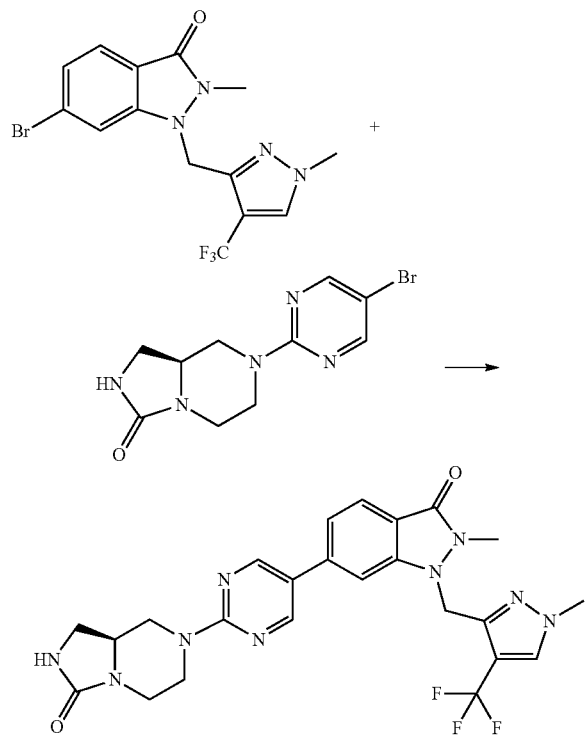

The reaction was performed in a similar manner to Example #8 using (S)-7-(5-bromopyrimidin-2-yl)hexahydroimidazo[1,5-a]pyrazin-3(2H)-one (0.108 g, 0.361 mmol (Preparation #13) and 6-bromo-2-methyl-1-((1-methyl-4-(trifluoromethyl)-1H-pyrazol-3-yl)methyl)-1H-indazol-3(2H)-one (0.108 g, 0.278 mmol) (synthesized in a similar fashion to Example #1 from 6-bromo-2-methyl-1H-indazol-3(2H)-one (Preparation #1) and 3-(bromomethyl)-1-methyl-4-(trifluoromethyl)-1H-pyrazole (synthesized in a similar fashion to Preparation #21, step 2 from (1-methyl-4-(trifluoromethyl)-1H-pyrazol-3-yl)methanol (Preparation #35, step 2) to give the title product (72%); (Table A, Method a) $R_t$=1.58 min; MS m/z: 528 (M+H)$^+$. (TNF IC$_{50}$=B).

Example #73*: (R)-6-(2-(4-Acetyl-3-methylpiperazin-1-yl)pyrimidin-5-yl)-2-methyl-1-((6-methyl-3-(trifluoromethyl)pyridin-2-yl)methyl)-1H-pyrazolo[3,4-b]pyridin-3(2H)-one

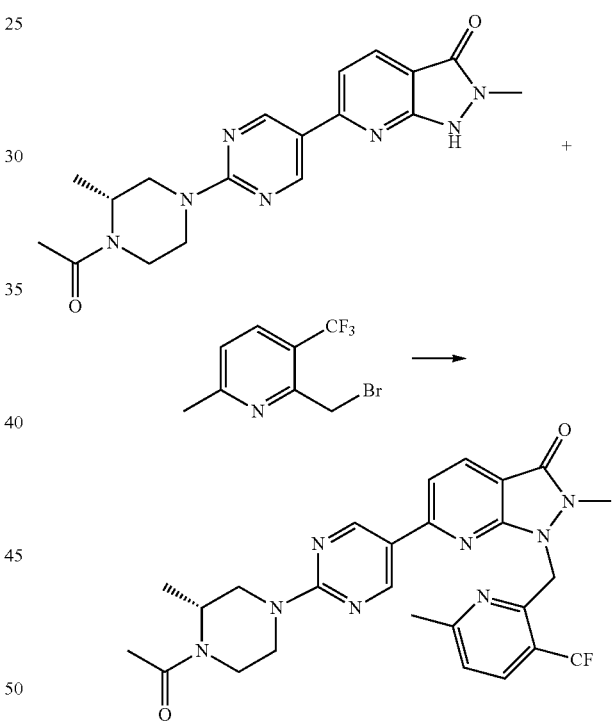

The reaction was performed in a similar manner to Example #1 using (R)-6-(2-(4-acetyl-3-methylpiperazin-1-yl)pyrimidin-5-yl)-2-methyl-1H-pyrazolo[3,4-b]pyridin-3(2H)-one (synthesized in a similar manner to Example #8 using 6-chloro-2-methyl-1H-pyrazolo[3,4-b]pyridin-3(2H)-one (Example #15, step 2) and (R)-1-(4-(5-bromopyrimidin-2-yl)-2-methylpiperazin-1-yl)ethanone (Preparation #16)) and 2-(bromomethyl)-6-methyl-3-(trifluoromethyl)pyridine (synthesized in a similar fashion to Preparation #14, step 6 from (6-methyl-3-(trifluoromethyl)pyridin-2-yl)methanol (Preparation #17)) to give the title product (20%); (Table A, Method a) $R_t$=1.92 min; MS m/z: 541 (M+H)$^+$. (TNF IC$_{50}$=A).

Example #74*: (R)-6-(2-(4-Acetyl-2-methylpiperazin-1-yl)pyrimidin-5-yl)-2-methyl-1-((6-methyl-3-(trifluoromethyl)pyridin-2-yl)methyl)-1H-indazol-3(2H)-one

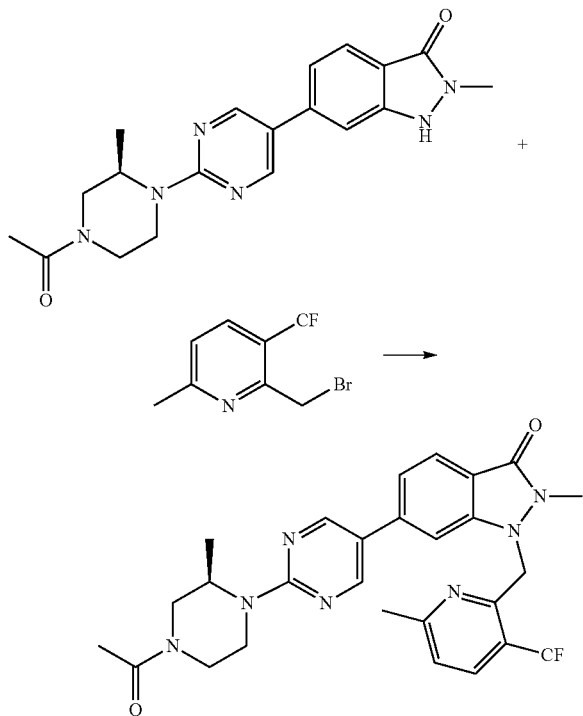

The reaction was performed in a similar manner to Example #1 using (R)-6-(2-(4-acetyl-2-methylpiperazin-1-yl)pyrimidin-5-yl)-2-methyl-1H-indazol-3(2H)-one (synthesized in a similar fashion to Example #8 from 6-bromo-2-methyl-1H-indazol-3(2H)-one (Preparation #1) and (R)-1-(4-(5-bromopyrimidin-2-yl)-3-methylpiperazin-1-yl)ethanone (prepared in a similar fashion to Preparation #13, step 1 using (R)-1-(3-methylpiperazin-1-yl)ethanone, trifluoroacetic acid salt (prepared in a similar fashion to Preparation #19, step 4 using (R)-tert-butyl 4-acetyl-2-methylpiperazine-1-carboxylate (prepared in a similar fashion to Preparation #16 using (R)-tert-butyl 2-methylpiperazine-1-carboxylate))) and 2-(bromomethyl)-6-methyl-3-(trifluoromethyl)pyridine (synthesized in a similar fashion to Preparation #14, step 6 from (6-methyl-3-(trifluoromethyl)pyridin-2-yl)methanol (Preparation #17)) to give the title product (63%); (Table A, Method a) R$_f$=1.89 min; MS m/z: 540 (M+H)$^+$. (TNF IC$_{50}$=A).

Example #75*: (R)-6-(2-(4-Acetyl-3-methylpiperazin-1-yl)pyrimidin-5-yl)-1-((3-(difluoromethoxy)-6-methylpyridin-2-yl)methyl)-2-methyl-1H-indazol-3(2H)-one

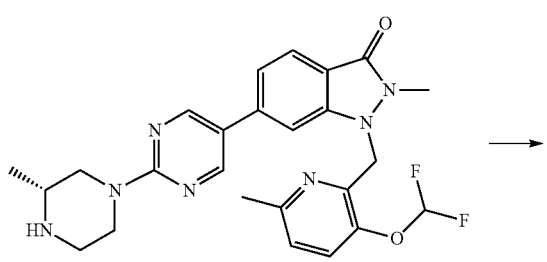

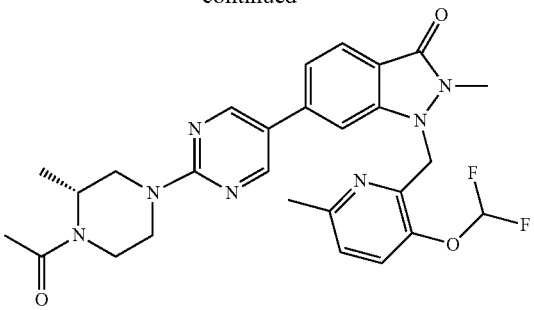

(R)-6-(2-(4-Acetyl-3-methylpiperazin-1-yl)pyrimidin-5-yl)-1-((3-(difluoromethoxy)-6-methylpyridin-2-yl)methyl)-2-methyl-1H-indazol-3(2H)-one was prepared in a similar fashion to Preparation #16 from (R)-1-((3-(difluoromethoxy)-6-methylpyridin-2-yl)methyl)-2-methyl-6-(2-(3-methylpiperazin-1-yl)pyrimidin-5-yl)-1H-indazol-3(2H)-one (prepared from tert-butyl (R)-2-methylpiperazine-1-carboxylate and 6-(2-chloropyrimidin-5-yl)-1-((3-(difluoromethoxy)-6-methylpyridin-2-yl)methyl)-2-methyl-1H-indazol-3(2H)-one (Preparation #57) in a similar fashion to Preparation #13, step 1); LC/MS (Table A, Method a) R$_f$=1.81 min; MS m/z: 539 (M+H)$^+$. (TNF IC$_{50}$=A).

Example #76*: (R)-1-((3-(Difluoromethoxy)-6-methylpyridin-2-yl)methyl)-6-(2-(4-(2-hydroxyacetyl)-3-methylpiperazin-1-yl)pyrimidin-5-yl)-2-methyl-1H-indazol-3(2H)-one

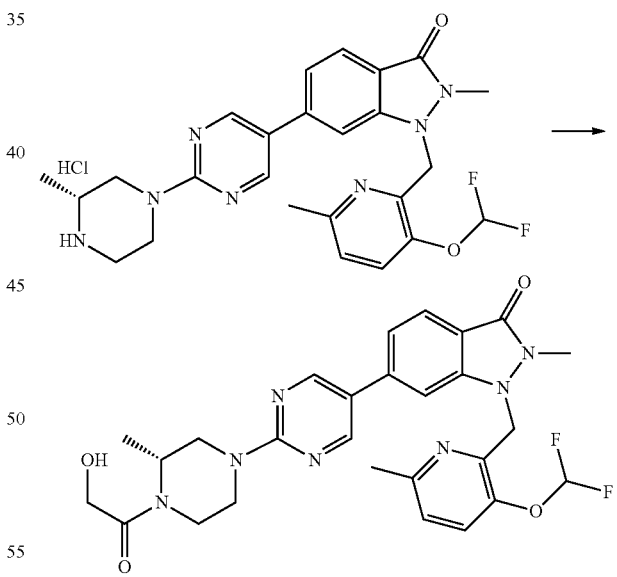

(R)-1-((3-(Difluoromethoxy)-6-methylpyridin-2-yl)methyl)-6-(2-(4-(2-hydroxyacetyl)-3-methylpiperazin-1-yl)pyrimidin-5-yl)-2-methyl-1H-indazol-3(2H)-one was prepared from (R)-1-((3-(difluoromethoxy)-6-methylpyridin-2-yl)methyl)-2-methyl-6-(2-(3-methylpiperazin-1-yl)pyrimidin-5-yl)-1H-indazol-3(2H)-one (prepared from tert-butyl (R)-2-methylpiperazine-1-carboxylate and 6-(2-chloropyrimidin-5-yl)-1-((3-(difluoromethoxy)-6-methylpyridin-2-yl)methyl)-2-methyl-1H-indazol-3(2H)-one (Preparation #57) in a similar fashion to Preparation

13, step 1) in a similar fashion to Preparation #15. LC/MS (Table A, Method a) $R_t$=1.72 min; MS m/z: 554 (M+H)$^+$. (TNF IC$_{50}$=A).

Example #77: 1-(2-(Difluoromethoxy)-6-(methoxymethyl)benzyl)-6-(2-(2-hydroxypropan-2-yl)pyrimidin-5-yl)-2-methyl-1H-indazol-3(2H)-one

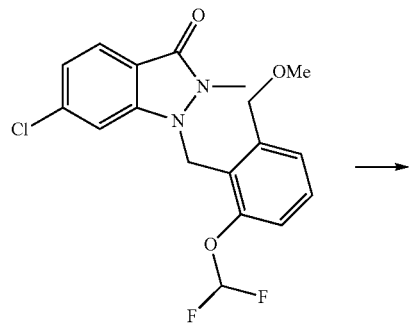

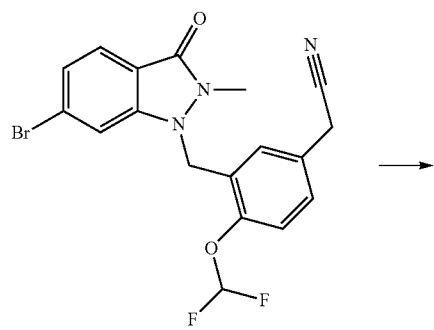

1-(2-(Difluoromethoxy)-6-(methoxymethyl)benzyl)-6-(2-(2-hydroxypropan-2-yl)pyrimidin-5-yl)-2-methyl-1H-indazol-3(2H)-one was prepared from 6-chloro-1-(2-(difluoromethoxy)-6-(methoxymethyl)benzyl)-2-methyl-1H-indazol-3(2H)-one (Example #33, step 8) and 2-(5-bromopyrimidin-2-yl)propan-2-ol in a similar fashion to Example #33, step 9. LC/MS (Table A, Method a) $R_t$=1.92 min; MS m/z: 485 (M+H)$^+$. (TNF IC$_{50}$=B).

Example #78*: (R)-2-(4-(difluoromethoxy)-3-((6-(2-(4-(2-hydroxy acetyl)-2-methylpiperazin-1-yl)pyrimidin-5-yl)-2-methyl-3-oxo-2,3-dihydro-1H-indazol-1-yl)methyl)phenyl)acetonitrile

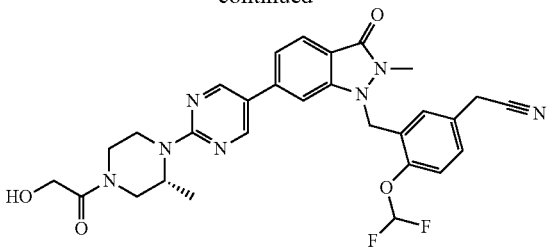

(R)-2-(4-(Difluoromethoxy)-3-((6-(2-(4-(2-hydroxyacetyl)-2-methylpiperazin-1-yl)pyrimidin-5-yl)-2-methyl-3-oxo-2,3-dihydro-1H-indazol-1-yl)methyl)phenyl)acetonitrile was prepared from 2-(3-((6-bromo-2-methyl-3-oxo-2,3-dihydro-1H-indazol-1-yl)methyl)-4-(difluoromethoxy)phenyl)acetonitrile (Preparation #20) and (R)-1-(4-(5-bromopyrimidin-2-yl)-3-methylpiperazin-1-yl)-2-hydroxyethanone (Preparation #22) in a similar fashion to Example #8. LC/MS (Table A, Method a) $R_t$=1.72 min; MS m/z: 578 (M+H)$^+$. (TNF IC$_{50}$=A).

Example #79*: (R)-2-(4-(Difluoromethoxy)-3-((2-methyl-3-oxo-6-(2-(3-oxotetrahydro-1H-oxazolo[3,4-a]pyrazin-7(3H)-yl)pyrimidin-5-yl)-2,3-dihydro-1H-indazol-1-yl)methyl)phenyl)acetonitrile

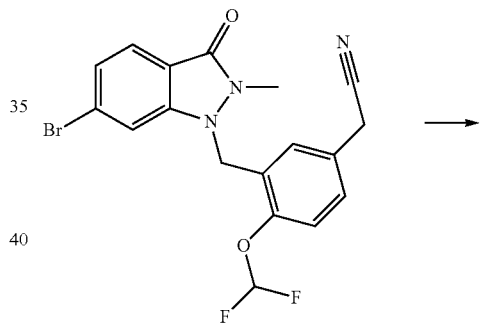

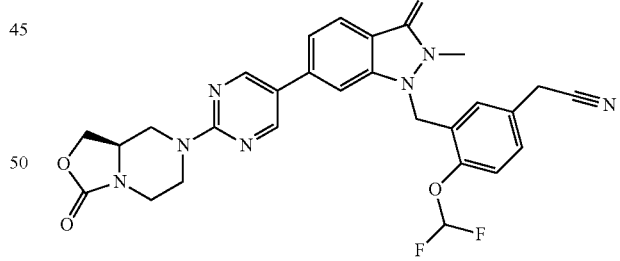

(R)-2-(4-(Difluoromethoxy)-3-((2-methyl-3-oxo-6-(2-(3-oxotetrahydro-1H-oxazolo[3,4-a]pyrazin-7(3H)-yl)pyrimidin-5-yl)-2,3-dihydro-1H-indazol-1-yl)methyl)phenyl)acetonitrile was prepared from 2-(3-((6-bromo-2-methyl-3-oxo-2,3-dihydro-1H-indazol-1-yl)methyl)-4-(difluoromethoxy)phenyl)acetonitrile (Preparation #20) and (R)-7-(5-bromopyrimidin-2-yl)tetrahydro-1H-oxazolo[3,4-a]pyrazin-3(5H)-one (prepared from 5-bromo-2-chloropyrimidine and (R)-tetrahydro-1H-oxazolo[3,4-a]pyrazin-3(5H)-one in a similar fashion to Preparation #13, step 1) in a similar fashion to Example #18. LC/MS (Table A, Method a) $R_t$=1.84 min; MS m/z: 562 (M+H)$^+$. (TNF IC$_{50}$=A).

Example #80*: (R)-1-(2-(Difluoromethoxy)-5-methylbenzyl)-6-(2-(4-(2-hydroxyacetyl)-2-methylpiperazin-1-yl)pyrimidin-5-yl)-2-methyl-1H-pyrazolo[3,4-b]pyridin-3(2H)-one

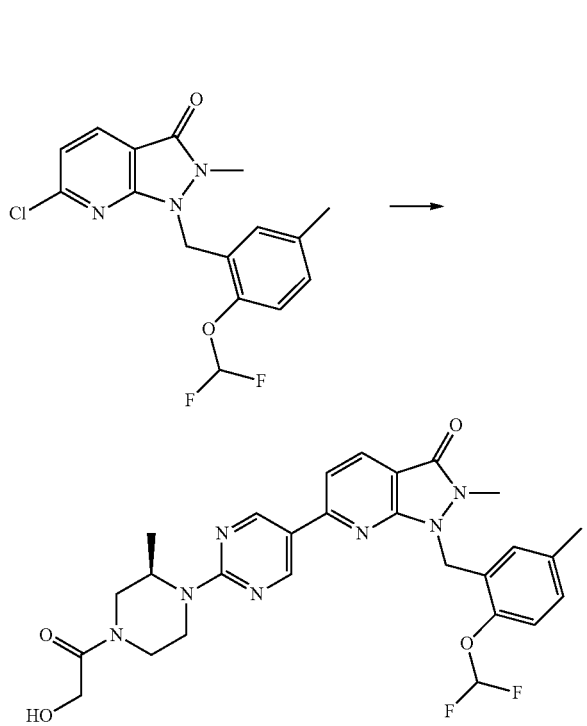

The compound was prepared in a manner similar to Example #8 from (R)-1-(4-(5-bromopyrimidin-2-yl)-3-methylpiperazin-1-yl)-2-hydroxyethanone (Preparation #22) and 6-chloro-1-(2-(difluoromethoxy)-5-methylbenzyl)-2-methyl-1H-pyrazolo[3,4-b]pyridin-3(2H)-one (prepared in a manner similar to Example #1 from 6-chloro-2-methyl-1H-pyrazolo[3,4-b]pyridin-3(2H)-one (Example #15, step 2) and 2-(bromomethyl)-1-(difluoromethoxy)-4-methylbenzene (prepared in a manner similar to Preparation #3, step 2 from (2-(difluoromethoxy)-5-methylphenyl)methanol)) (35%); LC/MS (Table A, Method e) R$_f$=1.93 min.; MS m/z 554 (M+H)$^+$. (TNF IC$_{50}$=A).

Example #81*: (R)-1-(2-Chloro-5-methylbenzyl)-6-(2-(4-(2-hydroxyacetyl)-2-methylpiperazin-1-yl)pyrimidin-5-yl)-2-methyl-1H-pyrazolo[3,4-b]pyridin-3(2H)-one

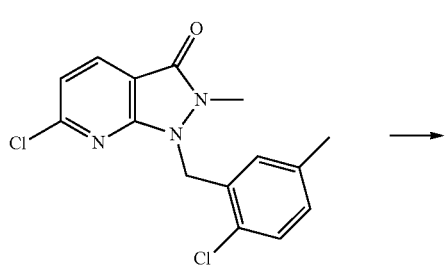

-continued

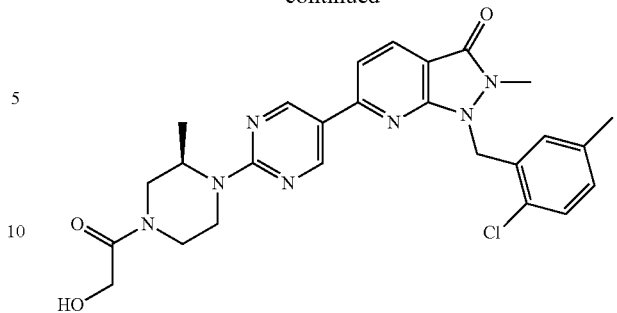

The compound was synthesized in a manner similar to Example #8 from (R)-1-(4-(5-bromopyrimidin-2-yl)-3-methylpiperazin-1-yl)-2-hydroxyethanone (Preparation #22) and 6-chloro-1-(2-chloro-5-methylbenzyl)-2-methyl-1H-pyrazolo[3,4-b]pyridin-3(2H)-one (prepared in a manner similar to Example #1 from 6-chloro-2-methyl-1H-pyrazolo[3,4-b]pyridin-3(2H)-one (Example #15, step 2) and 2-(bromomethyl)-1-chloro-4-methylbenzene (prepared in a manner similar to Preparation #3, step 2 from (2-chloro-5-methylphenyl)methanol (prepared in a manner similar to Preparation #32, step 4 from methyl 2-chloro-5-methylbenzoate))) (45%); LC/MS (Table A, Method e) R$_f$=2.02 min.; MS m/z: 522 (M+H)$^+$. (TNF IC$_{50}$=A).

Example #82*: (R)-6-(2-(4-Acetyl-3-methylpiperazin-1-yl)pyrimidin-5-yl)-1-(2-((difluoromethyl)thio)-4-methylbenzyl)-2-methyl-H-indazol-3(2H)-one

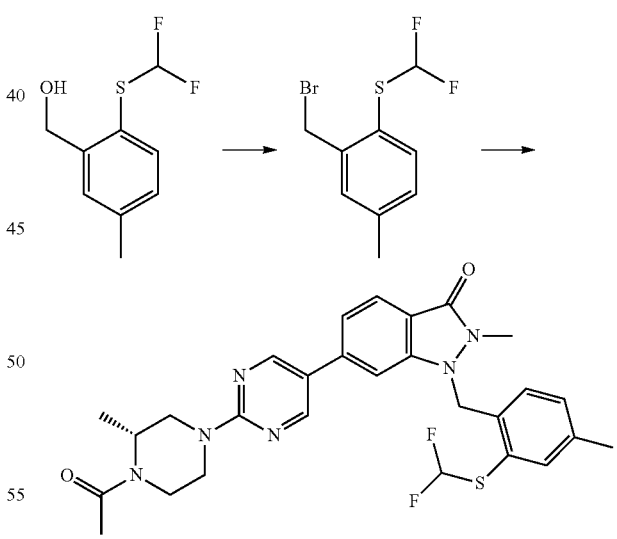

The compound was prepared in a manner similar to Example #1 from (R)-6-(2-(4-acetyl-3-methylpiperazin-1-yl)pyrimidin-5-yl)-2-methyl-1H-indazol-3(2H)-one (Preparation #28) and (2-(bromomethyl)-4-methylphenyl)(difluoromethyl)sulfane (prepared in a manner similar to Preparation #14, step 6 from (2-((difluoromethyl)thio)-5-methylphenyl)methanol (Preparation #18)) (63%); LC/MS (Table A, Method e) R$_f$=2.10 min; MS m/z 553(M+H)$^+$. (TNF IC$_{50}$=A).

Example #83: 1-(2-Chloro-5-((1-methyl-2-oxopiperidin-3-yl)amino)benzyl)-6-(2-(2-hydroxypropan-2-yl)pyrimidin-5-yl)-2-methyl-1H-indazol-3(2H)-one

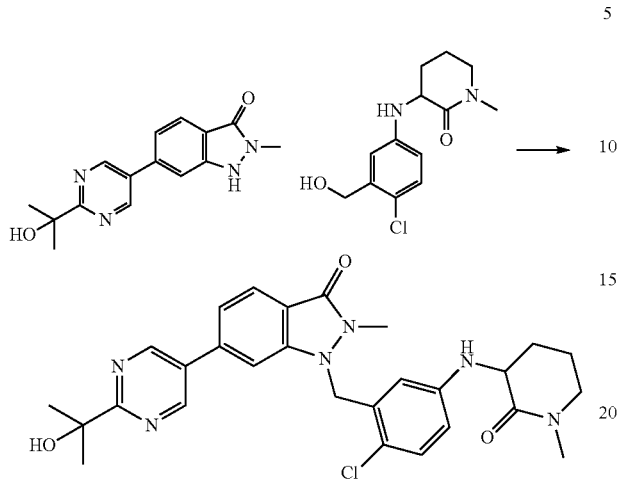

PPh$_3$ (156 mg, 0.600 mmol) and 3-((4-chloro-3-(hydroxymethyl)phenyl)amino)-1-methylpiperidin-2-one (Preparation #43) (0.100 g, 0.370 mmol) were combined in DCM (2 mL). Carbon tetrabromide (197 mg, 0.600 mmol) was added and the reaction was stirred for about 5 min at rt. K$_2$CO$_3$ (154 mg, 1.12 mmol), 6-(2-(2-hydroxypropan-2-yl)pyrimidin-5-yl)-2-methyl-1H-indazol-3(2H)-one (Preparation #19) (106 mg, 0.370 mmol), and DMF (2 mL) were added. DCM was removed in vacuo, then the reaction was heated to about 45° C. for about 90 min. The reaction was cooled and partitioned between EtOAc (10 mL) and water (10 mL). The organic layer was washed with water (10 mL) and sat. aq. NaCl (10 mL), then dried over MgSO$_4$, filtered, and concentrated in vacuo. Further purification via flash chromatography (0-10% MeOH in DCM) yielded the title compound (83 mg, 42%); LC/MS (Table A, Method e) R$_t$=1.75 min; MS m/z 535 (M+H)$^+$. (TNF IC$_{50}$=B).

Example #84: ((R)-7-(5-(1-((3-(Difluoromethoxy)-6-(hydroxymethyl)pyridin-2-yl)methyl)-2-methyl-3-oxo-2,3-dihydro-1H-indazol-6-yl)pyrimidin-2-yl)hexahydroimidazo[1,5-a]pyrazin-3(2H)-one

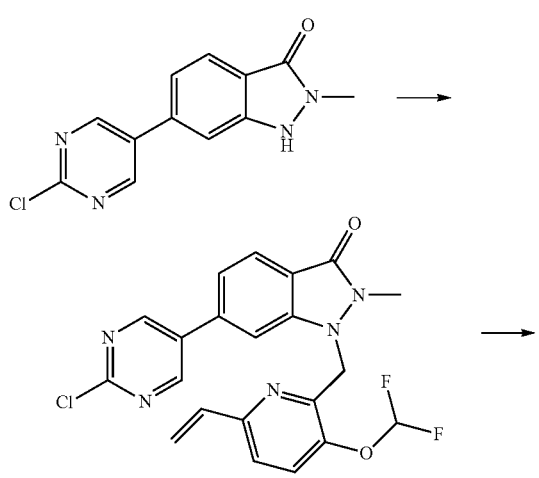

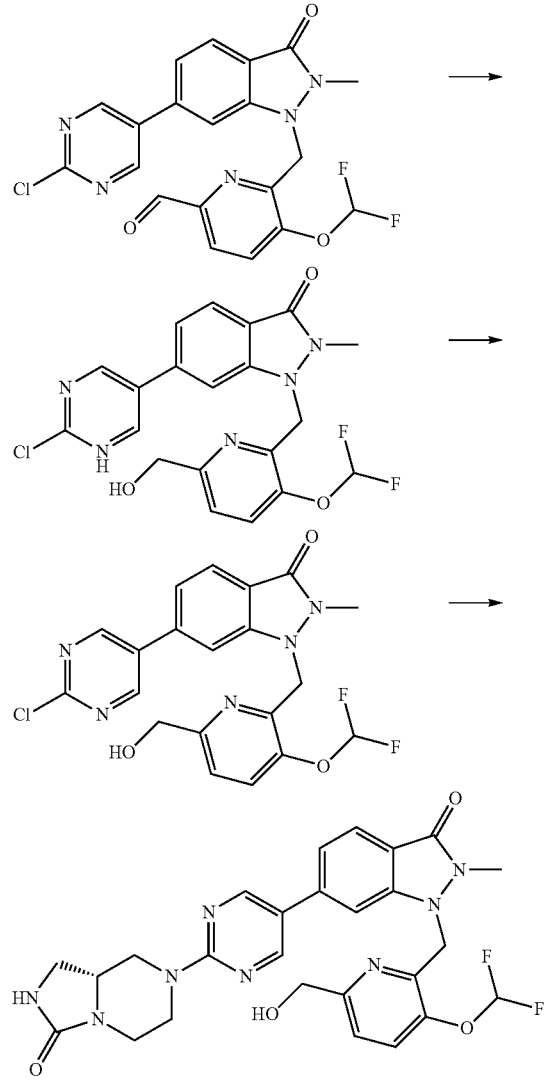

Step 1: 6-(2-Chloropyrimidin-5-yl)-1-((3-(difluoromethoxy)-6-vinylpyridin-2-yl)methyl)-2-methyl-1H-indazol-3(2H)-one The title compound was synthesized in a manner similar to Preparation #4, step 1 from 6-(2-chloropyrimidin-5-yl)-2-methyl-1H-indazol-3(2H)-one (Preparation #23) and 2-(bromomethyl)-3-(difluoromethoxy)-6-vinylpyridine (synthesized in a manner similar to Preparation #14, step 6 from (3-(difluoromethoxy)-6-vinylpyridin-2-yl)methanol (synthesized in a manner similar to Preparation #61, step 1 from tributyl(vinyl)stannane and (6-chloro-3-(difluoromethoxy)pyridin-2-yl)methanol (synthesized in a manner similar to Preparation #9 from 6-chloro-3-(difluoromethoxy)picolinaldehyde (synthesized in a manner similar to Example #4, step 1 from 6-chloro-3-(difluoromethoxy)-2-vinylpyridine (synthesized in a manner similar to Example #14, step 4 from 6-chloro-3-(difluoromethoxy)-2-iodopyridine and 4,4,5,5-tetramethyl-2-vinyl-1,3,2-dioxaborolane))))); LC/MS (Table A, Method i) R$_t$=1.19 min; MS m/z: 444 (M+H)$^+$.

Step 2: 6-((6-(2-Chloropyrimidin-5-yl)-2-methyl-3-oxo-2,3-dihydro-1H-indazol-1-yl)methyl)-5-(difluoromethoxy)picolinaldehyde The title compound was synthesized in a manner similar to Example #4, step 1 from 6-(2-chloropyrimidin-5-yl)-1-((3-(difluoromethoxy)-6-vinylpyridin-2-yl)methyl)-2-methyl-1H-indazol-3(2H)-one; LC/MS (Table A, Method i) $R_t$=1.05 min; MS m/z: 446 (M+H)$^+$.

Step 3: 6-(2-Chloro-1,6-dihydropyrimidin-5-yl)-1-((3-(difluoromethoxy)-6-(hydroxymethyl)pyridin-2-yl)methyl)-2-methyl-1H-indazol-3(2H)-one 6-((6-(2-Chloropyrimidin-5-yl)-2-methyl-3-oxo-2,3-dihydro-1H-indazol-1-yl)methyl)-5-(difluoromethoxy)picolinaldehyde (68 mg, 0.15 mmol) in MeOH (2 mL) was cooled in an ice/water bath then sodium tetrahydroborate (8.1 mg, 0.21 mmol) was added. After about 15 min, the mixture was concentrated under reduced pressure then partitioned between EtOAc and water. The organic solution was dried over magnesium sulfate, filtered and concentrated to give the title compound (60 mg, 87%); LC/MS (Table A, Method i) $R_t$=0.78 min; MS m/z: 450 (M+H)$^+$.

Step 4: 6-(2-Chloropyrimidin-5-yl)-1-((3-(difluoromethoxy)-6-(hydroxymethyl)pyridin-2-yl)methyl)-2-methyl-1H-indazol-3(2H)-one 6-(2-Chloro-1,6-dihydropyrimidin-5-yl)-1-((3-(difluoromethoxy)-6-(hydroxymethyl)pyridin-2-yl)methyl)-2-methyl-1H-indazol-3(2H)-one (55 mg, 0.12 mmol) suspended in 1,4-dioxane (10 mL) was treated with chloranil (58 mg, 0.24 mmol) then stirred at rt for about 12 h. The mixture was concentrated under reduced pressure then purified via flash chromatography on silica gel (0-10% DCM/MeOH) to give the title compound (22.2 mg, 41%); LC/MS (Table A, Method i) $R_t$=0.96 min; MS m/z: 448 (M+H)$^+$.

Step 5: ((R)-7-(5-(1-((3-(Difluoromethoxy)-6-(hydroxymethyl)pyridin-2-yl)methyl)-2-methyl-3-oxo-2,3-dihydro-1H-indazol-6-yl)pyrimidin-2-yl)hexahydroimidazo[1,5-a]pyrazin-3(2H)-one The title compound was synthesized in a manner similar to Preparation #13 from 6-(2-chloropyrimidin-5-yl)-1-((3-(difluoromethoxy)-6-(hydroxymethyl)pyridin-2-yl)methyl)-2-methyl-1H-indazol-3(2H)-one and (S)-hexahydroimidazo[1,5-a]pyrazin-3(2H)-one hydrochloride (Preparation #46); LC/MS (Table A, Method a) $R_t$=1.49 min; MS m/z: 553(M+H)$^+$. (TNF IC$_{50}$=A).

Example #85: 1-((S)-1-(2-Fluorophenyl)ethyl)-6-(2-((R)-4-(2-hydroxyacetyl)-3-methylpiperazin-1-yl)pyrimidin-5-yl)-2-methyl-1H-indazol-3(2H)-one

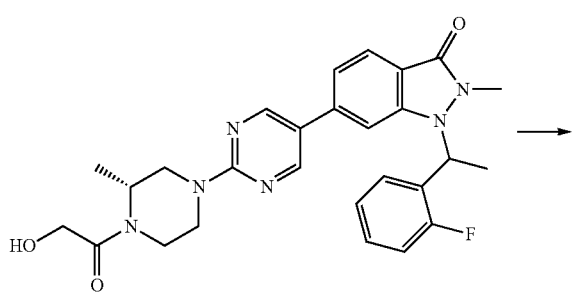

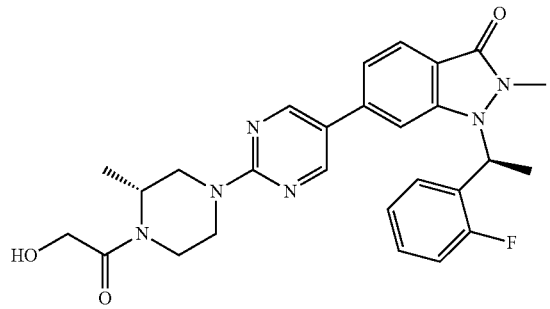

1-(1-(2-Fluorophenyl)ethyl)-6-(2-((R)-4-(2-hydroxyacetyl)-3-methylpiperazin-1-yl)pyrimidin-5-yl)-2-methyl-1H-indazol-3(2H)-one (0.154 g, 0.275 mmol) (Example #28.3) was submitted for chiral separation (Table C, Method d). Fractions from the first eluting component were combined, concentrated and frozen. The resulting solid was lyophilized to afford the title product (0.080 g, 58%) with undetermined optical rotation. LC/MS (Table A, Method e) $R_t$=1.81 min; MS m/z: 505 (M+H)$^+$. (TNF IC$_{50}$=A).

Example #86: 1-((R)-1-(2-Fluorophenyl)ethyl)-6-(2-((R)-4-(2-hydroxyacetyl)-3-methylpiperazin-1-yl)pyrimidin-5-yl)-2-methyl-1H-indazol-3(2H)-one

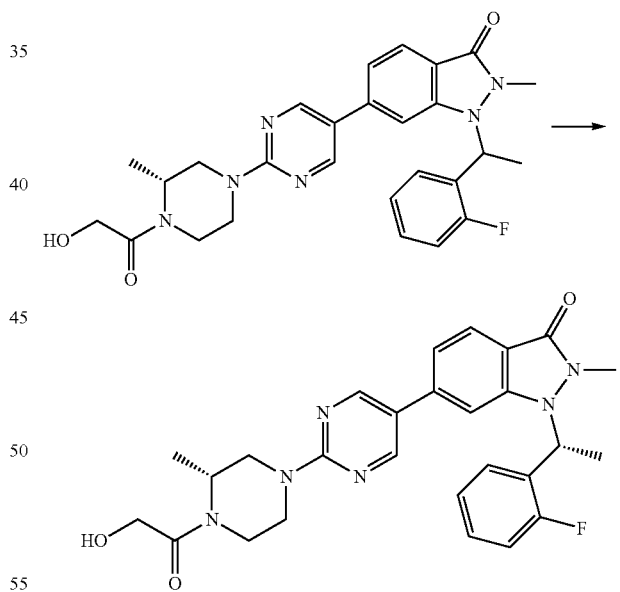

1-(1-(2-Fluorophenyl)ethyl)-6-(2-((R)-4-(2-hydroxyacetyl)-3-methylpiperazin-1-yl)pyrimidin-5-yl)-2-methyl-1H-indazol-3(2H)-one (0.154 g, 0.275 mmol) (Example #28.3) was submitted for chiral separation (Table C, Method d). Fractions from the second eluting component were combined, concentrated and frozen. The resulting solid was lyophilized to afford the title product (0.083 g, 60%) with undetermined optical rotation. LC/MS (Table A, Method e) $R_t$=1.81 min; MS m/z: 505 (M+H)$^+$. (TNF IC$_{50}$=B).

Example #87: 1-(2-(Difluoromethoxy)-5-methylbenzyl)-2-methyl-6-(2-(3-methylpyrrolidin-3-yl)pyrimidin-5-yl)-1H-indazol-3(2H)-one

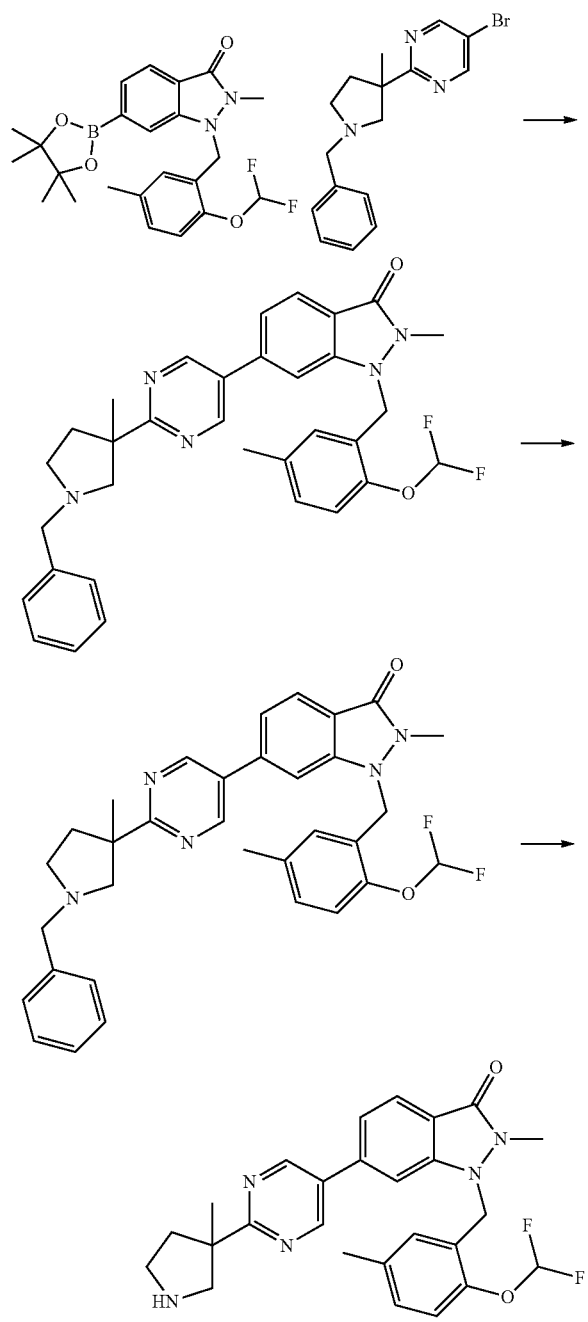

Step 1: 6-(2-(1-Benzyl-3-methylpyrrolidin-3-yl)pyrimidin-5-yl)-1-(2-(difluoromethoxy)-5-methylbenzyl)-2-methyl-1H-indazol-3(2H)-one 6-(2-(1-Benzyl-3-methylpyrrolidin-3-yl)pyrimidin-5-yl)-1-(2-(difluoromethoxy)-5-methylbenzyl)-2-methyl-1H-indazol-3(2H)-one was prepared in a similar fashion to Example #14, step 4 using 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, step 2) and 2-(1-benzyl-3-methylpyrrolidin-3-yl)-5-bromopyrimidine (Preparation #69) to give the title compound (0.127 g, 32%); LC/MS (Table A, Method j) $R_t$=1.24 min; MS m/z; 570 (M+H)$^+$.

Step 2: 1-(2-(Difluoromethoxy)-5-methylbenzyl)-2-methyl-6-(2-(3-methylpyrrolidin-3-yl)pyrimidin-5-yl)-1H-indazol-3(2H)-one A mixture of 6-(2-(1-benzyl-3-methylpyrrolidin-3-yl)pyrimidin-5-yl)-1-(2-(difluoromethoxy)-5-methylbenzyl)-2-methyl-1H-indazol-3(2H)-one (0.125 g, 0.219 mmol), TEA (44.0 µL, 0.316 mmol) in DCM (2 mL) was cooled to about 0° C. 1-Chloroethyl chloroformate (55 µL, 0.50 mmol) was added and the reaction was stirred at about 0° C. for about 1 h. The reaction was concentrated under reduced pressure to remove the DCM. MeOH (5 mL) was added and the reaction was stirred at about 60° C. for about 5 h. The reaction was allowed to cool to rt then was concentrated under reduced pressure. The reaction was partitioned between DCM (20 mL) and sat. aq. NaHCO$_3$(20 mL), the layers were separated and the aqueous layer was extracted with DCM (20 mL). The combined organic layers were dried over Na$_2$SO$_4$, filtered and concentrated under reduced pressure. The residue was purified on neutral alumina using a gradient of 1-5% MeOH/DCM to give the title compound (0.039 g, 36%); LC/MS (Table A, Method j) $R_t$=0.95 min; MS m/z: 480 (M+H)$^+$. (TNF IC$_{50}$=A).

Example #88: 1-(2-(Difluoromethoxy)-5-methylbenzyl)-6-(2-(1,3-dimethylpyrrolidin-3-yl)pyrimidin-5-yl)-2-methyl-1H-indazol-3(2H)-one

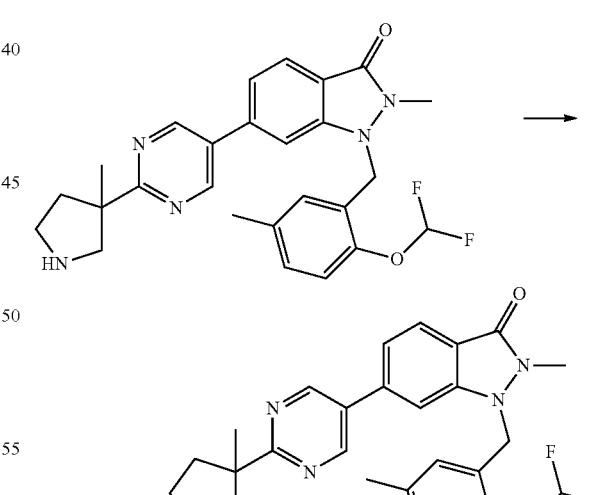

A drop of AcOH was added to a mixture of 1-(2-(difluoromethoxy)-5-methylbenzyl)-2-methyl-6-(2-(3-methylpyrrolidin-3-yl)pyrimidin-5-yl)-1H-indazol-3(2H)-one (0.030 g, 0.063 mmol) (Example #87, step 2), formaldehyde (0.025 g, 0.31 mmol) and sodium cyanotrihydroborate (9.8 mg, 0.16 mmol) in MeOH (0.5 mL). The reaction was stirred at rt for about 2 h. The reaction was diluted with MeOH (2×10 mL) and concentrated under reduced pressure. The residue was purified using reverse phase HPLC (Table A, Method l). The appropriate fractions were concentrated then frozen. The resulting solid was lyophilized to afford the acetic acid salt of the title product (0.006 g, 18%); LC/MS (Table A, Method j) $R_t$=0.96 min; MS m/z: 494 (M+H)$^+$. (TNF IC$_{50}$=B).

Example #89: 6-(6-(2-Aminopropan-2-yl)pyridin-3-yl)-1-(2-(difluoromethoxy)-5-methylbenzyl)-5-fluoro-2-methyl-1H-indazol-3(2H)-one 2,2,2-trifluoroacetate

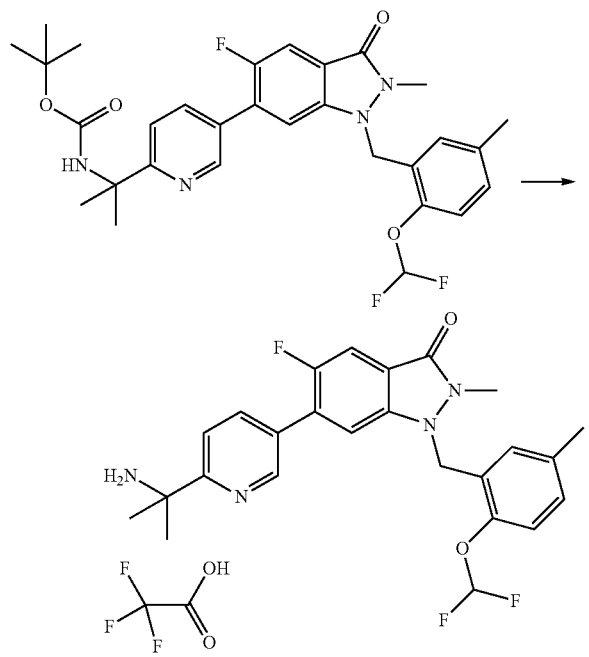

6-(6-(2-Aminopropan-2-yl)pyridin-3-yl)-1-(2-(difluoromethoxy)-5-methylbenzyl)-5-fluoro-2-methyl-1H-indazol-3(2H)-one 2,2,2-trifluoroacetate was prepared in a similar fashion to Preparation #19, step 4 using tert-butyl (2-(5-(1-(2-(difluoromethoxy)-5-methylbenzyl)-5-fluoro-2-methyl-3-oxo-2,3-dihydro-1H-indazol-6-yl)pyridin-2-yl)propan-2-yl)carbamate (prepared in a similar fashion to Example #8 using tert-butyl (2-(5-bromopyridin-2-yl)propan-2-yl)carbamate (Preparation #68) and 6-bromo-1-(2-(difluoromethoxy)benzyl)-5-fluoro-2-methyl-1H-indazol-3(2H)-one (synthesized in a similar fashion to Preparation #4, step 1 from 6-bromo-5-fluoro-2-methyl-1H-indazol-3(2H)-one (synthesized in a similar fashion to Preparation #1 from 4-bromo-2,5-difluorobenzoic acid) and 2-(bromomethyl)-1-(difluoromethoxy)-4-methylbenzene (synthesized in a similar fashion to Preparation #3, step 2 from (2-(difluoromethoxy)-5-methylphenyl)methanol (Preparation #11))) to give the title compound (0.061 g, 67%); LC/MS (Table A, Method e) $R_t$=0.99 min; MS m/z: 471 (M+H)$^+$. (TNF IC$_{50}$=A).

Example #90: 6-(2-(4-Acetylpiperazin-1-yl)pyrimidin-5-yl)-1-(2-(difluoromethoxy)-5-(methoxymethyl)benzyl)-2-methyl-1H-indazol-3(2H)-one

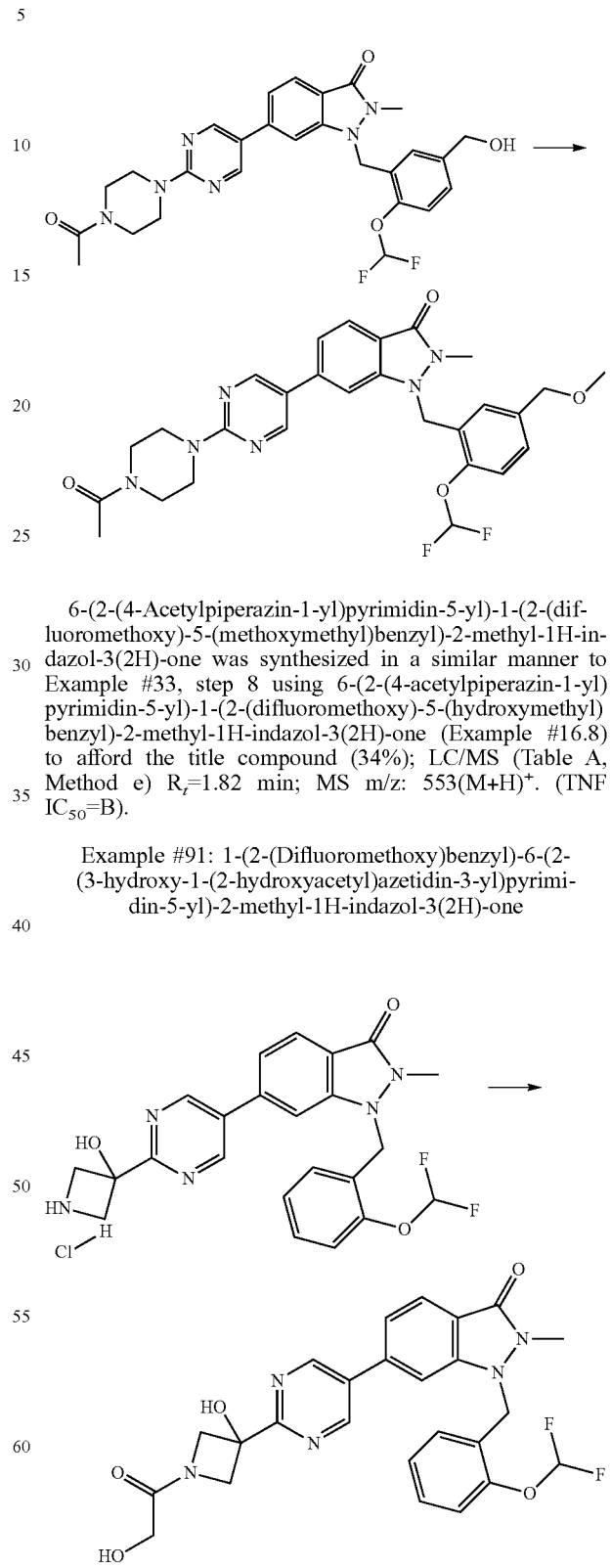

6-(2-(4-Acetylpiperazin-1-yl)pyrimidin-5-yl)-1-(2-(difluoromethoxy)-5-(methoxymethyl)benzyl)-2-methyl-1H-indazol-3(2H)-one was synthesized in a similar manner to Example #33, step 8 using 6-(2-(4-acetylpiperazin-1-yl)pyrimidin-5-yl)-1-(2-(difluoromethoxy)-5-(hydroxymethyl)benzyl)-2-methyl-1H-indazol-3(2H)-one (Example #16.8) to afford the title compound (34%); LC/MS (Table A, Method e) $R_t$=1.82 min; MS m/z: 553(M+H)$^+$. (TNF IC$_{50}$=B).

Example #91: 1-(2-(Difluoromethoxy)benzyl)-6-(2-(3-hydroxy-1-(2-hydroxyacetyl)azetidin-3-yl)pyrimidin-5-yl)-2-methyl-1H-indazol-3(2H)-one

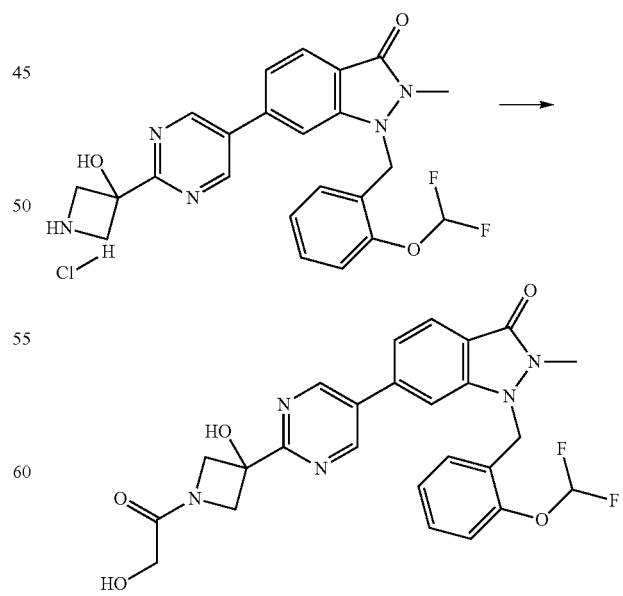

1-(2-(Difluoromethoxy)benzyl)-6-(2-(3-hydroxy-1-(2-hydroxyacetyl)azetidin-3-yl)pyrimidin-5-yl)-2-methyl-1H- indazol-3(2H)-one was prepared in a similar manner to Preparation #15 using 1-(2-(difluoromethoxy)benzyl)-6-(2-(3-hydroxyazetidin-3-yl)pyrimidin-5-yl)-2-methyl-1H-indazol-3(2H)-one hydrochloride (prepared in a similar manner to Example #3, step 1 using tert-butyl 3-(5-(1-(2-(difluoromethoxy)benzyl)-2-methyl-3-oxo-2,3-dihydro-1H-indazol-6-yl)pyrimidin-2-yl)-3-hydroxyazetidine-1-carboxylate (prepared in a similar manner to Example #14, step 4 using 1-(2-(difluoromethoxy)benzyl)-2-methyl-6-(4,4,5,5-tetramethyl-1,3,2-dioxaborolan-2-yl)-1H-indazol-3(2H)-one (Preparation #4, step 2) and tert-butyl 3-(5-bromopyrimidin-2-yl)-3-hydroxyazetidine-1-carboxylate (prepared in a similar manner to Example #20, step 1 using tert-butyl 3-oxoazetidine-1-carboxylate))) to afford the title compound (45%); LC/MS (Table A, Method a) R$_t$=1.46 min; MS m/z: 512 (M+H)$^+$. (TNF IC$_{50}$=B).

Example #92: 1-(2-(Difluoromethoxy)-((5-oxo-1H-1,2,4-triazol-4(5H)-yl)methy)benzyl)-6-(2-(2-hydroxypropan-2-yl)pyrimidin-5-yl)-2-methyl-1H-indazol-3(2H)-one

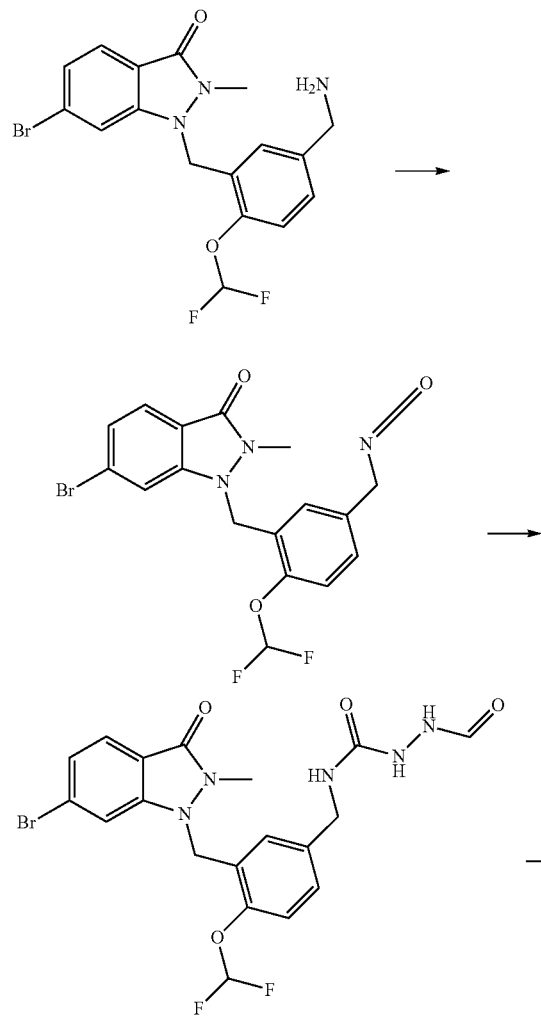

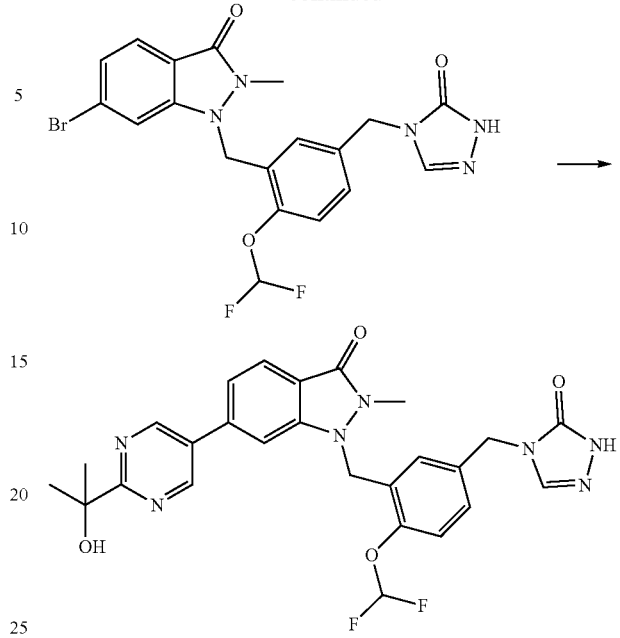

Step 1: 6-Bromo-1-(2-(difluoromethoxy)-5-(isocyanatomethyl)benzyl)-2-methyl-1H-indazol-3(2H)-one Phosgene (20% in toluene) (1.25 mL, 1.75 mmol) was added dropwise to a vigorously stirring mixture of 1-(5-(aminomethyl)-2-(difluoromethoxy)benzyl)-6-bromo-2-methyl-1H-indazol-3(2H)-one (0.180 g, 0.437 mmol) (Preparation #39, step 2) in DCM (2 mL) and sat. aq. NaHCO$_3$(2 mL) at about 0° C. After about 3 h, DCM and sat. aq. NH$_4$Cl were added. The layers were separated. The organic layer was filtered then concentrated at rt in vacuo. The residue (0.199 g) was used without further purification. LC/MS (Table A, Method j) R$_t$=1.51 min; MS m/z: 438 and 440 (M+H)$^+$.

Step 2: N-(3-((6-Bromo-2-methyl-3-oxo-2,3-dihydro-1H-indazol-1-yl)methyl)-4-(difluoromethoxy)benzyl)-2-formylhydrazinecarboxamide 6-Bromo-1-(2-(difluoromethoxy)-5-(isocyanatomethyl)benzyl)-2-methyl-1H-indazol-3(2H)-one (0.190 g, 0.434 mmol) was dissolved in MeCN (3 mL) and treated with formohydrazide (0.078 g, 1.3 mmol) at rt. After about 20 min, EtOAc and aq. HCl were added. The layers were separated and the organic layer was dried over Na$_2$SO$_4$, filtered, and concentrated under reduced pressure. The residue (192 mg) was used without further purification. LC/MS (Table A, Method j) R$_t$=1.06 min; MS m/z: 498 and 500 (M+H)$^+$.

Step 3: 6-Bromo-1-(2-(difluoromethoxy)-5-((5-oxo-1H-1,2,4-triazol-4(5H)-yl)methyl)benzyl)-2-methyl-1H-indazol-3(2H)-one Bromotrimethylsilane (0.500 mL, 3.85 mmol) was added to a stirring mixture of N-(3-((6-bromo-2-methyl-3-oxo-2,3-dihydro-1H-indazol-1-yl)methyl)-4-(difluoromethoxy)benzyl)-2-formylhydrazinecarboxamide (0.192 g, 0.385 mmol) and ammonium sulfate (0.020 g, 0.15 mmol) in hexamethyldisilazane (2.42 mL, 11.6 mmol). The mixture was warmed to about 114° C. After about 16 h, EtOAc (20 mL) was added then washed with 1M aq. HCl. The layers were separated and the organic layer was dried over Na$_2$SO$_4$, filtered, and concentrated. The residue was purified by flash chromatography on silica gel eluting with a gradient of 50-100% EtOAc/DCM to provide the title compound (25 mg, 14%); LC/MS (Table A, Method j) R$_t$=1.05 min; MS m/z: 480 and 482 (M+H)$^+$.

Step 4: 1-(2-(Difluoromethoxy)-5-((5-oxo-1H-1,2,4-triazol-4(5H)-yl)methyl)benzyl)-6-(2-(2-hydroxypropan-2-yl)pyrimidin-5-yl)-2-methyl-1H-indazol-3(2H)-one PdCl$_2$(dppf) (2.7 mg, 3.6 μmol) was added to a mixture of 2-(5-bromopyrimidin-2-yl)propan-2-ol (0.015 g, 0.068 mmol), 4,4,4',4',5,5,5',5'-octamethyl-2,2'-bi(1,3,2-dioxaborolane) (0.024 g, 0.094 mmol), KOAc (0.015 g, 0.16 mmol) and 1,4-dioxane (2 mL) under N$_2$. The reaction vessel was evacuated then back-filled with N$_2$ and flushed with N$_2$. The mixture heated to about 95° C. for about 2 h then cooled to rt. 6-Bromo-1-(2-(difluoromethoxy)-5-((5-oxo-1H-1,2,4-triazol-4(5H)-yl)methyl)benzyl)-2-methyl-1 1H-indazol-3(2H)-one (25 mg, 0.052 mmol), cesium carbonate (42 mg, 0.13 mmol). PdCl$_2$(PPh$_3$)$_2$(2.5 mg, 3.6 μmol), and water (0.5 mL) were added. The reaction vessel was evacuated then back-filled with N$_2$ and flushed with N$_2$. The mixture heated to about 80° C. for about 2 h. The mixture was cooled to rt. DCM (20 mL) and water were added. The layers were separated and the aqueous layer was extracted with DCM (20 mL). The combined organic layers were dried over Na$_2$SO$_4$, filtered, and concentrated. The residue was purified by flash chromatography on silica gel eluting with 100% EtOAc for 5 min then a gradient of 0-60% MeOH/DCM to afford the title compound (0.017 g, 61%); LC/MS (Table A, Method h) R$_t$=0.92 min; MS m/z: 538 (M+H)$^+$. (TNF IC$_{50}$=B).

Example #93: (S)-7-(5-(1-(5-((4H-1,2,4-triazol-4-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one

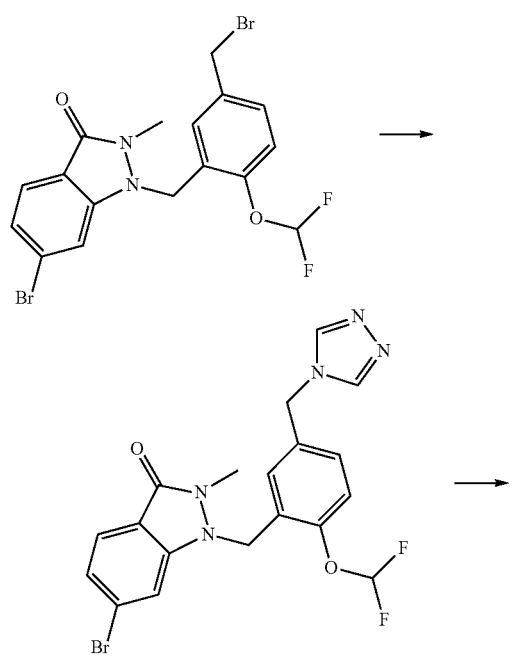

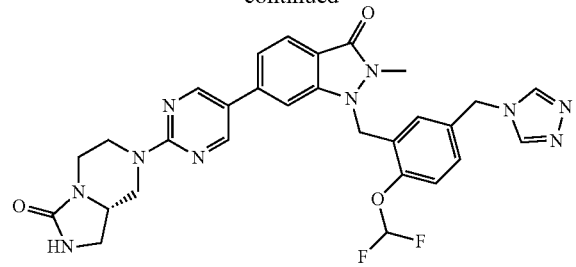

Step 1: 15-((4H-1,2,4-Triazol-4-yl)methyl)-2-(difluoromethoxy)benzyl)-6-bromo-2-methyl-1,2-dihydro-3H-indazol-3-one A mixture of 6-bromo-1-(5-(bromomethyl)-2-(difluoromethoxy)benzyl)-2-methyl-1,2-dihydro-3H-indazol-3-one (Preparation #20, step 3) (0.100 g, 0.210 mmol) and 2-(1H-1,2,4-triazol-1-yl)acetonitrile (*Synthesis* 1995, 9, 1183-1189) (0.026 g, 0.210 mmol) in MeCN (1 mL) was heated at about reflux for about 6 h, after which additional 2-(1H-1,2,4-triazol-1-yl)acetonitrile (0.020 g, 0.164 mmol) was added and heating continued for about 24 h. The reaction mixture was concentrated under reduced pressure and the residue was treated with 2 M aq. sodium hydroxide (2 mL, 4 mmol). After stirring for about 1 h, the mixture was extracted with EtOAc (3×5 mL) and the combined organic phases were washed with sat. aq. NaCl (5 mL), dried over Na$_2$SO$_4$, filtered, and concentrated under reduced pressure. The sample was purified on silica gel using 0-5% MeOH with DCM to give the title compound (0.053 g, 54%); LC/MS (Table A, Method i) R$_t$=1.04 min; MS m/z: 464 and 466 (M+H)$^+$.

Step 2: (S)-7-(5-(1-(5-((4H-1,2,4-Triazol-4-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one The reaction was performed using 1-(5-((4H-1,2,4-triazol-4-yl)methyl)-2-(difluoromethoxy)benzyl)-6-bromo-2-methyl-1,2-dihydro-3H-indazol-3-one and (S)-7-(5-bromopyrimidin-2-yl)hexahydroimidazo[1,5-a]pyrazin-3(2H)-one (Preparation #13) in a fashion similar to Example #8 to give the title product (13%); LC/MS (Table A, Method a) R$_t$=1.48 min; MS m/z: 603(M+H)$^+$. (TNF IC$_{50}$=A).

Example #94: (R)—N-(3-((6-(2-(4-Acetyl-3-methylpiperazin-1-yl)pyrimidin-5-yl)-2-methyl-3-oxo-2,3-dihydro-1H-indazol-1-yl)methyl)-4-(difluoromethoxy)benzyl)-N-ethylacetamide

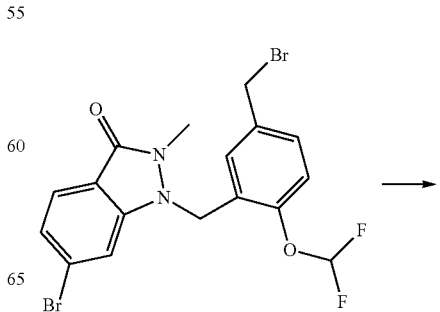

-continued

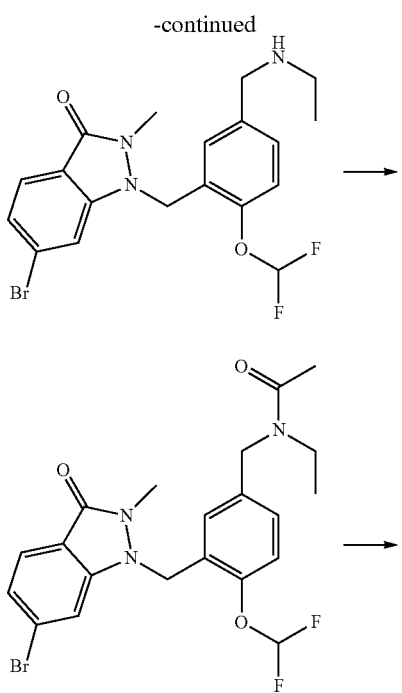

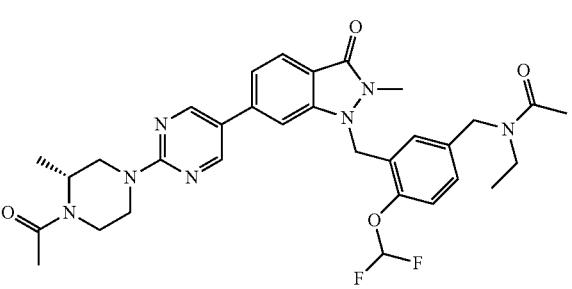

Step 1: 6-Bromo-1-(2-(difluoromethoxy)-5-((ethylamino)methyl)benzyl)-2-methyl-1,2-dihydro-3H-indazol-3-one A solution of 6-bromo-1-(5-(bromomethyl)-2-(difluoromethoxy)benzyl)-2-methyl-1,2-dihydro-3H-indazol-3-one (Preparation #20, step 3) (0.120 g, 0.252 mmol) in THF (2 mL) was added to ethylamine (2 M in THF) (10 mL, 20 mmol) and the resulting solution was stirred at about ambient temperature for about 2 min. The reaction mixture was concentrated under reduced pressure to give the title compound (0.11 g, 100%); LC/MS (Table A, Method i) $R_t$=0.94 min; MS m/z: 440 and 442 (M+H)$^+$.

Step 2: N-(3-((6-Bromo-2-methyl-3-oxo-2,3-dihydro-1H-indazol-1-yl)methyl)-4-(difluoromethoxy)benzyl)-N-ethylacetamide The reaction was performed using 6-bromo-1-(2-(difluoromethoxy)-5-((ethylamino)methyl)benzyl)-2-methyl-1,2-dihydro-3H-indazol-3-one with acetyl chloride in a fashion similar to Preparation #16 to give the title product (89%); LC/MS (Table A, Method i) $R_t$=1.26 min; MS m/z: 482 and 484 (M+H)$^+$.

Step 3: (R)—N-(3-((6-(2-(4-acetyl-3-methylpiperazin-1-yl)pyrimidin-5-yl)-2-methyl-3-oxo-2,3-dihydro-1H-indazol-1-yl)methyl)-4-(difluoromethoxy)benzyl)-N-ethylacetamide The reaction was performed using N-(3-((6-bromo-2-methyl-3-oxo-2,3-dihydro-1H-indazol-1-yl)methyl)-4-(difluoromethoxy)benzyl)-N-ethylacetamide and (R)-1-(4-(5-bromopyrimidin-2-yl)-2-methylpiperazin-1-yl)ethan-1-one (Preparation #16) in a fashion similar to Example #8 to give the title product (59%); LC/MS (Table A, Method a) $R_t$=1.75 min; MS m/z: 622 (M+H)$^+$. (TNF IC$_{50}$=B).

Example #95: 1-(2-(Difluoromethoxy)-5-methylbenzyl)-6-(2-(2-hydroxypropan-2-yl)-4-methylpyrimidin-5-yl)-2-methyl-1,2-dihydro-3H-pyrazolo[3,4-b]pyridin-3-one

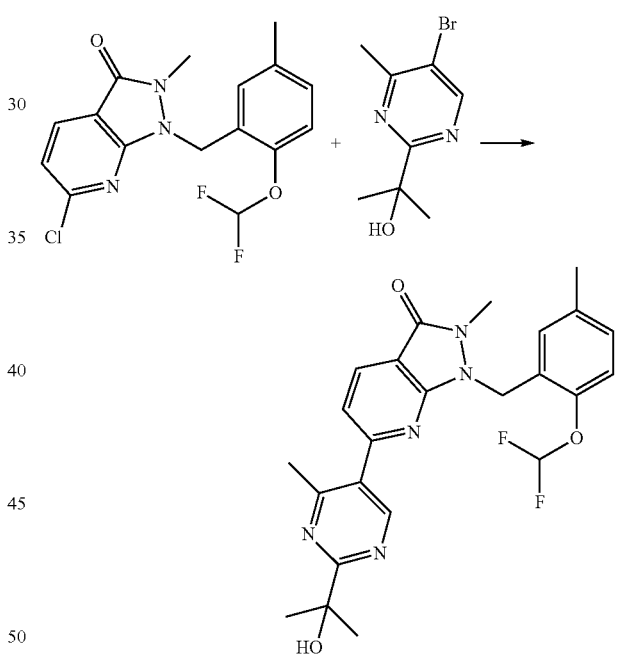

The reaction was performed using 6-chloro-1-(2-(difluoromethoxy)-5-methylbenzyl)-2-methyl-1,2-dihydro-3H-pyrazolo[3,4-b]pyridin-3-one (prepared using 2-(bromomethyl)-1-(difluoromethoxy)-4-methylbenzene (prepared from (2-(difluoromethoxy)-5-methylphenyl)methanol (Preparation #11) in a fashion similar to Preparation #3, step 2) and 6-chloro-2-methyl-1,2-dihydro-3H-pyrazolo[3,4-b]pyridin-3-one (Example #15, step 2) in a fashion similar to Example #14, step 2) and 2-(5-bromo-4-methylpyrimidin-2-yl)propan-2-ol (WO2015/86506 A1) in a fashion similar to Example #8 to give the title product (56%); LC/MS (Table A, Method a) $R_t$=2.12 min; MS m/z: 470 (M+H)$^+$. (TNF IC$_{50}$=B).

323

Example #96: rac-(R,3S)-3-(4-(Difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentane-1-carbonitrile and

Example #97: rac-(1R,3R)-3-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentane-1-carbonitrile

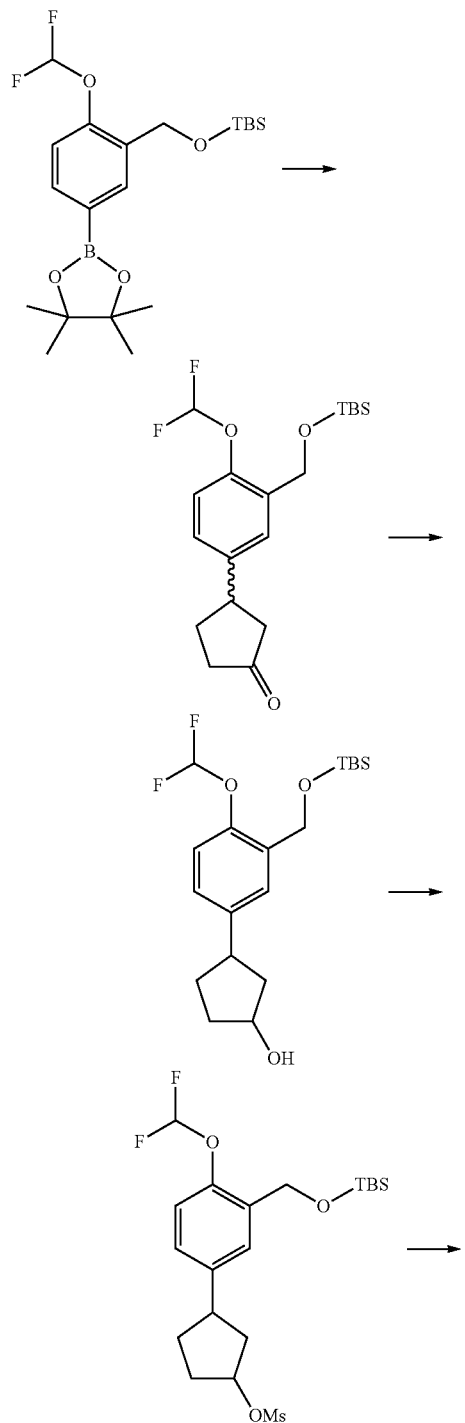

324

-continued

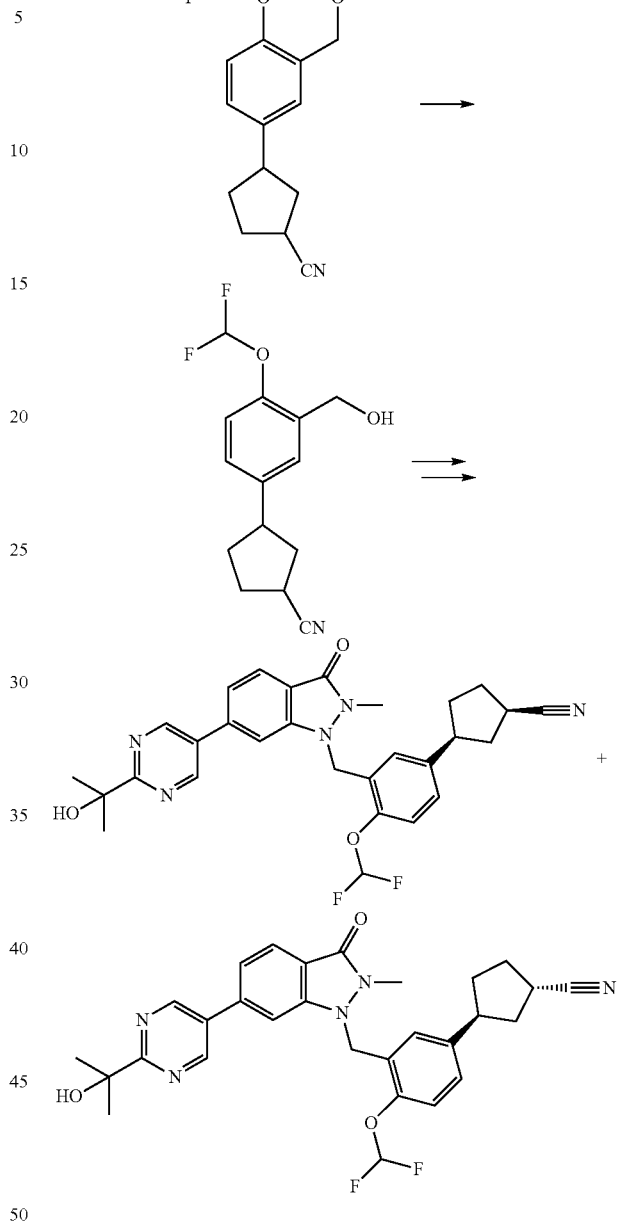

Step 1: 3-(3-(((tert-Butyldimethylsilyl)oxy)methyl)-4-(difluoromethoxy)phenyl)cyclopentan-1-one A solution of 2-cyclopenten-1-one (0.83 mL, 9.9 mmol), tert-butyl((2-(difluoromethoxy)-5-(4,4,5,5-tetramethyl-1,3,2-dioxaborolan-2-yl)benzyl)oxy)dimethylsilane (prepared from ((5-bromo-2-(difluoromethoxy)benzyl)oxy)(tert-butyl)dimethylsilane (prepared from (5-bromo-2-(difluoromethoxy)phenyl)methanol (Preparation #12) in a fashion similar to Preparation #43, step 1) in a fashion similar to Preparation #4, step 2) (2.05 g, 4.95 mmol) and DIEA (2.59 mL, 14.8 mmol) in 10:1 dioxane/water (22 mL) was degassed with nitrogen sparge for about 10 min and then added to a vessel containing chloro(1,5-cyclooctadiene)rhodium(I) dimer (0.122 g, 0.247 mmol) and 2,2'-bis(diphenylphosphanyl)-1,1'-binaphthalene (0.308 g, 0.495 mmol) under a nitrogen atmosphere. The reaction was heated at about 80° C. for about 1.5 h and then allowed to cool. The mixture was concentrated and the residue was purified on silica gel using 0-30% EtOAc in heptane to give the title compound (1.05 g, 57%); $^1$H NMR (400 MHz, CDCl$_3$) δ 7.45 (d. J=2.3 Hz, 1H), 7.13(dd, J=8.3, 2.3 Hz, 1H), 7.05 (d, J=8.3 Hz, 1H), 6.49 (t, J=74.3 Hz, 1H), 4.78 (s, 2H), 3.53-3.33(m, 1H), 2.75-2.57 (m, 1H), 2.54-2.39 (m, 2H), 2.38-2.22 (m, 2H), 2.07-1.87 (m, 1H), 0.95 (s, 9H), 0.12 (s, 6H).

Step 2: 3-(3-(((tert-Butyldimethylsilyl)oxy)methyl)-4-(difluoromethoxy)phenyl)cyclopentane-1-ol The reaction was performed using 3-(3-(((tert-butyldimethylsilyl)oxy)methyl)-4-(difluoromethoxy)phenyl)cyclopentane-1-one in a fashion similar to Preparation #14, step 2 to give the title product (100%) as a mixture of cis- and trans-isomers. $^1$H NMR (400 MHz, CDCl$_3$) δ 7.50-7.38 (m, 1H), 7.22-7.04 (m, 1H), 7.04-6.92 (m, 1H), 6.47 (t, J=74.6 Hz, 1H), 4.76 (s, 2H), 4.61-4.38 (m, 11H), 3.51-2.95 (m, 1H), 2.54-1.55 (m, 6H), 0.95 (s, 9H), 0.11 (s, 6H).

Step 3: 3-(3-(((tert-butyldimethylsilyl)oxy)methyl)-4-(difluoromethoxy)phenyl)cyclopentyl methanesulfonate The reaction was performed using 3-(3-(((tert-butyldimethylsilyl)oxy)methyl)-4-(difluoromethoxy)phenyl)cyclopentane-1-ol in a fashion similar to Example #24 to give the title product (92%) as a mixture of cis- and trans-isomers; LC/MS (Table A, Method i) R$_t$=2.20 min; MS m/z: 451 (M+H)$^+$.

Step 4: 3-(3-(((tert-Butyldimethylsilyl)oxy)methyl)-4-(difluoromethoxy)phenyl)cyclopentane-1-carbonitrile A solution of 3-(3-(((tert-butyldimethylsilyl)oxy)methyl)-4-(difluoromethoxy)phenyl)cyclopentyl methanesulfonate (0.480 g, 1.06 mmol) and sodium cyanide (0.078 g, 1.6 mmol) in DMF (6 mL) was heated at about 50° C. for about 21 h. The mixture was concentrated under reduced pressure and then the mixture was partitioned between EtOAc (50 mL) and water (50 mL). After separating the layers, the aqueous phase was extracted with EtOAc (2×25 mL). The combined organic phases were washed with sat. aq. NaCl (2×50 mL), dried over Na$_2$SO$_4$, filtered, and concentrated under reduced pressure. The sample was purified on silica gel using 0-50% EtOAc in heptane to give the title product (0.157 g, 39%). LC/MS (Table A, Method i) R$_t$=2.25 min; MS m/z: 382 (M+H)$^+$.

Step 5: 3-(4-(Difluoromethoxy)-3-(hydroxymethyl)phenyl)cyclopentane-1-carbonitrile The reaction was performed using 3-(3-(((tert-butyldimethylsilyl)oxy)methyl)-4-(difluoromethoxy)phenyl)cyclopentane-1-carbonitrile in a fashion similar to Example #35, step 3 to give the title product (96%) as a mixture of cis- and trans-isomers; LC/MS (Table A, Method i) R$_t$=1.25 min; MS m/z: 326 (M+AcO)$^-$.

Step 6: rac-(1R,3S)-3-(4-(Difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentane-1-carbonitrile and rac-(1R,3R)-3-(4-(difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentane-1-carbonitrile The reaction was performed using 3-(3-(bromomethyl)-4-(difluoromethoxy)phenyl)cyclopentane-1-carbonitrile (prepared from 3-(4-(difluoromethoxy)-3-(hydroxymethyl)phenyl)cyclopentane-1-carbonitrile in a fashion similar to Preparation #14, step 6) with 6-(2-(2-hydroxypropan-2-yl)pyrimidin-5-yl)-2-methyl-1,2-dihydro-3H-indazol-3-one (Preparation #19) in a fashion similar to Example #1 to give a mixture of cis- and trans-isomers. The mixture was separated using HPLC (Table A, Method m) to give (in a corresponding order of elution) the title compounds; (Table A, Method h) R$_t$=1.29 min; MS m/z: 534 (M+H)$^+$ (TNF IC$_{50}$=B) and R$_t$=1.29 min; MS m/z: 534 (M+H)$^+$ (TNF IC$_{50}$=A).

Example #98: 1-(2-(Difluoromethoxy)-5-methylbenzyl)-5-fluoro-6-(2-(2-hydroxypropan-2-yl)-4-methylpyrimidin-5-yl)-2-methyl-1,2-dihydro-3H-pyrazolo[3,4-b]pyridin-3-one

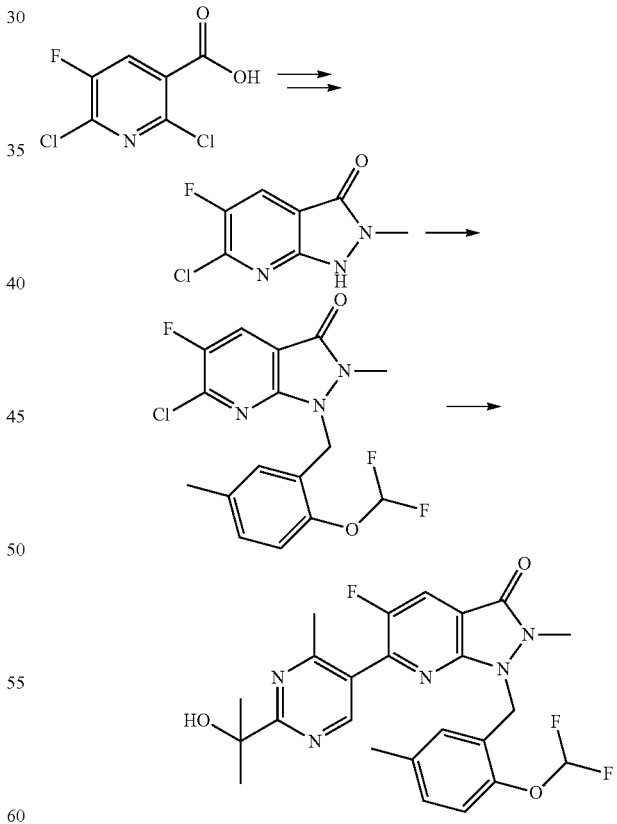

Step 1: 6-Chloro-5-fluoro-2-methyl-1,2-dihydro-3H-pyrazolo[3,4-b]pyridin-3-one 2,6-Dichloro-5-fluoronicotinic acid was treated in a fashion similar to Example #17, step 1 to afford 2,6-dichloro- 5-fluoro-N-methylnicotinohydrazide which was used in a fashion similar to Example #15, step 2 to give the title compound (33%); LC/MS (Table A, Method i) $R_t$=0.49 min; MS m/z: 200 (M−H)⁻.

Step 2: 6-Chloro-1-(2-(difluoromethoxy)-5-methyl-benzyl)-5-fluoro-2-methyl-1,2-dihydro-3H-pyrazolo [3,4-b]pyridin-3-one The reaction was performed using 6-chloro-5-fluoro-2-methyl-1,2-dihydro-3H-pyrazolo[3,4-b]pyridin-3-one and 2-(bromomethyl)-1-(difluoromethoxy)-4-methylbenzene (prepared from (2-(difluoromethoxy)-5-methylphenyl) methanol (Preparation #11) in a fashion similar to Preparation #3, step 2) in a fashion similar to Example #14, step 2 to give the title product (68%); LC/MS (Table A, Method i) $R_t$=1.54 min; MS m/z: 372 (M+H)⁺.

Step 3: 1-(2-(Difluoromethoxy)-5-methylbenzyl)-5-fluoro-6-(2-(2-hydroxypro pan-2-yl)-4-methylpy-rimidin-5-yl)-2-methyl-1,2-dihydro-3H-pyrazolo[3, 4-b]pyridin-3-one The reaction was performed using 6-chloro-1-(2-(difluoromethoxy)-5-methylbenzyl)-5-fluoro-2-methyl-1,2-dihydro-3H-pyrazolo[3,4-b]pyridin-3-one and 2-(5-bromo-4-methylpyrimidin-2-yl)propan-2-ol (WO2015/86506 A1) in a fashion similar to Example #8 to give the title product (63%); LC/MS (Table A, Method a) $R_t$=2.21 min; MS m/z: 488 (M+H)⁺. (TNF IC$_{50}$=A).

Example #99: 1-(2-Chloro-5-methylbenzyl)-6-(2-(2-hydroxypropan-2-yl)-4-methylpyrimidin-5-yl)-2-methyl-1,2-dihydro-3H-pyrazolo[3,4-b]pyridin-3-one

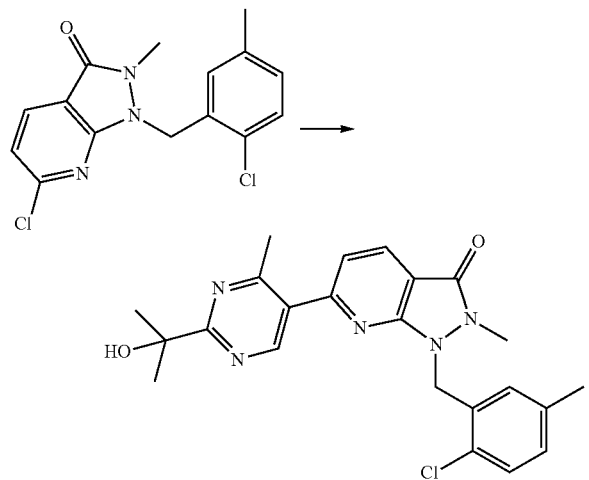

1-(2-Chloro-5-methylbenzyl)-6-(2-(2-hydroxypropan-2-yl)-4-methylpyrimidin-5-yl)-2-methyl-1,2-dihydro-3H-pyrazolo[3,4-b]pyridin-3-one was prepared from 6-chloro-1-(2-chloro-5-methylbenzyl)-2-methyl-1H-pyrazolo[3,4-b] pyridin-3(2H)-one (prepared in a manner similar to Example #1 from 6-chloro-2-methyl-1H-pyrazolo[3,4-b]pyridin-3 (2H)-one (Example #15, step 2) and 2-(bromomethyl)-1-chloro-4-methylbenzene (prepared in a manner similar to Preparation #3, step 2 from (2-chloro-5-methylphenyl) methanol (prepared in a manner similar to Preparation #32, step 4 from methyl 2-chloro-5-methylbenzoate))) and 2-(5-bromo-4-methylpyrimidin-2-yl)propan-2-ol (WO2015/86506 A1) in a manner similar to Example #8 to give the title product (62%); LC/MS (Table A, Method a) $R_t$=2.25 min; MS m/z: 438 (M+H)⁺. (TNF IC$_{50}$=A)

Example #100: 2-(4-(Difluoromethoxy)-3-((5-fluoro-6-(2-(2-hydroxypropan-2-yl)pyrimidin-5-yl)-2-methyl-3-oxo-2,3-dihydro-1H-indazol-1-yl) methyl)phenyl)acetonitrile

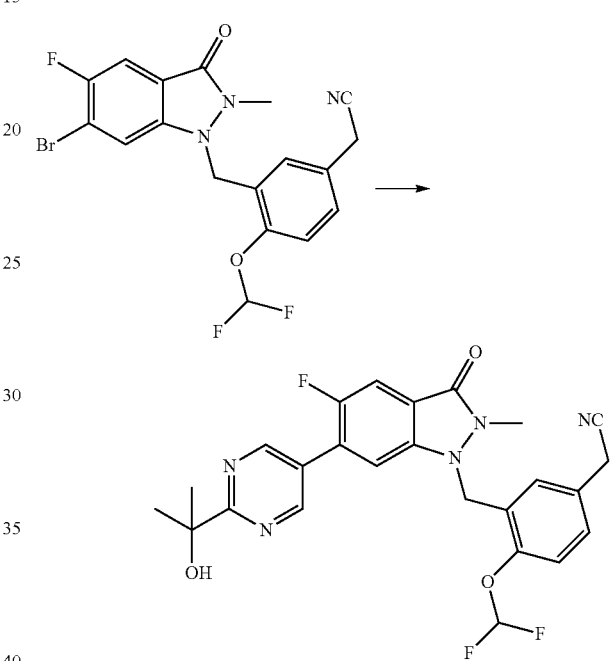

2-(4-(Difluoromethoxy)-3-((5-fluoro-6-(2-(2-hydroxy-propan-2-yl)pyrimidin-5-yl)-2-methyl-3-oxo-2,3-dihydro-1H-indazol-1-yl)methyl)phenyl)acetonitrile was prepared using 2-(3-((6-bromo-5-fluoro-2-methyl-3-oxo-2,3-dihydro-1H-indazol-1-yl)methyl)-4-(difluoromethoxy)phenyl)acetonitrile (prepared using 6-bromo-1-(5-(bromomethyl)-2-(difluoromethoxy) benzyl)-5-fluoro-2-methyl-1H-indazol-3(2H)-one (synthesized in a manner similar to Preparation #14, step 6 from 6-bromo-1-(2-(difluoromethoxy)-5-(hydroxymethyl)benzyl)-5-fluoro-2-methyl-1H-indazol-3(2H)-one (synthesized in a manner similar to Example #18 from 6-bromo-1-(2-(difluoromethoxy)-5-((trityloxy)methyl)benzyl)-5-fluoro-2-methyl-1H-indazol-3 (2H)-one (synthesized in a manner similar to Preparation #4, step 1 from 6-bromo-5-fluoro-2-methyl-1H-indazol-3(2H)-one (synthesized in a manner similar to Preparation #1 from 4-bromo-2,5-difluorobenzoic acid) and (((3-(bromomethyl)-4-(difluoromethoxy)benzyl)oxy)methanetriyl)tribenzene (Preparation #14)))) in a manner similar to Preparation #20) and 2-(5-bromopyrimidin-2-yl)propan-2-ol in a manner similar to Example #8 to give the title product (35%); LC/MS (Table A, Method a) $R_t$=1.87 min; MS m/z: 498 (M+H)⁺. (TNF IC$_{50}$=B)

Example #101: (R)-6-(2-(4-Acetyl-3-methylpiper-azin-1-yl)pyrimidin-5-yl)-1-(2-(difluoromethoxy)-5-((3-oxo-2,3-dihydro-H-pyrazol-1-yl)methyl)benzyl)-2-methyl-1,2-dihydro-3H-indazol-3-one and
Example #102: (R)-1-(5-((1H-pyrazol-5-yl)oxy)methyl)-2-(difluoromethoxy)benzyl)-6-(2-(4-acetyl-3-methylpiperazin-1-yl)pyrimidin-5-yl)-2-methyl-1,2-dihydro-3H-indazol-3-one

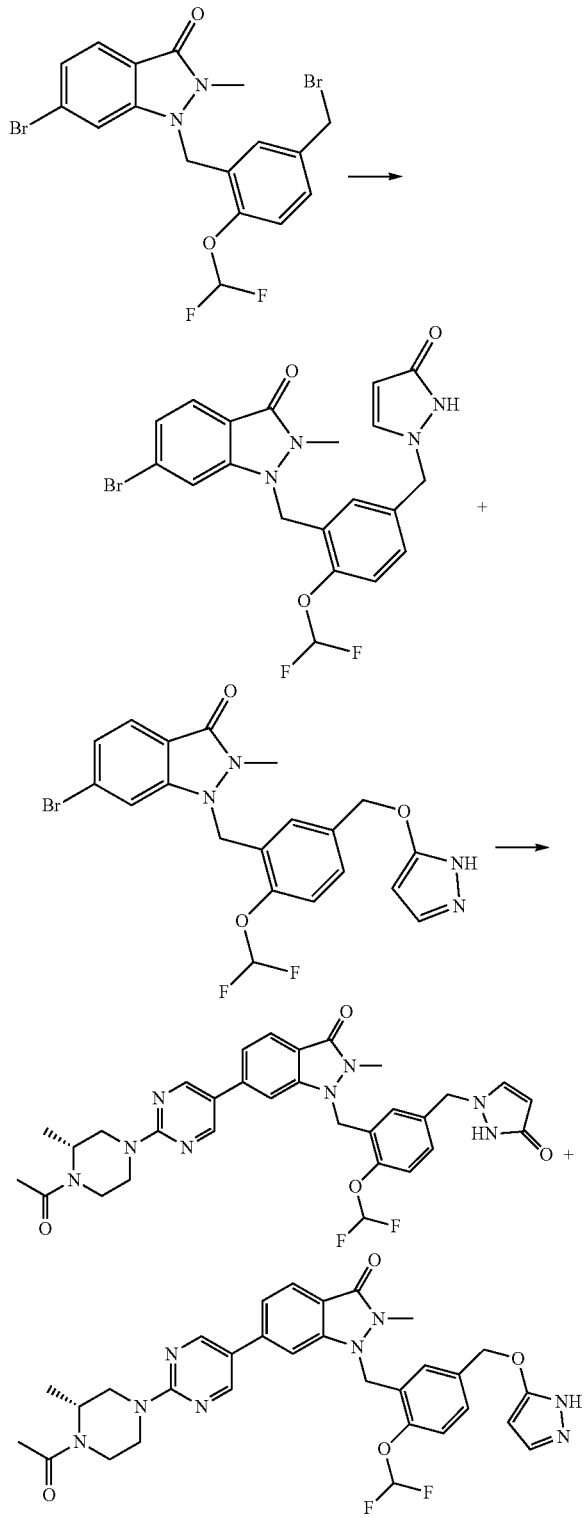

Step 1: 6-Bromo-1-(2-(difluoromethoxy)-5-((3-oxo-2,3-dihydro-1H-pyrazol-1-yl)methyl)benzyl)-2-methyl-1,2-dihydro-3H-indazol-3-one and 1-(5-((1H-pyrazol-5-yl)oxy)methyl)-2-(difluoromethoxy)benzyl)-6-bromo-2-methyl-1,2-dihydro-3H-indazol-3-one A solution of 1H-pyrazol-5-ol (0.047 g, 0.55 mmol) in DMF (1 mL) was cooled at about −15° C. before sodium hydride (60% dispersion in mineral oil) (12 mg, 0.30 mmol) was added in one portion and the mixture was stirred for about 5 min. The mixture was allowed to stir at ambient temperature for about 30 min and then was cooled to about −15° C. 6-Bromo-1-(5-(bromomethyl)-2-(difluoromethoxy)benzyl)-2-methyl-1,2-dihydro-3H-indazol-3-one (Preparation #20, step 3) (0.120 g, 0.252 mmol) in DMF (1 mL) was added drop-wise via syringe. The mixture was stirred in the bath for about 1.5 h. The reaction was quenched by addition of water (3 mL), followed by EtOAc (2 mL). The reaction mixture was partitioned between EtOAc (5 mL) and sat. aq. $NH_4Cl$ (5 mL). After separating the layers, the aqueous phase was extracted with EtOAc (2×5 mL). The combined organic phases were washed with sat. aq. NaCl (10 mL), dried over $Na_2SO_4$, filtered, and concentrated under reduced pressure. The material was purified on silica using 50-100% EtOAc in heptane to give the title compounds as a mixture (92 mg, 76%); LC/MS (Table A, Method i) $R_t$=1.08 and 1.17 min; MS m/z: 479 and 481 $(M+H)^+$.

Step 2: (R)-6-(2-(4-Acetyl-3-methylpiperazin-1-yl)pyrimidin-5-yl)-1-(2-(difluoromethoxy)-5-((3-oxo-2,3-dihydro-1H-pyrazol-1-yl)methyl)benzyl)-2-methyl-1,2-dihydro-3H-indazol-3-one and (R)-1-(5-(((1H-pyrazol-5-yl)oxy)methyl)-2-(difluoromethoxy)benzyl)-6-(2-(4-acetyl-3-methylpiperazin-1-yl)pyrimidin-5-yl)-2-methyl-1,2-dihydro-3H-indazol-3-one The reaction was performed using a mixture of 6-bromo-1-(2-(difluoromethoxy)-5-((3-oxo-2,3-dihydro-1H-pyrazol-1-yl)methyl)benzyl)-2-methyl-1,2-dihydro-3H-indazol-3-one and 1-(5-(((1H-pyrazol-5-yl)oxy)methyl)-2-(difluoromethoxy)benzyl)-6-bromo-2-methyl-1,2-dihydro-3H-indazol-3-one with (R)-1-(4-(5-bromopyrimidin-2-yl)-2-methylpiperazin-1-yl)ethan-1-one (Preparation #16) in a fashion similar to Example #8 to give (R)-6-(2-(4-acetyl-3-methylpiperazin-1-yl)pyrimidin-5-yl)-1-(2-(difluoromethoxy)-5-((3-oxo-2,3-dihydro-1H-pyrazol-1-yl)methyl)benzyl)-2-methyl-1,2-dihydro-3H-indazol-3-one (21%); LC/MS (Table A, Method a) $R_t$=1.69 min; MS m/z: 619 $(M+H)^+$; (TNF $IC_{50}$=B) and (R)-1-(5-(((1H-pyrazol-5-yl)oxy)methyl)-2-(difluoromethoxy)benzyl)-6-(2-(4-acetyl-3-methylpiperazin-1-yl)pyrimidin-5-yl)-2-methyl-1,2-dihydro-3H-indazol-3-one (13%); LC/MS (Table A, Method a) $R_t$=1.78 min; MS m/z: 619 $(M+H)^+$; (TNF $IC_{50}$=A).

Example #103: (S)-7-(5-(1(2-Chloro-5-methylbenzyl)-2-methyl-3-oxo-2,3-dihydro-1H-indazol-6-yl)pyrimidin-2-yl)hexahydroimidazo[1,5-a]pyrazin-3(2H)-one

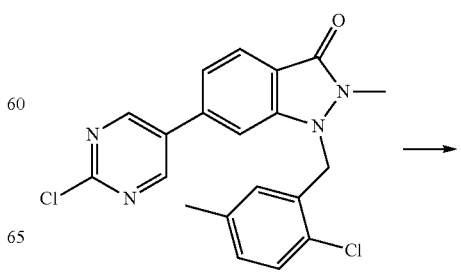

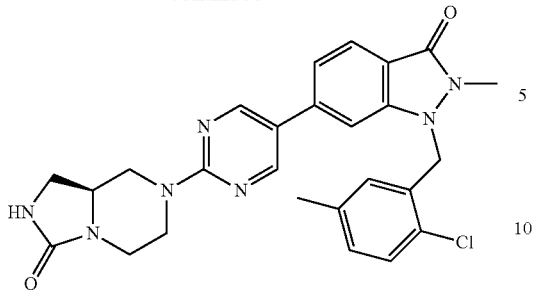

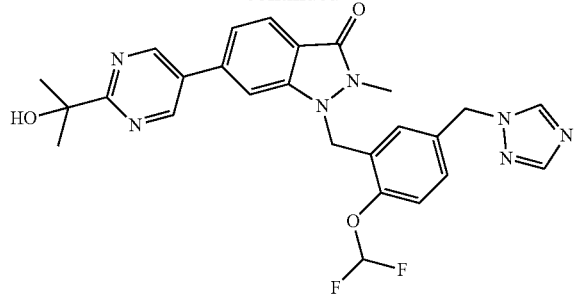

(S)-7-(5-(1-(2-Chloro-5-methylbenzyl)-2-methyl-3-oxo-2,3-dihydro-1H-indazol-6-yl)pyrimidin-2-yl)hexahydroimidazo[1,5-a]pyrazin-3(2H)-one was prepared using 1-(2-chloro-5-methylbenzyl)-6-(2-chloropyrimidin-5-yl)-2-methyl-1,2-dihydro-3H-indazol-3-one (prepared using 1-chloro-2-(chloromethyl)-4-methylbenzene (synthesized in a manner similar to Preparation #50, step 6 from (2-chloro-5-methylphenyl)methanol (synthesized in a manner similar to Preparation #32, step 4 from methyl 2-chloro-5-methylbenzoate)) with 6-(2-chloropyrimidin-5-yl)-2-methyl-1,2-dihydro-3H-indazol-3-one (Preparation #23) in a manner similar to Example #1) with (R)-hexahydroimidazo[1,5-a]pyrazin-3(2H)-one (Preparation #46) in a manner similar to Example #2 to give the title product (87%); LC/MS (Table A, Method a) $R_t$=1.94 min; MS m/z: 504 (M+H)$^+$. (TNF IC$_{50}$=A)

Example #104: 15-((1H-1,2,4-triazol-1-yl)methyl)-2-(difluoromethoxy)benzyl)-6-(2-(2-hydroxypropan-2-yl)pyrimidin-5-yl)-2-methyl-1,2-dihydro-3H-indazol-3-one

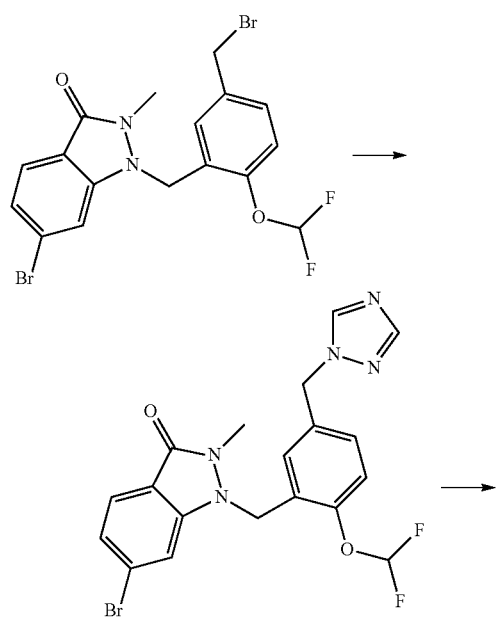

Step 1: 1-(5-(((1H-1,2,4-Triazol-1-yl)methyl)-2-(difluoromethoxy)benzyl)-6-bromo-2-methyl-1,2-dihydro-3H-indazol-3-one A mixture of 6-bromo-1-(5-(bromomethyl)-2-(difluoromethoxy)benzyl)-2-methyl-1,2-dihydro-3H-indazol-3-one (0.100 g, 0.210 mmol) (Preparation #20, step 3), 1,2,4-triazole (0.031 g, 0.449 mmol), and potassium carbonate (0.035 g, 0.25 mmol) in MeCN (2 mL) was heated at about 50° C. for about 1.5 h. The reaction mixture was partitioned between water (5 mL) and EtOAc (2 mL). After separating the layers, the aqueous phase was extracted with EtOAc (2×2 mL). The combined organic phases were washed with saturated aqueous NaCl (5 mL), dried over Na$_2$SO$_4$, filtered, and concentrated under reduced pressure to give the title compound (0.193 g, 99%) as a mixture together with a minor isomer; LC/MS (Table A, Method i) $R_t$=1.12 min; MS m/z: 464, 466 (M+H)$^+$.

Step 2: 1-(5-(((1H-1,2,4-Triazol-1-yl)methyl)-2-(difluoromethoxy)benzyl)-6-(2-(2-hydroxypropan-2-yl)pyrimidin-5-yl)-2-methyl-1,2-dihydro-3H-indazol-3-one The reaction was performed using 1-(5-((1H-1,2,4-triazol-1-yl)methyl)-2-(difluoromethoxy)benzyl)-6-(2-(2-hydroxypropan-2-yl)pyrimidin-5-yl)-2-methyl-1,2-dihydro-3H-indazol-3-one with 2-(5-bromopyrimidin-2-yl)propan-2-ol in a fashion similar to Example #8 to give the title product (54%); LC/MS (Table A, Method a) $R_t$=1.59 min; MS m/z: 522 (M+H)$^+$. (TNF IC$_{50}$=A).

Example #105*: (R)-6-(2-(4-Acetyl-3-methylpiperazin-1-yl)pyrimidin-5-yl)-1-((3-chloro-6-methylpyridin-2-yl)methyl)-2-methyl-1,2-dihydro-3H-indazol-3-one

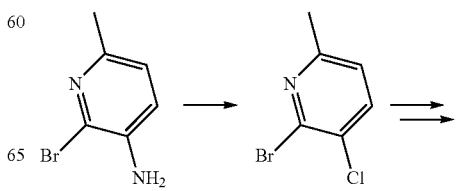

-continued

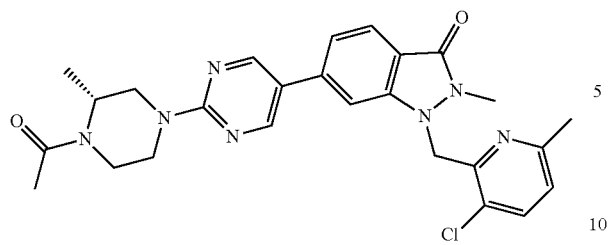

Step 1: 2-Bromo-3-chloro-6-methylpyridine

A suspension of 3-amino-2-bromo-6-picoline (2.50 g, 13.4 mmol) and copper(I) chloride (5.29 g, 53.5 mmol) in concentrated HCl (28 mL) at about 0° C. was treated with sodium nitrite (0.922 g, 13.4 mmol) and stirred for about 5 min. Water (28.0 mL) was added and the mixture was stirred for about 10 min, and then additional sodium nitrite (0.922 g, 13.4 mmol) in water (2 mL) was added drop-wise. The ice bath was removed and stirring was continued overnight. The reaction mixture was poured into ice water (100 mL) and then extracted with diethyl ether (3×50 mL). The combined organic phases were washed with sat. aq. NaHCO$_3$ and sat. aq. NaCl (75 mL each), dried over Na$_2$SO$_4$, filtered, and concentrated under reduced pressure to give the title compound (0.733 g, 27%); LC/MS (Table A, Method i) R$_t$=1.16 min; MS m/z: 206 and 208 (M+H)$^+$.

Step 2: (R)-6-(2-(4-Acetyl-3-methylpiperazin-1-yl)pyrimidin-5-yl)-1-((3-chloro-6-methylpyridin-2-yl)methyl)-2-methyl-1,2-dihydro-3H-indazol-3-one The reaction was performed using 2-(bromomethyl)-3-chloro-6-methylpyridine (prepared in a fashion similar to Preparation #3, step 2 from (3-chloro-6-methylpyridin-2-yl)methanol (prepared in a fashion similar to Preparation #9 from 3-chloro-6-methylpicolinaldehyde (prepared in a fashion similar to Example #4, step 1 from (E)-3-chloro-6-methyl-2-styrylpyridine (prepared in a fashion similar to Example #14, step 4 from 2-bromo-3-chloro-6-methylpyridine and (E)-styrylboronic acid)))) with (R)-6-(2-(4-acetyl-3-methylpiperazin-1-yl)pyrimidin-5-yl)-2-methyl-1,2-dihydro-3H-indazol-3-one (Preparation #28) in a fashion similar to Example #1 to give the title product (64%); (Table A, Method a) R$_t$=1.82 min; MS m/z: 506 (M+H)$^+$. (TNF IC$_{50}$=A).

Example #106: 1-(2-(Difluoromethoxy)-5-methylbenzyl)-6-(3-(1-hydroxyethyl)imidazo[1,2-b]pyridazin-7-yl)-2-methyl-1H-indazol-3(2H)-one

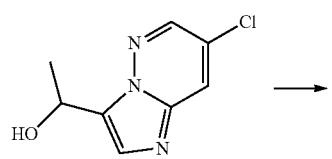

-continued

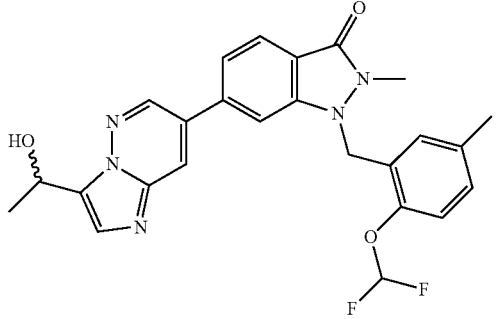

1-(7-Chloroimidazo[1,2-b]pyridazin-3-yl)ethanol (Preparation #45) (208 mg, 1.06 mmol), cesium carbonate (857 mg, 2.64 mmol), 2$^{nd}$ generation XPhos precatalyst (41 mg, 0.052 mmol), and 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, Step 2) (561 mg, 1.27 mmol) were combined in a reaction vessel. The vessel was evacuated and back-filled with N$_2$ three times, then a degassed mixture of 1,4-dioxane (5.5 mL) and water (1.1 mL) was added and the reaction was heated to about 80° C. for about 1 h. The reaction was cooled and partitioned between EtOAc (20 mL) and water (20 mL). The aqueous layer was extracted with additional EtOAc (20 mL), then the combined organic layers were washed with sat. aq. NaCl (10 mL), dried over MgSO$_4$, filtered, and concentrated in vacuo. Further purification via flash chromatography (0-8% DCM:MeOH) yielded the title compound (395 mg, 78%); LC/MS (Table A, Method h) R$_t$=1.15 min; MS m/z: 480 (M+H)$^+$. (TNF IC$_{50}$=A).

Example #107: (R)-1-(2-(Difluoromethoxy)-5-methylbenzyl)-6-(3-(1-hydroxyethyl)imidazo[1,2-b]pyridazin-7-yl)-2-methyl-1H-indazol-3(2H)-one

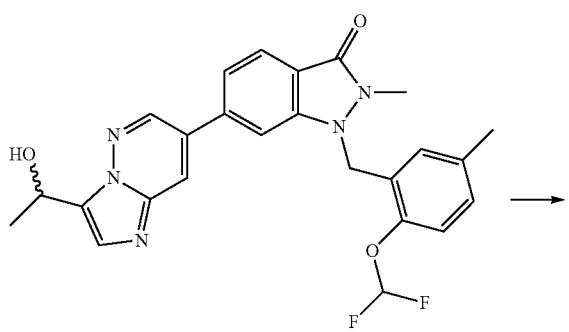

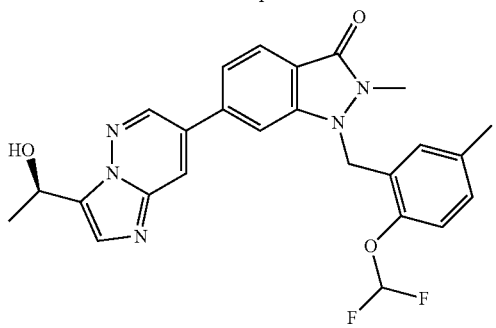

Racemic 1-(2-(difluoromethoxy)-5-methylbenzyl)-6-(3-(1-hydroxyethyl)imidazo[1,2-b]pyridazin-7-yl)-2-methyl- 1H-indazol-3(2H)-one (Example #106) (248 mg, 0.52 mmol) was submitted for chiral SFC HPLC separation (Table C, Method f). The fractions containing the first component to elute (positive optical rotation) were concentrated, then dried in a vacuum oven for about 3 h, yielding the title compound (107 mg, 43%); LC/MS (Table A, Method h) $R_t$=1.16 min; MS m/z; 480 (M+H)$^+$. (TNF IC$_{50}$=A).

Example #108: (S)-1-(2-(Difluoromethoxy)-5-methylbenzyl)-6-(3-(1-hydroxyethyl)imidazo[1,2-b]pyridazin-7-yl)-2-methyl-1H-indazol-3(2H)-one

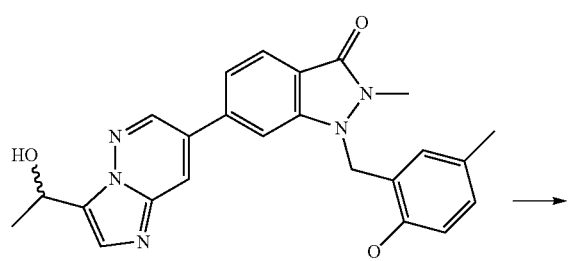

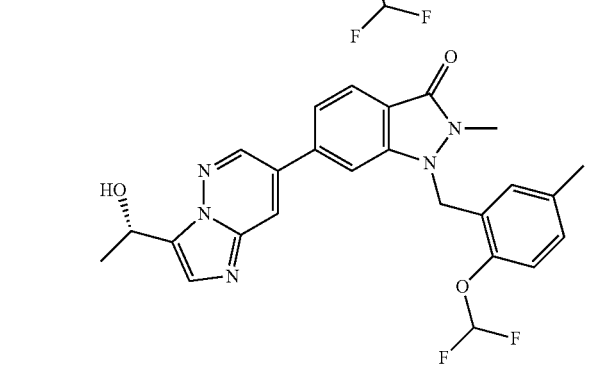

Racemic 1-(2-(difluoromethoxy)-5-methylbenzyl)-6-(3-(1-hydroxyethyl)imidazo[1,2-b]pyridazin-7-yl)-2-methyl-1H-indazol-3(2H)-one (Example #106) (248 mg, 0.52 mmol) was submitted for chiral SFC HPLC separation (Table C, Method f). Isolation of the second component to elute (negative optical rotation), followed by concentration and drying in a vacuum oven for about 3 h, yielded the title compound (112 mg, 45%); LC/MS (Table A, Method h) $R_t$=1.16 min; MS m/z: 480 (M+H)$^+$. (TNF IC$_{50}$=B)

Example #109: 1-(2-Chloro-5-((1-methyl-2-oxopyrrolidin-3-yl)amino)benzyl)-6-(2-(2-hydroxypropan-2-yl)pyrimidin-5-yl)-2-methyl-1H-indazol-3(2H)-one

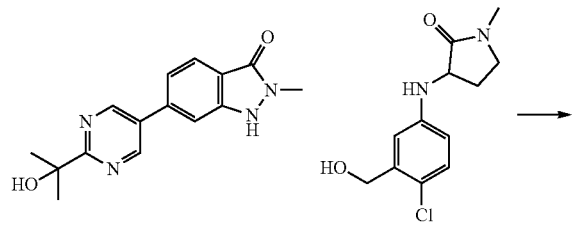

-continued

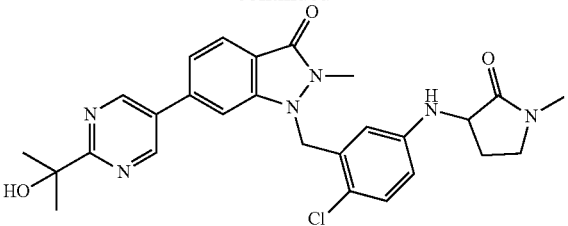

The compound was synthesized in a manner similar to Example #83 from 6-(2-(2-hydroxypropan-2-yl)pyrimidin-5-yl)-2-methyl-1H-indazol-3(2H)-one (Preparation #19) and 3-((4-chloro-3-(hydroxymethyl)phenyl)amino)-1-methylpyrrolidin-2-one (Preparation #44) (11%); LC/MS (Table A, Method e) $R_t$=1.70 min; MS m/z: 521 (M+H)$^+$. (TNF IC$_{50}$=B).

Example #110*: (R)-1-(5-((1H-Pyrazol-4-yl)methyl)-2-(difluoromethoxy)benzyl)-6-(2-(4-acetyl-3-methylpiperazin-1-yl)pyrimidin-5-yl)-2-methyl-1H-indazol-3(2H)-one

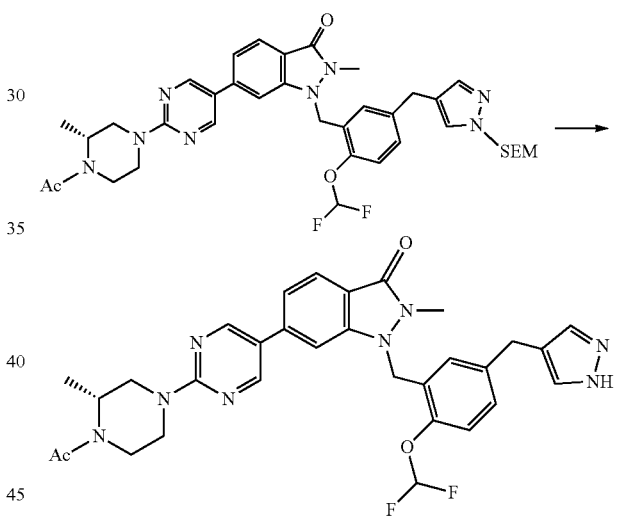

(R)-6-(2-(4-Acetyl-3-methylpiperazin-1-yl)pyrimidin-5-yl)-1-(2-(difluoromethoxy)-5-((1-((2-(trimethylsilyl)ethoxy)methyl)-1H-pyrazol-4-yl)methyl)benzyl)-2-methyl-1H-indazol-3(2H)-one (synthesized in a manner similar to Example #83 from (R)-6-(2-(4-acetyl-3-methylpiperazin-1-yl)pyrimidin-5-yl)-2-methyl-1H-indazol-3(2H)-one (Preparation #28) and (2-(difluoromethoxy)-5-((1-((2-(trimethylsilyl)ethoxy)methyl)-1H-pyrazol-4-yl)methyl)phenyl)methanol (Preparation #70)) (136 mg, 0.186 mmol) was dissolved in DCM (0.6 mL), then cooled to about 0° C. TFA (0.286 mL, 2.54 mmol) was added and the reaction was stirred at about 0° C. for about 5 h. The reaction was quenched with sat. aq. NaHCO$_3$ solution (6 mL), then additional DCM (6 mL) was added. The organic layer was washed with sat. aq. NaCl (5 mL) and concentrated. The resulting residue was purified via reverse phase preparative HPLC (Table A, Method l). The relevant fractions were concentrated to dryness, redissolved in EtOAc (10 mL), and washed with sat. aq. Na$_2$CO$_3$ (5 mL). The organic layer was dried over MgSO$_4$, filtered, and concentrated. The residue was redissolved in methanol (5 mL) and heated to about 40° C. for about 2 h. Removal of the solvent in vacuo yielded the title compound (72 mg, 65%); LC/MS (Table A, Method e) R$_t$=1.76 min; MS m/z: 603(M+H)$^+$. (TNF IC$_{50}$=A).

Example #111: 1-(5-((1H-Pyrazol-4-yl)methyl)-2-(difluoromethoxy)benzyl)-6-(2-(2-hydroxypropan-2-yl)pyrimidin-5-yl)-2-methyl-1H-indazol-3(2H)-one

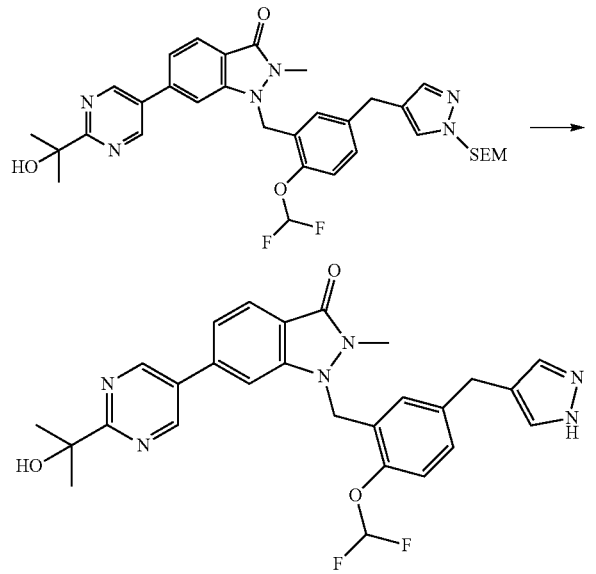

The compound was synthesized in a manner similar to Example #110 from 1-(2-(difluoromethoxy)-5-((1-((2-(trimethylsilyl)ethoxy)methyl)-1H-pyrazol-4-yl)methyl)benzyl)-6-(2-(2-hydroxypropan-2-yl)pyrimidin-5-yl)-2-methyl-1H-indazol-3(2H)-one (synthesized in a manner similar to Example #83 from 6-(2-(2-hydroxypropan-2-yl)pyrimidin-5-yl)-2-methyl-1H-indazol-3(2H)-one (Preparation #19) and (2-(difluoromethoxy)-5-((1-((2-(trimethylsilyl)ethoxy)methyl)-1H-pyrazol-4-yl)methyl)phenyl)methanol (Preparation #70)) (65%); LC/MS (Table A, Method e) R$_t$=1.73 min; MS m/z: 521 (M+H)$^+$. (TNF IC$_{50}$=A)

Example #112: 2-(4-(Difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentanecarbonitrile

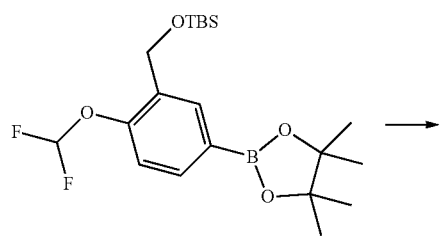

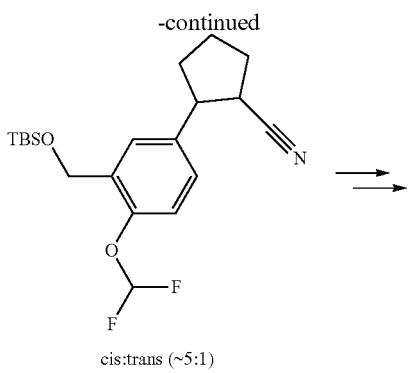

cis:trans (~5:1)

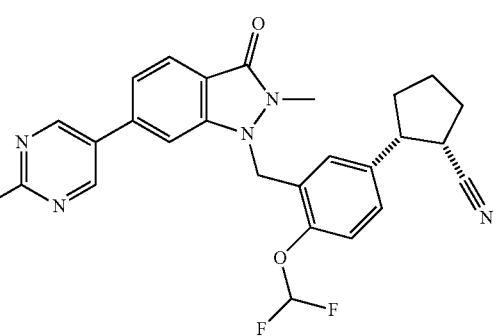

Step 1: 2-(3-(((tert-Butyldimethylsilyl)oxy)methyl)-4-(difluoromethoxy)phenyl)cyclopentanecarbonitrile A flask, purged with nitrogen, was charged with bis((1,5-cyclooctadiene)(hydroxo)rhodium) (145 mg, 0.317 mmol), dioxane (10 mL), H$_2$O (1.5 mL) and potassium hydroxide (36.0 mg, 0.642 mmol). The mixture was stirred at room temperature for about 15 min, then tert-butyl((2-(difluoromethoxy)-5-(4,4,5,5-tetramethyl-1,3,2-dioxaborolan-2-yl)benzyl)oxy)dimethylsilane (505 mg, 1.21 mmol) (prepared from ((5-bromo-2-(difluoromethoxy)benzyl)oxy)(tert-butyl)dimethylsilane (prepared from (5-bromo-2-(difluoromethoxy)phenyl)methanol (Preparation #12) in a similar fashion to Preparation #43, step 1) in a similar fashion to preparation #4, step 2) and 1-cyanocyclopentene (145 mg, 1.56 mmol) were added. The mixture was stirred at 60° C. for about 2 h, and then concentrated under reduced pressure. The residue was purified on silica gel (0-60% EtOAc/heptane) to afford the title product (152 mg, 33%); cis: $^1$H NMR (400 MHz, CDCl$_3$) δ 7.48 (s, 1H), 7.22 (dd, J=8.0, 4.0 Hz, 1H), 7.05 (d, J=8.0 Hz, 1H), 6.50 (d, J=76.0 Hz, 1H), 4.78 (s, 2H), 3.32-3.27 (m, 1H), 3.18 (ddd, J=12.0, 4.0, 4.0 Hz, 1H), 2.22-2.07 (m, 4H), 1.96-1.80 (m, 2H), 0.96 (s, 9H), 0.13(s, 6H).

Step 2: 2-(4-(Difluoromethoxy)-3-((6-(2-(2-hydroxypropan-2-yl)pyrimidin-5-yl)-2-methyl-3-oxo-2,3-dihydro-1H-indazol-1-yl)methyl)phenyl)cyclopentanecarbonltrile A flask was charged with 2-(3-(((tert-butyldimethylsilyl)oxy)methyl)-4-(difluoromethoxy)phenyl)cyclopentanecarbonitrile (150 mg, 0.39 mmol), THF (1 mL) and tetrabutylammonium fluoride (1 M in THF) (2 mL, 2 mmol) at room temperature. The solution was stirred for about 1 h, and then passed through a pad of silica. The filter cake was rinsed with EtOAc, and the filtrate was concentrated under reduced pressure. The residue was dissolved in DCM (2 mL) and carbon tetrabromide (130 mg, 0.39 mmol) and PPh$_3$(110 mg, 0.42 mmol) were added. The solution was stirred at room temperature for about 2 h. A solution of 6-(2-(2-hydroxypropan-2-yl)pyrimidin-5-yl)-2-methyl-1H-indazol-3(2H)-one (110 mg, 0.39 mmol) and potassium carbonate (64 mg, 0.46 mmol) in DMF (2 mL) was added and the mixture was stirred at about 40° C. for about 1 h. The mixture was diluted with H$_2$O (20 mL), and extracted with 10% MeOH in CH$_2$Cl$_2$ (3×10 mL). The organic layer was dried over Na$_2$SO$_4$, filtered and concentrated. The residue was purified on silica gel (0-10% MeOH/CH$_2$Cl$_2$) to afford the title product (110 mg, 56%); LC/MS (Table A, Method a) R$_t$=1.99 min; MS m/z: 534 (M+H)$^+$. (TNF IC$_{50}$=B)

Example #113: (R)-7-(5-(1-(5-((1H-1,2,4-Triazol-1-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one

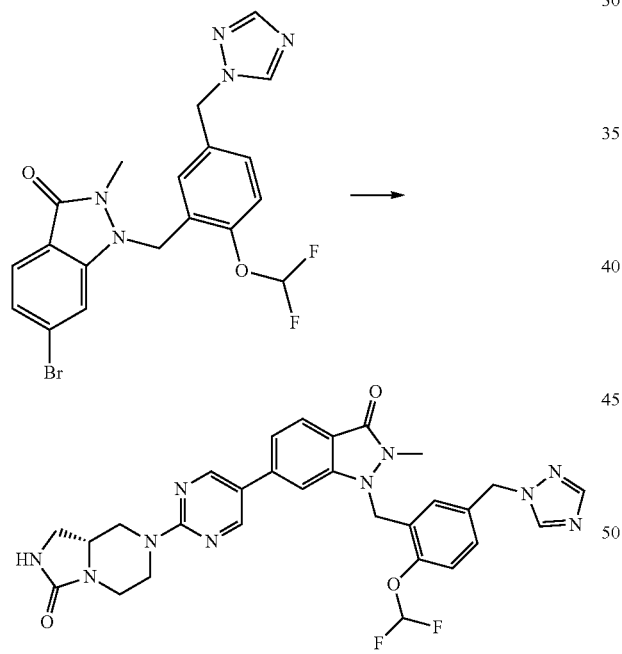

(R)-7-(5-(1-(5-((1H-1,2,4-Triazol-1-yl)methyl)-2-(difluoromethoxy)benzyl)-2-methyl-3-oxo-2,3-dihydro-1H-indazol-6-yl)pyrimidin-2-yl)hexahydroimidazo[1,5-a]pyrazin-3(2H)-one was prepared from 1-(5-((1H-1,2,4-triazol-1-yl)methyl)-2-(difluoromethoxy)benzyl)-6-bromo-2-methyl-1H-indazol-3(2H)-one (Example #104, step 1) and (R)-7-(5-bromopyrimidin-2-yl)hexahydroimidazo[1,5-a]pyrazin-3(2H)-one (Preparation #13) in a similar fashion to Example #8. LC/MS (Table A, Method a) R$_t$=1.52 min; MS m/z: 603(M+H)$^+$. (TNF IC$_{50}$=A)

Example #114: 6-(2-((R)-4-Acetyl-3-methylpiperazin-1-yl)pyrimidin-5-yl)-1-(2-(difluoromethoxy)-5-(2-hydroxypropyl)benzyl)-2-methyl-1H-indazol-3(2H)-one

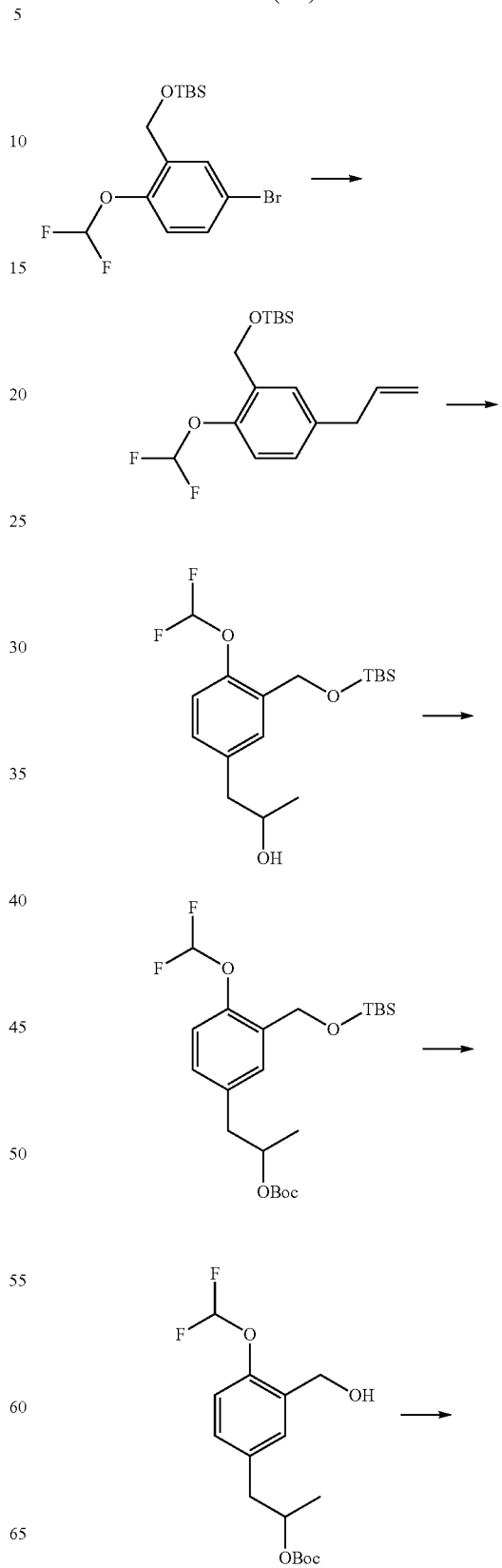

-continued

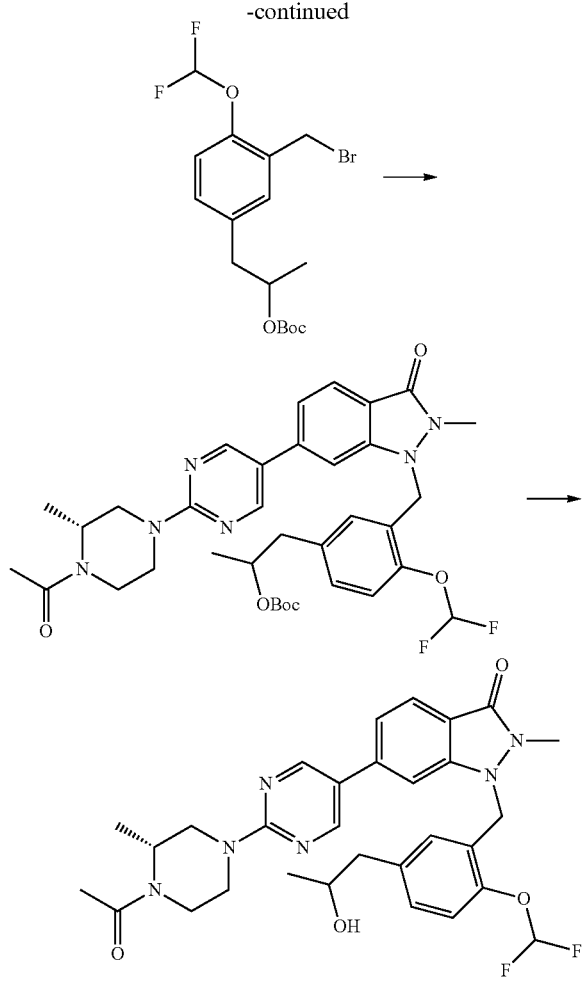

Step 1: ((5-Allyl-2-(difluoromethoxy)benzyl)oxy)(tert-butyl)dimethylsilane

A flask, purged with nitrogen, was charged with allyltributylstannane (126 mg, 0.381 mmol), ((5-bromo-2-(difluoromethoxy)benzyl)oxy)(tert-butyl)dimethylsilane (111 mg, 0.302 mmol) (prepared from (5-bromo-2-(difluoromethoxy)phenyl)methanol (Preparation #12) in a similar fashion to Preparation #43, step 1). DMF (2 mL), $Pd_2dba_3$ (9.0 mg, 9.8 μmol), $PPh_3$ (16 mg, 0.061 mmol) at rt. The mixture was stirred at 100° C. for about 4 h, cooled to rt, and then diluted with $H_2O$ (20 mL). The mixture was extracted with EtOAc (2×10 mL), dried over $Na_2SO_4$, filtered and concentrated. The residue was purified by flash chromatography on silica gel (0-50% EtOAc/heptane) to afford the title product (84 mg, 85%); $^1H$ NMR (400 MHz, $CDCl_3$) δ 7.36 (d, J=2.2 Hz, 1H), 7.07 (dd, J=8.3, 2.3 Hz, 1H), 6.99 (dt, J=8.2, 1.1 Hz, 1H), 6.47 (t, J=74.6 Hz, 1H), 6.06-5.76 (m, 1H), 5.13-5.08 (m, 1H), 5.07 (t, J=1.4 Hz, 1H), 4.76 (s, 2H), 3.38 (dt, J=6.8, 1.4 Hz, 2H), 0.95 (s, 9H), 0.11 (s, 6H).

Step 2: 1-(3-(((tert-Butyldimethylsilyl)oxy)methyl)-4-(difluoromethoxy)phenyl)propan-2-ol A flask was charged with mercuric acetate (2.8 g, 8.8 mmol), $H_2O$ (4 mL), and a solution of ((5-allyl-2-(difluoromethoxy)benzyl)oxy)(tert-butyl)dimethylsilane (2.02 g, 6.15 mmol) in THF (12 mL) at room temperature. The mixture was stirred for about 24 h then cooled to about 0° C. An aqueous solution of NaOH (5M, 15 mL) was added, followed by a solution of $NaBH_4$ (0.20 g, 5.3 mmol) in aqueous NaOH (2.5 M, 5 mL). The mixture was stirred at about 0° C. for about 30 min then at rt for about 16 h. The mixture was extracted with EtOAc (3×25 mL), dried over $Na_2SO_4$, filtered and concentrated. The residue was purified by flash chromatography on silica gel (0-60% EtOAc/heptane) to afford the title product (820 mg, 39%); $^1H$ NMR (400 MHz, $CDCl_3$) δ 7.38 (d, J=2.2 Hz, 1H), 7.10 (dd, J=8.5, 2.2 z, 1H), 7.02 (d, J=8.3 Hz, 1H), 6.49 (td, J=74.4, 0.9 Hz, 1H), 4.87-4.66 (m, 2H), 4.01 (q, J=5.7 Hz, 1H), 2.78 (dd, J=13.6, 5.0 Hz, 1H), 2.70 (dd, J=13.6, 7.8 Hz, 1H), 1.25 (dd, J=6.2, 0.9 Hz, 3H), 0.95 (d, J=0.9 Hz, 9H), 0.12 (d, J=0.8 Hz, 6H).

Step 3: tert-Butyl (1-(3-(((tert-butyldimethylsilyl)oxy)methyl)-4-(difluoromethoxy)phenyl)propan-2-yl)carbonate A flask was charged with 1-(3-(((tert-butyldimethylsilyl)oxy)methyl)-4-(difluoromethoxy)phenyl)propan-2-ol (390 mg, 1.1 mmol), $CH_2Cl_2$ (7 mL), $Boc_2O$ (310 mg, 1.4 mmol), DMAP (22 mg, 0.18 mmol) and TEA (0.05 mL, 0.4 mmol), and stirred at rt for about 1.5 h. The solution was diluted with $H_2O$ (10 mL), the layers were separated, and the aqueous layer was extracted with $CH_2Cl_2$ (5 mL). The combined organic layers were dried over $Na_2SO_4$, filtered and concentrated. The residue was purified by flash chromatography on silica gel (0-30% EtOAc/heptane) to afford the title product (440 mg, 88%); $^1H$ NMR (400 MHz, $CDCl_3$) δ 7.35 (d, J=2.3 Hz, 1H), 7.15-6.93(m, 2H), 6.69-6.24 (m, 1H), 4.90 (d, J=6.5 Hz, 1H), 4.74 (s, 2H), 3.05-2.89 (m, 1H), 2.75 (dt, J=14.2, 7.3 Hz, 1H), 1.45 (s, 9H), 1.25 (d, J=6.3 Hz, 3H), 0.94 (d, J=0.7 Hz, 9H), 0.11 (dd, J=1.3, 0.7 Hz, 6H).

Step 4: tert-Butyl (1-(4-(difluoromethoxy)-3-(hydroxymethyl)phenyl)propan-2-yl)carbonate A flask was charged with tert-butyl (1-(3-(((tert-butyldimethylsilyl)oxy)methyl)-4-(difluoromethoxy)phenyl)propan-2-yl)carbonate (440 mg, 0.99 mmol). THF (4 mL) then cooled to about 10° C. A solution of tetrabutylammonium fluoride in THF (1 M, 2.5 mL) was added and the solution was stirred for about 20 min then diluted with EtOAc (10 mL). The solution was filtered through a pad of silica gel and the filtrate was concentrated under reduced pressure. The residue was purified by flash chromatography on silica gel (0-50% EtOAc/heptane) to afford the title product (50 mg, 15%); $^1H$ NMR (400 MHz. $CDCl_3$) δ 7.31 (d, J=2.2 Hz, 1H), 7.15 (dd. J=8.3, 2.2 Hz, 11H), 7.08-7.01 (m, 1H), 6.52 (td, J=74.1, 1.0 Hz, 1H), 4.91 (h, J=6.4 Hz, 1H), 4.72 (d, J=5.0 Hz, 2H), 2.97 (dd, J=13.7, 6.6 Hz, 1H), 2.76 (dd, J=13.7, 6.7 Hz, 1H), 1.44 (d, J=1.0 Hz, 9H), 1.26 (d, J=6.4 Hz, 3H).

Step 5: 1-(3-(Bromomethyl)-4-(difluoromethoxy)phenyl)propan-2-yl tert-butyl carbonate 1-(3-(Bromomethyl)-4-(difluoromethoxy)phenyl)propan-2-yl tert-butyl carbonate was prepared in a similar fashion to Preparation #14, step 6. $^1H$ NMR (400 MHz, $CDCl_3$) δ 7.28 (d, J=2.2 Hz, 1H), 7.16 (d, J=2.2 Hz, 1H), 7.07 (d, J=8.5 Hz, 1H), 6.54 (t, J=73.8 Hz, 1H), 4.90 (q, J=6.4 Hz, 1H), 4.51 (d, J=1.6 Hz, 2H), 2.95 (dd, J=13.8, 6.7 Hz, 1H), 2.75 (dd, J=13.8, 6.5 Hz, 1H), 1.44 (s, 9H), 1.26 (d, J=6.3 Hz, 3H).

Step 6: 1-(3-((6-(2-((R)-4-Acetyl-3-methylpiper-azin-1-yl)pyrimidin-5-yl)-2-methyl-3-oxo-2,3-dihydro-1H-indazol-1-yl)methyl)-4-(difluoromethoxy)phenyl)propan-2-yl tert-butyl carbonate 1-(3-((6-(2-((R)-4-Acetyl-3-methylpiperazin-1-yl)pyrimidin-5-yl)-2-methyl-3-oxo-2,3-dihydro-1H-indazol-1-yl)methyl)-4-(difluoromethoxy)phenyl)propan-2-yl tert-butyl carbonate was prepared from (R)-6-(2-(4-acetyl-3-methyl-piperazin-1-yl)pyrimidin-5-yl)-2-methyl-1H-indazol-3 (2H)-one (Preparation #28) and 1-(3-(bromomethyl)-4-(difluoromethoxy)phenyl)propan-2-yl tert-butyl carbonate in a similar fashion to Example #1. LC/MS (Table A, Method i) $R_t$=2.31 min; MS m/z: 681 (M+H)$^+$.

Step 7: 6-(2-((R)-4-Acetyl-3-methylpiperazin-1-yl)pyrimidin-5-yl)-1-(2-(difluoromethoxy)-5-(2-hydroxypropyl)benzyl)-2-methyl-1H-indazol-3(2H)-one 6-(2-((R)-4-Acetyl-3-methylpiperazin-1-yl)pyrimidin-5-yl)-1-(2-(difluoromethoxy)-5-(2-hydroxypropyl)benzyl)-2-methyl-1H-indazol-3(2H)-one was prepared in a similar fashion to Example #3, step 1. LC/MS (Table A, Method a) $R_t$=1.75 min; MS m/z: 581 (M+H)$^+$. (TNF IC$_{50}$=B).

Example #115: 6-(2-(4-Acetylpiperazin-1-yl)pyrimidin-5-yl)-1-(5-(hydroxymethyl)-2-(trifluoromethyl)benzyl)-2-methyl-1H-indazol-3(2H)-one

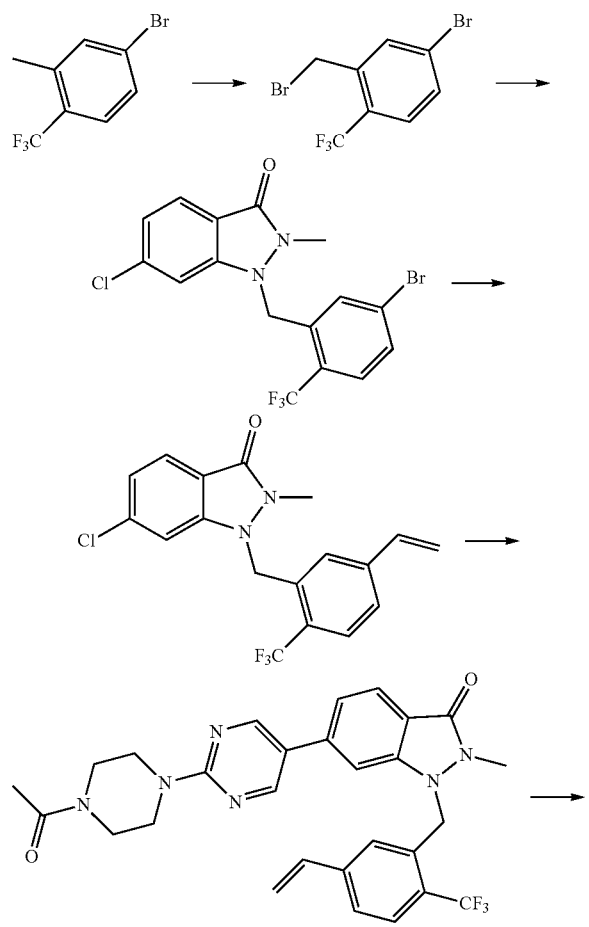

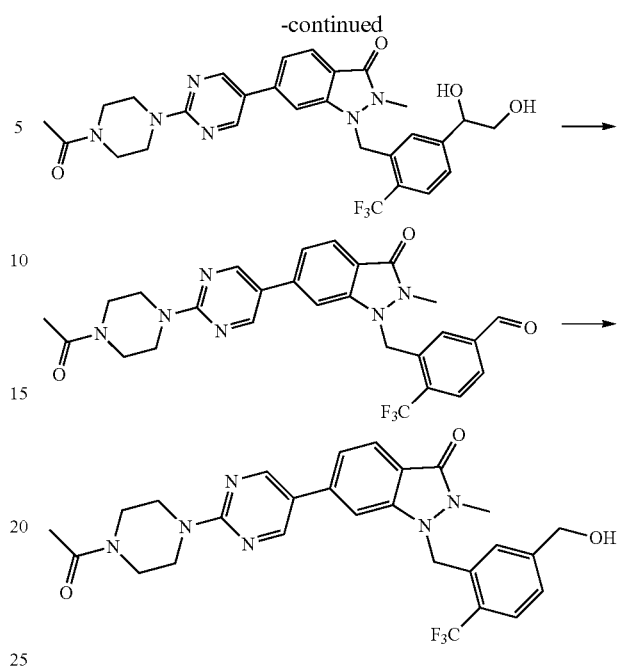

Step 1: 4-Bromo-2-(bromomethyl)-1-(trifluoromethyl)benzene

4-Bromo-2-methyl-1-(trifluoromethyl)benzene (2.00 g, 8.37 mmol), 1-bromopyrrolidine-2,5-dione (1.49 g, 8.37 mmol) and benzoic peroxyanhydride (0.101 g, 0.418 mmol) in CCl$_4$ (10 mL) was heated to reflux under nitrogen for about 48 h. The reaction was cooled to rt, diluted with DCM (25 mL) and washed with sat. aq. NaHCO$_3$ (20 mL) and water (20 mL). The organic layer was dried over MgSO$_4$, filtered, and concentrated. The residue was purified on silica gel (0-10% EtOAc/Heptane) to afford the title product (1.7 g, 64%); $^1$H NMR (400 MHz, CDCl$_3$) δ 7.77-7.74 (m, 1H), 7.59-7.38 (m, 2H), 4.57 (s, 2H).

Step 2: 1-(5-Bromo-2-(trifluoromethyl)benzyl)-6-chloro-2-methyl-1H-indazol-3(2H)-one The reaction was performed using 4-bromo-2-(bromomethyl)-1-(trifluoromethyl)benzene and 6-chloro-2-methyl-1H-indazol-3(2H)-one (Preparation #29) in a similar fashion to Example #1 to afford the title product (1.3 g, 58%); LC/MS (Table A, Method e) $R_t$=2.51 min; MS m/z: 419 and 421 (M+H)$^+$.

Step 3: 6-Chloro-2-methyl-1-(2-(trifluoromethyl)-5-vinylbenzyl)-1H-indazol-3(2H)-one The reaction was performed using 1-(5-bromo-2-(trifluoromethyl)benzyl)-6-chloro-2-methyl-1H-indazol-3(2H)-one in a similar fashion to Example #14, step 4 to afford the title product (0.70 g, 89%); LC/MS (Table A, Method i) $R_t$=1.67 min; MS m/z: 367 (M+H)$^+$.

Step 4: 6-(2-(4-Acetylpiperazin-1-yl)pyrimidin-5-yl)-2-methyl-1-(2-(trifluoromethyl)-5-vinylbenzyl)-1H-indazol-3(2H)-one The reaction was performed using 6-chloro-2-methyl-1-(2-(trifluoromethyl)-5-vinylbenzyl)-1H-indazol-3(2H)-one and 1-(4-(5-bromopyrimidin-2-yl)piperazin-1-yl)ethanone (prepared in a similar fashion to Preparation #13, step 1 using 1-(piperazin-1-yl)ethanone) in a similar fashion to Example #33, step 9 to afford the title product (0.15 g, 63%); LC/MS (Table A, Method i) $R_t$=1.40 min; MS m/z: 537 (M+H)$^+$.

Step 5: 6-(2-(4-Acetylpiperazin-1-yl)pyrimidin-5-yl)-1-(5-(1,2-dihydroxyethyl)-2-(trifluoromethyl)benzyl)-2-methyl-1H-indazol-3(2H)-one 4-Methylmorpholine 4-oxide (72.0 mg, 0.615 mmol) was added to a solution of 6-(2-(4-acetylpiperazin-1-yl)pyrimidin-5-yl)-2-methyl-1-(2-(trifluoromethyl)-5-vinylbenzyl)-1H-indazol-3(2H)-one (110 mg, 0.205 mmol) in THF (4 mL). After cooling to about 0° C., osmium tetroxide (4% in water) (65.2 mg, 10.3 µmol) was added. The reaction was stirred at about 0° C. for about 30 min and at rt for about 18 h. The reaction was quenched with 10% aq. $Na_2S_2O_5$ (10 mL). After stirring for about 15 min, EtOAc (20 mL) was added. The mixture was filtered. The layers were separated and the aqueous layer was extracted with EtOAc (2×10 mL). The combined organic layers were dried over $MgSO_4$, filtered and concentrated to give the title product (0.12 g, 100%); LC/MS (Table A, Method i) $R_t$=1.03 min; MS m/z: 571 (M+H)$^+$.

Step 6: 3-((6-(2-(4-Acetylpiperazin-1-yl)pyrimidin-5-yl)-2-methyl-3-oxo-2,3-dihydro-1H-indazol-1-yl)methyl)-4-(trifluoromethyl)benzaldehyde THF (4 mL) and water (1 mL) were added to 6-(2-(4-acetylpiperazin-1-yl)pyrimidin-5-yl)-1-(5-(1,2-dihydroxyethyl)-2-(trifluoromethyl)benzyl)-2-methyl-1H-indazol-3(2H)-one (175 mg, 0.307 mmol). Sodium periodate (98 mg, 0.46 mmol) was added. After about 20 min, the reaction was quenched with EtOAc (30 mL) and water (10 mL), the layers were separated, and the organic layer was washed with sat. aq. NaCl (10 mL), dried over $MgSO_4$, and concentrated to give the title product (0.10 g, 63%); LC/MS (Table A, Method i) $R_t$=1.18 min; MS m/z: 539 (M+H)$^+$.

Step 7: 6-(2-(4-Acetylpiperazin-1-yl)pyrimidin-5-yl)-1-(5-(hydroxymethyl)-2-(trifluoromethyl)benzyl)-2-methyl-1H-indazol-3(2H)-one The reaction was performed using 3-((6-(2-(4-acetylpiperazin-1-yl)pyrimidin-5-yl)-2-methyl-3-oxo-2,3-dihydro-1H-indazol-1-yl)methyl)-4-(trifluoromethyl)benzaldehyde in a similar fashion to Preparation #9 to afford the title product (38 mg, 35%); LC/MS (Table A, Method a) $R_t$=1.71 min; MS m/z: 541 (M+H)$^+$. (TNF IC$_{50}$=A).

Example #116: 6-(2-((R)-4-(2-hydroxyacetyl)-3-methylpiperazin-1-yl)pyrimidin-5-yl)-2-methyl-1-(1-(m-tolyl)ethyl)-1H-indazol-3(2H)-one

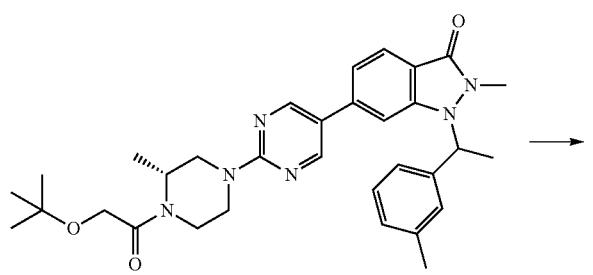

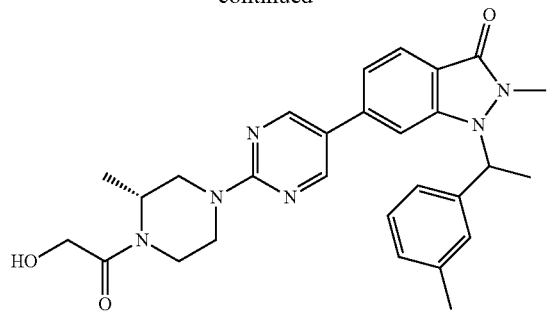

The reaction was performed using 6-(2-((R)-4-(2-(tert-butoxy)acetyl)-3-methylpiperazin-1-yl)pyrimidin-5-yl)-2-methyl-1-(1-(m-tolyl)ethyl)-1H-indazol-3(2H)-one (synthesized in a manner similar to Preparation #4, step 1 from (R)-6-(2-(4-(2-(tert-butoxy)acetyl)-3-methylpiperazin-1-yl)pyrimidin-5-yl)-2-methyl-1H-indazol-3(2H)-one (Preparation #60) and 1-(1-bromoethyl)-3-methylbenzene (synthesized in a manner similar to Preparation #21, step 2 from 1-(m-tolyl)ethanol (synthesized in a manner similar to Preparation #9 from 1-(m-tolyl)ethanone))) in a similar fashion to Example #30 to afford the title product (28 mg, 44%); LC/MS (Table A, Method a) $R_t$=1.94 min; MS m/z: 501 (M+H)$^+$. (TNF IC$_{50}$=A)

Example #117: 6-(2-((R)-4-(2-Hydroxyacetyl)-3-methylpiperazin-1-yl)pyrimidin-5-yl)-2-methyl-1-((S)-1-(m-tolyl)ethyl)-1H-indazol-3(2H)-one

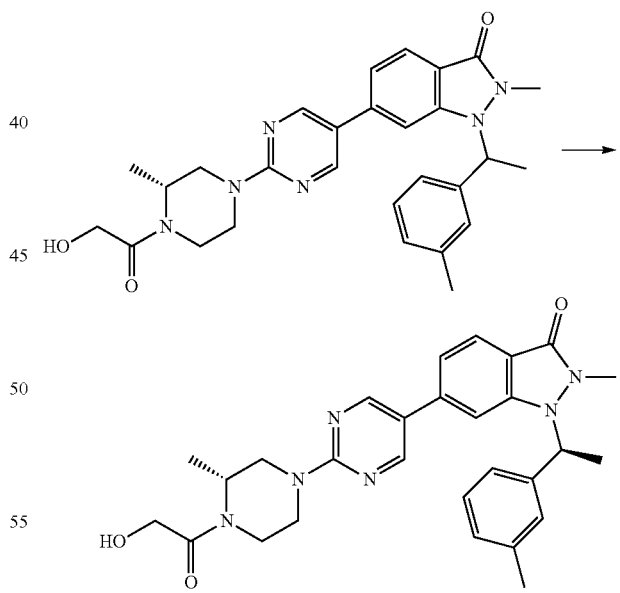

6-(2-((R)-4-(2-Hydroxyacetyl)-3-methylpiperazin-1-yl)pyrimidin-5-yl)-2-methyl-1-(1-(m-tolyl)ethyl)-1H-indazol-3(2H)-one (0.28 g, 0.54 mmol) (Example #116) was submitted for chiral separation (Table C, Method e). Fractions from the first eluding component were combined and concentrated. The residue was dissolved in MeCN (0.5 mL) then water (5 mL) was added. The mixture was sonicated then frozen. The resulting solid was lyophilized to afford the title product (0.085 g, 31%) with negative optical rotation. LC/MS (Table A, Method h) R_t=1.25 min; MS m/z: 501 (M+H)+. (TNF IC_{50}=A).

Example #118: 6-(2-((R)-4-(2-Hydroxyacetyl)-3-methylpiperazin-1-yl)pyrimidin-5-yl)-2-methyl-1-((R)-1-(m-tolyl)ethyl)-1H-indazol-3(2H)-one

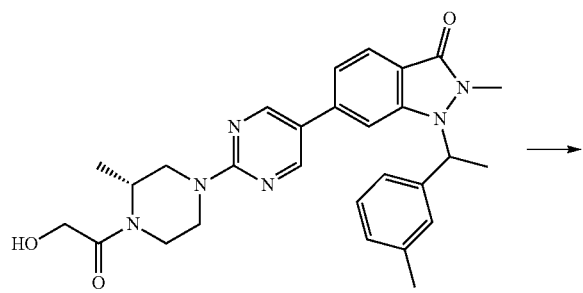

6-(2-((R)-4-(2-Hydroxyacetyl)-3-methylpiperazin-1-yl)pyrimidin-5-yl)-2-methyl-1-(1-(m-tolyl)ethyl)-1H-indazol-3(2H)-one (0.28 g, 0.54 mmol) (Example #116) was submitted for chiral separation (Table C, Method e). Fractions from the second eluding component were combined and concentrated. The residue was dissolved in MeCN (0.5 mL) then water (5 mL) was added. The mixture was sonicated then frozen. The resulting solid was lyophilized to afford the title product (0.090 g, 33%) with positive optical rotation. LC/MS (Table A, Method h) R_t=1.25 min; MS m/z: 501 (M+H)+. (TNF IC_{50}=B).

Example #119*: (R)-6-(2-(4-Acetyl-3-methylpiperazin-1-yl)pyrimidin-5-yl)-1-((1-acetyl-4-(trifluoromethyl)-1H-pyrrol-3-yl)methyl)-2-methyl-1H-indazol-3(2H)-one

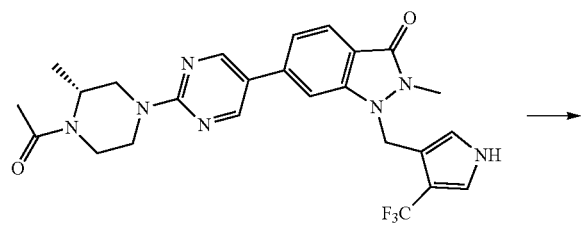

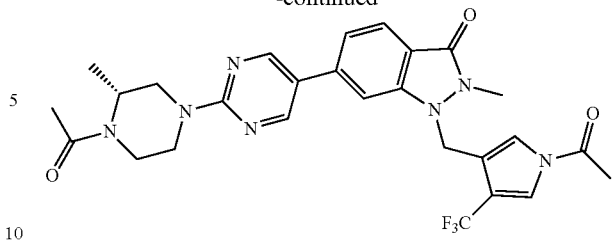

Sodium hydride (60% dispersion in mineral oil) (6.5 mg, 0.16 mmol) in THF (1 mL) was cooled to about 0° C. A solution of (R)-6-(2-(4-acetyl-3-methylpiperazin-1-yl)pyrimidin-5-yl)-2-methyl-1-((4-(trifluoromethyl)-1H-pyrrol-3-yl)methyl)-1H-indazol-3(2H)-one (120 mg, 0.234 mmol) (Example #27.5) in THF (1 mL) was added dropwise via syringe and the reaction was stirred for about 15 min at about 0° C. A solution of acetyl chloride (12.8 mg, 0.16 mmol) in THF (1 mL) was added dropwise via syringe at about 0° C. and the reaction was stirred at rt for about 18 h. The reaction was quenched with sat. aq. NH_4Cl (2 mL) and extracted with DCM (10 mL). The organic layer was dried over MgSO_4, filtered, and concentrated. The residue was purified on silica gel (0-8% MeOH/CH2Cl2) to afford the title product (14 mg, 10%); LC/MS (Table A, Method a) R_t=1.85 min; MS m/z: 556 (M+H)+. (TNF IC_{50}=A).

Example #120: 6-(2-(2-Aminopropan-2-yl)pyrimidin-5-yl)-1-(2-(difluoromethoxy)-5-methylbenzyl)-2-methyl-1H-indazol-3(2H)-one

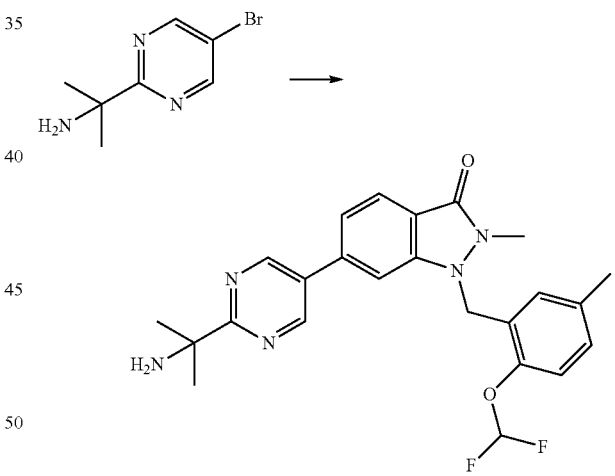

1-(2-(Difluoromethoxy)-5-methylbenzyl)-2-methyl-6-(4,4,5,5-tetramethyl-1,3,2-dioxaborolan-2-yl)-1H-indazol-3(2H)-one (Example #22, step 2) (452 mg, 1.02 mmol), 2-(5-bromopyrimidin-2-yl)propan-2-amine (prepared in a manner similar to conditions found in WO201586526 A1) (200 mg, 0.93 mmol), cesium carbonate (754 mg, 2.31 mmol), and bis(triphenylphosphine)palladium(II) dichloride (39 mg, 0.056 mmol) were combined, then the vessel was evacuated and back-filled with N_2 three times. A degassed mixture of dioxane (4.8 mL) and water (1.0 mL) was added and the reaction was heated to about 80° C. and stirred for about 90 min. Additional bis(triphenylphosphine)palladium (II) dichloride (39 mg, 0.056 mmol) was added and the reaction was stirred at about 85° C. for about 2.5 h. The

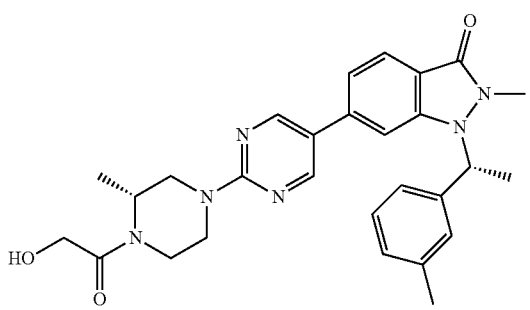 [SMILES: CC(c1ccccc1Cl)n1c2cc(-c3cnc(N4CCN(C(=O)CO)[C@H](C)C4)nc3)ccc2c(=O)n1C]

reaction was cooled and partitioned between EtOAc (20 mL) and water (20 mL). The aqueous layer was extracted with additional EtOAc (20 mL) then the combined organic layers were dried over MgSO$_4$, filtered, and concentrated. The resulting residue was purified via reverse phase preparative HPLC (Table A, Method I). The relevant fractions were concentrated, redissolved in DCM (20 mL) and washed with sat. aq. Na$_2$CO$_3$ solution (10 mL). The organic layer was dried over MgSO$_4$, filtered, and concentrated to yield the title compound (130 mg, 31%); LC/MS (Table A, Method h) R$_t$=0.95 min.; MS m/z: 454 (M+H)$^+$. (TNF IC$_{50}$=A)

Example #121*: (R)-1-(2-(Difluoromethoxy)benzyl)-7-fluoro-6-(2-(4-(2-hydroxyacetyl)-2-methylpiperazin-1-yl)pyrimidin-5-yl)-2-methyl-1H-indazol-3(2H)-one

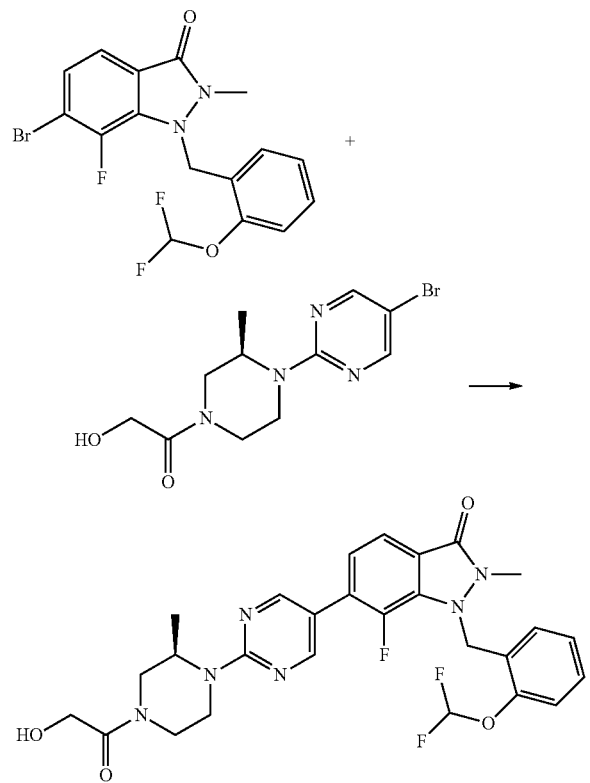

The reaction was performed in a similar manner to Example #8 using (R)-1-(4-(5-bromopyrimidin-2-yl)-3-methylpiperazin-1-yl)-2-hydroxyethanone (Preparation #22) and 6-Bromo-1-(2-(difluoromethoxy)benzyl)-7-fluoro-2-methyl-1H-indazol-3(2H)-one (prepared in a similar fashion to Preparation #4, step 1 using 6-bromo-7-fluoro-2-methyl-1H indazol-3(2H)-one (Preparation #38) and 1-(bromomethyl)-2-(difluoromethoxy)benzene)) to give the title product (34%); (Table A, Method a) R$_t$=1.87 min; MS m/z: 557 (M+H)$^+$. (TNF IC$_{50}$=A)

Example #122: 1-(2-Chloro-5-((2-hydroxy-2-methylpropyl)amino)benzyl)-6-(2-(2-hydroxypropan-2-yl)pyrimidin-5-yl)-2-methyl-1H-indazol-3(2H)-one

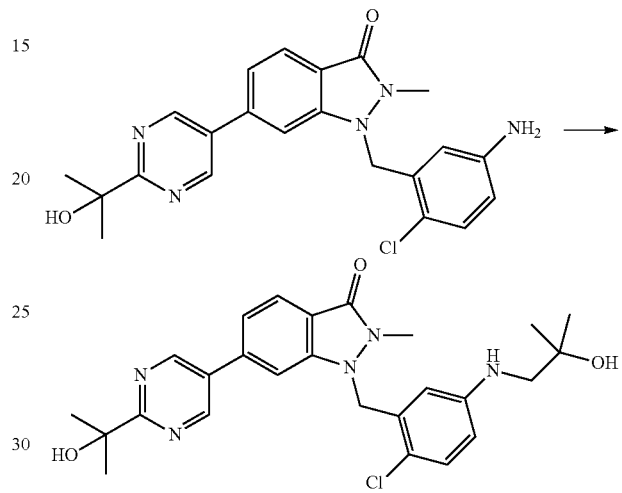

A scintillation vial was charged with 1-(5-amino-2-chlorobenzyl)-6-(2-(2-hydroxypropan-2-yl)pyrimidin-5-yl)-2-methyl-1H-indazol-3(2H)-one (0.140 g, 0.304 mmol) (Example #42, step 2), trifluoroethanol (0.65 mL) and 2,2-dimethyloxirane (0.136 mL, 1.52 mmol). The system was sealed then heated to about 60° C. for about 16 h. After cooling to rt, the solvent was removed under reduced pressure. The residue was concentrated from EtOAc (5 mL) twice. The material was purified via flash chromatography on silica gel (0-4% MeOH/DCM). The appropriate fractions were collected and concentrated under reduced pressure to provide the title product (0.025 g, 17%); LC/MS (Table A, Method h) R$_t$=1.14 min.; MS m/z: 496 (M+H)$^+$. (TNF IC$_{50}$=B)

The compounds shown in Table 30 were synthesized in a manner similar to Example #122 from 1-(5-amino-2-chlorobenzyl)-6-(2-(2-hydroxypropan-2-yl)pyrimidin-5-yl)-2-methyl-1H-indazol-3(2H)-one (Example #42, step 2) and the corresponding epoxide.

TABLE 30

| Epoxide | Product | Example # | R$_t$ min (Table A, Method) | m/z ESI+ (M + H)$^+$ | TNF IC$_{50}$ |
|---|---|---|---|---|---|
| (S)-2-Methyloxirane | | 30.1* | 1.08 (h) | 482 | B |

TABLE 30-continued

| Epoxide | Product | Example # | R, min (Table A, Method) | m/z ESI+ (M + H)+ | TNF IC50 |
|---|---|---|---|---|---|
| (R)-2-Metyhloxirane | | 30.2* | 1.08 (h) | 482 | B |

Example #123: (S)-7-(5-(2-Methyl-1-((1-methyl-4-(trifluoromethyl)-1H-pyrrol-3-yl)methyl)-3-oxo-2,3-dihydro-1H-indazol-6-yl)pyrimidin-2-yl)hexahydroimidazo[1,5-a]pyrazin-3(2H)-one

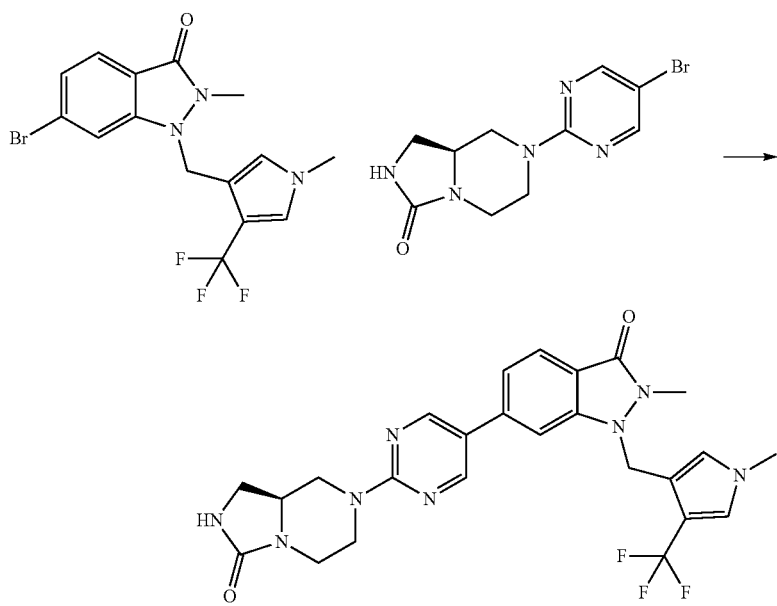

(S)-7-(5-(2-Methyl-1-((1-methyl-4-(trifluoromethyl)-1H-pyrrol-3-yl)methyl)-3-oxo-2,3-dihydro-1H-indazol-6-yl)pyrimidin-2-yl)hexahydroimidazo[1,5-a]pyrazin-3(2H)-one was prepared in a manner similar to Example #8 using (S)-7-(5-bromopyrimidin-2-yl)hexahydroimidazo[1,5-a]pyrazin-3(2H)-one (Preparation #13) and 6-bromo-2-methyl-1-((1-methyl-4-(trifluoromethyl)-1H-pyrrol-3-yl)methyl)-1H-indazol-3(2H)-one (prepared in a similar manner to Example #1 using 6-bromo-2-methyl-1H-indazol-3(2H)-one (Preparation #1) and 3-(chloromethyl)-1-methyl-4-(trifluoromethyl)-1H-pyrrole, hydrochloric acid (prepared in a similar manner to Preparation #50, step 6 using (1-methyl-4-(trifluoromethyl)-1H-pyrrol-3-yl)methanol (prepared in a similar manner to Preparation #32, step 4 using ethyl 1-methyl-4-(trifluoromethyl)-1H-pyrrole-3-carboxylate (WO 2001049664 A1)))) to afford the title compound (84%); LC/MS (Table A, Method a) R$_t$=1.75 min; MS m/z: 527 (M+H)+. (TNF IC$_{50}$=A).

Example #124: 1-(2-(Difluoromethoxy)-5-methylbenzyl)-6-(2-isopropylpyrimidin-5-yl)-2-methyl-1H-indazol-3(2H)-one

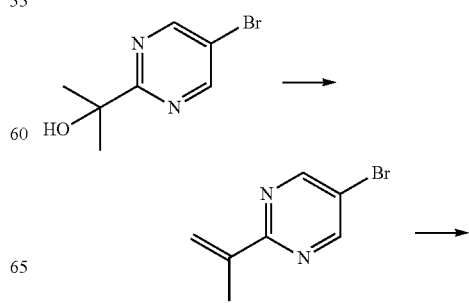

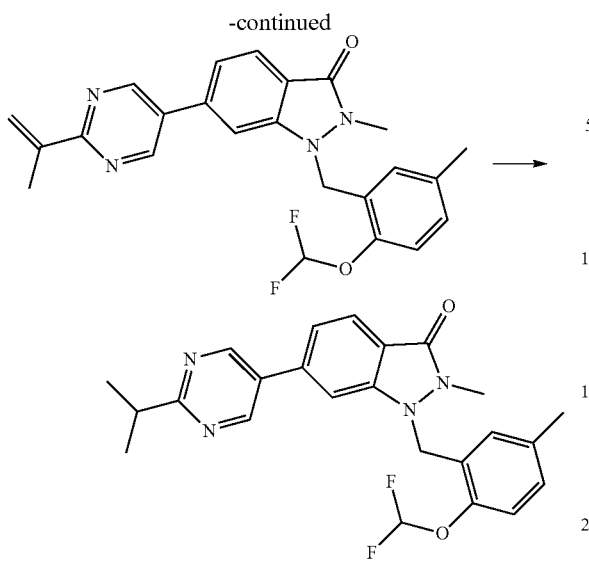

Step 1: 5-Bromo-2-(prop-1-en-2-yl)pyrimidine

SOCl$_2$ (3.50 mL, 48.0 mmol) was added to a solution of 2-(5-bromopyrimidin-2-yl)propan-2-ol (1.00 g, 4.61 mmol) and DCM (10.0 mL). After about 90 min, pyridine (1.10 mL, 13.6 mmol) was added in one portion. After about 18 h, the volatiles were removed under reduced pressure. The residue was dissolved in DCM (50 mL), sat. aq. NH$_4$Cl (50 mL), and water (10 mL). The layers were separated. The organic layer was dried over Na$_2$SO$_4$, filtered, and concentrated under reduced pressure. The residue was purified using flash chromatography on silica gel (0-15% EtOAc/heptane). The appropriate fractions were collected and concentrated under reduced pressure to afford the title product (54%); $^1$H NMR (400 MHz, DMSO-d$_6$) δ 8.95 (s, 2H), 6.37 (dq, J=2.2, 0.9 Hz, 1H), 5.58 (dq, J=2.3, 1.6 Hz, 1H), 2.14 (dd, J=1.5, 0.9 Hz, 3H).

Step 2: 1-(2-(Difluoromethoxy)-5-methylbenzyl)-2-methyl-6-(2-(prop-1-en-2-yl)pyrimidin-5-yl)-1H-indazol-3(2H)-one 1-(2-(Difluoromethoxy)-5-methylbenzyl)-2-methyl-6-(2-(prop-1-en-2-yl)pyrimidin-5-yl)-1H-indazol-3(2H)-one was prepared in a manner similar to Example #15, step 4 using 5-bromo-2-(prop-1-en-2-yl)pyrimidine and 1-(2-(difluoromethoxy)-5-methylbenzyl)-2-methyl-6-(4,4,5,5-tetramethyl-1,3,2-dioxaborolan-2-yl)-1H-indazol-3(2H)-one (Example #22, step 2) to afford the title product (51%); LC/MS (Table A, Method i) R$_t$=1.64 min; MS m/z: 437 (M+H)$^+$.

Step 3: 1-(2-(Difluoromethoxy)-5-methylbenzyl)-6-(2-Isopropylpyrimidin-5-yl)-2-methyl-1H-indazol-3(2H)-one MeOH (3.50 mL) was added to a mixture of 1-(2-(difluoromethoxy)-5-methylbenzyl)-2-methyl-6-(2-(prop-1-en-2-yl)pyrimidin-5-yl)-1H-indazol-3(2H)-one (0.150 g, 0.344 mmol) and 10% palladium on carbon (wet) (0.073 g) under N$_2$. The mixture was placed under H$_2$ (balloon). After about 2 h, the atmosphere was evacuated and the reaction mixture was filtered through Celite® rinsing with 50% MeOH/DCM (30 mL). The volatiles were removed under reduced pressure. The residue was purified on silica gel using a gradient of 0-80% EtOAc/DCM. The appropriate fractions were collected and concentrated to afford the title product (95.8 mg, 63%); LC/MS (Table A, Method a) R$_t$=2.28 min; MS m/z: 439 (M+H)$^+$. (TNF IC$_{50}$=A).

Example #125: 1-(2-(Difluoromethoxy)-5-morpholinobenzyl)-6-(2-(2-hydroxypropan-2-yl)pyrimidin-5-yl)-2-methyl-1H-indazol-3(2H)-one

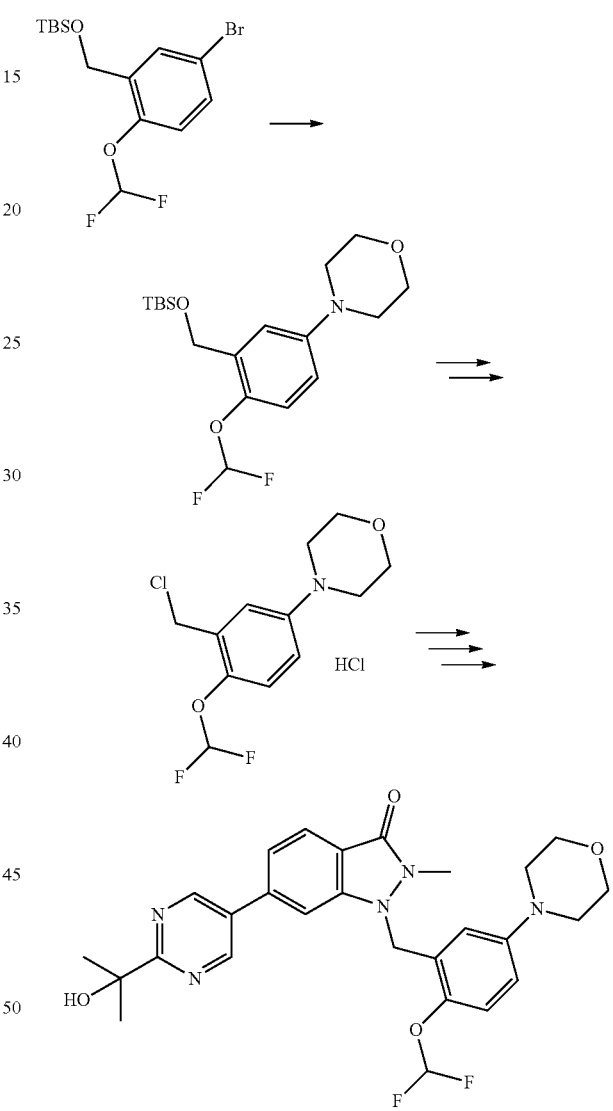

Step 1: 4-(3-(((tert-Butyldimethylsilyl)oxy)methyl)-4-(difluoromethoxy)phenyl)morpholine Sodium tert-butoxide (1.60 g, 16.65 mmol) was added to a solution of ((5-bromo-2-(difluoromethoxy)benzyl)oxy)(tert-butyl)dimethylsilane (2.46 g, 6.70 mmol) (prepared in a similar manner to Preparation #43, step 1 from (5-bromo-2-(difluoromethoxy)phenyl)methanol (Preparation #12)), morpholine (1.80 mL, 20.1 mmol), and toluene (60.0 mL) under N$_2$. Pd$_2$dba$_3$ (0.305 g, 0.333 mmol) and 1,1'-binaphthalene-2,2'-diyl)bis(diphenylphosphine (0.628 g, 1.009 mmol) were added. The reaction vessel was evacuated and back-filled with N₂ three times then purged with N₂ for about 20 min. The mixture was warmed to about 100° C. After about 3 h, the mixture was allowed to cool to rt. Water (50 mL) and EtOAc (100 mL) were added. The layers were separated and the organic layer was washed with sat. aq. NaCl (50 mL). The organic layer was dried over Na₂SO₄, filtered, and concentrated under reduced pressure. The residue was purified by flash chromatography on silica gel eluding with a gradient of 0-20% EtOAc/heptane. The appropriate fractions were collected and concentrated under reduced pressure to afford the title compound (0.689 g, 28%); LC/MS (Table A, Method i) $R_f$=2.22 min; MS m/z: 374 (M+H)⁺.

Step 2: 4-(3-(Chloromethyl)-4-(difluoromethoxy) phenyl)morpholine, hydrochloric acid 4-(3-(Chloromethyl)-4-(difluoromethoxy)phenyl)morpholine, hydrochloric acid was prepared in a similar manner to Preparation #50, step 6 using (2-(difluoromethoxy)-5-morpholinophenyl)methanol (prepared in a similar manner to Preparation #43, step 1 using 4-(3-(((tert-butyldimethylsilyl)oxy)methyl)-4-(difluoromethoxy)phenyl)morpholine) to afford the title product; (95%); LC/MS (Table A, Method i) $R_f$=1.46 min; MS m/z: 278 (M+H)⁺.

Step 3: 1-(2-(Difluoromethoxy)-5-morpholinobenzyl)-6-(2-(2-hydroxypropan-2-yl)pyrimidin-5-yl)-2-methyl-1H-indazol-3(2H)-one 1-(2-(Difluoromethoxy)-5-morpholinobenzyl)-6-(2-(2-hydroxypropan-2-yl)pyrimidin-5-yl)-2-methyl-1H-indazol-3(2H)-one was prepared in a similar manner to Example #15, step 4 using 2-(5-bromopyrimidin-2-yl)propan-2-ol and 1-(2-(difluoromethoxy)-5-morpholinobenzyl)-2-methyl-6-(4,4,5,5-tetramethyl-1,3,2-dioxaborolan-2-yl)-1H-indazol-3(2H)-one (prepared in a similar manner to Preparation #4, step 2 using 6-bromo-1-(2-(difluoromethoxy)-5-morpholinobenzyl)-2-methyl-1H-indazol-3 (2H)-one (prepared in a similar manner to Example 1 using 6-bromo-2-methyl-1H-indazol-3(2H)-one (Preparation #1) and 4-(3-(chloromethyl)-4-(difluoromethoxy)phenyl)morpholine, hydrochloric acid)) to afford the title product (71%); LC/MS (Table A, Method a) $R_f$=1.81 min; MS m/z: 526 (M+H)⁺. (TNF IC₅₀=B).

Example #126*: (R)-1-(2-(Difluoromethoxy)benzyl)-5-fluoro-6-(2-(4-(2-hydroxyacetyl)-2-methylpiperazin-1-yl)pyrimidin-5-yl)-2-methyl-1H-indazol-3(2H)-one

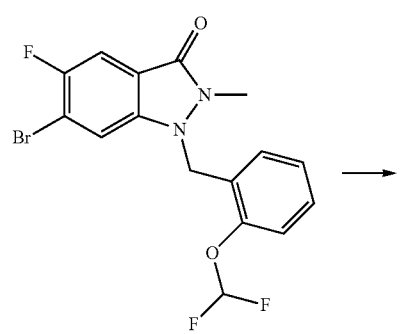

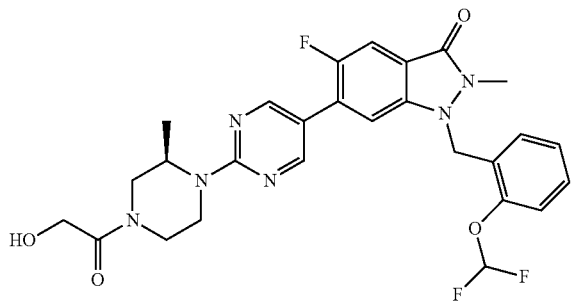

(R)-1-(2-(Difluoromethoxy)benzyl)-5-fluoro-6-(2-(4-(2-hydroxyacetyl)-2-methylpiperazin-1-yl)pyrimidin-5-yl)-2-methyl-1H-indazol-3(2H)-one was synthesized in a manner similar to Example #8 from 6-bromo-1-(2-(difluoromethoxy)benzyl)-5-fluoro-2-methyl-1H-indazol-3(2H)-one (Preparation #40) and (R)-1-(4-(5-bromopyrimidin-2-yl)-3-methylpiperazin-1-yl)-2-hydroxyethanone (Preparation #22) to afford the title compound (37%); LC/MS (Table A, Method a) $R_f$=1.84 min; MS m/z: 557 (M+H)⁺. (TNF IC₅₀=A).

Example #127: 6-(2-(2-Hydroxypropan-2-yl)pyrimidin-5-yl)-2-methyl-1-((1-(pyridin-3-ylmethyl)-4-(trifluoromethyl)-1H-pyrrol-3-yl)methyl)-1H-indazol-3(2H)-one

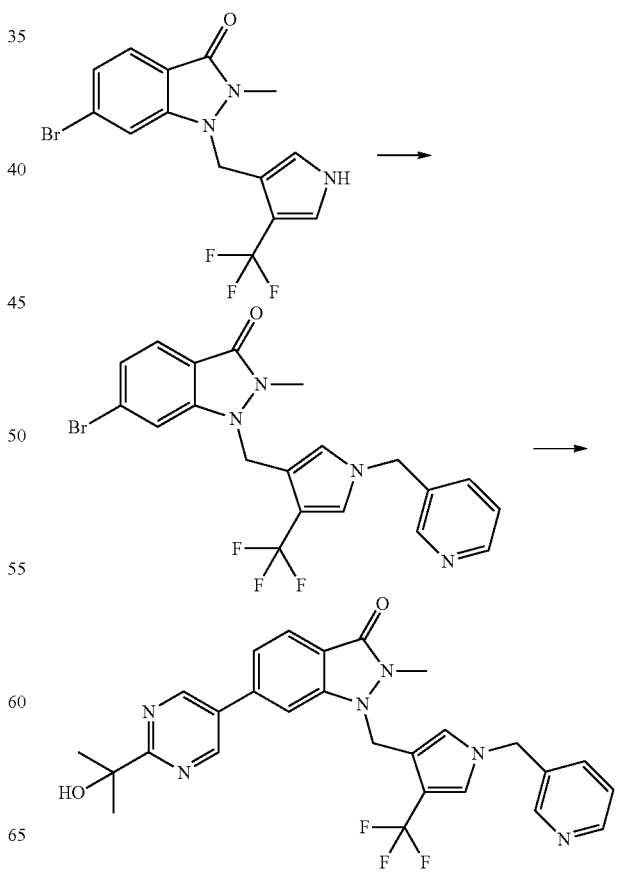

Step 1: 6-Bromo-2-methyl-1-((1-(pyridin-3-ylmethyl)-4-(trifluoromethyl)-1H-pyrrol-3-yl)methyl)-1H-indazol-3(2H)-one NaH (60% dispersion in mineral oil) (0.0240 g, 0.600 mmol) was added in one portion to a mixture of 6-bromo-2-methyl-1-((4-(trifluoromethyl)-1H-pyrrol-3-yl)methyl)-1H-indazol-3(2H)-one (0.100 g, 0.267 mmol) (Preparation #72), 3-(bromomethyl)pyridine hydrobromide (0.0890 g, 0.352 mmol), and THF (2.50 mL) under $N_2$ at about 0° C. After about 1 h, sat. aq. $NaHCO_3$(2.5 mL), water (2.5 mL) and DCM (10 mL) were added. The layers were separated and the aqueous layer was extracted with DCM (2×5 mL). The combined organic layers were dried over $Na_2SO_4$, filtered, and concentrated. The residue was purified by flash chromatography on silica gel eluding with a gradient of 10-80% (10% MeOH/DCM)/DCM). The appropriate fractions were collected and concentrated under reduced pressure to afford the title compound (0.080 g, 65%); LC/MS (Table A, Method i) $R_t$=1.35 min; MS m/z: 465 and 467 $(M+H)^+$.

Step 2: 6-(2-(2-Hydroxypropan-2-yl)pyrimidin-5-yl)-2-methyl-1-((1-(pyridin-3-ylmethyl)-4-(trifluoromethyl)-1H-pyrrol-3-yl)methyl)-1H-indazol-3(2H)-one 6-(2-(2-Hydroxypropan-2-yl)pyrimidin-5-yl)-2-methyl-1-((1-(pyridin-3-ylmethyl)-4-(trifluoromethyl)-1H-pyrrol-3-yl)methyl)-1H-indazol-3(2H)-one was prepared in a similar manner to Example #8 using 6-bromo-2-methyl-1-((1-(pyridin-3-ylmethyl)-4-(trifluoromethyl)-1H-pyrrol-3-yl)methyl)-1H-indazol-3(2H)-one and 2-(5-bromopyrimidin-2-yl)propan-2-ol to afford the title compound (61%); LC/MS (Table A, Method a) $R_t$=1.78 min; MS m/z: 523$(M+H)^+$. (TNF $IC_{50}$=A).

Example #128: 1-((1-((4-Ethylpyridin-3-yl)methyl)-4-(trifluoromethyl)-1H-pyrrol-3-yl)methyl)-6-(2-(2-hydroxypropan-2-yl)pyrimidin-5-yl)-2-methyl-1H-indazol-3(2H)-one

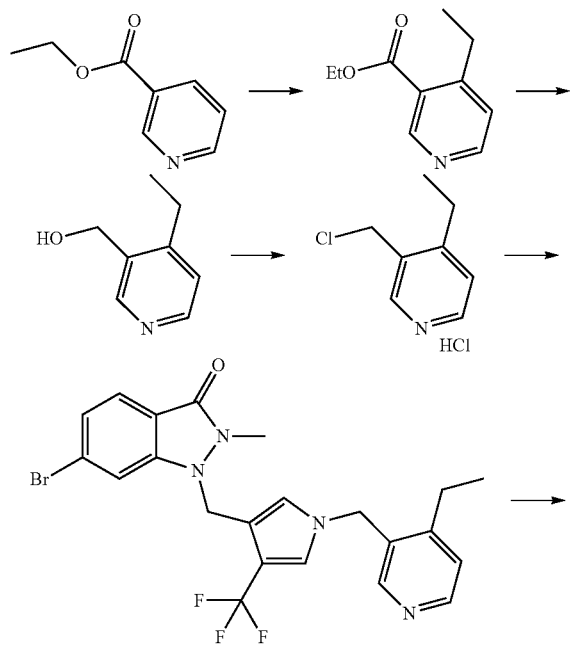

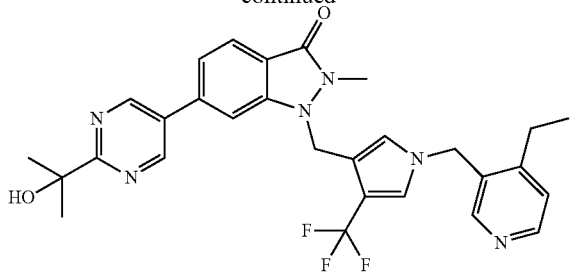

Step 1: Ethyl 4-ethylnicotinate

Copper(I) bromide dimethyl sulfide complex (0.753 g, 3.66 mmol) was added to a solution of ethyl nicotinate (5.00 mL, 36.6 mmol) and THF (80 mL) under $N_2$. The solution was cooled to about −78° C. Phenyl chloroformate (5.00 mL, 39.8 mmol) was added over about 10 min. After about 20 min, ethylmagnesium bromide (1 M solution in THF) (40.0 mL, 40.0 mmol) was added dropwise over about 40 min. After about 1 h, the cold bath was removed and sat. aq. $NH_4Cl$ (120 mL) then isopropyl acetate (80 mL) were added. After warming to about rt, the layers were separated. The organic layer was washed with 1 M aq. HCl (120 mL). The aqueous layers were extracted with isopropyl acetate (80 mL). The combined organic layers were dried over $Na_2SO_4$, filtered, and concentrated under reduced pressure. The residue was dissolved in isopropyl acetate (80 mL), 2,3-Dichloro-5,6-dicyano-1,4-benzoquinone (5.82 g, 25.6 mmol) was added. After about 30 min, 1 M aq. HCl (100 mL) was added. The layers were separated and the organic layer was extracted with 1 M aq. HCl (100 mL). The combined aqueous layers were adjusted to about pH 10 with 5 N aq. NaOH (45 mL). The aqueous mixture was extracted with DCM (2×100 mL). The combined organic layers were dried over $Na_2SO_4$, filtered, and concentrated under reduced pressure. The residue was purified on silica gel (0-20% EtOAc/DCM). The appropriate fractions were collected and concentrated under reduced pressure to afford the title compound (2.36 g, 36%); LC/MS (Table A, Method i) $R_t$=1.03 min; MS m/z: 180 $(M+H)^+$.

Step 2: (4-Ethylpyridin-3-yl)methanol (4-Ethylpyridin-3-yl)methanol was prepared in a similar manner to Preparation #32, step 4 using ethyl 4-ethylnicotinate to afford the title compound (99%); LC/MS (Table A, Method i) R=0.12 min; MS m/z: 138 $(M+H)^+$.

Step 3: 3-(Chloromethyl)-4-ethylpyridine, hydrochloric acid 3-(Chloromethyl)-4-ethylpyridine, hydrochloric acid was prepared in a similar manner to Preparation #50, step 6 using (4-ethylpyridin-3-yl)methanol to afford the title compound (86%); LC/MS (Table A, Method i) $R_t$=0.74 min; MS m/z: 156 $(M+H)^+$.

Step 4: 6-Bromo-1-((1-((4-ethylpyridin-3-yl)methyl)-4-(trifluoromethyl)-1H-pyrrol-3-yl)methyl)-2-methyl-1H-indazol-3(2H)-one 6-Bromo-1-((1-((4-ethylpyridin-3-yl)methyl)-4-(trifluoromethyl)-1H-pyrrol-3-yl)methyl)-2-methyl-1H-indazol-3

(2H)-one was prepared in a similar manner to Example #127, step 1 using 3-(chloromethyl)-4-ethylpyridine, hydrochloric acid and 6-bromo-2-methyl-1-((4-(trifluoromethyl)-1H-pyrrol-3-yl)methyl)-1H-indazol-3(2H)-one (Preparation #72) to afford the title compound (50%); LC/MS (Table A, Method i) $R_f$=1.47 min; MS m/z: 493 and 495 (M+H)$^+$.

Step 5: 1-((1-((4-Ethylpyridin-3-yl)methyl)-4-(trifluoromethyl)-1H-pyrrol-3-yl)methyl)-6-(2-(2-hydroxypropan-2-yl)pyrimidin-5-yl)-2-methyl-1H-indazol-3(2H)-one 1-((1-((4-Ethylpyridin-3-yl)methyl)-4-(trifluoromethyl)-1H-pyrrol-3-yl)methyl)-6-(2-(2-hydroxypropan-2-yl)pyrimidin-5-yl)-2-methyl-1H-indazol-3(2H)-one was prepared in a similar manner to Example #8 using 6-bromo-1-((1-((4-ethylpyridin-3-yl)methyl)-4-(trifluoromethyl)-1H-pyrrol-3-yl)methyl)-2-methyl-1H-indazol-3(2H)-one and 2-(5-bromopyrimidin-2-yl)propan-2-ol to afford the title compound (68%); LC/MS (Table A, Method a) $R_f$=1.90 min; MS m/z: 551 (M+H)$^+$. (TNF IC$_{50}$=B).

Example #128: 6-(2-(2-Hydroxypropan-2-yl)pyrimidin-5-yl)-2-methyl-1-((1-(pyridazin-4-ylmethyl)-4-(trifluoromethyl)-1H-pyrrol-3-yl)methyl)-1H-indazol-3(2H)-one

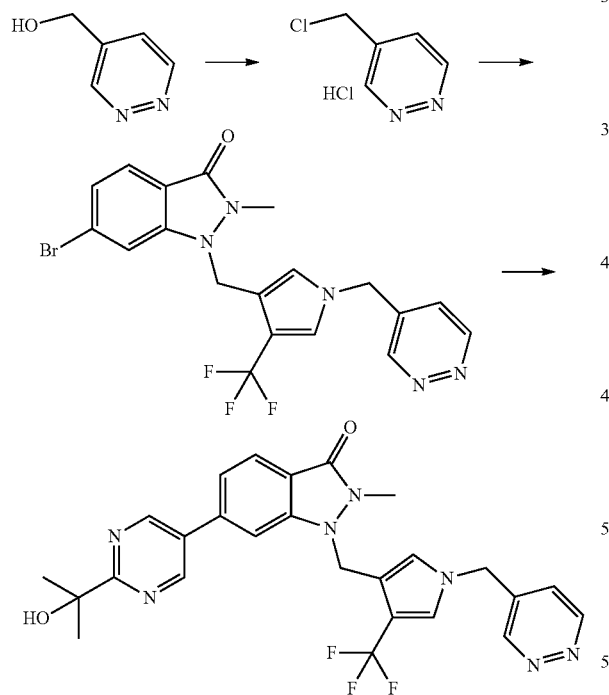

Step 1: 4-(Chloromethyl)pyridazine, hydrochloric acid 4-(Chloromethyl)pyridazine, hydrochloric acid was prepared in a similar manner to Preparation #50, step 6 using 4-pyridazinemethanol to afford the title compound (84%); LC/MS (Table A, Method j) $R_f$=0.23 min; MS m/z: 129 (M+H)$^+$.

Step 2: 6-Bromo-2-methyl-1-((1-(pyridazin-4-ylmethyl)-4-(trifluoromethyl)-1H-pyrrol-3-yl)methyl)-1H-indazol-3(2H)-one 6-Bromo-2-methyl-1-((1-(pyridazin-4-ylmethyl)-4-(trifluoromethyl)-1H-pyrrol-3-yl)methyl)-1H-indazol-3(2H)-one was prepared in a similar manner to Example #127, step 1 using 4-(chloromethyl)pyridazine, hydrochloric acid and 6-bromo-2-methyl-1-((4-(trifluoromethyl)-1H-pyrrol-3-yl)methyl)-1H-indazol-3(2H)-one (Preparation #72) to afford the title compound (11%); LC/MS (Table A, Method i) $R_f$=1.22 min; MS m/z: 466 and 468 (M+H)$^+$.

Step 3: 6-(2-(2-Hydroxypropan-2-yl)pyrimidin-5-yl)-2-methyl-1-((1-(pyridazin-4-ylmethyl)-4-(trifluoromethyl)-1H-pyrrol-3-yl)methyl)methyl)-1H-indazol-3(2H)-one 6-(2-(2-Hydroxypropan-2-yl)pyrimidin-5-yl)-2-methyl-1-((1-(pyridazin-4-ylmethyl)-4-(trifluoromethyl)-1H-pyrrol-3-yl)methyl)-1H-indazol-3(2H)-one was prepared in a similar manner to Example #8 using 6-bromo-2-methyl-1-((1-(pyridazin-4-ylmethyl)-4-(trifluoromethyl)-1H-pyrrol-3-yl)methyl)-1H-indazol-3(2H)-one and 2-(5-bromopyrimidin-2-yl)propan-2-ol to afford the title compound (68%); LC/MS (Table A, Method a) $R_f$=1.63 min; MS m/z: 524 (M+H)$^+$. (TNF IC$_{50}$=B).

Example #129*: (R)-6-(2-(4-Acetyl-3-methylpiperazin-1-yl)pyrimidin-5-yl)-1-(2-(difluoromethoxy)-5-((3-methyl-2-oxoimidazolidin-1-yl)methyl)benzyl)-2-methyl-1H-indazol-3(2H)-one

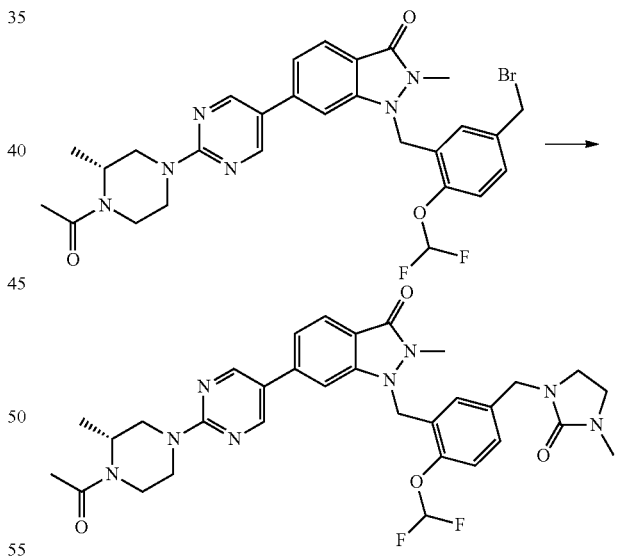

A flask was charged with sodium hydride (13.2 mg, 0.330 mmol), DMF (1 mL) and 1-methylimidazolidin-2-one (41 mg, 0.41 mmol) at rt. After about 30 min, the mixture was cooled to about −7° C. After about 20 min, (R)-6-(2-(4-acetyl-3-methylpiperazin-1-yl)pyrimidin-5-yl)-1-(5-(bromomethyl)-2-(difluoromethoxy)benzyl)-2-methyl-1H-indazol-3(2H)-one (prepared from (R)-6-(2-(4-acetyl-3-methylpiperazin-1-yl)pyrimidin-5-yl)-1-(2-(difluoromethoxy)-5-(hydroxymethyl)benzyl)-2-methyl-1H-indazol-3(2H)-one (prepared from (R)-6-(2-(4-acetyl-3-methylpiperazin-1-yl)pyrimidin-5-yl)-1-(2-

(difluoromethoxy)-5-((trityloxy)methyl)benzyl)-2-methyl-1H-indazol-3(2H)-one (prepared from (R)-6-(2-(4-acetyl-3-methylpiperazin-1-yl)pyrimidin-5-yl)-2-methyl-1H-indazol-3(2H)-one (Preparation #28) and (((3-(bromomethyl)-4-(difluoromethoxy)benzyl)oxy)methanetriyl)tribenzene (Preparation #14) in a similar fashion to Example #1) in a similar fashion to Example #18) in a similar fashion to Preparation #14, step 6) was added. After about 1 min, the reaction was quenched with H$_2$O (10 mL) and diluted further with additional H$_2$O (10 mL). The mixture was extracted with 10% MeOH in CH$_2$Cl$_2$ (2×10 mL), dried over Na$_2$SO$_4$, filtered and concentrated. The residue was purified by flash chromatography on silica gel (0-10% MeOH/CH$_2$Cl$_2$) to afford the title product (18 mg, 29%); LC/MS (Table A, Method a) R$_t$ =1.72 min; MS m/z: 635 (M+H)$^+$. (TNF IC$_{50}$=B).

Example #130: 6-(2-(2-Hydroxypropan-2-yl)pyrimidin-5-yl)-1-((1-((4-methoxy-1H-pyrazol-3-yl)methyl)-4-(trifluoromethyl)-1H-pyrrol-3-yl)methyl)-2-methyl-1H-indazol-3(2H)-one

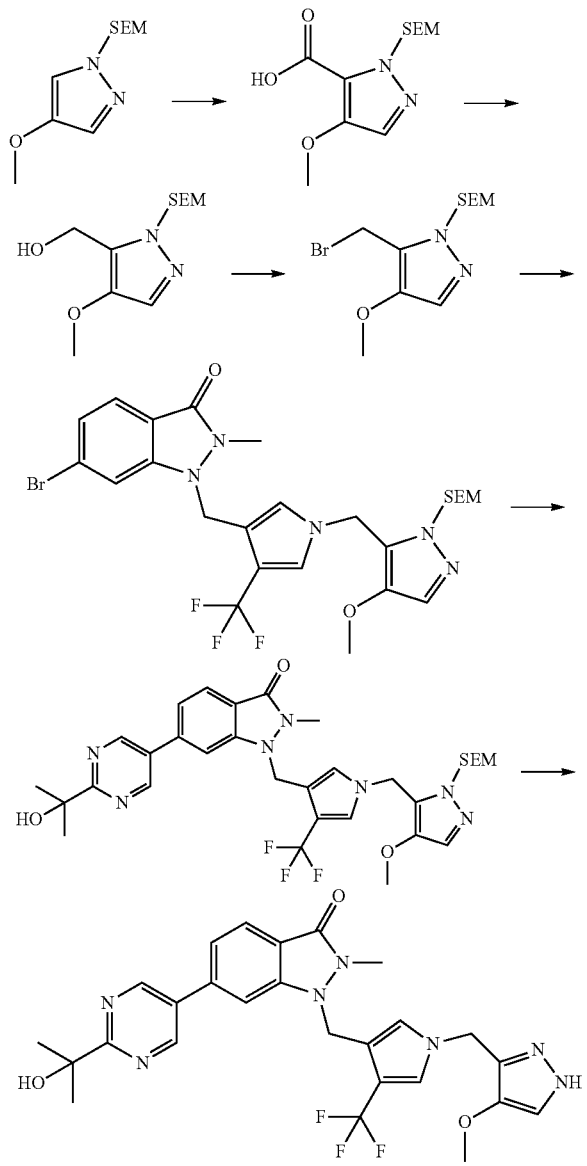

Step 1: 4-Methoxy-1-((2-(trimethylsilyl)ethoxy)methyl)-1H-pyrazole-3-carboxylic acid n-Butyllithium (2.5 M solution in hexanes) (15.0 mL, 37.5 mmol) was added dropwise over about 15 min to a solution of 4-methoxy-1-((2-(trimethylsilyl)ethoxy)methyl)-1H-pyrazole (6.92 g, 30.3 mmol) (WO 2015095767 A1) and THF (100 mL) under N$_2$ at about −65° C. After stirring at about −60 to −65° C. for about 1 h, the solution was cooled to about −78° C. The solution was saturated with carbon dioxide by bubbling carbon dioxide through the solution for about 15 min. The cold bath was allowed to thaw to rt over about 2 h. After stirring at rt for about 1 h, sat. aq. NH$_4$Cl (14 mL) was added, 1 M aq. HCl (31.5 mL) was added to adjust the pH to about 4. EtOAc (150 mL) was added. The layers were separated and the aqueous layer was extracted with EtOAc (150 mL). The combined organic layers were dried over Na$_2$SO$_4$, filtered, and concentrated. The resulting solid was dried under reduced pressure for about 15 h to afford the title compound (7.95 g, 96%); LC/MS (Table A, Method i) R$_t$=1.01 min; MS m/z: 271 (M−H)$^-$.

Step 2: (4-Methoxy-1-((2-(trimethylsilyl)ethoxy)methyl)-1H-pyrazol-3-yl)methanol (4-Methoxy-1-((2-(trimethylsilyl)ethoxy)methyl)-1H-pyrazol-3-yl)methanol was prepared in a similar manner to Preparation #32, step 4 using 4-methoxy-1-((2-(trimethylsilyl)ethoxy)methyl)-1H-pyrazole-3-carboxylic acid to afford the title compound (78%); LC/MS (Table A, Method i) R$_t$=1.23 min; MS m/z: 259 (M+H)$^+$.

Step 3: 3-(Bromomethyl)-4-methoxy-1-((2-(trimethylsilyl)ethoxy)methyl)-1H-pyrazole 3-(Bromomethyl)-4-methoxy-1-((2-(trimethylsilyl)ethoxy)methyl)-1H-pyrazole was prepared in a similar manner to Preparation #20, step 3 using (4-methoxy-1-((2-(trimethylsilyl)ethoxy)methyl)-1H-pyrazol-3-yl)methanol acid to afford the title compound (28%); LC/MS (Table A, Method i) R$_t$=1.77 min; MS m/z: 321 and 323(M+H)$^+$.

Step 4: 6-Bromo-1-((1-((4-methoxy-1-((2-(trimethylsilyl)ethoxy)methyl)-1H-pyrazol-3-yl)methyl)-4-(trifluoromethyl)-1H-pyrrol-3-yl)methyl)-2-methyl-1H-indazol-3(2H)-one 6-Bromo-1-((1-((4-methoxy-1-((2-(trimethylsilyl)ethoxy)methyl)-1H-pyrazol-3-yl)methyl)-4-(trifluoromethyl)-1H-pyrrol-3-yl)methyl)-2-methyl-1H-indazol-3(2H)-one was prepared in a similar manner to Example #127, step 1 using 3-(bromomethyl)-4-methoxy-1-((2-(trimethylsilyl)ethoxy)methyl)-1H-pyrazole and 6-bromo-2-methyl-1-((4-(trifluoromethyl)-1H-pyrrol-3-yl)methyl)-1H-indazol-3(2H)-one (Preparation #72) to afford the title compound (49%); LC/MS (Table A, Method i) R$_t$=2.02 min; MS m/z: 614 and 616 (M+H)$^+$.

Step 5: 6-(2-(2-Hydroxypropan-2-yl)pyrimidin-5-yl)-1-((1-((4-methoxy-1H-pyrazol-3-yl)methyl)-4-(trifluoromethyl)-1H-pyrrol-3-yl)methyl)-2-methyl-1H-indazol-3(2H)-one TFA (0.900 mL, 11.7 mmol) was added to a solution of 6-(2-(2-hydroxypropan-2-yl)pyrimidin-5-yl)-1-((1-((4-methoxy-1-((2-(trimethylsilyl)ethoxy)methyl)-1H-pyrazol-3-yl)methyl)-4-(trifluoromethyl)-1H-pyrrol-3-yl)methyl)-2- methyl-1H-indazol-3(2H)-one (0.153 g, 0.228 mmol) and DCM (0.900 mL). After about 2.5 h, the volatiles were removed under reduced pressure. The residue was concentrated from MeOH (5 mL) twice. The residue was purified by flash chromatography on silica gel (2-8% MeOH/DCM). The appropriate fractions were combined and concentrated to afford a pale yellow film. The residue was dissolved in 0.5 mL MeCN, 5 mL of water was added. The mixture was frozen and the resulting solid was lyophilized to afford the title compound (109 mg, 87%); LC/MS (Table A, Method a) $R_t$=1.78 min; MS m/z: 542 (M+H)$^+$. (TNF IC$_{50}$=A).

Example #131: 1-(2-(Difluoromethoxy)-5-methylbenzyl)-5-fluoro-6-(6-(1-hydroxyethyl)-5,6-dihydro-2H-pyran-3-yl)-2-methyl-1H-indazol-3(2H)-one

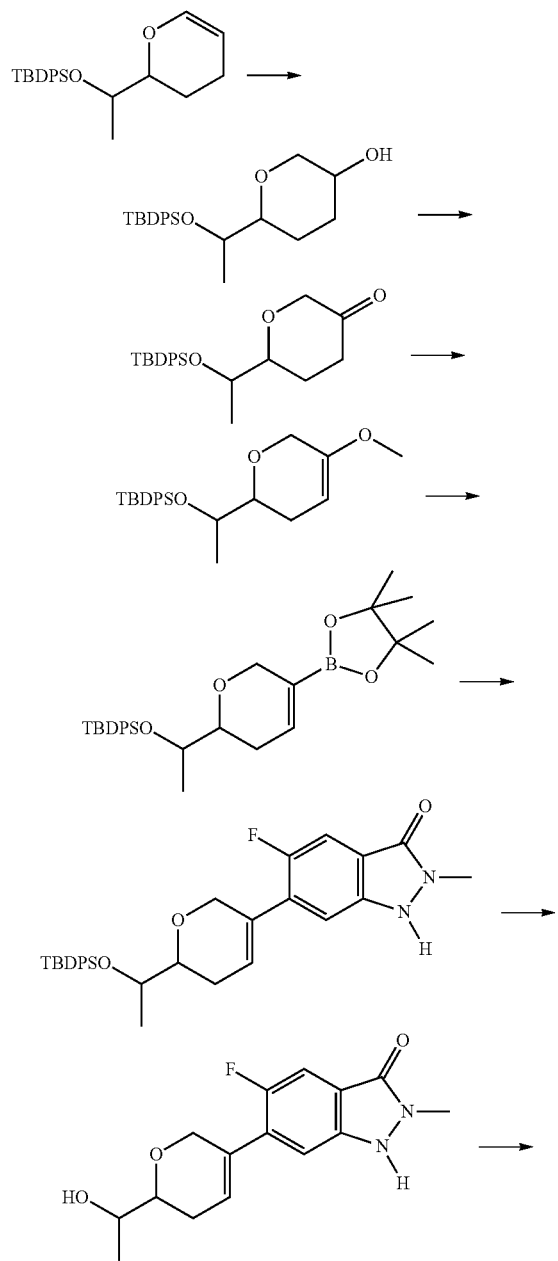

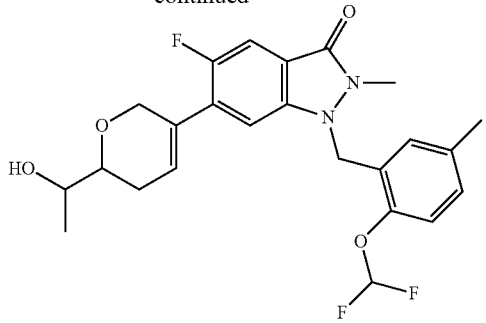

Step 1: 6-(1-((tert-Butyldiphenylsilyl)oxy)ethyl)tetrahydro-2H-pyran-3-ol

Borane tetrahydrofuran complex (1 M solution in THF) (84.0 mL, 84 mmol) was added over about 20 min to a solution of tert-butyl(1-(3,4-dihydro-2H-pyran-2-yl)ethoxy)diphenylsilane (20.6 g, 56.2 mmol) (prepared in a similar manner to Preparation #43, step 1 using TBDPSCl and 1-(3,4-dihydro-2H-pyran-2-yl)ethanol (prepared in a similar manner to Preparation #21, step 1 using 3,4-dihydro-2H-pyran-2-carbaldehyde and methylmagnesium bromide)) and THF (280 mL) under N$_2$ at about 0° C. After completion of the addition, the ice bath was removed. After stirring at rt for about 15 h, the solution was cooled to about 0° C. A solution of 2 M aq. sodium hydroxide (50.0 mL, 100 mmol) and hydrogen peroxide (30 wt %) (14.0 mL, 137 mmol) was added dropwise over about 45 min. After completion of addition, the ice bath was removed. After about 30 min, the mixture was warmed to about 55° C. After about 1 h, the mixture was allowed to cool to rt. Sat. aq. NaHCO$_3$(100 mL), water (200 mL) and EtOAc (200 mL) were added. The layers were separated and the organic layer was washed with water (200 mL) and sat. aq. NaCl (200 mL). The combined organic layers were dried over Na$_2$SO$_4$, filtered, and concentrated under reduced pressure. The residue was purified by flash chromatography on silica gel (0-40% EtOAc/heptane). The appropriate fractions were collected and concentrated to afford, after drying under reduced pressure for about 5 h, the title compound (16.9 g, 78%); $^1$H NMR (400 MHz, CDCl$_3$) δ 7.75-7.62 (m, 4H), 7.46-7.31 (m, 6H), 4.03-2.88 (m, 5H), 2.21-1.20 (m, 7H), 1.12-0.98 (m, 12H).

Step 2: 6-(1-((tert-Butyldiphenylsilyl)oxy)ethyl)dihydro-2H-pyran-3(4H)-one

Dess-Martin periodinane (24.6 g, 58.0 mmol) was added in one portion to a solution of 6-(1-((tert-butyldiphenylsilyl)oxy)ethyl)tetrahydro-2H-pyran-3-ol (16.9 g, 43.9 mmol) and DCM (200 mL) under N$_2$ at about 0° C. After about 5 min, the ice bath was removed. After about 23 h, a solution of 10% aq. Na$_2$S$_2$O$_3$(200 mL) and sat. aq. NaHCO$_3$(200 mL) was slowly added. After vigorously stirring for about 2 h, the layers were separated and the organic layer was washed with water (200 mL) then sat. aq. NaCl (200 mL). The aqueous layers were extracted with DCM (200 mL). The combined organic layers were dried over Na$_2$SO$_4$, filtered, and concentrated. The residue was purified on silica gel (0-40% EtOAc/heptane). The appropriate fractions were collected and concentrated to afford the title compound (15.3 g, 91%); $^1$H NMR (400 MHz, CDCl$_3$) δ 7.77-7.62 (m, 4H), 7.49-7.31 (m, 6H), 4.16-3.68 (m, 3H), 3.59-3.45 (m, 1H), 2.65-2.49 (m, 1H), 2.45-2.33(m, 1H), 2.17-1.84 (m, 2H), 1.14-0.99 (m, 12H).

Step 3: 6-(1-((tert-Butyldiphenylsilyl)oxy)ethyl)-5,6-dihydro-2H-pyran-3-yl trifluoromethanesulfonate A solution of 6-(1-((tert-butyldiphenylsilyl)oxy)ethyl)dihydro-2H-pyran-3(4H)-one (14.8 g, 38.7 mmol), 2-[N,N-bis(trifluoromethanesulfonyl)amino]-5-chloropyridine (17.2 g, 43.8 mmol), and THF (300 mL) under $N_2$ was cooled to about −78° C. Potassium bis(trimethylsilyl)amide (1 M solution in tert-butyl methyl ether) (43.0 mL, 43.0 mmol) was added dropwise over about 25 min. After about 2 h, the cold bath was removed. Sat. aq. $NH_4Cl$ (300 mL) was added. EtOAc (300 mL) was added. The mixture was allowed to warm to rt. Water (50 mL) was added and the layers were separated. The organic layer was dried over $Na_2SO_4$, filtered and concentrated. The material was slurried in DCM (20 mL) and filtered rinsing with DCM (2×10 mL). The organic volatiles were removed under reduced pressure. The material was slurried in DCM (5 mL) then filtered rinsing with DCM (5 mL). The solution was purified on silica gel (0-10% EtOAc/heptane). The appropriate fractions were collected and concentrated to afford the title product (15.8 g, 79%); $^1$H NMR (400 MHz, $CDCl_3$) δ 7.75-7.59 (m, 4H), 7.46-7.28 (m, 6H), 5.91-5.76 (m, 1H), 4.20-4.07 (m, 1H), 4.07-3.94 (m, 1H), 3.95-3.77 (m, 1H), 3.47-3.28 (m, 11H), 2.41-2.08 (m, 2H), 1.09-1.00 (m, 12H).

Step 4: tert-Butyldiphenyl(1-(5-(4,4,5,5-tetramethyl-1,3,2-dioxaborolan-2-yl)-3,6-dihydro-2H-pyran-2-yl)ethoxy)silane $PdCl_2$(dppf) DCM complex (2.51 g, 3.07 mmol) was added to a mixture of 6-(1-((tert-butyldiphenylsilyl)oxy)ethyl)-5,6-dihydro-2H-pyran-3-yl trifluoromethanesulfonate (15.8 g, 30.7 mmol), KOAc (9.21 g, 94 mmol), bis(pinacolato)diboron (9.46 g, 37.3 mmol), and dioxane (250 mL) under $N_2$. The reaction vessel was evacuated then back-filled with $N_2$ three times then purged with $N_2$ for about 15 min. The reaction mixture was warmed to about 95° C. After about 15 h, the mixture was allowed to cool to rt. The mixture was diluted with water (300 mL) and EtOAc (300 mL). The layers were separated. The organics were dried over $Na_2SO_4$, filtered, and concentrated. The residue was purified on silica gel (0-5% EtOAc/heptane). The appropriate fractions were collected and concentrated to afford the title product (11.6 g, 77%); LC/MS (Table A, Method k) $R_t$=1.88 min; MS m/z: 415 $(M+H)^+$.

Step 5: 6-(6-(1-((tert-Butyldiphenylsilyl)oxy)ethyl)-5,6-dihydro-2H-pyran-3-yl)-5-fluoro-2-methyl-1H-indazol-3(2H)-one Bis(triphenylphosphine)palladium(II) dichloride (0.231 g, 0.329 mmol) was added to a mixture of 6-bromo-5-fluoro-2-methyl-1H-indazol-3(2H)-one (1.00 g, 4.08 mmol) (prepared in a similar manner to Preparation #1 using 4-bromo-2,5-difluorobenzoic acid), tert-butyldiphenyl(1-(5-(4,4,5,5-tetramethyl-1,3,2-dioxaborolan-2-yl)-3,6-dihydro-2H-pyran-2-yl)ethoxy)silane (3.01 g, 6.12 mmol), cesium carbonate (3.45 g, 10.6 mmol), dioxane (32.0 mL), and water (8.00 mL). The mixture was evacuated then back-filled with $N_2$ three times then purged with $N_2$ for about 15 min. The mixture was warmed to about 75° C. After about 2 h, the mixture was warmed to about 85° C. After about 5 h, the mixture was allowed to cool to it. Water (40 mL) and EtOAc (40 mL) were added. The layers were separated and the aqueous layer was extracted with EtOAc (20 mL). The combined organic layers were dried over $Na_2SO_4$, filtered and concentrated. The residue was purified on silica gel (0-8% (MeOH/DCM). The appropriate fractions were collected and concentrated to afford the title product (1.76 g, 81%); LC/MS (Table A, Method j) $R_t$=2.16 min; MS m/z: 531 $(M+H)^+$.

Step 6: 5-Fluoro-6-(6-(1-hydroxyethyl)-5,6-dihydro-2H-pyran-3-yl)-2-methyl-1H-indazol-3(2H)-one Tetrabutylammonium fluoride (1.0 M solution in THF) (10.0 mL, 10.00 mmol) was added in one portion to a mixture of 6-(6-(1-((tert-butyldiphenylsilyl)oxy)ethyl)-5,6-dihydro-2H-pyran-3-yl)-5-fluoro-2-methyl-1H-indazol-3(2H)-one (2.00 g, 3.77 mmol) and THF (10.0 mL). The reaction vessel was sealed and the solution was warmed to about 60° C. After about 20 h, EtOAc (50 mL) was added. AcOH (1 mL) was added. The solution was washed with water (2×50 mL) and sat. aq. NaCl (50 mL). The aqueous layers were extracted with EtOAc (3×50 mL). The combined organic layers were dried over $Na_2SO_4$, filtered, and concentrated. The residue was purified on silica gel (2-10% (MeOH/DCM). The appropriate fractions were collected and concentrated to afford the title compound (0, 502 g, 44%); LC/MS (Table A, Method j) $R_t$=0.64 min; MS m/z: 293$(M+H)^+$.

Step 7: 1-(2-(Difluoromethoxy)-5-methylbenzyl)-5-fluoro-6-(6-(1-hydroxyethyl)-5,6-dihydro-2H-pyran-3-yl)-2-methyl-1H-indazol-3(2H)-one 1-(2-(Difluoromethoxy)-5-methylbenzyl)-5-fluoro-6-(6-(1-hydroxyethyl)-5,6-dihydro-2H-pyran-3-yl)-2-methyl-1H-indazol-3(2H)-one was prepared in a similar manner to Example #1 using 5-fluoro-6-(6-(1-hydroxyethyl)-5,6-dihydro-2H-pyran-3-yl)-2-methyl-1H-indazol-3(2H)-one and 2-(bromomethyl)-1-(difluoromethoxy)-4-methylbenzene (prepared in a similar manner to Preparation #3, step 2 using (2-(difluoromethoxy)-5-methylphenyl)methanol (Preparation #11)) to afford the title compound (67%); LC/MS (Table A, Method h) $R_t$=1.29 min; MS m/z: 463$(M+H)^+$. (TNF $IC_{50}$=A).

Example #132: 1-(2-(Difluoromethoxy)-5-methylbenzyl)-5-fluoro-6-(6-(2-hydroxypropan-2-yl)-5,6-dihydro-2H-pyran-3-yl)-2-methyl-1H-indazol-3(2H)-one

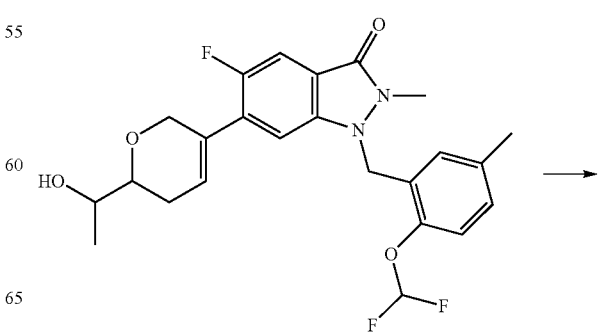

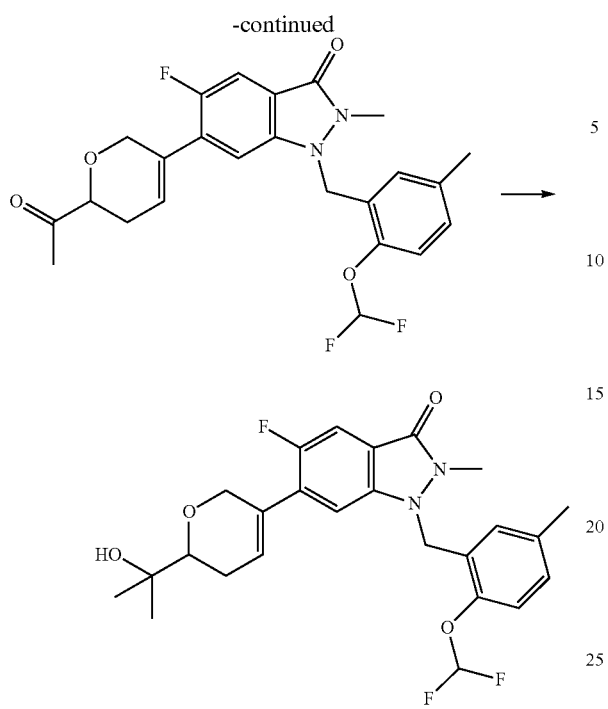

Step 1: 6-(6-Acetyl-5,6-dihydro-2H-pyran-3-yl)-1-(2-(difluoromethoxy)-5-methylbenzyl)-5-fluoro-2-methyl-1H-indazol-3(2H)-one 6-(6-Acetyl-5,6-dihydro-2H-pyran-3-yl)-1-(2-(difluoromethoxy)-5-methylbenzyl)-5-fluoro-2-methyl-1H-indazol-3(2H)-one was prepared in a similar manner to Example #131, step 2 using 1-(2-(difluoromethoxy)-5-methylbenzyl)-5-fluoro-6-(6-(1-hydroxyethyl)-5,6-dihydro-2H-pyran-3-yl)-2-methyl-1H-indazol-3(2H)-one (Example #131) to afford the title product (63%); LC/MS (Table A, Method j) $R_t$=1.44 min; MS m/z: 461 (M+H)$^+$.

Step 2: 1-(2-(Difluoromethoxy)-5-methylbenzyl)-5-fluoro-6-(6-(2-hydroxypropan-2-yl)-5,6-dihydro-2H-pyran-3-yl)-2-methyl-1H-indazol-3(2H)-one Methylmagnesium bromide (3.0 M in diethyl ether) (0.030 mL, 0.090 mmol) was added dropwise to a solution of 6-(6-acetyl-5,6-dihydro-2H-pyran-3-yl)-1-(2-(difluoromethoxy)-5-methylbenzyl)-5-fluoro-2-methyl-1H-indazol-3(2H)-one (0.0506 g, 0.110 mmol) and THF (1.50 mL) under N$_2$ at about −78° C. After about 30 min, sat. aq. NH$_4$Cl (5 mL) was added. The cold bath was removed. EtOAc (5 mL) was added. After warming to rt, the layers were separated and the aqueous layer was extracted with EtOAc (5 mL). The combined organic layers were dried over Na$_2$SO$_4$, filtered, and concentrated. The residue was purified on silica gel (25-100% EtOAc/heptane). The appropriate fractions were collected and concentrated to afford the title compound (22 mg, 42%); LC/MS (Table A, Method h) $R_t$=1.40 min; MS m/z: 477 (M+H)$^+$. (TNF IC$_{50}$=A).

Example #133: 1-(5-((1H-Pyrazol-5-yl)methyl)-2-(difluoromethoxy)benzyl)-6-(2-(2-hydroxypropan-2-yl)pyrimidin-5-yl)-2-methyl-1H-indazol-3(2H)-one

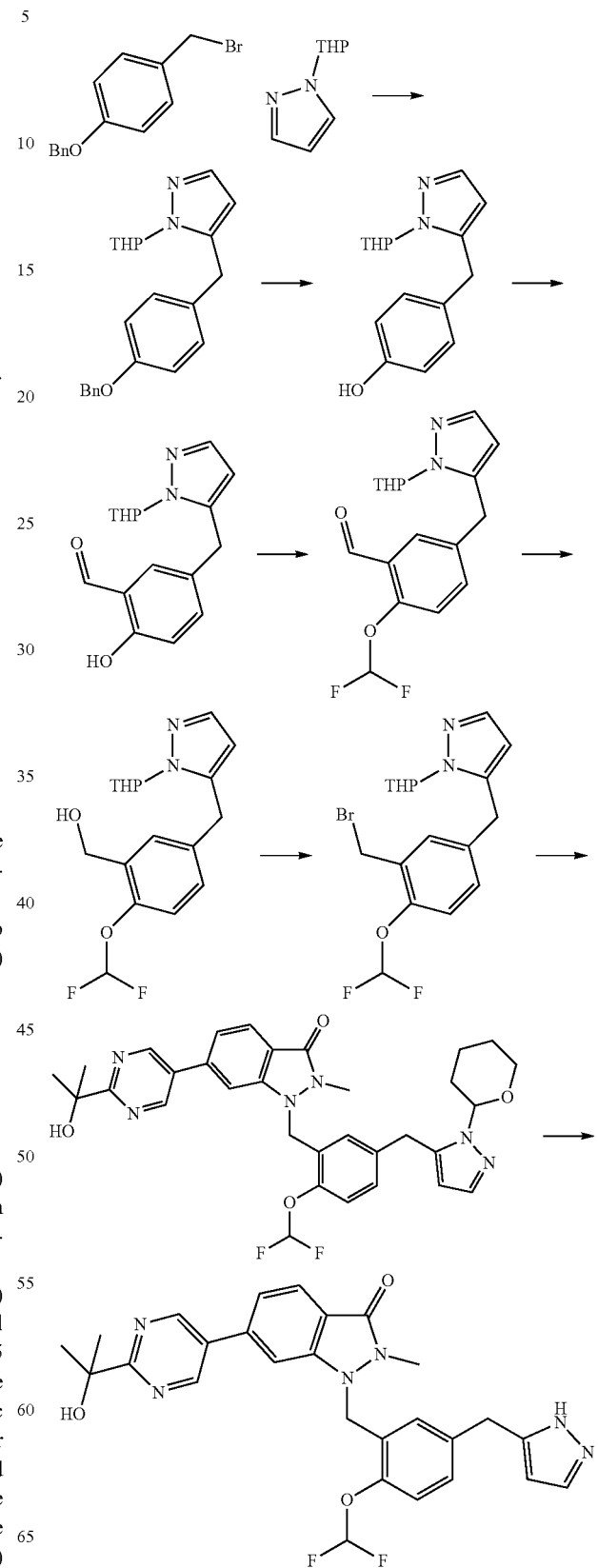

Step 1: 5-(4-(Benzyloxy)benzyl)-1-(tetrahydro-2H-pyran-2-yl)-1H-pyrazole 1-(Tetrahydro-2H-pyran-2-yl)-1H-pyrazole (6.00 g, 39.4 mmol) in THF (180 mL) was cooled to about −78° C. n-Butyllithium (1.6 M in hexane) (27.1 mL, 43.4 mmol) was added dropwise over about 1 h. The reaction was stirred at about −78° C. for about 1 h, 1-(Benzyloxy)-4-(bromomethyl)benzene (12.0 g, 43.4 mmol) (prepared in a similar fashion to Preparation #3, step 2 from (4-(benzyloxy)phenyl)methanol) was added and the reaction was allowed to warm to about −50° C. The mixture was diluted with sat. aq. $NaHCO_3$ (75 mL) and water (50 mL). The aqueous layer was extracted with DCM (3×50 mL). The combined organic layers were dried over $MgSO_4$, filtered, and concentrated. The residue was purified on silica gel (5-20% EtOAc/heptane) to give the title product (10.2 g, 74.3%); LC/MS (Table A, Method j) $R_t$=1.77 min; MS m/; 347 $(M+H)^+$.

Step 2: 4-((1-(Tetrahydro-2H-pyran-2-yl)-1H-pyrazol-5-yl)methyl)phenol 5-(4-(Benzyloxy)benzyl)-1-(tetrahydro-2H-pyran-2-yl)-1H-pyrazole (10.2 g, 29.3 mmol) and 10% dihydroxypalladium on carbon (4.11 g) in MeOH (500 mL) were evacuated and purged with $N_2$ three times. The reaction vessel was evacuated and back-filled with $H_2$ then the reaction mixture was stirred under a balloon of $H_2$ for about 1 h at rt. The suspension was filtered through Celite® and washed with MeOH (50 mL). The filtrate was concentrated and purified on silica gel (0-4% MeOH/DCM) to give the title product (6.5 g, 86%); LC/MS (Table A, Method j) $R_t$=0.99 min; MS m/z: 257 $(M+H)^+$.

Step 3: 2-Hydroxy-5-((1-(tetrahydro-2H-pyran-2-yl)-1H-pyrazol-5-yl)methyl)benzaldehyde 4-((1-(Tetrahydro-2H-pyran-2-yl)-1H-pyrazol-5-yl)methyl)phenol (2.00 g, 7.74 mmol), anhydrous $MgCl_2$ (1.11 g, 11.6 mmol), anhydrous TEA (3.13 g, 31.0 mmol) and paraformaldehyde (1.63 g, 54.2 mmol) were suspended in anhydrous MeCN (30 mL). The resulting suspension was stirred vigorously and heated to about 77° C. for about 30 min. The reaction was cooled to rt, quenched with water (50 mL), and extracted with EtOAc (150 mL). The aqueous layer was acidified with 1 N HCl to about pH 7 and extracted with EtOAc (50 mL). The combined organic layers were dried over $MgSO_4$, filtered, and concentrated. The residue was purified on silica gel (0-10% EtOAc/DCM) to give the title product (1.7 g, 77%); LC/MS (Table A, Method j) $R_t$=1.18 min; MS m/z: 285 $(M+H)^+$.

Step 4: 2-(Difluoromethoxy)-5-((1-(tetrahydro-2H-pyran-2-yl)-1H-pyrazol-5-yl)methyl)benzaldehyde The reaction was performed using 2-hydroxy-5-((1-(tetrahydro-2H-pyran-2-yl)-1H-pyrazol-5-yl)methyl)benzaldehyde in a similar fashion to Example #33, step 1 to afford the title product (0.95 g, 48%); LC/MS (Table A, Method j) $R_t$=1.38 min; MS m/z: 337 $(M+H)^+$.

Step 5: (2-(Difluoromethoxy)-5-((1-(tetrahydro-2H-pyran-2-yl)-1H-pyrazol-5-yl)methyl)phenyl)methanol The reaction was performed using 2-(difluoromethoxy)-5-((1-(tetrahydro-2H-pyran-2-yl)-1H-pyrazol-5-yl)methyl) benzaldehyde in a similar fashion to Preparation #9 to afford the title product (0.96 g, 100%); LC/MS (Table A, Method j) $R_t$=1.20 min; MS m/z: 339 $(M+H)^+$.

Step 6: 5-(3-(Bromomethyl)-4-(difluoromethoxy)benzyl)-1-(tetrahydro-2H-pyran-2-yl)-1H-pyrazole The reaction was performed using (2-(difluoromethoxy)-5-((1-(tetrahydro-2H-pyran-2-yl)-1H-pyrazol-5-yl)methyl)phenyl)methanol in a similar fashion to Preparation #21, step 2 to afford the title product (82 mg, 38%); LC/MS (Table A, Method j) $R_t$=1.65 min; MS m/z: 317 and 319 $(M+H)^+$.

Step 7: 1-(2-(Difluoromethoxy)-5-((1-(tetrahydro-2H-pyran-2-yl)-H-pyrazol-5-yl)methyl)benzyl)-6-(2-(2-hydroxypropan-2-yl)pyrimidin-5-yl)-2-methyl-1H-indazol-3(2H)-one The reaction was performed using 5-(3-(bromomethyl)-4-(difluoromethoxy)benzyl)-1-(tetrahydro-2H-pyran-2-yl)-1H-pyrazole and 6-(2-(2-hydroxypropan-2-yl)pyrimidin-5-yl)-2-methyl-1H-indazol-3(2H)-one (Preparation #19) in a similar fashion to Preparation #4, step 1 to afford the title product (100 mg, 94%); LC/MS (Table A, Method j) $R_t$=1.25 min; MS m/z: 605 $(M+H)^+$.

Step 8: 1-(5-((1H-Pyrazol-5-yl)methyl)-2-(difluoromethoxy)benzyl)-6-(2-(2-hydroxypropan-2-yl)pyrimidin-5-yl)-2-methyl-1H-indazol-3(2H)-one 1-(2-(Difluoromethoxy)-5-((1-(tetrahydro-2H-pyran-2-yl)-1H-pyrazol-5-yl)methyl)benzyl)-6-(2-(2-hydroxypropan-2-yl)pyrimidin-5-yl)-2-methyl-1H-indazol-3(2H)-one (100 mg, 0.165 mmol) in THF (2 mL) was added 1 N aq. HCl (0.992 mL, 0.992 mmol) and stirred for about 2 h at rt. 1 N aq. HCl (0.992 mL, 0.992 mmol) was added and the reaction was stirred for about 20 h at rt then quenched with sat. aq. $NaHCO_3$ to about pH 8 and extracted with EtOAc (50 mL). The organic layer was washed with water (5 mL), sat. aq. NaCl (5 mL), dried over $MgSO_4$, filtered, and concentrated. The residue was purified on silica gel (0-9% MeOH/DCM) to afford the title product (48 mg, 55%); LC/MS (Table A, Method h) $R_t$=1.07 min; MS m/z: 521 $(M+H)^+$. (TNF $IC_{50}$=A).

Example #134*: (R)-3-((6-(2-(4-Acetyl-3-methyl-piperazin-1-yl)pyrimidin-5-yl)-1-(2-chlorobenzyl)-3-oxo-1H-indazol-2(3H)-yl)methyl)benzonitrile

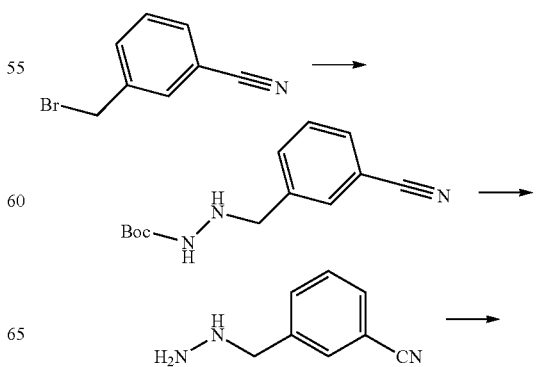

-continued

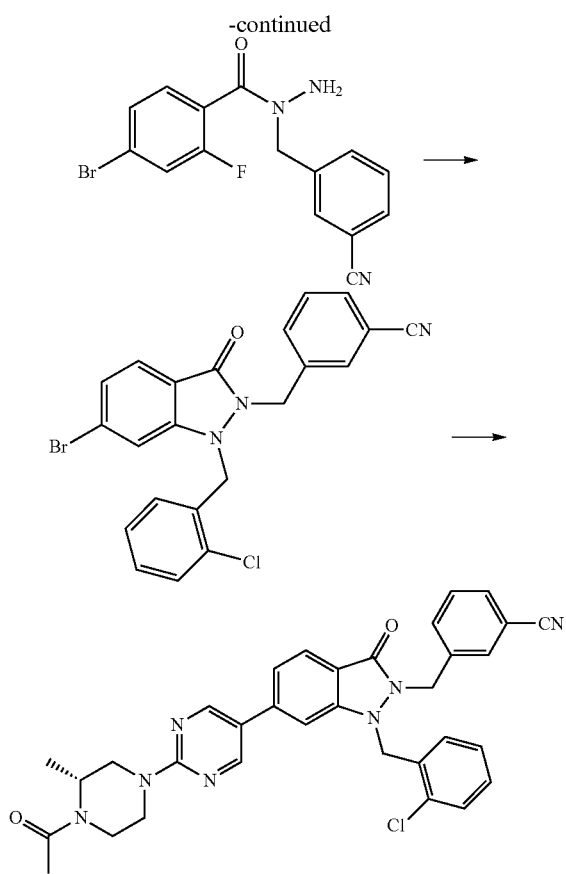

Step 1: tert-Butyl
2-(3-cyanobenzyl)hydrazinecarboxylate

3-Cyanobenzyl bromide (4.9 g, 25 mmol) and tert-butyl carbazate (6.61 g, 50.0 mmol) were dissolved in MeCN (100 mL). Potassium carbonate (6.91 g, 50.0 mmol) was added. The mixture was heated to about 70° C. for about 3 h. The mixture was cooled to rt then concentrated. Water (100 mL) was added to the residue. The mixture was extracted with EtOAc (2×200 mL). The combined organic layers were dried over sodium sulfate, filtered and concentrated under reduced pressure. The material was purified on silica gel (0-30% EtOAc/DCM). The appropriate fractions were combined and concentrated under reduced pressure to afford the title product (3.47 g, 52% yield); LC/MS (Table A, Method i) $R_t$=1.07 min; MS m/z: 248 (M+H)$^+$.

Step 2: 3-(Hydrazinylmethyl)benzonitrile, 2
hydrochloric acid tert-Butyl 2-(3-cyanobenzyl)hydrazinecarboxylate (3.47 g, 12.9 mmol) was dissolved in DCM (25.8 mL). Hydrogen chloride (4 M in dioxane) (12.9 mL, 51.6 mmol) was added. After about 4 h, additional hydrogen chloride (4 M in dioxane) (12.9 mL, 51.6 mmol) was added. After about 16 h, the mixture was diluted with diethyl ether (50 mL) and the solid was collected by filtration. The solid was dried in a vacuum oven at about 55° C. for about 2 h to afford the title product (2.61 g, 92%); LC/MS (Table A, Method i) $R_t$=0.12 min; MS m/z: 148 (M+H)$^+$.

Step 3:
4-Bromo-N-(3-cyanobenzyl)-2-fluorobenzohydrazide 3-(Hydrazinylmethyl)benzonitrile, 2 hydrochloric acid (0.500 g, 2.27 mmol) was suspended in DCM (5.0 mL). DIEA (1.6 mL, 9.0 mmol) was added. After cooling to about −50° C. a solution of 4-bromo-2-fluorobenzoyl chloride (0.539 g, 2.27 mmol) in DCM (5.0 mL) was added dropwise over about 5 min. The mixture was allowed to warm to ambient temperature over about 30 min. MeOH (5 mL) was added. The mixture was diluted with sat. aq. sodium bicarbonate (150 mL) and then extracted with DCM (2×100 mL). The combined organic layers were dried over sodium sulfate, filtered and concentrated under reduced pressure to afford the title product (0.79 g, 100%); LC/MS (Table A, Method i) $R_t$=1.27 min; MS m/z: 348 and 350 (M+H)$^+$.

Step 4: 3-((6-Bromo-1-(2-chlorobenzyl)-3-oxo-1H-
indazol-2(3H)-yl)methyl)benzonitrile Potassium tert-butoxide (0.560 g, 4.99 mmol) was added in one portion to a solution of 4-bromo-N-(3-cyanobenzyl)-2-fluorobenzohydrazide (0.79 g, 2.3 mmol) and DMF (5.4 mL). After about 30 min, the reaction vessel was transferred to an ice bath and after about 5 min, 2-chlorobenzyl bromide (0.32 mL, 2.5 mmol) in DMF (0.5 mL) was added dropwise over about 1 min. The ice bath was removed. After warming to rt, the mixture was diluted with sat. aq. sodium bicarbonate (75 mL) and then extracted with DCM (3×50 mL). The combined organic layers were dried over sodium sulfate, filtered and concentrated under reduced pressure. The material was purified on silica gel (0-50% EtOAc/DCM) to afford the title product (189 mg, 18%); LC/MS (Table A, Method i) $R_t$=1.73 min; MS m/z: 452 and 454 (M+H)$^+$.

Step 5: (R)-3-((6-(2-(4-Acetyl-3-methylpiperazin-1-
yl)pyrimidin-5-yl)-1-(2-chlorobenzyl)-3-oxo-1H-
indazol-2(3H)-yl)methyl)benzonitrile (R)-3-((6-(2-(4-Acetyl-3-methylpiperazin-1-yl)pyrimidin-5-yl)-1-(2-chlorobenzyl)-3-oxo-1H-indazol-2(3H)-yl) methyl)benzonitrile was prepared in a similar manner to Example #8 using 3-((6-bromo-1-(2-chlorobenzyl)-3-oxo-1H-indazol-2(3H)-yl)methyl)benzonitrile and (R)-1-(4-(5-bromopyrimidin-2-yl)-2-methylpiperazin-1-yl)ethanone (Preparation #16) to afford the title compound (50%); LC/MS (Table A, Method a) $R_t$=2.17 min; MS m/z: 592 (M+H)$^+$. (TNF IC$_{50}$=B).

Example #135: 1-(2-(Difluoromethoxy)-5-methyl-
benzyl)-6-(3-(2-hydroxypropan-2-yl)imidazo[1,2-b]
pyridazin-7-yl)-2-methyl-1H-indazol-3(2H)-one

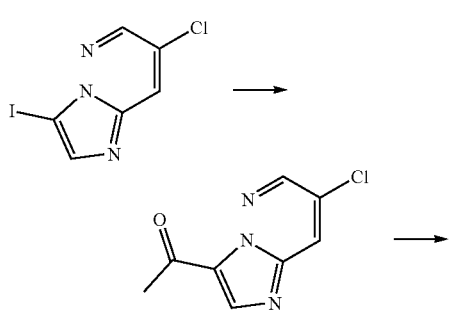

-continued

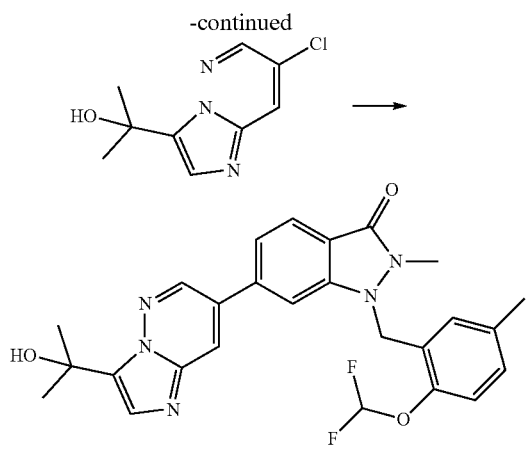

Step 1: 1-(7-Chloroimidazo[1,2-b]pyridazin-3-yl)ethanone

7-Chloro-3-iodoimidazo[1,2-b]pyridazine (1.5 g, 5.37 mmol) (synthesized as described in US2012/165305 A1, 2012), dioxane (30 mL), tributyl(1-ethoxyvinyl)stannane (2.03 g, 5.64 mmol) and PdCl$_2$(PPh$_3$)$_2$ (0.188 g, 0.268 mmol) were heated at about 100° C. for about 14 h. The mixture was cooled to rt then 6 N hydrochloric acid (2 mL, 12 mmol) was added. The mixture was stirred for about 5 min then EtOAc (75 mL) and sat. aq. NaHCO$_3$ were added. The layers were separated then the aqueous layer was extracted three times with EtOAc (40 mL). The combined organic layers were dried over magnesium sulfate, filtered and concentrated. The material was purified via flash chromatography on silica gel (0-100% EtOAc/CH$_2$Cl$_2$) to give the title compound (0.615 g, 59%); LC/MS (Table A, Method j) R$_t$=0.50 min; MS m/z: 196 (M+H)$^+$.

Step 2: 2-(7-Chloroimidazo[1,2-b]pyridazin-3-yl)propan-2-ol 1-(7-Chloroimidazo[1,2-b]pyridazin-3-yl)ethanone (0.615 g, 3.14 mmol) in THF (15 mL) was cooled to about 0° C. then methylmagnesium iodide (3M in ether) (1.20 mL, 3.60 mmol) was added. The mixture was warmed to rt for about 30 min then AcOH (~1 mL), water (~20 mL) and sat. aq. NaCl (15 mL) were added. The mixture was extracted with EtOAc (2×25 mL) then the combined organic layers were dried over magnesium sulfate, filtered and concentrated under reduced pressure. The material was purified via flash chromatography on silica gel (0-10% MeOH/CH$_2$Cl$_2$) to give the title compound (0.365 g, 55%); LC/MS (Table A, Method j) R$_t$=0.74 min; MS m/z: 212 (M+H)$^+$.

Step 3: 1-(2-(Difluoromethoxy)-5-methylbenzyl)-6-(3-(2-hydroxypropan-2-yl)imidazo[1,2-b]pyridazin-7-yl)-2-methyl-1H-indazol-3(2H)-one A mixture of 2-(7-chloroimidazo[1,2-b]pyridazin-3-yl)propan-2-ol (0.140 g, 0.661 mmol), 1-(2-(difluoromethoxy)-5-methylbenzyl)-2-methyl-6-(4,4,5,5-tetramethyl-1,3,2-dioxaborolan-2-yl)-1H-indazol-3(2H)-one (0.280 g, 0.630 mmol) (Example #22, step 2), 1,4-dioxane (5 mL), water (1.25 mL), cesium carbonate (0.513 g, 1.58 mmol) and 2nd generation XPhos precatalyst (0.025 g, 0.032 mmol) was heated at about 80° C. under an atmosphere of nitrogen for about 30 min. The mixture was cooled to rt then diluted with EtOAc (25 mL) and water (20 mL). The layers were separated then the aqueous layer was extracted with EtOAc (20 mL). The organic layers were combined then dried over magnesium sulfate, filtered and concentrated. The material was purified via flash chromatography on silica gel (0-10% MeOH/CH$_2$Cl$_2$) to give the title compound (0.133 g, 42%); LC/MS (Table A, Method h) R$_t$=0.50 min; MS m/z: 196 (M+H)$^+$. (TNF IC$_{50}$=A).

What is claimed:
1. A method for measuring TNF-alpha competitive binding of a test compound,
the method comprising:
(i) treating TNF-alpha trimer with a mixture of the test compound and a fluorescent probe, and measuring the fluorescence polarization;
(ii) treating TNF-alpha trimer with the fluorescent probe, and measuring the fluorescence polarization; and
(ii) subtracting the fluorescence polarization of (ii) from (i), wherein the subtracted result is used to determine the competitive binding of the test compound to TNF-alpha;
wherein the fluorescent probe is a compound of Formula:

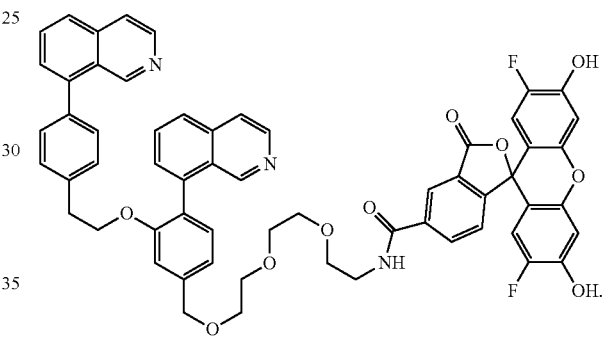

2. The method of claim 1, wherein the test compound is a compound of Formula (I):

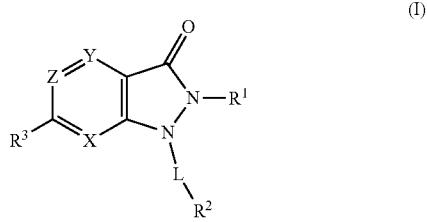

or a pharmaceutically acceptable salt or stereoisomer thereof,
wherein:
X, Y and Z are independently CR$^4$ or N;
provided that Y and Z are not both N;
L is a bond, optionally substituted (C$_1$-C$_3$)alkylene, or —C(O)—;
R$^1$ is H, CD$_3$, optionally substituted (C$_1$-C$_3$)alkyl, or optionally substituted (C$_3$-C$_6$)cycloalkyl;
R$^2$ is optionally substituted aryl or optionally substituted heteroaryl;
R$^3$ is —R$^{3a}$-R$^{3b}$, wherein:
R$^{3a}$ is an optionally substituted saturated, unsaturated, or partially saturated heterocyclyl or optionally substituted heteroaryl;

$R^{3b}$ is —N($R^a$)($R^b$), —O($R^a$), optionally substituted ($C_1$-$C_5$)alkyl, optionally substituted ($C_3$-$C_6$)cycloalkyl, —(CH$_2$)$_p$-optionally substituted heterocyclyl, or —(CH$_2$)$_p$-optionally substituted oxetanyl; wherein $R^a$ and $R^b$ are independently selected from the group consisting of H, optionally substituted ($C_1$-$C_5$)alkyl, —(CH$_2$)$_n$-optionally substituted heterocyclyl, and —(CH$_2$)$_n$-optionally substituted oxetanyl;

$R^4$ is independently H, Cl, CN, F, CF$_3$, methoxy, or optionally substituted ($C_1$-$C_3$)alkyl;

n is 0 or 1; and p is 0, 1 or 2;

wherein heterocyclyl is:
(i) a non-aromatic monocylic, bicyclic, tricyclic, or spirocyclic ring having 5 to 12 ring atoms including at least one nitrogen, oxygen, or sulfur ring atom; or
(ii) an azetidinyl ring.

3. A method for measuring TNF-alpha competitive binding of a test compound, the method comprising:
(i) treating TNF-alpha trimer with a mixture of the test compound and a fluorescent probe, and measuring the fluorescence polarization;
(ii) treating TNF-alpha trimer with the fluorescent probe, and measuring the fluorescence polarization; and
(ii) subtracting the fluorescence polarization of (ii) from (i), wherein the subtracted result is used to determine the competitive binding of the test compound to TNF-alpha;

wherein the test compound is a compound of Formula (I):

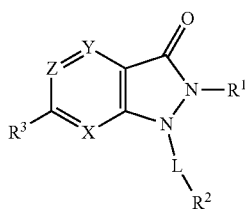

(I)

or a pharmaceutically acceptable salt or stereoisomer thereof,
wherein:
X, Y and Z are independently CR$^4$ or N;
provided that Y and Z are not both N;
L is a bond, optionally substituted ($C_1$-$C_3$)alkylene, or —C(O)—;
$R^1$ is H, CD$_3$, optionally substituted ($C_1$-$C_3$)alkyl, or optionally substituted ($C_3$-$C_6$)cycloalkyl;
$R^2$ is optionally substituted aryl or optionally substituted heteroaryl;
$R^3$ is —$R^{3a}$-$R^{3b}$, wherein:
$R^{3a}$ is an optionally substituted saturated, unsaturated, or partially saturated heterocyclyl or optionally substituted heteroaryl;
$R^{3b}$ is —N($R^a$)($R^b$), —O($R^a$), optionally substituted ($C_1$-$C_5$)alkyl, optionally substituted ($C_3$-$C_6$)cycloalkyl, —(CH$_2$)$_p$-optionally substituted heterocyclyl, or —(CH$_2$)$_p$-optionally substituted oxetanyl; wherein $R^a$ and $R^b$ are independently selected from the group consisting of H, optionally substituted ($C_1$-$C_5$)alkyl, —(CH$_2$)$_n$-optionally substituted heterocyclyl, and —(CH$_2$)$_n$-optionally substituted oxetanyl;

$R^4$ is independently H, Cl, CN, F, CF$_3$, methoxy, or optionally substituted ($C_1$-$C_3$)alkyl;

n is 0 or 1; and p is 0, 1 or 2;

wherein heterocyclyl is:
(i) a non-aromatic monocylic, bicyclic, tricyclic, or spirocyclic ring having 5 to 12 ring atoms including at least one nitrogen, oxygen, or sulfur ring atom; or
(ii) an azetidinyl ring.

4. A compound of Formula (I):

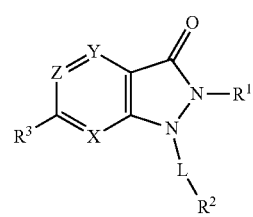

(I)

or a pharmaceutically acceptable salt or stereoisomer thereof,
wherein:
X, Y and Z are independently CR$^4$ or N;
provided that Y and Z are not both N;
L is a bond, optionally substituted ($C_1$-$C_3$)alkylene, or —C(O)—;
$R^1$ is H, CD$_3$, optionally substituted ($C_1$-$C_3$)alkyl, or optionally substituted ($C_3$-$C_6$)cycloalkyl;
$R^2$ is optionally substituted aryl or optionally substituted heteroaryl;
$R^3$ is —$R^{3a}$—$R^{3b}$, wherein:
$R^{3a}$ is an optionally substituted saturated, unsaturated, or partially saturated heterocyclyl or optionally substituted heteroaryl;
$R^{3b}$ is —N($R^a$)($R^b$), —O($R^a$), optionally substituted ($C_1$-$C_5$)alkyl, optionally substituted ($C_3$-$C_6$)cycloalkyl, —(CH$_2$)$_p$-optionally substituted heterocyclyl, or —(CH$_2$)$_p$-optionally substituted oxetanyl; wherein $R^a$ and $R^b$ are independently selected from the group consisting of H, optionally substituted ($C_1$-$C_5$)alkyl, —(CH$_2$)$_n$-optionally substituted heterocyclyl, and —(CH$_2$)$_n$-optionally substituted oxetanyl;

$R^4$ is independently H, Cl, CN, F, CF$_3$, methoxy, or optionally substituted ($C_1$-$C_3$)alkyl;

n is 0 or 1; and p is 0, 1 or 2;

wherein heterocyclyl is:
(i) a non-aromatic monocylic, bicyclic, tricyclic, or spirocyclic ring having 5 to 12 ring atoms including at least one nitrogen, oxygen, or sulfur ring atom; or
(ii) an azetidinyl ring.

5. A pharmaceutical composition comprising a compound of claim 4, or a pharmaceutically acceptable salt or stereoisomer thereof, and one or more pharmaceutically acceptable excipients.

6. The compound of claim 4 of Formula (Ia):

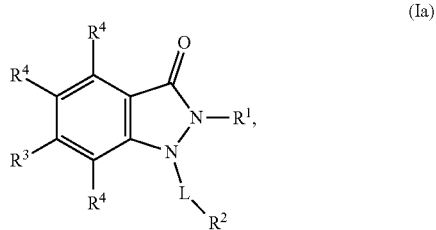

(Ia)

or a pharmaceutically acceptable salt or stereoisomer thereof.

7. The compound of claim 4 of Formula (Ie):

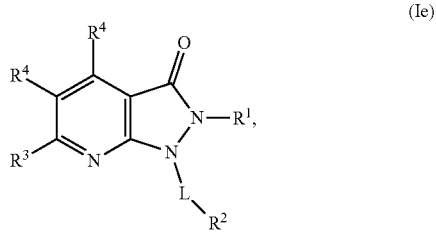

(Ie)

or a pharmaceutically acceptable salt or stereoisomer thereof.

8. The compound of claim 4, or a pharmaceutically acceptable salt or stereoisomer thereof, wherein $R^1$ is optionally substituted ($C_1$-$C_3$)alkyl or optionally substituted cyclopropyl.

9. The compound of claim 4, or a pharmaceutically acceptable salt or stereoisomer thereof, wherein $R^2$ is optionally substituted heteroaryl or optionally substituted phenyl.

10. The compound of claim 4, or a pharmaceutically acceptable salt or stereoisomer thereof, wherein $R^{3a}$ is optionally substituted 1,2,4-oxadiazolyl, optionally substituted pyrazolyl, optionally substituted pyridinyl, optionally substituted pyrimidinyl, optionally substituted pyrazinyl, or optionally substituted 1,2,4-thiadiazolyl.

11. The compound of claim 4, or a pharmaceutically acceptable salt or stereoisomer thereof, wherein $R^{3b}$ is —N($R^a$)($R^b$), —O($R^a$), optionally substituted ($C_1$-$C_3$)alkyl, —($CH_2$)$_p$-optionally substituted 2-oxa-6-azaspiro[3.3]heptanyl, —($CH_2$)$_p$-optionally substituted 2-azaspiro[3.3]heptanyl, —($CH_2$)$_p$-optionally substituted 5-azaspiro[2.3]hexanyl, —($CH_2$)$_p$-optionally substituted azetidinyl, —($CH_2$)$_p$-optionally substituted morpholinyl, —($CH_2$)$_p$-optionally substituted oxetanyl, —($CH_2$)$_p$-optionally substituted piperazinyl, —($CH_2$)$_p$-optionally substituted piperidinyl, —($CH_2$)$_p$-optionally substituted pyrrolidinyl, —($CH_2$)$_p$-optionally substituted tetrahydropyranyl, —($CH_2$)$_p$-optionally substituted 6-oxohexahydropyrrolo[1,2-a]pyrazinyl, —($CH_2$)$_p$-optionally substituted tetrahydro-1H-oxazolo[3,4-a]pyrazin-3(5H)-one, or —($CH_2$)$_p$-optionally substituted hexahydroimidazo[1,5-a]pyrazin-3(2H)-one;
wherein $R^a$ and $R^b$ are independently selected from the group consisting of H, optionally substituted ($C_1$-$C_3$) alkyl, —($CH_2$)$_n$-oxoazepanyl, —($CH_2$)$_n$-optionally substituted tetrahydrofuranyl, —($CH_2$)$_n$-optionally substituted oxetanyl, —($CH_2$)-optionally substituted tetrahydropyranyl, and —($CH_2$)$_n$-optionally substituted pyrrolidinyl.

12. The compound of claim 4, or a pharmaceutically acceptable salt or stereoisomer thereof, wherein L is a bond or optionally substituted ($C_1$-$C_2$)alkylene.

13. The compound of claim 4, or a pharmaceutically acceptable salt or stereoisomer thereof, wherein $R^2$ is phenyl, pyridinyl, or pyrimidinyl, and $R^2$ is optionally substituted by one or more substituents independently selected from the group consisting of halogen, CN, haloalkoxy, $CF_3$, and optionally substituted ($C_1$-$C_3$)alkyl.

14. The compound of claim 4, or a pharmaceutically acceptable salt or stereoisomer thereof, wherein $R^{3b}$ is —N(H)$CH_2$-optionally substituted pyrrolidinyl, —O($R^a$), —N(H)-optionally substituted oxetanyl, optionally substituted ($C_1$-$C_3$)alkyl, optionally substituted 2-oxa-6-azaspiro[3.3]heptanyl, optionally substituted 5-azaspiro[2.3]hexanyl, optionally substituted azetidinyl, optionally substituted morpholinyl, —($CH_2$)$_p$-optionally substituted oxetanyl, optionally substituted piperazinyl, optionally substituted piperidinyl, —($CH_2$)$_p$-optionally substituted pyrrolidinyl, or optionally substituted tetrahydropyranyl;
wherein $R^a$ is selected from the group consisting of H, optionally substituted ($C_1$-$C_3$)alkyl, —($CH_2$)$_n$-oxoazepanyl, —($CH_2$)$_n$-optionally substituted tetrahydrofuranyl, —($CH_2$)$_n$-optionally substituted oxetanyl, —($CH_2$)$_n$-optionally substituted tetrahydropyranyl, and —($CH_2$)$_n$-optionally substituted pyrrolidinyl.

15. The compound of claim 4, or a pharmaceutically acceptable salt or stereoisomer thereof, wherein $R^{3b}$ is optionally substituted by one or more substituents independently selected from the group consisting of halogen, CN, —C(O)OH, —C(O)$CH_3$, —C(O)$NH_2$, $NH_2$, =O, —OH, optionally substituted ($C_1$-$C_3$)alkyl, optionally substituted ($C_1$-$C_3$)alkoxy, and optionally substituted oxetanyl.

16. The compound of claim 4, or a pharmaceutically acceptable salt or stereoisomer thereof, wherein Y is $CR^4$.

17. The compound of claim 4, or a pharmaceutically acceptable salt or stereoisomer thereof, wherein Z is $CR^4$.

18. The compound of claim 4, or a pharmaceutically acceptable salt or stereoisomer thereof, wherein optionally substituted refers to optional substitution with one or more substituents selected from the group consisting of ($C_1$-$C_8$) alkyl optionally substituted with —OH; ($C_2$-$C_8$)alkenyl; ($C_2$-$C_8$)alkynyl; ($C_3$-$C_{10}$)cycloalkyl optionally substituted with —CN; halogen; halogenated ($C_1$-$C_8$)alkyl; —O—($C_1$-$C_8$)alkyl; —($C_1$-$C_6$)alkyl-C(O)OH; =O; =$CH_2$; —OH; —$CH_2$OH; —$CH_2NH_2$; ($C_1$-$C_4$)alkyl-OH; —$CH_2CH_2OCH_2CH_3$; —S—($C_1$-$C_8$)alkyl; —SH; —NH($C_1$-$C_8$)alkyl; —N(($C_1$-$C_8$)alkyl)$_2$; —$NH_2$; —C(O)$NH_2$; —C(O)$CH_2NH_2$; —C(O)CH($CH_3$)$NH_2$; —C(O)CH(OH)$CH_2NH_2$; —C(O)CH(OH)$CH_2$C(O)OH; —C(O)$CH_2$OC(O)CH($NH_2$)($C_1$-$C_6$)alkyl; —C(O)($C_1$-$C_6$)alkyl($C_1$-$C_6$)alkoxy; —($C_1$-$C_6$)alkyl($C_1$-$C_6$)alkoxy; —C(O)($C_1$-$C_6$)alkyl-CN; —($C_1$-$C_6$)alkyl-CN; —C(O)CH(OH)$CH_2$OH; —C(O)($C_1$-$C_6$)alkyl-P(O)$_4$; —$CH_2$NHC(O)($C_1$-$C_4$)alkyl; —$CH_2$NHC(O)($C_1$-$C_4$)alkoxy; —$CH_2$NHC(O)$CH_2$Cl; —$CH_2$NHC(O)$CH_2$CN; —$CH_2$NHC(O)$CH_2CH_2$N($CH_3$)$_2$; —$CH_2$OC(O)N($CH_3$)$_2$; —$CH_2$OC(O)(($C_1$-$C_6$)alkyl wherein alkyl is optionally substituted with $NH_2$; —$CH_2$NHC(O)C(=$CH_2$)$CH_3$; —$CH_2$NHC(O)($C_2$-$C_4$) alkynyl; —$CH_2$NHC(O)$CH_2CH_2$-piperidinyl; —($C_1$-$C_4$) alkyl-morpholinyl; —$CH_2$NHC(O)$CH_2$O-phenyl wherein the phenyl is optionally substituted with halogen; ($C_1$-$C_4$) alkoxy; —C(O)($C_1$-$C_4$)alkyl; —C(O)($C_1$-$C_4$)alkyl-OH; —C(O)N($CH_3$)$_2$; —N($CH_3$)$_2$; —NHC(O)($C_1$-$C_4$)alkyl; —NHC(O)($C_2$-$C_4$)alkenyl; —NHC(O)$CH_2$CN; —S(O)$_2$($C_1$-$C_4$)alkyl; 4-methylpiperazinecarbonyl; —($C_1$-$C_4$)alkyl-C(O)$NH_2$; —C(O)NH($C_1$-$C_8$)alkyl; —C(O)N(($C_1$-$C_8$)

alkyl)₂; —C(O)N(H)(C₃-C₈)cycloalkyl; —C(O)(C₁-C₄)alkoxy; —NHC(O)H; —NHC(O)(C₁-C₈)alkyl; —NHC(O)(C₃-C₈)cycloalkyl; —N((C₁-C₈)alkyl)C(O)H; —N((C₁-C₈)alkyl)C(O)(C₁-C₈)alkyl; —NHC(O)NH₂; —NHC(O)NH(C₁-C₈)alkyl; —N((C₁-C₈)alkyl)C(O)NH₂; —NHC(O)N((C₁-C₈)alkyl)₂; —N((C₁-C₈)alkyl)C(O)N((C₁-C₈)alkyl)₂; —N((C₁-C₈)alkyl)C(O)NH((C₁-C₈)alkyl); —NH(C₁-C₆)alkyl wherein alkyl is optionally substituted with —OH; —NHCH₂-heteroaryl; benzyl; —OCH₂-heteroaryl; —C(O)H; —C(O)(C₁-C₈)alkyl; —CN; —NO₂; —S(O)(C₁-C₈)alkyl; —S(O)₂(C₁-C₈)alkyl; —S(O)₂N((C₁-C₈)alkyl)₂; —S(O)₂NH(C₁-C₈)alkyl; —S(O)₂NH(C₃-C₈)cycloalkyl; —S(O)₂NH₂; —NHS(O)₂(C₁-C₈)alkyl; —N((C₁-C₈)alkyl)S(O)₂(C₁-C₈)alkyl; —(C₁—C)alkyl-O—(C₁-C₈)alkyl; —O—(C₁-C₈)alkyl-O—(C₁-C₈)alkyl; —C(O)OH; —C(O)O(C₁-C₈)alkyl; NHOH; NHO(C₁-C₈)alkyl; —O-halogenated (C₁-C₈)alkyl; —S(O)₂-halogenated (C₁-C₈)alkyl; —S-halogenated (C₁-C₈)alkyl; pyrrolidine; tetrahydrofuran; pyran; morpholine; —NH— heterocyclyl; tetrazole; imidazole; furan; pyrazine; pyrazole; —(C₁-C₆)alkyl-heteroaryl; —(C₁-C₆)alkyl-O-heteroaryl; phenyl; —NHC(O)O—(C₁-C₆)alkyl; —N((C₁-C₆)alkyl)C(O)O—(C₁-C₆)alkyl; —C(=NH)—(C₁-C₆)alkyl; —C(=NOH)—(C₁-C₆)alkyl; and —C(=N—O—(C₁-C₆)alkyl)-(C₁-C₆)alkyl.

19. The compound of claim 4 selected from the group consisting of:

1

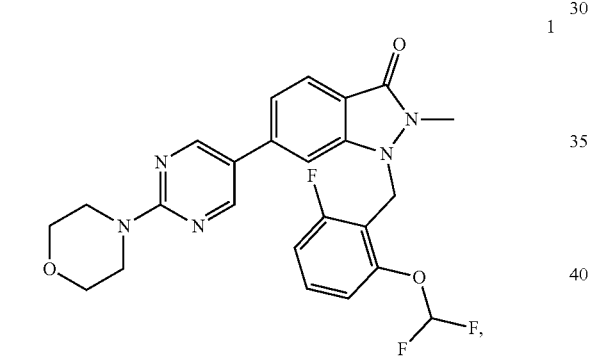

1.1

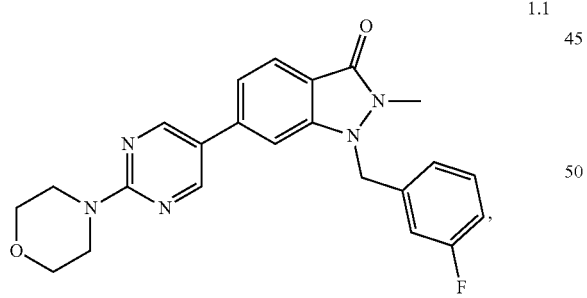

1.2

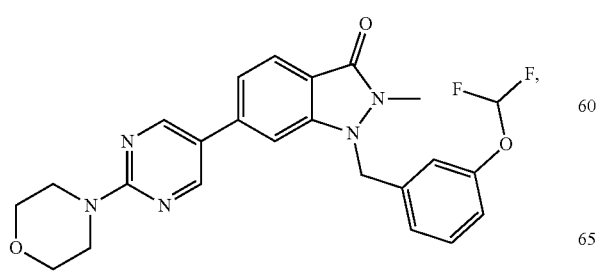

1.3

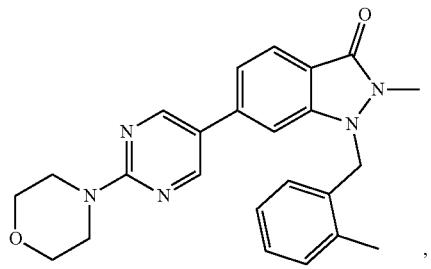

1.4

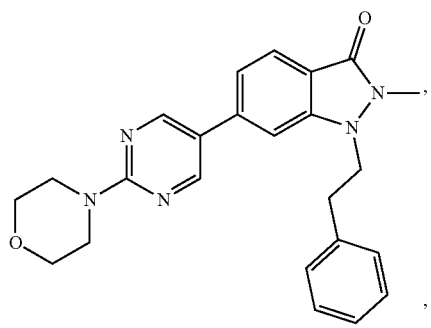

1.5

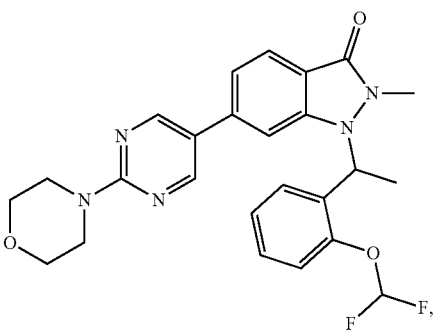

1.6

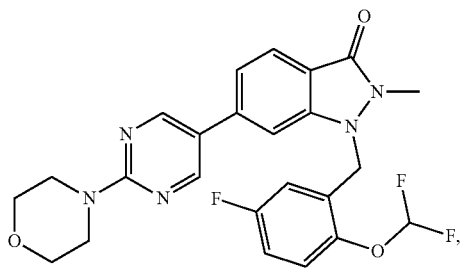

1.7

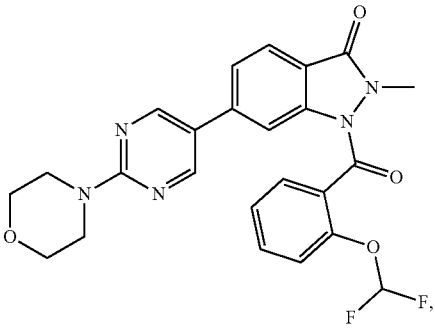

1.8
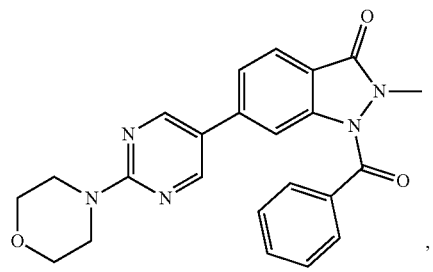
1.9
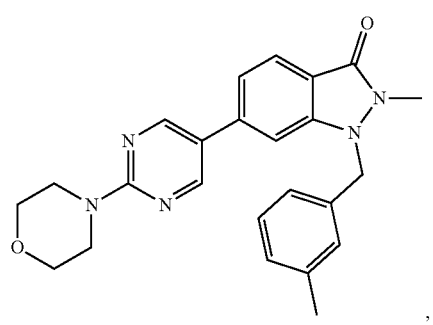
1.10
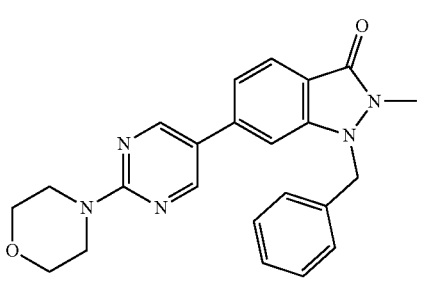
1.11
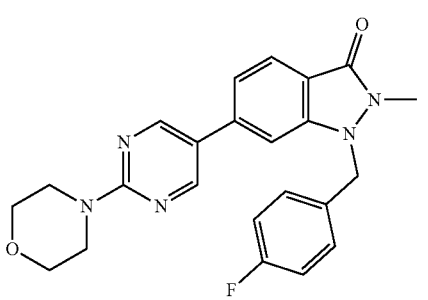
1.12
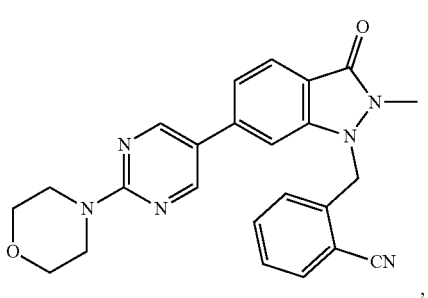
1.13
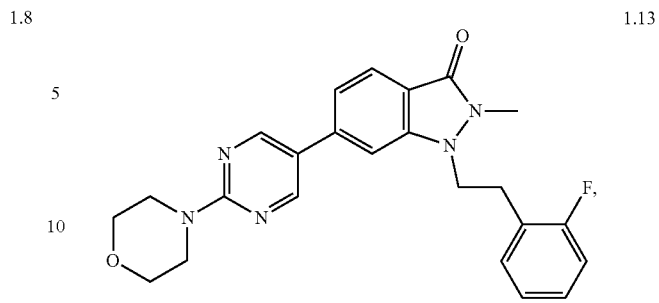
1.14
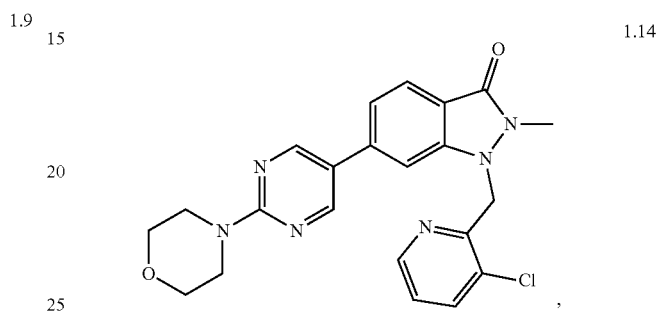
1.15
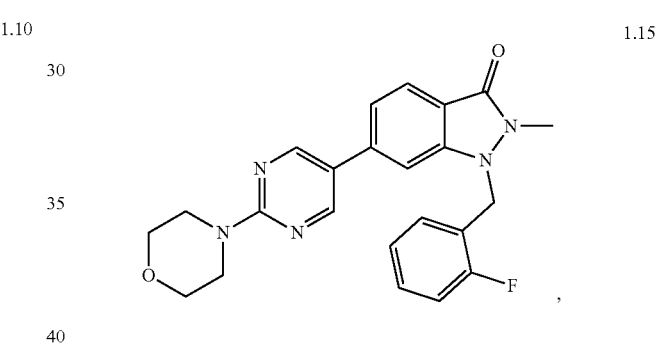
1.16
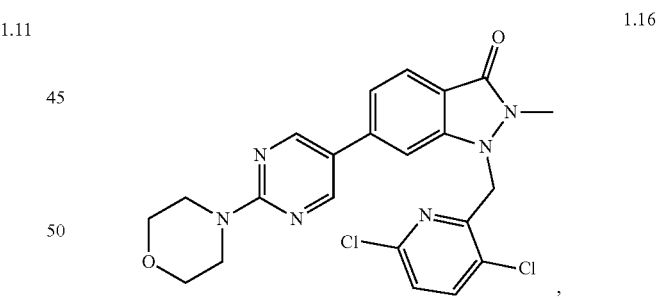
1.17
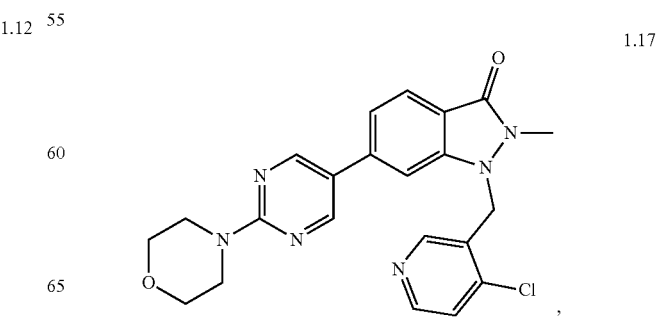

| | |
|---|---|
| 1.18 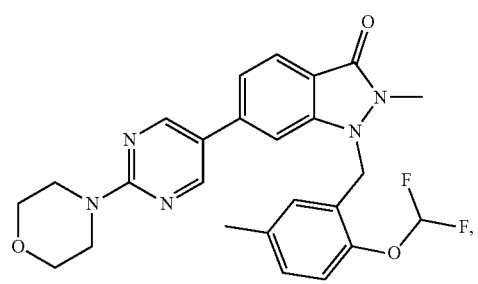 | 2.3 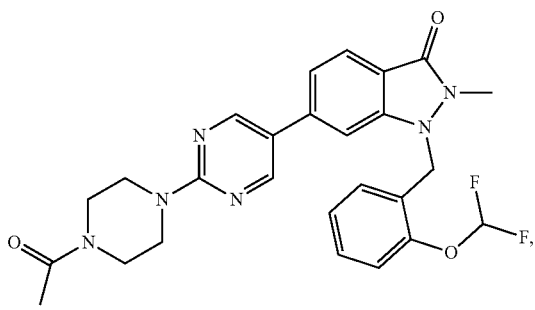 |
| 1.19 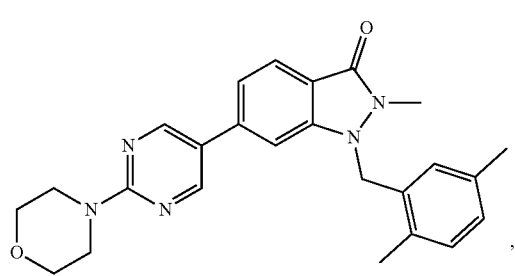 | 2.4 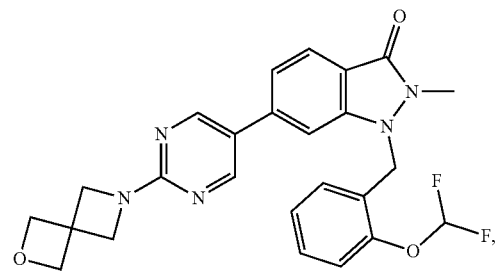 |
| 2 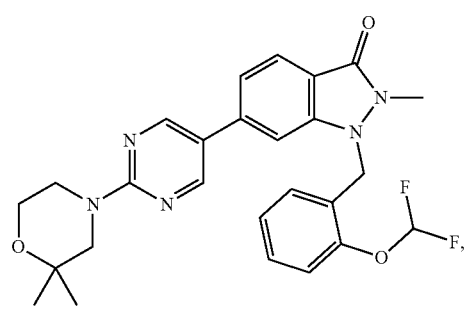 | 2.5 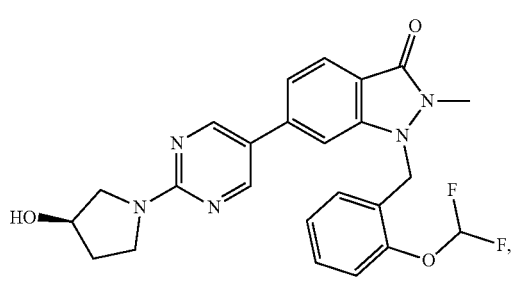 |
| 2.1 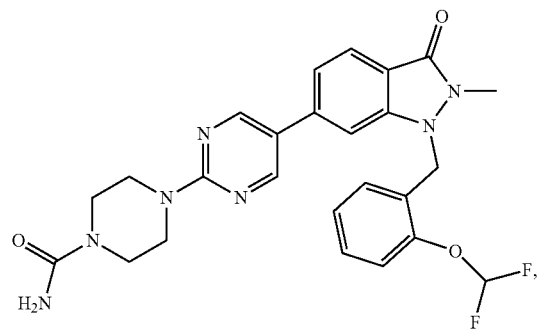 | 2.6 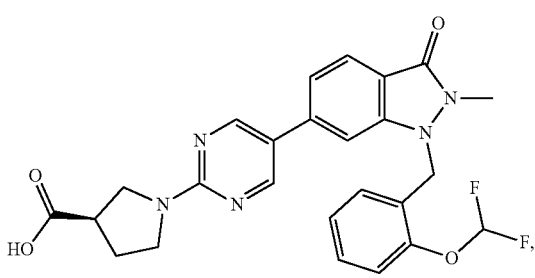 |
| 2.2 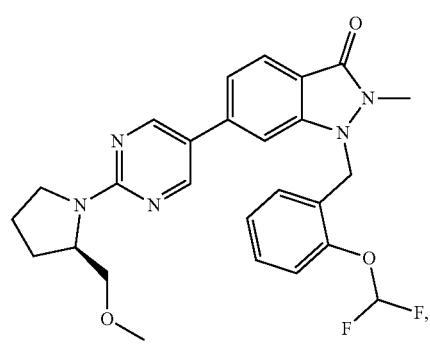 | 2.7 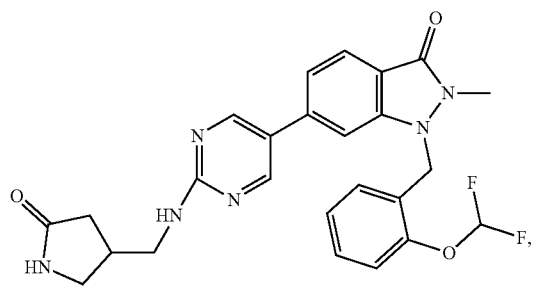 |

2.8
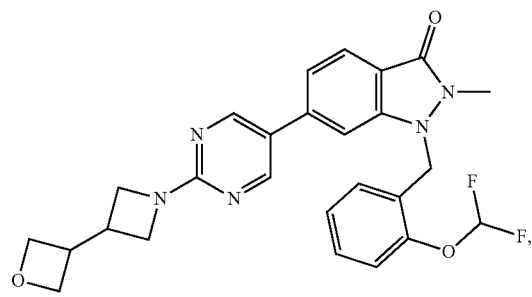
2.13
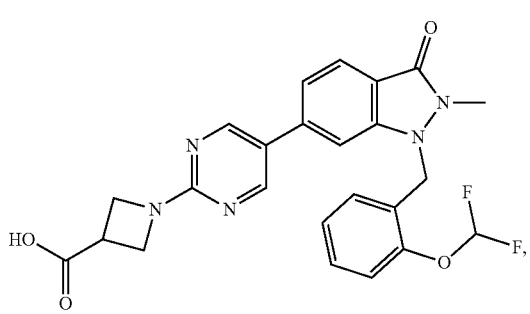
2.9
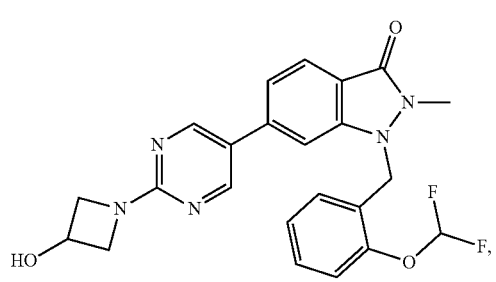
2.14
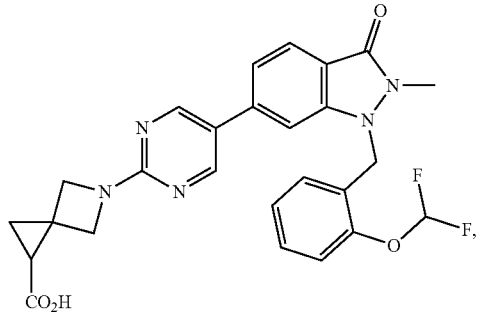
2.10
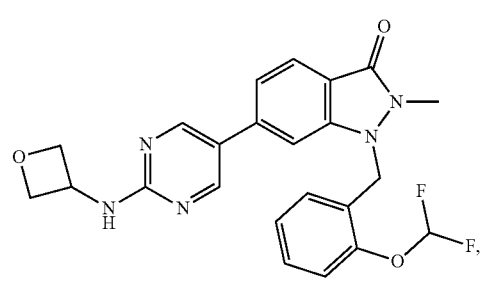
2.15
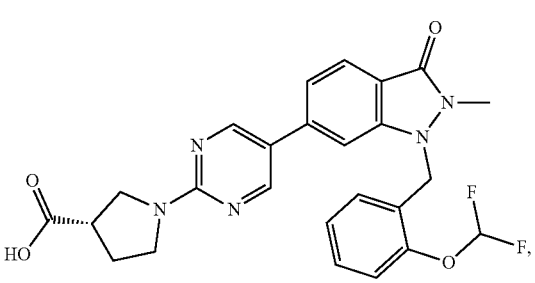
2.11
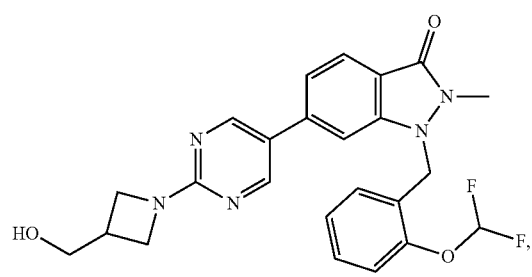
2.16
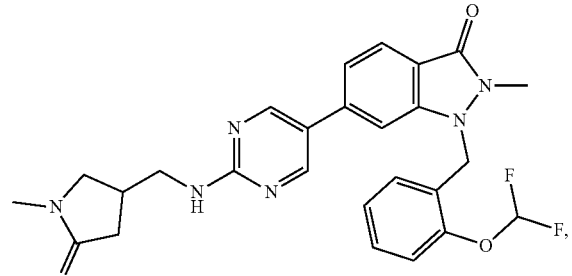
2.12
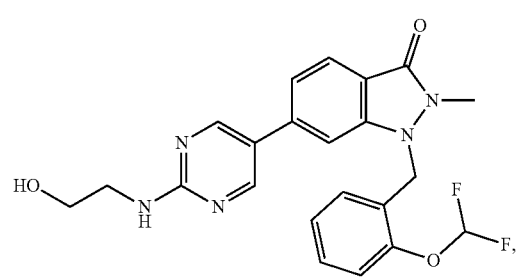
2.17
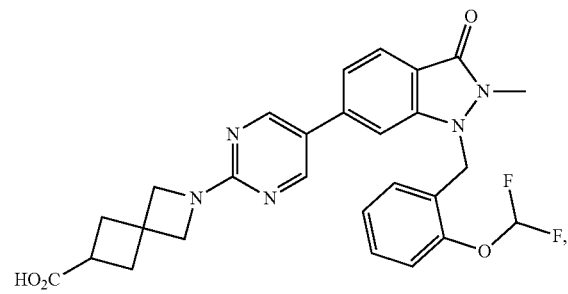

2.18 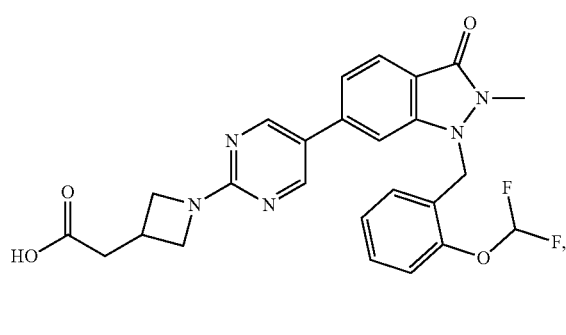
2.22 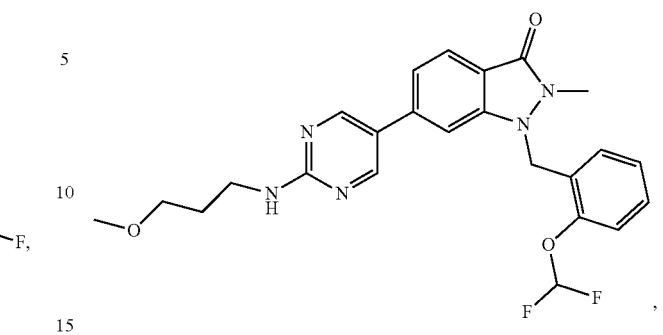
2.19 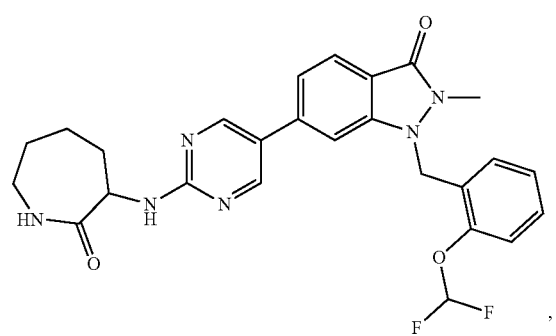
2.23 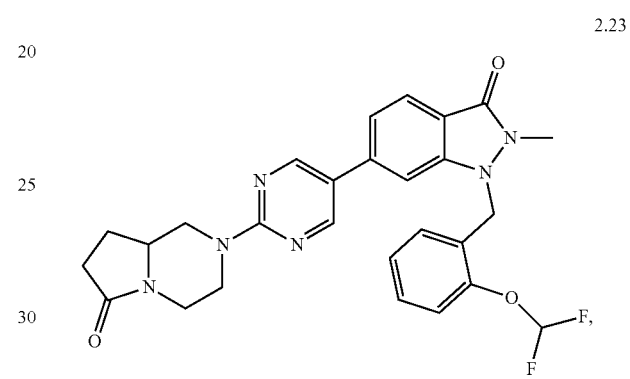
2.20 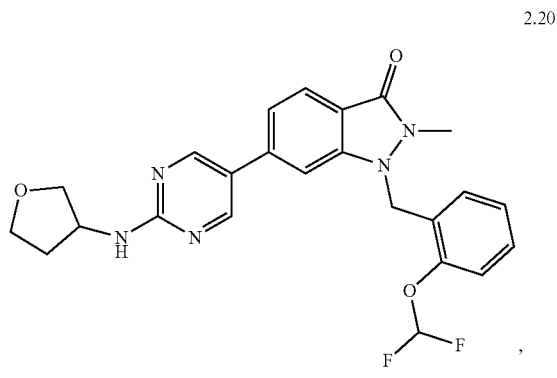
2.24 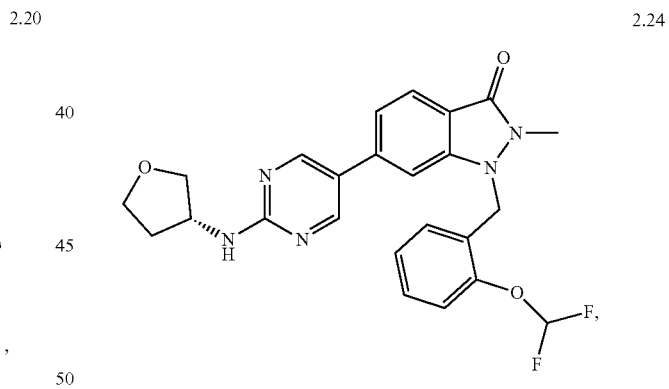
2.21 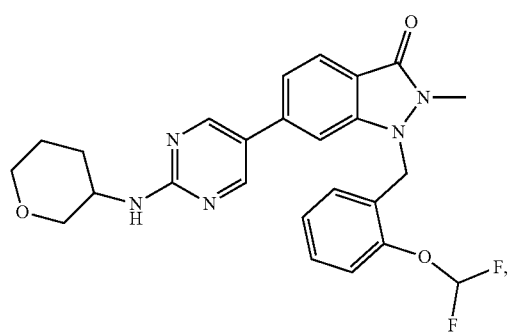
2.25 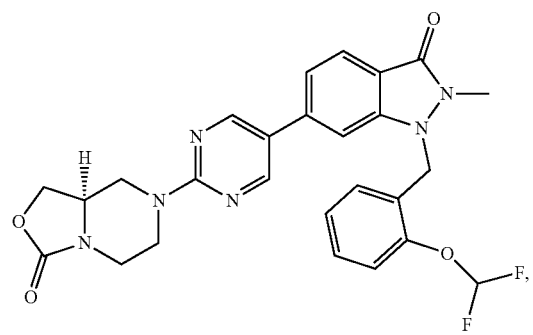

2.26
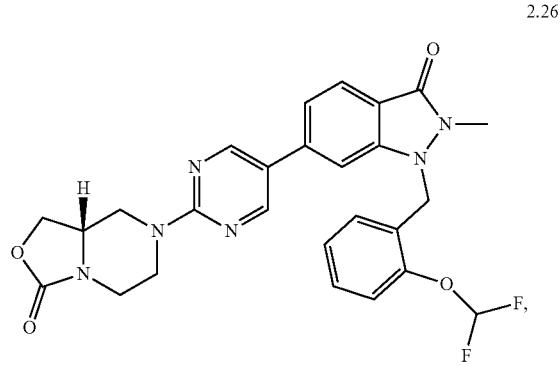
3.1
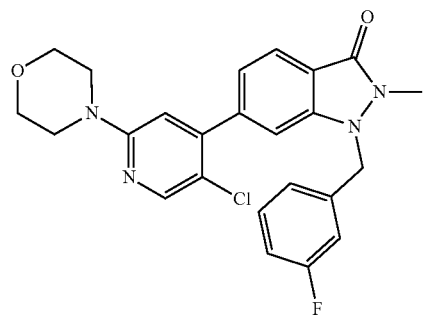
2.27
4
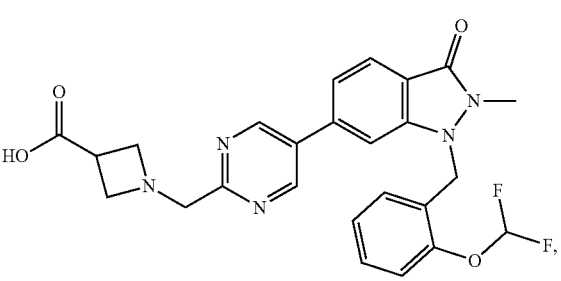
2.28
4.1
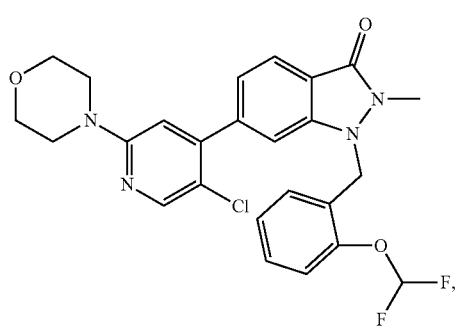
3
5
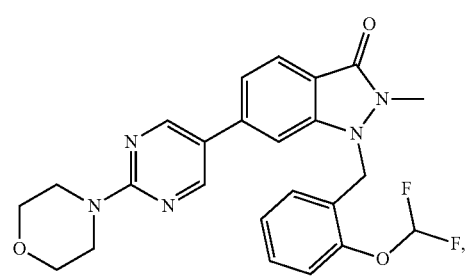
5.1
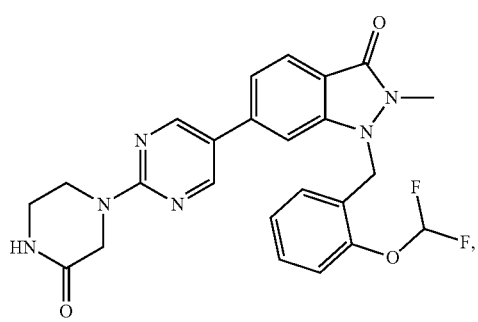

391
-continued
5.2
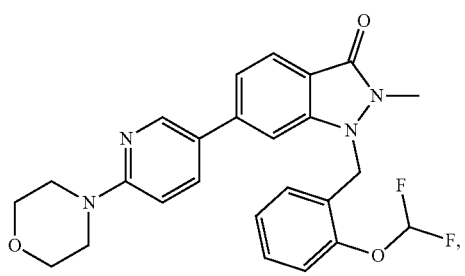
5.3
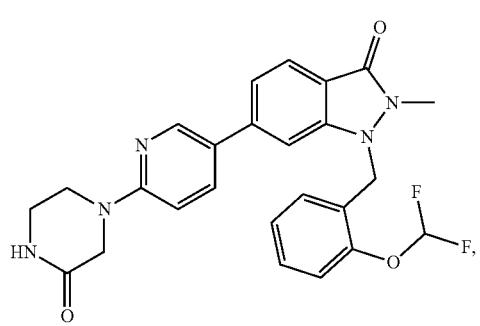
5.4
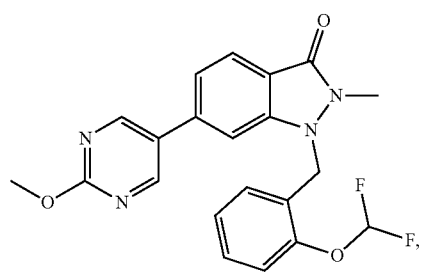
5.5
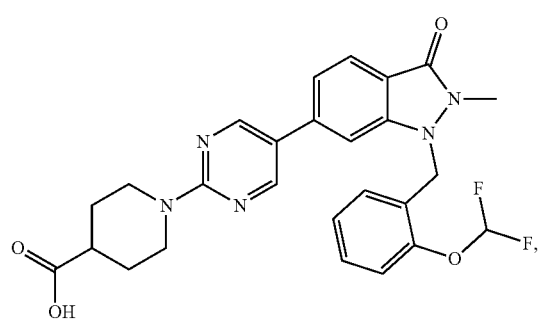
5.6
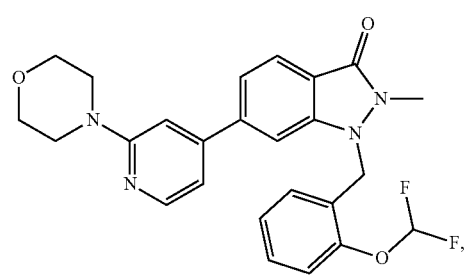
392
-continued
5.7
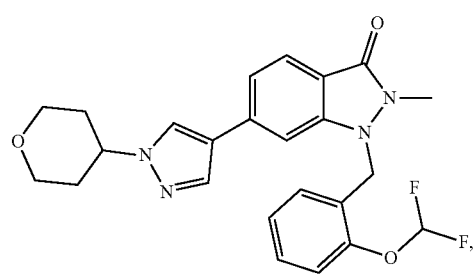
6
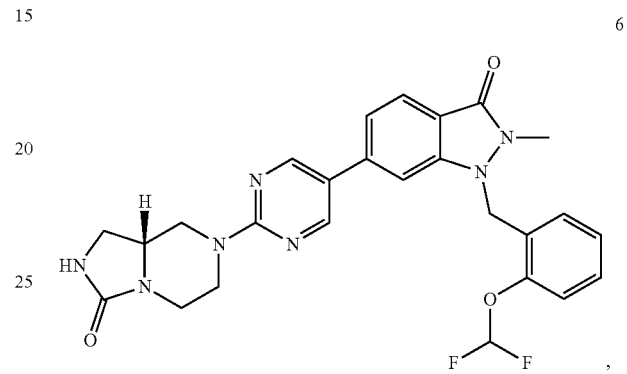
6.1
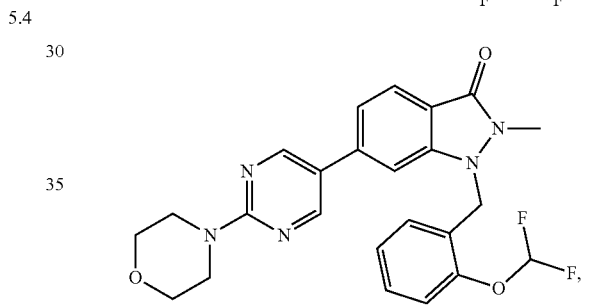
7
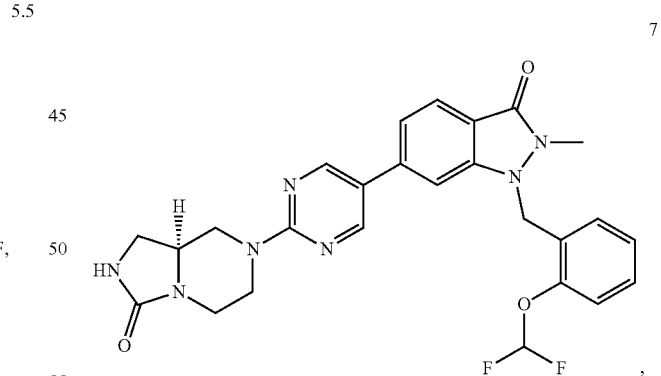
7.1
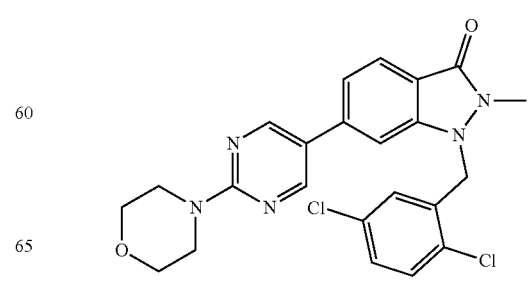

7.2
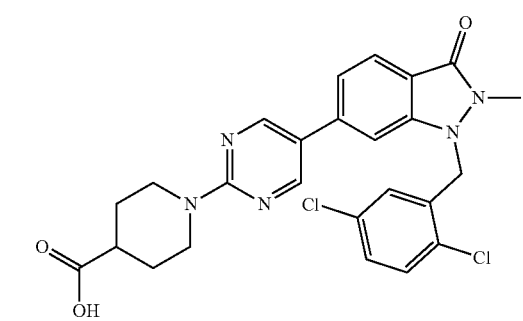
8
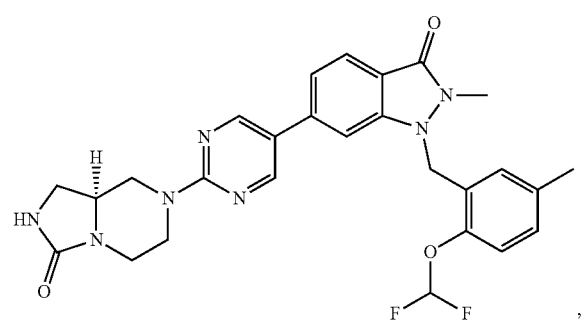
8.1
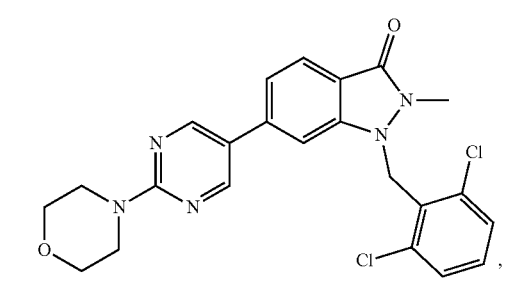
8.2
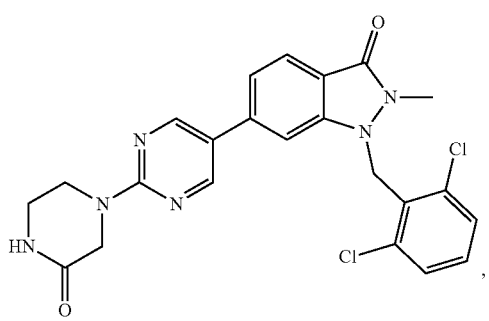
9
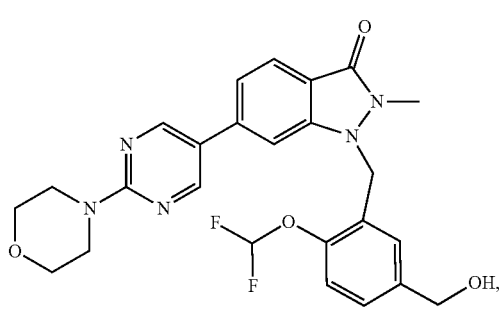
9.1
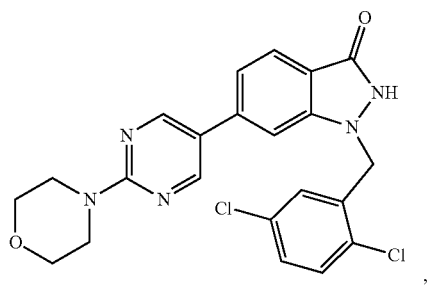
10
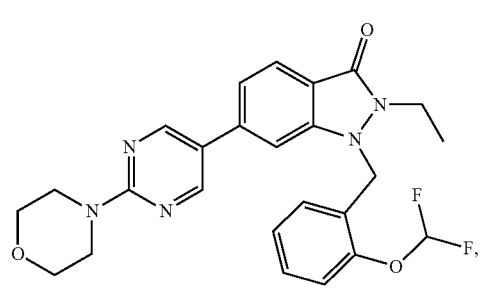
10.1
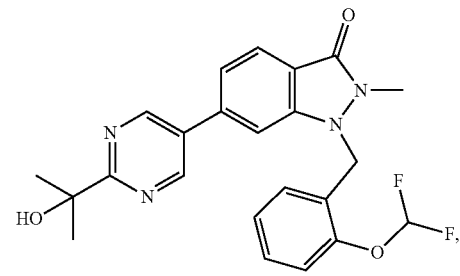
10.2
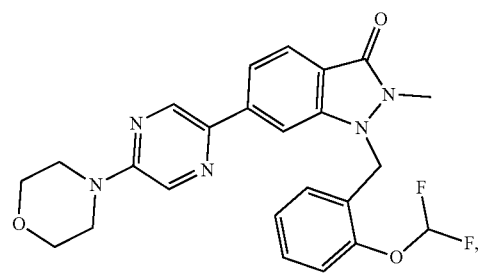
10.3
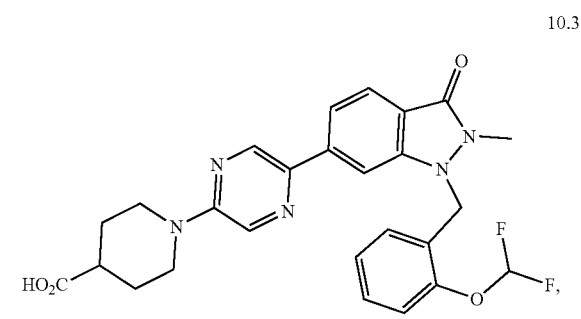

10.4
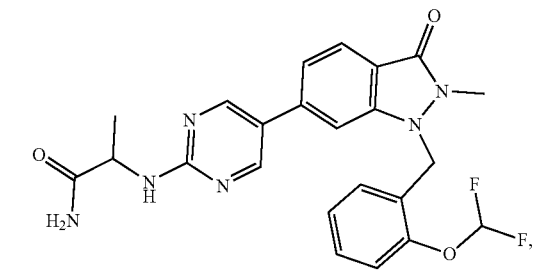
10.5
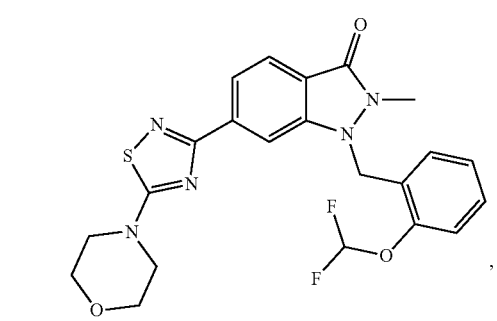
10.6
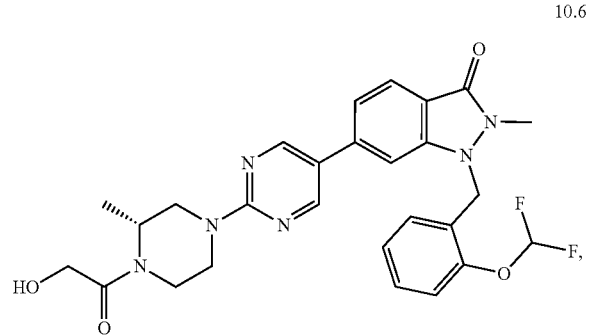
10.7
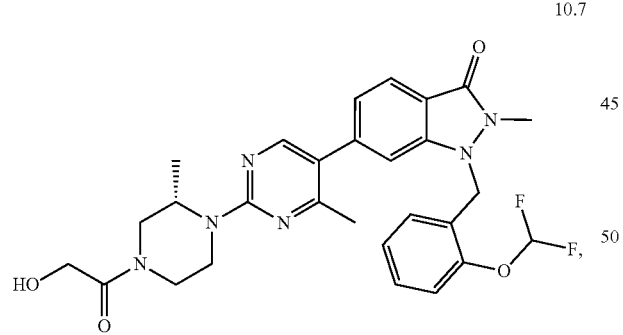
10.8
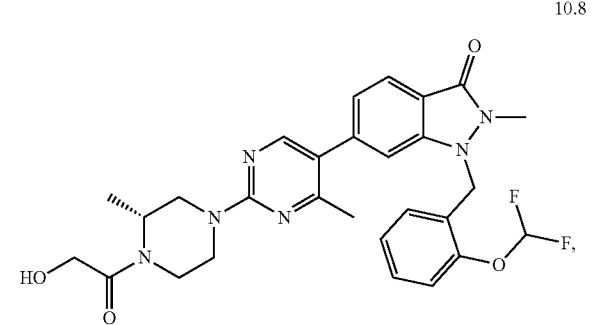
10.9
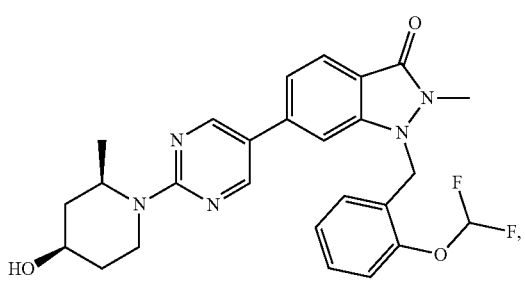
10.10
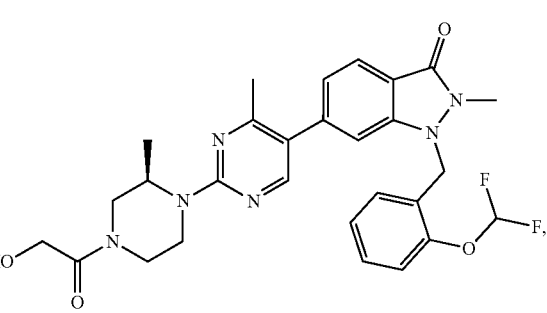
10.11
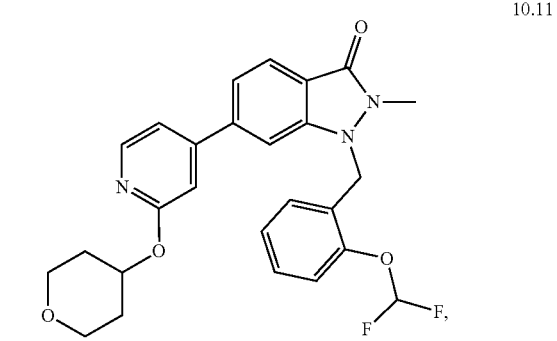
10.12
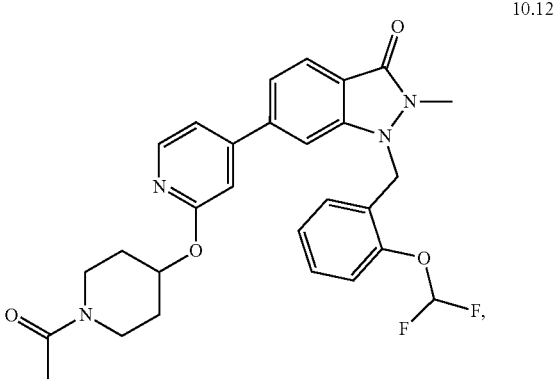

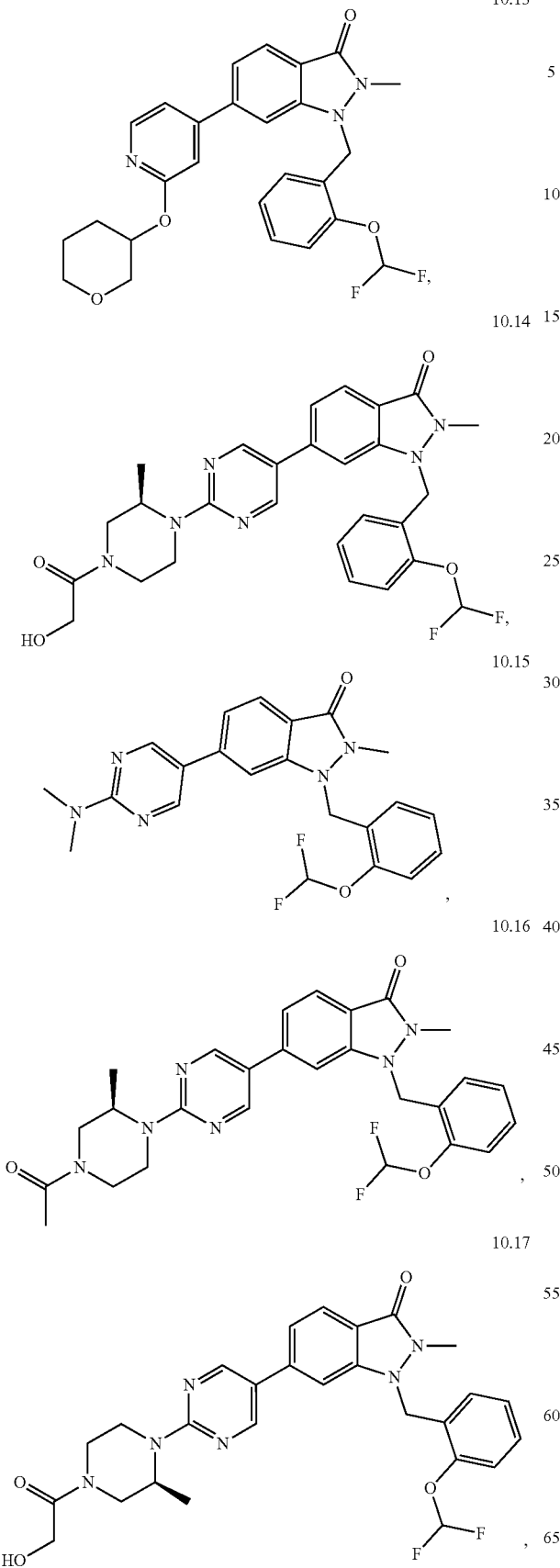
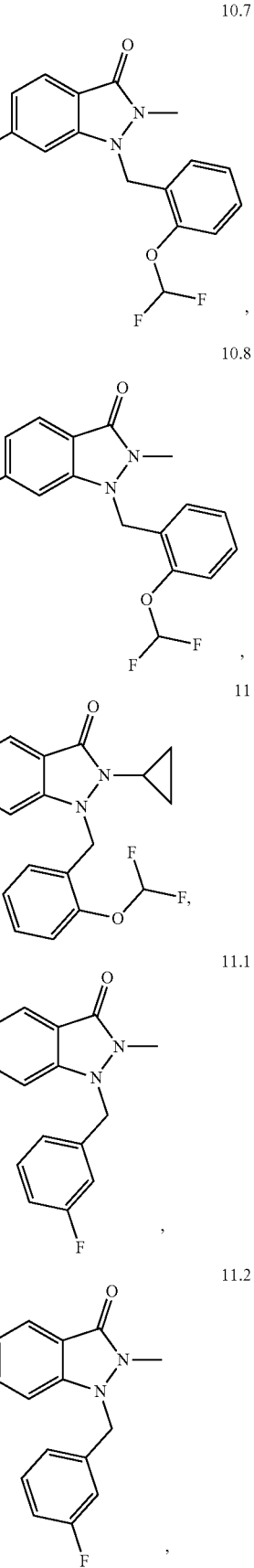

12
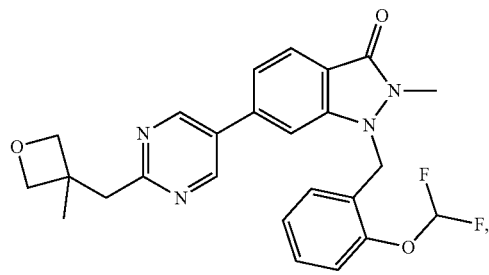
12.1
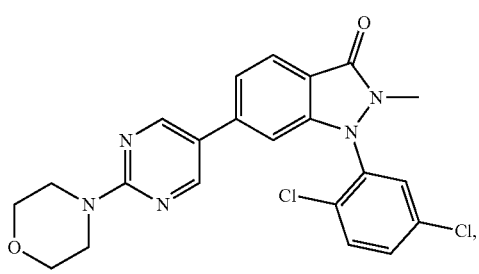
13
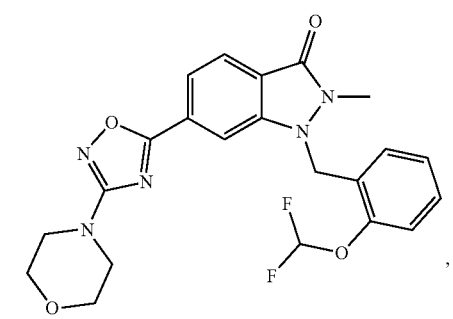
13.1
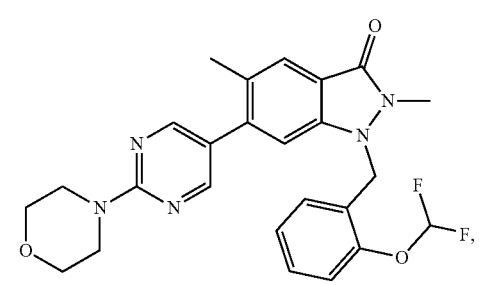
13.2
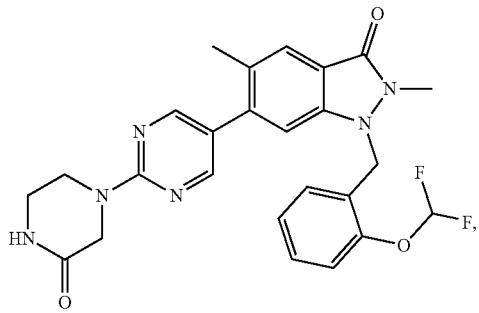
13.3
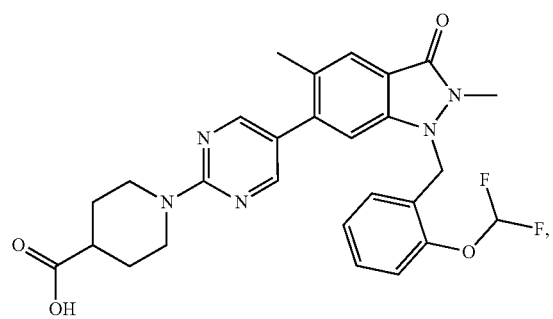
14
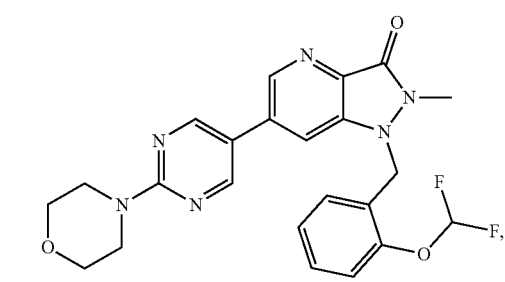
14.1
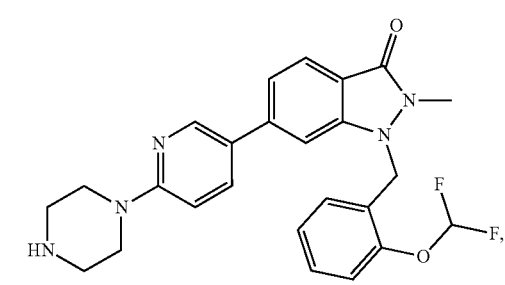
14.2
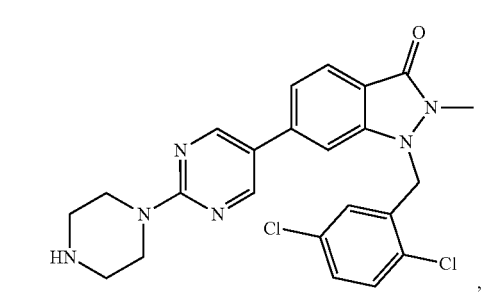
14.3
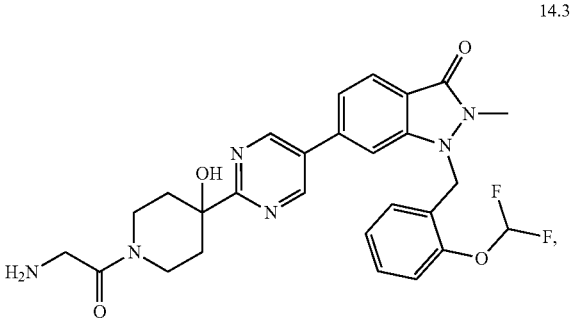

14.4
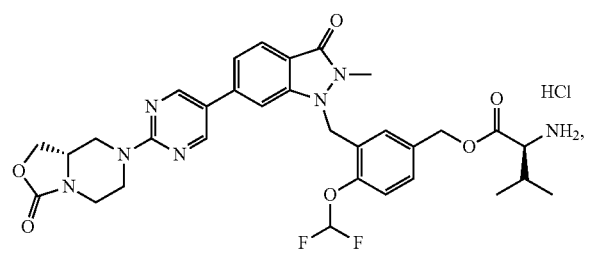
HCl
14.5
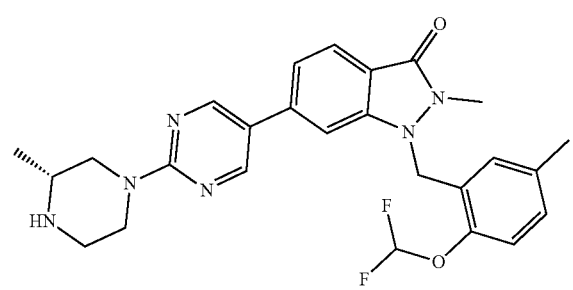
,
14.6
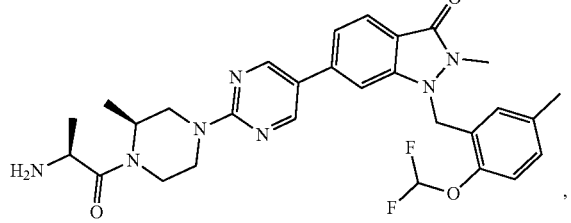
,
14.7
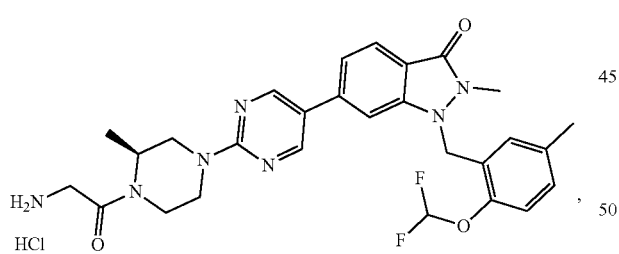
HCl
,
14.8
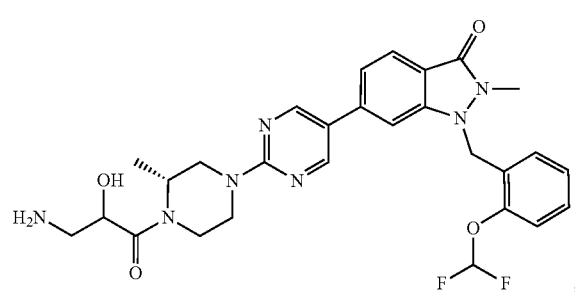
,
14.9
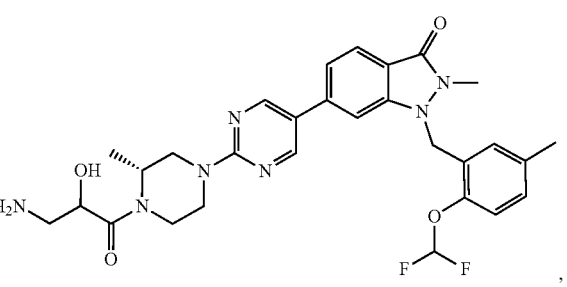
,
14.10
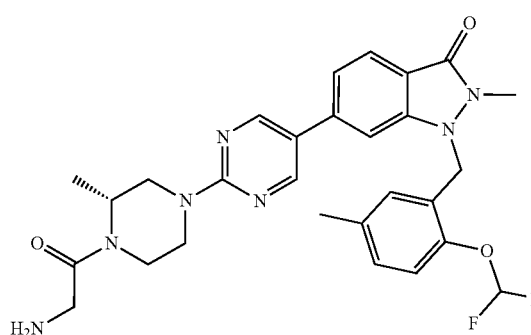
,
14.11
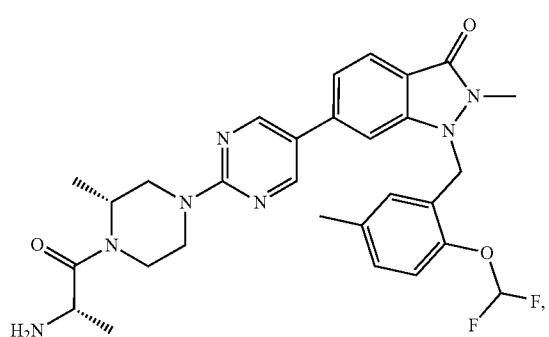
,
14.12
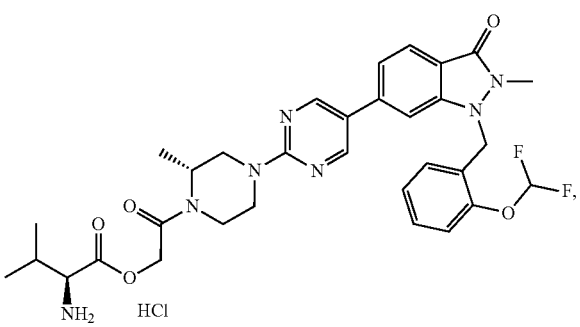
HCl 14.13
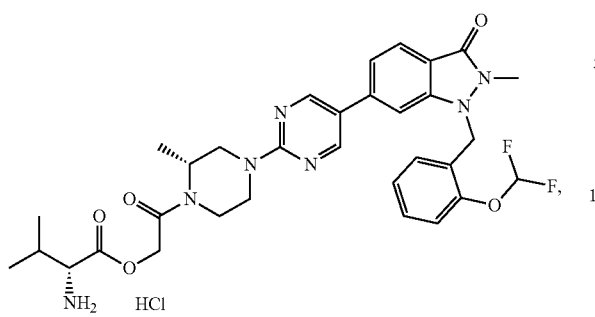
14.14
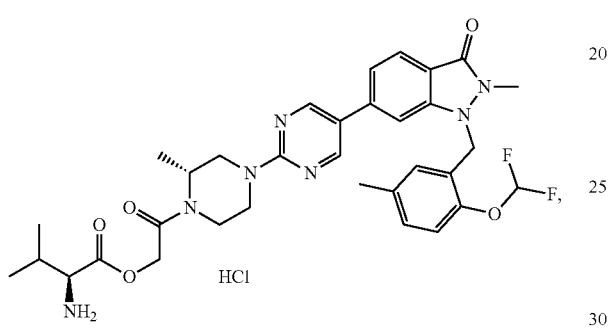
14.15
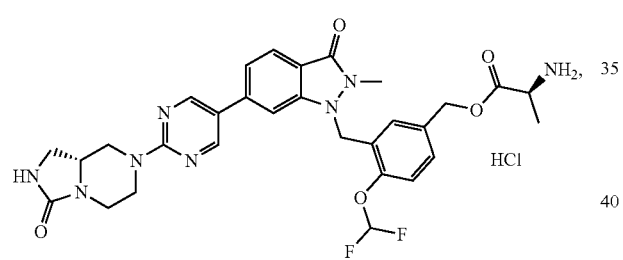
14.16
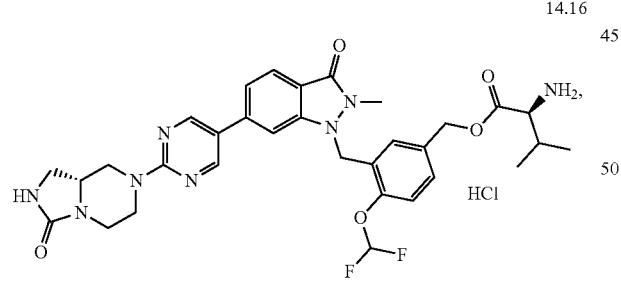
15
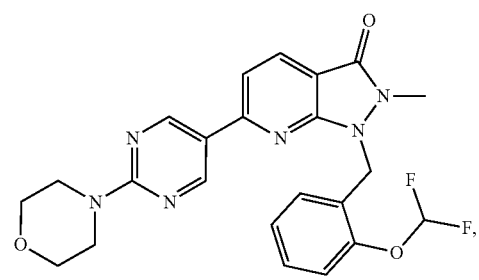
15.1
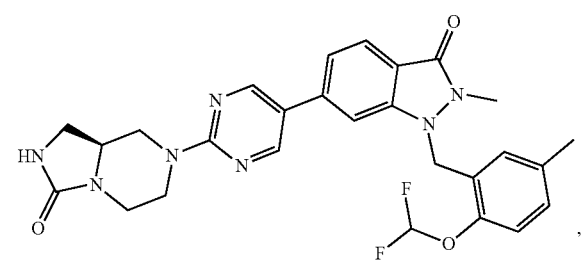
16
16.1
16.2
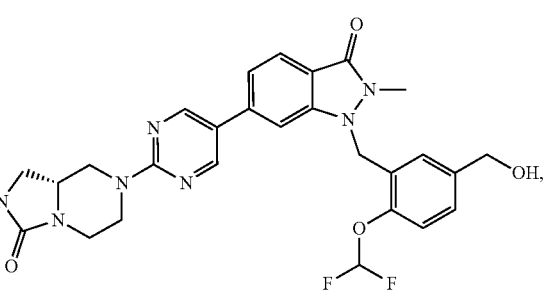
16.3

16.4
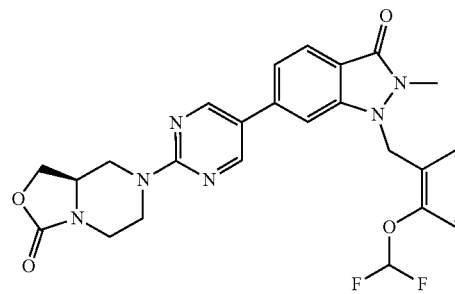
16.8
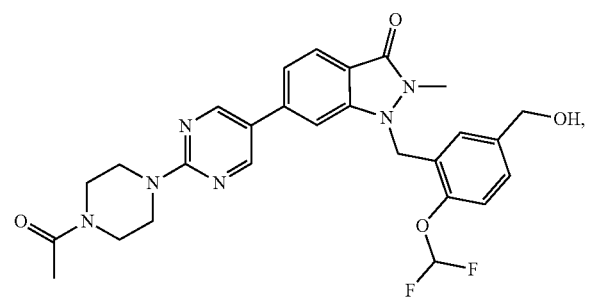
16.5
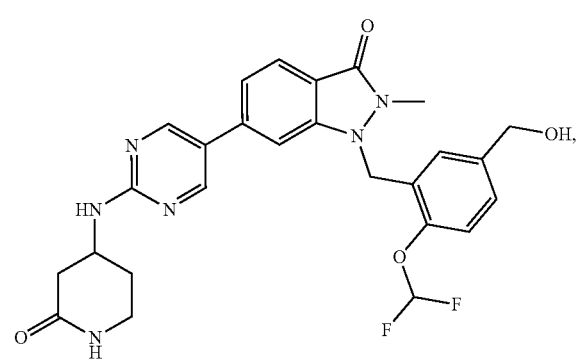
16.9
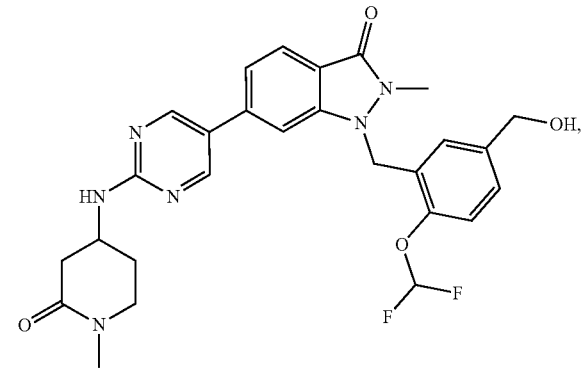
16.6
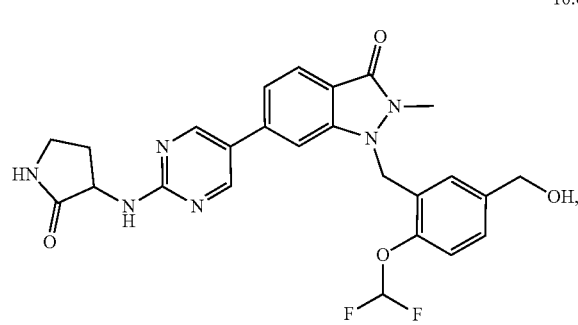
16.10
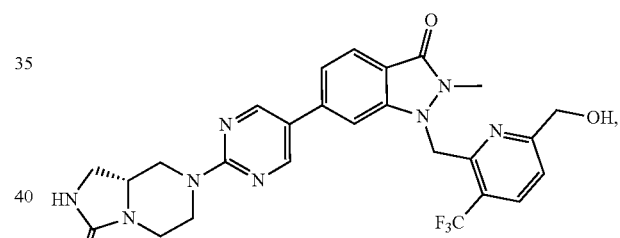
17
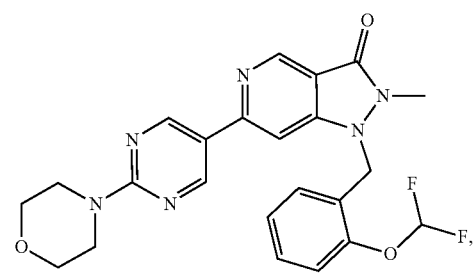
16.7
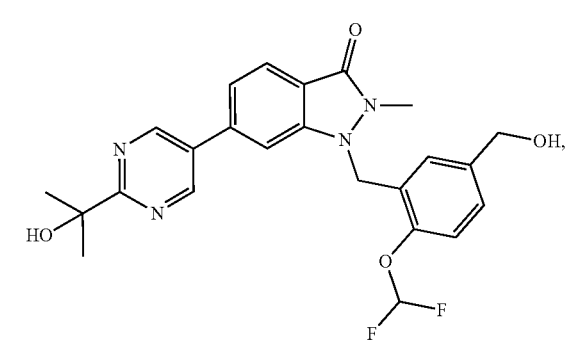
17.1
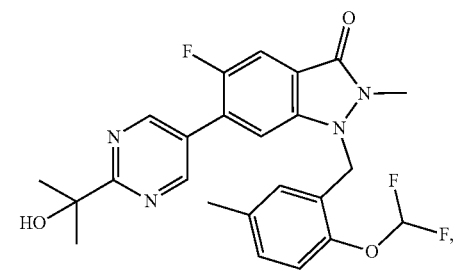

17.2 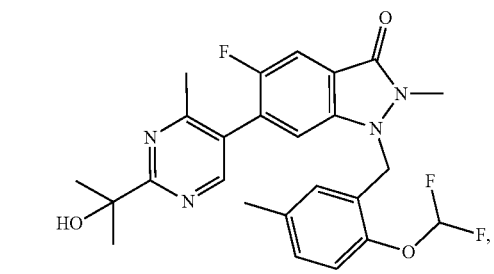
17.3 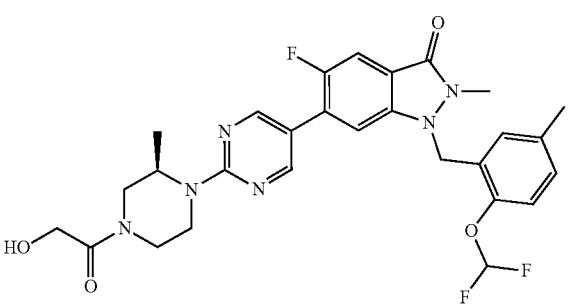
17.4 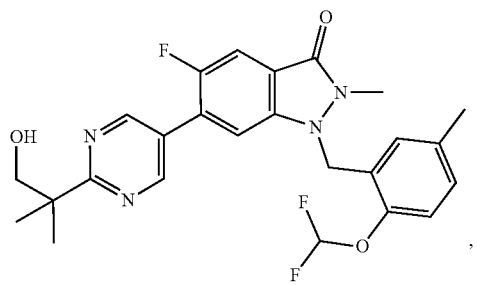
18 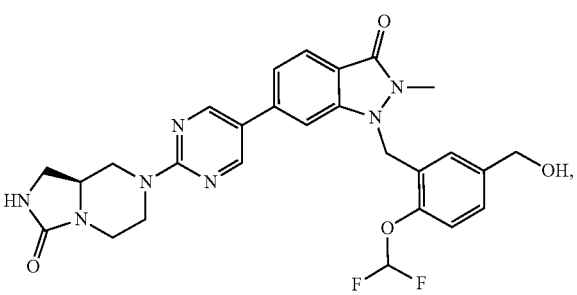
18.1 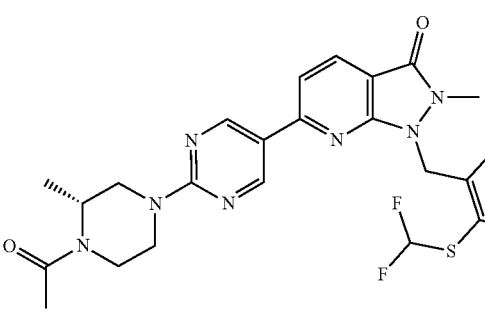
18.2 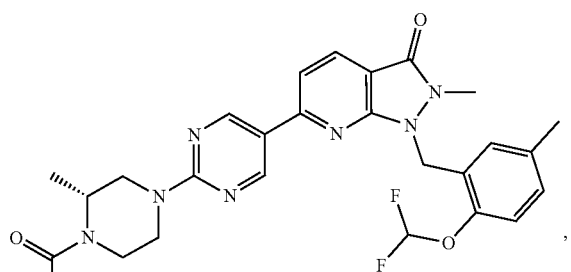
18.3 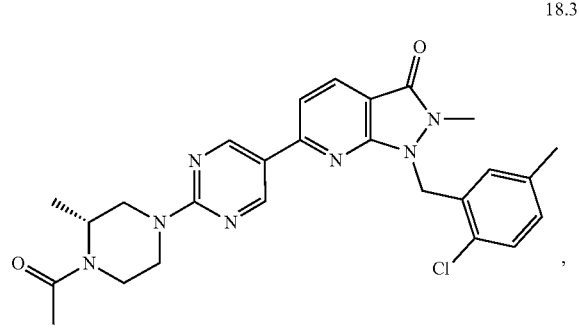
19 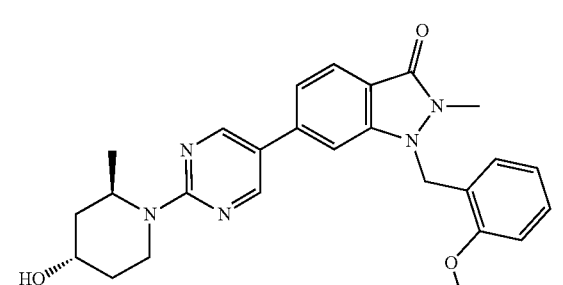
19.1 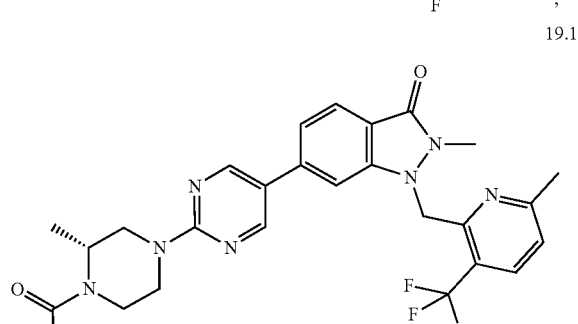
19.2 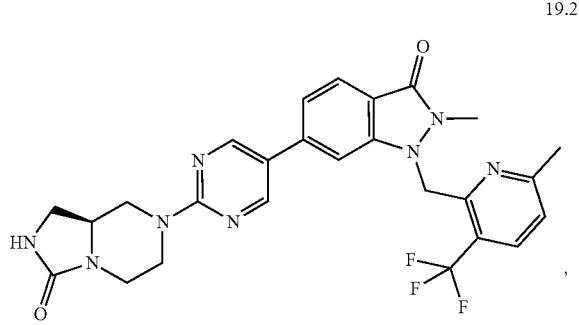

19.3
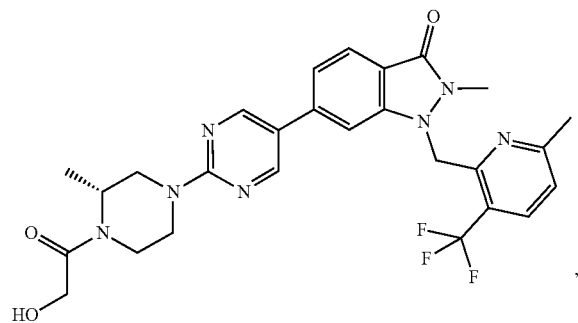
19.4
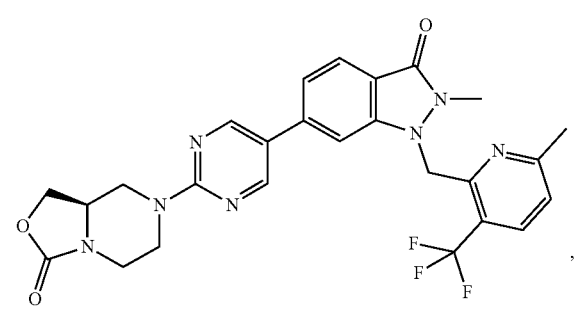
19.5
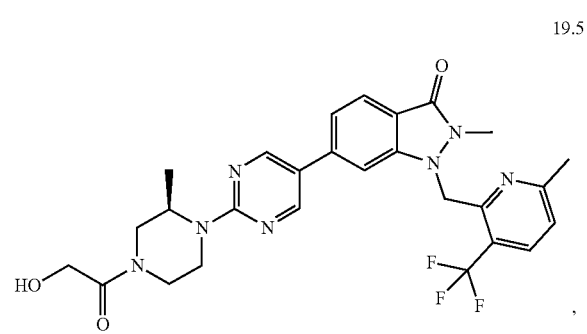
20.0
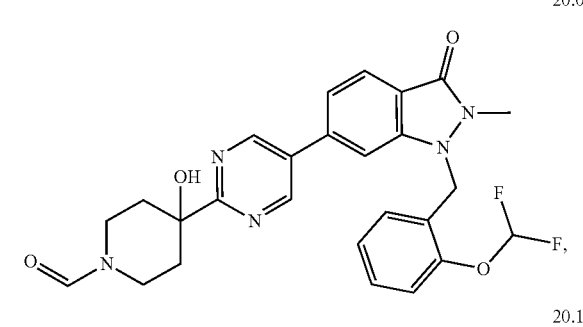
20.1
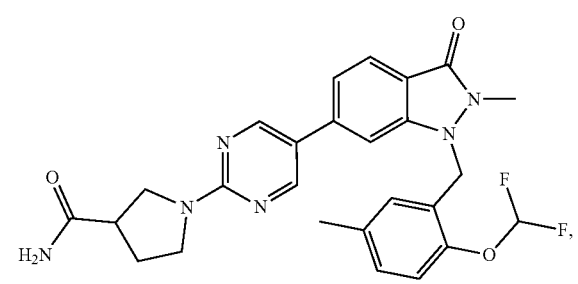
20.2
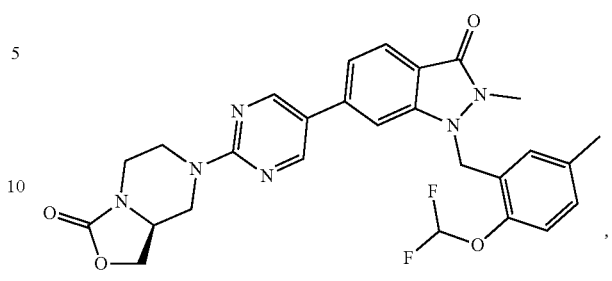
20.3
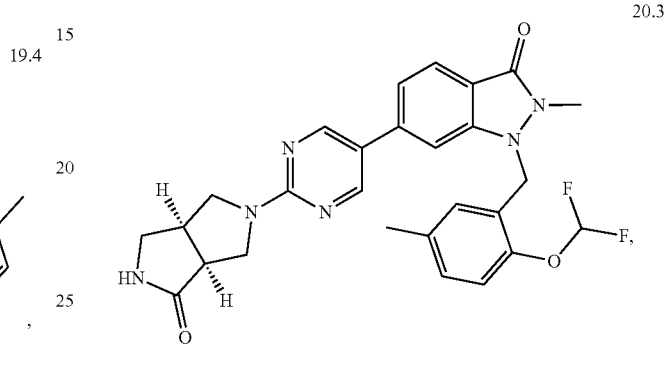
20.4
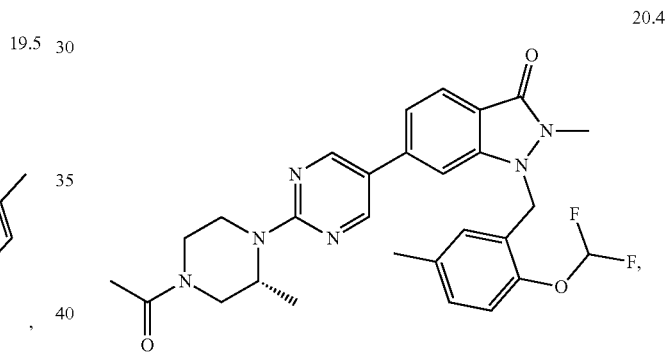
20.5
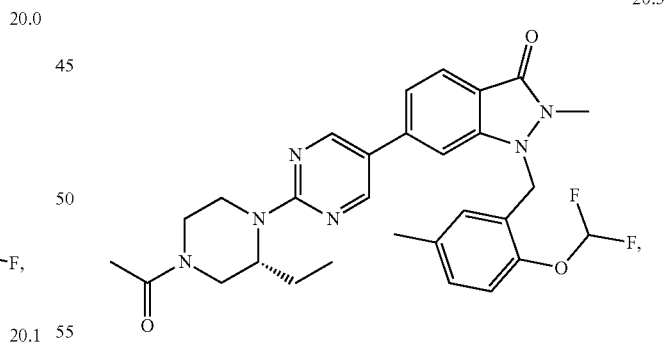
21
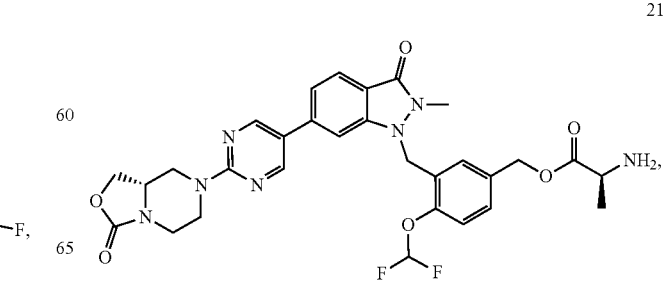

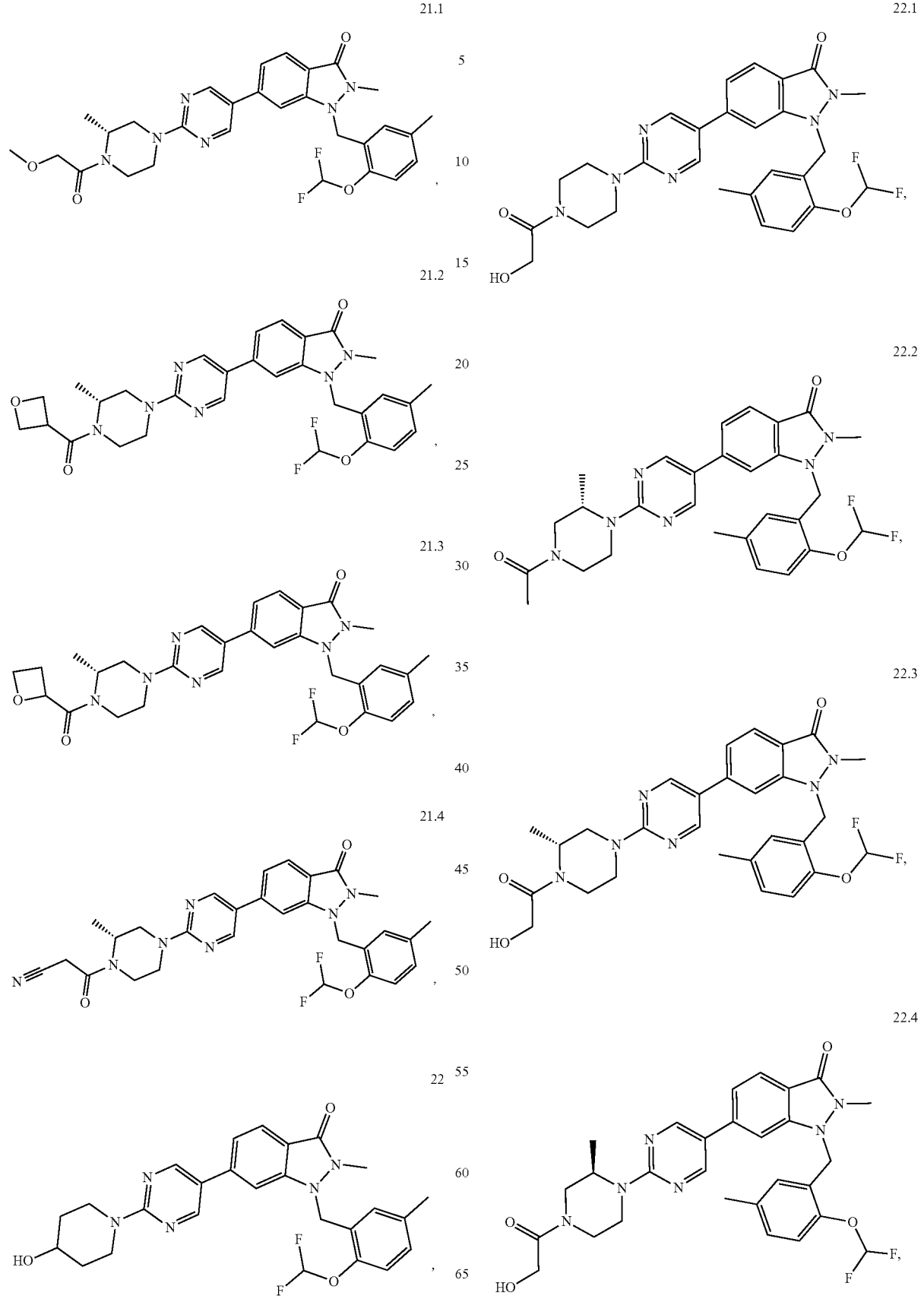

| | |
|---|---|
| 22.5 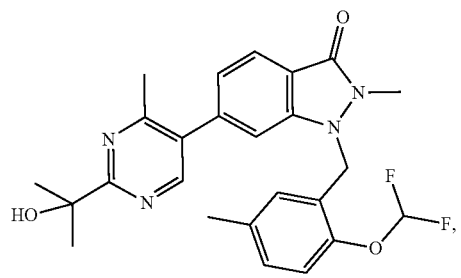 | 22.10 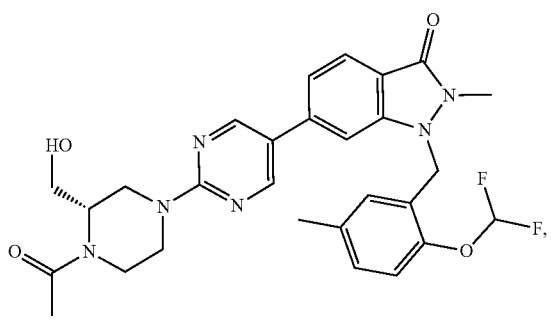 |
| 22.6 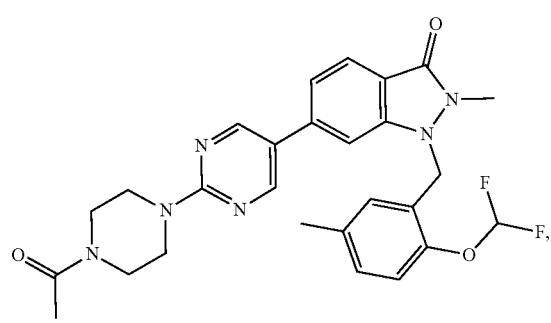 | 22.11 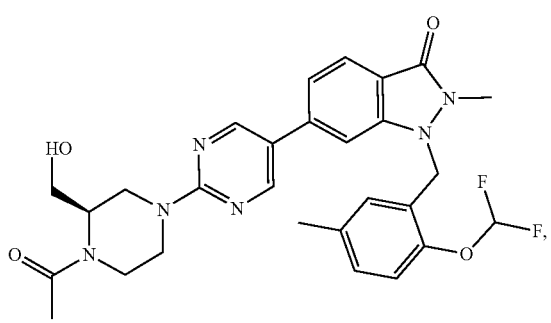 |
| 22.7 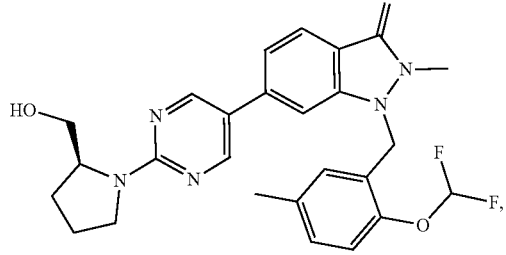 | 22.12 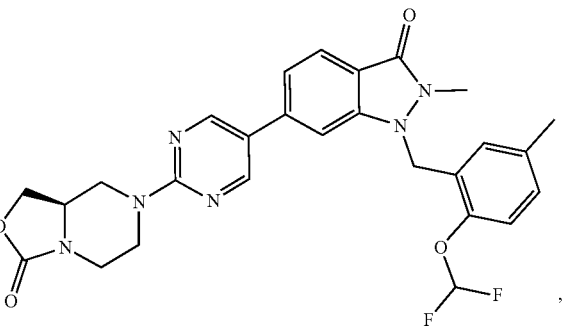 |
| 22.8 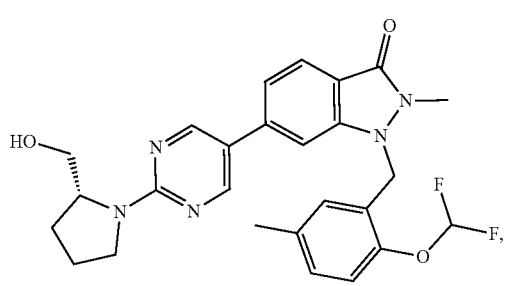 | 22.13 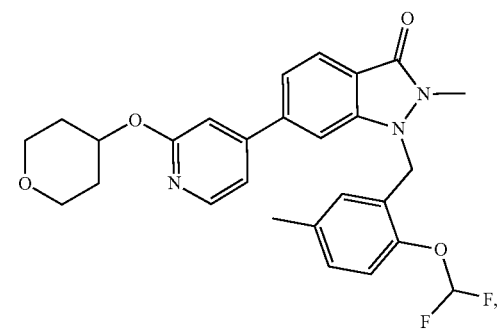 |
| 22.9 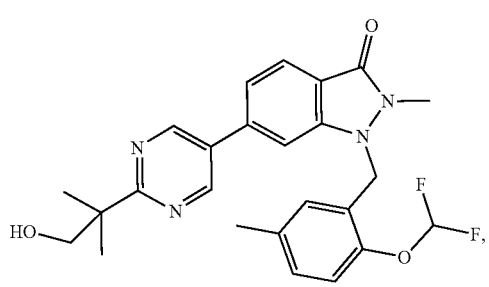 | |

22.14
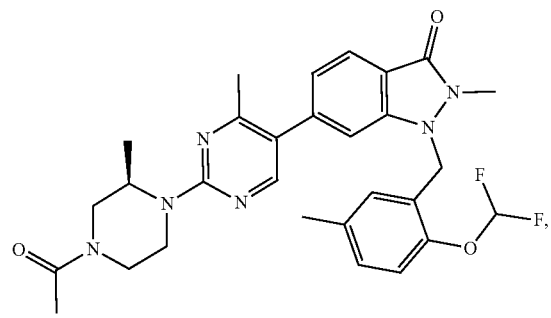
22.15
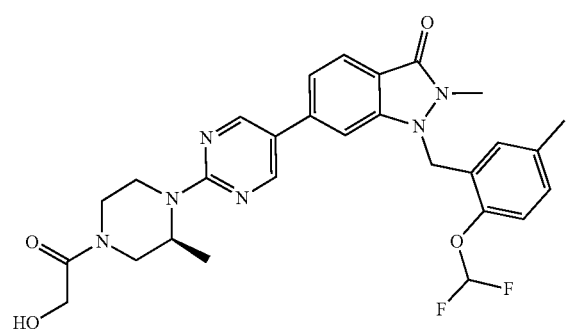
23
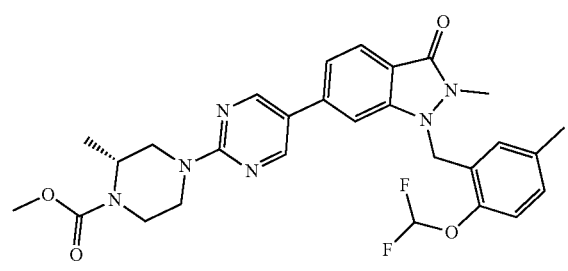
23.1
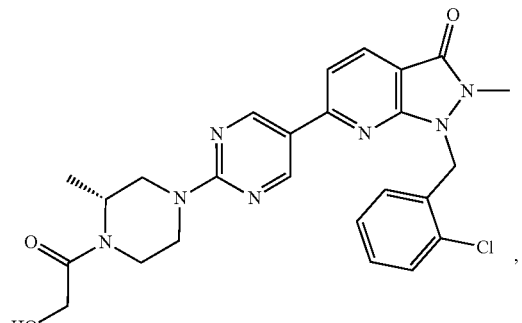
23.2
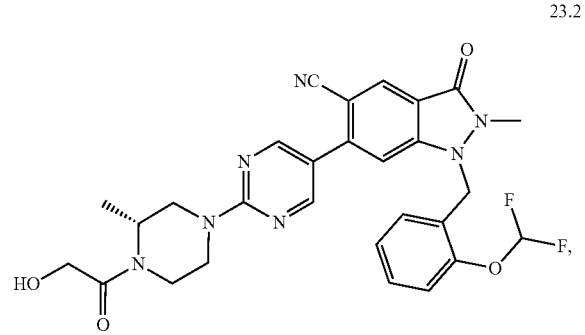
23.3
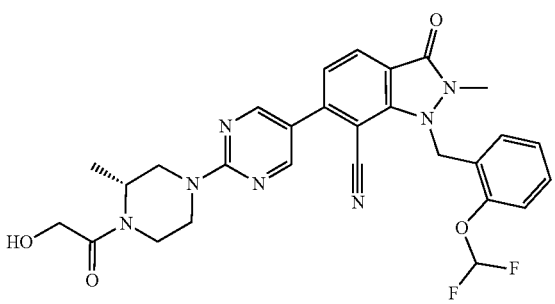
24.1
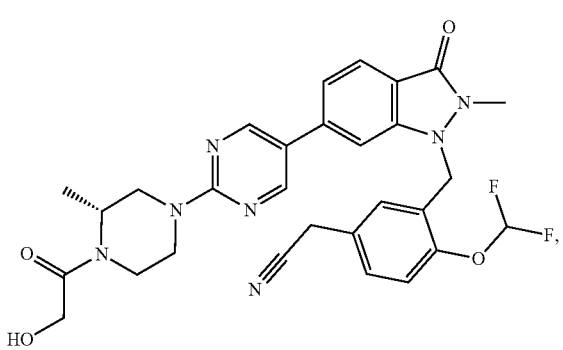
24.2
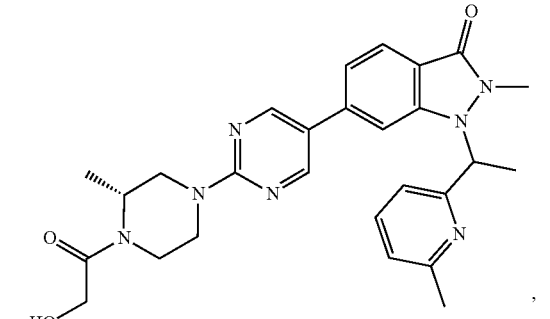
24.3
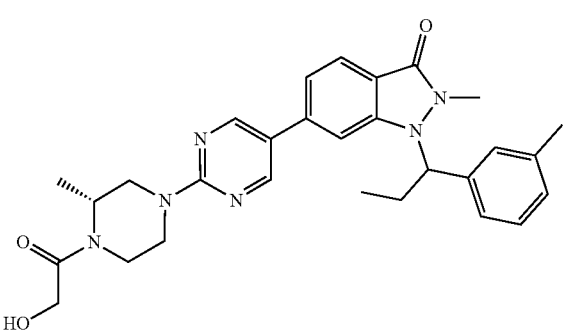

417
-continued
24.4
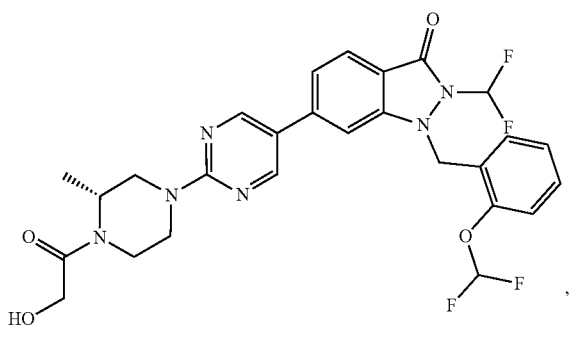
24.5
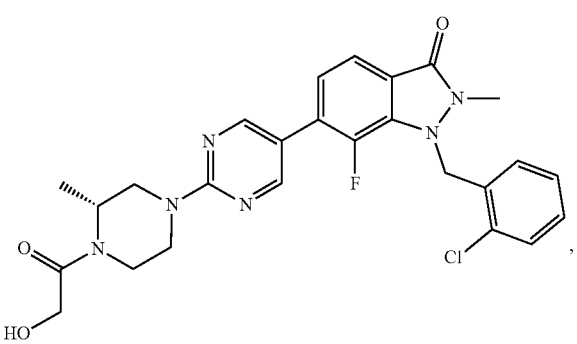
24.6
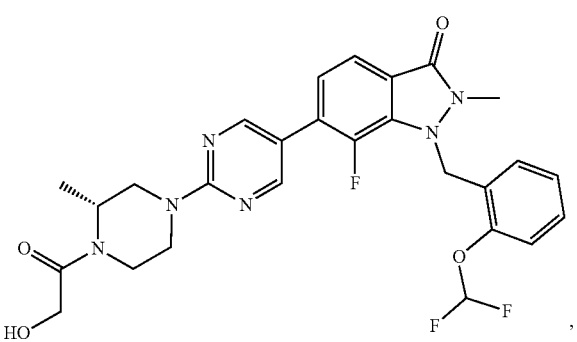
24.7
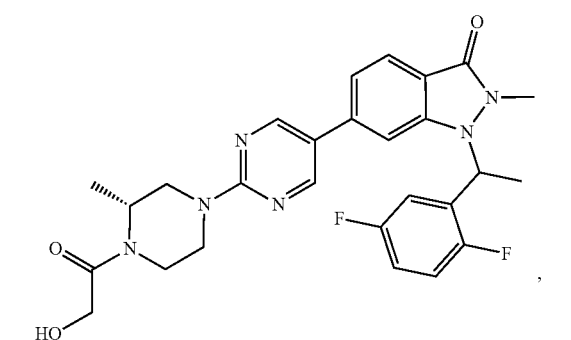
418
-continued
24.8
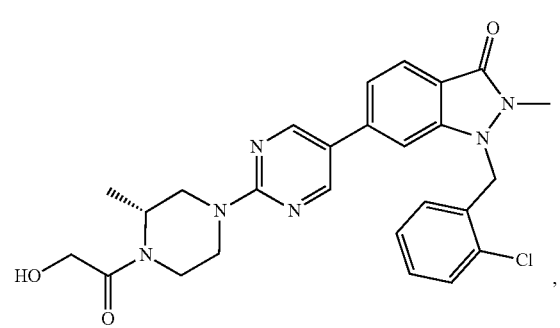
24.9
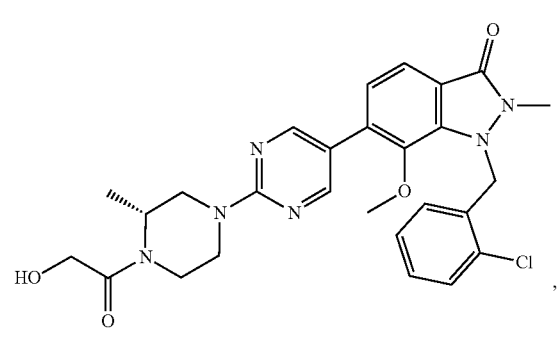
24.10
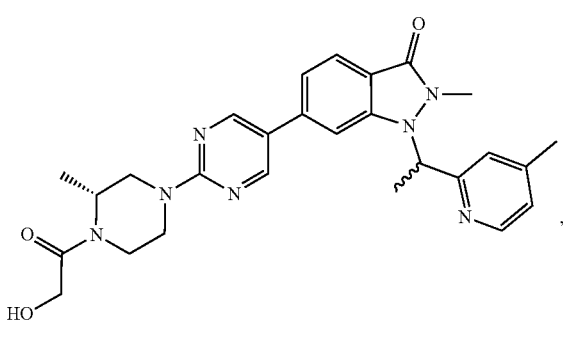
24.11
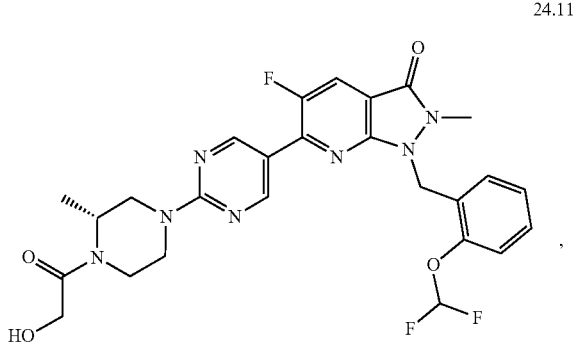

24.12
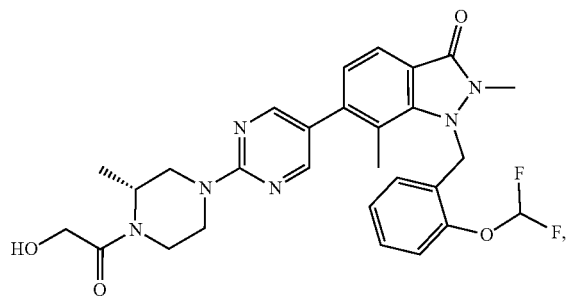
24.13
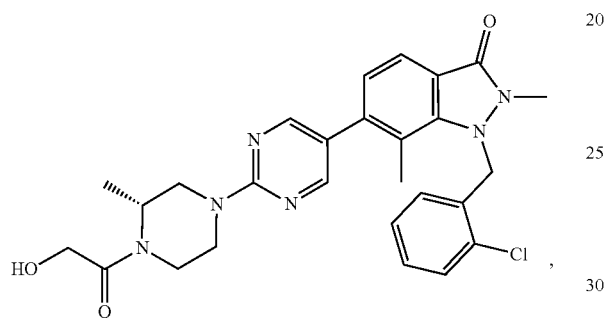
25
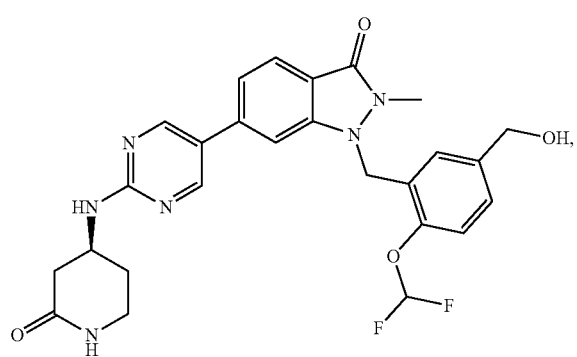
25.1
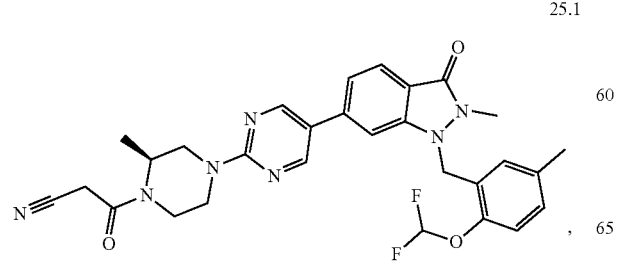
26
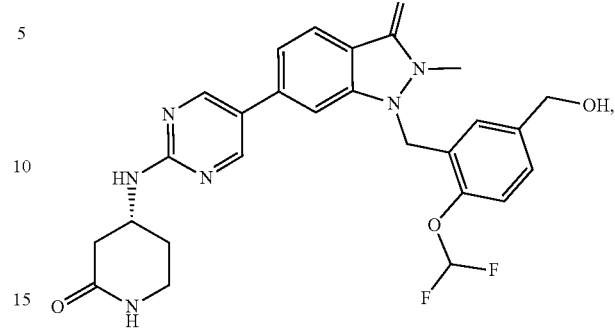
26.1
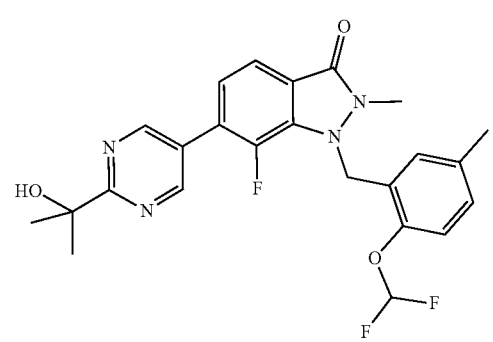
26.2
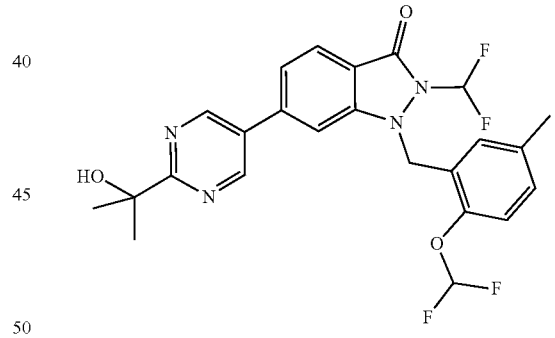
26.3
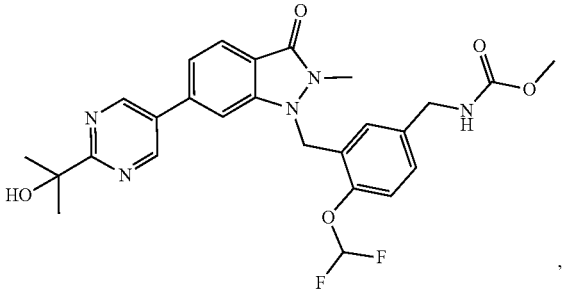

26.4
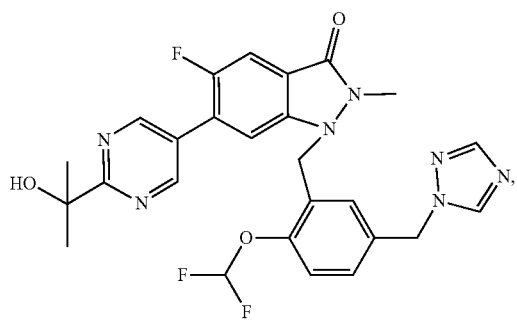
26.5
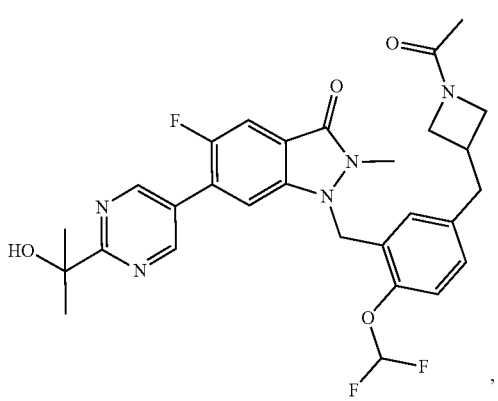
26.6
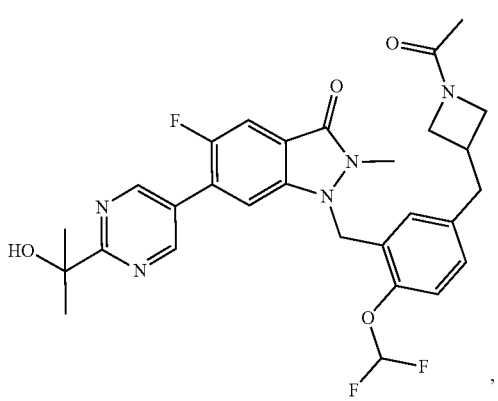
26.7
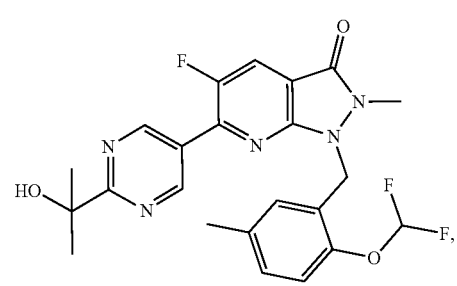
26.8
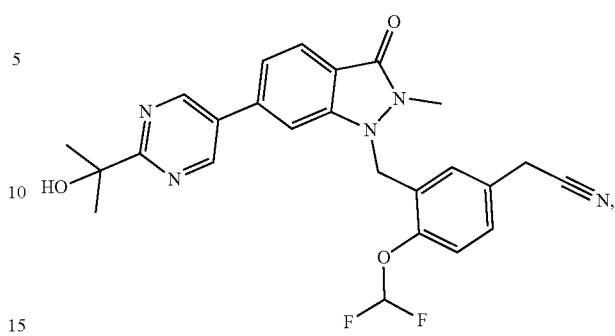
27
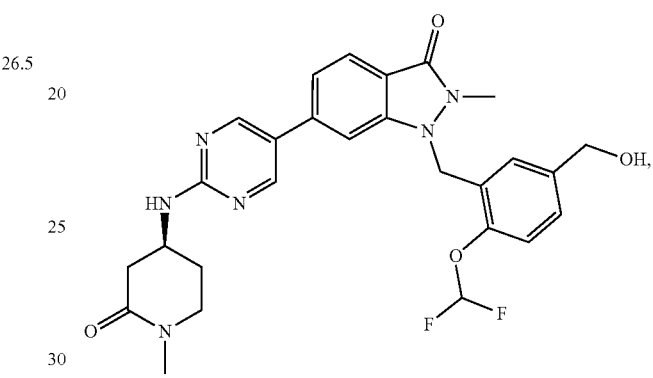
27.1
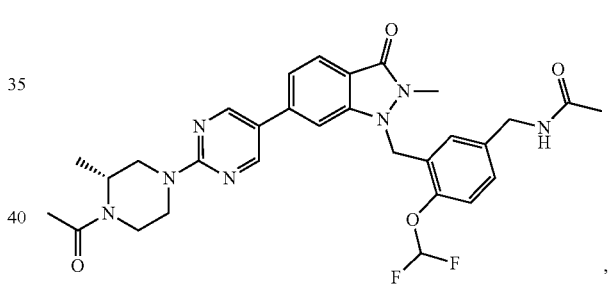
27.2
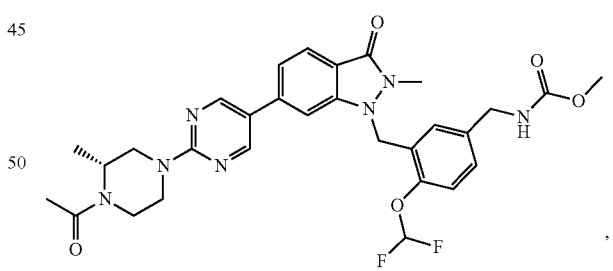
27.3
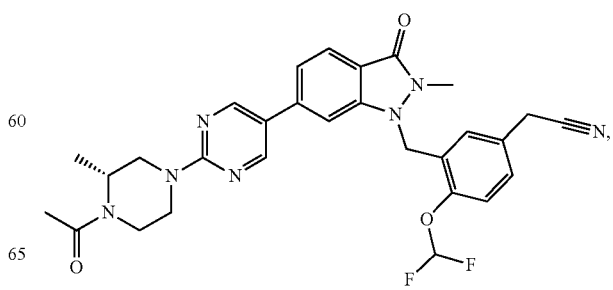

27.4
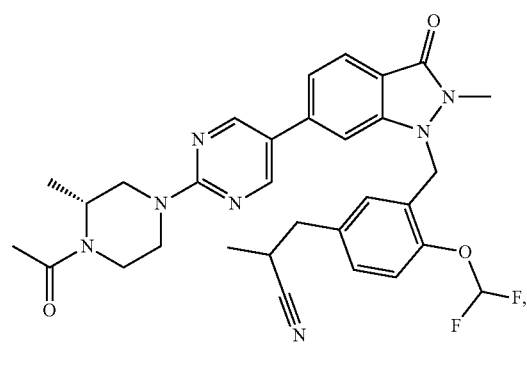
27.5
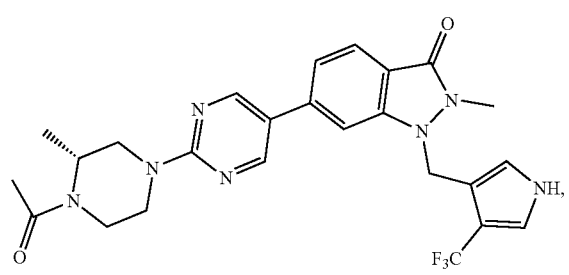
27.6
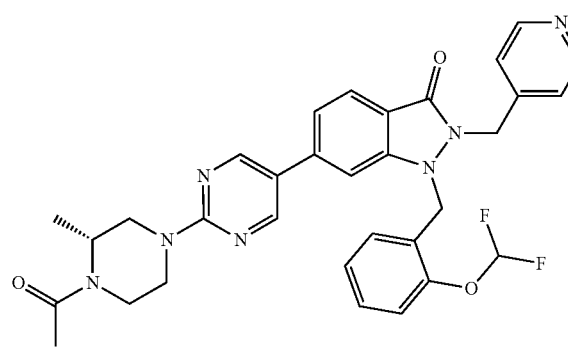
27.7
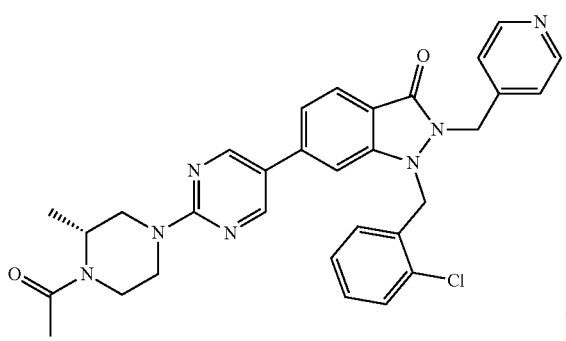
28
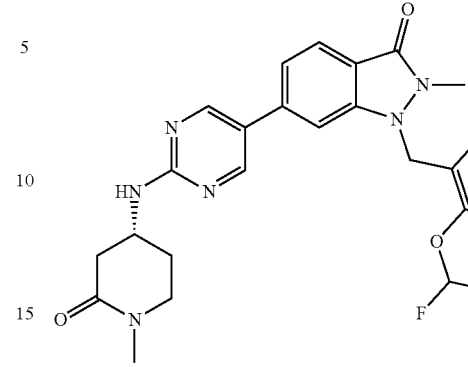
28.1
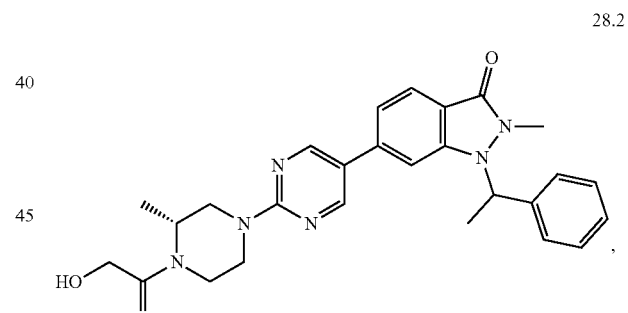
28.2
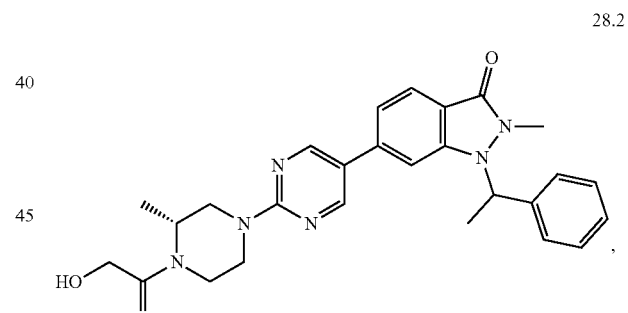
28.3
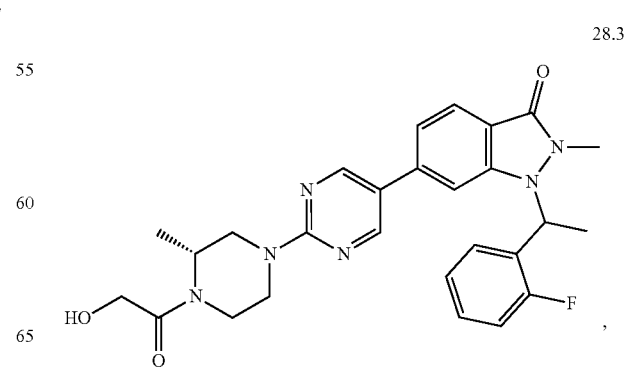

28.4
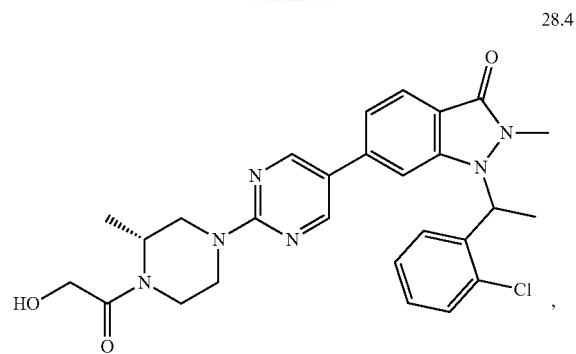
29
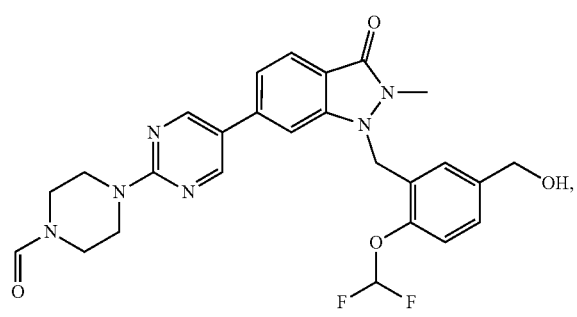
29.1
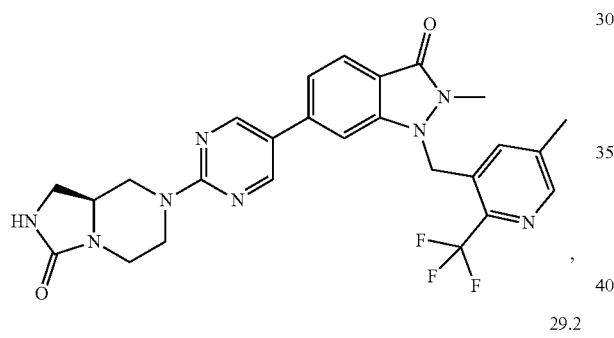
29.2
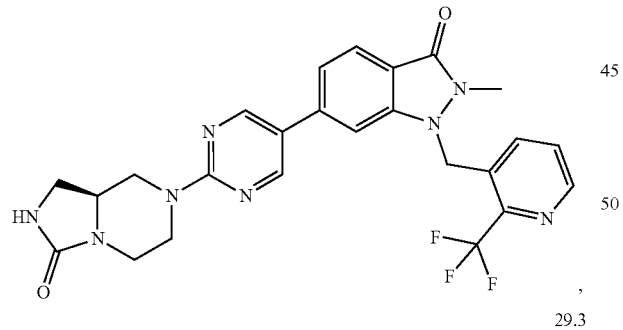
29.3
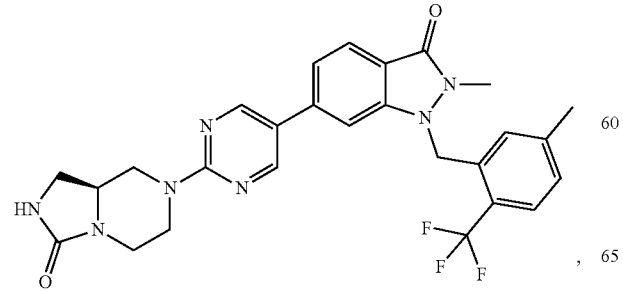
29.4
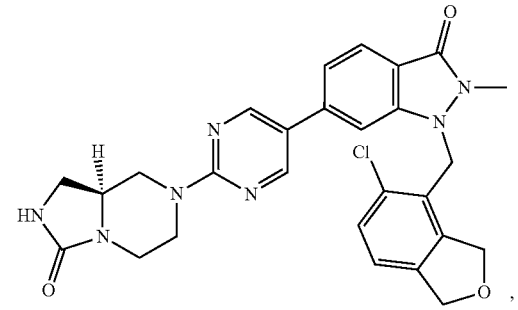
29.5
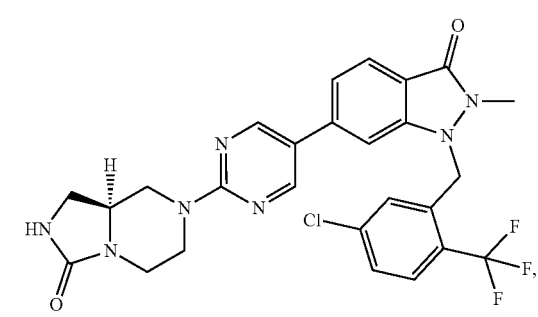
29.6
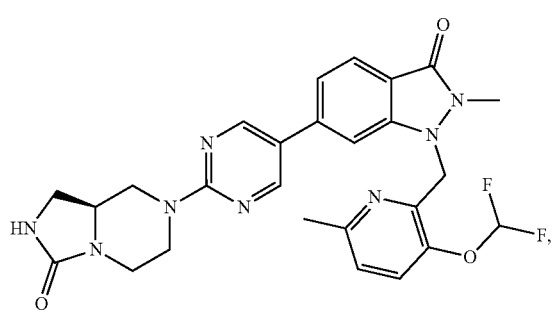
30
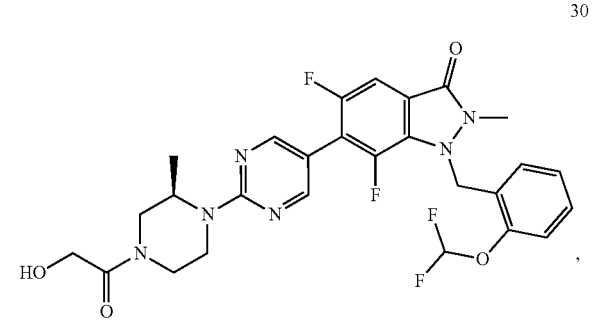
30.1
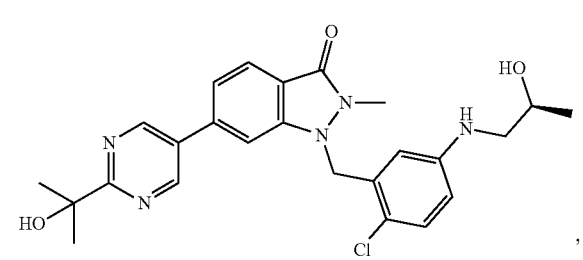

30.2
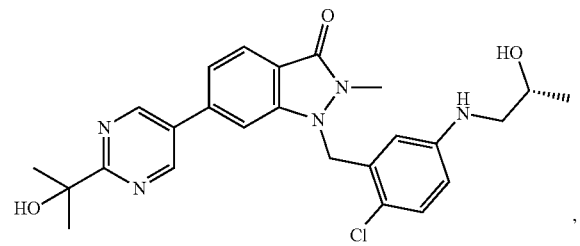
31
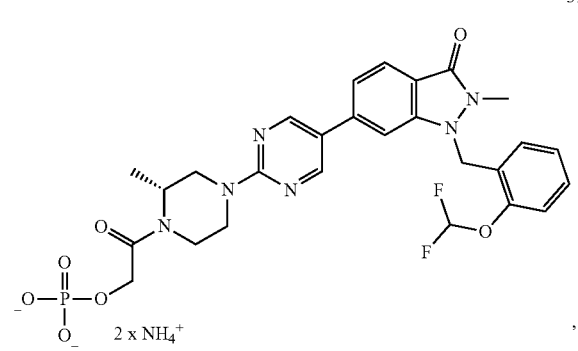
32
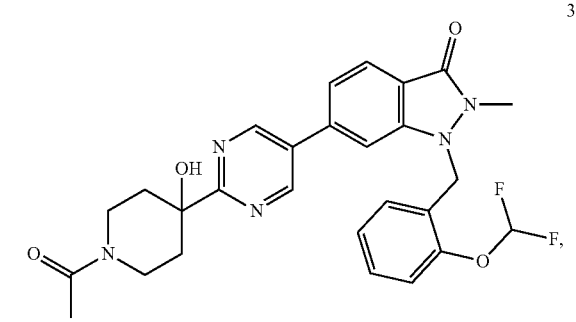
33
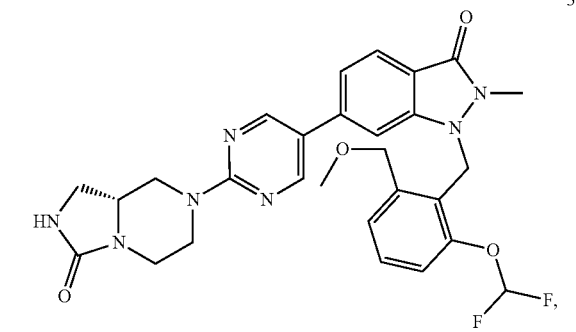
34
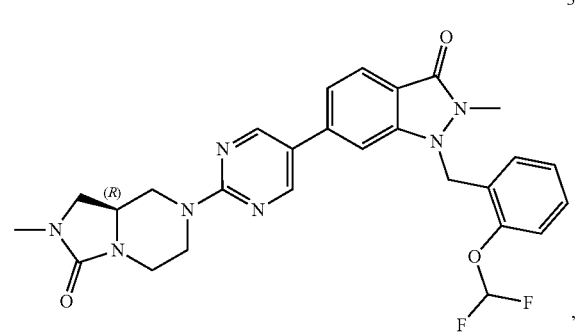
35
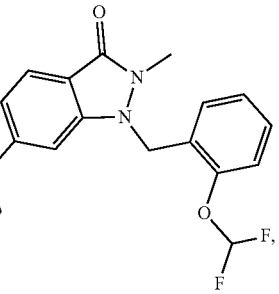
,
36
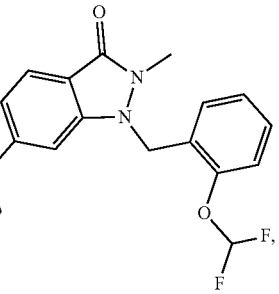
,
37
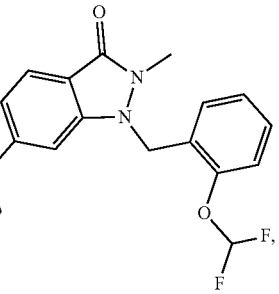
,
38
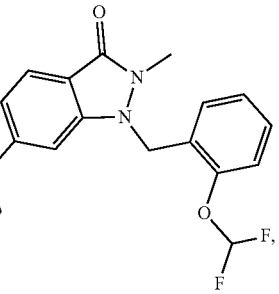
,

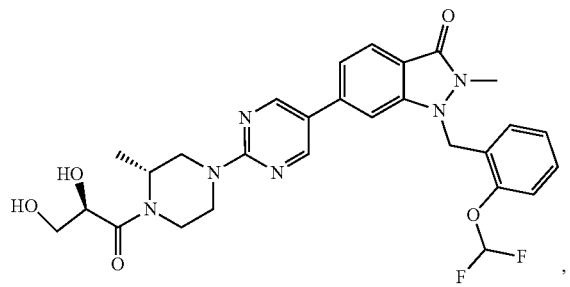
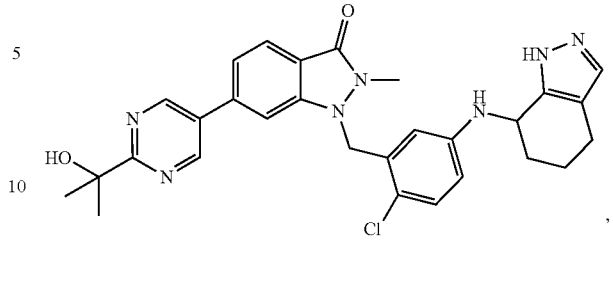
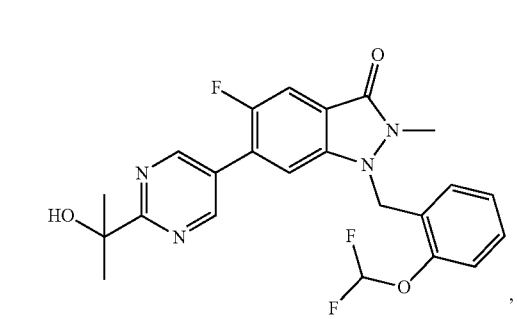
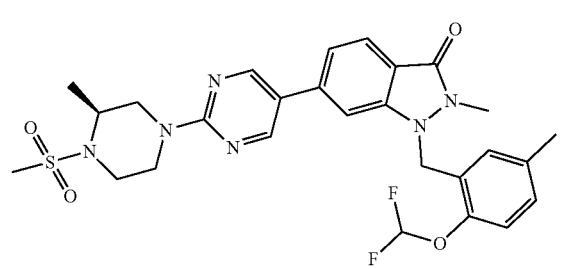
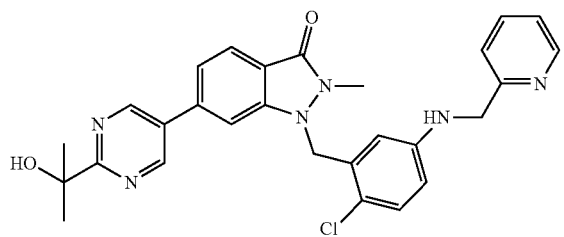
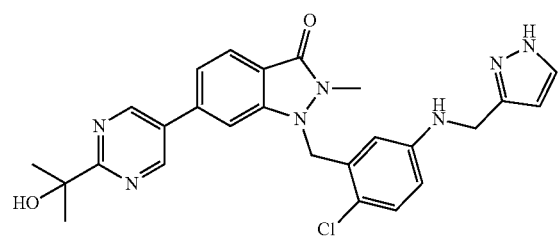

49
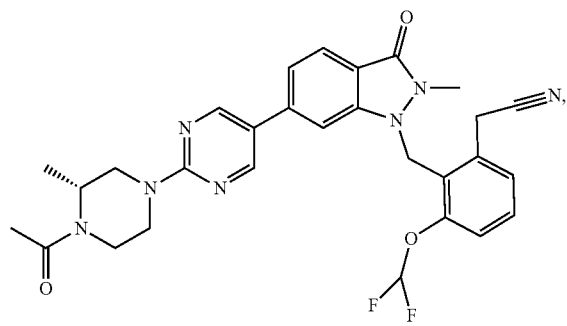
,
50
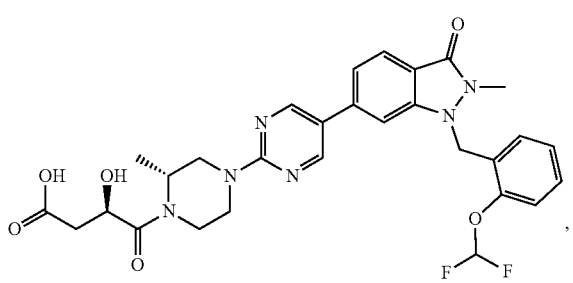
,
51
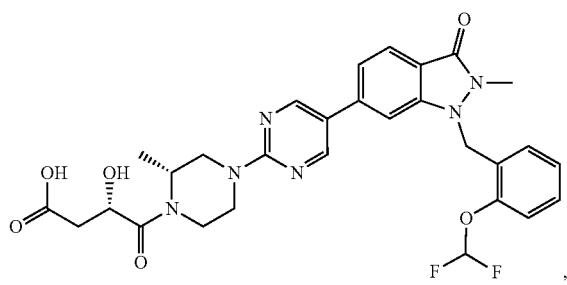
,
52
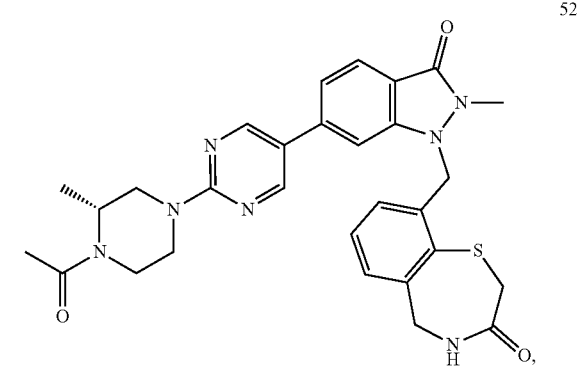
,
53
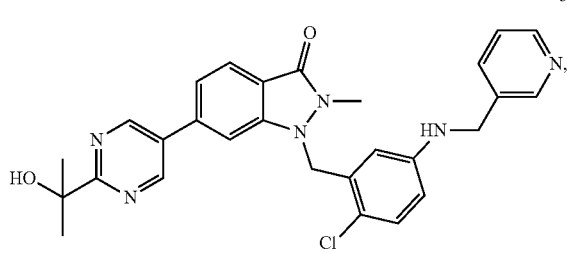
54
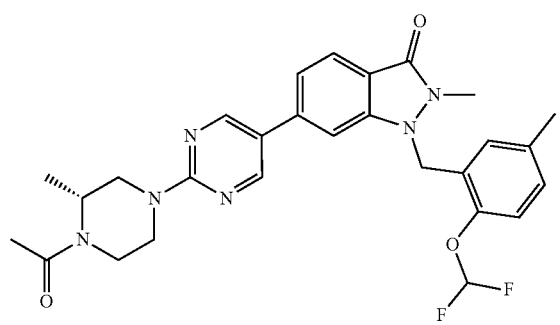
,
55
56
57
58

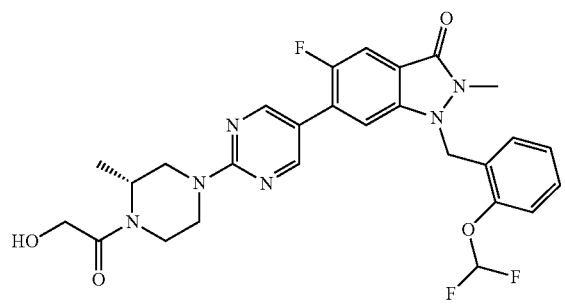
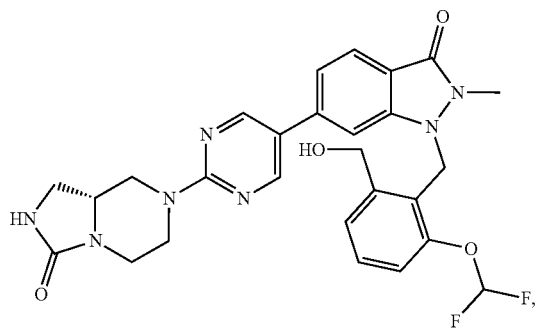
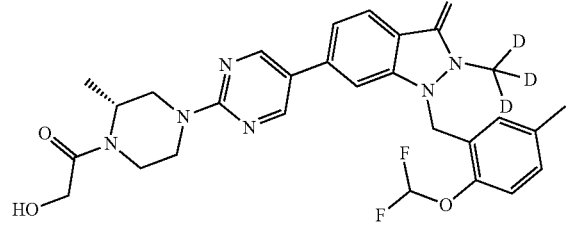
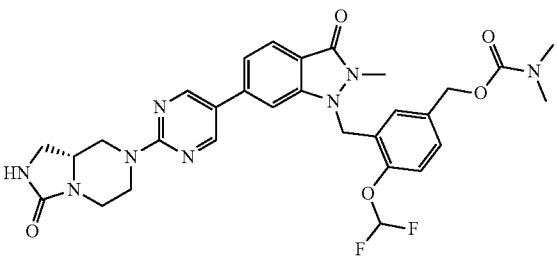
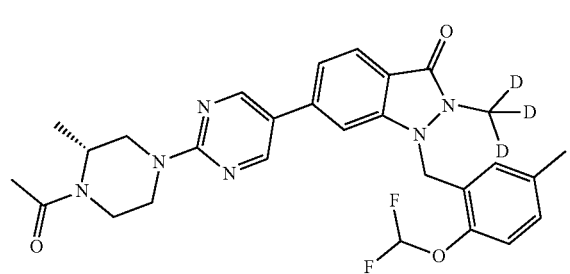

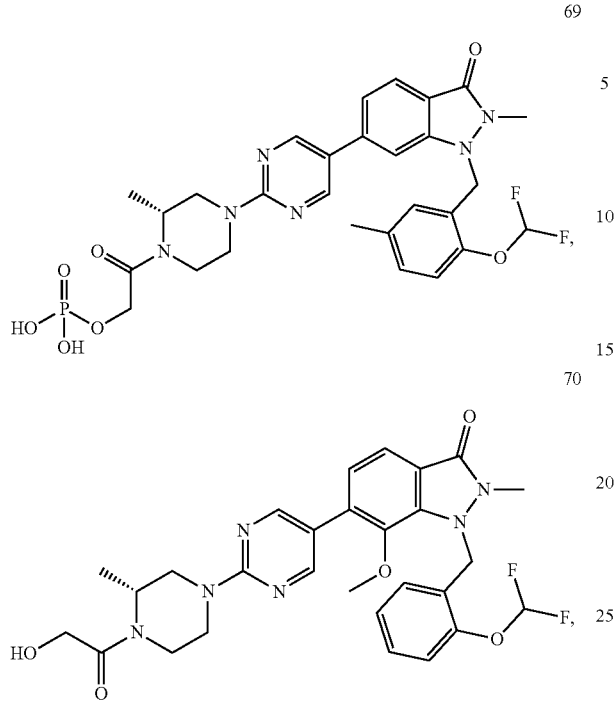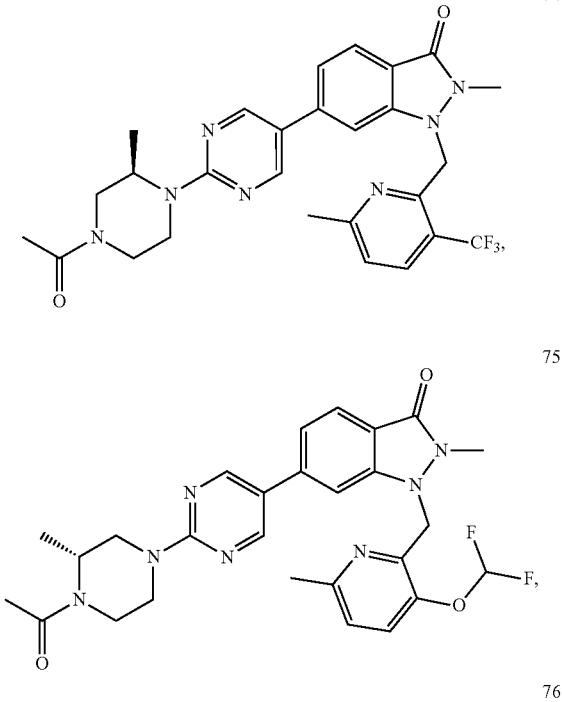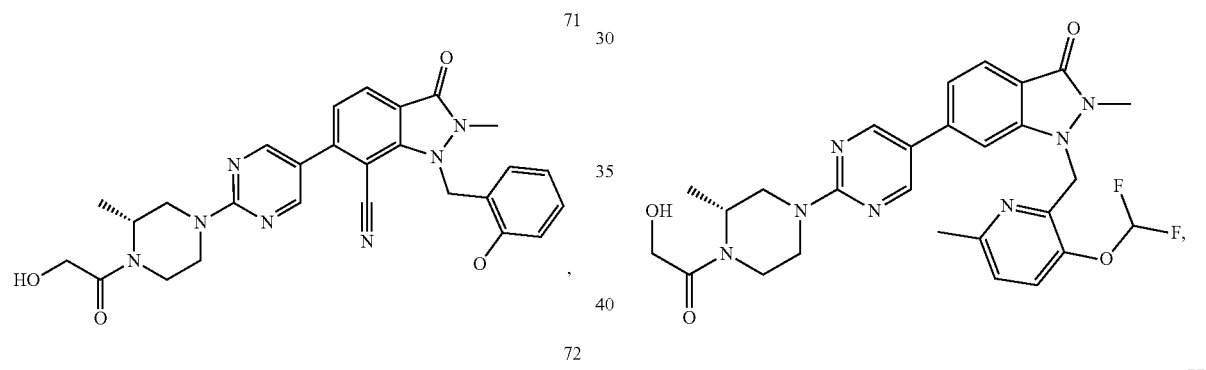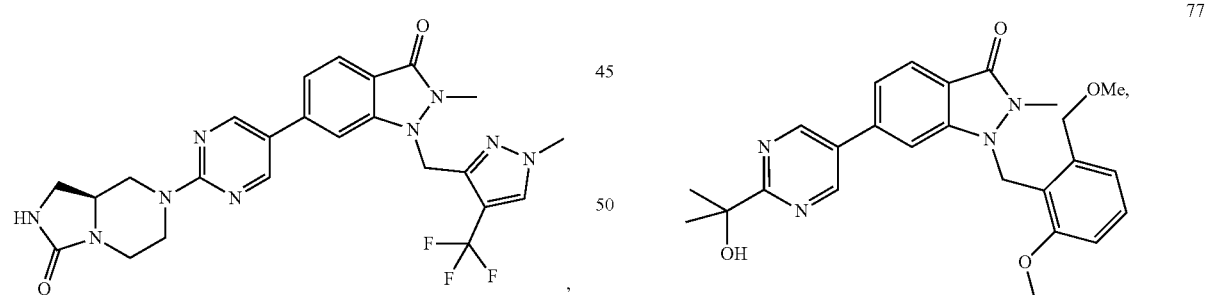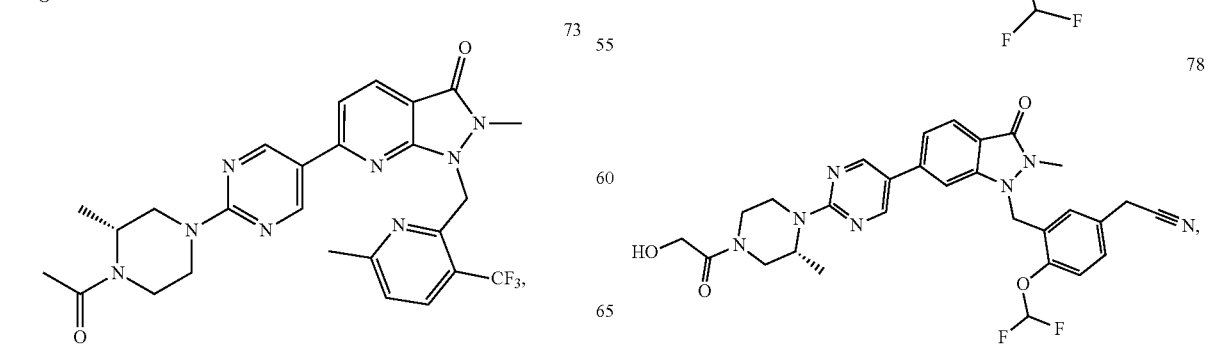

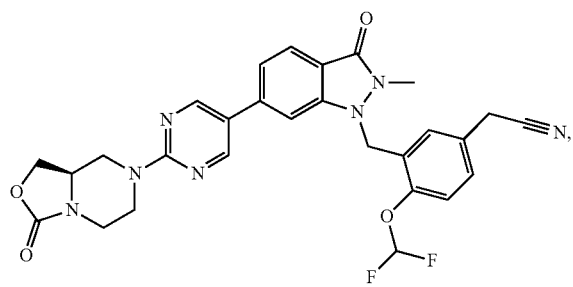
79
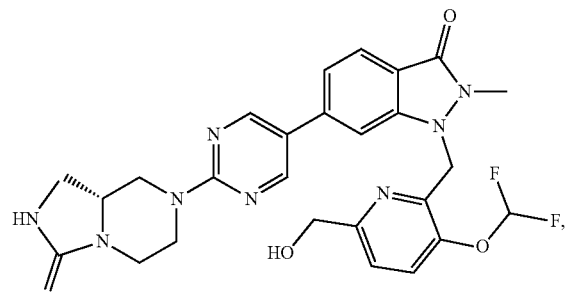
84
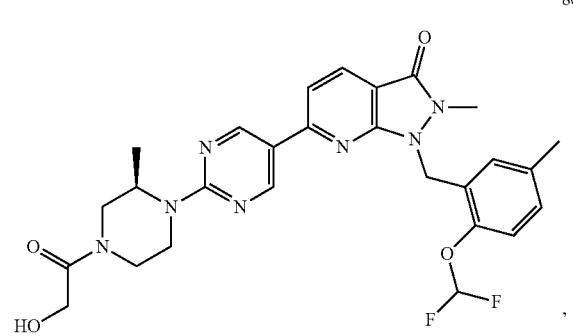
80
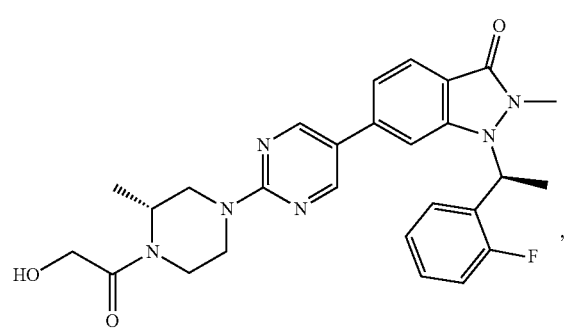
85
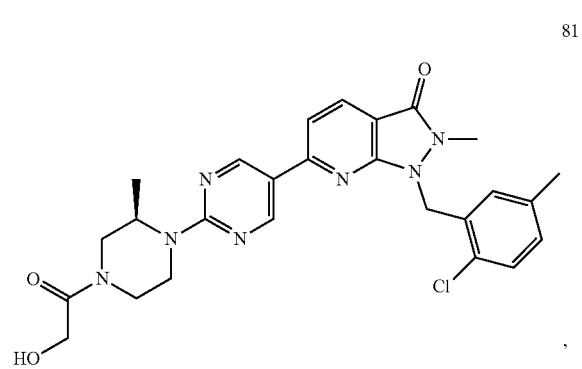
81
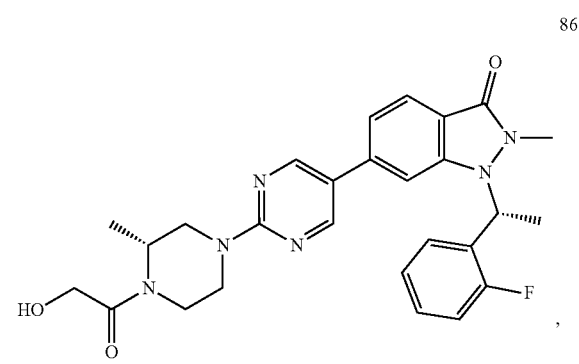
86
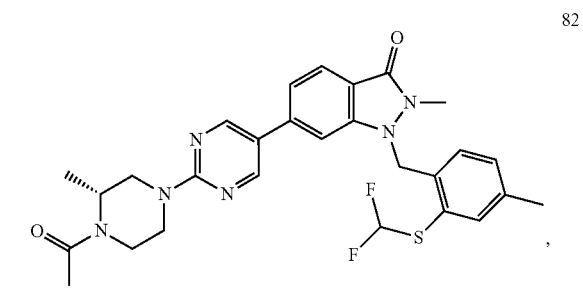
82
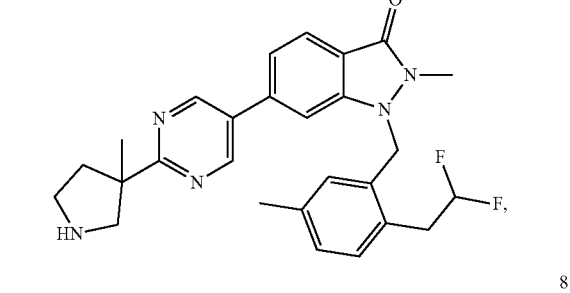
87
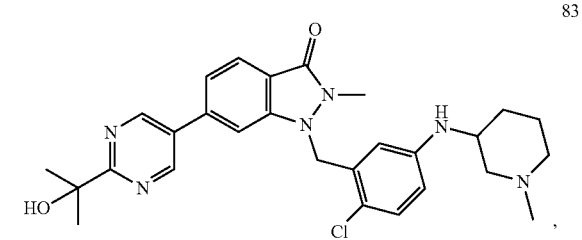
83
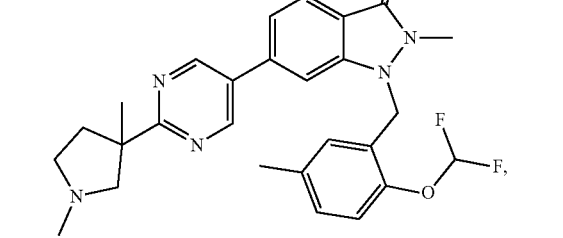
88

89
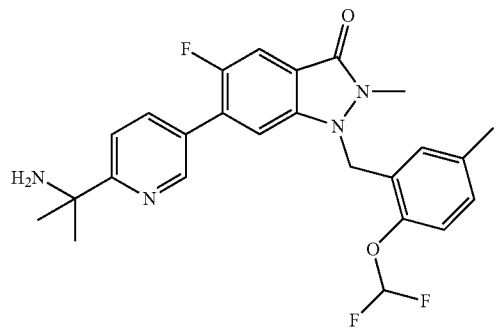
94
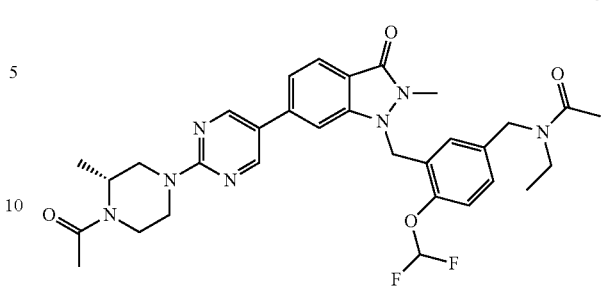
90
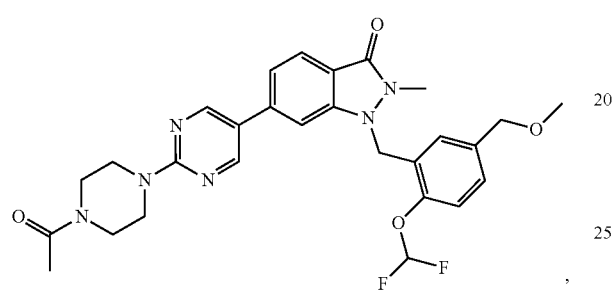
95
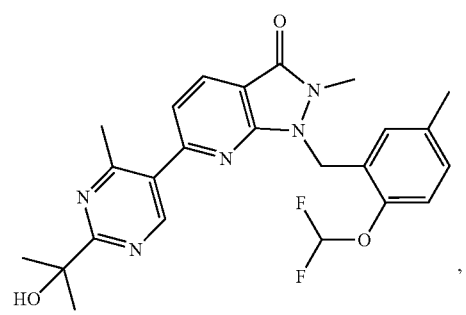
91
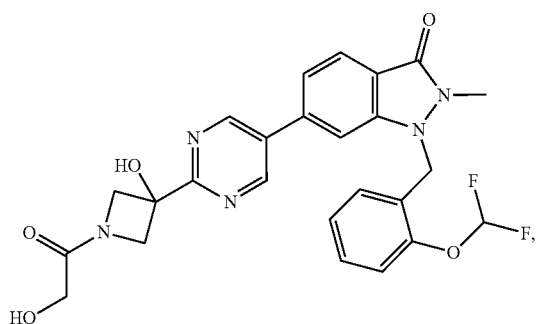
96
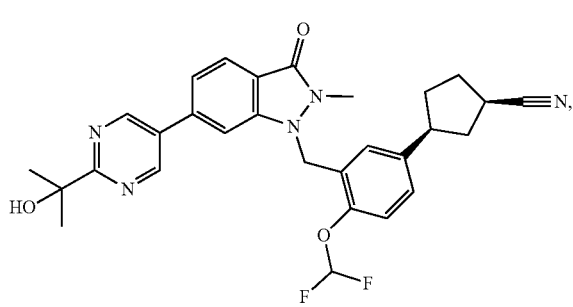
92
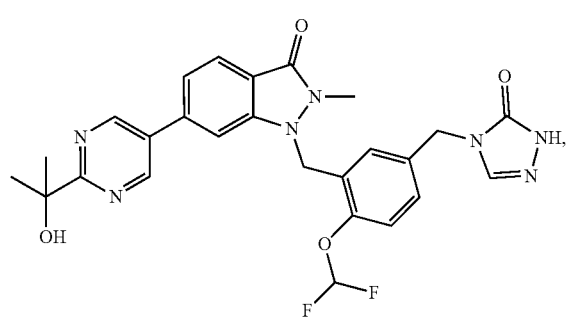
97
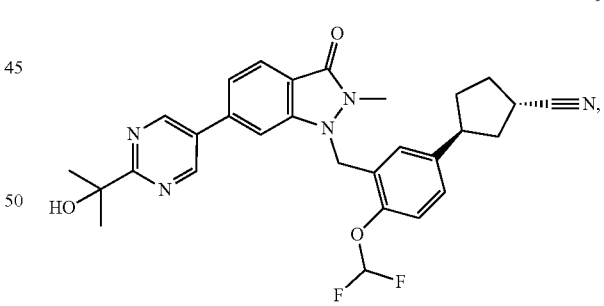
93
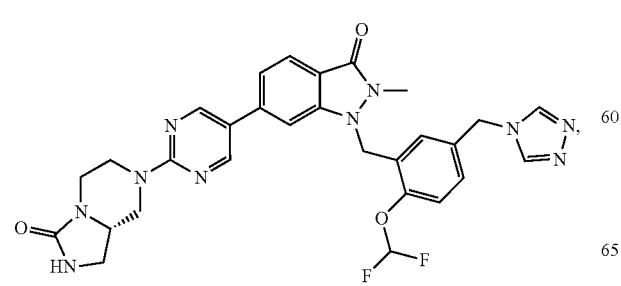
98
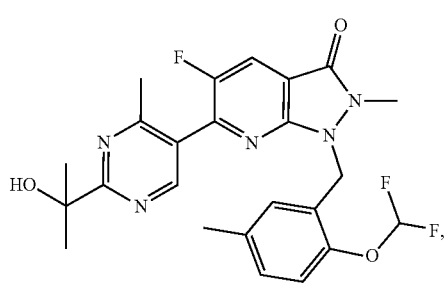

99
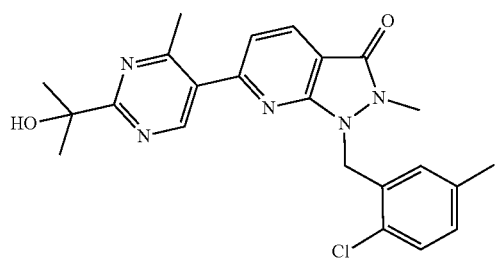
100
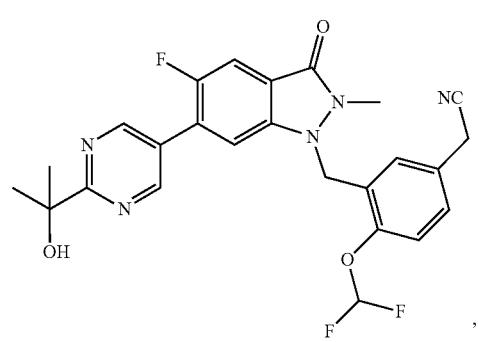
101
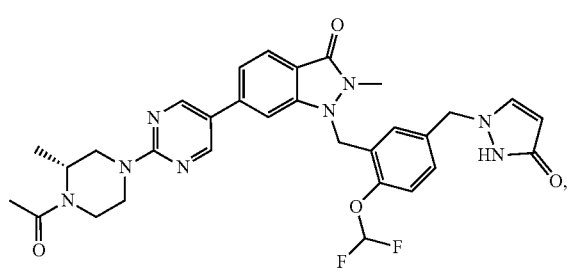
102
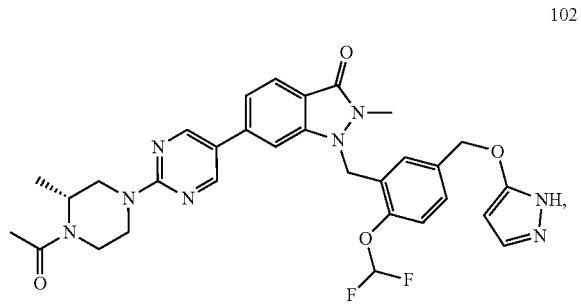
103
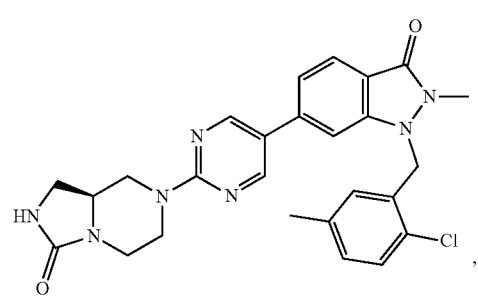
104
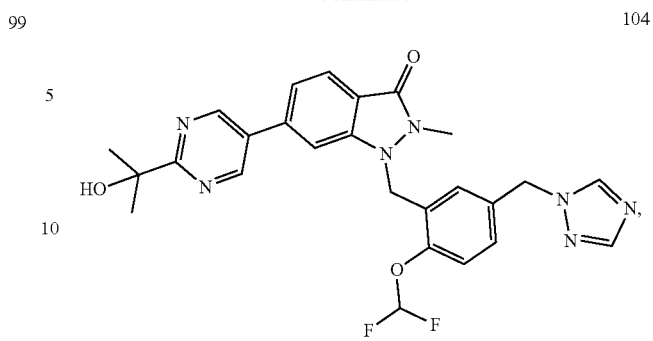
105
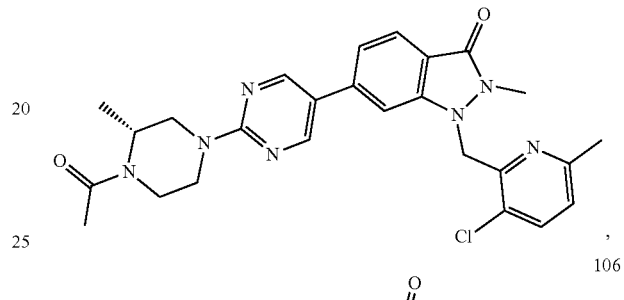
106
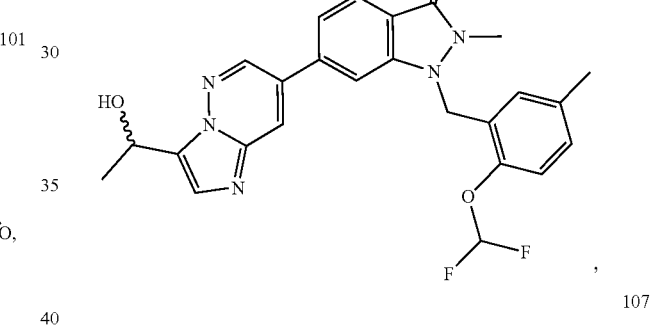
107
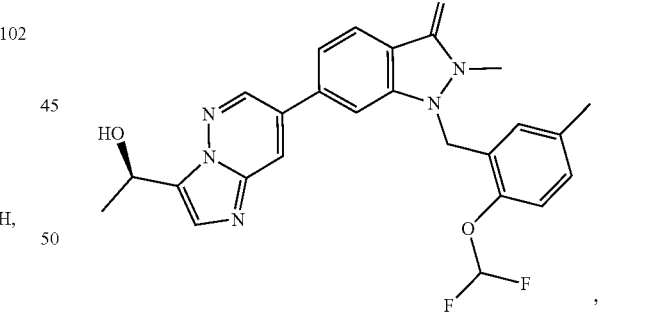
108
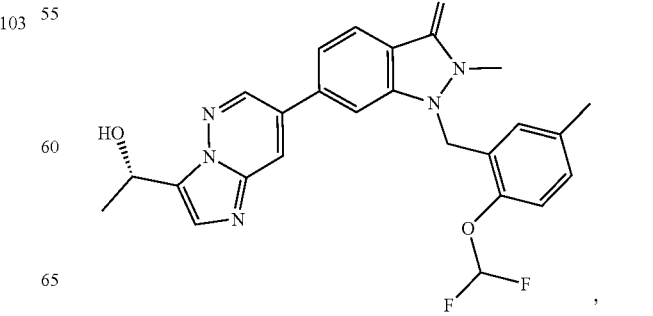

-continued
109
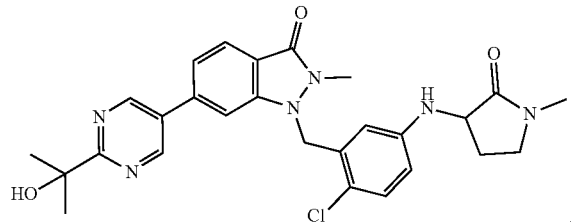,
110
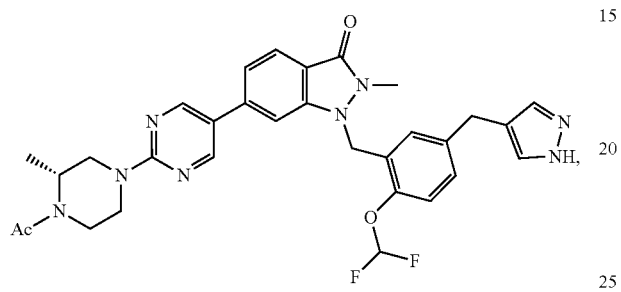,
111
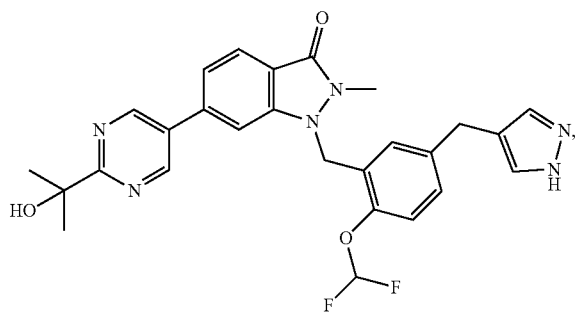,
112
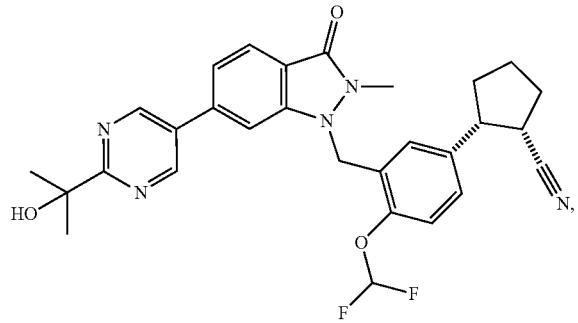,
113
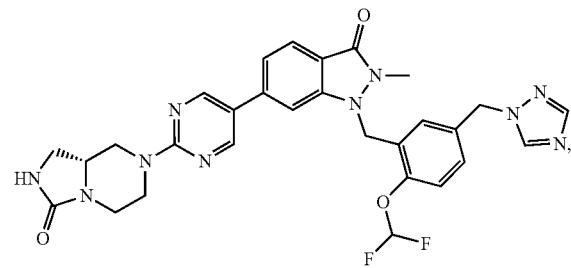,
-continued
114
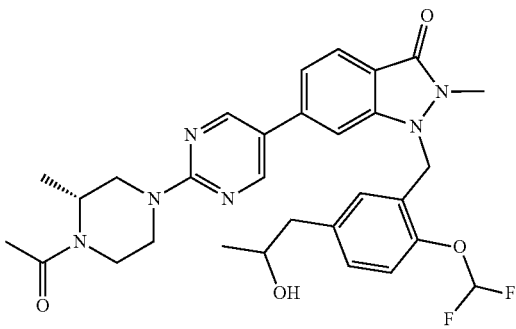,
115
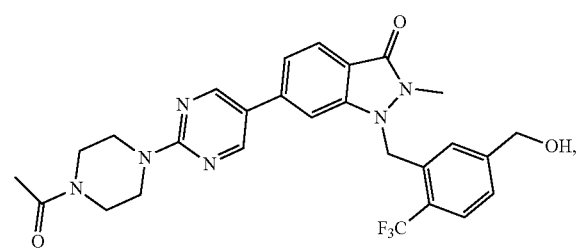,
116
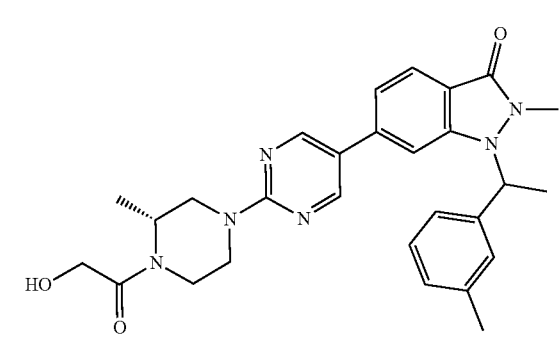,
117
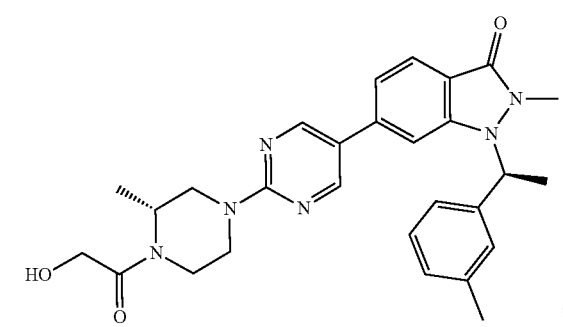,
118
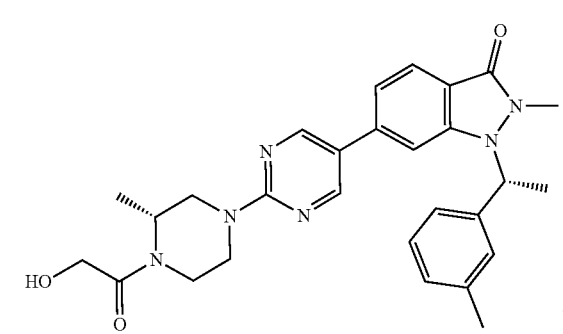, 119
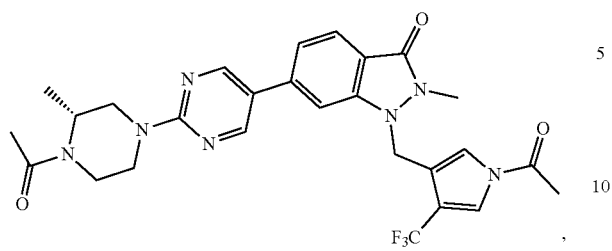
120
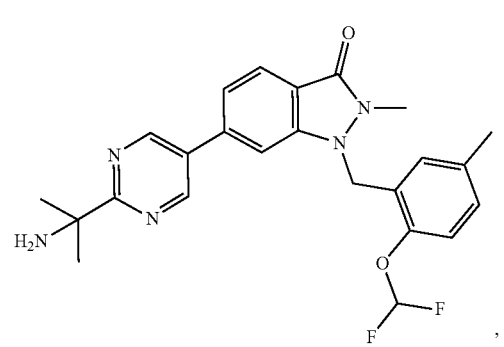
121
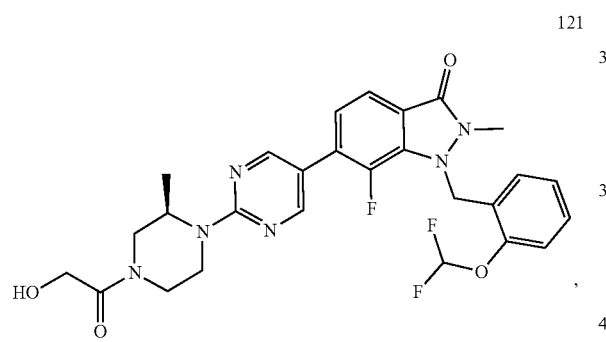
122
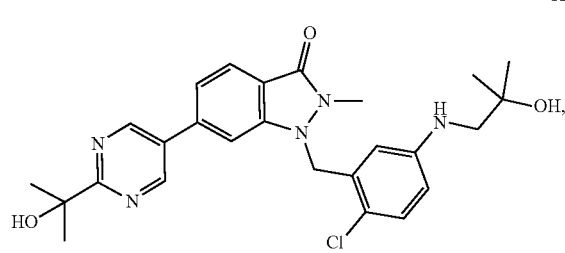
123
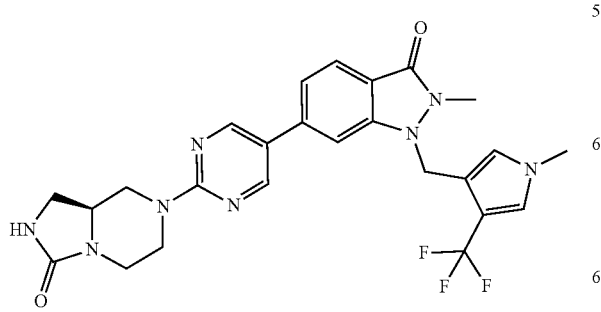
124
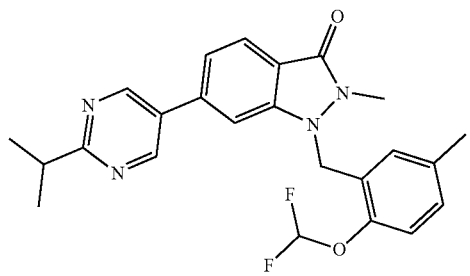
125
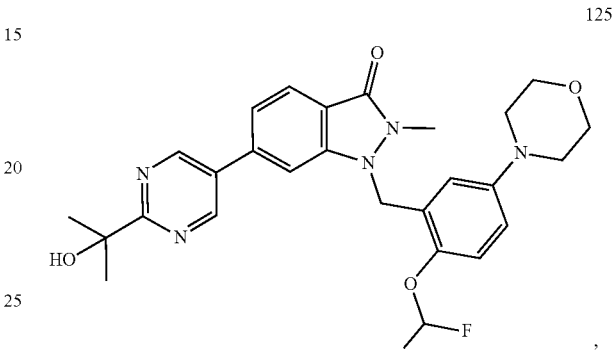
126
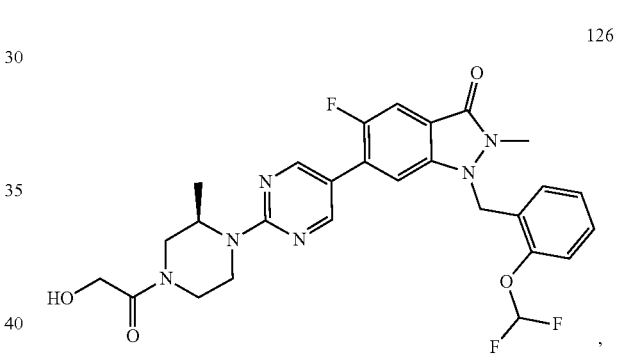
127
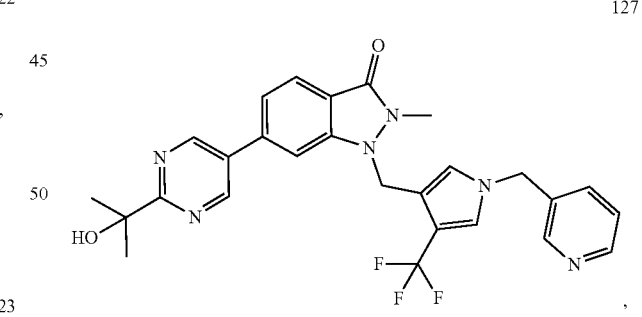
128
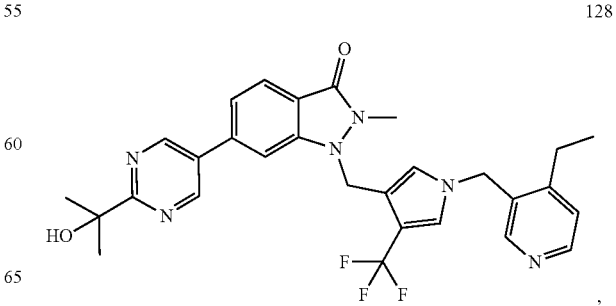

128
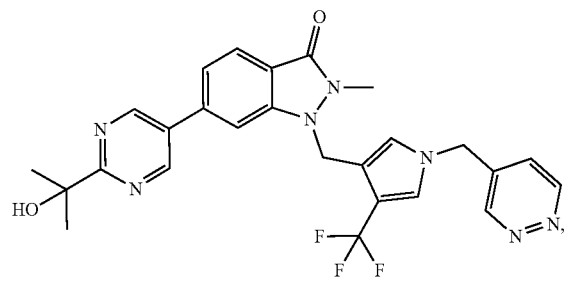
129
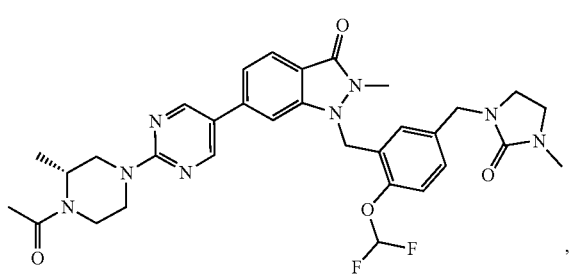
130
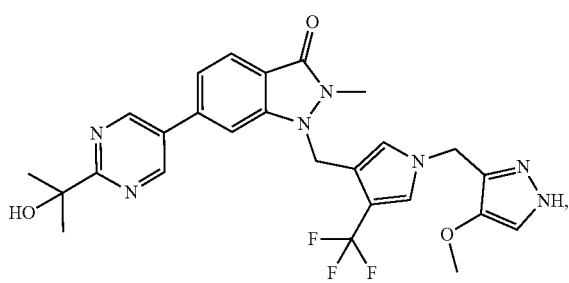
131
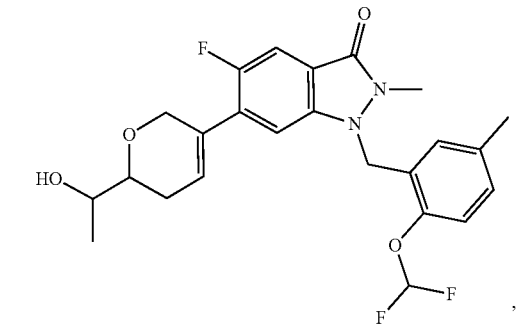
132
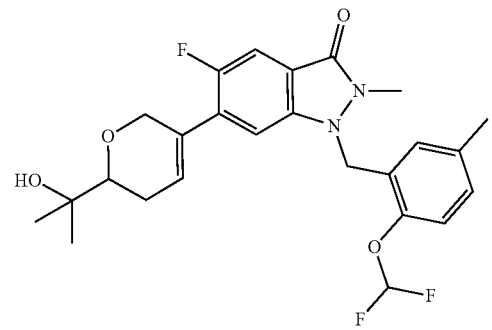
133
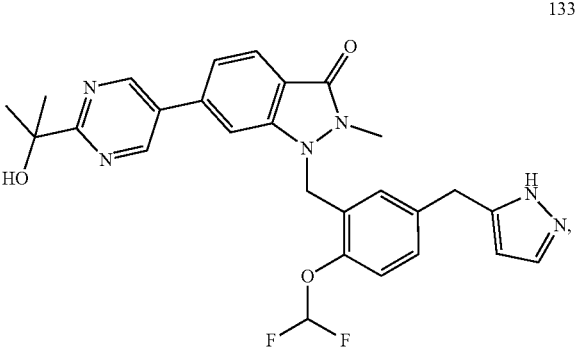
134
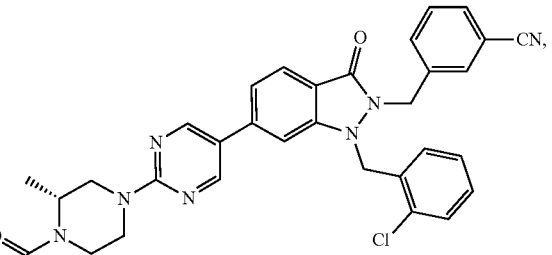
135
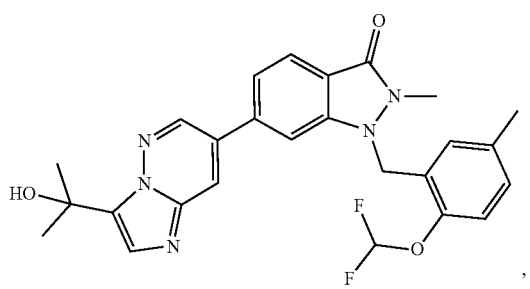
and pharmaceutically acceptable salts thereof.
20. A pharmaceutical composition comprising a compound of claim 19, or a pharmaceutically acceptable salt thereof, and one or more pharmaceutically acceptable excipients.
* * * * *